United States Patent
Lakins et al.

(10) Patent No.: US 12,344,672 B2
(45) Date of Patent: Jul. 1, 2025

(54) ANTIBODY MOLECULES THAT BIND PD-L1 AND CD137

(71) Applicant: INVOX PHARMA LIMITED, London (GB)

(72) Inventors: Matthew Lakins, Cambridge (GB); Jose Munoz-Olaya, Cambridge (GB); Francisca Wollerton, Cambridge (GB); Sarah Batey, Cambridge (GB); Mihriban Tuna, Cambridge (GB); Alexander Koers, Cambridge (GB)

(73) Assignee: INVOX PHARMA LIMITED, London (GB)

( * ) Notice: Subject to any disclaimer, the term of this patent is extended or adjusted under 35 U.S.C. 154(b) by 954 days.

(21) Appl. No.: 17/259,791

(22) PCT Filed: Jul. 12, 2019

(86) PCT No.: PCT/EP2019/068793
§ 371 (c)(1),
(2) Date: Jan. 12, 2021

(87) PCT Pub. No.: WO2020/011964
PCT Pub. Date: Jan. 16, 2020

(65) Prior Publication Data
US 2022/0049007 A1   Feb. 17, 2022

(30) Foreign Application Priority Data

Jul. 12, 2018 (GB) .................................. 1811405
Nov. 9, 2018 (GB) .................................. 1818283
Feb. 26, 2019 (GB) .................................. 1902594

(51) Int. Cl.
C07K 16/28 (2006.01)
A61K 39/00 (2006.01)
A61P 35/00 (2006.01)

(52) U.S. Cl.
CPC .......... *C07K 16/2878* (2013.01); *A61P 35/00* (2018.01); *C07K 16/2827* (2013.01); *A61K 2039/507* (2013.01); *A61K 2039/545* (2013.01); *C07K 2317/24* (2013.01); *C07K 2317/31* (2013.01); *C07K 2317/33* (2013.01); *C07K 2317/34* (2013.01); *C07K 2317/526* (2013.01); *C07K 2317/60* (2013.01); *C07K 2317/75* (2013.01); *C07K 2317/92* (2013.01); *C07K 2317/94* (2013.01)

(58) Field of Classification Search
None
See application file for complete search history.

(56) References Cited

U.S. PATENT DOCUMENTS

| | | |
|---|---|---|
| 3,909,459 A | 9/1975 | Friese et al. |
| 3,967,230 A | 6/1976 | Kamigaito et al. |
| 4,004,183 A | 1/1977 | Oki et al. |
| 5,595,756 A | 1/1997 | Bally et al. |
| 6,380,664 B1 | 4/2002 | Pollner |
| 7,288,638 B2 | 10/2007 | Jure-Kunkel et al. |
| 7,592,426 B2 | 9/2009 | Ebel et al. |
| 8,217,149 B2 | 7/2012 | Irving et al. |
| 8,383,796 B2 | 2/2013 | Korman et al. |
| 8,911,732 B2 | 12/2014 | Dennis et al. |
| 9,567,399 B1 * | 2/2017 | Campbell ............ C07K 16/468 |
| 9,617,338 B1 | 4/2017 | Campbell et al. |
| 10,090,646 B2 | 10/2018 | Takaoka et al. |
| 10,205,305 B2 | 2/2019 | Uegaki et al. |
| 10,233,258 B2 | 3/2019 | Akamatsu et al. |
| 10,604,576 B2 | 3/2020 | Campbell et al. |
| 11,214,618 B2 | 1/2022 | Tuna et al. |
| 11,214,620 B2 | 1/2022 | Campbell et al. |
| 11,548,948 B2 | 1/2023 | Tuna et al. |
| 11,629,193 B2 | 4/2023 | Tuna et al. |
| 12,103,976 B2 | 10/2024 | Lakins et al. |
| 2003/0030355 A1 | 2/2003 | Honda |
| 2007/0071675 A1 | 3/2007 | Wu et al. |
| 2009/0055944 A1 | 2/2009 | Korman et al. |
| 2012/0237498 A1 | 9/2012 | Ahrens et al. |
| 2012/0276104 A1 | 11/2012 | Woisetschlager |
| 2013/0034559 A1 | 2/2013 | Queva et al. |
| 2014/0004121 A1 | 1/2014 | Fanslow, III et al. |
| 2014/0341917 A1 | 11/2014 | Nastri et al. |
| 2015/0214697 A1 | 7/2015 | Yoshida et al. |

(Continued)

FOREIGN PATENT DOCUMENTS

| | | |
|---|---|---|
| CN | 101802006 A | 8/2010 |
| CN | 104955845 A | 9/2015 |

(Continued)

OTHER PUBLICATIONS

U.S. Appl. No. 16/955,450, filed Jun. 18, 2020, Tuna et al.
U.S. Appl. No. 17/259,634, filed Jan. 12, 2021, Munoz-Olaya et al.
U.S. Appl. No. 17/259,680, filed Jan. 12, 2021, Pechouckova et al.
U.S. Appl. No. 17/259,677, filed Jan. 12, 2021, Munoz-Olaya et al.
U.S. Appl. No. 17/259,754, filed Jan. 12, 2021, Lakins et al.
U.S. Appl. No. 17/259,642, filed Jan. 12, 2021, Wollerton et al.

(Continued)

*Primary Examiner* — Daniel E Kolker
*Assistant Examiner* — Brianna K Swartwout
(74) *Attorney, Agent, or Firm* — Wolf, Greenfield & Sacks, P.C.

(57) ABSTRACT

The present application relates to antibody molecules that bind both PD-L1 and CD137 and are able to induce agonism of CD137. The antibody molecules comprise a CDR-based binding site for PD-L1, and a CD137 antigen-binding site that is located in a constant domain of the antibody molecule. The antibody molecules of the invention find application, for example, in the treatment of diseases, such as cancer.

25 Claims, 36 Drawing Sheets

Specification includes a Sequence Listing.

(56) References Cited

U.S. PATENT DOCUMENTS

| | | |
|---|---|---|
| 2015/0259420 A1 | 9/2015 | Triebel et al. |
| 2015/0307620 A1 | 10/2015 | Vella et al. |
| 2016/0043531 A1 | 2/2016 | Firstenberg et al. |
| 2016/0137740 A1 | 5/2016 | Hammond et al. |
| 2016/0244528 A1 | 8/2016 | Gray et al. |
| 2017/0198050 A1 | 7/2017 | Eckelman et al. |
| 2017/0355756 A1 | 12/2017 | Julien et al. |
| 2017/0362321 A1 | 12/2017 | Campbell et al. |
| 2018/0118841 A1 | 5/2018 | Ellmark et al. |
| 2018/0175592 A1 | 6/2018 | Uegaki et al. |
| 2018/0194862 A1 | 7/2018 | Akamatsu et al. |
| 2018/0339031 A1 | 11/2018 | Masternak et al. |
| 2019/0106494 A1 | 4/2019 | Wang et al. |
| 2019/0202920 A1 | 7/2019 | Tuna et al. |
| 2019/0256602 A1 | 8/2019 | Campbell et al. |
| 2019/0330344 A1 | 10/2019 | Tuna et al. |
| 2019/0330351 A1 | 10/2019 | Campbell et al. |
| 2019/0338032 A1 | 11/2019 | Campbell et al. |
| 2019/0338049 A1 | 11/2019 | Tuna et al. |
| 2020/0407446 A1 | 12/2020 | McCourt et al. |
| 2021/0139590 A1 | 5/2021 | Tuna et al. |
| 2021/0237498 A1 | 8/2021 | Yoda et al. |
| 2021/0238299 A1 | 8/2021 | Pechouckova et al. |
| 2021/0277134 A1 | 9/2021 | Lakins et al. |
| 2021/0301022 A1 | 9/2021 | Wollerton et al. |
| 2021/0309753 A1 | 10/2021 | Tuna et al. |
| 2021/0355228 A1 | 11/2021 | Lakins et al. |
| 2022/0048996 A1 | 2/2022 | Tuna et al. |
| 2022/0185890 A1 | 6/2022 | Tuna et al. |
| 2022/0185894 A1 | 6/2022 | Campbell et al. |
| 2022/0267421 A1 | 8/2022 | Munoz-Olaya et al. |
| 2022/0275092 A1 | 9/2022 | Morrow et al. |
| 2023/0357413 A1 | 11/2023 | Tuna et al. |
| 2023/0406935 A1 | 12/2023 | Tuna et al. |

FOREIGN PATENT DOCUMENTS

| | | |
|---|---|---|
| CN | 104968364 A | 10/2015 |
| CN | 107523546 A | 12/2017 |
| CN | 109563171 A | 4/2019 |
| EP | 1025230 B1 | 2/2006 |
| EP | 1180123 B1 | 7/2008 |
| EP | 2407487 A1 | 1/2012 |
| EP | 2546268 A1 | 1/2013 |
| EP | 2242771 B1 | 7/2013 |
| EP | 2905030 A1 | 8/2015 |
| EP | 2215121 B1 | 2/2016 |
| EP | 3354661 A1 | 8/2018 |
| EP | 3470426 A1 | 4/2019 |
| JP | S51-046628 A | 4/1976 |
| JP | 2003-022886 A | 1/2003 |
| JP | 2011-521905 A | 7/2011 |
| JP | 2012-500006 A | 1/2012 |
| JP | 2016-513467 A | 5/2016 |
| JP | 2016-533395 A | 10/2016 |
| JP | 2017-010741 A | 1/2017 |
| JP | 2018-508475 A | 3/2018 |
| RU | 2017112379 A | 10/2018 |
| TW | 201642897 A | 12/2016 |
| WO | 2001/077342 | 10/2001 |
| WO | WO 2005/035584 A1 | 4/2005 |
| WO | WO 2006/072620 A1 | 7/2006 |
| WO | WO 2006/088447 A1 | 8/2006 |
| WO | WO 2006/099141 A2 | 9/2006 |
| WO | WO 2008/003103 A2 | 1/2008 |
| WO | WO 2008/068048 A2 | 6/2008 |
| WO | WO 2009/000006 A1 | 12/2008 |
| WO | WO 2009/068204 A1 | 6/2009 |
| WO | WO 2009/126944 A1 | 10/2009 |
| WO | WO 2009/132876 A1 | 11/2009 |
| WO | WO 2010/019570 A2 | 2/2010 |
| WO | WO 2010/057047 A1 | 5/2010 |
| WO | WO 2010/111282 A1 | 9/2010 |
| WO | WO 2010/124797 A1 | 11/2010 |
| WO | WO 2012/130831 A1 | 10/2012 |
| WO | WO 2013/181634 A2 | 12/2013 |
| WO | WO 2014/004549 A2 | 1/2014 |
| WO | WO 2014/008218 A1 | 1/2014 |
| WO | WO 2014/052064 A1 | 4/2014 |
| WO | WO 2014/089113 A1 | 6/2014 |
| WO | WO 2014/140180 A1 | 9/2014 |
| WO | WO 2014/151910 A1 | 9/2014 |
| WO | WO 2015/048312 A1 | 4/2015 |
| WO | WO 2015/049537 A1 | 4/2015 |
| WO | WO 2015/119923 A1 | 8/2015 |
| WO | WO 2015/138920 A1 | 9/2015 |
| WO | WO 2015/198312 A1 | 12/2015 |
| WO | WO 2015/200119 A1 | 12/2015 |
| WO | WO 2016/028672 A1 | 2/2016 |
| WO | WO 2016/040880 A1 | 3/2016 |
| WO | 2016/110584 | 7/2016 |
| WO | WO 2016/111645 A1 | 7/2016 |
| WO | WO 2016/162505 A1 | 10/2016 |
| WO | WO 2016/177802 A1 | 11/2016 |
| WO | WO 2016/185016 A1 | 11/2016 |
| WO | WO 2016/200782 A1 | 12/2016 |
| WO | WO 2017/009456 A1 | 1/2017 |
| WO | WO 2017/015560 A2 | 1/2017 |
| WO | WO 2017/019846 A8 | 2/2017 |
| WO | WO 2017/025498 A1 | 2/2017 |
| WO | WO 2017/049452 A1 | 3/2017 |
| WO | WO 2017/052241 A1 | 3/2017 |
| WO | WO 2017/055398 A2 | 4/2017 |
| WO | WO 2017/062888 A1 | 4/2017 |
| WO | WO 2017/077085 A2 | 5/2017 |
| WO | WO 2017/087589 A2 | 5/2017 |
| WO | WO 2017/087901 A2 | 5/2017 |
| WO | WO 2017/123650 A2 | 7/2017 |
| WO | WO 2017/182672 A1 | 10/2017 |
| WO | WO 2017/193032 A2 | 11/2017 |
| WO | WO 2017/205738 A1 | 11/2017 |
| WO | WO 2017/220555 A1 | 12/2017 |
| WO | WO 2017/220569 A1 | 12/2017 |
| WO | WO 2017/220990 A9 | 12/2017 |
| WO | WO 2018/017673 A1 | 1/2018 |
| WO | WO 2018/056821 A1 | 3/2018 |
| WO | WO 2018/060480 A1 | 4/2018 |
| WO | WO 2018/091740 A2 | 5/2018 |
| WO | WO 2018/115859 A1 | 6/2018 |
| WO | WO 2018/127610 A1 | 7/2018 |
| WO | WO 2018/222711 A2 | 12/2018 |
| WO | WO 2019/025545 A1 | 2/2019 |

OTHER PUBLICATIONS

U.S. Appl. No. 17/259,714, filed Jan. 12, 2021, Tuna et al.
U.S. Appl. No. 17/259,796, filed Jan. 12, 2021, Tuna et al.
PCT/EP2019/068793, Oct. 18, 2019, International Search Report and Written Opinion.
PCT/EP2019/068793, Jan. 21, 2021, International Preliminary Report on Patentability.
International Search Report and Written Opinion for Application No. PCT/EP2019/068793, mailed Oct. 18, 2019.
International Preliminary Report on Patentability for Application No. PCT/EP2019/068793, mailed Jan. 21, 2021.
[No Author Listed] F-star Alpha: A new asset centric company. Retrieved from http://www.onenucleus.com/media/Events/LSLS/11%20feb%202014/Jane%20Dancer.pdf on Jan. 8, 2015. 15 pages.
Asgarov et al., A new anti-mesothelin antibody targets selectively the membrane-associated form. MAbs. Apr. 2017;9(3):567-577. doi: 10.1080/19420862.2017.1288770.
Bacac et al., Abstract 1494: CEA TCB: A novel head-to-tail 2:1 T cell bispecific antibody for treatment of CEA-positive solid tumors. Oncoimmunology. Aug. 2016; 5(Abstract): e1203498. Epub Jun. 24, 2016. doi: 10.1080/2162402X.2016.1203498.
Chester et al., 4-1BB agonism: adding the accelerator to cancer immunotherapy. Cancer Immunol Immunother. Oct. 2016;65(10):1243-8. doi: 10.1007/s00262-016-1829-2. Epub Mar. 31, 2016.
Chester et al., Dual antibody therapy to harness the innate anti-tumor immune response to enhance antibody targeting of tumors. Curr Opin Immunol. Apr. 2015;33:1-8. doi: 10.1016/j.coi.2014.12.010. Epub Jan. 7, 2015.

(56) References Cited

OTHER PUBLICATIONS

Goding et al., Combination of adoptive cell transfer, anti-PD-L1 and anti-LAG-3 antibodies for the treatment of recurrent tumors: better with more. OncoImmunology. Oct. 22, 2013;2(8):e25050-1-e25050-3.

Hasenhindl et al., Creating stable stem regions for loop elongation in Fcabs—insights from combining yeast surface display, in silico loop reconstruction and molecular dynamics simulations. Biochim Biophys Acta. 2014;1844(9):1530-1540. doi:10.1016/j.bbapap.2014.04.020.

Hasenhindl et al., Stability assessment on a library scale: a rapid method for the evaluation of the commutability and insertion of residues in C-terminal loops of the CH3 domains of IgG1-Fc. Protein Eng Des Sel. 2013;26(10):675-682.

Jing et al., Combined immune checkpoint protein blockade and low dose whole body irradiation as immunotherapy for myeloma. Journal of Immunotherapy of Cancer. doi: 10.1186/S40425-014-0043-Z. Jan. 20, 2015. 15 pages.

Kraman et al., A LAG-3/PD-L1 bispecific antibody inhibits tumor growth in two syngeneic colon carcinoma models. Journal of ImmunoTherapy of Cancer. 2016;4(Suppl 1):82(abstract P124).

Kraman et al., A LAG-3/PD-L1 bispecific antibody inhibits tumor growth in two syngeneic colon carcinoma models. Retrieved from http://www.f-star.com/media/73722/A-LAG-3-PD-L1-bispecific-antibody-inhibits-tumour-growth-in-two-syngeneic-colon-carcinoma-models.pdf. Nov. 9-13, 2016. 1 page.

Lakins et al., A Novel CD137/PD-L1 Bispecific Antibody Modulates the Tumour Microenvironmentby Activating CD8+ T cells and Results in Tumour Growth Inhibition. F-Star Poster. Nov. 7, 2018. 1 page. Retrieved from https://www.f-star.com/media/87488/201811-SITC-2018-F-star-FS222-Poster-ONLINE.pdf.

Lee et al., 4-1BB and OX40 dual costimulation synergistically stimulate primary specific CD8 T cells for robust effector function. J Immunol. Sep. 1, 2004;173(5):3002-12. doi: 10.4049/jimmunol.173.5.3002.

Leung et al., A HER2-specific Modified Fc Fragment (Fcab) Induces Antitumor Effects Through Degradation of HER2 and Apoptosis. Mol Ther. Nov. 2015;23(11):1722-1733. doi: 10.1038/mt.2015.127. Epub Aug. 3, 2015. Erratum in: Mol Ther. Nov. 2015;23(11):1794.

Lobner et al., Engineered IgG1-Fc—one fragment to bind them all. Immunol Rev. Mar. 2016;270(1):113-31. doi: 10.1111/imr.12385.

Lobner et al., Two-faced Fcab prevents polymerization with VEGF and reveals thermodynamics and the 2.15 Å crystal structure of the complex. MAbs. Oct. 2017;9(7):1088-1104. doi: 10.1080/19420862.2017.1364825. Epub Aug. 17, 2017.

Lundqvist et al., 31st Annual Meeting and Associated Programs of the Society for Immunotherapy of Cancer (SITC 2016): Part One. Journal for Immunotherapy of Cancer. Nov. 16, 2016;4(1):74(abstract P. 124).

Qui et al., CD134 plus CD137 dual costimulation induces Eomesodermin in CD4 T cells to program cytotoxic Th1 differentiation. J Immunol. Oct. 1, 2011;187(7):3555-64. doi: 10.4049/jimmunol.1101244. Epub Aug. 31, 2011.

Ramelet et al., Beneficial outcome of combination therapy with 4-1BB targeting antibody. Eur J Cancer. Nov. 29, 2016;69(Suppl 1):S96-S97.

Sallin et al., The anti-lymphoma activities of anti-CD137 monoclonal antibodies are enhanced in FcγRIII(−/−) mice. Cancer Immunol Immunother. Sep. 2014;63(9):947-58. doi: 10.1007/s00262-014-1567-2. Epub Jun. 14, 2014.

Schlothauer et al., Novel human IgG1 and IgG4 Fc-engineered antibodies with completely abolished immune effector functions. Protein Eng Des Sel. Oct. 2016;29(10):457-466. doi: 10.1093/protein/gzw040. Epub Aug. 29, 2016.

Shindo et al., Combination immunotherapy with 4-1BB activation and PD-1 blockade enhances antitumor efficacy in a mouse model of subcutaneous tumor. Anticancer Res. Jan. 2015;35(1):129-36.

Vilgelm et al., Combinatorial approach to cancer immunotherapy: strength in numbers. Journal of Leukocyte Biology. 2016;100(2):275-90. Epub Jun. 2, 2016.

Wozniak-Knopp et al., Designing Fcabs: well-expressed and stable high affinity antigen-binding Fc fragments. Protein Eng Des Sel. Sep. 1, 2017;30(9):657-671. doi: 10.1093/protein/gzx042.

Wozniak-Knopp et al., Introducing antigen-binding sites in structural loops of immunoglobulin constant domains: Fc fragments with engineered HER2/neu-binding sites and antibody properties. Protein Eng Des Sel. 2010;23(4):289-297. doi:10.1093/protein/gzq005.

Xu et al., In vitro characterization of five humanized OKT3 effector function variant antibodies. Cell Immunol. Feb. 25, 2000;200(1):16-26.

[No Author Listed], FS118 First in Human Study in Patients With Advanced Malignancies. Sponsored by F-star Therapeutics Limited. Clinical Trial. Retrieved from https://clinicaltrials.gov/ct2/show/NCT03440437. Feb. 22, 2018. 7 pages.

Asgarov et al., A new anti-mesothelin antibody targets selectively the membrane-associated form. MAbs. Apr. 2017;9(3):Supplementary Data. doi: 10.1080/19420862.2017.1288770. 6 pages.

Awuah et al., Reduced Shedding of Surface Mesothelin Improves Efficacy of Mesothelin-Targeting Recombinant Immunotoxins. Mol Cancer Ther. Jul. 2016;15(7):1648-55. doi: 10.1158/1535-7163. MCT-15-0863. Epub May 18, 2016.

Callahan et al., Targeting T Cell Co-receptors for Cancer Therapy. Immunity. May 17, 2016;44(5):1069-78. doi: 10.1016/j.immuni.2016.04.023.

Chatterjee et al., Noninvasive Imaging of Immune Checkpoint Ligand PD-L1 in Tumors and Metastases for Guiding Immunotherapy. Mol Imaging. Jan.-Dec. 2017;16:1536012117718459. doi: 10.1177/1536012117718459. 5 pages.

Chu et al., An Update on Anti-CD137 Antibodies in Immunotherapies for Cancer. Int J Mol Sci. Apr. 1, 20192;20(8):1822. doi: 10.3390/ijms20081822. 17 pages.

Dahlén et al., Bispecific antibodies in cancer immunotherapy. Ther Adv Vaccines Immunother. Feb. 2018;6(1):3-17. doi: 10.1177/2515135518763280. Epub Mar. 28, 2018.

Del Bano et al., A Bispecific Antibody-Based Approach for Targeting Mesothelin in Triple Negative Breast Cancer. Front Immunol. Jul. 10, 2019;10:1593. doi: 10.3389/fimmu.2019.01593.

El-Khoueiry et al., The relationship of pharmacodynamics (PD) and pharmacokinetics (PK) to clinical outcomes in a phase I study of OX40 agonistic monoclonal antibody (mAb) PF-04518600 (PF-8600). J Clin Oncol. May 20, 2017. 35(15_suppl):3027-3027. Meeting Abstract. 2017 ASCO Annual Meeting I. doi: 10.1200/JCO.2017.35.15_suppl.3027. 4 pages.

Faroudi et al., Abstract 2399: LAG-3/PD-L1 mAb2 can overcome PD-L1-mediated compensatory upregulation of LAG-3 induced by single-agent checkpoint blockade. Proceedings: AACR Annual Meeting 2019; Mar. 29-Apr. 3, 2019. Atlanta, GA. Doi: 10.1158/1538-7445.AM2019-2399. Published Jul. 2019.

Faroudi et al., Abstract B009: FS118, a LAG-3/PD-L1 bispecific antibody, capable of driving potent anti-tumour immune responses and overcome PD-(L)1-mediated compensatory. Sep. 25-28, 2019. Fifth CRI-CIMT-EATI-AACR International Cancer Immunotherapy Conference (2019): Translating Science into Survival. Paris. 1 page.

Faroudi et al., FS118, a LAG-3/PD-L1 bispecific antibody, capable of driving potent anti- tumour immune responses and overcome PD-(L)1-mediated compensatory. Sep. 25-28, 2019. Poster. Fifth CRI-CIMT-EATI-AACR International Cancer Immunotherapy Conference (2019): Translating Science into Survival. Paris. 1 page.

Frenzel et al., Phage display-derived human antibodies in clinical development and therapy. MAbs. Oct. 2016;8(7):1177-1194. doi: 10.1080/19420862.2016.1212149. Epub Jul. 14, 2016.

F-Star, Next-Generation Bispecifics for Cancer Immunotherapy. Feb. 2020. Presented on Mar. 11, 2020 at Immuno-Oncology Summit Europe 2020. London. 46 pages.

F-Star, Redirecting T Cells. Overcoming Cancer. Improving Lives. Oct. 2019 Presentation in Investor Meeting. 36 pages.

F-Star, Redirecting T Cells. Overcoming Cancer. Improving Lives. Apr. 2020 Presentation in Investor Meeting. 43 pages.

F-Star, Redirecting T Cells. Overcoming Cancer. Improving Lives. Jan. 2020 Presentation in Investor Meeting. 41 pages.

(56) References Cited

OTHER PUBLICATIONS

Gaspar et al., FS120 mAb2, a dual agonist bispecific antibody targeting OX40 and CD137, activates T cells in vitro and induces FcγR-independent anti-tumour activity. SITC 2018. Nov. 7, 2018. Poster. 10 pages.

Gaspar, FS120 mAb2, a dual agonist bispecific antibody targeting OX40 and CD137. SITC 2018. Nov. 11, 2018. Presentation. 12 pages.

Geuijen et al., Abstract 541: An unbiased screen identifies a CD137xPD-L1 bispecific IgG1 antibody with unique T cell activation and binding properties. Cancer Res. 2019;79(13_Supplement):541. Poster Presentation AACR Conference 2019. Jul. 1, 2019. doi: 10.1158/1538-7445.AM2019-541. 4 pages.

Glisson et al., Phase 1 study of MEDI0562, a humanized OX40 agonist monoclonal antibody (mAb), in adult patients (pts) with advanced solid tumors. Annals Onocol. Oct. 1, 2016;27(6):vi361. doi: 10.1093/annonc/mdw378.07.

Golfier et al., Anetumab ravtansine: a novel mesothelin-targeting antibody-drug conjugate cures tumors with heterogeneous target expression favored by bystander effect. Mol Cancer Ther. Jun. 2014;13(6):1537-48. doi: 10.1158/1535-7163.MCT-13-0926. Epub Apr. 8, 2014.

Gunde et al., Abstract 1532: A novel, monovalent tri-specific antibody-based molecule that simultaneously modulates PD-L1 and 4-1BB exhibits potent anti-tumoral activity in vivo. Cancer Res. 2019;79(13_Supplement): 1532. AACR Conference 2019. Jul. 1, 2019. doi: 10.1158/1538-7445.AM2019-1532. 4 pages.

Han et al., Bispecific anti-CD3 x anti-HER2 antibody mediates T cell cytolytic activity to HER2-positive colorectal cancer in vitro and in vivo. Int J Oncol. Dec. 2014;45(6):2446-54. doi: 10.3892/ijo.2014.2663. Epub Sep. 18, 2014.

Hassan et al., Mesothelin Immunotherapy for Cancer: Ready for Prime Time? J Clin Oncol. Dec. 2016;34(34):4171-4179. doi: 10.1200/JCO.2016.68.3672. Epub Oct. 31, 2016.

Hassan et al., Phase II clinical trial of amatuximab, a chimeric antimesothelin antibody with pemetrexed and cisplatin in advanced unresectable pleural mesothelioma. Clin Cancer Res. Dec. 1, 2014;20(23):5927-36. doi: 10.1158/1078-0432.CCR-14-0804. Epub Sep. 17, 2014.

Hebb et al., Administration of low-dose combination anti-CTLA4, anti-CD137, and anti-OX40 into murine tumor or proximal to the tumor draining lymph node induces systemic tumor regression. Cancer Immunol Immunother. Jan. 2018;67(1):47-60. doi: 10.1007/s00262-017-2059-y. Epub Sep. 13, 2017. Author Manuscript. 20 pages.

Ho et al., A novel high-affinity human monoclonal antibody to mesothelin. Int J Cancer. May 1, 2011;128(9):2020-30. doi: 10.1002/ijc.25557.

Kraman et al., Dual blockade of PD-L1 and LAG-3 with FS118, a unique bispecific antibody, induces CD8+ T-cell activation and modulates the tumour microenvironment to promote anti-tumour immune responses. Apr. 14-18, 2018. Poster 2719. Proceedings of the American Association for Cancer Research Annual Meeting 2018. Chicago, IL. 2 pages.

Kraman et al., Dual blockade of PD-L1 and LAG-3 with FS118, a unique bispecific antibody, induces T-cell activation with the potential to drive potent anti-tumour immune responses. Nov. 7, 2017;5 Suppl 2 (87): Abstract P348. 32nd Annual Meeting and Pre-Conference Programs of the Society for Immunotherapy of Cancer (SITC). Part II. Nov. 8-12, 2017. National Harbor, MD. 2 pages.

Kraman et al., Dual blockade of PD-L1 and LAG-3 with FS118, a unique bispecific antibody, induces T-cell activation with the potential to drive potent anti-tumour immune responses. Apr. 14-18, 2018;78(13 Suppl);Abstract 2719. Proceedings of the American Association for Cancer Research Annual Meeting 2018. Chicago, IL. 5 pages.

Kraman et al., Dual blockade of PD-L1 and LAG-3 with FS118, a unique bispecific antibody, induces T-cell activation with the potential to drive potent anti-tumour immune responses. Poster P348. 32nd Annual Meeting and Pre-Conference Programs of the Society for Immunotherapy of Cancer (SITC). Part II. Nov. 8-12, 2017. National Harbor, MD. 1 page.

Kraman et al., FS118, a Bispecific Antibody Targeting LAG-3 and PD-L1, Enhances T-Cell Activation Resulting in Potent Antitumor Activity. Clin Cancer Res. Jul. 1, 2020;26(13):3333-3344. doi: 10.1158/1078-0432.CCR-19-3548. Epub Apr. 16, 2020.

Kunik et al., Structural consensus among antibodies defines the antigen binding site. PLoS Comput Biol. 2012;8(2):e1002388. doi: 10.1371/journal.pcbi.1002388. Epub Feb. 23, 2012. 12 pages.

Kvarnhammar et al., The CTLA-4 x OX40 bispecific antibody ATOR-1015 induces anti-tumor effects through tumor-directed immune activation. J Immunother Cancer. Apr. 11, 2019;7(1):103. doi: 10.1186/s40425-019-0570-8.

Lakins et al., FS222 mAb2, a bispecific conditional agonist antibody targeting CD137 and PD-L1, induces potent lymphocyte activation and has a favourable safety profile. F-star, Cambridge, UK. Poster Presentation. AACR Annual Meeting Mar. 29-Apr. 3, 2019. Atlanta, GA. Poster No. 1540. 1 page.

Lakins et al., Optimising TNFRSF agonism and checkpoint blockade with a novel CD137/PD-L1 bispecific antibody. Abstracts Therapeutic Development. Dec. 1, 2018;29(Supplement 10):X30. doi: 10.1093/annonc/mdy487.014. 1 page.

Lamberts et al., ImmunoPET with Anti-Mesothelin Antibody in Patients with Pancreatic and Ovarian Cancer before Anti-Mesothelin Antibody-Drug Conjugate Treatment. Clin Cancer Res. Apr. 1, 2016;22(7):1642-52. doi: 10.1158/1078-0432.CCR-15-1272. Epub Nov. 20, 2015.

Li et al., Discovery and preclinical characterization of the antagonist anti-PD-L1 monoclonal antibody LY3300054. J Immunother Cancer. Apr. 30, 2018;6(1):31. doi: 10.1186/s40425-018-0329-7. Erratum in: J Immunother Cancer. Jun. 4, 2018;6(1):45.

Lin et al., Fc-dependent expression of CD137 on human NK cells: insights into "agonistic" effects of anti-CD137 monoclonal antibodies. Blood. Aug. 1, 2008;112(3):699-707. doi: 10.1182/blood-2007-11-122465. Epub Jun. 2, 2008.

Link et al., Abstract 3752: Preclinical pharmacology of MP0310: A 4-1BB/FAP bispecific DARPin drug candidate promoting tumor-restricted T-cell costimulation. Cancer Res. Jul. 1, 2018;78(13_Supplement):3752.

Liu et al., Abstract 3642: Tumor-antigen expression-dependent activation of the CD137 costimulatory pathway by bispecific DART® proteins. Cancer Res. Jul. 1, 2017;77(13_Supplement):3642.

Ma et al., Recognition of mesothelin by the therapeutic antibody MORAb-009: structural and mechanistic insights. J Biol Chem. Sep. 28, 2012;287(40):33123-31. doi: 10.1074/jbc.M112.381756. Epub Jul. 11, 2012.

Mayes et al., Abstract 539: A bispecific Fc-silenced IgG1 antibody (MCLA-145) requires PD-L1 binding to activate CD137. Cancer Res. 2019;79(13_Supplement):539. AACR Presentation 2019. Jul. 1, 2019. doi: 10.1158/1538-7445.AM2019-539. 4 pages.

McCourt, Development of an ICOS/PD-L1 Bispecific, Mar. 18-22, 2019. Abstract. Cambridge Healthtech Institute's 4th Annual Immuno-Oncology Summit Europe 2019 (London).

Melero et al., Clinical development of immunostimulatory monoclonal antibodies and opportunities for combination. Clin Cancer Res. Mar. 1, 2013;19(5):997-1008. doi: 10.1158/1078-0432.CCR-12-2214.

Perez-Ruiz et al., Anti-CD137 and PD-1/PD-L1 Antibodies En Route toward Clinical Synergy. Clin Cancer Res. Sep. 15, 2017;23(18):5326-5328. doi: 10.1158/1078-0432.CCR-17-1799. Epub Aug. 8, 2017.

Poon et al., Dual agonist bispecific antibody targeting OX40 and DC137 mediates anti-tumour immunity and synergises with PD-1/PD-L1 blockade to improve survival in a syngeneic mouse model. AACR 2019. Mar. 29, 2019. Poster. 9 pages.

Reichen et al., Abstract 3029: FAP-mediated tumor accumulation of a T-cell agonistic FAP/4-1BB DARPin drug candidate analyzed by SPECT/CT and quantitative biodistribution. Cancer Res. Jul. 1, 2018;78(13_Supplement):3029.

Ryan et al., A novel biologic platform elicits profound T cell costimulatory activity and antitumor immunity in mice. Cancer

(56) References Cited

OTHER PUBLICATIONS

Immunol Immunother. Apr. 2018;67(4):605-613. doi: 10.1007/s00262-018-2116-1. Epub Jan. 11, 2018.
Schroeder, Chapter 13: Immunoglobulins and Their Genes. From Arthritis and Allied Conditions: A Textbook of Rheumatology. 15th Ed. vol 1. Eds Koopman et al.Lippincot Williams & Wilkins. pp. 289-304. Supplied by the British Library Jul. 31, 2023.
Segal et al., Results from an Integrated Safety Analysis of Urelumab, an Agonist Anti-CD137 Monoclonal Antibody. Clin Cancer Res. Apr. 15, 2017;23(8):1929-1936. doi: 10.1158/1078-0432.CCR-16-1272. Epub Oct. 18, 2016.
Tang et al., A human single-domain antibody elicits potent antitumor activity by targeting an epitope in mesothelin close to the cancer cell surface. Mol Cancer Ther. Apr. 2013;12(4):416-26. doi: 10.1158/1535-7163.MCT-12-0731. Epub Jan. 31, 2013.
Tuna, Delivering the next immuno-oncology breakthrough. PEGS Europe 2018. Nov. 11, 2018. Presentation. 24 pages.
Wang et al., Retargeting T cells for HER2-positive tumor killing by a bispecific Fv-Fc antibody. PLoS One. Sep. 23, 2013;8(9):e75589. doi: 10.1371/journal.pone.0075589. eCollection 2013.
Yap et al., A first-in-human phase I study of FS118, an anti-LAG-3/PD-L1 bispecific antibody in patients with solid tumors that have progressed on prior PD-1/PD-L1 therapy. Journal of Clinical Oncology. Jun. 1, 2019. Poster TPS2652. 2019 ASCO Annual Meeting Proceedings. 20 pages.
Yap et al., A first-in-human phase I study of FS118, an anti-LAG-3/PD-L1 bispecific antibody in patients with solid tumors that have progressed on prior PD-1/PD-L1 therapy. Journal of Clinical Oncology. May 26, 2019;37(15_suppl). 3 pages.
Yonezawa et al., Boosting Cancer Immunotherapy with Anti-CD137 Antibody Therapy. Clin Cancer Res. Jul. 15, 2015;21(14):3113-20. doi: 10.1158/1078-0432.CCR-15-0263. Epub Apr. 23, 2015.
Zhao et al., Novel Antibody Therapeutics Targeting Mesothelin in Solid Tumors. Clin Cancer Drugs. Oct. 2016;3(2):76-86. doi: 10.2174/2212697X03666160218215744.
[No Author Listed] Abstract for CHI Immuno-Oncology Summit Europe. Mar. 18-22, 2019. 1 page. PDR303.
[No Author Listed] F-Star Modular Bispecific Antibodies. Summary for Atlas deck. Presented at JP Morgan. Jan. 2017. 1 page. PDR159.
[No Author Listed] First-in-Class bispecific antibodies for cancer immunotherapy. Presentation at Takeda. Dec. 1, 20163. 24 pages. PDR160.
[No Author Listed], Pipeline Overview: F-star is developing a pipeline of bispecific antibodies focused on oncology and immuno-oncology. F-Start website update. Sep. 2016. 2 pages. PDR126.
Ascierto et al., Initial efficacy of anti-lymphocyte activation gene-3 (anti-LAG-3:BMS-986016) in combination with nivolumab (nivo) in pts with melanoma (MEL) previously treated with anti-PD-1/PD-L1 therapy. J Clin Oncology. May 20, 2017;35(15):9520-9520. Abstract only. doi: 10.1200/JCO.2017.35.15_suppl.9520. EPub May 30, 2017.
Berg et al., Biochemistry. 5th ed. New York. 2002. Accessible at https://www.ncbi.nlm.nih.gov/books/NBK22358/section5.5. Accessed Jun. 9, 2021. 4 pages.
Bernett et al., Abstract P122: Multiple bispecific checkpoint combinations enhance T cell activity. J Immunother Cancer. 2016;4(Suppl 1):P122. 2 pages.
Bernett et al., Multiple bispecific checkpoint combinations enhance T cell activity. Xencor Poster Presentation. 2016. 1 page.
Bodhankar et al., PD-L1 Monoclonal Antibody Treats Ischemic Stroke by Controlling Central Nervous System Inflammation. Stroke. Oct. 2015;46(10):2926-34. doi: 10.1161/STROKEAHA.115.010592. Epub Aug. 25, 2015.
Borlak et al., Immune-mediated liver injury of the cancer therapeutic antibody catumaxomab targeting EpCAM, CD3 and Fc? receptors. Oncotarget. May 10, 2016;7(19):28059-74. doi: 10.18632/oncotarget.8574.
Brewis, Development of an anti-PD-L1 Fcab. Presentation. Human Antibodies and Hybrodomas Conference. Oct. 2018. 22. PDR 312.
Brewis, Identification of a PD-L1 binding Fcab: a potent inhibitor of immunosuppressive signals. Abstract. Huamn Antibodies and Hybridomas 2018. Jun. 11, 2018. 1 page. PDR282.
Brewis, The use of bispecific antibodies to modulate anti-tumour immune responses. Oral Presentation at ELRIG-Research and Innovation. Mar. 29, 2017. 33 pages. PDR177.
Brewis, The use of bispecific antibodies to modulate anti-tumour immune responses. Oral Presentation at PEPtalk. Jan. 12, 2017. 26 pages. PDR163.
Burova et al., Abstract 1484: Combined treatment with anti-LAG-3 and anti-PD-1 fully human monoclonal antibodies inhibits tumor growth in immunocompetent double-humanized LAG-3/PD-1 mice. Proceedings: AACR 107th Annual Meeting 2016. Apr. 16-20, 2016. New Orleans, LA. doi: 10.1158/1538-7445.AM2016-1484. Published Jul. 2016. 8 pages.
Burova et al., Abstract P195: A novel anti-human LAG-3 antibody in combination with anti-human PD-1 (REGN2810) shows enhanced anti-tumor activity in PD-1 x LAG-3 dual-humanized mice and favorable pharmacokinetic and safety profiles in cynomolgus monkey. J Immunother Cancer. 2016;4(Suppl 1):P195. 2 pages.
Camisaschi et al., LAG-3 expression defines a subset of CD4(+)CD25(high)Foxp3(+) regulatory T cells that are expanded at tumor sites. J Immunol. Jun. 1, 2010;184(11):6545-51. doi: 10.4049/jimmunol.0903879. Epub Apr. 26, 2010.
Cemerski et al., T cell activation and anti-tumor efficacy of anti-LAG-3 antibodies is independent of LAG-3-MHCII blocking capacity. Poster Presentation. 30th Annual Meeting and Associated Programs of the Society for Immunotherapy of Cancer (SITC 2015). National Harbor, MD. Nov. 4-8, 2015. 1 page.
Chen et al., Molecular mechanisms of T cell co-stimulation and co-inhibition. Nat Rev Immunol. Apr. 2013;13(4):227-42. doi: 10.1038/nri3405. Epub Mar. 8, 2013. Erratum in: Nat Rev Immunol. Jul. 2013;13(7):542.
Chiu et al., Antibody Structure and Function: The Basis for Engineering Therapeutics. Antibodies (Basel). Dec. 3, 2019;8(4):55. doi: 10.3390/antib8040055.
Curran et al., PD-1 and CTLA-4 combination blockade expands infiltrating T cells and reduces regulatory T and myeloid cells within B16 melanoma tumors. Proc Natl Acad Sci U S A. Mar. 2, 2010;107(9):4275-80. doi: 10.1073/pnas.0915174107. Epub Feb. 16, 2010.
Davies, Analytical challenges for next generation biologics. Oral Presentation at Waters Biopharma Mini-Seminar. May 24, 2017. 20 pages. PDR191.
Davies, Bispecific Antibodies: New Opportunities for Novel Therapies. Oral Presentation at Bioprocess UK 2016. Nov. 26, 2016. 14 pages. PDR 135.
Davies, Overcoming the Manufacturing Challenges for Bisepcific mAbs. Oral Presentation at 5th Annual Cell Culture and Bioprocessing Congress. Nov. 6, 2016. 16 pages. PDR142.
Davies, Overcoming the Manufacturing Challenges for Bisepcific mAbs. Oral Presentation at Biopronet 3rd Annual Scientific Symposium. Oct. 20, 2016. 16 pages. PDR136.
Daxini et al., Vasculitis associated with immune checkpoint inhibitors-a systematic review. Clin Rheumatol. Sep. 2018;37(9):2579-2584. doi: 10.1007/s10067-018-4177-0. Epub Jun. 19, 2018.
Demeure et al., T Lymphocytes infiltrating various tumour types express the MHC class II ligand lymphocyte activation gene-3 (LAG-3): role of LAG-3/MHC class II interactions in cell-cell contacts. Eur J Cancer. Sep. 2001;37(13):1709-18. doi: 10.1016/s0959-8049(01)00184-8.
Deng et al., LAG-3 confers poor prognosis and its blockade reshapes antitumor response in head and neck squamous cell carcinoma. Oncoimmunology. Oct. 7, 2016;5(11):e1239005. doi: 10.1080/2162402X.2016.1239005.
Doody et al., Abstract B091: A LAG-3/PD-L1 bispecific antibody inhibits tumor growth in two syngeneic colon carcinoma models. Second CRI-CIMT-EATI-AACR International Cancer Immunotherapy Conference: Translating Science into Survival. Sep. 25-28, 2016. New York, NY. doi: 10.1158/23/26-6066.IMM2016-B091. Published Nov. 2016. 8 pages.
Doody, An anti-murine LAG-3/PD-L1 bispecific antibody which modulates T cell activity and inhibits tumour growth. Oral Presen-

(56) References Cited

OTHER PUBLICATIONS tation at 2nd Annual Advances in Immuno-Oncology Congress. May 16, 2017. 17 pages. PDR188.
Doody, In vivo Efficacy of bispecific antibodies targeting two immmune-modulatory receptors. Oral Presentation at PEGS Europe. Nov. 4, 2016. 16 pages. PDR144.
Everett et al., A LAG-3/PD-L1 bispecific antibody inhibits tumour growth in two syngeneic colon carcinoma models. Poster Presentation. AACR Tumor Immunology and Immunotherapy. Oct. 21, 2016. 1 page. PDR137.
Everett et al., Abstract PR06: a LAG-3/PD-L1 bispecific antibody inhibits tumour growth in two syngeneic colon carcinoma models. AACR Special Conference on Tumor Immunology and Immunotherapy. Oct. 20-23, 2016. Boston, MA. Doi: 10.1158/2326-6074.TUMIMM16-PR06. Published Mar. 2017. 8 pages.
Everett, A LAG-3/PD-L1 Bispecific Antibody Inhibits Tumour Growth in Two Syngeneic Colon Carcinoma Models. Oral Presentation at AACR Tumor Immunology and Immunotherapy. Boston, MA. Oct. 20-23, 2016. 5 pages. PDR141.
F-Star, First-in-Class Bispecific Antibodies for Cance Immunotherapy. Jul. 2016. Presentation. 14 pages. PDR119.
Fiehler, Development of an anti-PD-L1 Fcab. Presentation. European Antibody Congress. Oct. 29, 2018. 26 pages. PDR312.
Foy et al., Poxvirus-Based Active Immunotherapy with PD-1 and LAG-3 Dual Immune Checkpoint Inhibition Overcomes Compensatory Immune Regulation, Yielding Complete Tumor Regression in Mice. PLoS One. Feb. 24, 2016;11(2):e0150084. doi: 10.1371/journal.pone.0150084.
Gandhi et al., Expression of LAG-3 by tumor-infiltrating lymphocytes is coincident with the suppression of latent membrane antigen-specific CD8+ T-cell function in Hodgkin lymphoma patients. Blood. Oct. 1, 2006;108(7):2280-9. doi: 10.1182/blood-2006-04-015164. Epub Jun. 6, 2006.
Gliddon, Pushing all the buttons: innovating in immuno-oncology with mAb. Oral Presentation at Phacilitate Immunotherapy World 2017. Jan. 18, 2017. 11 pages. PDR165.
Grosso et al., Programmed death-ligand 1 (PD-L1) expression in various tumor types. J Immunother Cancer. 2013;1(Suppl 1):P53. http://www.immunotherapyofcancer.org/content/1/S1/P53. 1 page.
Haines et al., Abstract 4714: Blockade of LAG-3 amplifies immune activation signatures and augments curative antitumor responses to anti-PD-1 therapy in immune competent mouse models of cancer. Proceedings: AACR Annual Meeting 2017. Apr. 1-5, 2017. Washington, DC. doi: 10.1158/1538-7445.AM2017-4714. Published Jul. 2017. 8 pages.
Herbst et al., Predictive correlates of response to the anti-PD-L1 antibody MPDL3280A in cancer patients. Nature. Nov. 27, 2014;515(7528):563-7. doi: 10.1038/nature14011. Author Manuscript.
Hid Cadena et al., Checks and Balances in Autoimmune Vasculitis. Front Immunol. Feb. 22, 2018;9:315. doi: 10.3389/fimmu.2018.00315.
Horn et al., CD3xPDL1 bi-specific T cell engager (BiTE) simultaneously activates T cells and NKT cells, kills PDL1+ tumor cells, and extends the survival of tumor-bearing humanized mice. Oncotarget. Aug. 3, 2017;8(35):57964-57980. doi: 10.18632/oncotarget.19865.
Huang et al., Abstract PR03: Combinatorial blockade of PD-1, CTLA-4, and LAG-3 pathways inhibits murine ovarian tumor growth. Abstracts: AACR Special Conference: Advances in Ovarian Cancer Research: Exploiting Vulnerabilites. Oct. 17-20, 2015. Orlando, FL. doi: 10.1158/1557-3265.OVCA15-PR03. Published Jan. 2016. 8 pages.
Iwai et al., Involvement of PD-L1 on tumor cells in the escape from host immune system and tumor immunotherapy by PD-L1 blockade. Proc Natl Acad Sci U S A. Sep. 17, 2002;99(19):12293-7. doi: 10.1073/pnas.192461099. Epub Sep. 6, 2002.
Jochems et al., Analyses of functions of an anti-PD-L1/TGF?R2 bispecific fusion protein (M7824). Oncotarget. Sep. 8, 2017;8(43):75217-75231. doi: 10.18632/oncotarget.20680.

Kehry et al., Abstract 271: Targeting PD-1, TIM-3 and LAG-3 in combination for improved immunotherapy combinations. AACR 106th Annual Meeting. Apr. 18-22, 2015. Philadelphia, PA. doi: 10.1158/1538-7445.AM2015-271. 8 pages.
Klooster et al., Abstract B088: Generation of immuno-modulatory receptor binding bispecific antibodies to modulate tumor immunity. Second CRI-CIMT-EATI-AACR International Cancer Immunotherapy Conference: Translating Science into Survival. Sep. 25-28, 2016. New York, NY. doi: 10.1158/2326-6066.IMM2016-B088. 4 pages.
Koopmans et al., A novel bispecific antibody for EGFR-directed blockade of the PD-1/PD-L1 immune checkpoint. Oncoimmunology. May 31, 2018;7(8):e1466016. doi: 10.1080/2162402X.2018.1466016.
Kraman et al., A LAG-3/PD-L1 bispecific antibody inhibits tmour growth in two syngeneic colon carcinoma models. Poster Presentation. BSI/NVVI Congress. Dec. 6, 2016. 1 page. PDR153.
Kraman et al., A LAG-3/PD-L1 bispecific antibody inhibits tumour growth in two syngeneic colon carcinoma models. Abstract B091. Poster Presentation. CRI-CIMT-EATI-AACR Cancer Immunotherapy Conference. Sep. 26, 2016. 1 page. PDR129.
Kraman et al., A LAG-3/PD-L1 bispecific antibody inhibits tumour growth in two syngeneic colon carcinoma models. Poster 003. Poster Presentation. 2nd Annual Advances in Immuno-Oncology Congress. May 15, 2017. 1 page. PDR185.
Kraman et al., A LAG-3/PD-L1 bispecific antibody inhibits tumour growth in two syngeneic colon carcinoma models. Poster 1103. Poster Presentation. Keystone Symposium—Cancer Immunology and Immunotherapy. Mar. 19, 2017. 1 page. PDR174.
Kraman et al., A LAG-3/PD-L1 bispecific antibody inhibits tumour growth in two syngeneic colon carcinoma models. Poster 128. Poster Presentation at SITC. Nov. 9, 2016. 1 page. PDR143.
Kraman et al., A LAG-3/PD-L1 bispecific antibody inhibits tumour growth in two syngeneic colon carcinoma models. Poster 5651. Poster Presentation. AACR Annual Meeting. Apr. 1, 2017. 1 page. PDR176.
Kraman et al., A Lag-3/PD-L1 bispecific antibody inhibits tumour growth in two syngeneic colon carcinoma models. Poster Presentation. International Conference on Human & Translational Immunology. Sep. 16, 2016. 1 page. PDR123.
Kraman et al., A LAG-3/PD-L1 bispecific antibody inhibits tumour growth in two syngeneic coon carcinoma models. Poster 3005. Poster Presentation. Keystome Symposium—Biobetters and Next-Generation Biologics. Jan. 22-26, 2017. 1 page. PDR164.
Kraman et al., Abstract 5651:A LAG-3/PD/L1 bispecific antibody inhibits tumor growth in two syngeneic colon carcinoma models. AACR Annual Meeting 2017. Apr. 1-5, 2017. Washington, DC. Doi: 10.1158/1538-7445.AM2017-5651. 8 pages.
La Motte-Mohs et al., Abstract 3217: MGD013, a bispecific PD-1 x LAG-3 Dual-Affinity Re-Targeting (Dart®) protein with T-cell immunomodulatory activity for cancer treatment. AACR 107th Annual Meeting. Apr. 16-20, 2016. New Orleans, LA. Doi: 10.1158/1538-7445.AM2016-3217. 8 pages.
La Motte-Mohs et al., MGD013, a bispecific PD-1xLAG-3 Dual-Affinity Re-Targeting (Dart®) protein with T-cell immunomodulatory activity for cancer treatment. Poster Presentation. 2016. http://ir.macrogenics.com/events.cfm. 1 page.
Larkin et al., Combined Nivolumab and Ipilimumab or Monotherapy in Untreated Melanoma. N Engl J Med. Jul. 2, 2015;373(1):23-34. doi: 10.1056/NEJMoa1504030. Epub May 31, 2015. Erratum in: N Engl J Med. Nov. 29, 2018;379(22):2185.
Levitan, Amgen Halts Rilotumumab Development Due to Increased Death Signal. Cancer Network. Nov. 26, 2014. Retrieved from www.cancernetwork.com/view/amgen-halts-rilotumumab-development-due-increased-death-signal. 3 pages.
Liu et al., Dual Targeting of Innate and Adaptive Checkpoints on Tumor Cells Limits Immune Evasion. Cell Rep. Aug. 21, 2018;24(8):2101-2111. doi: 10.1016/j.celrep.2018.07.062.
McCourt et al., KY1055; a novel ICOS/PD-L1 bispecific antibody, enhance T cell activation and delivers potent monotherapy antitumour response in vivo. Abstract. CIMT 2018. Feb. 28, 2018. 1 page. PDR245.

(56) References Cited

OTHER PUBLICATIONS

McCourt et al., KY1055; a novel ICOS/PD-L1 bispecific antibody, enhance T cell activation and delivers potent monotherapy anti-tumour response in vivo. Poster Presentation. CIMT Conference. May 9, 2018. 1 page. PDR 264.
McCourt et al., KY1055; a novel ICOS/PD-L1 bispecific antibody, enhance T cell activation and delivers potent monotherapy anti-tumour response in vivo. Presentation. CIMT Conference. May 9, 2018. 13 pages. PDR265.
Michaelson et al., Anti-tumor activity of stability-engineered IgG-like bispecific antibodies targeting TRAIL-R2 and LTbetaR. MAbs. Mar.-Apr. 2009; 1(2):128-41. doi: 10.4161/mabs.1.2.7631. Epub Mar. 11, 2009.
Munoz-Olaya, Development of an anti-PD-L1Fcab. Presentation. PEGS Lisbon. Nov. 16, 2018. 24 pages. PDR321.
Nalivaiko et al., A Recombinant Bispecific CD20×CD95 Antibody With Superior Activity Against Normal and Malignant B-cells. Mol Ther. Feb. 2016;24(2):298-305. doi: 10.1038/mt.2015.209. Epub Nov. 19, 2015.
Pavlidou et al., Simultaneous costimulatory T-cell engagement and checkpoint inhibition by PRS-344/ONC0055, a 4-1BB/PD-L1 bispecific compound for tumor localized activation of the immune system. SITC 2018. Poster Presentation. 2018. 1 page.
Powles et al., MPDL3280A (anti-PD-L1) treatment leads to clinical activity in metastatic bladder cancer. Nature. Nov. 27, 2014;515(7528):558-62. doi: 10.1038/nature13904.
Sainson et al., KY1055, a novel ICOS/PD-L1 bispecific antibody, efficiently enhances T cell activation and delivers a potent anti-tumour response in vivo. Abstract. AACR. Jan. 22, 2018. 1 page. PDR236.
Sainson et al., KY1055, a novel ICOS/PD-L1 bispecific antibody, efficiently enhances T cell activation and delivers a potent anti-tumour response in vivo. Poster Presentation. AACR 2018. Apr. 4, 2018. 1 page. PDR254.
Strauss et al., Phase I Trial of M7824 (MSB0011359C), a Bifunctional Fusion Protein Targeting PD-L1 and TGF?, in Advanced Solid Tumors. Clin Cancer Res. Mar. 15, 2018;24(6):1287-1295. doi: 10.1158/1078-0432.CCR-17-2653. Epub Jan. 3, 2018.
Tuna, Identification of a PD-L1 binding FCAB: a potent inhibitor of immunosuppressive signals. Abstract. European Antibody Congress. May 3, 2018. 1 page. PDR270.
Tuna, The use of bispecific antibodies to modulate anti-tumour immune responses. Oral Presentation at 10th Annual Proteins and Antibodies Congress. Apr. 24, 2017. 26 pages. PDR183.
Vanamee et al., Structural principles of tumor necrosis factor superfamily signaling. Sci Signal. Jan. 2, 2018;11(511):eaao4910. doi: 10.1126/scisignal.aao4910. 12 pages.
Weismann, A LAG-3/PD-L1 Bispecific Antibody Inhibits Tumour Growth in Two Syngeneic Colon Carcinoma Models. International Conference on Human and Translational Immunology. Rhodes, Greece. Sep. 16-21, 2016. Presentation. 6 pages. PDR128.
Wherry, T cell exhaustion. Nat Immunol. Jun. 2011;12(6):492-9. doi: 10.1038/ni.2035.
Wilton, KY1055, a bispecific mAb2 targeting ICOS and PD-L1. Presentation. Feb. 21, 2018. 17 pages. PDR238.
Wolchok et al., Nivolumab plus ipilimumab in advanced melanoma. N Engl J Med. Jul. 11, 2013;369(2):122-33. doi: 10.1056/NEJMoa1302369. Epub Jun. 2, 2013. Erratum in: N Engl J Med. Nov. 29, 2018;379(22):2185. Author Manuscript.
Woo et al., Immune inhibitory molecules LAG-3 and PD-1 synergistically regulate T-cell function to promote tumoral immune escape. Cancer Res. Feb. 15, 2012;72(4):917-27. doi: 10.1158/0008-5472.CAN-11-1620. Epub Dec. 20, 2011.
Workman et al., Negative regulation of T cell homeostasis by lymphocyte activation gene-3 (CD223). J Immunol. Jan. 15, 2005;174(2):688-95. doi: 10.4049/jimmunol.174.2.688.
Workman et al., The CD4-related molecule, LAG-3 (CD223), regulates the expansion of activated T cells. Eur J Immunol. Apr. 2003;33(4):970-9. doi: 10.1002/eji.200323382.
Wydro, Bispecific antibodies: new opportunities for novel therapies. Oral Presentation at 7th Annual Biologics Symposium. Mar. 1, 2017. 24 pages. PDR172.
Wykes et al., Immune checkpoint blockade in infectious diseases. Nat Rev Immunol. Feb. 2018;18(2):91-104. doi: 10.1038/nri.2017.112. Epub Oct. 9, 2017.
Zhang et al., Structural basis of a novel PD-L1 nanobody for immune checkpoint blockade. Cell Discov. Mar. 7, 2017;3:17004. doi: 10.1038/celldisc.2017.4.
[No Author Listed], Molecular biological basis of immunotherapy. New and Orphan Drugs for Leukemia Therapeutics. Sep. 30, 2016. 387-390. Retrieved on Dec. 18, 2023. 7 pages.
Brinkmann et al., The making of bispecific antibodies. MAbs. Feb./Mar. 2017;9(2):182-212. doi: 10.1080/19420862.2016.1268307.
Chen et al., Enhancement and destruction of antibody function by somatic mutation: unequal occurrence is controlled by V gene combinatorial associations. EMBO J. Jun. 15, 1995;14(12):2784-94. doi: 10.1002/j.1460-2075.1995.tb07278.x.
Cooper, The Development and Causes of Cancer. From the Cell: Molecular Approach. 2nd Ed. Sunderland, MA. Sinauer Associates. 2000. 9 pages.
Edwards et al., The remarkable flexibility of the human antibody repertoire; isolation of over one thousand different antibodies to a single protein, BLyS. J Mol Biol. Nov. 14, 2003;334(1):103-18. doi: 10.1016/j.jmb.2003.09.054.
Heppner et al., Tumor heterogeneity: biological implications and therapeutic consequences. Cancer Metastasis Rev. 1983;2(1):5-23. doi: 10.1007/BF00046903.
Koenig et al., Mutational landscape of antibody variable domains reveals a switch modulating the interdomain conformational dynamics and antigen binding. Proc Natl Acad Sci U S A. Jan. 24, 2017;114(4):E486-E495. doi: 10.1073/pnas.1613231114. Epub Jan. 5, 2017.
Kussie et al., A single engineered amino acid substitution changes antibody fine specificity. J Immunol. Jan. 1, 1994;152(1):146-52.
Lo et al., Effector-attenuating Substitutions That Maintain Antibody Stability and Reduce Toxicity in Mice. J Biol Chem. Mar. 3, 2017;292(9):3900-3908. doi: 10.1074/jbc.M116.767749. Epub Jan. 11, 2017.
Seckinger et al., Development and characterization of NILK-2301, a novel CEACAM5xCD3 κλ bispecific antibody for immunotherapy of CEACAM5-expressing cancers. J Hematol Oncol. Dec. 12, 2023;16(1):117. doi: 10.1186/s13045-023-01516-3.
Yap et al., Abstract TPS2652: A first-in-human phase I study of FS118, an anti-LAG-3/PD-L1 bispecific antibody in patients with solid tumors that have progressed on prior PD-1/PD-L1 therapy. Journal of Clinical Oncology. May 15, 2019;37(15_suppl). 2019 ASCO Annual Meeting Proceedings. 4 pages.
[No. Author Listed], mesothelin isoform 1 preproprotein [Homo sapiens]. NCBI Reference Sequence: NP_001170826.1. May 2, 2024. Retrieved from https://www.ncbi.nlm.nih.gov/protein/NP_001170826.1/. 4 pages.
[No. Author Listed], mesothelin isoform 1 preproprotein [Mus musculus]. NCBI Reference Sequence: NP_001343215.1. Jun. 18, 2024. Retrieved from https://www.ncbi.nlm.nih.gov/protein/NP_001343215.1. 3 pages.
[No. Author Listed], Predicted: mesothelin isoform X4 [Macaca fascicularis]. NCBI Reference Sequence: XP_005590874.2. Jan. 25, 2016. Retrieved from https://www.ncbi.nlm.nih.gov/protein/XP_005590874.2. 2 pages.
[No. Author Listed], tumor necrosis factor receptor superfamily member 9 precursor [Homo sapiens]. NCBI Reference Sequence: NP_001552.2. Jun. 9, 2024. Retrieved from https://www.ncbi.nlm.nih.gov/protein/NP_001552.2. 4 pages.
Badri et al., Optimization of radiation dosing schedules for proneural glioblastoma. J Math Biol. Apr. 2016;72(5):1301-36. doi: 10.1007/s00285-015-0908-x.
Baylot et al., TCTP Has a Crucial Role in the Different Stages of Prostate Cancer Malignant Progression. Results Probl Cell Differ. 2017;64:255-261. doi: 10.1007/978-3-319-67591-6_13.

(56) References Cited

OTHER PUBLICATIONS

Durham et al., Lymphocyte Activation Gene 3 (LAG-3) modulates the ability of CD4 T-cells to be suppressed in vivo. PLoS One. Nov. 5, 2014;9(11):e109080. doi: 10.1371/journal.pone.0109080. 13 pages.

Gide et al., Distinct Immune Cell Populations Define Response to Anti-PD-1 Monotherapy and Anti-PD-1/Anti-CTLA-4 Combined Therapy. Cancer Cell. Feb. 11, 2019;35(2):238-255.e6. doi: 10.1016/j.ccell.2019.01.003.

Gough et al., OX40 agonist therapy enhances CD8 infiltration and decreases immune suppression in the tumor. Cancer Res. Jul. 1, 2008;68(13):5206-15. doi: 10.1158/0008-5472.CAN-07-6484.

Hong et al., An Agonistic Anti-CD137 Antibody Disrupts Lymphoid Follicle Structure and T-Cell-Dependent Antibody Responses. Cell Rep Med. Jun. 23, 2020;1(3):100035. doi: 10.1016/j.xcrm.2020.100035.

Kaas et al., IG, TR and IgSF, MHC and MhcSF: what do we learn from the IMGT Colliers de Perles? Brief Funct Genomic Proteomic. Dec. 2007;6(4):253-64. doi: 10.1093/bfgp/elm032. Epub Jan. 21, 2008.

Koyama et al., Adaptive resistance to therapeutic PD-1 blockade is associated with upregulation of alternative immune checkpoints. Nat Commun. Feb. 17, 2016;7:10501. doi: 10.1038/ncomms10501. 9 pages.

Matsuzaki et al., Tumor-infiltrating NY-ESO-1-specific CD8+ T cells are negatively regulated by LAG-3 and PD-1 in human ovarian cancer. Proc Natl Acad Sci U S A. Apr. 27, 2010;107(17):7875-80. doi: 10.1073/pnas.1003345107. Epub Apr. 12, 2010.

Muller et al., Spliceosomal peptide P140 for immunotherapy of systemic lupus erythematosus: results of an early phase II clinical trial. Arthritis Rheum. Dec. 2008;58(12):3873-83. doi: 10.1002/art.24027.

Otano et al., CD137 (4-1BB) costimulation of CD8+ T cells is more potent when provided in cis than in trans with respect to CD3-TCR stimulation. Nat Commun. Dec. 15, 2021;12(1):7296. doi: 10.1038/s41467-021-27613-w.

Shen, et al. Single variable domain-IgG fusion. A novel recombinant approach to Fc domain-containing bispecific antibodies. J Biol Chem. Apr. 21, 2006;281(16):10706-14. doi: 10.1074/jbc.M513415200. Epub Feb. 15, 2006.

Shepherd et al., T Cell Immunity to Bacterial Pathogens: Mechanisms of Immune Control and Bacterial Evasion. Int J Mol Sci. Aug. 26, 2020;21(17):6144. doi: 10.3390/ijms21176144.

Torres et al., The immunoglobulin constant region contributes to affinity and specificity. Trends Immunol. Feb. 2008;29(2):91-7. doi: 10.1016/j.it.2007.11.004. Epub Jan. 10, 2008.

Turaj et al., Augmentation of CD134 (OX40)-dependent NK antitumour activity is dependent on antibody cross-linking. Sci Rep. Feb. 2, 2018;8(1):2278. doi: 10.1038/s41598-018-20656-y.

Ye et al., CD137, an attractive candidate for the immunotherapy of lung cancer. Cancer Sci. May 2020;111(5):1461-1467. doi: 10.1111/cas.14354. Epub Apr. 3, 2020.

Yuan et al., Contributions of Costimulatory Molecule CD137 in Endothelial Cells. J Am Heart Assoc. Jun. 2021;10(11):e020721. doi: 10.1161/JAHA.120.020721. Epub May 22, 2021.

* cited by examiner

| IMGT | IMGT exon numbering | EU numbering | Kabat numbering | Wt Fcab | FS22-053 | FS22-053-008 | FS22-053-009 | FS22-053-010 | FS22-053-011 | FS22-053-012 | FS22-053-013 | FS22-053-014 | FS22-053-015 | FS22-053-016 | FS22-053-017 | FS22-172 | FS22-172-001 | FS22-172-002 | FS22-172-003 | FS22-172-004 | FS22-172-005 | FS22-172-006 |
|---|---|---|---|---|---|---|---|---|---|---|---|---|---|---|---|---|---|---|---|---|---|---|
| 1.4 | 1 | 341 | 361 | G | | | | | | | | | | | | | | | | | | |
| 1.3 | 2 | 342 | 363 | Q | | | | | | | | | | | | | | | | | | |
| 1.2 | 3 | 343 | 364 | P | | | | | | | | | | | | | | | | | | |
| 1.1 | 4 | 344 | 365 | R | | | | | | | | | | | | | | | | | | |
| 1 | 5 | 345 | 366 | E | | | | | | | | | | | | | | | | | | |
| 2 | 6 | 346 | 367 | P | | | | | | | | | | | | | | | | | | |
| 3 | 7 | 347 | 368 | Q | | | | | | | | | | | | | | | | | | |
| 4 | 8 | 348 | 369 | V | | | | | | | | | | | | | | | | | | |
| 5 | 9 | 349 | 370 | Y | | | | | | | | | | | | | | | | | | |
| 6 | 10 | 350 | 371 | T | | | | | | | | | | | | | | | | | | |
| 7 | 11 | 351 | 372 | L | | | | | | | | | | | | | | | | | | |
| 8 | 12 | 352 | 373 | P | | | | | | | | | | | | | | | | | | |
| 9 | 13 | 353 | 374 | P | | | | | | | | | | | | | | | | | | |
| 10 | 14 | 354 | 375 | S | | | | | | | | | | | | | | | | | | |
| 11 | 15 | 355 | 376 | R | | | | | | | | | | | | | | | | | | |
| 12 | 16 | 356 | 377 | D | | | | | | | | | | | | | | | | | | |
| 13 | 17 | 357 | 378 | E | | | | | | | | | | | | | | | | | | |
| 14 | 18 | 358 | 381 | L | | | | | | | | | | | | | | | | | | |
| 15 | 19 | 359 | 382 | T | N | N | N | N | N | N | N | N | N | N | R | P | P | P | N | Q | R |
| 16 | 20 | 360 | 383 | K | P | P | P | P | P | P | P | P | P | P | F | F | Y | Y | Q | | |
| 16.5 | | | | | P | P | P | P | P | P | P | P | P | P | Y | V | Q | L | V | Y | |
| 16.4 | | | | | Y | Y | Y | Y | Y | Y | Y | Y | Y | Y | Y | M | M | L | Y | Y | |
| 16.3 | | | | | L | L | L | L | L | L | L | L | L | L | P | P | P | P | P | P | |
| 16.2 | | | | | F | F | F | F | F | F | F | F | F | F | P | P | P | P | P | P | |
| 16.1 | | | | | S | S | S | S | S | S | S | S | S | S | Y | Y | Y | Y | Y | Y | |
| 17 | 21 | 361 | 384 | N | | | | | | | | | | | | | | | | | | |
| 18 | 22 | 362 | 385 | Q | | | | | | | | | | | | | | | | | | |
| 19 | 23 | 363 | 386 | V | | | | | | | | | | | | | | | | | | L |
| 20 | 24 | 364 | 387 | S | | | | | | | | | | | | | | | | | | |
| 21 | 25 | 365 | 388 | L | | | | | | | | | | | | | | | | | | |
| 22 | 26 | 366 | 389 | T | | | | | | | | | | | | | | | | | | |
| 23 | 27 | 367 | 390 | C | | | | | | | | | | | | | | | | | | |
| 24 | 28 | 368 | 391 | L | | | | | | | | | | | | | | | | | | |
| 25 | 29 | 369 | 392 | V | | | | | | | | | | | | | | | | | | |
| 26 | 30 | 370 | 393 | K | | | | | | | | | | | | | | | | | | |
| 27 | 31 | 371 | 394 | G | | | | | | | | | | | | | | | | | | |
| 28 | 32 | 372 | 395 | F | | | | | | | | | | | | | | | | | | |

| IMGT | IMGT exon numbering | EU numbering | Kabat numbering | Wt Fab | FS22-053 | FS22-053-008 | FS22-053-009 | FS22-053-010 | FS22-053-011 | FS22-053-012 | FS22-053-013 | FS22-053-014 | FS22-053-015 | FS22-053-016 | FS22-053-017 | FS22-172 | FS22-172-001 | FS22-172-002 | FS22-172-003 | FS22-172-004 | FS22-172-005 | FS22-172-006 |
|---|---|---|---|---|---|---|---|---|---|---|---|---|---|---|---|---|---|---|---|---|---|---|
| 29 | 33 | 373 | 396 | Y | | | | | | | | | | | | | | | | | | |
| 30 | 34 | 374 | 397 | P | | | | | | | | | | | | | | | | | | |
| 35 | 35 | 375 | 398 | S | | | | | | | | | | | | | | | | | | |
| 36 | 36 | 376 | 399 | D | | | | | | | | | | | | | | | | | | |
| 37 | 37 | 377 | 400 | I | | | | | | | | | | | | | | | | | | |
| 38 | 38 | 378 | 401 | A | | | | | | | | | | | | | | | | | | |
| 39 | 39 | 379 | 402 | V | | | | | | | | | | | | | | | | | | |
| 40 | 40 | 380 | 405 | E | | | | | | | | | | | | | | | | | | |
| 41 | 41 | 381 | 406 | W | | | | | | | | | | | | | | | | | | |
| 42 | 42 | 382 | 407 | E | | | | | | | | | | | | | | | | | | |
| 43 | 43 | 383 | 408 | S | | | | | | | | | | | | | | | | | | |
| 44 | 44 | 384 | 410 | N | | | | | | | | | | | | | | | | | | |
| 45 | 45 | 385 | 411 | G | | | | | | | | | | | | | | | | | | |
| 45.1 | 46 | 386 | 414 | Q | | | | | | | | | | | | | | | | | | |
| 45.2 | 47 | 387 | 415 | P | | | | | | | | | | | | | | | | | | |
| 45.3 | 48 | 388 | 416 | E | | | | | | | | | | | | | | | | | | |
| 45.4 | 49 | 389 | 417 | N | | | | | | | | | | | | | | | | | | |
| 77 | 50 | 390 | 418 | N | | | | | | | | | | | | | | | | | | |
| 78 | 51 | 391 | 419 | Y | | | | | | | | | | | | | | | | | | |
| 79 | 52 | 392 | 420 | K | | | | | | | | | | | | | | | | | | |
| 80 | 53 | 393 | 421 | T | | | | | | | | | | | | | | | | | | |
| 81 | 54 | 394 | 422 | T | | | | | | | | | | | | | | | | | | |
| 82 | 55 | 395 | 423 | P | | | | | | | | | | | | | | | | | | |
| 83 | 56 | 396 | 424 | P | | | | | | | | | | | | | | | | | | |
| 84 | 57 | 397 | 425 | V | | | | | | | | | | | | | | | | | | |
| 84.1 | 58 | 398 | 426 | L | | | | | | | | | | | | | | | | | | |
| 84.2 | 59 | 399 | 427 | D | | | | | | | | | | | | | | | | | | |
| 84.3 | 60 | 400 | 428 | S | | | | | | | | | | | | | | | | | | |
| 84.4 | 61 | 401 | 430 | D | | | | | | | | | | | | | | | | | | |
| 85.4 | 62 | 402 | 433 | G | | | | | | | | | | | | | | | | | | |
| 85.3 | 63 | 403 | 434 | S | | | | | | | | | | | | | | | | | | |
| 85.2 | 64 | 404 | 435 | F | | | | | | | | | | | | | | | | | | |
| 85.1 | 65 | 405 | 436 | F | | | | | | | | | | | | | | | | | | |
| 85 | 66 | 406 | 437 | L | | | | | | | | | | | | | | | | | | |
| 86 | 67 | 407 | 438 | Y | | | | | | | | | | | | | | | | | | |
| 87 | 68 | 408 | 439 | S | | | | | | | | | | | | | | | | | | |
| 88 | 69 | 409 | 440 | K | | | | | | | | | | | | | | | | | | |

| IMGT | 89 | 90 | 91 | 92 | 93 | 94 | 95 | 96 | 97 | 98 | 99 | 100 | 101 | 102 | 103 | 104 | 105 | 106 | 107 | 108 | 109 | 110 | 111 | 112 | 113 | 114 | 115 | 116 | 117 | 118 | 119 | 120 | 121 | 122 | 123 | 124 | 125 | CH3 10 |
|---|---|---|---|---|---|---|---|---|---|---|---|---|---|---|---|---|---|---|---|---|---|---|---|---|---|---|---|---|---|---|---|---|---|---|---|---|---|---|
| IMGT exon numbering | 70 | 71 | 72 | 73 | 74 | 75 | 76 | 77 | 78 | 79 | 80 | 81 | 82 | 83 | 84 | 85 | 86 | 87 | 88 | 89 | 90 | 91 | 92 | 93 | 94 | 95 | 96 | 97 | 98 | 99 | 100 | 101 | 102 | 103 | 104 | 105 | CH3 10 | 129 |
| EU numbering | 410 | 411 | 412 | 413 | 414 | 415 | 416 | 417 | 418 | 419 | 420 | 421 | 422 | 423 | 424 | 425 | 426 | 427 | 428 | 429 | 430 | 431 | 432 | 433 | 434 | 435 | 436 | 437 | 438 | 439 | 440 | 441 | 442 | 443 | 444 | 445 | 446 | |
| Kabat numbering | 441 | 442 | 443 | 444 | 445 | 446 | 447 | 448 | 449 | 450 | 451 | 452 | 453 | 454 | 455 | 456 | 457 | 458 | 459 | 460 | 461 | 462 | 463 | 464 | 465 | 466 | 467 | 468 | 469 | 470 | 471 | 472 | 473 | 474 | 475 | 476 | 477 | |
| Wt Fcab | L | T | V | D | K | S | R | W | Q | Q | G | N | V | F | S | C | S | V | M | H | E | A | L | H | N | H | Y | T | Q | K | S | L | S | L | S | P | G | |
| FS22-053 | | | | Y | Y | N | | | | D | | | | | | | | | | | | | | | | | | | | | | | | | | | | |
| FS22-053-008 | | | | Y | Y | W | | | | E | | | | | | | | | | | | | | | | | | | | | | | | | | | | |
| FS22-053-009 | | | | E | H | T | | | | D | | | | | | | | | | | | | | | | | | | | | | | | | | | | |
| FS22-053-010 | | | | | Y | M | | | | D | | | | | | | | | | | | | | | | | | | | | | | | | | | | |
| FS22-053-011 | | | | G | Y | W | | | | D | | | | | | | | | | | | | | | | | | | | | | | | | | | | |
| FS22-053-012 | | | | Y | H | M | | | | E | | | | | | | | | | | | | | | | | | | | | | | | | | | | |
| FS22-053-013 | | | | | Y | E | | | | E | | | | | | | | | | | | | | | | | | | | | | | | | | | | |
| FS22-053-014 | | | | Y | H | W | | | | D | | | | | | | | | | | | | | | | | | | | | | | | | | | | |
| FS22-053-015 | | | | | | L | | | | | | | | | | | | | | | | | | | | | | | | | | | | | | | | |
| FS22-053-016 | | | | Y | Y | W | | | | N | | | | | | | | | | | | | | | | | | | | | | | | | | | | |
| FS22-053-017 | | | | | H | | | | | | | | | | | | | | | | | | | | | | | | | | | | | | | | | |
| FS22-172 | | | | G | A | D | | | | E | | | | | | | | | | | | | | | | | | | | | | | | | | | | |
| FS22-172-001 | | | | G | A | D | | | | E | | | | | | | | | | | | | | | | | | | | | | | | | | | | |
| FS22-172-002 | | | | G | A | D | | | | E | | | | | | | | | | | | | | | | | | | | | | | | | | | | |
| FS22-172-003 | | | | G | A | D | | | | E | | | | | | | | | | | | | | | | | | | | | | | | | | | | |
| FS22-172-004 | | | | G | A | D | | | | E | | | | | | | | | | | | | | | | | | | | | | | | | | | | |
| FS22-172-005 | | | | G | A | D | | | | E | | | | | | | | | | | | | | | | | | | | | | | | | | | | |
| FS22-172-006 | | | | G | A | D | | | | E | | | | | | | | | | | | | | | | | | | | | | | | | | | | |

Figure 1C

ANTIBODY MOLECULES THAT BIND PD-L1 AND CD137

RELATED APPLICATIONS

This application is a national stage filing under 35 U.S.C. § 371 of International Patent Application Serial No. PCT/EP2019/068793, filed Jul. 12, 2019, the entire content of which is incorporated herein by reference in its entirety.

REFERENCE TO AN ELECTRONIC SEQUENCE LISTING

The contents of the electronic sequence listing (F083170011US00-SUBSEQ-ZJG.txt; Size: 249,027 bytes; and Date of Creation: Dec. 19, 2024) is herein incorporated by reference in its entirety.

FIELD OF THE INVENTION

The present invention relates to antibody molecules that bind both PD-L1 and CD137 and are able to induce agonism of CD137. The antibody molecules comprise a CDR-based binding site for PD-L1, and a CD137 antigen-binding site that is located in a constant domain of the antibody molecule. The antibody molecules of the invention find application, for example, in the treatment of diseases, such as cancer.

BACKGROUND TO THE INVENTION

Programmed cell death 1 (PD-1) and its ligands PD-L 1 (CD274, B7-H1) and PD-L2 (B7-DC) deliver inhibitory signals that regulate the balance between T cell activation, tolerance, and immunopathology. PD-L 1 is transiently expressed on all immune cells and some tumour cells. PD-L 1 is a member of the B7 protein family and shares approximately 20% amino acid sequence identity with B7.1 and B7.2. Human PD-L1 shares 70% and 93% amino acid identity with the murine and cynomolgus orthologs of PD-L1, respectively.

PD-L1 binds to its receptor PD-1 with an affinity ($K_D$) of 770 nM. PD-1 is expressed on activated T cells, B cells and myeloid cells, and modulates activation or inhibition of cellular immune responses. Binding of PD-L1 to PD-1 delivers an inhibitory signal, reducing cytokine production and proliferation of T cells. Consequently, PD-L1 expression by cells can mediate protection against cytotoxic T lymphocyte (CTL) killing and is a regulatory mechanism that dampens chronic immune responses during viral infections. Cancer, as a chronic and pro-inflammatory disease, subverts this immune-protective pathway through up-regulation of PD-L1 expression to evade the host immune response. In the context of an active immune response, interferon-gamma (IFN-γ) also upregulates the expression of PD-L1.

PD-L1 also mediates immune suppression through interaction with another protein, B7.1 (also known as CD80), blocking its ability to deliver one of the secondary signals of activation on T cells through CD28. In terms of PD-L1 expression on tumour cells and its engagement with B7.1, the relevance of this specific interaction in tumour immune resistance is still unclear.

PD-L1 expression has been shown in a wide variety of solid tumours. Of 654 samples examined in one study, spanning 19 tumours from different sites, 89 (14%) were PD-L1 positive (~5% frequency). The highest PD-L1 positive frequencies were seen in head and neck (17/54; 31%), cervical (10/34; 29%), cancer of unknown primary origin (CUP; 8/29; 28%), glioblastoma multiforme (GBM; 5/20; 25%), bladder (8/37; 21%), oesophageal (16/80; 20%), triple negative (TN) breast (6/33; 18%), and hepatocarcinoma (6/41; 15%) (Grosso et al, 2013). Tumour-associated expression of PD-L1 has been shown to confer immune resistance and potentially protect tumour cells from T cell mediated apoptosis.

Clinical trials have shown the clinical benefit of targeting PD-L1 in patients leading to the approval of three anti-PD-L1 targeting monoclonal antibodies to date. Atezolizumab (MPDL3280A, RG7466, Tecentriq™), a humanised IgG1 antibody which binds PD-L1, is approved for first line treatment of non-small-cell lung carcinoma (NSCLC) and first and second line treatment of bladder cancer after clinical trials showed objective response rates (ORR) of 38% and 43%, respectively, in patients with PD-L1 positive tumours (Iwai et al., 2017). Avelumab (MSB0010718C, Bavencio™) is a fully human IgG1 antibody which binds to PD-L1 and is approved for the treatment of Merkel-cell carcinoma and second line treatment of bladder cancer, whereas the fully human IgG1 antibody durvalumab (MEDI4736, Imfinzi™) is approved for the treatment of second line bladder cancer. Additional trials with these antibodies and other anti-PD-L1 therapeutics are ongoing focusing on expanding the range of solid cancers that can be treated, including colorectal cancer, gastric cancer, breast cancer, head and neck, pancreatic, ovarian and renal cell carcinoma.

CD137 (4-1 BB; TNFRSF9) is a co-stimulatory molecule of the tumour necrosis factor receptor superfamily (TNFRSF). CD137 is widely known to be upregulated on $CD8^+$ T cells following activation, and can also be expressed on activated $CD4^+$ helper T cells, B cells, regulatory T cells, natural killer (NK) cells, natural killer T (NKT) cells and dendritic cells (DCs) (Bartkowiak & Curran, 2015). The primary functional role of CD137 in enhancing T cell cytotoxicity was first described in 1997 (Shuford et al., 1997), and soon thereafter anti-CD137 mAbs were proposed as anti-cancer therapeutics.

CD137 is a transmembrane protein with four extracellular cysteine-rich domains, referred to as CRD1-4, and a cytoplasmic region responsible for CD137 signalling. The ligand for CD137 is CD137L. Although no crystal structure exists for the CD137/CD137L complex, it is predicted that CD137 forms a trimer/trimer complex with CD137L (Won et al., 2010). Engagement of CD137L results in receptor trimer formation and subsequent clustering of multiple receptor trimers, and leads to the activation of the CD137 signalling cascade. This signalling cascade provides a survival signal to T cells against activation-induced cell death (Hurtado et al., 1997) thereby playing a critical role in sustaining effective T cell immune responses and generating immunological memory (Bartkowiak & Curran, 2015).

CD137 is expressed by activated T cells and has been used as a marker to identify antigen-specific $CD4^+$ and $CD8^+$ T cells (Wolfl et al., 2007; Ye et al., 2014). Typically, expression of CD137 is higher on $CD8^+$ T cells than $CD4^+$ T cells (Wen et al., 2002). In the case of $CD8^+$ T cells, proliferation, survival and cytotoxic effector function via the production of interferon gamma and interleukin 2 have been attributed to CD137 crosslinking. CD137 crosslinking also contributes to the differentiation and maintenance of memory $CD8^+$ T cells (Chacon et al., 2013). In some subsets of $CD4^+$ T cells, CD137 crosslinking similarly leads to proliferation and activation and results in the release of cytokines such as interleukin 2 (Makkouk et al., 2016). CD137 has also been demonstrated to be expressed on tumour-reactive subsets of tumour-infiltrating lymphocytes (TILs). CD137 monotherapy has been shown to be efficacious in several preclinical immunogenic tumour models such as MC38, CT26 and B cell lymphomas.

Clinical development of CD137 mAbs has been slow due to dose-limiting high-grade liver inflammation associated with CD137 agonist antibody treatment. Urelumab (BMS-663513), a non-ligand blocking human IgG4 isotype antibody (Chester et al, 2018), was the first anti-CD137 antibody to enter clinical trials but these were halted after significant, on target, dose-dependent liver toxicity was observed (Chester et al., 2018; Segal et al., 2017; and Segal et al., 2018). More recently, clinical trials of urelumab in the treatment of solid cancers was recommenced in which urelumab treatment was combined with radiotherapy (NCT03431948) or with other therapeutic antibodies, such as rituximab (NCT01775631), cetuximab (NCT02110082), anti-PD-1 antibody nivolumab (NCT02253992, NCT02534506, NCT02845323), and a combination of nivolumab and the anti-LAG-3 antibody BMS986016 (NCT02658981). However, to reduce liver toxicity associated with urelumab treatment, dosing of urelumab in these trials had to be limited and efficacy results were disappointing (Chester et al., 2018).

No dose-limiting toxicity has been observed with Pfizer's anti-CD137 antibody utomilumab (PF-05082566), a human IgG2 isotype antibody, in the dose range 0.03 mg/kg up to 10 mg/kg in Phase I clinical trials of advanced cancer (Chester et al. 2016; Segal et al., 2018). However, the overall objective response rate with this antibody was only 3.8% in patients with solid tumours, potentially indicating that utomilumab has a weaker potency and clinical efficacy than urelumab, whilst having a more favourable safety profile (Chester et al., 2018; Segal et al., 2018). Utomilumab has been tested in combination with radiotherapy (NCT03217747) or chemotherapy, as well as in combination with other antibody therapies, including anti-PD-L1 antibody avelumab (NCT02554812), and anti-PD-1 antibody pembrolizumab (NCT02179918), to assess the safety, tolerability, dose-limiting toxicities (DLTs), maximum tolerated dose (MTD) and efficacy of the different treatment combinations. These trials are ongoing with early results showing no DLTs for doses up to 5 mg/kg and a 26% patient response rate for the combination of utomilumab and pembrolizumab. (Tolcher et al., 2016) (Pérez-Ruiz et al, 2017).

Clinical trials are ongoing to test anti-CD137 antibody, utomilumab, in combination with anti-PD-L1 antibody, avelumab (NCT02554812, NCT3390296). Triple combinations of utomilumab with avelumab and other therapies are also being tested (NCT02554812, NCT03217747, NCT03440567, NCT03414658).

A number of bispecific molecules targeting CD137 are also in early stage development, for example those targeting CD137 as well as FAP-alpha (Link et al., 2018; Reichen et al., 2018), HER2 (Hinner et al., 2015 and WO 2016/177802 A1), or EphA2 (Liu et al., 2017). CD137L fusion proteins which target tumours for example via FAP-alpha (Claus et al., 2017) are also being developed. The most clinically advanced CD137 bispecific is PRS-343, a CD137/HER2 bispecific molecule which has recently entered Phase I clinical trials for treatment of a range of solid tumours to assess its safety, tolerability and efficacy (NCT03330561).

There are other approaches to combine anti-CD137 activity and anti-PD-L1 activity into bispecific therapies. One approach utilized the biclonics technology to produce a full length heterodimeric human IgG with monovalent binding to both CD137 and PD-L1 (WO2018056821) resulting in a molecule that can bind to both CD137 and PD-L1 and induce CD137 agonism in the presence of high levels of PD-L1. A second approach has been described using sdAb-Fc fusions to target both CD137 and PD-L1 (WO2017123650). Both approaches are capable of binding CD137 in the absence of PD-L1 binding and induce low levels of CD137 agonism in the absence of PD-L1, this agonism is increased in the presence of high levels of PD-L1. A further heterodimeric bispecific antibody has been described with monovalent binding to both CD137 and PD-L1 (WO2019/025545 A1), containing a humanised anti-CD137 binding region and a human anti-PD-L1 region that induces CD137 agonism in the presence of levels of PD-L1.

Current data shows that overall treatment with anti-PD-L1 monotherapy results in a response in less than 50% of cancer patients. Thus, there remains a need in the art for additional molecules which can target PD-L1 and which find application in cancer therapy. PD-1/PD-L1 blockade has strong clinical validation however less than 50% of patients respond in a monotherapy setting. Combinations of PD-L1 and additional immune modulators are expected to demonstrate improved efficacy. However, such combinations may be linked to an increase in treatment related adverse events and as a result the efficacy can be restricted by the limited therapeutic window. CD137-targeting agonistic molecules have yet to demonstrate significant responses in cancer patients, this may in part be due to relatively low dose levels due to a limited therapeutic index. Thus, there remains a need in the art to develop treatments which combine PD-L1 blockade and elicit CD137 agonism in safe and efficacious therapies.

STATEMENTS OF INVENTION

As explained in the background section above, clinical development of CD137 agonist molecules has been held back due to treatment being either associated with dose-limiting high-grade liver inflammation (urelumab) or low clinical efficacy (utomilumab).

The present inventors recognised that there is a need in the art for CD137 agonist molecules which exhibit high activity and where agonism can be localised to the tumour microenvironment. Such molecules could be administered to individuals at doses which optimize the potency and therefore efficacy of the molecule, and could be employed in the treatment of cancer as immunotherapeutic agents, for example.

The antibody molecules of the present invention comprise a CD137 antigen-binding site that is located in a constant domain of the antibody molecule. The present inventors performed an extensive selection and affinity maturation program to isolate a panel of CD137 antigen-binding site containing molecules (also referred to as "Fcabs" herein) which bind to dimeric CD137 with a higher affinity than to monomeric CD137.

'Affinity' as referred to herein may refer to the strength of the binding interaction between an antibody molecule and its cognate antigen as measured by $K_D$. As would be readily apparent to the skilled person, where the antibody molecule is capable of forming multiple binding interactions with an antigen (e.g. where the antibody molecule is capable of binding the antigen bivalently and, optionally, the antigen is dimeric) the affinity, as measured by $K_D$, may also be influenced by avidity, whereby avidity refers to the overall strength of an antibody-antigen complex.

Expression of CD137 by T cells is upregulated on activation. Without wishing to be bound by theory, it is thought that due to the high expression of CD137 on activated T cells, CD137 will be in the form of dimers, trimers and higher-order multimers on the surface of such cells. In contrast, naïve immune cells, such as naïve T cells, express low or negligible levels of CD137 on their cell surface and any CD137 present is therefore likely to be in monomeric form. It is therefore expected that antibody molecules comprising a CD137 antigen-binding site which bind to dimeric or multimeric CD137 with high avidity, will preferentially bind to activated immune cells, such as activated T cells, as opposed to naïve immune cells, for example.

These features of the CD137 antigen-binding site are believed to distinguish the antibody molecules of the present invention from known antibodies that bind CD137, for example, the antibody described in WO2018056821. WO2018056821 describes an antibody containing a monovalent CD137 binding domain that binds to CD137 with a high affinity (low nM range, see Table 6 of WO2018056821). Since these antibodies do not distinguish between monomeric and dimeric or multimeric CD137, it is not expected that these prior art antibodies would display the same preferential binding to activated immune cells.

As described in the background section above, it is thought that initial ligation of CD137 ligand to CD137 initiates a chain of events that leads to receptor trimerisation, followed by receptor clustering, activation and subsequent initiation of potent anti-tumour T cell activity. For a therapeutic agent to efficiently achieve activation of CD137, it is therefore expected that several receptor monomers need to be bridged together in a way that mimics bridging by the trimeric ligand.

Utomilumab is an IgG2 molecule and is dependent on crosslinking by Fcγ receptors for its agonist activity. Urelumab is an IgG4 molecule with constitutive activity and so does not require crosslinking by Fcγ receptors for activity, although its agonist activity is enhanced on crosslinking by some Fcγ receptors. Fcγ receptors are found throughout the human body. The immune cell activation activity of utomilumab and urelumab is therefore not limited to particular sites in the body and thus may occur in locations other than the tumour microenvironment, such as the liver.

The present inventors have shown that the CD137 antigen-binding site present in the antibody molecules of the invention requires crosslinking in order to cluster and activate CD137. However, it should be noted that this is not an intrinsic feature of CD137 binders. Rather, many of the CD137 binders isolated during the screening program bound to CD137 but did not require crosslinking for CD137 clustering and activation or induced limited CD137 clustering and activation in the absence of crosslinking.

As mentioned above, Fcγ receptor-mediated crosslinking has the disadvantage that Fcγ receptors are found throughout the human body and thus CD137 activation is not limited to a particular site. The present inventors therefore introduced mutations into the CH2 domain of the Fcabs to reduce or abrogate Fcγ receptor binding. Thus, in the absence of crosslinking through an agent other than Fcγ receptors, the antibody molecules of the invention do not exhibit CD137 agonist activity. Further, it is expected that these mutations will result in the antibody molecules of the present invention being unable to induce antibody cellular cytotoxicity, so the antibody molecules will not elicit killing of the immune cells they activate.

The present inventors have demonstrated that antibody molecules which contain the CD137 antigen-binding site described above and a CDR-based binding site for PD-L1 are highly effective in activating immune cells in locations where CD137 and PD-L1 are co-expressed, for example in a tumour microenvironment. Co-expression in this sense encompasses situations where CD137 and PD-L1 are expressed on the same cells, e.g. a T cell, and situations where CD137 and PD-L1 are expressed on different cells, for example a T cell and a tumour cell, respectively.

The antibody molecules are capable of binding simultaneously to CD137 and PD-L1. Thus, in locations where PD-L1 and CD137 are co-expressed, it is thought that binding of the antibody molecules to PD-L1 causes cross-linking of the antibody molecules, which in turn leads to clustering and activation of bound CD137 on the T cell surface.

As demonstrated by the present inventors, by reducing or abrogating Fcγ receptor binding, the agonistic activity of the antibody molecules is dependent on both the PD-L1 and CD137 being present. In other words, the agonistic activity is conditional and the antibody molecules are therefore expected to be capable of only activating immune cells in locations where PD-L1 is present, such as in the tumour microenvironment. This targeted activation of immune cells is expected to be beneficial in avoiding the liver inflammation seen with urelumab treatment, for example.

Indeed, the present inventors demonstrate that antibody molecules having the features described above do not show exhibit severe hepatotoxicity when administered in a mouse model at therapeutic doses. Only minimal liver pathology was observed in mice that had been administered with these antibody molecules, which was not deemed to represent the severe hepatotoxicity that has been previously reported for other anti-CD137 agonist antibodies. Preliminary studies in cynomolgus monkeys also showed that the antibody molecules are safe and well tolerated up to 30 mg/kg. Without wishing to be bound by theory, it is expected that the results from these animal models will translate to the clinic in predicting the risk of hepatotoxicity in human patients and therefore that the antibody molecules of the invention would have low risk of inducing hepatotoxicity in human patients treated at therapeutic doses.

The present inventors also provide in vitro evidence that the level of CD137 agonistic activity induced by the antibody molecule correlates with the amount of PD-L1 expression on the cell surface. The inventors demonstrate that the antibody molecule is capable of agonising CD137 even where there is a low level of PD-L1 expression and that as the level of PD-L1 in the system increases, so does the CD137 agonistic activity. This result further supports the evidence that CD137 agonistic activity is dependent on PD-L1 expression and suggests that the antibody molecules of the invention will have a broad range of activity on tumours that express varying levels of PD-L1 on the tumour cell surface.

The CDR-based binding sites for PD-L1 described above are able to efficiently block binding of PD-L1 to its receptor PD-1. PD-1 is expressed on activated T cells, B cells, and myeloid cells, and modulates activation or inhibition of cellular immune responses. Binding of PD-L1 to PD-1 delivers an inhibitory signal, reducing cytokine production and proliferation of T cells, thereby dampening the immune response. In cancer, the interaction of PD-L1 on a tumour cell with PD-1 on a T cell reduces T cell activity to prevent the immune system from attacking the tumour cells. Therefore, it is expected that by blocking the binding of PD-L1 to PD-1, the antibody molecules of the invention can prevent the tumour cells from evading the immune system in this way. Without wishing to be bound by theory, it is believed that this efficient blocking of PD-L1 binding to PD-1 functions together with the CD137 agonistic activity described above to increase anti-tumour potency of the antibody molecule.

The present inventors have also shown that such bispecific antibody molecules comprising the CD137 antigen-binding site and CDR-based binding site for PD-L1 described above are capable of supressing tumour growth in vivo. Furthermore, more effective tumour growth suppression was observed with the bispecific antibody molecules as compared to a combination of two monospecific antibody molecules where one of the antibody molecules comprised a CDR-based antigen-binding site for PD-L1 and the other molecule comprised a CDR-based antigen-binding site for CD137, demonstrating that enhanced clustering and signalling of CD137, and thus T cell activation and corresponding anti-tumour effects, are seen with the antibody molecules of the invention.

Antibody molecules comprising a CD137 antigen-binding site of the invention may additionally be able to bind PD-L1 bivalently, such that the antibody molecules bind both CD137 and PD-L1 bivalently. This is expected to be advantageous, as the bivalent binding of both targets is expected to make the bridging between the T cell expressing CD137 and the PD-L1 expressing cell more stable and thereby extend the time during which the T cell is localised at sites where PD-L1 is co-expressed with CD137, such as in the tumour microenvironment, and can act on the disease, e.g. the tumour. This is different to the vast majority of conventional bispecific antibody formats which are heterodimeric and bind each target antigen monovalently via one Fab arm. Such a monovalent interaction is expected to not only be less stable but also to be less efficient at inducing clustering of TNF receptors such as CD137 and/or to require higher expression of one or both targets to induce such clustering, and thus T cell activation. This is supported by experiments conducted by the present inventors, which showed that mAb$^2$ molecules comprising a bivalent Fab binding site for PD-L1 and a monovalent binding site for CD137 in one of the CH3 domains of the molecule induced lower levels of T cell activation, as measured by IFN-γ release, than a mAb$^2$ binding both targets bivalently.

A further feature of the antibody molecules identified by the inventors is that the antigen-binding site for CD137 and the CDR-based binding site for PD-L1 are both contained within the antibody structure itself. In particular, the antibody molecules do not require other proteins to be fused to the antibody molecule via linkers or other means to result in molecule that binds bivalently to both of its targets. This has a number of advantages. Specifically, the antibody molecules can be produced using methods similar to those employed for the production of standard antibodies, as they do not comprise any additional fused portions. The structure is also expected to result in improved antibody stability, as linkers may degrade overtime, resulting in a heterogeneous population of antibody molecules. In such heterogeneous populations, those antibodies in the population having only one protein fused to them, and thus binding one target only monovalently, are expected not to induce conditional agonism of TNF receptors such as CD137 as efficiently, as those antibodies which have two proteins fused to them and which are thus capable of binding both targets bivalently. Cleavage/degradation of the linker could take place prior to administration or after administration of the therapeutic to the patient (e.g. through enzymatic cleavage or the in vivo pH of the patient), thereby resulting in a reduction of its effectiveness whilst circulating in the patient. As there are no linkers in the antibody molecules of the invention, the antibody molecules are expected to retain the same number of binding sites both before and after administration. Furthermore, the structure of the antibody molecules is also preferred from the perspective of immunogenicity of the molecules, as the introduction of fused proteins or linkers or both may induce immunogenicity when the molecules are administered to a patient, resulting in reduced effectiveness of the therapeutic.

Thus, the present invention provides:

[1] An antibody molecule that binds to programmed death-ligand 1 (PD-L1) and CD137, comprising
  (a) a complementarity determining region (CDR)-based antigen-binding site for PD-L1; and
  (b) a CD137 antigen-binding site located in a CH3 domain of the antibody molecule;
    wherein the CDR-based antigen-binding site comprises CDRs 1-6 set forth in:
(i) SEQ ID NOs 1, 2, 3, 4, 5 and 6, respectively [E12v2];
(ii) SEQ ID NOs 1, 2, 3, 18, 19 and 20, respectively [E05v2]; or
(iii) SEQ ID NOs 1, 2, 3, 18, 19 and 29, respectively [G12v2]; and
    wherein the CD137 antigen-binding site comprises a first sequence and a second sequence located in the AB and EF structural loops of the CH3 domain, respectively, wherein the first and second sequence have the sequence set forth in SEQ ID NOs 113 and 114 [FS22-172-003], or 79 and 80 [FS22-53-008], respectively.

[2] An antibody molecule that binds to programmed death-ligand 1 (PD-L1) and CD137, comprising
  (a) a complementarity determining region (CDR)-based antigen-binding site for PD-L1; and
  (b) a CD137 antigen-binding site located in a CH3 domain of the antibody molecule;
    wherein the CDR-based antigen-binding site comprises CDRs 1-6 according to IMGT] set forth in:
(i) SEQ ID NOs 7, 8, 9, 10, 11 and 6, respectively [E12v2];
(ii) SEQ ID NOs 21, 8, 9, 22, 11 and 20, respectively [E05v2]; or
(iii) SEQ ID NOs 21, 8, 9, 22, 11 and 29, respectively [G12v2]; and
    wherein the CD137 antigen-binding site comprises a first sequence and a second sequence located in the AB and EF structural loops of the CH3 domain, respectively, wherein the first and second sequence have the sequence set forth in SEQ ID NOs 113 and 114 [FS22-172-003], or 79 and 80 [FS22-53-008], respectively.

[3] The antibody molecule according to [1] or [2], wherein the antibody molecule comprises CDRs 1-6 set out in (i) or (ii) of [1] or [2].

[4] The antibody molecule according to [1] or [2], wherein the antibody molecule comprises CDRs 1-6 set out in (i) of [1] or [2].

[5] The antibody molecule according to any one of [1] to [4], wherein the antibody molecule comprises a heavy chain variable (VH) domain and/or light chain variable (VL) domain, preferably a VH domain and a VL domain.

[6] The antibody molecule according to any one of [1] to [5], wherein the antibody molecule comprises an immunoglobulin heavy chain and/or an immunoglobulin light chain, preferably an immunoglobulin heavy chain and an immunoglobulin light chain.

[7] The antibody molecule according to any one of [5] to [6], wherein the antibody molecule comprises the VH domain and/or VL domain, preferably the VH domain and the VL domain set forth in:
- (i) SEQ ID NOs 12 and 14, respectively [E12v2];
- (ii) SEQ ID NOs 23 and 25, respectively [E05v2]; or
- (iii) SEQ ID NOs 23 and 30, respectively [G12v2].

[8] The antibody molecule according to [7], wherein the antibody molecule comprises the VH domain and VL domain set out in (i) or (ii).

[9] The antibody molecule according to [8], wherein the antibody molecule comprises the VH domain and VL domain set out in (i).

[10] The antibody molecule according to any one of [1] to [9], wherein the first sequence is located between positions 14 and 17 of the CH3 domain of the antibody molecule, wherein the amino acid residue numbering is according to the IMGT numbering scheme.

[11] The antibody molecule according to [10], wherein the first sequence is located at positions 15, 16, 16.5, 16.4, 16.3, 16.2, and 16.1 of the CH3 domain of the antibody molecule, wherein the amino acid residue numbering is according to the IMGT numbering scheme.

[12] The antibody molecule according to any one of [1] to [11], wherein the second sequence is located at positions 92 to 98 of the CH3 domain of the antibody molecule, wherein the amino acid residue numbering is according to the IMGT numbering scheme.

[13] The antibody molecule according to any one of [1] to [12], wherein the antibody molecule further comprises a third sequence located in the CD structural loop of the CH3 domain.

[14] The antibody molecule according to [13], wherein the third sequence is located at positions 43 to 78 of the CH3 domain of the antibody molecule, wherein the amino acid residue numbering is according to the IMGT numbering scheme.

[15] The antibody molecule according to any one of [13] to [14], wherein the third sequence has the sequence set forth in SEQ ID NO: 73.

[16] The antibody molecule according to any one of [1] to [15], wherein the antibody molecule comprises the CH3 domain sequence set forth in:
- (i) SEQ ID NO: 115 [FS22-172-003]; or
- (ii) SEQ ID NO: 81 [FS22-53-008].

[17] The antibody molecule according to any one of [1] to [15], wherein the first and second sequence have the sequence set forth in SEQ ID NOs 113 and 114 [FS22-172-003], respectively.

[18] The antibody molecule according to any one of [1] to [15] and [17], wherein the antibody molecule comprises the CH3 domain sequence set forth in SEQ ID NO: 115 [FS22-172-003].

[19] An antibody molecule according to any one of [1] to [18], wherein the antibody molecule is a human IgG1 molecule.

[20] The antibody molecule according to any one of [1] to [19], wherein the antibody molecule comprises the heavy chain and light chain of antibody:
- (i) FS22-172-003-AA/E12v2 set forth in SEQ ID NOs 134 and 17, respectively;
- (ii) FS22-172-003-AA/E05v2 set forth in SEQ ID NOs 137 and 28, respectively;
- (iii) FS22-172-003-AA/G12v2 set forth in SEQ ID NOs 140 and 33, respectively;
- (iv) FS22-053-008-AA/E12v2 set forth in SEQ ID NOs 143 and 17, respectively;
- (v) FS22-053-008-AA/E05v2 set forth in SEQ ID NOs 146 and 28, respectively; or
- (vi) FS22-053-008-AA/G12v2 set forth in SEQ ID NOs 149 and 33, respectively.

[21] The antibody molecule according to [20], wherein the antibody molecule comprises light chain and heavy chain set out in any one of (i)-(iv) of [20].

[22] The antibody molecule according to [20], wherein the antibody molecule comprises light chain and heavy chain set out in (i) of [20].

[23] The antibody molecule according to any one of [20] to [22], wherein the proline (P) at position 114 of the CH2 domain of the antibody is substituted with alanine (A), and wherein the amino acid residue numbering is according to the IMGT numbering scheme.

[24] The antibody molecule according to any one of [1] to [23], wherein the antibody molecule binds human PD-L1 and human CD137.

[25] The antibody molecule according to [24], wherein the PD-L1 consists of or comprises the sequence set forth in SEQ ID NO: 180.

[26] The antibody molecule according to [24] or [25], wherein the human CD137 consists of or comprises the sequence set forth in SEQ ID NO: 186.

[27] The antibody molecule according to any one of [1] to [26], wherein the antibody molecule is capable of activating CD137 on an immune cell in the presence of tumour cell-surface bound PD-L1.

[28] The antibody molecule according to any one of [1] to [26], wherein binding of the antibody molecule to CD137 on an immune cell and to tumour cell-surface bound PD-L1 causes clustering of CD137 on the immune cell.

[29] The antibody molecule according to [27] or [28], wherein the immune cell is a T cell, B cell, natural killer (NK) cell, natural killer T (NKT) cell, or dendritic cell (DC).

[30] The antibody molecule according to [29], wherein the immune cell is a T cell.

[31] The antibody molecule according to any one of [1] to [30], wherein the antibody molecule has been modified to reduce or abrogate binding of the CH2 domain of the antibody molecule to one or more Fcγ receptors.

[32] The antibody molecule according to any one of [1] to [31], wherein the antibody molecule does not bind to one or more Fcγ receptors.

[33] The antibody molecule according to [31] or [32], wherein the Fcγ receptor is selected from the group consisting of: FcγRI, FcγRIIa, FcγRIIb and FcγRIII.

[34] A conjugate comprising the antibody molecule according to any one of [1] to [33] and a bioactive molecule.

[35] A conjugate comprising the antibody molecule according to any one of [1] to [33] and a detectable label.

[36] A nucleic acid molecule or molecules encoding the antibody molecule according to any one of [1] to [33].

[37] A nucleic acid molecule or molecules encoding the antibody molecule according to any one of [1] to [2], [5] to [7], [10] to [16], [19] to [20] and [23] to [33], wherein the nucleic acid molecule(s) comprise(s) the heavy chain nucleic acid sequence and/or light chain nucleic acid sequence of:
- (i) FS22-172-003-AA/E12v2 set forth in SEQ ID NOs 32 and 39, or 135 and 136, respectively, preferably SEQ ID NOs 32 and 39, respectively;
- (ii) FS22-172-003-AA/E05v2 set forth in SEQ ID NOs 138 and 139, respectively;
- (iii) FS22-172-003-AA/G12v2 set forth in SEQ ID NOs 141 and 142, respectively;

(iv) FS22-053-008-AA/E12v2 set forth in SEQ ID NOs 144 and 145, respectively;

(v) FS22-053-008-AA/E05v2 set forth in SEQ ID NOs 147 and 148, respectively; or (vi) FS22-053-008-AA/G12v2 set forth in SEQ ID NOs 150 and 151, respectively.

[38] A vector or vectors comprising the nucleic acid molecule or molecules according to any one of [36] to [37].

[39] A recombinant host cell comprising the nucleic acid molecule(s) according to any one of [36] to [37], or the vector(s) according to [38].

[40] A method of producing the antibody molecule according to any one of [1] to [33] comprising culturing the recombinant host cell of [39] under conditions for production of the antibody molecule.

[41] The method according to [40] further comprising isolating and/or purifying the antibody molecule.

[42] A pharmaceutical composition comprising the antibody molecule or conjugate according to any one of [1] to [35] and a pharmaceutically acceptable excipient.

[43] The antibody molecule or conjugate according to any one of [1] to [35] for use in a method of treating cancer in an individual.

[44] A method of treating cancer in an individual comprising administering to the individual a therapeutically effective amount of the antibody molecule or conjugate according to any one of [1] to [35].

[45] The use of the antibody molecule or conjugate according to any one of [1] to [35] in the preparation of a medicament for the treatment of cancer.

[46] The antibody molecule or conjugate for use, the method, or the use according to any one of [43] to [45], wherein the cancer is selected from the list consisting of: melanoma, bladder cancer, brain cancer, breast cancer, ovarian cancer, lung cancer, colorectal cancer, cervical cancer, liver cancer, head and neck cancer, pancreatic cancer, renal cancer, stomach cancer and Gastrointestinal Stromal Tumours (GISTs).

[47] The antibody molecule or conjugate for use according to [43], where the treatment comprises administering the antibody molecule or conjugate to the individual in combination with a second therapeutic.

[48] The method according to [44], wherein the method further comprises administering a therapeutically effective amount of a second therapeutic to the individual.

BRIEF DESCRIPTION OF THE FIGURES

FIG. 1: FIGS. 1A, B and C show an alignment of the sequences of the CH3 domains of Fcabs FS22-053, FS22-053-008, FS22-053-009, FS22-053-010, FS22-053-011, FS22-053-012, FS22-053-013, FS22-053-014, FS22-053-015, FS22-053-016, FS22-053-017, FS22-172, FS22-172-001, FS22-172-002, FS22-172-003, FS22-172-004, FS22-172-005 and FS22-172-006 as well as the wild-type (WT) Fcab. The numbers of the residues according to the IMGT, IMGT exon (consecutive numbering), EU and Kabat numbering systems is indicated.

This indicated that better maximum activity was achieved with the mAb² overall when 100% of HEK cells express PD-L1.

Figure 7:
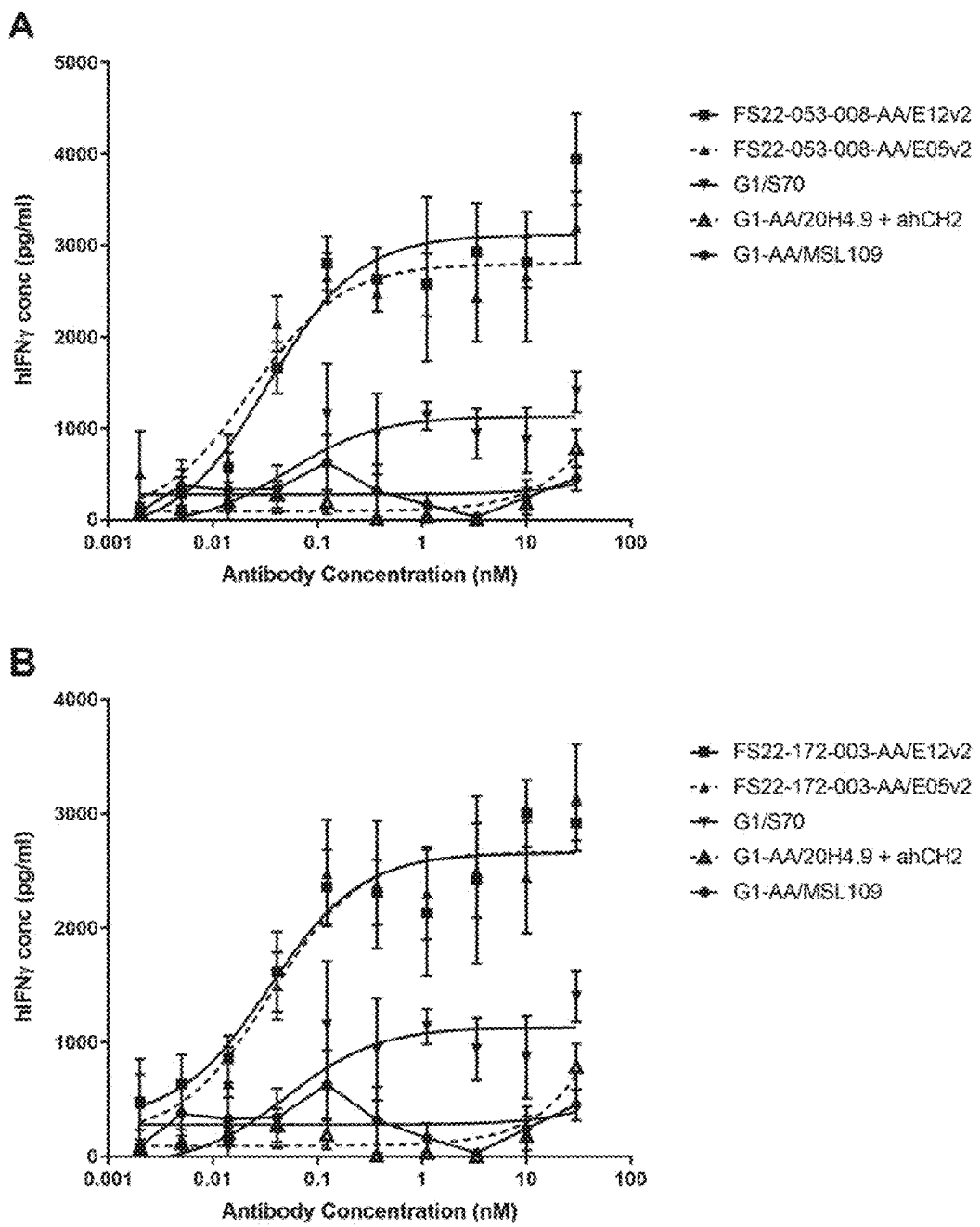
Figure 7:
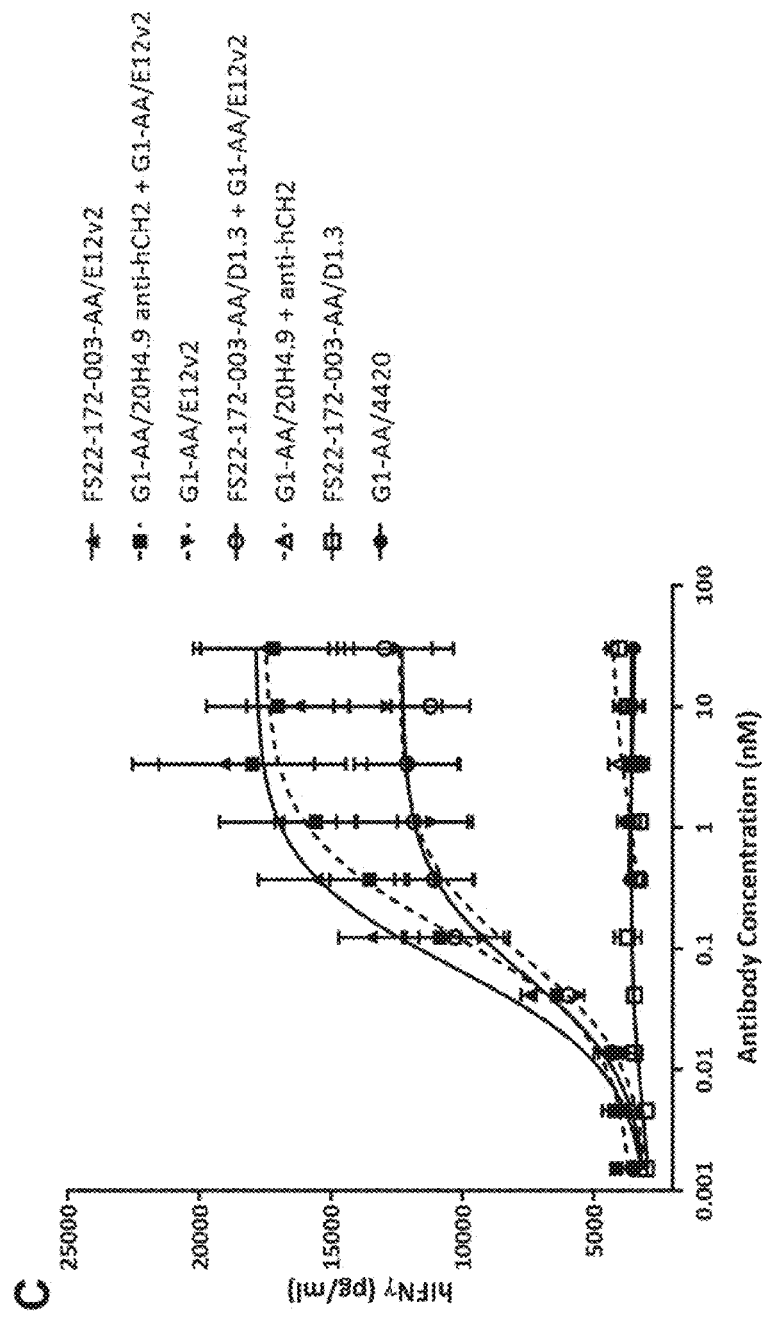

FIG. 7 shows that anti-human CD137/PD-L1 mAb² are capable of activating T cells. (A) and (B): Release of IFN-γ in a primary human Mixed Lymphocyte Reaction (MLR) assay was tested in the presence of anti-human CD137/PD-L1 mAb², anti-human PD-L1 positive control antibody G1/S70 or anti-human CD137 positive control antibody G1-AA/20H4.9 (crosslinked with an anti-human CH2 antibody). (A) FS22-053-008 Fcab-based mAb² and (B) FS22-172-003 Fcab-based mAb² showed higher activity in this assay than either of the positive control antibodies, indicating that PD-L1 blockade and CD137 agonism in the same molecule elicits greater T cell activation, presumably through PD-L1-based clustering and activation of CD137. (C) Release of IFN-γ in a primary human MLR assay was tested in the presence of anti-human CD137/PD-L1 mAb², anti-human PD-L1 antibody G1-AA/E12v2, anti-human CD137 positive control antibody G1-AA/20H4.9 (crosslinked with an anti-human CH2 antibody), or anti-human CD137 Fcab in mock mAb² format (FS22-172-003-AA/D1.3). FS22-172-003-AA/E12v2 mAb² showed higher T cell activation activity in this assay than either of the positive control antibodies or its component Fcab in mock mAb² format, indicating that PD-L1 blockade and CD137 agonism in the same molecule elicits greater T cell activation, presumably through PD-L1-based crosslinking leading to clustering and activation of CD137.

Figure 8:
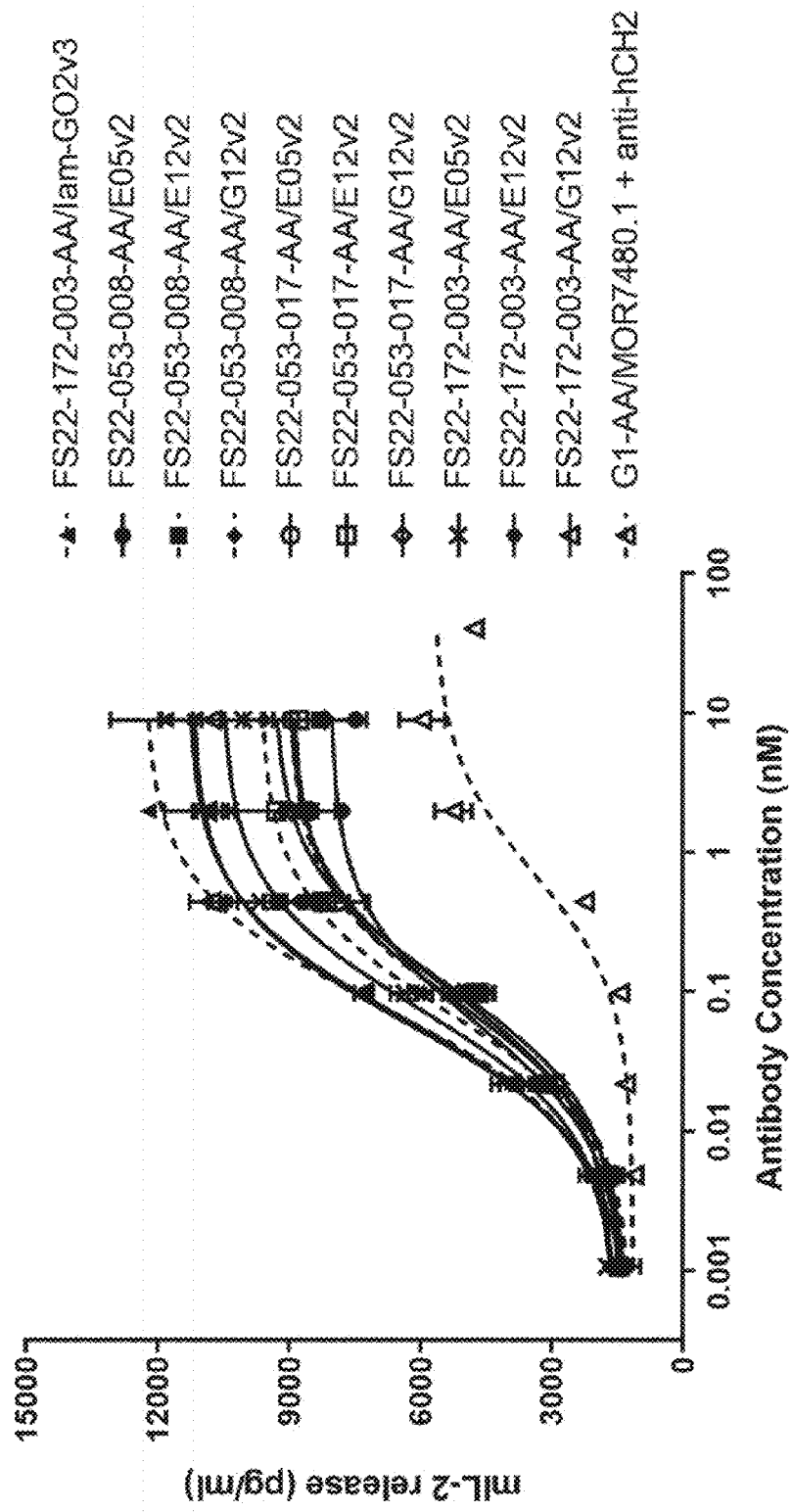

FIG. 8 shows IL-2 release in a T cell activation assay, wherein the T cells have been engineered to overexpress cynomolgus CD137, in the presence of anti-human CD137/PD-L1 mAb² and positive control anti-human CD137 antibody G1-AA/MOR7480.1. All mAb² tested drove clustering and activation of CD137 only when crosslinked with HEK cells overexpressing cynomolgus PD-L1 (open and closed black and grey symbols with solid connecting lines) leading to a release of mouse interleukin-2 (mIL-2) in a DO11.10 T cell activation assay. At increasing concentrations, the positive control anti-human CD137 antibody, G1-AA/MOR7480.1 which has previously been shown by others to by cynomolgus cross-reactive to cynomolgus CD137, shows an increase in mIL-2 release (solid black circles, dotted line), however the maximal release was significantly less than that of all anti-human CD137/PD-L1 mAb². All anti-human CD137/PD-L1 mAb² without HEK cells overexpressing PD-L1 to crosslink show significantly lower mIL-2 release compared to when crosslinked (data not shown).

Figure 9:
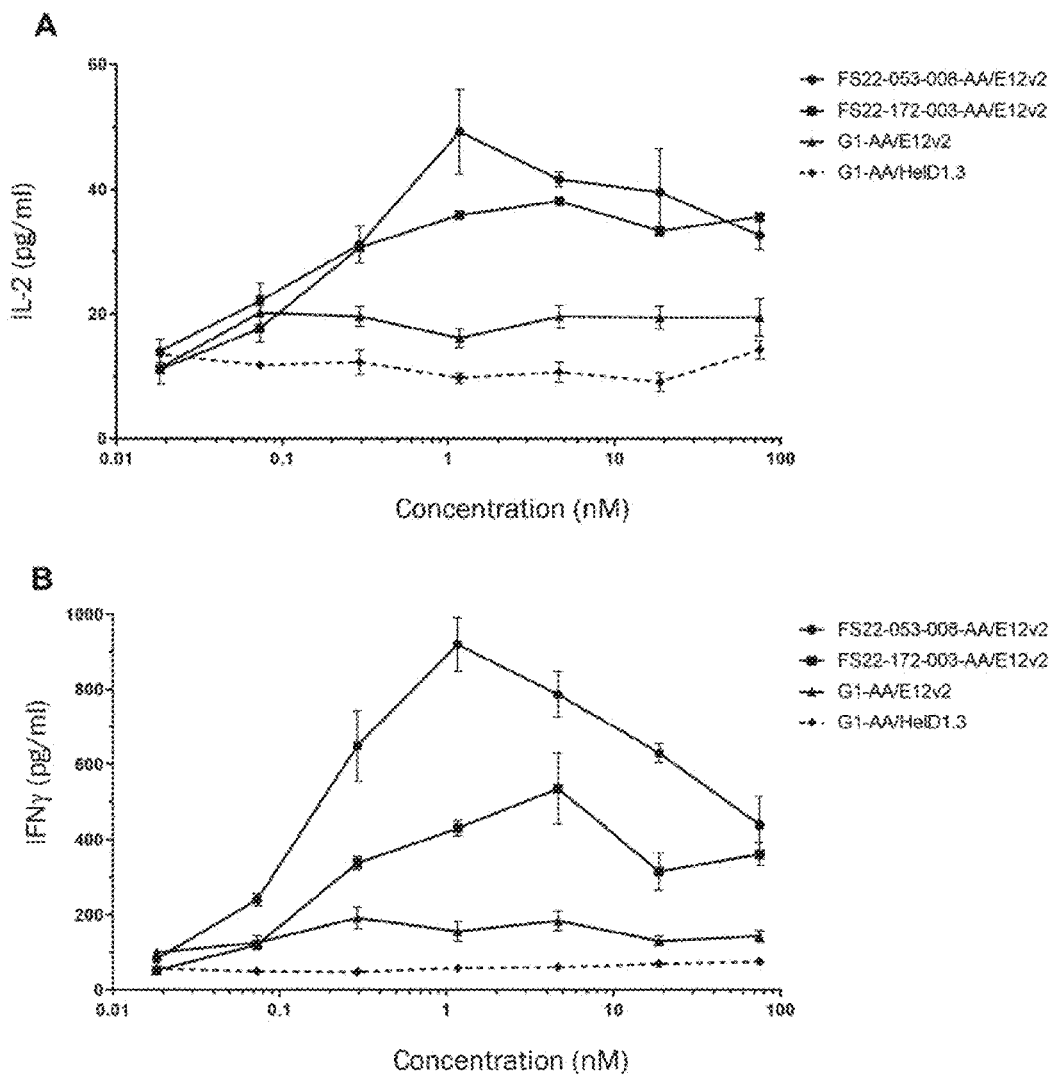

FIG. 9 shows IL-2 release at day 2 (FIG. 9A) or IFN-γ release at day 6 (FIG. 9B) from cynomolgus CD4⁺ T cells cultured with allogeneic cynomolgus monocytes in the presence of a titration of anti-human CD137/PD-L1 mAb² FS22-053-008-AA/E12v2 or 172-003-AA/E12v2 or anti-human PD-L1 positive control antibody G1-AA/E12v2 or isotype control antibody G1-AA/HeID1.3.

Figure 10:
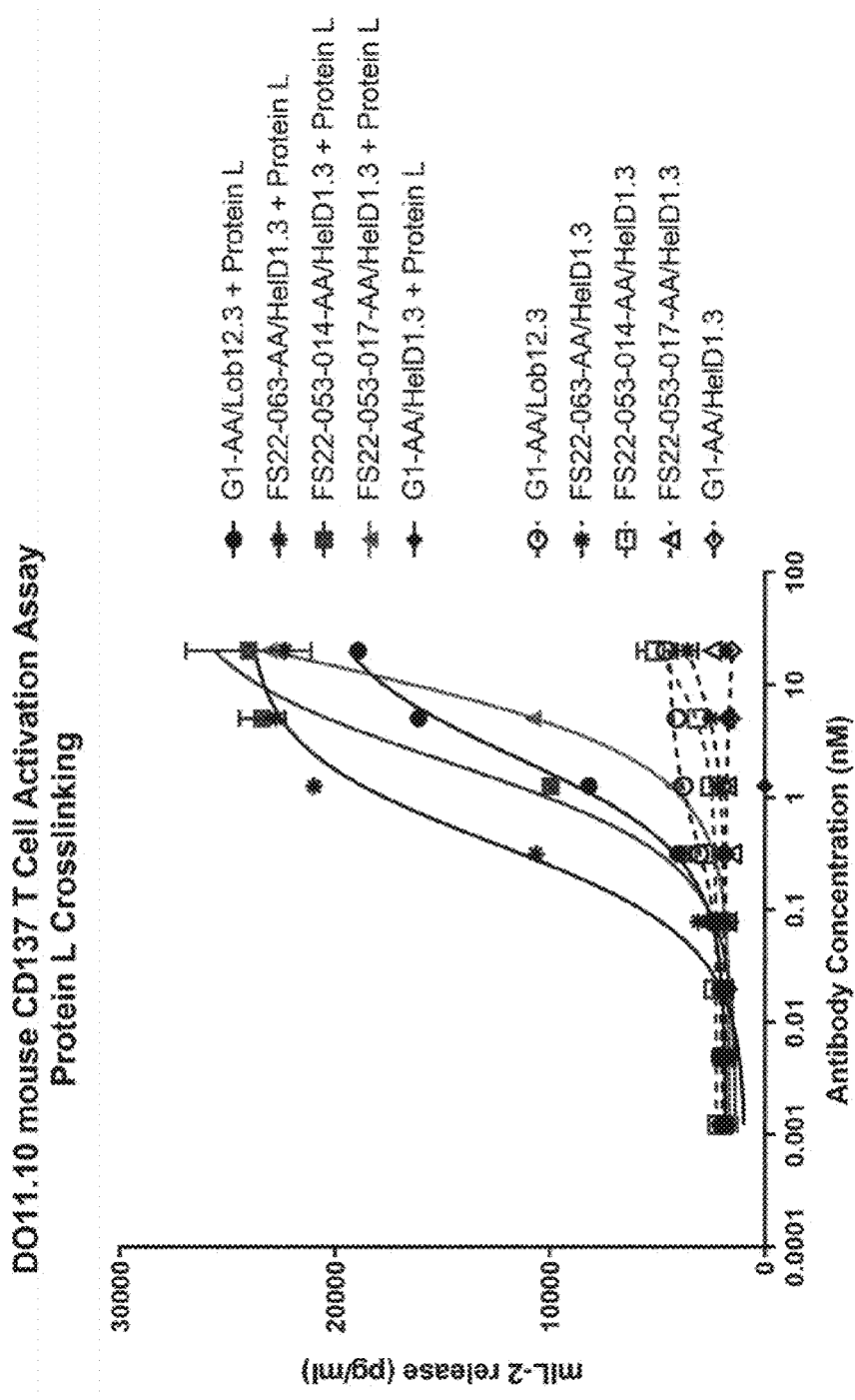

FIG. 10 shows mouse IL-2 release in a DO11.10 mouse CD137 T cell activation assay testing the mouse and human cross-reactive CD137 Fcabs FS22-053-014 and FS22-053-017 in mock mAb² format when crosslinked with Protein L. FS22-053-014 and FS22-053-017, and anti-mouse CD137 Fcab FS22m-063, all in HeID1.3 mock mAb² format activated CD137 when crosslinked with Protein L leading to a release of mIL-2. The positive control anti-mouse CD137 mAb, Lob12.3, showed an increase in mIL-2 release as expected. All anti-CD137 Fcabs in mock mAb² format without Protein L to crosslink (dotted lines) showed greatly reduced mIL-2 release compared to when crosslinked.

FS22-053-017 had lower activity in this assay (8-fold worse $EC_{50}$ compared to FS22-053-014) but still showed activity in the assay.

Figure 11:
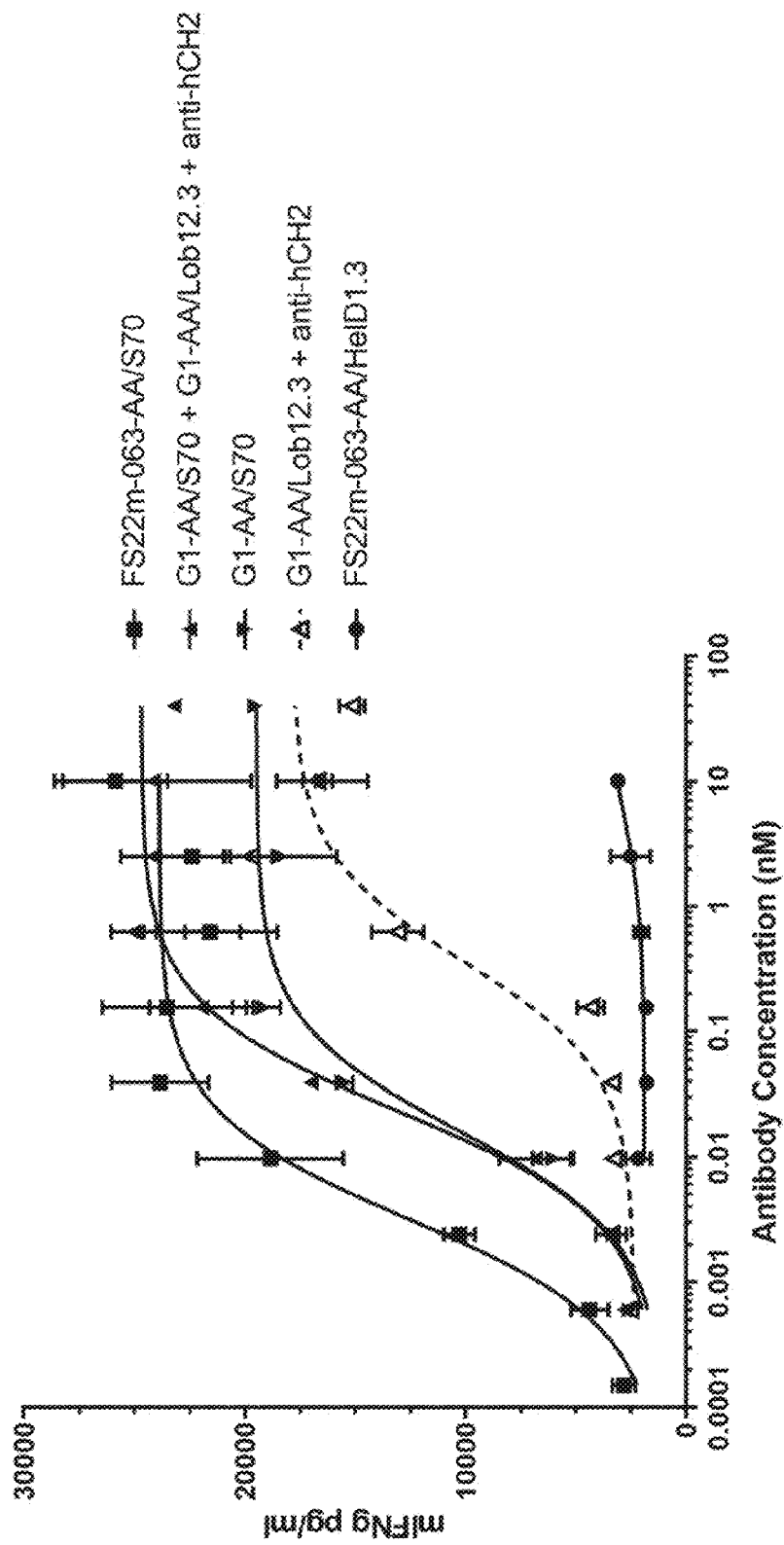

FIG. 11 shows release of mouse IFNγ which is an indication of CD8⁺ T cell activation. The anti-mouse CD137/PD-L1 mAb² shows the greatest potency in this assay above either of the positive control antibodies against human CD137 and PD-L1, or the combination of the two. As expected, the FS22m-063-AA Fcab in mock mAb² format (FS22m-063-AA/HeID1.3) does not show any activity.

Figure 12:
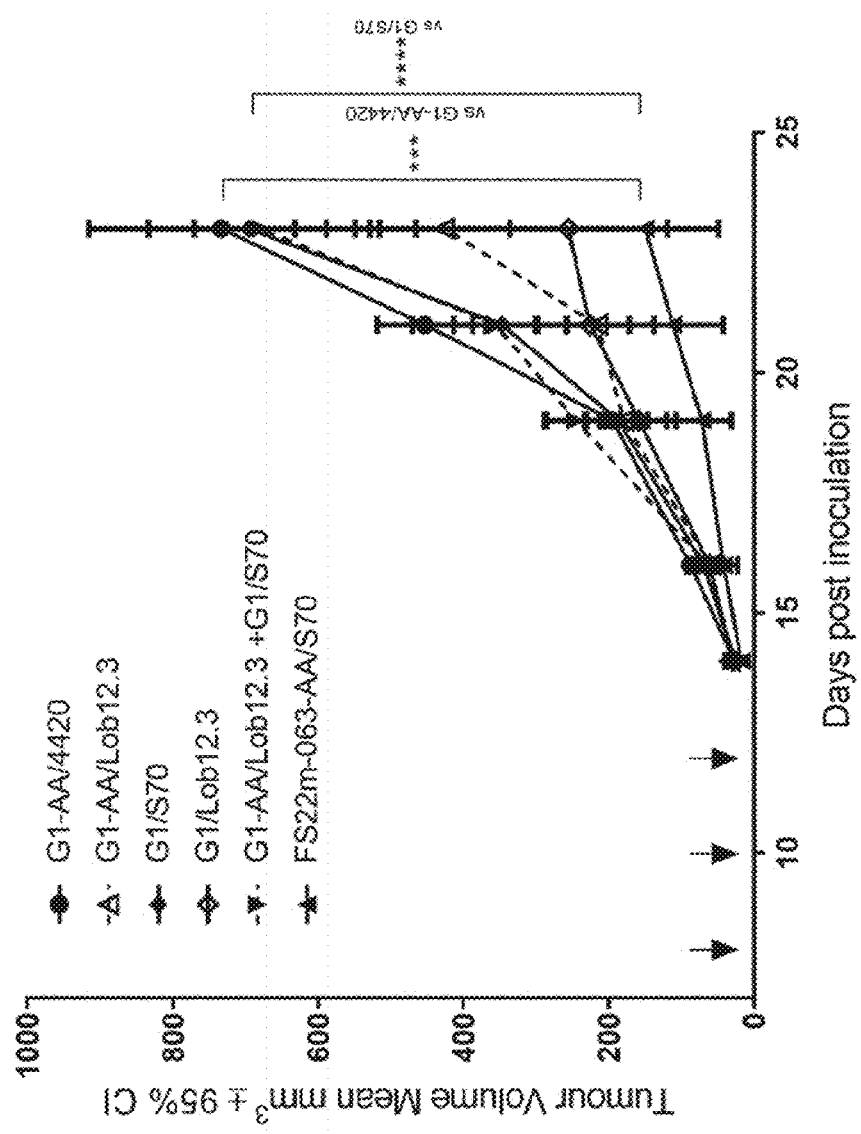

FIG. 12 shows tumour volume measurements of the CT26 syngeneic tumour model grown subcutaneously in Balb/c mice treated with G1-AA/4420 (IgG control), G1/S70 (PD-L1 positive control), G1-AA/Lob12.3 and G1/Lob12.3 (CD137 positive control with the LALA mutation and without), the combination of G1/S70 plus G1-AA/Lob12.3 and FS22m-063-AA/S70 (the anti-mouse CD137 Fcab FS22m-063 in a model PD-L1 mAb² format). The mean tumour volume plus or minus 95% confidence interval is plotted. FS22m-063-AA/S70 is able to significantly reduce tumour growth in a CT26 syngeneic tumour model compared to IgG control treated mice and anti-PD-L1 positive control mAb. Statistical significance shown pairwise for growth rates over the full time of study using the Mixed Model analysis.

Mean tumour volume shown as geometric or arithmetic mean as appropriate based on data normality testing. *$P \leq 0.05$; $P \leq 0.01$; *$P \leq 0.001$; ****$P \leq 0.0001$.

Figure 13:
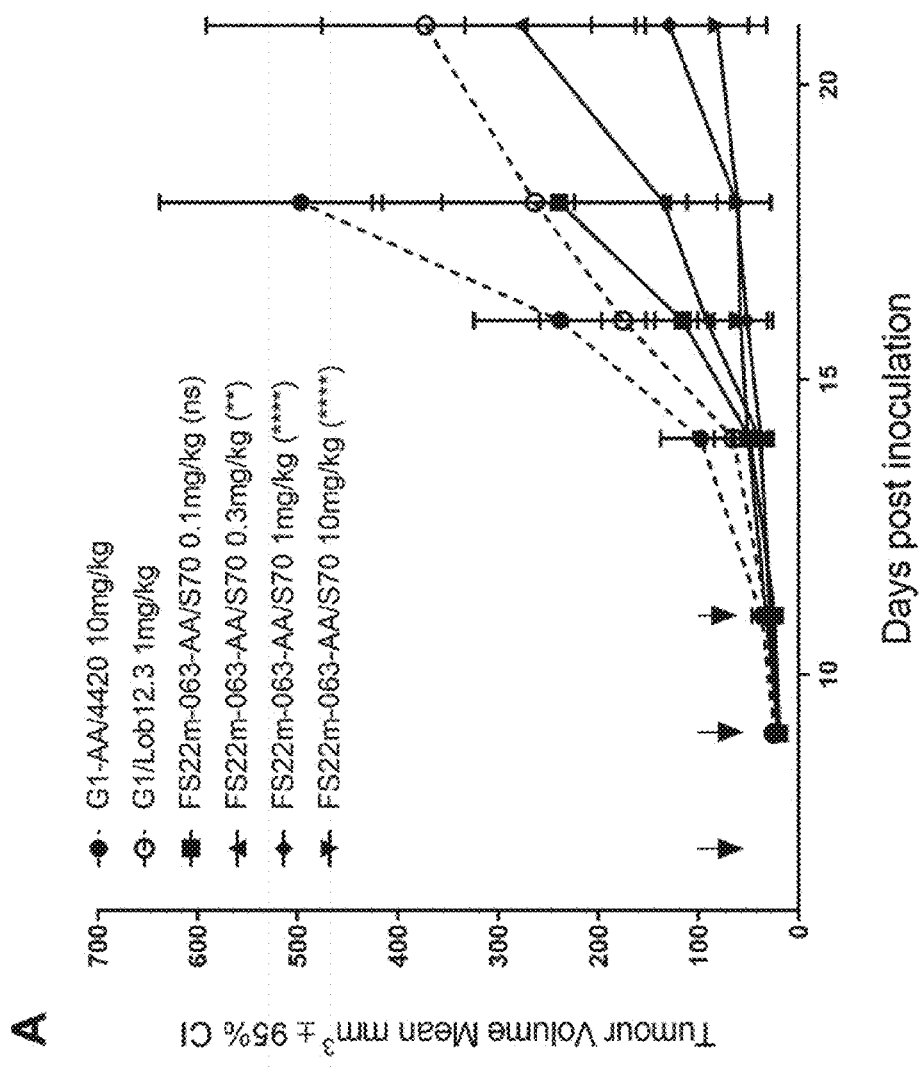
Figure 13:
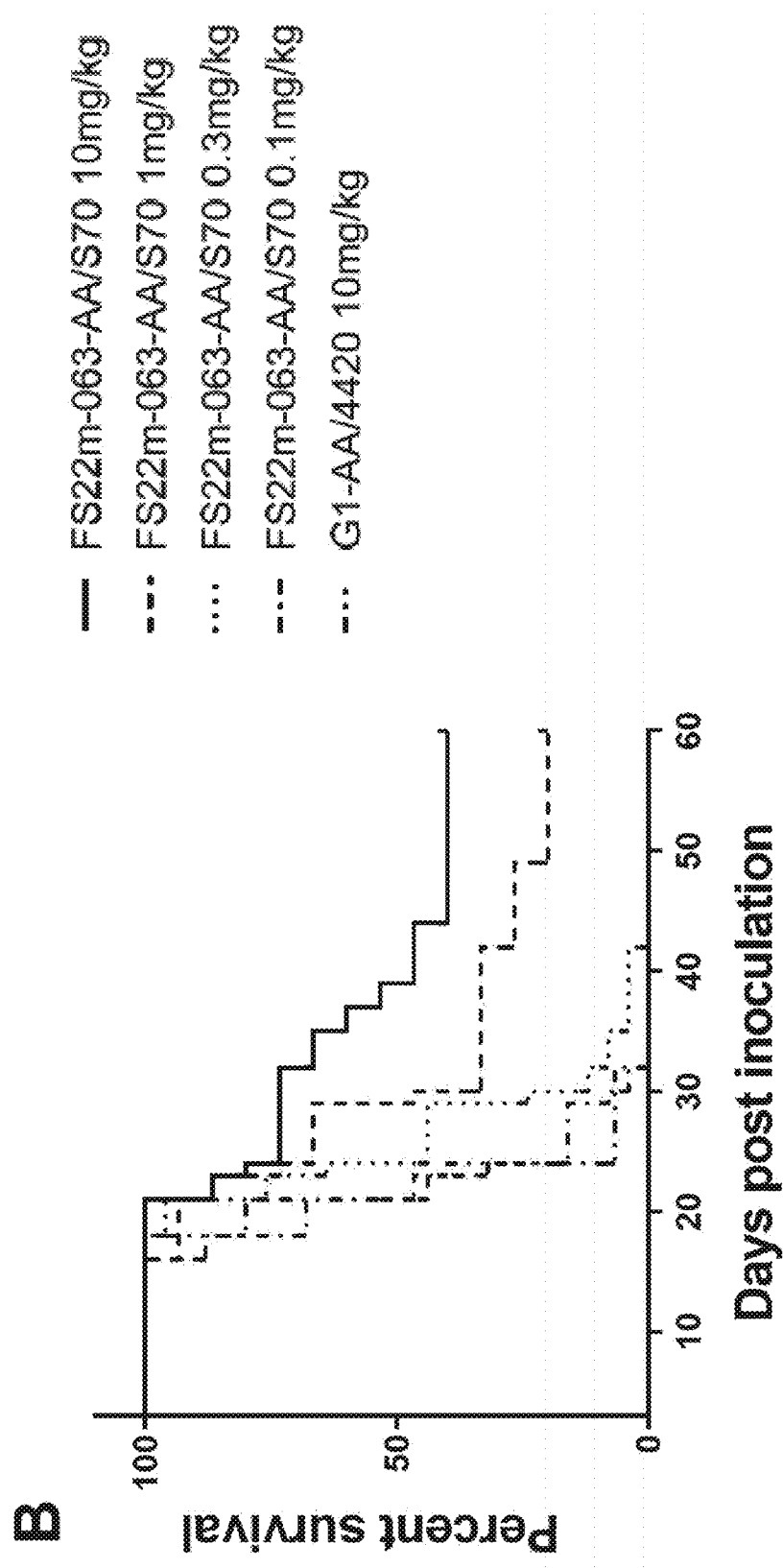

FIG. 13 shows the results of a dose-response study of anti-mouse CD137/PD-L1 mAb² in a CT26 syngeneic mouse tumour model. A: shows tumour volume measurements of the CT26 syngeneic tumour model grown subcutaneously in Balb/c mice treated with 3 doses of G1-AA/4420 (IgG control, 10 mg/kg), G1/Lob12.3 (CD137 positive control, 1 mg/kg), and the anti-mouse CD137/PD-L1 mAb² FS22m-063-AA/S70 at 4 different doses (0.1 mg/kg, 0.3 mg/kg, 1.0 mg/kg, and 10.0 mg/kg). Each dose is indicated by a vertical black arrow on the x-axis. The mean tumour volume plus or minus 95% confidence interval is plotted. FS22m-063-AA/S70 is able to significantly reduce tumour growth in a CT26 syngeneic tumour model compared to IgG control treated mice and anti-PD-L1 positive control mAb. Statistical significance shown pairwise for growth rates over the full time of study using the Mixed Model analysis. Mean tumour volume shown as geometric or arithmetic mean as appropriate based on data normality testing. $P \leq 0.01$; *****$P \leq 0.0001$. B: shows a Kaplan Meier plot of the CT26 syngeneic tumour model grown subcutaneously in Balb/c mice treated with 3 doses of G1-AA/4420 (IgG control, ~10 mg/kg) and the anti-mouse CD137/PD-L1 mAb² FS22m-063-AA/S70 at 4 different doses 2 µg, 6 µg, 20 µg, and 200 µg (equivalent to approximately 0.1 mg/kg, 0.3 mg/kg, 1.0 mg/kg, and 10.0 mg/kg). FS22m-063-AA/S70 induces a dose dependent increase of survival in a CT26 syngeneic tumour model compared to IgG control treated mice.

Figure 14:
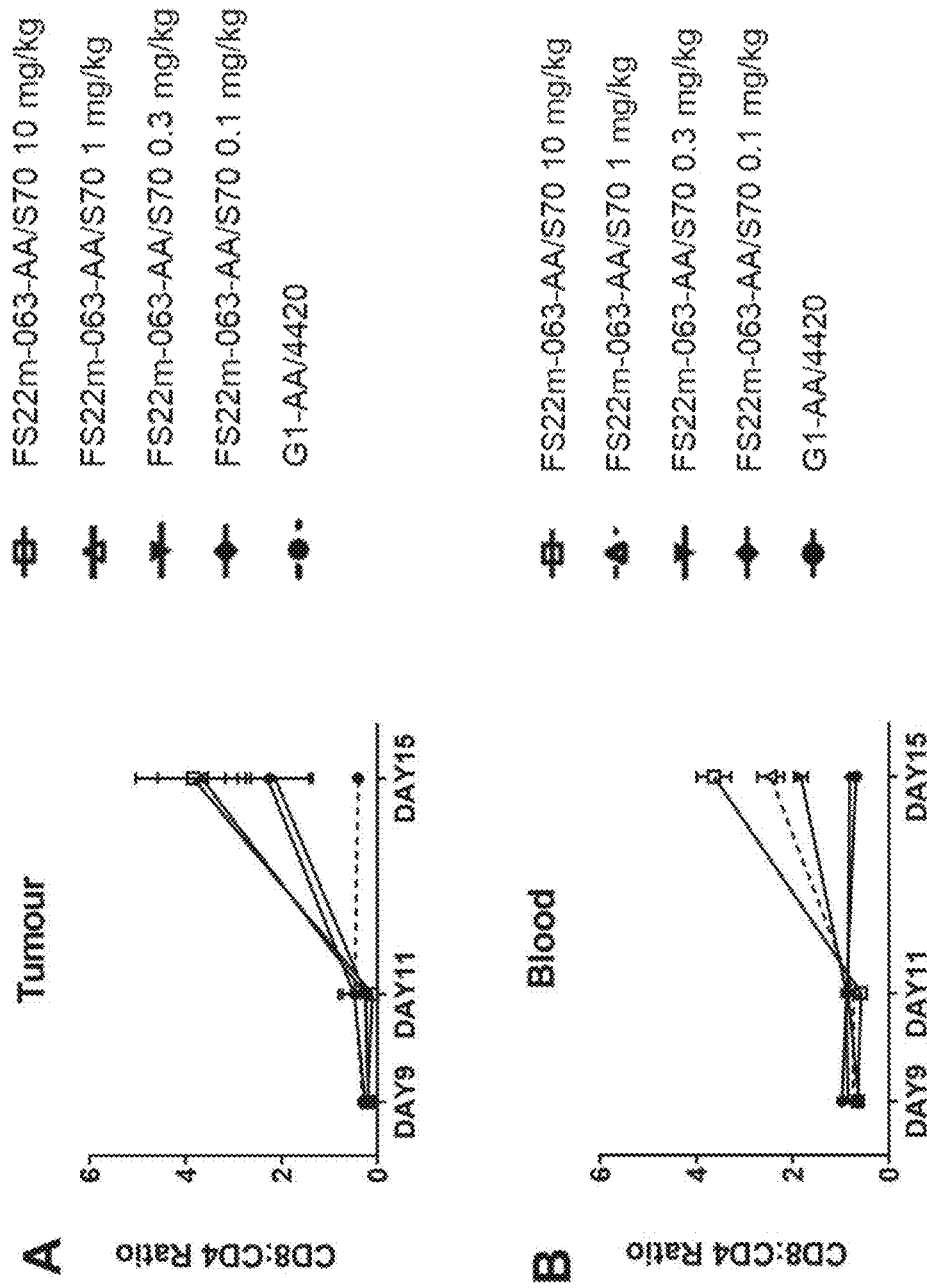
Figure 14:
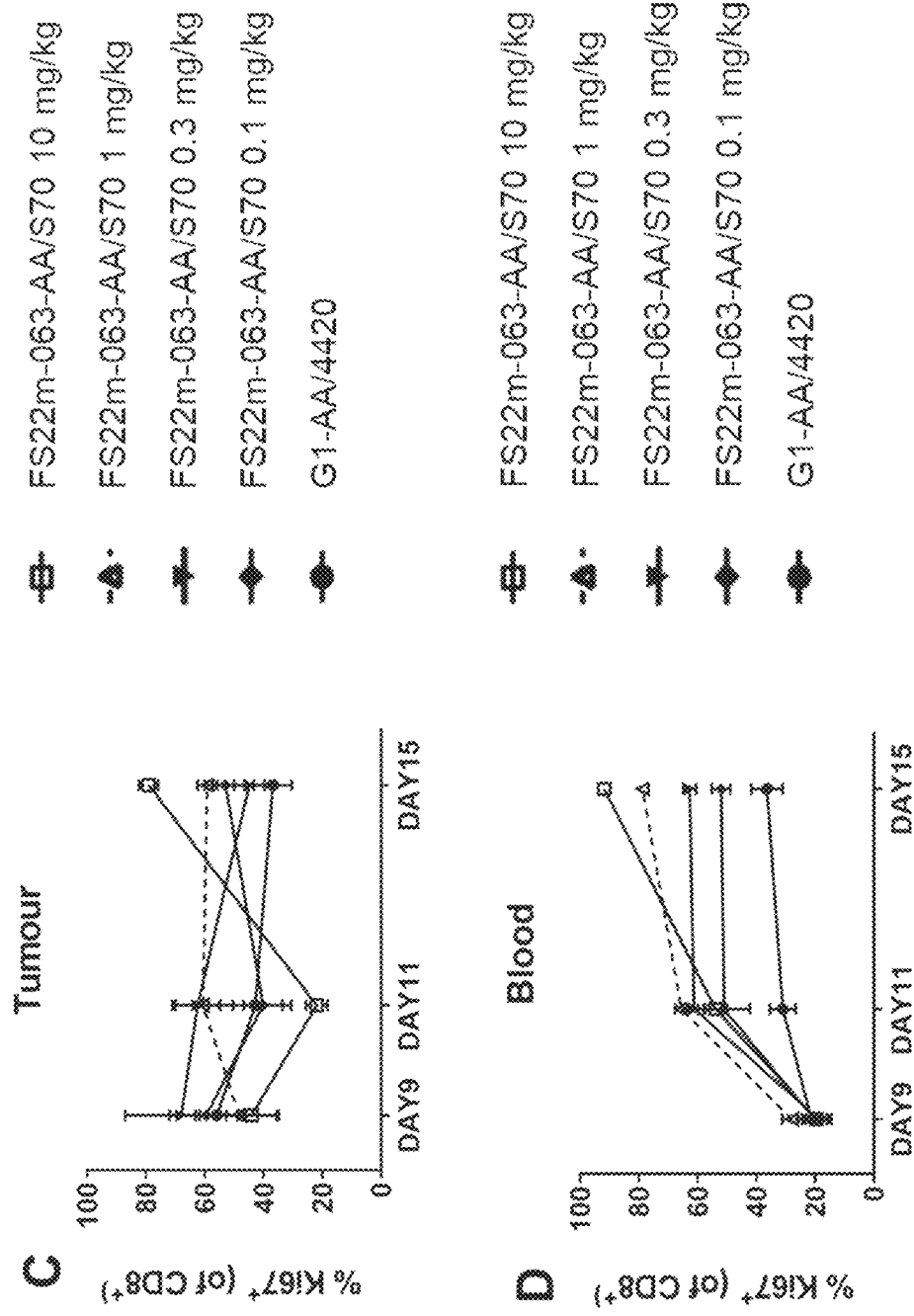

FIG. 14 shows a dose dependent increase in CD8⁺:CD4⁺ percentage ratio in tumour and blood of mice administered q2dx3 with anti-mouse CD137/PD-L1 mAb² FS22m-063-AA/S70 at four different dose levels is shown in panel A and B and Ki67 expression on CD8⁺ T cells is shown in panels C and D.

Figure 15:
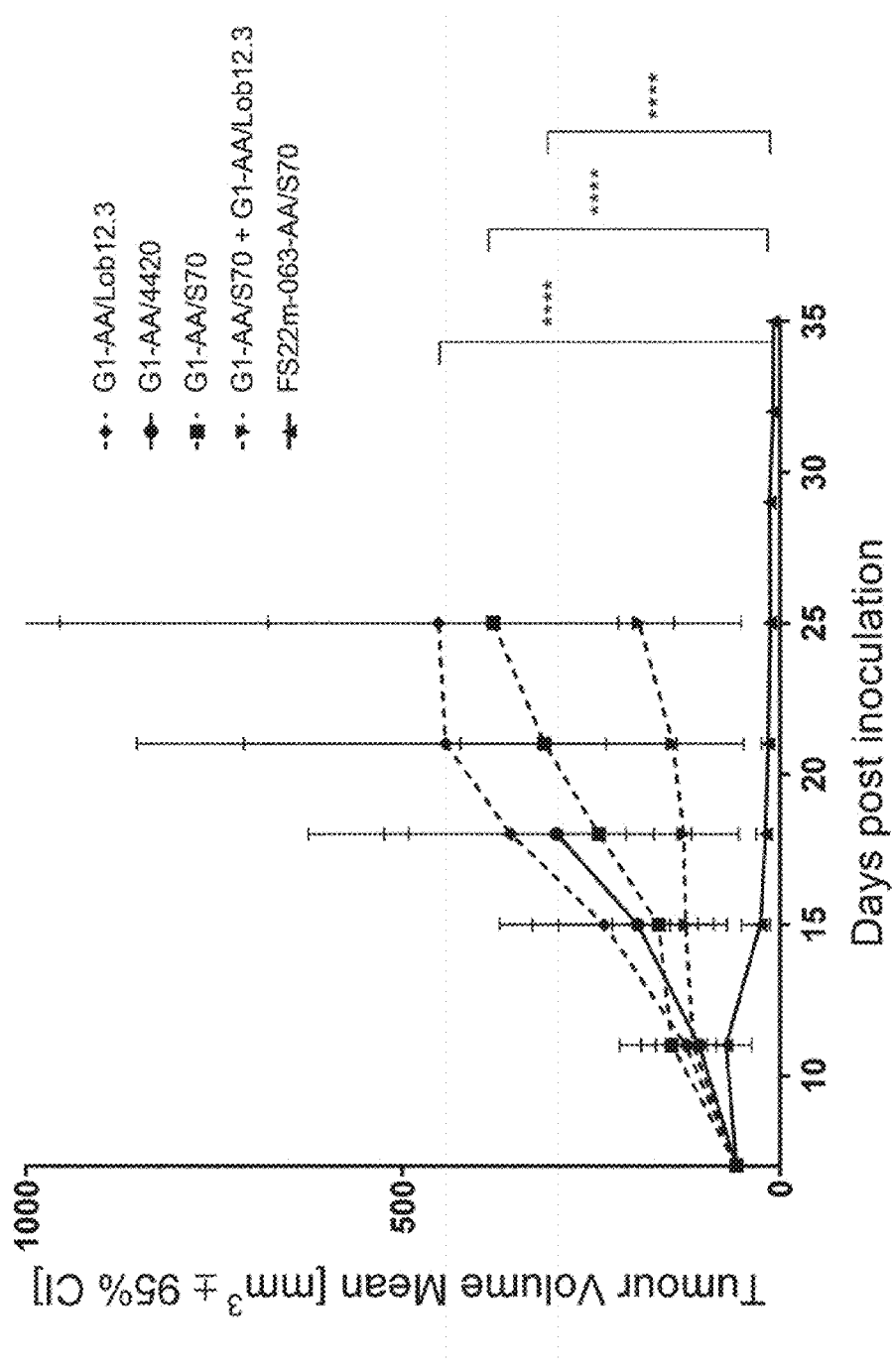

FIG. 15 shows tumour volume measurements of the MC38 syngeneic tumour model grown subcutaneously in C57BL/6 mice treated with G1-AA/4420 (isotype control), G1-AA/S70 (PD-L1 positive control), G1-AA/Lob12.3 (CD137 positive control), the combination of G1-AA/S70 plus G1-AA/Lob12.3, and FS22m-063-AA/S70 (the anti-mouse CD137 Fcab FS22m-063 in a model PD-L1 mAb$^2$ format). The mean tumour volume [in mm$^3$] plus or minus the 95% Confidence Interval is plotted. FS22m-063-AA/S70 is able to significantly reduce tumour growth in a MC38 syngeneic tumour model compared to IgG control treated mice, anti-PD-L1 positive control mAb treated mice, anti-CD137 positive control treated mice. Statistical significance shown pairwise for growth rates over the full time of study using the Mixed Model analysis. ****≤0.0001 p-value.

Figure 16:
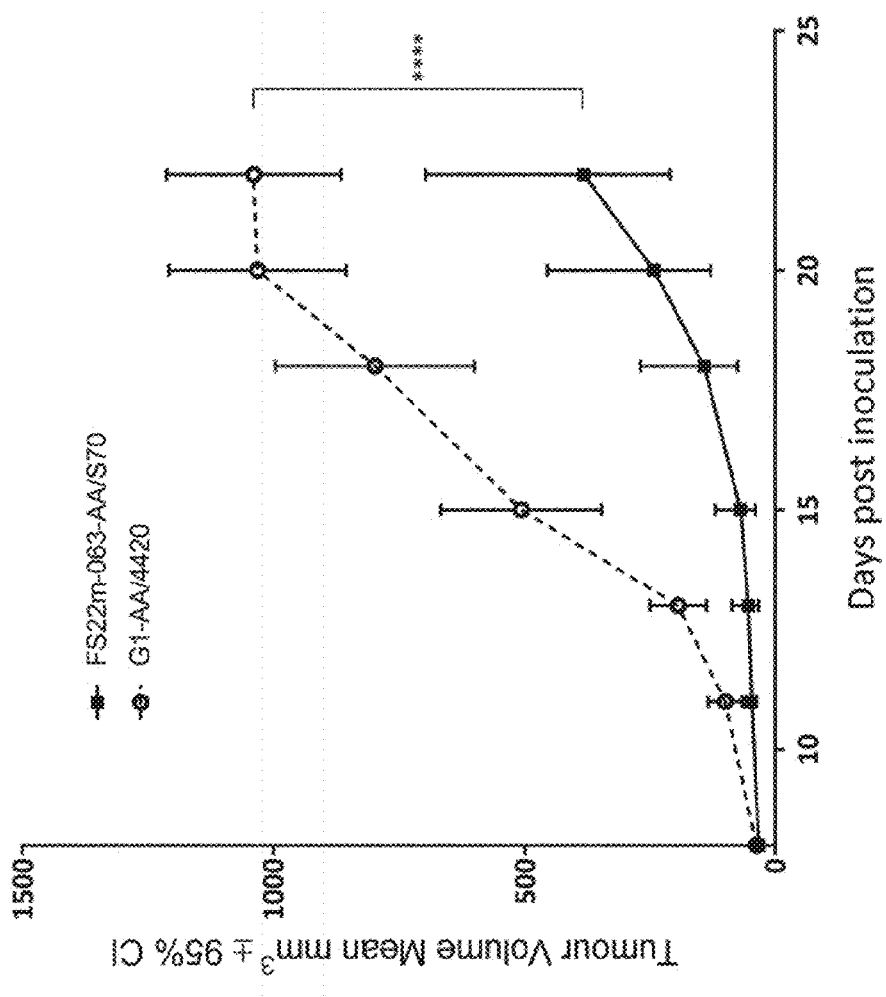

FIG. 16 shows tumour volume measurements of the B16.F10 syngeneic tumour model grown subcutaneously in C57BL/6 mice treated with G1-AA/4420 (isotype control) and the anti-mouse CD137/PD-L1 mAb$^2$ FS22m-063-AA/S70. Both compositions were dosed at 1 mg/kg. The mean tumour volume [in mm$^3$] plus or minus the 95% Confidence Interval is plotted. FS22m-063-AA/S70 treatment significantly reduced tumour growth in a B16.F10 syngeneic tumour model compared to IgG control treated mice. Statistical significance shown pairwise for growth rates over the full time of study using the Mixed Model analysis. Mean tumour volume shown as geometric or arithmetic mean as appropriate based on data normality testing. *P≤0.05; P≤0.01; *P≤0.001; ****P≤0.0001.

Figure 17:
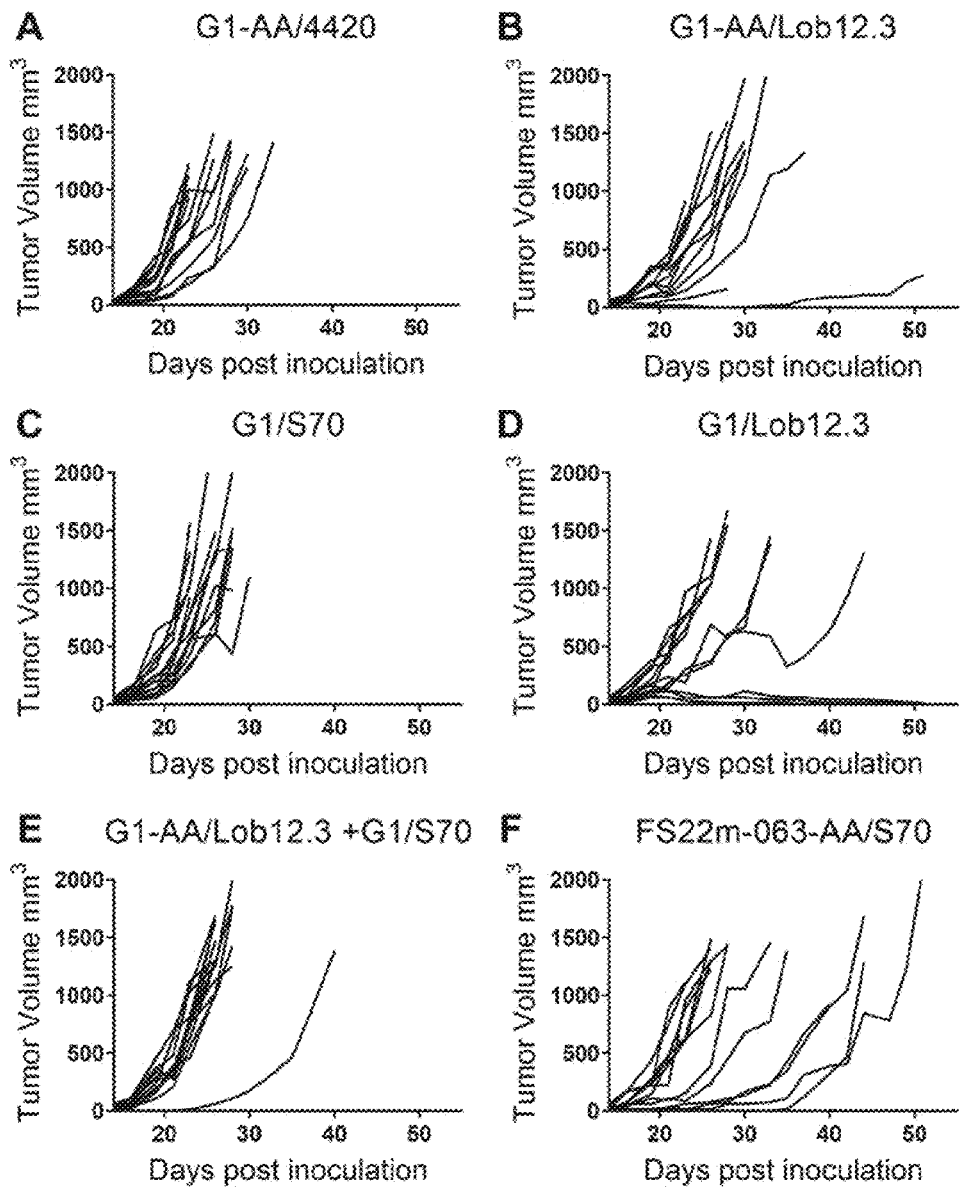

FIG. 17 shows the spaghetti plots for individual mice in the CT26 syngeneic tumour model grown subcutaneously in Balb/c mice treated with (A) G1-AA/4420 (IgG control), (C) G1/S70 (anti-PD-L1 positive control), (B) G1-AA/Lob12.3 and (D) G1/Lob12.3 (anti-CD137 positive control with and without the LALA mutation), or (E) a combination of G1/S70 plus G1-AA/Lob12.3 and (F) FS22m-063-AA/S70 (the anti-mouse CD137 Fcab FS22m-063 in a model PD-L1 mAb$^2$ format). FS22m-063-AA/S70 induced significant tumour growth inhibition in a CT26 syngeneic tumour model compared to IgG control treated mice.

Figure 18:
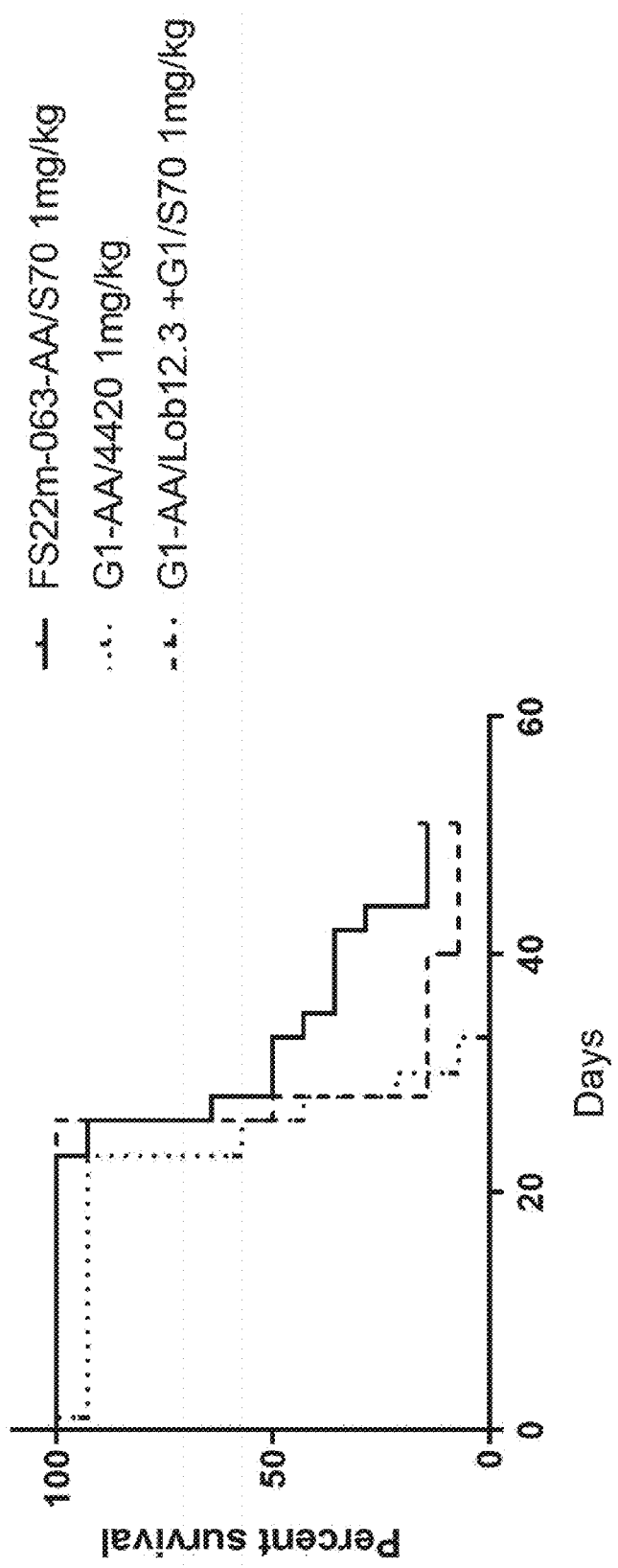

FIG. 18 shows a Kaplan Meier plot of the CT26 syngeneic tumour model grown subcutaneously in Balb/c mice treated with G1-AA/4420 (IgG control), the combination of G1/S70 plus G1-AA/Lob12.3, and FS22m-063-AA/S70 (the anti-mouse CD137 Fcab FS22m-063 in a model PD-L1 mAb$^2$ format) all at 1 mg/kg. FS22m-063-AA/S70 induced significant survival in a CT26 syngeneic tumour model compared to IgG control treated mice.

Figure 19:
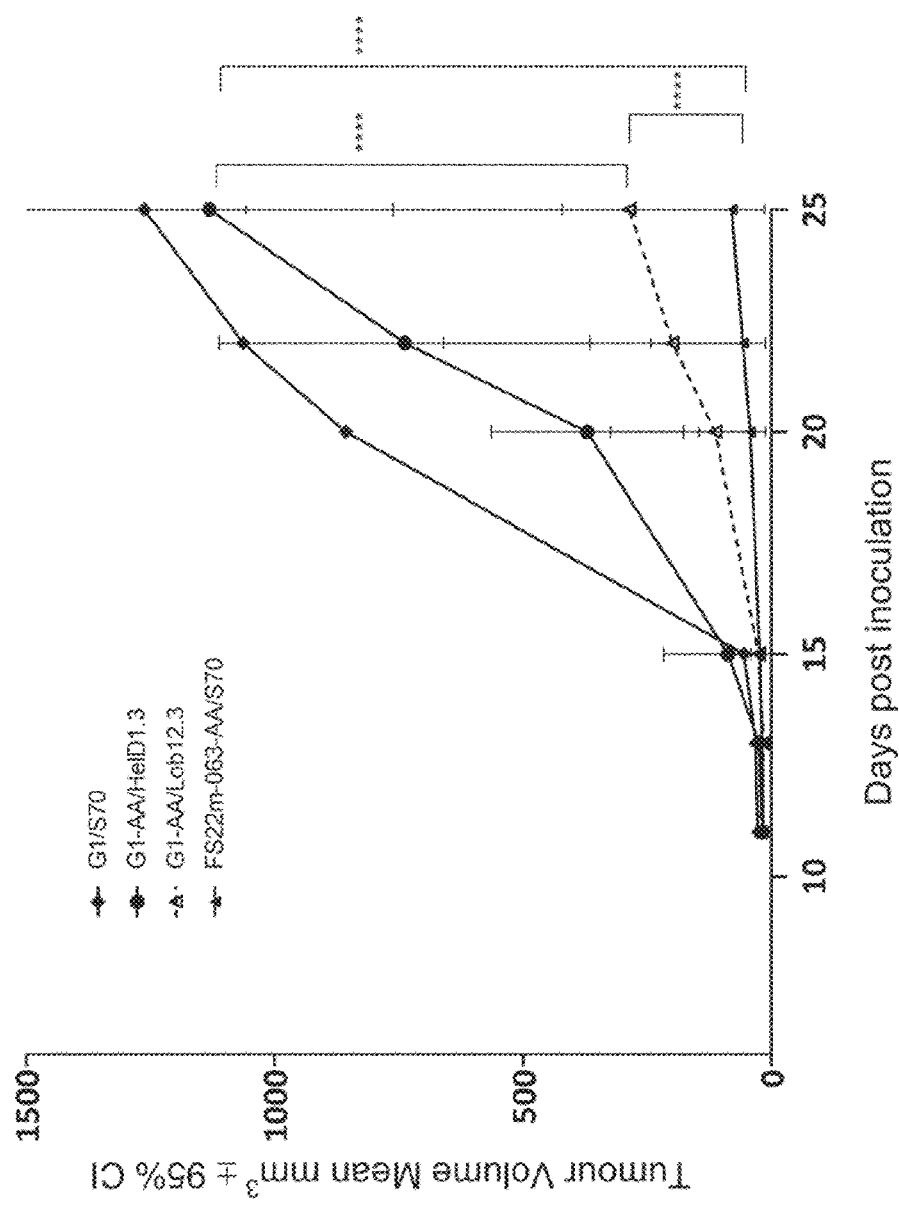

FIG. 19 shows tumour volume measurements of the CT26 syngeneic tumour model grown subcutaneously in Balb/c mice treated with G1-AA/HeID1.3 (IgG control), G1/S70 (anti-PD-L1 positive control), G1-AA/Lob12.3 (anti-CD137 positive control), and FS22m-063-AA/S70 (the anti-mouse CD137 Fcab FS22m-063 in a model PD-L1 mAb$^2$ format). The mean tumour volume plus or minus 95% confidence interval is plotted. FS22m-063-AA/S70 was able to significantly reduce tumour growth in a CT26 syngeneic tumour model compared to IgG control treated mice, anti-PD-L1 positive control mAb treated mice and anti-CD137 positive control treated mice. Statistical significance shown pairwise for growth rates over the full time of study using the Mixed Model analysis. Mean tumour volume shown as geometric or arithmetic mean as appropriate based on data normality testing. *P≤0.05; P≤0.01; *P≤0.001; ****P≤0.0001.

Figure 20:
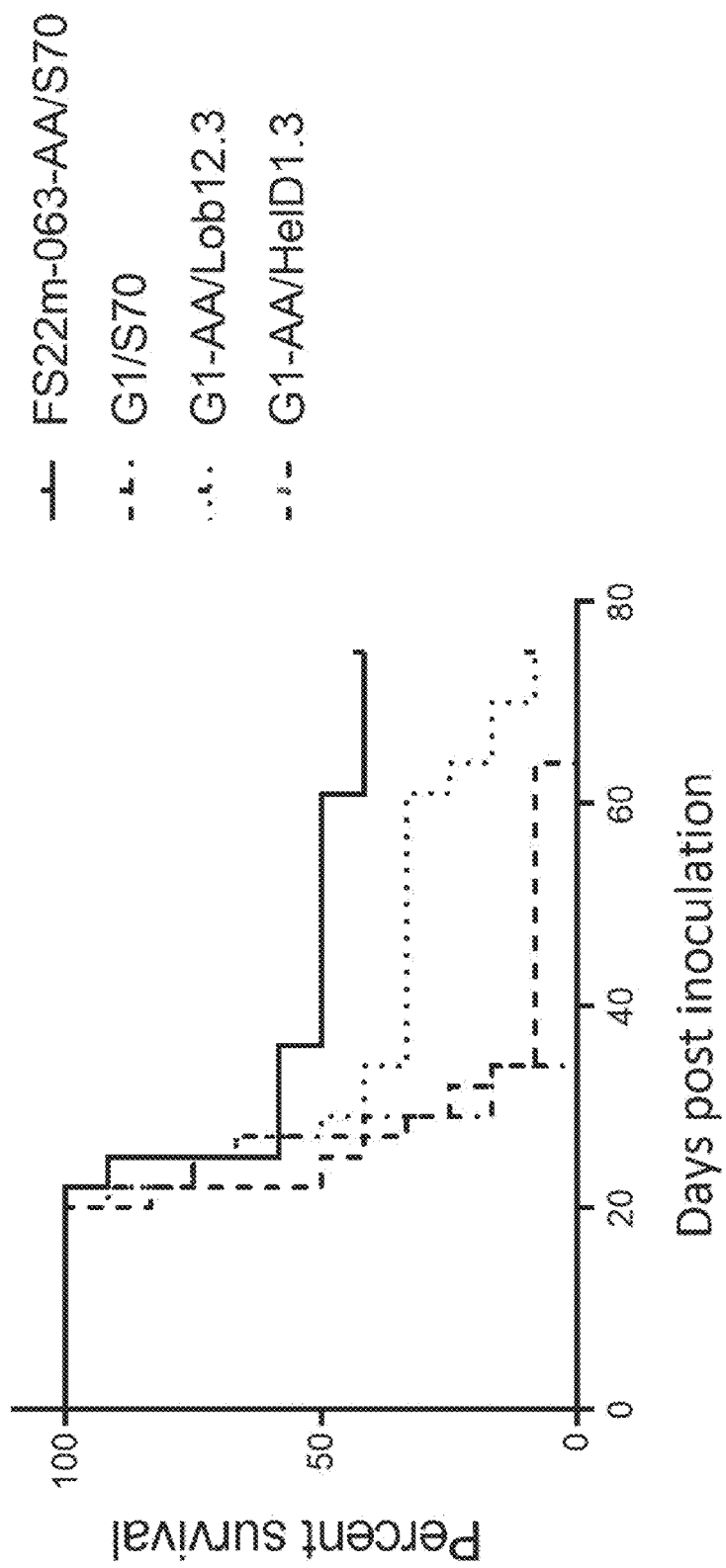

FIG. 20 shows a Kaplan Meier plot of the CT26 syngeneic tumour model grown subcutaneously in Balb/c mice treated with G1-AA/HeID1.3 (IgG control), G1/S70 (anti-PD-L1 positive control), G1-AA/Lob12.3 (anti-CD137 positive control) and FS22m-063-AA/S70 (the anti-mouse CD137 Fcab FS22m-063 in a model PD-L1 mAb$^2$ format). FS22m-063-AA/S70 induces significant survival in a CT26 syngeneic tumour model compared to IgG control treated mice and CD137 positive control treated mice.

Figure 21:
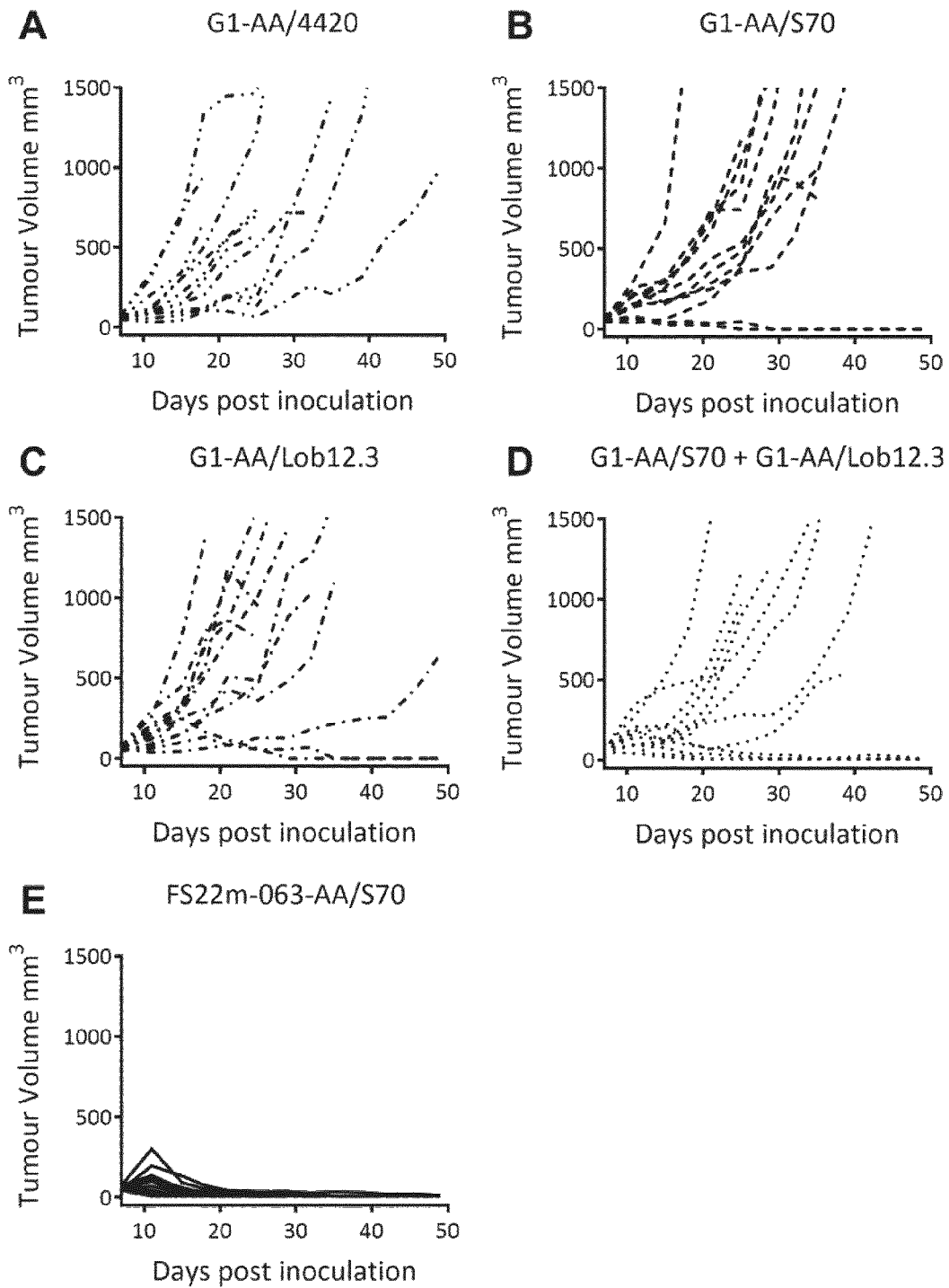

FIG. 21 shows the spaghetti plots for individual mice in the MC38 syngeneic tumour model grown subcutaneously in C57BL/6 mice treated with 3 doses of (A) G1-AA/4420 (isotype control), (B) G1-AA/S70 (anti-PD-L1 positive control), (C) G1-AA/Lob12.3 (anti-CD137 positive control), (D) the combination of G1-AA/S70 plus G1-AA/Lob12.3, and (E) FS22m-063-AA/S70 (the anti-mouse CD137 Fcab FS22m-063 in a model PD-L1 mAb$^2$ format). FS22m-063-AA/S70 induces full tumour growth inhibition, resulting in 100% tumour-free mice, in a MC38 syngeneic tumour model compared to IgG control treated mice.

Figure 22:
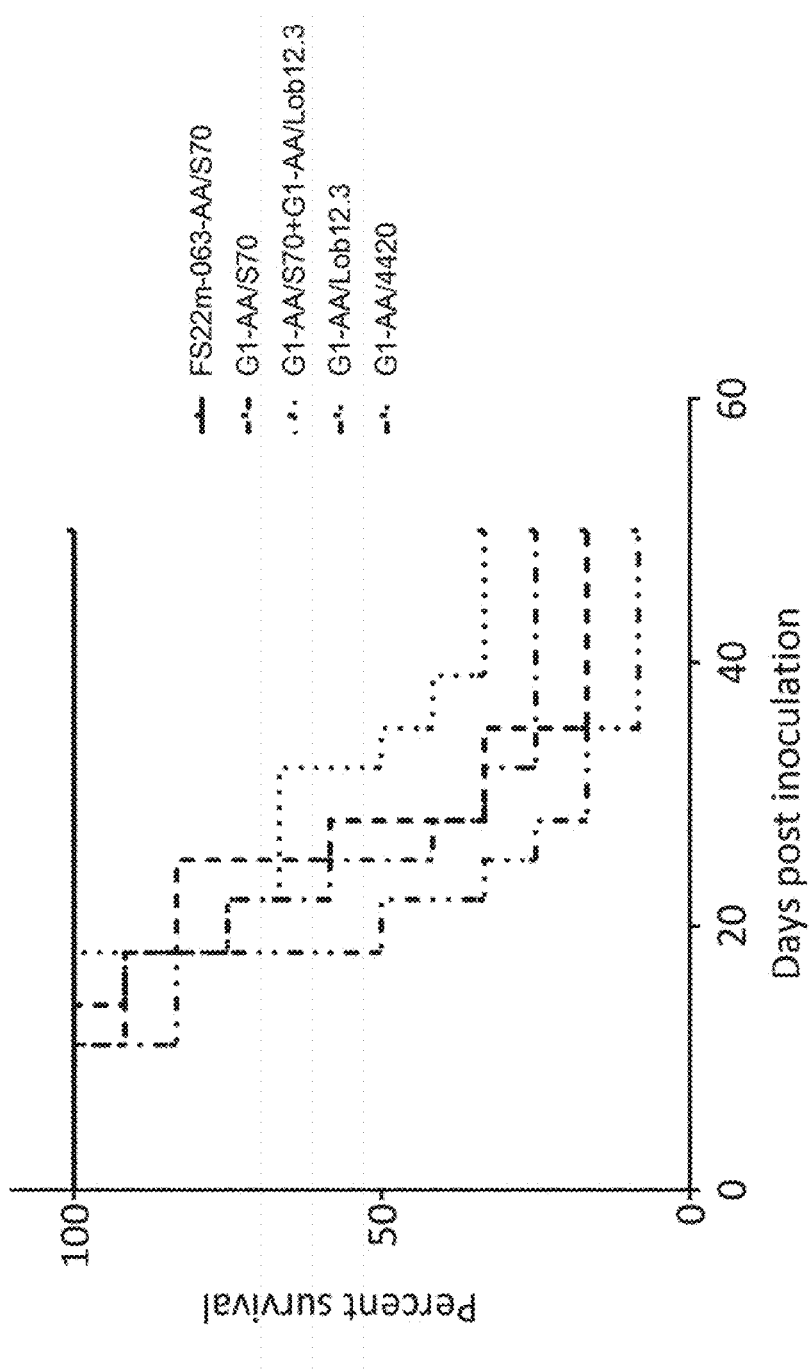

FIG. 22 shows a Kaplan Meier plot of the MC38 syngeneic tumour model grown subcutaneously in C57BL/6 mice treated with 3 doses of G1-AA/4420 (isotype control), G1-AA/S70 (anti-PD-L1 positive control), G1-AA/Lob12.3 (anti-CD137 positive control), the combination of G1-AA/S70 plus G1-AA/Lob12.3, and FS22m-063-AA/S70 (the anti-mouse CD137 Fcab FS22m-063 in a model PD-L1 mAb$^2$ format). FS22m-063-AA/S70 induces full survival in a MC38 syngeneic tumour model compared to IgG control treated mice.

Figure 23:
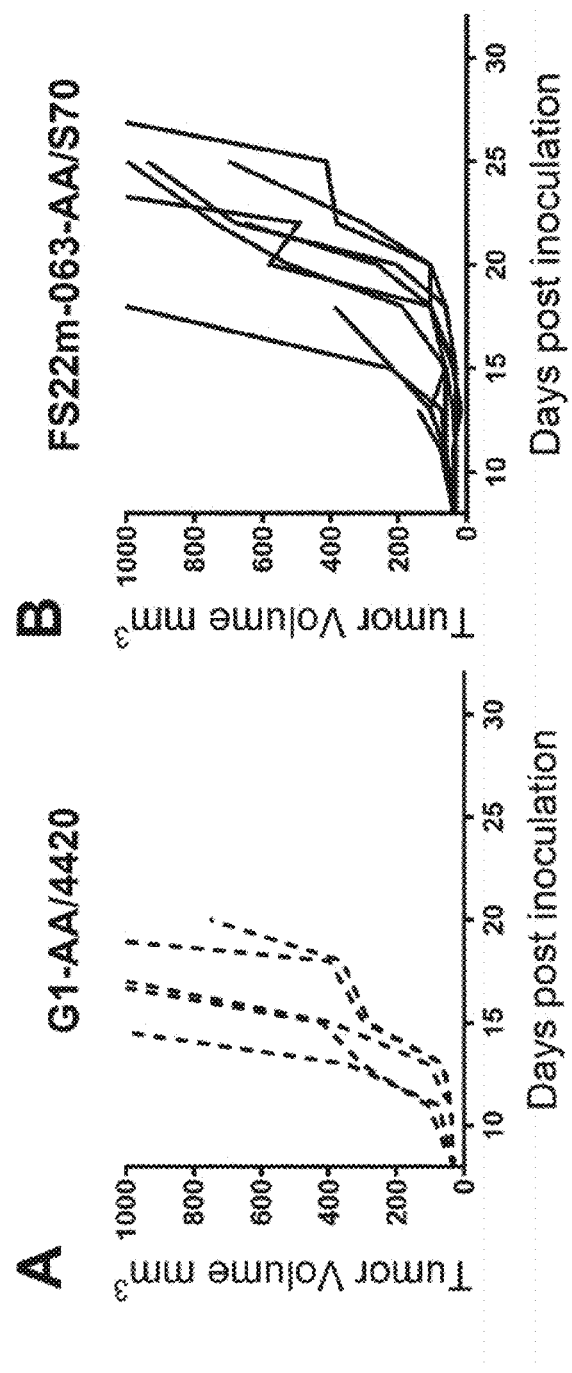

FIG. 23 shows the spaghetti plots for individual mice in the B16.F10 syngeneic tumour model grown subcutaneously in C57BL/6 mice treated with G1-AA/4420 (isotype control) (FIG. 23A) and the anti-mouse CD137/PD-L1 mAb$^2$ FS22m-063-AA/S70 (FIG. 23B). FS22m-063-AA/S70 induced partial tumour growth inhibition in a B16.F10 syngeneic tumour model compared to IgG control treated mice.

Figure 24:
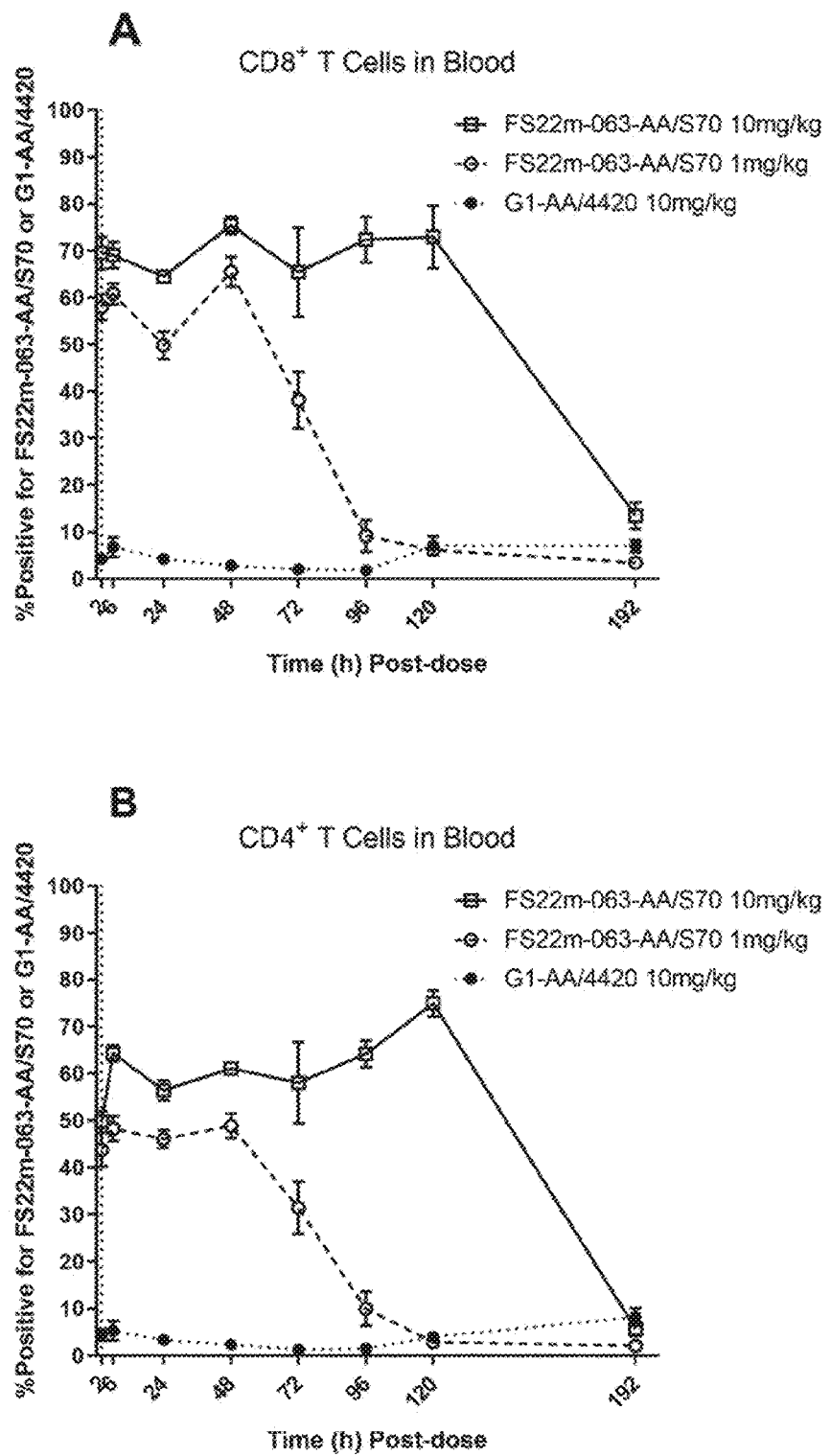
Figure 24:
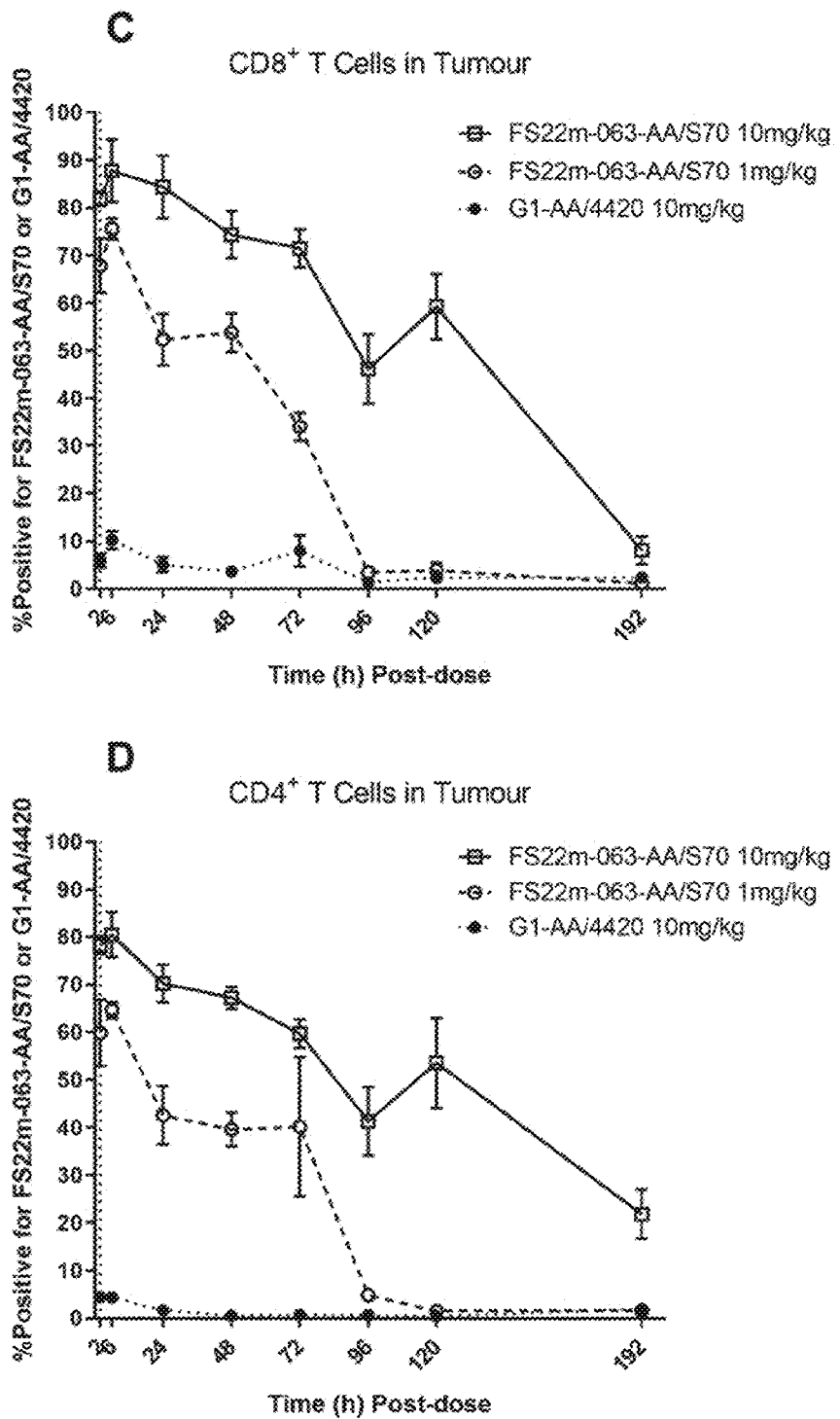

FIG. 24 shows anti-mCD137/PD-L1 mAb$^2$ binding data to T cells ex vivo, determined by flow cytometry. The Mean Fluorescent Intensity (MFI) values were measured from anti-human Fc secondary antibody conjugated with Alexa Fluor 488 that detected the human Fc region of the anti-mCD137/PDI-L1 mAb$^2$ bound to cells. Positive cells that had an MFI greater than that of an unstained control sample were identified as positive for anti-mCD137/PD-L1 and the data presented shows the positive population as a percentage of (A) all CD8$^+$ or (B) all CD4$^+$ T cells from the blood, or (C) all CD8$^+$ or (D) all CD4$^+$ T cells from the tumour. These results show that anti-mCD137/PD-L1 mAb$^2$ rapidly binds both CD8' and CD4$^+$ T cells present in both tumour and blood and that the percentage positive T cell population decreases over time dependent on dose level.

Figure 25:
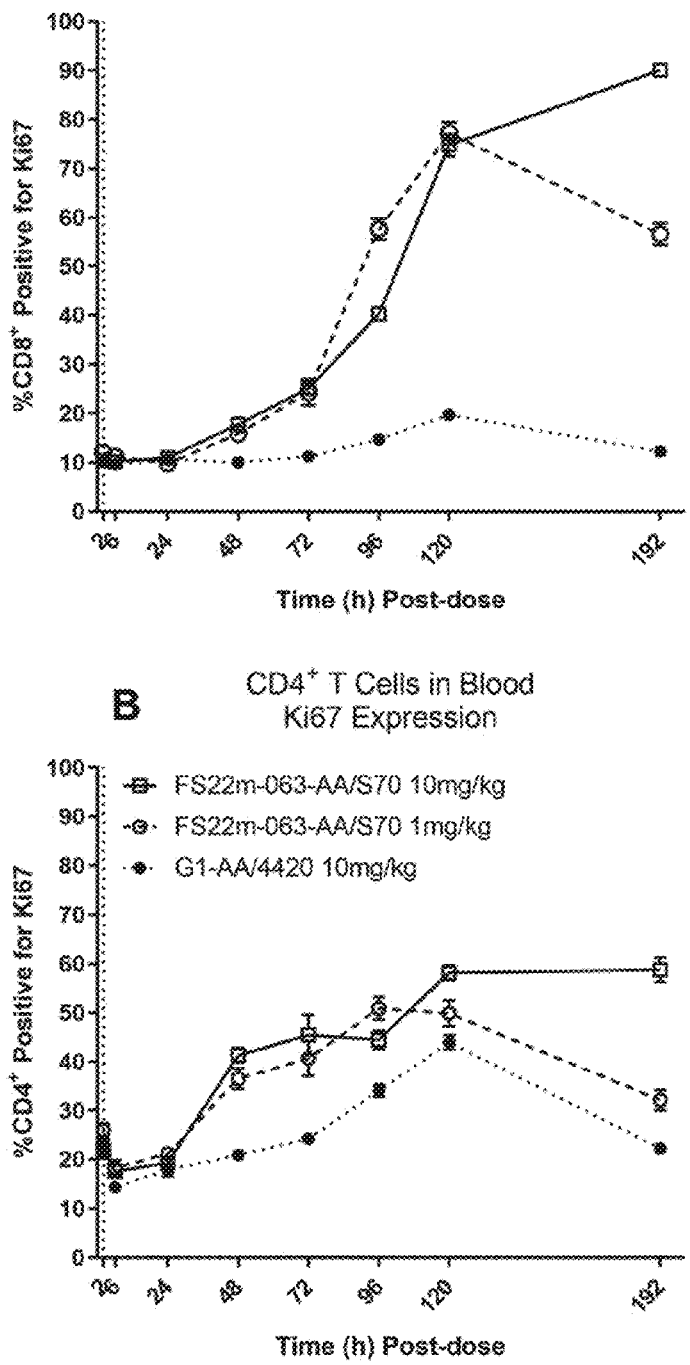
Figure 25:
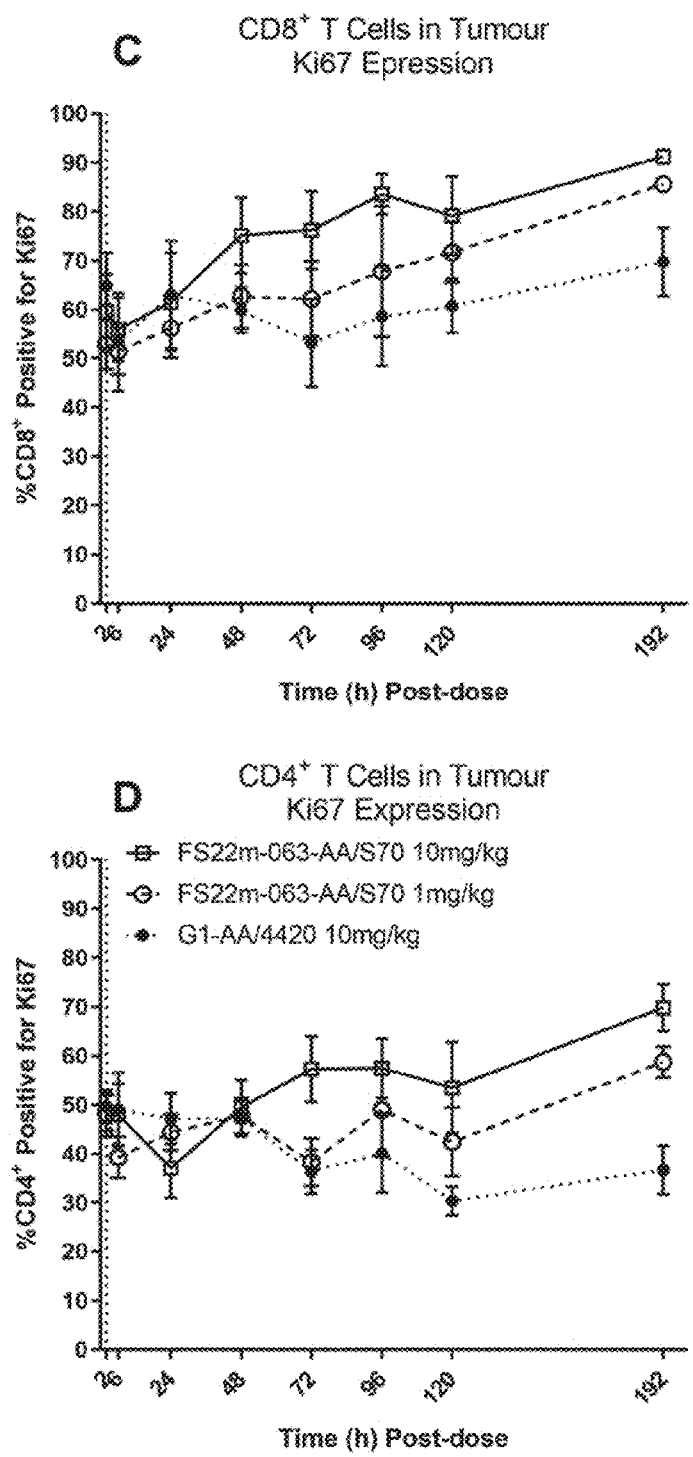

FIG. 25 shows Ki67 expression data by T cells ex vivo, determined by flow cytometry. The Mean Fluorescent Intensity (MFI) values were measured from anti-Ki67 antibody conjugated with PE-Cy7 bound to cells. Positive cells that had an MFI greater than that of an unstained control sample were identified as positive for Ki67 expression and the data presented shows the positive population as a percentage of (A) all CD8$^+$ or (B) all CD4$^+$ T cells from the blood, or (C) all CD8$^+$ or (D) all CD4$^+$ T cells from the tumour. These results show that T cells in mice dosed with anti-mCD137/PD-L1 mAb$^2$ rapidly express Ki67 both on CD8$^+$ and CD4$^+$ T cells in the blood and that a high percentage of Ki67 positive T cells are already present in a sample from the tumour microenvironment. An increase in Ki67 expression over time dependent on dose level was observed.

Figure 26:
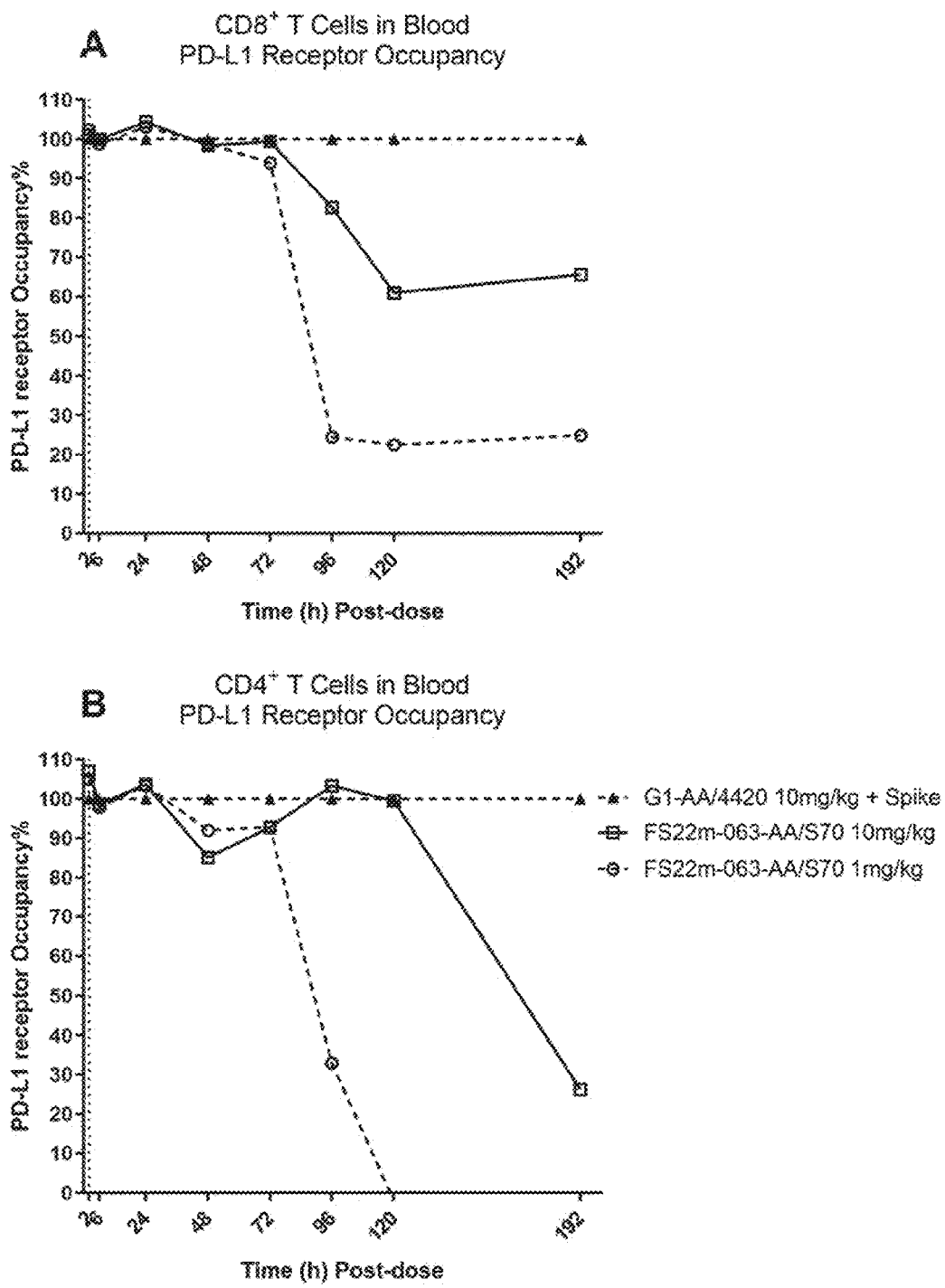
Figure 26:
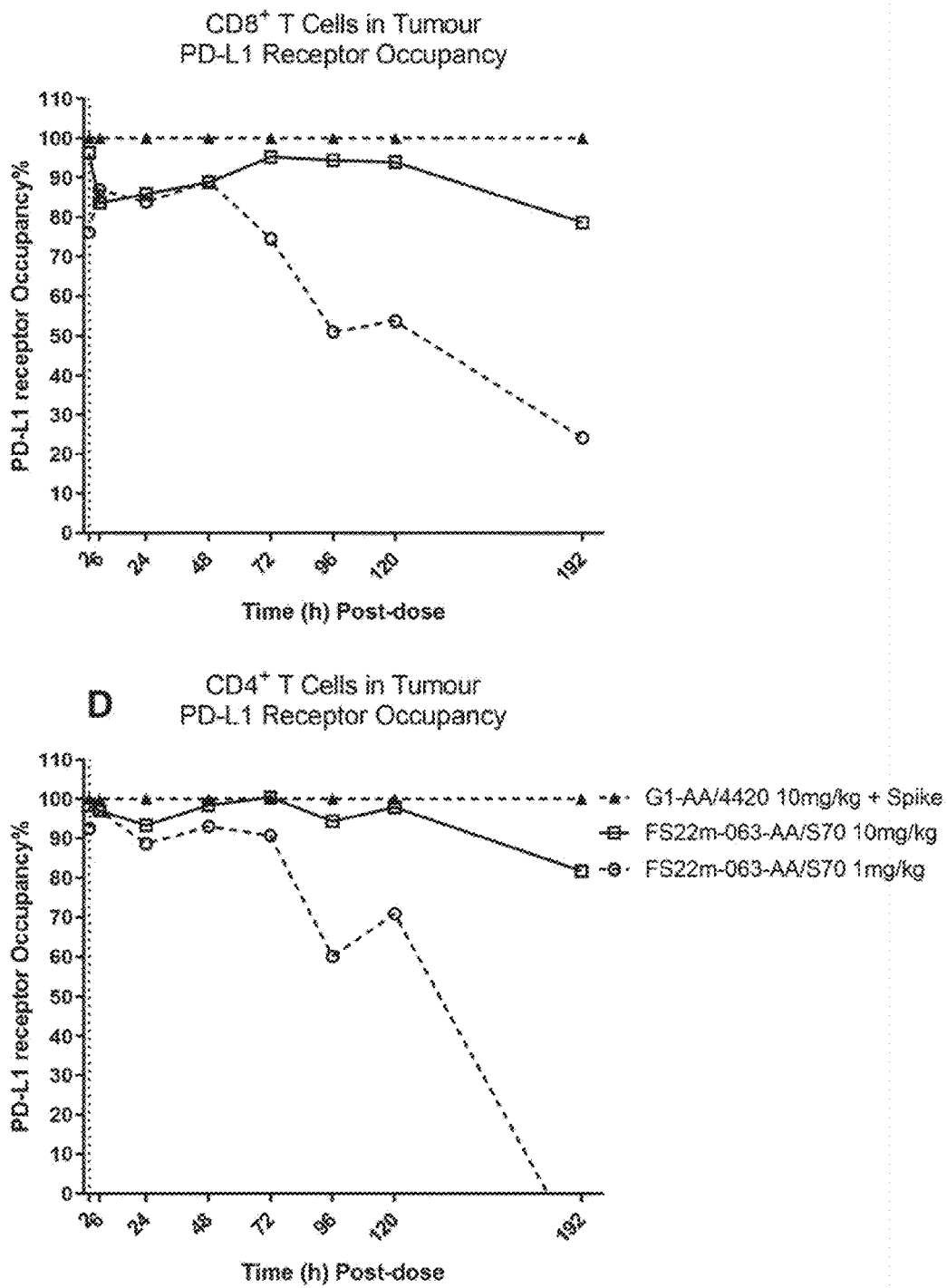

FIG. 26 shows PD-L1 receptor occupancy relative to a time-matched sample from mice dosed with control antibody G1-AA/4420 that was then spiked with 100 nM anti-mCD137/PD-L1 mAb$^2$ ex vivo to saturate all PD-L1 receptors, thus indicating a 100% PD-L1 receptor occupancy level (triangle symbols with dashed line). Free PD-L1 receptors were detected using the Mean Fluorescent Intensity (MFI) values of a competing anti-mPD-L1 antibody conjugated with Bv605. Positive cells that had an MFI greater than that of an unstained control sample were identified as positive for free PD-L1. The results show the positive population as a percentage of PD-L1 receptor occupancy compared to the 100% saturated sample of (A) $CD8^+$ or (B) $CD4^+$ T cells from the blood, or (C) $CD8^+$ or (D) $CD4^+$ T cells from the tumour. These results demonstrate that PD-L1 receptor occupancy reached 100% rapidly in the blood before decreasing in line with dose level over time. PD-L1 receptor occupancy on T cells was maintained longer in the tumour microenvironment than in the blood.

Figure 27:
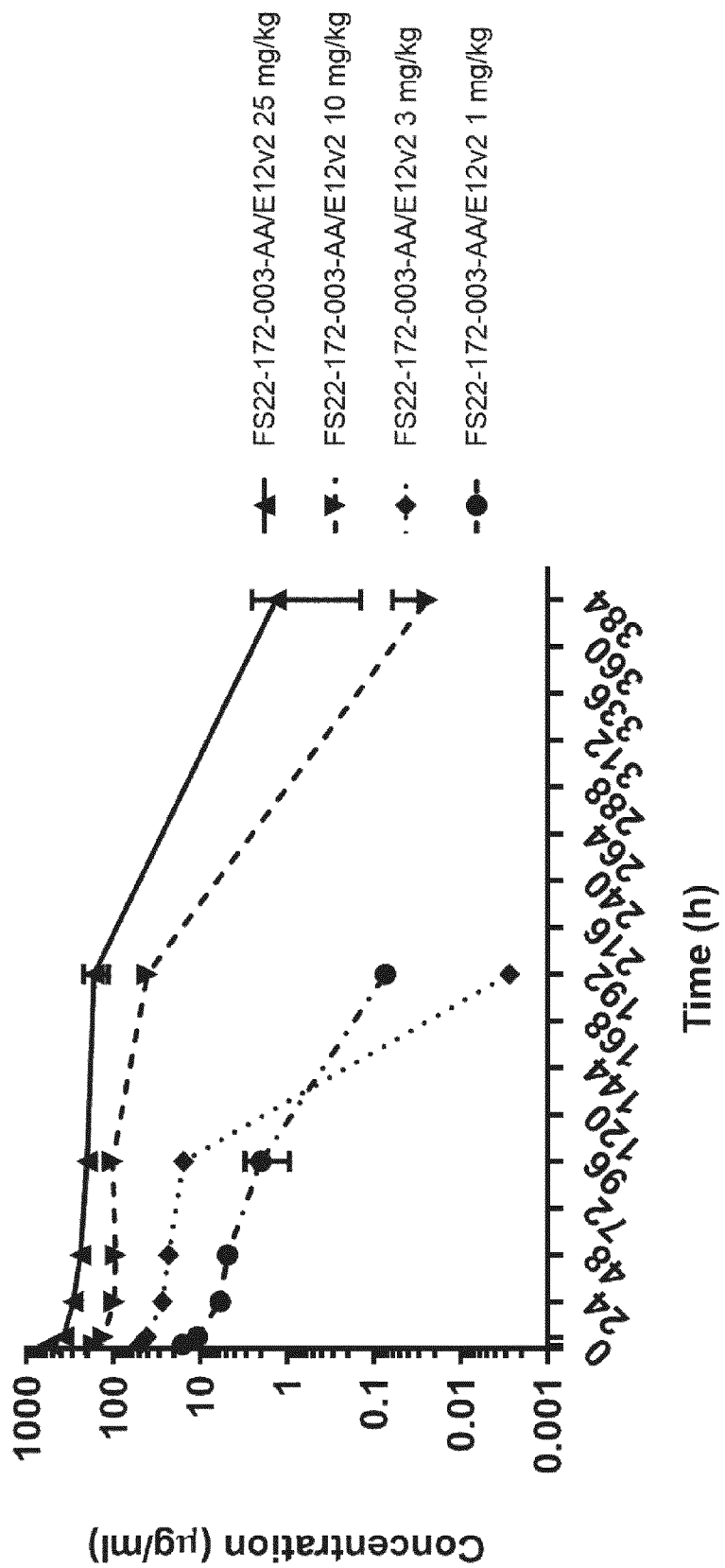

FIG. 27 shows the pharmacokinetic profile of anti-CD137/PD-L1 $mAb^2$ at 25, 10, 3, and 1 mg/kg after a single intravenous single-dose administered to C57BL/6 naïve mice. The concentration of CD137/PD-L1 $mAb^2$ in the mice over time is shown. FIG. 27 demonstrates that the rate of clearance of the anti-CD137/PD-L1 $mAb^2$ at each dose is comparable to clearance of a standard human IgG in mice.

Figure 28:
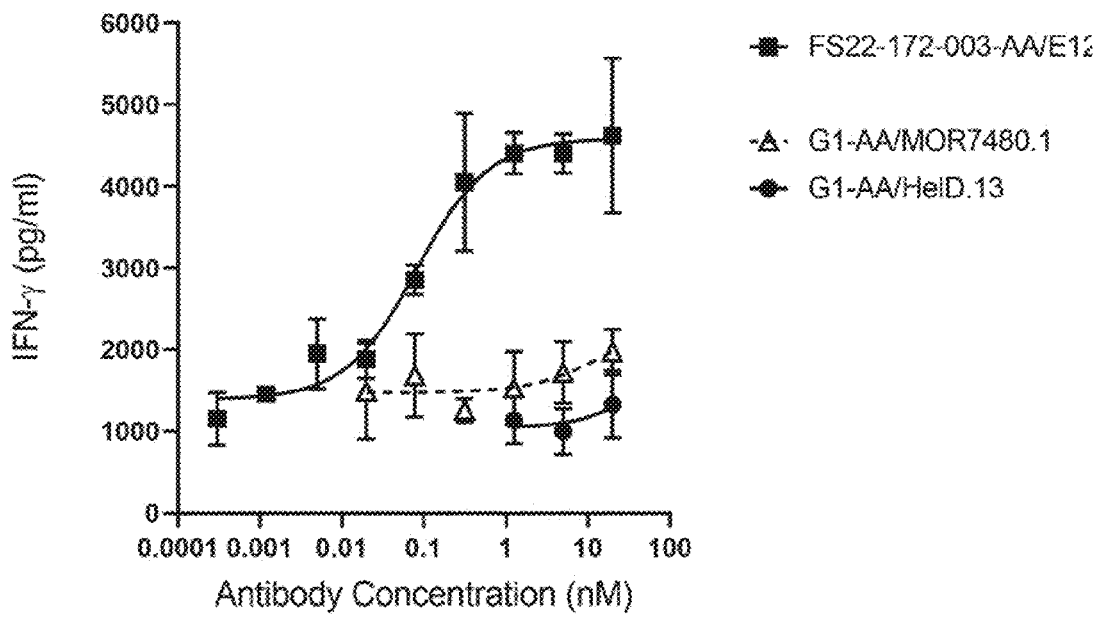
Figure 28:
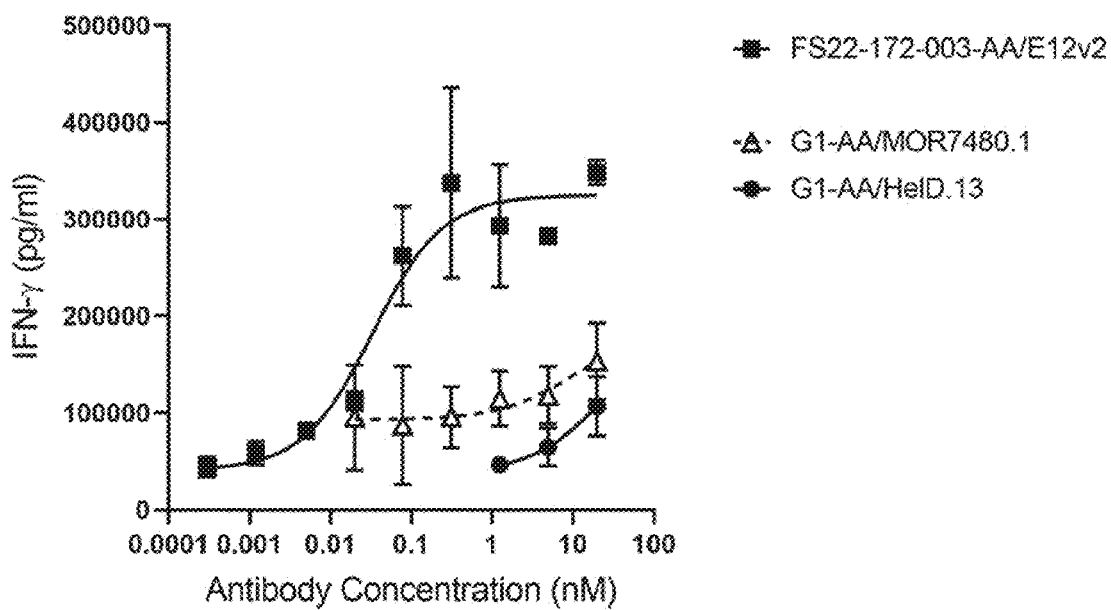

FIG. 28 shows that anti-human CD137/PD-L1 $mAb^2$ FS22-172-003-AA/E12v2 is capable of activating T cells in a PBMC T cell activation assay using (A) cynomolgus monkey PBMCs or (B) human PBMCs. Release of IFN-γ in a PBMC assay was tested in the presence of anti-human CD137/PD-L1 $mAb^2$, anti-human CD137 positive control antibody G1-AA/MOR7480.1 (crosslinked with an anti-human CH2 antibody). The mAb2 showed activity in both assays and showed activation levels higher than the positive control antibody, indicating that PD-L1 blockade and CD137 agonism by the same molecule elicits greater T cell activation, presumably through PD-L1-based clustering and activation of CD137, in both cynomolgus monkey and humans.

DETAILED DESCRIPTION

Aspects and embodiments of the present invention will now be discussed with reference to the accompanying figures. Further aspects and embodiments will be apparent to those skilled in the art. All documents mentioned in this text are incorporated herein by reference.

The present invention relates to antibody molecules which bind both to PD-L1 and CD137. Specifically, the antibody molecules of the present invention comprise a CDR-based antigen-binding site for PD-L1 and a CD137 antigen-binding site located in a constant domain of the antibody molecule. The terms "PD-L1" and "CD137" may refer to human PD-L1 and human CD137, murine PD-L1 and murine CD137, and/or cynomologus monkey PD-L1 and cynomologus monkey CD137, unless the context requires otherwise. Preferably the terms "PD-L1" and "CD137" refer to human PD-L1 and human CD137, unless the context requires otherwise.

The term "antibody molecule" describes an immunoglobulin whether natural or partly or wholly synthetically produced. The antibody molecule may be human or humanised, preferably human. The antibody molecule is preferably a monoclonal antibody molecule. Examples of antibodies are the immunoglobulin isotypes, such as immunoglobulin G, and their isotypic subclasses, such as IgG1, IgG2, IgG3 and IgG4, as well as fragments thereof. The antibody molecule may be isolated, in the sense of being free from contaminants, such as antibodies able to bind other polypeptides and/or serum components.

The term "antibody molecule", as used herein, thus includes antibody fragments, provided said fragments comprise a CDR-based antigen binding site for PD-L1 and a CD137 antigen binding site located in a constant domain. Unless the context requires otherwise, the term "antibody molecule", as used herein, is thus equivalent to "antibody molecule or fragment thereof".

It is possible to take monoclonal and other antibodies and use techniques of recombinant DNA technology to produce other antibodies or chimeric molecules which retain the specificity of the original antibody. Such techniques may involve introducing the CDRs, or variable regions, and/or the constant domain sequences providing the CD137 antigen binding site, into a different immunoglobulin. Introduction of the CDRs of one immunoglobulin into another immunoglobulin is described for example in EP-A-184187, GB 2188638A or EP-A-239400. Similar techniques could be employed for the relevant constant domain sequences. Alternatively, a hybridoma or other cell producing an antibody molecule may be subject to genetic mutation or other changes, which may or may not alter the binding specificity of antibodies produced.

As antibodies can be modified in a number of ways, the term "antibody molecule" should be construed as covering antibody fragments, derivatives, functional equivalents and homologues of antibodies, including any polypeptide comprising an immunoglobulin binding domain, whether natural or wholly or partially synthetic. Chimeric molecules comprising an immunoglobulin binding domain, or equivalent, fused to another polypeptide are therefore included. Cloning and expression of chimeric antibodies are described in EP-A-0120694 and EP-A-0125023.

An example of an antibody fragment comprising both CDR sequences and CH3 domain is a minibody, which comprises an scFv joined to a CH3 domain (Hu et al. (1996), Cancer Res., 56(13):3055-61).

The antibody molecule of the present invention binds to PD-L1 and CD137. Binding in this context may refer to specific binding. The term "specific" may refer to the situation in which the antibody molecule will not show any significant binding to molecules other than its specific binding partner(s), here PD-L1 and CD137. The term "specific" is also applicable where the antibody molecule is specific for particular epitopes, such as epitopes on PD-L1 and CD137, that are carried by a number of antigens in which case the antibody molecule will be able to bind to the various antigens carrying the epitope.

The present inventors demonstrated that antibody molecules described herein showed a high level of specificity for human PD-L1 and did not show any significant binding to other T cells targets PD-L1, CD80, PD-1 or B7-H3. See Example 9.3. Thus, in a preferred embodiment, the antibody molecule does not bind, or does not show any significant binding, to any one of, preferably all of, PD-L2, CD80, PD-1, and B7-H3. The present inventors also demonstrated that the CD137 antigen-binding site did not show any significant binding to the human TNFRSF receptors CD40, OX40 and GITR. See Example 3.6. Thus, in a more preferred embodiment, the antibody molecule does not bind, or does show any significant binding, to any one of, preferably all of, PD-L2, CD80, PD-1, B7-H3, CD40, OX40 and GITR. Antibodies and methods for their construction and use are well-known in the art and are described in, for example, Holliger & Hudson (2005). It is possible to take monoclonal and other antibodies and use techniques of recombinant DNA technology to produce other antibodies or chimeric molecules which retain the specificity of the original antibody. Such techniques may involve introducing CDRs or variable regions of one antibody molecule into a different antibody molecule (EP-A-184187, GB 2188638A and EP-A-239400).

A CDR-based antigen-binding site is an antigen-binding site in an antibody variable region. A CDR-based antigen-binding site, may be formed by three CDRs, such as the three light chain variable domain (VL) CDRs or three heavy chain variable domain (VH) CDRs. Preferably the CDR-based antigen-binding site is formed by six CDRs, three VL CDRs and three VH CDRs. The contributions of the different CDRs to the binding of the antigen may vary in different antigen binding sites.

The three VH domain CDRs of the antigen-binding site may be located within an immunoglobulin VH domain and the three VL domain CDRs may be located within an immunoglobulin VL domain. For example, the CDR-based antigen-binding site may be located in an antibody variable region.

The antibody molecule may have one or preferably more than one, for example two, CDR-based antigen binding sites for the first antigen. The antibody molecule thus may comprise one VH and one VL domain but preferably comprises two VH and two VL domains, i.e. two VHNL domain pairs, as is the case in naturally-occurring IgG molecules, for example.

The CDR-based antigen-binding site may comprise the three VH CDRs or three VL CDRs, preferably the three VH CDRs and the three VL CDRs, of antibody E12v2, E05v2, G12v2, or lam-G02v3, preferably antibody E12v2, E05v2, or G12v2, more preferably E12v2 or E05v2, most preferably E12v2.

The VH and VL domain sequences of these antibodies are set forth as follows:
(i) the VH and VL domain sequences for antibody E12v2 are shown in SEQ ID NOs 12 and 14, respectively;
(ii) the VH and VL domain sequences for antibody E05v2 are shown in SEQ ID NOs 23 and 25, respectively;
(iii) the VH and VL domain sequences for antibody G12v2 are shown in SEQ ID NOs 23 and 30, respectively; and
(iv) the VH and VL domain sequences for antibody lam-G02v3 are shown in SEQ ID NOs 23 and 41, respectively.

The skilled person would have no difficulty in determining the sequences of the CDRs from the VH and VL domain sequences of the antibodies set out above. The CDR sequences may, for example, be determined according to Kabat (Kabat, E. A et al. (1991). Sequences of Proteins of Immunological Interest, 5th edit., NIH Publication no. 91-3242. U.S. Department of Health and Human Services) or the international ImMunoGeneTics information system (IMGT: Lefranc, M.-P. et al. *Nucleic Acids Res.* 43, D413-22 (2015)).

The VH domain CDR1, CDR2 and CDR3 sequences of the antibody molecule according to Kabat numbering may be the sequences at located positions 31-35, 50-65, and 95-102 of the VH domain, respectively.

The VH domain CDR1, CDR2 and CDR3 sequences of the antibody molecule according to IMGT numbering may be the sequences located at positions 27-38, 56-65, and 105-117, of the VH domain of the antibody molecule, respectively.

The VL domain CDR1, CDR2 and CDR3 sequences of the antibody molecule according to Kabat numbering may be the sequences at located positions 24-34, 50-56, and 89-97 of the VL domain, respectively.

The VL domain CDR1, CDR2 and CDR3 sequences of the antibody molecule according to IMGT numbering may be the sequences located at positions 27-38, 56-65, and 105-117, of the VL domain, respectively.

The antibody molecule may comprise the sequence of the VH domain CDR1 of SYGIS (SEQ ID NO: 1), the VH domain CDR2 of WISAYSGGTNYAQKLQG (SEQ ID NO: 2), and the VH domain CDR3 of DLFPTIFGVSYYYY (SEQ ID NO: 3) wherein the CDR sequences are defined according to the Kabat numbering scheme.

In preferred embodiments, the antibody molecule comprises a proline at position 28 according to the Kabat numbering scheme.

The antibody molecule may comprise the sequence of the VH domain CDR1 of GYX$_1$FTSYG (SEQ ID NO: 45), the VH domain CDR2 of ISAYSGGT (SEQ ID NO: 8), and the VH domain CDR3 of ARDLFPTIFGVSYYYY (SEQ ID NO: 9);
wherein X$_1$ is P or T, preferably wherein X$_1$ is P;
and wherein the CDR sequences are defined according to the IMGT numbering scheme.

The antibody molecule may comprise the sequence of the VH domain CDR1, CDR2 and CDR3 of:
(i) SEQ ID NOs 7, 8 and 9, respectively [E12v2]; or
(ii) SEQ ID NOs 21, 8 and 9, respectively [E05v2, G12v2 or lam-G02v3],
wherein the CDR sequences are defined according to the IMGT numbering scheme.

The CDRs of the VH domain may be flanked by framework (FW) sequences (HFW1, HFW2, HFW3 and HFW4). The VH domain may comprise the HFW1, HFW2, HFW3 and HFW4 sequences of SEQ ID NO: 51, 52, 53 and 54, respectively, wherein the FW and CDR sequences are defined according to the Kabat numbering scheme. Alternatively, the VH domain may comprise the HFW1, HFW2, HFW3 and HFW4 sequences of SEQ ID NO: 55, 56, 57 and 54, respectively, wherein the FW and CDR sequences are defined according to the IMGT numbering scheme.

The antibody molecule may comprise the sequence of the VL domain CDR1 of TGTSSDVGGYNYVS (SEQ ID NO: 34), the VL CDR2 of EVTNRPS (SEQ ID NO: 35), and the VL CDR3 of SSFKRGSTLVV (SEQ ID NO: 36); wherein the CDR sequences are defined according to the Kabat numbering scheme. The VL domain may be derived from a lambda VL domain. For example, each of the VL domain CDRs may be flanked by framework (FW) sequences (LFW1, LFW2, LFW3 and LFW4) that are derived from a lambda VL domain. Specifically, the VL domain may comprise the LFW1, LFW2, LFW3 and LFW4 sequences of SEQ ID NO: 65, 66, 67 and 68, respectively, wherein the FW sequences are defined according to the Kabat numbering scheme.

The antibody molecule may comprise the sequence of the VL domain CDR1 of RASQSIX$_2$X$_3$RLA (SEQ ID NO: 46), the VL CDR2 of EASX$_4$X$_5$EX$_6$ (SEQ ID NO: 47), and the VL CDR3 of QQSYSX$_7$PX$_8$X$_9$T (SEQ ID NO: 48);
wherein X$_2$ is S or G, X$_3$ is N or G; X$_4$ is T or N; X$_5$ is S or L; X$_6$ is T or S; X$_7$ is T or W; X$_8$ is absent or R; X$_9$ is Y, R, or V; and
wherein the CDR sequences and position numbering are defined according to the Kabat numbering scheme.

Preferably, the antibody molecule comprises the sequence of the VH domain CDR1 of RASQSIGNRLA (SEQ ID NO: 4), the VL CDR2 of EASTSET (SEQ ID NO: 5), and the VL CDR3 of QQSYSTPYT (SEQ ID NO: 6), wherein the CDR sequences are defined according to the Kabat numbering scheme. The VL domain may be derived from a kappa VL domain. For example, each of the VL domain CDRs may be flanked by framework (FW) sequences (LFW1, LFW2, LFW3 and LFW4) that are derived from a kappa VL domain. Specifically, the VL domain may comprise the LFW1, LFW2, LFW3 and LFW4 sequences of SEQ ID NO: 58, 59, 60 and 61, respectively, wherein the FW sequences are defined according to the Kabat numbering scheme.

For example, the antibody molecule may comprise the sequence of the VL domain CDR1, CDR2 and CDR3 of:
(i) SEQ ID NOs 4, 5 and 6, respectively [E12v2];
(ii) SEQ ID NOs 18, 19 and 20, respectively [E05v2];
(iii) SEQ ID NOs 18, 19 and 29, respectively [G12v2]; or
(iv) SEQ ID NOs 34, 35 and 36, respectively [lam-G02v3],
wherein the CDR sequences are defined according to the Kabat numbering scheme.

The antibody molecule may comprise the sequence of the VL domain CDR1 of SSDVGGYNY (SEQ ID NO: 37), the VL CDR2 of EVT (SEQ ID NO: 38), and the VL CDR3 of SSFKRGSTLVV (SEQ ID NO: 36), wherein the CDR sequences are defined according to the IMGT numbering scheme. The VL domain may be derived from a lambda VL domain. For example, each of the VL domain CDRs may be flanked by framework (FW) sequences (LFW1, LFW2, LFW3 and LFW4) that are derived from a lambda VL domain. Specifically, the VL domain may comprise the LFW1, LFW2, LFW3 and LFW4 sequences of SEQ ID NO: 69, 70, 71 and 68, respectively, wherein the FW sequences are defined according to the IMGT numbering scheme.

Alternatively, the antibody molecule may comprise the sequence of the VL domain CDR1 of $QSIX_{10}X_{11}R$ (SEQ ID NO: 49), the VL CDR2 of EAS (SEQ ID NO: 11), and the VL CDR3 of $QQSYSX_{12}X_{13}X_{14}X_{15}T$ (SEQ ID NO: 50);
wherein $X_{10}$ is G or S; $X_{11}$ is N or G; $X_{12}$ is absent or T; $X_{13}$ is T, W, or P; $X_{14}$ is P or R; $X_{15}$ is Y or R; and
wherein the CDR sequences and position numbering are defined according to the IMGT numbering scheme.

Preferably, the antibody molecule comprises the sequence of the VH domain CDR1 of QSIGNR (SEQ ID NO: 10), the VL CDR2 of EAS (SEQ ID NO: 11), and the VL CDR3 of QQSYSTPYT (SEQ ID NO: 6), wherein the CDR sequences are defined according to the IMGT numbering scheme. The VL domain may be derived from a kappa VL domain. For example, each of the VL domain CDRs may be flanked by framework (FW) sequences (LFW1, LFW2, LFW3 and LFW4) that are derived from a kappa VL domain. Specifically, the VL domain may comprise the LFW1, LFW2, LFW3 and LFW4 sequences of SEQ ID NO: 62, 63, 64 and 61, respectively, wherein the FW sequences are defined according to the IMGT numbering scheme.

For example, the antibody molecule may comprise the sequence of the VL domain CDR1, CDR2 and CDR3 of:
(i) SEQ ID NOs 10, 11 and 6, respectively [E12v2];
(ii) SEQ ID NOs 22, 11 and 20, respectively [E05v2];
(iii) SEQ ID NOs 22, 11 and 29, respectively [G12v2]; or
(iv) SEQ ID NOs 37, 38 and 36, respectively [lam-G02v3],
wherein the CDR sequences are defined according to the IMGT numbering scheme.

The CDR-based antigen-binding site may comprise the VH or VL domains, preferably the VH and VL domains, of antibody E12v2, E05v2, G12v2, or lam-G02v3, preferably antibody E12v2, E05v2, or G12v2, more preferably E12v2 or E05v2, most preferably E12v2.

The VH domain of antibodies E12v2, E05v2, G12v2, and lam-G02v3 may have the sequence set forth in SEQ ID NOs 12, 23, 23, and 23, respectively. The VL domain of antibodies E12v2, E05v2, G12v2, and lam-G02v3 may have the sequence set forth in SEQ ID NOs 14, 25, 30, and 41, respectively.

The antibody molecule of the invention comprises a CD137 antigen-binding site located in the constant domain of the antibody molecule. The constant domain may be a CL, CH1, CH2, CH3, or CH4 domain, preferably the constant domain is a CH1, CH2, or CH3 domain, more preferably a CH2 or CH3 domain, most preferably a CH3 domain. The CD137 antigen-binding site comprises one or more modified structural loops in a constant domain of the antibody molecule. Engineering antibody constant domain structural loops to create antigen-binding sites for target antigens is known in the art and is described, for example, Wozniak-Knopp G et al. (2010); WO20061072620 and WO2009/132876.

The CD137 antigen-binding site of the antibody molecule may comprise a first and second sequence, preferably a first and second sequence, wherein the first and second sequence are located in the AB and EF structural loops of the constant domain, preferably the CH3 domain, of the antibody molecule, respectively.

In a preferred embodiment, the residues at positions 95 and 96 of the CH3 domain of the antibody molecule are wild-type, i.e. are preferably arginine (R) and tryptophan (W), respectively. Both of these residues are located in the EF structural loop. Amino acid residue positions are numbered herein according to the ImMunoGeneTics (IMGT) numbering scheme, unless otherwise indicated. The IMGT numbering scheme is described in Lefranc et al., 2005.

The first sequence preferably comprises the sequence PPY (SEQ ID NO: 78).

The PPY sequence may be located between positions 10 and 19, preferably positions 15 and 17 of the CH3 domain of the antibody molecule. In a preferred embodiment, the PPY sequence is located at positions 16, 16.5 and 16.4 of the CH3 domain. Alternatively, the PPY sequence may be located between positions 16 and 17 of the CH3 domain. In an alternative preferred embodiment, the PPY sequence is located at positions 16.3, 16.2 and 16.1 of the CH3 domain. In the IMGT numbering scheme, inserted residues are numbered according to the direction of the loop in which they are located. If the loop goes "up" the inserted residues take the number of the residue immediately preceding the insertion with the number of the inserted residue in the sequence being indicated by an ascending decimal number, e.g. 16, 16.1, 16.2, 16.3, where there are three mutations following residue 16. If the loop goes "down", the inserted residues take the number of the residue immediately preceding the insertion with the number of the inserted residue in the sequence being indicated by descending decimal number, e.g. 16, 16.3, 16.2, 16.1, where again there are three mutations following residue 16 (LeFranc et al., 2005, and LeFranc et al. 2015).

In a preferred embodiment, the AB structural loop comprises an amino acid insertion. The insertion may be 1 to 10, 2 to 9, 3 to 7, 4 to 6 or 5 amino acids in length. Preferably, the insertion is 5 amino acids in length.

The insertion may be located between positions 10 and 19, preferably between positions 14 and 17, more preferably between positions 16 and 17 of the CH3 domain of the antibody molecule. In a preferred embodiment, the insertion is located at positions 16.5 to 16.1 of the CH3 domain of the antibody molecule. FIG. 1 shows Fcabs comprising a CH3 domain where the insetion is located at postitions 16.5 to 16.1 of the CH3 domain.

The majority of the Fcabs identified following affinity maturation comprised a leucine (L) residue at position 97 of the CH3 domain. Many of these Fcabs also comprised an aspartic acid (D) residue or glutamic acid (E) residue at positions 98 of the CH3 domain. Both of these amino acid changes are located in the EF structural loop. These results suggest that one or both of these residues may be important for CD137 binding. Thus, the second sequence preferably comprises the sequence LD or LE, wherein the LD or LE sequence is preferably located at positions 97 and 98 of the CH3 domain of the antibody molecule.

The first sequence and second sequence may be a first and second sequence of the CH3 domain of: FS22-053-008, FS22-053-009, FS22-053-011, FS22-053-017, FS22-053-014, FS22-053-010, FS22-053-012, FS22-053-013, FS22-053-015, FS22-053-016, FS22-053, preferably FS22-053-008, FS22-053-009, FS22-053-011, FS22-053-017, or FS22-053-014, more preferably FS22-053-008, FS22-053-009, FS22-053-011, or FS22-053-017, yet more preferably specific binding member FS22-053-008.

The first sequence and second sequence may be a first and second sequence of the CH3 domain of: FS22-053-008, FS22-053-009, FS22-053-011, FS22-053-017, FS22-053-014, FS22-053-010, FS22-053-012, FS22-053-013, FS22-053-015, FS22-053-016, FS22-053, FS22-172-003, FS22-172-002, FS22-172-004, FS22-172-001, FS22-172-005, FS22-172-006, or FS22-172, preferably FS22-053-008, FS22-053-009, FS22-053-011, FS22-053-017, FS22-053-014, FS22-172-003, FS22-172-002, FS22-172-004, FS22-172-001, FS22-172-005, or FS22-172-006, more preferably FS22-053-008, FS22-053-009, FS22-053-011, FS22-053-017, FS22-172-003, FS22-172-002, or FS22-172-004, even more preferably FS22-053-008 or FS22-172-003, still more preferably FS22-172-003. In an alternatively preferred embodiment, the first sequence and second sequence may be a first and second sequence of the CH3 domain of FS22-053-017.

The CH3 domain sequence of FS22-053-008, FS22-053-009, FS22-053-011, FS22-053-017, FS22-053-014, FS22-053-010, FS22-053-012, FS22-053-013, FS22-053-015, FS22-053-016, FS22-053, FS22-172-003, FS22-172-002, FS22-172-004, FS22-172-001, FS22-172-005, FS22-172-006, and FS22-172, is set forth in SEQ ID NOs: 81, 84, 87, 90, 93, 96, 99, 102, 105, 108, 111, 115, 118, 121, 124, 127, 130 and 132, respectively.

The first and second sequence of FS22-053-008, FS22-053-009, FS22-053-011, FS22-053-017, FS22-053-014, FS22-053-010, FS22-053-012, FS22-053-013, FS22-053-015, FS22-053-016, FS22-053, FS22-172-003, FS22-172-002, FS22-172-004, FS22-172-001, FS22-172-005, FS22-172-006, and FS22-172 may be the sequence between positions 14 and 17, and positions 91 and 99, of the CH3 domain of FS22-053-008, FS22-053-009, FS22-053-011, FS22-053-017, FS22-053-014, FS22-053-010, FS22-053-012, FS22-053-013, FS22-053-015, FS22-053-016, FS22-053, FS22-172-003, FS22-172-002, FS22-172-004, FS22-172-001, FS22-172-005, FS22-172-006, and FS22-172, respectively.

Alternatively, the first and second sequence of FS22-053-008, FS22-053-010, FS22-053-011, FS22-053-012, and FS22-053-016 may be the sequence between positions 14 and 17, and positions 92 and 99, of the CH3 domain of FS22-053-008, FS22-053-010, FS22-053-011, FS22-053-012, and FS22-053-016, respectively.

The first and second sequence of FS22-053-015 may alternatively be the sequence between positions 14 and 17, and positions 92 and 98, of the CH3 domain of FS22-053-015, respectively.

The CD loop sequence of the antibody molecule is preferably unmodified, i.e. wild type. The CD loop sequence therefore preferably has the sequence set forth in SEQ ID NO: 73. The CD loop sequence is preferably located at positions 43 to 78 of the CH3 domain.

The first and second sequences may be the complete AB and EF structural loop sequences, of FS22-053-008, FS22-053-009, FS22-053-011, FS22-053-017, FS22-053-014, FS22-053-010, FS22-053-012, FS22-053-013, FS22-053-015, FS22-053-016, FS22-053, FS22-172-003, FS22-172-002, FS22-172-004, FS22-172-001, FS22-172-005, FS22-172-006, or FS22-172, respectively. Determination of the location of the AB, CD, and EF structural loops in a CH3 domain sequence, for example in accordance with the IMGT, IMGT exon, EU, or Kabat numbering systems, is within the capabilities of the skilled person and described in Hasenhindl et al. (2013). In a preferred embodiment, the AB, CD and EF structural loops according to the IMGT numbering system are located between positions 10 and 19, 42 and 79, and 91 and 102 of the CH3 domain, respectively. In a preferred embodiment, the first, second and third sequence are therefore the sequence between positions 10 and 19, 42 and 79, and 91 and 102 of the CH3 domain of FS22-053-008, FS22-053-009, FS22-053-011, FS22-053-017, FS22-053-014, FS22-053-010, FS22-053-012, FS22-053-013, FS22-053-015, FS22-053-016, FS22-053, FS22-172-003, FS22-172-002, FS22-172-004, FS22-172-001, FS22-172-005, FS22-172-006, or FS22-172, respectively.

Thus, in one preferred embodiment, the first and second sequence of the CD137 antigen-binding site comprise the AB and EF loop sequence set forth in SEQ ID NOs 171 and 172 [FS22-172-003], respectively, or the AB and EF structural loop sequence set forth in SEQ ID NOs 173 and 174 [FS22-53-008], respectively. In a more preferred embodiment, the first and second sequence of the CD137 antigen-binding site comprise the AB and EF structural loop set forth in SEQ ID NOs 171 and 172 [FS22-172-003], respectively.

In an alternatively preferred embodiment, the first and second sequence of the CD137 antigen-binding site comprise the AB and EF structural loop sequence set forth in SEQ ID NOs 173 and 175 [FS22-053-017], respectively.

In a preferred embodiment, the CD137 antigen-binding site comprises a first and/or second, preferably the first and second sequence set forth in:

(i) SEQ ID NOs 79 and 80, respectively [FS22-053-008];
(ii) SEQ ID NOs 79 and 83, respectively [FS22-053-009];
(iii) SEQ ID NOs 79 and 86, respectively [FS22-053-011];
(iv) SEQ ID NOs 79 and 89, respectively [FS22-053-017];
(v) SEQ ID NOs 79 and 92, respectively [FS22-053-014];
(vi) SEQ ID NOs 79 and 95, respectively [FS22-053-010];
(vii) SEQ ID NOs 79 and 98, respectively [FS22-053-012];
(viii) SEQ ID NOs 79 and 101, respectively [FS22-053-013];
(ix) SEQ ID NOs 79 and 104, respectively [FS22-053-015];
(x) SEQ ID NOs 79 and 107, respectively [FS22-053-016];
(xi) SEQ ID NOs 79 and 110, respectively [FS22-053];

(xii) SEQ ID NOs 113 and 114, respectively [FS22-172-003];
(xiii) SEQ ID NOs 117 and 114, respectively [FS22-172-002];
(xiv) SEQ ID NOs 120 and 114, respectively [FS22-172-004];
(xv) SEQ ID NOs 123 and 114, respectively [FS22-172-001];
(xvi) SEQ ID NOs 126 and 114, respectively [FS22-172-005];
(xvii) SEQ ID NOs 129 and 114, respectively [FS22-172-006]; or
(xviii) SEQ ID NOs 129 and 114, respectively [FS22-172]; wherein the first and second sequence are preferably located between positions 14 and 17, and 91 and 99 of the CH3 domain of the antibody molecule, respectively.

In a yet more preferred embodiment, the antibody molecule comprises the first and/or second, preferably the first and second sequence set forth in:
(i) SEQ ID NOs 79 and 80, respectively [FS22-053-008];
(ii) SEQ ID NOs 79 and 83, respectively [FS22-053-009];
(iii) SEQ ID NOs 79 and 86, respectively [FS22-053-011];
(iv) SEQ ID NOs 79 and 89, respectively [FS22-053-017];
(v) SEQ ID NOs 113 and 114, respectively [FS22-172-003];
(vi) SEQ ID NOs 117 and 114, respectively [FS22-172-002]; or
(vii) SEQ ID NOs 120 and 114, respectively [FS22-172-004].

In an even more preferred embodiment, the CD137 antigen-binding site of the antibody molecule comprises the first and second sequence set forth in SEQ ID NOs 113 and 114 [FS22-172-003], respectively, or the first and second sequence set forth in SEQ ID NOs 79 and 80 [FS22-53-008], respectively. In a still more preferred embodiment, the CD137 antigen-binding site of the antibody molecule comprises the first and second sequence set forth in SEQ ID NOs 113 and 114 [FS22-172-003], respectively. For example, the CD137 antigen-binding site may comprise the AB and EF structural loop sequences set forth in SEQ ID NOs 171 and 172 [FS22-172-003], respectively.

In an embodiment, the antibody molecule, in particular an antibody molecule comprising the first and/or second, preferably the first and second, sequence set forth in SEQ ID NO: 129 and 114 [FS22-172-006], may comprise a leucine (L) at position 19 of the CH3 domain of the antibody molecule.

As an alternative to IMGT numbering, amino acid residue positions, including the position of amino acid sequences, substitutions, deletions and insertions as described herein, may be numbered according to IMGT exon numbering (also referred to as consecutive numbering), EU numbering, or Kabat numbering. The concordance between IMGT numbering, IMGT exon numbering, EU numbering, and Kabat numbering of the residue positions of the CH3 domain are shown in FIG. 1. Thus, for example, where the present application refers to the first sequence being located between positions 14 and 17 of the CH3 domain of the clone, respectively, where the residue positions are numbered in accordance with the IMGT numbering scheme, the first sequence is located between positions 18 and 21 of the CH3 domain, where the residue positions are numbered in accordance with the IMGT exon numbering scheme, as shown in FIG. 1. Alternatively, the position of amino acid residues in the CH3 domain, including the position of amino acid sequences, substitutions, deletions and insertions in the CH3 domain, as described herein, may be defined by reference to their position in the wild-type CH3 domain sequence set forth in SEQ ID NO: 75. The concordance between IMGT numbering and the wild-type CH3 domain sequence is also shown in FIG. 1.

In one embodiment, the antibody molecule comprises a CH3 domain which comprises, has, or consists of the CH3 domain sequence of FS22-053-008, FS22-053-009, FS22-053-011, FS22-053-017, FS22-053-014, FS22-053-010, FS22-053-012, FS22-053-013, FS22-053-015, FS22-053-016, FS22-053, FS22-172-003, FS22-172-002, FS22-172-004, FS22-172-001, FS22-172-005, FS22-172-006, or FS22-172, wherein the CH3 domain sequence of FS22-053-008, FS22-053-009, FS22-053-011, FS22-053-017, FS22-053-014, FS22-053-010, FS22-053-012, FS22-053-013, FS22-053-015, FS22-053-016, FS22-053, FS22-172-003, FS22-172-002, FS22-172-004, FS22-172-001, FS22-172-005, FS22-172-006, and FS22-172 is set forth in SEQ ID NOs 81, 84, 87, 90, 93, 96, 99, 102, 105, 108, 111, 115, 118, 121, 124, 127, 130 and 132, respectively.

In a preferred embodiment, the antibody molecule comprises a CH3 domain which comprises, has, or consists of the CH3 domain sequence of FS22-172-003 or FS22-053-008 set forth in SEQ ID NO 115 and 81, respectively. In a more preferred embodiment, the antibody molecule comprises a CH3 domain which comprises, has, or consists of the CH3 domain sequence of FS22-172-003 set forth in SEQ ID NO 115.

In an alternatively preferred embodiment, the antibody molecule comprises a CH3 domain which comprises, has, or consists of the CH3 domain sequence of FS22-053-017 set forth in SEQ ID NO 90, respectively.

The CH3 domain of the antibody molecule may optionally comprise an additional lysine residue (K) at the immediate C-terminus of the CH3 domain sequence.

In addition, the antibody molecule of the invention may comprise a CH2 domain of an immunoglobulin G molecule, such as a CH2 domain of an IgG1, IgG2, IgG3, or IgG4 molecule. Preferably the antibody molecule of the invention comprises a CH2 domain of an IgG1 molecule. The CH2 domain may have the sequence set forth in SEQ ID NO: 76.

The CH2 domain is known bind to Fcγ receptors and complement. Binding of the CH2 domain to Fcγ receptors is required antibody-dependent cell-mediated cytotoxicity (ADCC), while binding to complement is required complement-dependent cytotoxicity (CDC). The CH2 domain of the antibody molecule preferably comprise one or more mutations that reduce or abrogate binding of the CH2 domain to one or more Fcγ receptors, such as FcγRI, FcγRIIa, FcγRIIb, FcγRIII, and/or to complement. The inventors postulate that reducing or abrogating binding to Fcγ receptors will decrease or eliminate ADCC mediated by the antibody molecule. Similarly, reducing or abrogating binding to complement is expected to reduce or eliminate CDC mediated by the antibody molecule. Without wishing to be bound by theory, this is expected to reduce or avoid liver toxicity when the antibody molecule is administered to a patient. In addition, reducing or abrogating binding to Fcγ receptors is expected to be useful where the antibody molecule comprises a second antigen-binding site for an immune cell antigen, where ADCC and/or CDC-mediated killing of immune cells bound by the antibody molecule should be avoided. Mutations to decrease or abrogate binding of the CH2 domain to one or more Fcγ receptors and/or complement are known in the art (Wang et al., 2018). These mutations include the "LALA mutation" described in Bruhns et al., 2009 and Hezareh et al., 2001, which involves substitution of the leucine residues at positions 1.3 and 1.2 of the CH2 domain with alanine (L1.3A and L1.2A). Alternatively, the generation of a-glycosyl antibodies through mutation of the conserved N-linked glycosylation site by mutating the aparagine (N) at position 84.4 of the CH2 domain to alanine, glycine or glutamine (N84.4A, N84.4G or N84.4Q) is also known to decrease IgG1 effector function (Wang et al., 2018). As a further alternative, complement activation (C1q binding) and ADCC are known to be reduced through mutation of the proline at position 114 of the CH2 domain to alanine or glycine (P114A or P114G) (Idusogie et al., 2000; Klein et al., 2016). These mutations may also be combined in order to generate antibody molecules with further reduced or no ADCC or CDC activity.

Thus, the antibody molecule may comprise a CH2 domain, wherein the CH2 domain preferably comprises:
(i) alanine residues at positions 1.3 and 1.2; and/or
(ii) an alanine or glycine at position 114; and/or
(iii) an alanine, glutamine or glycine at position 84.4;
wherein the amino acid residue numbering is according to the IMGT numbering scheme.

In a preferred embodiment, the antibody molecule comprises a CH2 domain, wherein the CH2 domain comprises:
(i) an alanine residue at position 1.3; and
(ii) an alanine residue at position 1.2;
wherein the amino acid residue numbering is according to the IMGT numbering scheme.

For example, the CH2 domain may have the sequence set forth in SEQ ID NO: 77.

In an alternative preferred embodiment, the antibody molecule comprises a CH2 domain, wherein the CH2 domain comprises:
(i) an alanine residue at position 1.3;
(ii) an alanine residue at position 1.2; and
(iii) an alanine at position 114;
wherein the amino acid residue numbering is according to the IMGT numbering scheme.

For example, the CH2 domain may have the sequence set forth in SEQ ID NO: 176.

In a preferred embodiment, the antibody molecule that binds to PD-L1 and CD137 comprises
(a) a CDR-based antigen-binding site for PD-L1; and
(b) a CD137 antigen-binding site located in a CH3 domain of the antibody molecule;
wherein the CDR-based antigen-binding site comprises the three VH CDRs and three VL CDRs (CDRs 1-6) of antibody E12v2, E05v2, or G12v2, preferably E12v2; and
wherein the CD137 antigen-binding site comprises a first sequence and a second sequence located in the AB and EF structural loops of the CH3 domain, respectively; wherein the first and second sequence have the sequence set forth in SEQ ID NOs 113 and 114 [FS22-172-003], or 79 and 80 [FS22-53-008], respectively, preferably wherein the first and second sequence have the sequence set forth in SEQ ID NOs 113 and 114 [FS22-172-003].

As described in the Examples, an antibody molecule having a CD137 antigen-binding site comprising the first sequence and a second sequence set forth in SEQ ID NOs 79 and 89, respectively [FS22-053-017] was able to bind human, cynomolgus and, unexpectedly, mouse CD137. The inventors demonstrated that this antibody molecule had activity in human, cynomolgus and mouse T cell activation assays when crosslinked.

In an alternatively preferred embodiment, the antibody molecule that binds to PD-L1 and CD137 comprises
(a) a CDR-based antigen-binding site for PD-L1; and
(b) a CD137 antigen-binding site located in a CH3 domain of the antibody molecule;
wherein the CDR-based antigen-binding site comprises the three VH CDRs and three VL CDRs (CDRs 1-6) of antibody E12v2, E05v2, or G12v2, preferably E12v2; and
wherein the CD137 antigen-binding site comprises a first sequence and a second sequence located in the AB and EF structural loops of the CH3 domain, respectively, wherein the first and second sequence have the sequence set forth in SEQ ID NOs 79 and 89 [FS22-053-017].

In some embodiments, the antibody molecule comprises
(a) a CDR-based antigen-binding site for PD-L1; and
(b) a CD137 antigen-binding site located in a CH3 domain of the antibody molecule;
wherein the wherein the CDR-based antigen-binding site comprises the three VH CDRs and three VL CDRs (CDRs 1-6) of antibody E12v2, E05v2, or G12v2, preferably E12v2; and
wherein the CD137 antigen-binding site comprises a first sequence and a second sequence located in the AB and EF structural loops of the CH3 domain, respectively, wherein the first and second sequence have the sequence set forth in SEQ ID NOs 113 and 114 [FS22-172-003], or 79 and 80 [FS22-53-008], respectively, preferably wherein the first and second sequence have the sequence set forth in SEQ ID NOs 113 and 114 [FS22-172-003], with the proviso that the antibody molecule does not comprise the CDRs 1-6 of antibody G12v2 paired with the CD137 antigen-binding site having the first and second sequence set forth in in SEQ ID NOs 79 and 80 [FS22-053-008].

In a further preferred embodiment, the antibody molecule that binds to PD-L1 and CD137 comprises
(a) a CDR-based antigen-binding site for PD-L1; and
(b) a CH3 domain which comprises, has, or consists of the sequence set forth in SEQ ID NOs 115 [FS22-172-003], or 81 [FS22-53-008], preferably SEQ ID NO 115 [FS22-172-003];
wherein the CDR-based antigen-binding site comprises the three VH CDRs and three VL CDRs (CDRs 1-6) of antibody E12v2, E05v2, or G12v2, preferably E12v2.

In a further alternatively preferred embodiment, the antibody molecule that binds to PD-L1 and CD137 comprises
(a) a CDR-based antigen-binding site for PD-L1; and
(b) a CH3 domain which comprises, has, or consists of the sequence set forth in SEQ ID NOs 90 [FS22-053-017];
wherein the CDR-based antigen-binding site comprises the three VH CDRs and three VL CDRs (CDRs 1-6) of antibody E12v2, E05v2, or G12v2, preferably E12v2.

In a yet further preferred embodiment, the antibody molecule that binds to PD-L1 and CD137 comprises
(a) a VH domain and a VL domain comprising the CDR-based antigen binding site for PD-L1; and
(b) a CH3 domain which comprises, has, or consists of the sequence set forth in SEQ ID NOs 115 [FS22-172-003], or 81 [FS22-53-008], preferably SEQ ID NO 115 [FS22-172-003];
wherein the VH and VL domain comprises, has, or consists of the VH and VL of antibody E12v2, E05v2, or G12v2, preferably E12v2.

In a yet further alternatively preferred embodiment, the antibody molecule that binds to PD-L1 and CD137 comprises
   (a) a VH domain and a VL domain comprising the CDR-based antigen binding site for PD-L1; and
   (b) a CH3 domain which comprises, has, or consists of the sequence set forth in SEQ ID NOs 90 [FS22-053-017];
   wherein the VH and VL domain comprises, has, or consists of the VH and VL of antibody E12v2, E05v2, or G12v2, preferably E12v2.

In a still further preferred embodiment, the antibody molecule that binds to PD-L1 and CD137 comprises—
   (a) a VH domain and a VL domain comprising the CDR-based antigen binding site for PD-L1;
   (b) a CH3 domain which comprises, has, or consists of the sequence set forth in SEQ ID NOs 115 [FS22-172-003], or 81 [FS22-53-008], preferably SEQ ID NO 115 [FS22-172-003];
   (c) a CH2 domain which comprises, has or consists of the sequence set forth in SEQ ID NO: 76, wherein the CH2 domain comprises:
      (i) an alanine residue at position 1.3;
      (ii) an alanine residue at position 1.2;
      wherein the amino acid residue numbering is according to the IMGT numbering scheme; and
   wherein the VH and VL domain comprises, has, or consists of the VH and VL of antibody E12v2, E05v2, or G12v2, preferably E12v2.

In a further embodiment, the antibody molecule the antibody molecule that binds to PD-L1 and CD137 comprises:
   (a) a VH and VL domain comprising a CDR-based antigen-binding site for PD-L1, wherein the CDR-based antigen-binding site comprises CDRs 1-6; and
   (b) a CD137 antigen-binding site located in a CH3 domain of the antibody molecule, the CD137 antigen binding site comprising a first sequence and a second sequence located in the AB and EF structural loops of the CH3 domain;
wherein the CDRs 1-6, first sequence and second sequence have the sequence set forth in:
(i) SEQ ID NOs 1, 2, 3, 4, 5, 6, 113 and 114, respectively [FS22-172-003-AA/E12v2];
(ii) SEQ ID NOs 1, 2, 3, 18, 19, 20, 113 and 114, respectively [FS22-172-003-AA/E05v2];
(iii) SEQ ID NOs 1, 2, 3, 18, 19, 29, 113 and 114, respectively [FS22-172-003-AA/G12v2];
(iv) SEQ ID NOs 1, 2, 3, 4, 5, 6, 79 and 80, respectively [FS22-053-008-AA/E12v2]; or
(v) SEQ ID NOs 1, 2, 3, 18, 19, 20, 79 and 80, respectively [FS22-053-008-AA/E05v2], or
wherein the VH domain, VL domain, first sequence and second sequence have the sequence set forth in:
(i) SEQ ID NOs 12, 14, 113 and 114, respectively [FS22-172-003-AA/E12v2];
(ii) SEQ ID NOs 23, 25, 113 and 114, respectively [FS22-172-003-AA/E05v2];
(iii) SEQ ID NOs 23, 30, 113 and 114, respectively [FS22-172-003-AA/G12v2];
(iv) SEQ ID NOs 12, 14, 79 and 80, respectively [FS22-053-008-AA/E12v2]; or
(v) SEQ ID NOs 23, 25, 79 and 80, respectively [FS22-053-008-AA/E05v2]; or
wherein the VH domain, VL domain, and CH3 domain have the sequence set forth in:
(i) SEQ ID NOs 12, 14, and 115, respectively [FS22-172-003-AA/E12v2];
(ii) SEQ ID NOs 23, 25, and 115, respectively [FS22-172-003-AA/E05v2];
(iii) SEQ ID NOs 23, 30, and 115, respectively [FS22-172-003-AA/G12v2];
(iv) SEQ ID NOs 12, 14, and 81, respectively [FS22-053-008-AA/E12v2]; or
(v) SEQ ID NOs 23, 25, and 81, respectively [FS22-053-008-AA/E05v2].

In a yet further preferred embodiment, the antibody molecule that binds to PD-L1 and CD137 comprises a heavy chain which comprises, has, or consists of the heavy chain and light chain of antibody:
   (i) FS22-172-003-AA/E12v2 set forth in SEQ ID NOs 134 and 17, respectively;
   (ii) FS22-172-003-AA/E05v2 set forth in SEQ ID NOs 137 and 28, respectively;
   (iii) FS22-172-003-AA/G12v2 set forth in SEQ ID NOs 140 and 33, respectively;
   (iv) FS22-053-008-AA/E12v2 set forth in SEQ ID NOs 143 and 17, respectively;
   (v) FS22-053-008-AA/E05v2 set forth in SEQ ID NOs 146 and 28, respectively; or
   (vi) FS22-053-008-AA/G12v2 set forth in SEQ ID NOs 149 and 33, respectively.

In an even more preferred embodiment, the antibody molecule that binds to PD-L1 and CD137 comprises a heavy chain which comprises, has, or consists of the heavy chain and light chain of antibody:
   (i) FS22-172-003-AA/E12v2 set forth in SEQ ID NOs 134 and 17, respectively;
   (ii) FS22-172-003-AA/E05v2 set forth in SEQ ID NOs 137 and 28, respectively;
   (iii) FS22-172-003-AA/G12v2 set forth in SEQ ID NOs 140 and 33, respectively;
   (iv) FS22-053-008-AA/E12v2 set forth in SEQ ID NOs 143 and 17, respectively; or
   (v) FS22-053-008-AA/E05v2 set forth in SEQ ID NOs 146 and 28, respectively.

In a still more preferred embodiment, the antibody molecule that binds to PD-L1 and CD137 comprises a heavy chain which comprises, has, or consists of the heavy chain and light chain of antibody:
   (i) FS22-172-003-AA/E12v2 set forth in SEQ ID NOs 134 and 17, respectively; or
   (iv) FS22-053-008-AA/E12v2 set forth in SEQ ID NOs 143 and 17, respectively.

In a yet still more preferred embodiment, the antibody molecule that binds to PD-L1 and CD137 comprises a heavy chain which comprises, has, or consists of the heavy chain and light chain of antibody FS22-172-003-AAIE12v2 set forth in SEQ ID NOs 134 and 17, respectively.

In a yet further alternatively preferred embodiment, the antibody molecule that binds to PD-L1 and CD137 comprises a heavy chain which comprises, has, or consists of the heavy chain and light chain of antibody:
   (i) FS22-053-017-AA/E12v2 set forth in SEQ ID NOs 152 and 17, respectively;
   (ii) FS22-053-017-AA/E05v2 set forth in SEQ ID NOs 153 and 28, respectively; or
   (iii) FS22-053-017-AA/G12v2 set forth in SEQ ID NOs 154 and 33, respectively.

The antibody molecules of the present invention may also comprise variants of a first, second or third sequence, AB, CD or EF structural loop sequence, CH3 domain, CH2 domain, CH2 and CH3 domain, CDR, FW, VH domain, VL domain, light chain and/or heavy chain sequences disclosed herein. Suitable variants can be obtained by means of methods of sequence alteration, or mutation, and screening. In a preferred embodiment, an antibody molecule comprising one or more variant sequences retains one or more of the functional characteristics of the parent antibody molecule, such as binding specificity and/or binding affinity for PD-L1 and CD137. For example, an antibody molecule comprising one or more variant sequences preferably binds to PD-L1 and/or CD137 with the same affinity, or a higher affinity, than the (parent) antibody molecule. The parent antibody molecule is an antibody molecule which does not comprise the amino acid substitution(s), deletion(s), and/or insertion(s) which have been incorporated into the variant antibody molecule.

For example, an antibody molecule of the invention may comprise a first, second or third sequence, AB, CD or EF structural loop sequence, CH3 domain, CH2 domain, CH2 and CH3 domain, CDR, FW, VH domain, VL domain, light chain and/or heavy chain sequence which has at least 70%, at least 75%, at least 80%, at least 85%, at least 90%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, or at least 99.9% sequence identity to a structural loop, CH3 domain, CH2 domain, CH2 and CH3 domain, CDR, FW, VH domain, VL domain, light chain or heavy chain sequence disclosed herein.

In a preferred embodiment, the antibody molecule of the invention comprises a CH3 domain sequence which has at least 97%, at least 98%, at least 99%, at least 99.1%, at least 99.2%, at least 99.3%, at least 99.4%, at least 99.5%, at least 99.6%, at least 99.7%, at least 99.8%, or at least 99.9% sequence identity to the CH3 domain sequence set forth in SEQ ID NO: 115 [FS22-172-003] or 81 [FS22-053-008], preferably SEQ ID NO: 115 [FS22-172-003].

In a further preferred embodiment, the antibody molecule has or comprises a CH2 domain sequence, which has at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, or at least 99.9% sequence identity to the CH2 domain sequence set forth in SEQ ID NO: 76 or 77.

Sequence identity is commonly defined with reference to the algorithm GAP (Wisconsin GCG package, Accelerys Inc, San Diego USA). GAP uses the Needleman and Wunsch algorithm to align two complete sequences, maximising the number of matches and minimising the number of gaps. Generally, default parameters are used, with a gap creation penalty equalling 12 and a gap extension penalty equalling 4. Use of GAP may be preferred but other algorithms may be used, e.g. BLAST (which uses the method of Altschul et al., 1990), FASTA (which uses the method of Pearson and Lipman, 1988), or the Smith-Waterman algorithm (Smith and Waterman, 1981), or the TBLASTN program, of Altschul et al., 1990 supra, generally employing default parameters. In particular, the psi-Blast algorithm (Altschul et al., 1997) may be used.

An antibody molecule of the invention may also comprise a first, second or third sequence, AB, CD or EF structural loop sequence, CH3 domain, CH2 domain, CH2 and CH3 domain, CDR, FW, VH domain, VL domain, light chain and/or heavy chain which has one or more amino acid sequence alterations (addition, deletion, substitution and/or insertion of an amino acid residue), preferably 20 alterations or fewer, 15 alterations or fewer, 10 alterations or fewer, 5 alterations or fewer, 4 alterations or fewer, 3 alterations or fewer, 2 alterations or fewer, or 1 alteration compared with a first, second or third sequence, AB, CD or EF structural loop sequence, CH3 domain, CH2 domain, CH2 and CH3 domain, CDR, FW, VH domain, VL domain, light chain or heavy chain sequence disclosed herein. In particular, alterations may be made in one or more framework regions of the antibody molecule outside the VH and VL domain sequences and/or in one or more framework regions of the CH3 domain. For example, the alterations may be in the CH3 domain outside of the sequences described herein as a first, second and third sequences, or as AB, CD or EF structural loop sequences.

In a preferred embodiment, the antibody molecule of the invention may comprise a CH3 domain sequence with one or more amino acid sequence alterations (addition, deletion, substitution and/or insertion of an amino acid residue), preferably 20 alterations or fewer, 15 alterations or fewer, 10 alterations or fewer, 5 alterations or fewer, 4 alterations or fewer, 3 alterations or fewer, 2 alterations or fewer, or 1 alteration compared with the CH3 domain sequence set forth in SEQ ID NOs 81, 84, 87, 90, 93, 96, 99, 102, 105, 108, 111, 115, 118, 121, 124, 127, 130, or 132. In a more preferred embodiment, the antibody molecule of the invention may comprise a CH3 domain sequence with one or more amino acid sequence alterations (addition, deletion, substitution and/or insertion of an amino acid residue), preferably 20 alterations or fewer, 15 alterations or fewer, 10 alterations or fewer, 5 alterations or fewer, 4 alterations or fewer, 3 alterations or fewer, 2 alterations or fewer, or 1 alteration compared with the CH3 domain sequence set forth in SEQ ID NOs: 115 [FS22-172-003] or 81 [FS22-053-008], preferably SEQ ID NO: 115 [FS22-172-003].

In a further preferred embodiment, the antibody molecule comprises a CH2 domain sequence, with one or more amino acid sequence alterations (addition, deletion, substitution and/or insertion of an amino acid residue), preferably 20 alterations or fewer, 15 alterations or fewer, 10 alterations or fewer, 5 alterations or fewer, 4 alterations or fewer, 3 alterations or fewer, 2 alterations or fewer, or 1 alteration compared with the CH2 domain sequence set forth in SEQ ID NO: 76 or 77.

In preferred embodiments in which one or more amino acids are substituted with another amino acid, the substitutions may conservative substitutions, for example according to the following Table. In some embodiments, amino acids in the same category in the middle column are substituted for one another, i.e. a non-polar amino acid is substituted with another non-polar amino acid for example. In some embodiments, amino acids in the same line in the rightmost column are substituted for one another.

| ALIPHATIC | Non-polar | G A P |
| | | I L V |
| | Polar-uncharged | C S T M |
| | | N Q |
| | Polar-charged | D E |
| | | K R |
| AROMATIC | | H F W Y |

In some embodiments, substitution(s) may be functionally conservative. That is, in some embodiments the substitution may not affect (or may not substantially affect) one or more functional properties (e.g. binding affinity) of the antibody molecule comprising the substitution as compared to the equivalent unsubstituted antibody molecule.

Where the antibody molecule comprises a variant of a first sequence, AB structural loop sequence, CH3 domain, or heavy chain sequence as disclosed herein, the antibody molecule preferably retains the sequence PPY between positions 11 and 19, preferably positions 15 and 17, of the CH3 domain of the antibody molecule. In addition, the antibody molecule preferably retains an insertion, preferably a 5 amino acid insertion between positions 16 and 17 of the CH3 domain of the antibody molecule. In a further preferred embodiment, the antibody molecule preferably retains the sequence at positions 97 and 98 of the CH3 domain of the antibody molecule.

In addition, or alternatively, where the antibody molecule comprises a variant of CH3 domain, CH2 and CH3 domain, light chain or heavy chain sequence disclosed herein, the variant preferably does not comprise any amino acid alterations in the first and second located in the AB and EF structural loops of the CH3 domain of the antibody molecule. For example, the variant may not comprise any amino acid alterations in the AB and EF structural loops of the CH3 domain of the antibody molecule. Additionally, the variant may not comprise any amino acid alterations in the CD structural loop of the CH3 domain of the antibody molecule. That is, the variant may not comprise any amino acid alterations in the AB and EF structural loops of the CH3 domain of the antibody molecule.

Where the antibody molecule comprises a variant of a VH domain, VL domain, light chain or heavy chain sequence disclosed herein, the antibody molecule preferably does not comprise any amino acid alterations in the CDR sequences. That is, any amino acid alterations present may be in the FW sequences, e.g. HFW1, HFW2, HFW3, HFW4, LFW1, LFW2, LFW3 and/or LFW4. For example, the variant may not comprise any amino acid alterations in the CDR1, CDR2, CDR3, CDR4, CDR5 and/or CDR6 sequences.

The antibody molecule preferably binds to human PD-L1 and human CD137. Preferably, the antibody molecule is capable of simultaneously binding to human PD-L1 and human CD137, wherein human CD137 and human PD-L1 are co-expressed. As used herein, co-expression means that the two targets are expressed on the surface of a single cell, or on the surface of two separate cells. For example, the antibody molecule may be capable of binding to human PD-L1 and human CD137 when human PD-L1 and human CD137 are co-expressed on a single cell, e.g. an immune cell, as well as being capable of binding to human PD-L1 and human CD137 when human PD-L1 and human CD137 are co-expressed on two separate cells, e.g. an immune cell expressing CD137 and a separate tumour cell expressing PD-L1 in the tumour microenvironment.

The antibody molecule preferably binds to human PD-L1 with an affinity ($K_D$) of 8 nM, 7 nM, 6 nM, 5 nM, 4 nM, 3 nM, 2 nM, 1 nM, 0.5 nM, 0.4 nM, or 0.3 nM or with a higher affinity. Preferably, the antibody molecule binds to human PD-L1, with an affinity ($K_D$) of 0.3 nM, or with a higher affinity.

The human PD-L1 may, for example, have the sequence set forth in SEQ ID NO: 180. The human PD-L1 may, for example, be recombinant human PD-L1 with an Avi Tag (hPD-L1-Avi-His), available from Acro Biosystems (catalogue number: PD1-H82E5). The recombinant human PD-L1 may be biotinylated.

The antibody molecule preferably binds to dimeric human CD137 with an affinity ($K_D$) of 60 nM, 50 nM, 40 nM, 30 nM, 20 nM, 10 nM, 5 nM, 4 nM, 3 nM, or 2 nM, or with a higher affinity. Preferably, the antibody molecule binds to dimeric human CD137, with an affinity ($K_D$) of 2 nM, or with a higher affinity.

In a preferred embodiment, the antibody molecule binds to dimeric CD137 with a higher affinity than monomeric CD137. In a preferred embodiment, the antibody molecule binds to dimeric CD137 with an affinity which is at least 50-fold, 60-fold, 70-fold, 80-fold, 90-fold, 100-fold, 110-fold, 120-fold, 130-fold, 140-fold, 150-fold, 160-fold, 170-fold or 200-fold higher than the affinity of the antibody molecule for monomeric CD137.

The human CD137 may, for example, have the sequence set forth in SEQ ID NO: 186. Methods for producing dimeric and monomeric CD137 antigens are described in the examples.

The antibody molecule preferably binds to cynomolgus PD-L1 and cynomolgus CD137. Preferably, the antibody molecule is capable of simultaneously binding to cynomolgus PD-L1 and cynomolgus CD137, wherein cynomolgus PD-L1 and cynomolgus CD137 are expressed on the surface of a single cell, or on the surface of two separate cells.

In a preferred embodiment, the antibody molecule may bind to cynomolgus PD-L1 with an affinity ($K_D$) of 8 nM, 7 nM, 6 nM, 5 nM, 4 nM, 3 nM, 2 nM, 1 nM, 0.5 nM, 0.4 nM, or 0.3 nM or with a higher affinity. Preferably, the antibody molecule binds to cynomolgus PD-L1, with an affinity ($K_D$) of 1 nM, or with a higher affinity.

The cynomolgus PD-L1 may, for example, have the sequence set forth in SEQ ID NO: 184.

In a preferred embodiment, the antibody molecule may bind to dimeric cynomolgus CD137 with an affinity ($K_D$) of 60 nM, 50 nM, 40 nM, 30 nM, 20 nM, 10 nM, 5 nM, 4 nM, 3 nM, or 2 nM or with a higher affinity. Preferably, the antibody molecule binds to dimeric cynomolgus CD137, with an affinity ($K_D$) of 2 nM, or with a higher affinity.

The antibody molecule may bind to human PD-L1 and cynomolgus PD-L1 with a similar affinity, and/or bind to dimeric human CD137 and dimeric cynomolgus CD137 with similar affinity. This is thought to be beneficial for ensuring that efficacy and toxicity studies carried out with the antibody molecule in cynomolgus monkeys are predictive of the efficacy and toxicity of the antibody molecule in humans.

Thus, in a preferred embodiment, the antibody molecule binds to cynomolgus PD-L1 with an affinity which is no more than 10-fold, preferably no more than 5-fold lower or higher than the affinity with which the antibody molecule binds to human PD-L1. In a preferred embodiment, the antibody molecule binds to dimeric cynomolgus CD137 with an affinity which is no more than 10-fold, preferably no more than 5-fold lower or higher than the affinity with which the antibody molecule binds dimeric human CD137.

The binding affinity of an antibody molecule to a cognate antigen, such as human PD-L1, human CD137, cynomolgus PD-L1, or cynomolgus CD137 can be determined by surface plasmon resonance (SPR), such as Biacore, for example. Further details of suitable methods are described in the Examples.

The ability of an antibody molecule to simultaneously bind to two cognate antigens, e.g. human PD-L1 and human CD137, or cynomolgus PD-L1 and cynomolgus CD137, can be determined by SPR, such as Biacore for example. Further details of suitable methods are described in the Examples.

The antibody molecule may be capable of blocking the interaction between PD-L1 and its receptor, PD-1, preferably human PD-L1 and human PD-1.

The PD-1/PD-L1 signalling pathway is known to be important in mediating immune suppression. Thus, antibody molecules that are capable of blocking this pathway are expected to be advantageous in that they may reduce immune suppression and help to increase the anti-tumour response. PD-1/PD-L1 signalling inhibition and CD137 activation may work together in order to increase anti-tumour potency.

The ability of an antibody molecule to block the binding of PD-L1 to PD-1 may be determined using a bioluminescent cell-based assay, for example using a PD-1/PD-L1 Blockade Bioassay product, e.g. from Promega. The ability of an antibody molecule to block the binding of PD-L1 to PD-1 may be determined using ELISA. Further details of these assays are described in the Examples.

The ability of an antibody molecule to block the binding of PD-L1 to PD-1, also referred to as the PD-1/PD-L1 blocking activity herein, may be determined by reference to an antibody molecule comprising or consisting of the heavy chain and light chain of antibody 2.14H9OPT set forth in WO2011/066389 A1, respectively, or the heavy chain and light chain of antibody G11280_02_G02 set forth in SEQ ID NOs 177 and 178, respectively.

For example, the antibody molecule may have a similar or higher level of PD-1/PD-L1 blocking activity than an antibody molecule comprising or consisting of the heavy chain and light chain of antibody 2.14H9OPT set forth in WO2011/066389 A1, or the heavy chain and light chain of antibody G11280_02_G02 set forth in SEQ ID NOs 177 and 178, respectively.

The antibody molecule may have a PD-1/PD-L1 blocking activity that is at least 70%, 80%, or 90% of the PD-1/PD-L1 blocking activity of an antibody molecule comprising or consisting of the heavy chain sequence and light chain sequence of antibody 2.14H9OPT set forth in WO2011/066389 A1, or the heavy chain and light chain of antibody G11280_02_G02 set forth in SEQ ID NOs 177 and 178, respectively.

The antibody molecule may have a PD-1/PD-L1 blocking activity that is between 70% and 130%, 80% and 120%, or 90% and 110% of the PD-1/PD-L1 blocking activity of an antibody molecule comprising or consisting of the heavy chain sequence and light chain sequence of antibody 2.14H9OPT set forth in WO2011/066389 A1, or the heavy chain and light chain of antibody G1/280_02_G02 set forth in SEQ ID NOs 177 and 178, respectively.

As described above, the antibody molecules of the invention are capable of simultaneously bind PD-L1 and CD137, which results in the activation (agonism) of CD137. In a preferred embodiment, the antibody molecule is capable of simultaneously binding to both human PD-L1 and human CD137, wherein such binding causes activation of human CD137. In an additionally preferred embodiment, the antibody molecule is capable of simultaneously binding to both cynomolgus PD-L1 and cynomolgus CD137, wherein such binding causes activation of cynomolgus CD137. Exemplary methods of testing simultaneous binding and activation include T cell activation assays, as described in more detail below.

The ability of an antibody molecule to activate T cells can be measured using a T cell activation assay. T cells release IL-2 on activation. A T cell activation assay may therefore measure IL-2 release to determine the level of T cell activation induced by the antibody molecule.

For example, the ability of the antibody molecule to activate T cells is determined by measuring the concentration of the antibody molecule required to achieve half-maximal release of IL-2 by the T cells in a T cell activation assay. This is referred to as the $EC_{50}$ below.

In a preferred embodiment, the antibody molecule has an $EC_{50}$ in a T cell activation assay which is within 50-fold, 40-fold, 30-fold, 20-fold, 10-fold, 5-fold, 4-fold, 3-fold, or 2-fold of the $EC_{50}$ of FS22-172-003-AA/E12v2 in the same assay, wherein FS22-172-003-AA/E12v2 consists of the heavy chain of SEQ ID NO: 134 and the light chain of SEQ ID NO: 17.

For example, the antibody molecule may have an $EC_{50}$ in a T cell activation assay of 30 nM or less, 25 nM or less, 20 nM or less, 14 nM or less, 10 nM or less, 5 nM or less, 4 nM or less, 3 nM or less, 2 nM or less, 1.5 nM or less, 1 nM or less, 0.4 nM or less, 0.4 nM or less, or 0.3 nM or less, preferably 1 nM or less, more preferably 1.5 nM or less when the antibody molecule is crosslinked.

In addition, or alternatively, the ability of an antibody molecule to activate T cells may be determined by measuring the maximum concentration of IL-2 released by the T cells in a T cell activation assay in the presence of the antibody molecule ($E_{max}$).

The antibody molecule may have a maximum concentration of IL-2 released by the T cells in a T cell activation assay in the presence of the antibody molecule of at least 1500 μg/ml, 2000 μg/ml, 2500 μg/ml, 3000 μg/ml, or 3250 μg/ml or more, preferably 2500 μg/ml or more.

In a preferred embodiment, the maximum concentration of IL-2 released by the T cells in a T cell activation assay in the presence of the antibody molecule is within 20%, or 10% of the maximum concentration of IL-2 released by the T cells in the presence of FS22-172-003-AA/E12v2 in the same assay, wherein FS22-172-003-AA/E12v2 consists of the heavy chain of SEQ ID NO: 134 and the light chain of SEQ ID NO: 17.

The T cell activation assay preferably comprises T cells expressing CD137 and cells expressing PD-L1, for example, HEK293 cells overexpressing human PD-L1 (HEK.hPD-L1) may be prepared and used as described in the Examples. Alternatively, or additionally, cells expressing a different level of PD-L1 may be used, such as the human breast adenocarcinoma cell line MDA-MB-231 (ATCC HTB-26) cells and/or SKBR3 cells. As described in the Examples, HEK.hPD-L1 express a high level of human PD-L1, MDA-MB-231 cells express a medium level of human PD-L1 and SKBR3 cells express a low level of PD-L1.

In a preferred embodiment, the T cell activation assay does not comprise any agents capable of crosslinking the antibody molecule other than CD137 and PD-L1 expressing cells. Examples of agents capable of crosslinking the antibody molecule include an anti-human CH2 antibody, as described in the Examples.

The T cell activation assay may be a T cell assay as described herein, such as a pan-T cell assay as described in the present Examples.

For example, a T cell activation assay may be an IL-2 release assay based on T cells isolated from human Peripheral Blood Mononuclear Cells (PBMCs). For example, the T cell activation assay may comprise isolating human PBMCs from leucocyte depletion cones. Methods for isolating PBMCs are known in the art and described in the present examples. The T cells may then be isolated from the PBMCs. Methods for isolating T cells (all T cells) from PBMCs are known in the art and described in the present Examples.

The activation assay may involve preparing the required number of T cells for example in experimental media, such as a T cell medium. The required number of T cells may be prepared at a concentration of $1.0 \times 10^6$ cells/ml. T cells may then be stimulated using a suitable T cell activation reagent that provides the signals required for T cell activation. For example, the T cell activation reagent may be a reagent comprising CD3 and CD28, such as beads comprising CD3 and CD28. Isolated T cells may be incubated overnight with the T cell activation reagent to activate the T cells. Following this, the activated T cells may be washed to separate the T cells from the T cell activation reagent and resuspended in T cell medium at a suitable concentration, such as $2.0 \times 10^6$ cells/ml. Activated T cells may then be added to plates coated with anti-human CD3 antibody.

The cells (e.g. HEK.hPD-L1 cells) may be plated at, e.g. $2 \times 10^5$ cells per well on to anti-CD3 antibody-coated tissue culture plates in T cell culture medium. After, e.g. 4 hours of incubation, all T cell culture medium may be removed and replaced with 100 μl T cell culture medium containing T cells, e.g. at a concentration of $5.0 \times 10^5$ cells/ml resulting in $5.0 \times 10^4$ cells/well.

A suitable dilution of each test antibody molecule may be prepared and added to the wells. The T cells may then be incubated at 37° C., 5% $CO_2$ for 24 hours with the test antibody. Supernatants may be collected and assayed to determine the concentration of IL-2 in the supernatant. Methods for determining the concentration of IL-2 in a solution are known in the art and described in the present examples. The concentration of human IL-2 may be plotted versus the log concentration of the antibody molecule. The resulting curves may be fitted using the log (agonist) versus response equation.

The antibody molecule may be conjugated to a bioactive molecule or a detectable label. In this case, the antibody molecule may be referred to as a conjugate. Such conjugates find application in the treatment of diseases as described herein.

For example, the bioactive molecule may be an immune system modulator, such as a cytokine, preferably a human cytokine. For example, the cytokine may be a cytokine which stimulates T cell activation and/or proliferation. Examples of cytokines for conjugation to the antibody molecule include IL-2, IL-10, IL-12, IL-15, IL-21, GM-CSF and IFN-γ.

Alternatively, the bioactive molecule may be a ligand trap, such as a ligand trap of a cytokine, e.g. of TGF-beta or IL-6.

Alternatively, the bioactive molecule may be a therapeutic radioisotope.

Radioimmunotherapy is used in cancer treatment, for example. Therapeutic radioisotopes suitable for radioimmunotherapy are known in the art and include yttrium-90, iodine-131, bismuth-213, astatine-211, lutetium 177, rhenium-188, copper-67, actinium-225, and iodine-125 and terbium-161.

Suitable detectable labels which may be conjugated to antibody molecules are known in the art and include radioisotopes such as iodine-125, iodine-131, yttrium-90, indium-111 and technetium-99; fluorochromes, such as fluorescein, rhodamine, phycoerythrin, Texas Red and cyanine dye derivatives for example, Cy7 and Alexa750; chromogenic dyes, such as diaminobenzidine; latex beads; enzyme labels such as horseradish peroxidase; phosphor or laser dyes with spectrally isolated absorption or emission characteristics; and chemical moieties, such as biotin, which may be detected via binding to a specific cognate detectable moiety, e.g. labelled avidin.

The antibody molecule may be conjugated to the bioactive molecule or detectable label by means of any suitable covalent or non-covalent linkage, such as a disulphide or peptide bond. Where the bioactive molecule is a cytokine, the cytokine may be joined to the antibody molecule by means of a peptide linker. Suitable peptide linkers are known in the art and may be 5 to 25, 5 to 20, 5 to 15, 10 to 25, 10 to 20, or 10 to 15 amino acids in length.

In some embodiments, the bioactive molecule may be conjugated to the antibody molecule by a cleavable linker. The linker may allow release of the bioactive molecule from the antibody molecule at a site of therapy. Linkers may include amide bonds (e.g. peptidic linkers), disulphide bonds or hydrazones. Peptide linkers for example may be cleaved by site specific proteases, disulphide bonds may be cleaved by the reducing environment of the cytosol and hydrazones may be cleaved by acid-mediated hydrolysis.

The invention also provides an isolated nucleic acid molecule or molecules encoding an antibody molecule of the invention. The skilled person would have no difficulty in preparing such nucleic acid molecules using methods well-known in the art.

The nucleic acid molecule or molecules may, for example, comprise the sequence set forth in SEQ ID NO: 82, 85, 88, 91, 94, 97, 100, 103, 106, 109, 112, 116, 119, 122, 125, 128, 131, or 133, which encode the CH3 domains of FS22-053-008, FS22-053-009, FS22-053-011, FS22-053-017, FS22-053-014, FS22-053-010, FS22-053-012, FS22-053-013, FS22-053-015, FS22-053-016, FS22-053, FS22-172-003, FS22-172-002, FS22-172-004, FS22-172-001, FS22-172-005, FS22-172-006, and FS22-172, respectively. Preferably, the nucleic acid molecule or molecules comprise the sequence set forth in SEQ ID NO: 116 or 82, which encode the CH3 domain of FS22-172-003 or FS22-053-008, respectively. More preferably, the nucleic acid molecule or molecules comprise the sequence set forth in SEQ ID NO: 116, which encodes the CH3 domain of FS22-172-003.

The nucleic acid molecule or molecules may encode the VH domain and/or VL domain, preferably the VH domain and VL domain of antibody E12v2, E05v2, G12v2, or lam-G02v3, preferably antibody E12v2, E05v2, or G12v2, more preferably E12v2 or E05v2, most preferably E12v2. The VH and VL domain sequences of these antibodies are described herein.

For example, the nucleic acid molecule(s) may comprise:
(i) the VH domain nucleic acid sequence of antibody E12v2 set forth in SEQ ID NO: 13, and/or the VL domain nucleic acid sequence of antibody E12v2 set forth in SEQ ID NO: 15; or
(ii) the VH domain nucleic acid sequence of antibody E05v2 set forth in SEQ ID NO: 24, and/or the VL domain nucleic acid sequence of antibody E05v2 set forth in SEQ ID NO: 26;
(iii) the VH domain nucleic acid sequence of antibody G12v2 set forth in SEQ ID NO: 24, and/or the VL domain nucleic acid sequence of antibody G12v2 set forth in SEQ ID NO: 31; or
(v) the VH domain nucleic acid sequence of antibody lam-G02v3 set forth in SEQ ID NO: 24, and/or the VL domain nucleic acid sequence of antibody lam-G02v3 set forth in SEQ ID NO: 42.

The nucleic acid molecule or molecules may encode the heavy chain and/or light chain, preferably the heavy chain and light chain of antibody FS22-172-003-AA/E12v2, FS22-172-003-AA/E05v2, FS22-172-003-AA/G12v2, FS22-053-008-AA/E12v2, FS22-053-008-AA/E05v2, or FS22-053-008-AA/G12v2, preferably antibody FS22-172-003-AA/E12v2, FS22-172-003-AA/E05v2, FS22-172-003-AA/G12v2, FS22-053-008-AA/E12v2, or FS22-053-008-AA/E05v2, even more preferably antibody FS22-172-003-AA/E12v2. The heavy chain and light chain sequences of these antibodies are described herein.

For example, the nucleic acid molecule(s) may comprise:
(i) the heavy chain nucleic acid sequence of antibody FS22-172-003-AA/E12v2 set forth in SEQ ID NO: 32 or 135, and/or the light chain nucleic acid sequence of antibody FS22-172-003-AA/E12v2 set forth in SEQ ID NO: 39 or 136; or
(ii) the heavy chain nucleic acid sequence of antibody FS22-172-003-AA/E05v2 set forth in SEQ ID NO: 138, and/or the light chain nucleic acid sequence of antibody FS22-172-003-AA/E05v2 set forth in SEQ ID NO: 139;
(iii) the heavy chain nucleic acid sequence of antibody FS22-172-003-AA/G12v2 set forth in SEQ ID NO: 141, and/or the light chain nucleic acid sequence of antibody FS22-172-003-AA/G12v2 set forth in SEQ ID NO: 142;
(iv) the heavy chain nucleic acid sequence of antibody FS22-053-008-AA/E12v2 set forth in SEQ ID NO: 144, and/or the light chain nucleic acid sequence of antibody FS22-053-008-AA/E12v2 set forth in SEQ ID NO: 145;
(v) the heavy chain nucleic acid sequence of antibody FS22-053-008-AA/E05v2 set forth in SEQ ID NO: 147, and/or the light chain nucleic acid sequence of antibody FS22-053-008-AA/E05v2 set forth in SEQ ID NO: 148; or
(vi) the heavy chain nucleic acid sequence of antibody FS22-053-008-AA/G12v2 set forth in SEQ ID NO: 150, and/or the light chain nucleic acid sequence of antibody FS22-053-008-AA/G12v2 set forth in SEQ ID NO: 151.

Where the nucleic acid encodes the VH and VL domain, or heavy and light chain, of an antibody molecule of the invention, the two domains or chains may be encoded on two separate nucleic acid molecules.

An isolated nucleic acid molecule may be used to express an antibody molecule of the invention. The nucleic acid will generally be provided in the form of a recombinant vector for expression. Another aspect of the invention thus provides a vector comprising a nucleic acid as described above. Suitable vectors can be chosen or constructed, containing appropriate regulatory sequences, including promoter sequences, terminator fragments, polyadenylation sequences, enhancer sequences, marker genes and other sequences as appropriate. Preferably, the vector contains appropriate regulatory sequences to drive the expression of the nucleic acid in a host cell. Vectors may be plasmids, viral e.g. phage, or phagemid, as appropriate.

A nucleic acid molecule or vector as described herein may be introduced into a host cell. Techniques for the introduction of nucleic acid or vectors into host cells are well established in the art and any suitable technique may be employed. A range of host cells suitable for the production of recombinant antibody molecules are known in the art, and include bacterial, yeast, insect or mammalian host cells. A preferred host cell is a mammalian cell, such as a CHO, NS0, or HEK cell, for example a HEK293 cell.

Another aspect of the invention provides a method of producing an antibody molecule of the invention comprising expressing a nucleic acid encoding the antibody molecule in a host cell and optionally isolating and/or purifying the antibody molecule thus produced. Methods for culturing host cells are well-known in the art. The method may further comprise isolating and/or purifying the antibody molecule. Techniques for the purification of recombinant antibody molecules are well-known in the art and include, for example HPLC, FPLC or affinity chromatography, e.g. using Protein A or Protein L. In some embodiments, purification may be performed using an affinity tag on antibody molecule. The method may also comprise formulating the antibody molecule into a pharmaceutical composition, optionally with a pharmaceutically acceptable excipient or other substance as described below.

PD-L1 is known to be expressed on many cancer cells and is expressed on cell of the immune system. CD137 is expressed on cells of the immune system, including T cells, in particular $CD8^+$ T cells, B cells, NK cells and tumour-infiltrating lymphocytes (TILs). CD137 is expressed at a lower level on $CD4^+$ T cells than $CD8^+$ T cells but has also been shown to be involved in inducing proliferation and activation of some subsets of $CD4^+$ T cells.

CD137 activation has been shown to play a role in enhancing proliferation, survival and the cytotoxic effector function of $CD8^+$ T cells, as well as $CD8^+$ T cell differentiation and maintenance of memory $CD8^+$ T cells. Activation of CD137 has also been demonstrated to enhance NK cell-mediated ADCC, as well as B cell proliferation, survival and cytokine production.

As described in detail herein, the present inventors have demonstrated that antibody molecules of the invention are capable of simultaneously binding to PD-L1 and CD137 in order to induce agonism of CD137. In this way, the antibody molecule drives agonism autonomously, based on the expression of the PD-L1 and CD137, and without the need for additional crosslinking agents. Since PD-L1 is expressed on many cancer cells and CD137 is expressed on immune cells, where it has a known role in enhancing the proliferation and survival of immune cells, it is expected that antibody molecules of the invention will be able to enhance an immune response at locations where PD-L1 is expressed, e.g. in the tumour microenvironment. Furthermore, the present inventors have shown that the use of an antibody molecule having these properties, is effective in suppressing tumour growth in syngeneic mouse models of cancer, and that such antibody molecules are more effective than the administration of two binding molecules which bind PD-L1 and CD137, respectively.

The antibody molecules as described herein may thus be useful for therapeutic applications, in particular in the treatment of cancer.

An antibody molecule as described herein may be used in a method of treatment of the human or animal body. Related aspects of the invention provide;
(i) an antibody molecule described herein for use as a medicament,
(ii) an antibody molecule described herein for use in a method of treatment of a disease or disorder,
(iii) the use of an antibody molecule described herein in the manufacture of a medicament for use in the treatment of a disease or disorder; and,
(iv) a method of treating a disease or disorder in an individual, wherein the method comprises administering to the individual a therapeutically effective amount of an antibody molecule as described herein.

The individual may be a patient, preferably a human patient.

Treatment may be any treatment or therapy in which some desired therapeutic effect is achieved, for example, the inhibition or delay of the progress of the condition, and includes a reduction in the rate of progress, a halt in the rate of progress, amelioration of the condition, cure or remission (whether partial or total) of the condition, preventing, ameliorating, delaying, abating or arresting one or more symptoms and/or signs of the condition or prolonging survival of an individual or patient beyond that expected in the absence of treatment.

Treatment as a prophylactic measure (i.e. prophylaxis) is also included. For example, an individual susceptible to or at risk of the occurrence or re-occurrence of a disease such as cancer may be treated as described herein. Such treatment may prevent or delay the occurrence or re-occurrence of the disease in the individual.

A method of treatment as described may be comprise administering at least one further treatment to the individual in addition to the antibody molecule. The antibody molecule described herein may thus be administered to an individual alone or in combination with one or more other treatments. Where the antibody molecule is administered to the individual in combination with another treatment, the additional treatment may be administered to the individual concurrently with, sequentially to, or separately from the administration of the antibody molecule. Where the additional treatment is administered concurrently with the antibody molecule, the antibody molecule and additional treatment may be administered to the individual as a combined preparation. For example, the additional therapy may be a known therapy or therapeutic agent for the disease to be treated.

Whilst an antibody molecule may be administered alone, antibody molecules will usually be administered in the form of a pharmaceutical composition, which may comprise at least one component in addition to the antibody molecule. Another aspect of the invention therefore provides a pharmaceutical composition comprising an antibody molecule as described herein. A method comprising formulating an antibody molecule into a pharmaceutical composition is also provided.

Pharmaceutical compositions may comprise, in addition to the antibody molecule, a pharmaceutically acceptable excipient, carrier, buffer, stabilizer or other materials well known to those skilled in the art. The term "pharmaceutically acceptable" as used herein pertains to compounds, materials, compositions, and/or dosage forms which are, within the scope of sound medical judgement, suitable for use in contact with the tissues of a subject (e.g., human) without excessive toxicity, irritation, allergic response, or other problem or complication, commensurate with a reasonable benefit/risk ratio. Each carrier, excipient, etc. must also be "acceptable" in the sense of being compatible with the other ingredients of the formulation. The precise nature of the carrier or other material will depend on the route of administration, which may be by infusion, injection or any other suitable route, as discussed below.

For parenteral, for example subcutaneous or intravenous administration, e.g. by injection, the pharmaceutical composition comprising the antibody molecule may be in the form of a parenterally acceptable aqueous solution which is pyrogen-free and has suitable pH, isotonicity and stability. Those of relevant skill in the art are well able to prepare suitable solutions using, for example, isotonic vehicles, such as Sodium Chloride Injection, Ringer's Injection, Lactated Ringer's Injection. Preservatives, stabilizers, buffers, antioxidants and/or other additives may be employed as required including buffers such as phosphate, citrate and other organic acids; antioxidants, such as ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens, such as methyl or propyl paraben; catechol; resorcinol; cyclohexanol; 3'-pentanol; and m-cresol); low molecular weight polypeptides; proteins, such as serum albumin, gelatin or immunoglobulins; hydrophilic polymers, such as polyvinylpyrrolidone; amino acids, such as glycine, glutamine, asparagines, histidine, arginine, or lysine; monosaccharides, disaccharides and other carbohydrates including glucose, mannose or dextrins; chelating agents, such as EDTA; sugars, such as sucrose, mannitol, trehalose or sorbitol; salt-forming counter-ions, such as sodium; metal complexes (e.g. Zn-protein complexes); and/or non-ionic surfactants, such as TWEEN™, PLURONICS™ or polyethylene glycol (PEG).

In some embodiments, antibody molecules may be provided in a lyophilised form for reconstitution prior to administration. For example, lyophilised antibody molecules may be re-constituted in sterile water and mixed with saline prior to administration to an individual. Administration may be in a "therapeutically effective amount", this being sufficient to show benefit to an individual. The actual amount administered, and rate and time-course of administration, will depend on the nature and severity of what is being treated, the particular individual being treated, the clinical condition of the individual, the cause of the disorder, the site of delivery of the composition, the type of antibody molecule, the method of administration, the scheduling of administration and other factors known to medical practitioners. Prescription of treatment, e.g. decisions on dosage etc., is within the responsibility of general practitioners and other medical doctors, and may depend on the severity of the symptoms and/or progression of a disease being treated. Appropriate doses of antibody molecules are well known in the art (Ledermann et al. (1991) Int. J. Cancer 47: 659-664; and Bagshawe et al. (1991) Antibody, Immunoconjugates and Radiopharmaceuticals 4: 915-922). Specific dosages indicated herein, or in the Physician's Desk Reference (2003) as appropriate for an antibody molecule being administered, may be used. A therapeutically effective amount or suitable dose of an antibody molecule can be determined by comparing in vitro activity and in vivo activity in an animal model. Methods for extrapolation of effective dosages in mice and other test animals to humans are known. The precise dose will depend upon a number of factors, including whether the size and location of the area to be treated, and the precise nature of the antibody molecule.

A typical antibody dose is in the range 100 µg to 1 g for systemic applications, and 1 µg to 1 mg for topical applications. An initial higher loading dose, followed by one or more lower doses, may be administered. This is a dose for a single treatment of an adult individual, which may be proportionally adjusted for children and infants, and also adjusted for other antibody formats in proportion to molecular weight.

Treatments may be repeated at daily, twice-weekly, weekly or monthly intervals, at the discretion of the physician. The treatment schedule for an individual may be dependent on the pharmocokinetic and pharmacodynamic properties of the antibody composition, the route of administration and the nature of the condition being treated.

Treatment may be periodic, and the period between administrations may be about two weeks or more, e.g. about three weeks or more, about four weeks or more, about once a month or more, about five weeks or more, or about six weeks or more. For example, treatment may be every two to four weeks or every four to eight weeks. Suitable formulations and routes of administration are described above.

In a preferred embodiment, an antibody molecule as described herein may be for use in a method of treating cancer.

Cancer may be characterised by the abnormal proliferation of malignant cancer cells. Where a particular type of cancer, such as breast cancer, is referred to, this refers to an abnormal proliferation of malignant cells of the relevant tissue, such as breast tissue. A secondary cancer which is located in the breast but is the result of abnormal proliferation of malignant cells of another tissue, such as ovarian tissue, is not a breast cancer as referred to herein but an ovarian cancer.

The cancer may be a primary or a secondary cancer. Thus, an antibody molecule as described herein may be for use in a method of treating cancer in an individual, wherein the cancer is a primary tumour and/or a tumour metastasis.

A tumour of a cancer to be treated using an antibody molecule as described herein may comprise TILs that express CD137, e.g. on their cell surface. In one embodiment, the tumour may have been determined to comprise TILs that express CD137. Methods for determining the expression of an antigen on a cell surface are known in the art and include, for example, flow cytometry.

For example, the cancer to be treated using an antibody molecule as described herein may be selected from the group consisting of leukaemias, such as acute myeloid leukaemia (AML), chronic myeloid leukaemia (CML), acute lymphoblastic leukaemia (ALL) and chronic lymphocytic leukaemia (CLL); lymphomas, such as Hodgkin lymphoma, non-Hodgkin lymphoma and multiple myeloma; and solid cancers, such as sarcomas (e.g. soft tissue sarcomas), skin cancer (e.g. Merkel cell carcinoma), melanoma, bladder cancer (e.g. urothelial carcinoma), brain cancer (e.g. glioblastoma multiforme), breast cancer, uterine/endometrial cancer, ovarian cancer (e.g. ovarian serous cystadenoma), prostate cancer, lung cancer (e.g. non-small cell lung carcinoma (NSCLC) and small cell lung cancer (SCLC), colorectal cancer (e.g. colorectal adenocarcinoma), cervical cancer (e.g. cervical squamous cell cancer and cervical adenocarcinoma), liver cancer (e.g. hepatocellular carcinoma), head and neck cancer (e.g. head and neck squamous-cell carcinoma), oesophageal cancer, pancreatic cancer, renal cancer (e.g. renal cell cancer), adrenal cancer, stomach cancer (e.g. stomach adenocarcinoma), testicular cancer, cancer of the gall bladder and biliary tracts (e.g. cholangiocarcinoma), thyroid cancer, thymus cancer, bone cancer, and cerebral cancer.

In a preferred embodiment, the cancer to be treated using an antibody molecule as described herein is a solid cancer.

More preferably, the cancer to be treated using an antibody molecule as described herein is a solid cancer selected from the group consisting of melanoma, bladder cancer, brain cancer, breast cancer, ovarian cancer, lung cancer, colorectal cancer, cervical cancer, liver cancer, head and neck cancer, pancreatic cancer, renal cancer, stomach cancer and Gastrointestinal Stromal tumours (GISTs).

In a further preferred embodiment, the cancer to be treated using an antibody molecule as described herein may be a cancer which is responsive to treatment with one or more check-point inhibitors, such as an antibody which binds PD-1, PD-L1 or CTLA4. Such tumours are thought to have higher TIL levels and/or higher tumour mutational burden than tumours which are not responsive to check-point inhibitor therapy. Such tumours are also referred to as warm or hot tumours.

Examples of such tumours include head and neck squamous-cell carcinoma (HNSCC), melanoma, lung cancer (such as squamous lung cancer, lung adenocarcinoma, non-small cell lung carcinoma [NSCLC], or small-cell lung carcinoma [SCLC]), prostate cancer, cervical cancer (such as cervical squamous cell carcinoma or endocervical adenocarcinoma), bladder cancer, breast cancer, thyroid cancer, kidney cancer, colorectal cancer (MSI or MSS; e.g. colorectal adenocarcinoma), oesophageal cancer, non-Hodgkin's lymphoma (NHL), gastric cancer, endometrial cancer, pancreatic cancer, ovarian cancer, hepatocellular carcinoma, mesothelioma, urothelial cancer, Merkel cell carcinoma, and stomach adenocarcinoma. In a preferred embodiment, the cancer is HNSCC. The cancer may further be a cancer which has not previously been treated with a chemotherapeutic or radiotherapetic agent, i.e. the individual to be treated may be a cancer patient which has not received treatment with a chemotherapeutic or radiotherapeutic agent for the cancer in question.

Alternatively, the cancer to be treated using an antibody molecule as described herein may be a cancer, such as pancreatic cancer or prostate cancer which is not responsive to treatment with one or more check-point inhibitors, such as an antibody which binds PD-1, PD-L1 or CTLA4. An individual treated with an antibody of the invention may thus be a cancer patient, such as a pancreatic cancer or prostate cancer patient, with a previous inadequate response to one or more check-point inhibitors, such as an anti-PD-L1 or anti-PD-1 antibody.

Tumours which are not responsive to treatment with one or more check-point inhibitors are also referred to as cold tumours. Without wishing to be bound by theory, it is thought that treatment of a cancer, which is not responsive to treatment with one or more check-point inhibitors alone, with chemotherapy, radiotherapy, an immunotherapeutic agent, such as an immunostimulatory agent, or an anti-tumour vaccine will result in cancer cell death which in turn will result in an increase in TILs in the tumour and higher expression of immunosuppressive receptors, which in turn will make the cancer responsive to treatment with check-point inhibitors, i.e. turn a cold tumour into a warm tumour. Thus, the antibody molecule of the invention may be for use in a method of treating cancer in an individual, wherein the cancer is not responsive, or refractory, to treatment with one or more check-point inhibitors alone, and wherein the method comprises administering the antibody molecule to the individual in combination with a chemotherapeutic, radiotherapeutic, or immunostimulatory agent, or an anti-cancer vaccine. A method of treating a cancer in an individual, wherein the cancer is not responsive, or refractory, to treatment with one or more check-point inhibitors alone, and wherein the method comprises administering the antibody molecule to the individual in combination with a chemotherapeutic, radiotherapeutic, or immunostimulatory agent, or an anti-cancer vaccine is also contemplated.

In the context of cancer, treatment may include inhibiting cancer growth, including complete cancer remission, and/or inhibiting cancer metastasis, as well as inhibiting cancer recurrence. Cancer growth generally refers to any one of a number of indices that indicate change within the cancer to a more developed form. Thus, indices for measuring an inhibition of cancer growth include a decrease in cancer cell survival, a decrease in tumour volume or morphology (for example, as determined using computed tomographic (CT), sonography, or other imaging method), a delayed tumour growth, a destruction of tumour vasculature, improved performance in delayed hypersensitivity skin test, an increase in the activity of anti-cancer immune cells or other anti-cancer immune responses, and a decrease in levels of tumour-specific antigens. Activating or enhancing immune responses to cancerous tumours in an individual may improve the capacity of the individual to resist cancer growth, in particular growth of a cancer already present in the subject and/or to decrease the propensity for cancer growth in the individual.

In the context of cancer treatment, an antibody molecule as described herein may be administered to an individual in combination with another anti-cancer therapy or therapeutic agent, such as an anti-cancer therapy or therapeutic agent which has been shown to be suitable, or potentially suitable, for the treatment of the cancer in question. For example, the antibody molecule may be administered to the individual in combination with a chemotherapeutic agent, radiotherapy, a radionuclide, an immunotherapeutic agent, an anti-tumour vaccine, an oncolytic virus, an adoptive cell transfer (ACT) therapy, such as adoptive NK cell therapy or therapy with chimeric antigen receptor (CAR) T-cells, autologous TILs or gamma/delta T cells, or an agent for hormone therapy.

Without wishing to be bound by theory, it is thought that the antibody molecule described herein may act as an adjuvant in anti-cancer therapy. Specifically, it is thought that administration of the antibody molecule to an in individual in combination with chemotherapy or radiotherapy, for example, will trigger a greater immune response against the cancer than is achieved with chemotherapy or radiotherapy alone.

One or more chemotherapeutic agents for administration in combination with an antibody molecule as described herein may be selected from the group consisting of: taxanes, cytotoxic antibiotics, tyrosine kinase inhibitors, PARP inhibitors, B-Raf enzyme inhibitors, MEK inhibitors, c-MET inhibitors, VEGFR inhibitors, PDGFR inhibitors, alkylating agents, platinum analogues, nucleoside analogues, antifolates, thalidomide derivatives, antineoplastic chemotherapeutic agents and others. Taxanes include docetaxel, paclitaxel and nab-paclitaxel; cytotoxic antibiotics include actinomycin, bleomycin, and anthracyclines such as doxorubicin, mitoxantrone and valrubicin; tyrosine kinase inhibitors include erlotinib, gefitinib, axitinib, PLX3397, imatinib, cobemitinib and trametinib; PARP inhibitors include piraparib; B-Raf enzyme inhibitors include vemurafenib and dabrafenib; alkylating agents include dacarbazine, cyclophosphamide and temozolomide; platinum analogues include carboplatin, cisplatin and oxaliplatin; nucleoside analogues include azacitidine, capecitabine, fludarabine, fluorouracil and gemcitabine and; antifolates include methotrexate and pemetrexed. Other chemotherapeutic agents suitable for use in the present invention include defactinib, entinostat, eribulin, irinotecan and vinblastine.

Preferred therapeutic agents for administration with an antibody molecule as described herein are doxorubicin, mitoxantrone, cyclophosphamide, cisplatin, and oxaliplatin.

A radiotherapy for administration in combination with an antibody molecule as described herein may be external beam radiotherapy or brachytherapy.

Radionuclides for administration with an antibody molecule as described herein may be selected from the group consisting of: yttrium-90, iodine-131, bismuth-213, astatine-211, lutetium 177, rhenium-188, copper-67, actinium-225, iodine-125 and terbium-161.

An immunotherapeutic agent for administration in combination with an antibody molecule as described herein may be a therapeutic antibody molecule, nucleotide, cytokine, or cytokine-based therapy. For example, the therapeutic antibody molecule may bind to an immune regulatory molecule, e.g. an inhibitory checkpoint molecule or an immune costimulatory molecule, a receptor of the innate immune system, or a tumour antigen, e.g. a cell surface tumour antigen or a soluble tumour antigen. Examples of immune regulatory molecules to which the therapeutic antibody molecule may bind include CTLA-4, LAG-3, TIGIT, TIM-3, VISTA, PD-L1, PD-1, CD47, CD73, CSF-1R, KIR, CD40, HVEM, IL-10 and CSF-1. Examples of receptors of the innate immune system to which the therapeutic antibody molecule may bind include TLR4, TLR7, TLR9, RIG-1-like receptors (e.g. RIG-1 and MDA-5), and STING. Examples of tumour antigens to which the therapeutic antibody molecule may bind include HER2, EGFW, CD20 and TGF-beta.

The nucleotide for administration in combination with an antibody molecule as described herein may be an siRNA.

The cytokines or cytokine-based therapy may be selected from the group consisting of: IL-2, prodrug of conjugated IL-2, GM-CSF, IL-7, IL-12, IL-9, IL-15, IL-18, IL-21, and type I interferon.

Anti-tumour vaccines for the treatment of cancer have both been implemented in the clinic and discussed in detail within scientific literature (such as Rosenberg, S. 2000 Development of Cancer Vaccines). This mainly involves strategies to prompt the immune system to respond to various cellular markers expressed by autologous or allogenic cancer cells by using those cells as a vaccination method, both with or without granulocyte-macrophage colony-stimulating factor (GM-CSF). GM-CSF provokes a strong response in antigen presentation and works particularly well when employed with said strategies.

The features disclosed in the foregoing description, or in the following claims, or in the accompanying drawings, expressed in their specific forms or in terms of a means for performing the disclosed function, or a method or process for obtaining the disclosed results, as appropriate, may, separately, or in any combination of such features, be utilised for realising the invention in diverse forms thereof.

While the invention has been described in conjunction with the exemplary embodiments described above, many equivalent modifications and variations will be apparent to those skilled in the art when given this disclosure. Accordingly, the exemplary embodiments of the invention set forth above are considered to be illustrative and not limiting. Various changes to the described embodiments may be made without departing from the spirit and scope of the invention.

For the avoidance of any doubt, any theoretical explanations provided herein are provided for the purposes of improving the understanding of a reader. The inventors do not wish to be bound by any of these theoretical explanations.

Any section headings used herein are for organizational purposes only and are not to be construed as limiting the subject matter described.

Throughout this specification, including the claims which follow, unless the context requires otherwise, the word "comprise" and "include", and variations such as "comprises", "comprising", and "including" will be understood to imply the inclusion of a stated integer or step or group of integers or steps but not the exclusion of any other integer or step or group of integers or steps.

It must be noted that, as used in the specification and the appended claims, the singular forms "a," "an," and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment. The term "about" in relation to a numerical value is optional and means for example +/−10%.

EXAMPLES

Example 1: Antigen Selection and Characterisation

The selection and screening methods used to identify mAb[2] that are capable of binding PD-L1 and CD137 and agonising CD137 required the use of various PD-L1 and CD137 antigens. The production of these antigens is described in more detail below.

1.1 Recombinant CD137 Antigens

Tumour necrosis factor receptor superfamily (TNFRSF) members, such as CD137, are known for their tendency to form multimers which cluster together when bound to their cognate ligands (Croft, M. 2003). This propensity to aggregate for their functionality makes it challenging to produce soluble recombinant proteins that do not aggregate in solution for use in in vitro selections such as phage and yeast display and for characterisation of selected proteins.

Several commercially available recombinant antigens were tested and the majority found to be unsuitable for use in these selections due to the levels of aggregates present. Of those tested only the biotinylated, human secreted CD137, hFc-fusion protein (BPS Biosciences, catalogue no. 71171), designated 'hCD137-hFc-Avi-BPS' hereinafter, had sufficiently low aggregation to be suitable and was used in selections, though with limited success (see Example 2).

As the majority of commercially available antigens were deemed unsuitable, the following recombinant dimeric and monomeric CD137 antigens (see Table 1), were produced in-house for use in selections:

TABLE 1

CD137 Antigens

| Type | Designation | Species | Soluble or cell | Bio- tinylated | Antigen Format |
|---|---|---|---|---|---|
| Recombinant | mCD137-mFc-Avi | Mouse | Soluble | Yes | Dimer |
| Recombinant | mCD137-Avi-His | Mouse | Soluble | Yes | Monomer |
| Recombinant | hCD137-mFc-Avi | Human | Soluble | Yes | Dimer |
| Recombinant | hCD137-Avi-His | Human | Soluble | Yes | Monomer |
| Recombinant | cCD137-mFc-Avi | Cyno | Soluble | Yes | Dimer |

Monomeric antigens were produced by cloning DNA encoding the extracellular domain of the human (SEQ ID NO: 186) or mouse CD137 (SEQ ID NO: 188) along with an Avi sequence and six C-terminal histidine residues into modified pFUSE vectors (Invivogen cat no pfuse-mg2afc2) using EcoRI-HF and BamHI-HF restriction enzymes. The vectors were transfected into HEK293-6E cells (National Research Council of Canada), and expressed CD137 was purified using HisTrap™ excel nickel column (GE Life-Sciences 29048586) and size-exclusion chromatography (SEC) to ensure antigen was a single species and did not contain aggregates.

To produce the dimeric antigens, DNA constructs encoding the extracellular domain of the human, mouse or cynomolgus CD137 fused with the mIgG2a Fc domain along with an Avi sequence were cloned into modified pFUSE vectors and transfected into HEK293-6E cells. Recombinant CD137 was purified using MabSelect SuRe™ protein A column (GE Healthcare, 11003494) and size-exclusion chromatography (SEC) to ensure antigen was a single species and did not contain aggregates.

Each of the dimeric and monomeric antigens were biotinylated using a BirA biotin-biotin protein ligase reaction kit (Avidity LLC, BirA500) to produce monomeric CD137 antigens labelled with a single biotin molecule and dimeric CD137 antigens labelled with two biotin molecules, one per each of the two monomers. 3 mg of antigen was mixed with 7.8 µl BirA enzyme mix to a molar ratio of enzyme to substrate of 1:50. Additives were then added in accordance with the manufacturer's recommendations (142 µl Biomix A, 142 µl Biomix B, 142µ Biotin) and the reaction mix was incubated for two hours at room temperature. To maintain the integrity of the biotinylated protein, the reaction mix was immediately buffer exchanged to DPBS (Life Technologies 14190-169) using Amicon 30 µm filters (Merck Millipore UFC503096).

Proteins were further purified by SEC to ensure removal of the BirA enzyme and production of a final high quality monodispersed protein preparation with no high molecular weight aggregates. In more detail, materials from the same production lot were mixed together and analysed for stability and purity by size-exclusion high-performance liquid chromatography (SE-HPLC), SDS polyacrylamide gel electrophoresis (SDS-PAGE), and size-exclusion chromatography with multi-angle light scattering (SEC-MALS). Complete biotinylation of the proteins was confirmed in a streptavidin-shifting SDS-PAGE gel. The recombinant human and mouse antigens were confirmed to bind anti-CD137 positive-control antibodies (20H4.9 (U.S. Pat. No. 7,288,638)) and Lob12.3 (University of Southampton), respectively) in vitro by surface-plasmon resonance (SPR) and to DO11.10 cells expressing human and mouse CD137 ligand by flow cytometry. Cells were incubated with the CD137 antigens for 1 hour, and then a fluorescently-labelled anti mouse Fc fragment antibody was used to detect cell binding. The recombinant cyno antigen was confirmed to bind to DO11.10 cells (National Jewish Health) expressing cyno CD137 ligand by flow cytometry as described above. To ensure as high a purity as possible for the materials used in selection protocols, thorough protein characterisation of the antigens was performed to ensure the presence of protein aggregates did not exceed 2%.

1.2 Cell-Expressed CD137 Antigens

DO11.10 cells (National Jewish Health) expressing full-length mouse CD137 (SEQ ID NO: 187) or human CD137 (SEQ ID NO: 185), designated 'DO11.10.mCD137' and 'DO11.10.hCD137' respectively, were produced in order to present the antigen in a membrane-bound conformation, most similar to its natural form, for selections and further characterisation of selected Fcabs, as listed in Table 2.

Lentiviral transduction was used to generate these DO11.10 cells over-expressing human or mouse CD137 receptors using the Lenti-X HTX Packaging System (Clontech, catalogue no. 631249). Lenti-X expression vector (pLVX) (Clontech, catalogue no. 631253) containing cDNA encoding the human CD137 (SEQ ID NO: 185) or encoding the mouse CD137 (SEQ ID NO: 187) was co-transfected with a Lenti-X HTX Packaging Mix into the Lenti-X 293T Cell Line (Clontech, catalogue no. 632180) to generate virus. The DO11.10 cell line was then transduced with these lentiviral vectors.

Expression of human CD137 or mouse CD137 on these cells was confirmed by binding of 20H4.9 and Lob12.3 anti-CD137 positive control antibodies, respectively, to the cells by flow cytometry. Cells were incubated with the human or mouse positive control antibodies for 1 hour and then a fluorescently-labelled anti-human Fc detection antibody (Stratech Scientific Ltd, catalogue no. 109-546-098-JIR) was used to detect cell binding.

DO11.10 cells expressing cynomolgus CD137 (SEQ ID NO: 189), designated 'DO11.10.cCD137', were also generated using the same lentiviral transduction methodology and used to test cross-reactivity of anti-human CD137 Fcabs with cynomolgus CD137. Expression of cynomolgus CD137 was confirmed by binding of an anti-CD137 positive control antibody (MOR7480.1, US 2012/0237498 A1) to the cells by flow cytometry as described earlier.

TABLE 2

Cell-expressed CD137

| Type | Designation | Species | Presentation |
|---|---|---|---|
| Cell | DO11.10.hCD137 | Human | Cell-expressed |
| Cell | DO11.10.mCD137 | Mouse | Cell-expressed |
| Cell | DO11.10.cCD137 | Cyno | Cell-expressed |

1.3 CD4+ and Fc Tagged Mouse and Human PD-L1

Human and mouse PD-L1 antigens with fusion proteins were generated for use in antibody selections and screening. Antigens were expressed with either a C-terminal His tag as well as either a monomeric rat CD4+, domains 3 and 4 (rCD4) tag (Brown and Barclay, 1994), a dimeric human IgG1 Fc domain or, for human PD-L1 only, an Avi tag (resulting in hPD-L1-rCD4-His (SEQ ID NO: 195), hPD-L1-Fc-His (SEQ ID NO: 196), mPD-L1-rCD4-His (SEQ ID NO: 197), mPD-L1-Fc-His (SEQ ID NO: 198) and hPD-L1-His-Avi (SEQ ID NO: 199). The production of antigens in different formats enabled the elimination of tag binders during sequential rounds of antibody phage display panning. Expression plasmids encoding the antigens were transfected into HEK293 cells as described by Chapple et al., 2006. Supernatants were harvested 5 days after transfection and the secreted antigens were purified by Ni-NTA sepharose affinity chromatography (Schofield et al., 2007). rCD4 and Fc-containing PD-L1 antigens were biotinylated using EZ-link Sulfo-NHS-Biotin reagent (Thermo Fisher Scientific, product code 21326) following the manufacturer's recommendations. The biotinylation reaction product was gel filtered and the monomeric fraction was collected. The monomeric fraction was used for all solution-phase phage-display selections. The average number of biotins per molecule was 1 to 3 biotins per PD-L1 monomer as determined using Fluorescence Biotin Quantitation kit (Thermo Fisher Scientific, product code 46610).

Example 2: Selection and Characterisation of Anti-Human CD137 Fcabs 2.1 Naïve Selection of Anti-Human CD137 Fcabs In order to select Fcabs that bind to human CD137, yeast and phage display selection campaigns were employed, to maximise the diversity of Fcabs identified. Both cell surface displayed human CD137 and recombinant dimeric human CD137 and were used to provide a variety of antigen formats, in order to exert avidity-driven selection pressure against dimeric or multimeric CD137 proteins. Obtaining an Fcab which bound avidly to CD137 complexes rather than with high affinity to monomeric CD137 was deemed beneficial because such Fcab would preferentially target activated and primed T cells only, where upregulation of CD137 occurs after T cell stimulation. Without wishing to be bound by theory, it was hypothesised that T cells with very low or negligible levels of CD137 membrane expression would be more likely to have CD137 in monomeric state, unlike activated T cells with highly upregulated CD137 where most of the protein would be in dimeric, trimeric, or higher multimeric states. As a result of the avidity-driven selections, the Fcab would preferentially bind activated T cells and not bind well to naïve T cells that display only monomeric CD137. By selecting an avid CD137 Fcab potential off-targeted T cell activation would be reduced, with associated reduced toxicity.

Six naïve phage libraries displaying the CH3 domain of human IgG1 were used for selections by phage display. All six libraries comprised randomised AB loops (comprising residues at positions 14-18 according to IMGT numbering) and randomised EF loops (comprising residues at positions 92-101 according to IMGT numbering). One of the libraries comprised clones with an insertion of either two or four amino acids (encoded by two or four NNK codons) at position 101 in the EF loop (inserted residues are at positions 101.4-101.1 according to IMGT numbering).

3230 phage clones were screened by phage ELISA for binding to dimeric recombinant hCD137 antigen and recombinant Fc was used as a negative control. 1140 phage clones were screened by phage FACS for specific binding to DO11.10.hCD137 cells. Individual hits were then sequenced and the resulting 76 unique sequences were assigned an Fcab clone identifier and subcloned into a pTT5 expression vector (National Research Council of Canada) containing a HeID1.3 IgG1 heavy chain expression cassette for the purpose of expressing the Fcab clones in mAb$^2$ format (see Example 3.2).

Four naïve yeast libraries displaying CH1 to CH3 domains of human IgG1 were used for selection by yeast display. All four libraries comprised randomised AB loops (comprising residues at positions 14 to 18 according to IMGT numbering) and randomised EF loops (comprising residues at positions 92 to 101 according to IMGT numbering) in the CH3 domain. Two of the libraries further comprised an insertion of five amino acid residues at position 16 in the AB loop of the CH3 domain (residues at positions 16.5 to 16.1 according to IMGT numbering).

2784 yeast single clones identified from library selections were screened for antigen binding using a flow cytometry antigen binding assay that involved incubating the cells with biotinylated recombinant dimeric human antigen or mouse Fc fragment to discriminate against yeast clones binding to the Fc portion of the recombinant hCD137 antigen. Selections were repeated with varying antigen concentrations and conditions, such as increasing induction temperature, decreasing the selection stringency or reducing the number of rounds in order to increase the number of hits. Hit sequencing revealed considerably low output diversity, with only 9 Fcab clones having unique sequences identified: FS22-053, FS22-172, FS22-173, FS22-174, FS22-175, FS22-176, FS22-177, FS22-178 and FS22-179.

2.2 Preparation of Anti-Human CD137 Fcabs in "Mock" mAb$^2$ Format

"Mock" mAb$^2$ antibodies consisting of IgG1 molecules comprising the 76 anti-human CD137 Fcab clones isolated from phage and 9 clones isolated from yeast selections were produced to allow characterisation of the Fcabs in a mAb$^2$ format. The mock mAb$^2$ were prepared by substituting part of the CH3 domain Fcabs comprising the AB, CD and EF loops, for the corresponding region of the CH3 domain of the anti-hen egg lysozyme antibody HeID1.3. Generation of the HeID1.3 antibody is described in Tello et al. 1993. The heavy and light chain sequences of antibody HeID1.3 are shown in SEQ ID 191 and 159, respectively. The mock mAb² molecules were produced by transient expression in HEK293-6E cells. To assess the amount of protein produced, IgG protein content was quantified by BioLayer Interferometry using the Octet QKe platform with Protein A quantitation biosensors from PALL (18-5021). Proteins were purified by protein A affinity chromatography using mAb SelectSure columns. 53 phage-derived CD137 mAb² proteins presented measurements below the detection threshold and therefore determined to be unsuitable for further analysis. 32 mAb² were purified using mAb Select SuRe protein A columns (GE Healthcare, 11003494).

A selection of these mAb² were then tested for binding to human recombinant antigen (biotinylated hCD137-mFc-Avi) using BioLayer Interferometry (BLI) using the Octet QKe platform. 12 mAb² did not bind and 19 bound CD137-coated sensors (FS22-007, FS22-033, FS22-042, FS22-049, FS22-050, FS22-052, FS22-053, FS22-054, FS22-169, FS22-172, FS22-173, FS22-174, FS22-179, FS22-180, FS22-181, FS22-183, FS22-187, FS22-194, FS22-195).

2.3 Activity of Selected Anti-CD137 Mock mAb² in a Human NF-κB Reporter Assay

Multimerisation and clustering is required for TNFR signalling (Bitra et al., 2017). CD137 clusters and activates the NF-κB signalling pathway when it interacts with its cognate ligand, CD137L. Agonist molecules mimic the ligand in driving clustering and activation of CD137, thereby activating the NF-κB signalling pathway. It is known that some agonistic antibodies can inherently cause CD137 clustering upon binding for example, urelumab, whereas as others require additional crosslinking of the antibody itself to induce CD137 clustering, such as utomilumab (Fisher et al, 2012). Fc gamma receptors on effector cells are known to induce such crosslinking in vivo, though this is inefficient and may occur away from the site of therapeutic interest. Since dose limiting toxicities have been associated with urelumab but not utolimumab, it was decided to select for anti-CD137 binding Fcabs which did not have the ability to inherently agonise, but to select only those that required additional crosslinking in order to induce CD137 clustering. Therefore, an assay that can detect the activation of the NF-κB signalling pathway in a cell upon clustering of CD137 expressed on the cell surface by cross-linked antibodies, but that showed little activity when the antibodies were not crosslinked, was developed. This assay was then used to test the agonistic functional activity of 27 anti-CD137 Fcab clones in mock mAb² format, and 6 anti-CD137 Fcab clones in anti-CD20 mAb² format, irrespective of whether the Fcabs were found to bind recombinant antigen by BLI or not.

This can be measured by activation of the NF-κB signalling pathway in the assay. Protein L was used as a crosslinking agent to drive cross linking of the mock mAb² via the Fab portions in the assay and NF-κB activation was measured.

cDNA encoding human CD137 (SEQ ID NO: 185) was subcloned into pMSCV-neomycin vector (Takara Clontech, Cat. 634401) using EcoRI-HF and XhoI restriction enzymes. RetroPack PT67 cell line (Clontech, Cat. 631510) was used to produce retroviral particles following the manufacturer's protocol. This retro virus was subsequently used to transduce HEK.FRT.luc cells that were previously generated by transducing a FIp-In T-REx 293 HEK cell line (Life Technologies, R780-07) with Qiagen Cignal Lenti NFkB Reporter (luc) (Qiagen, cat no 336851) lentivirus containing a NF-κB-sensitive promoter controlling the expression of luciferase. These HEK.FRT.luc.hCD137 cells were used to screen the mock mAb² containing the CD137 binders identified in selections.

A 2 μM dilution of each mock mAb² was prepared in DPBS (Life Technologies, 14190169) and further diluted 1:3 in reporter cell medium (DMEM (Gibco, Cat. 61965-026); 10% FCS (Gibco, Cat. 10270-106); 1× PennStrep (Gibco, Cat. 15140-122); Blasticidin 15 μg/ml (Melford Laboratories Ltd. Cat. B1105); Puromycin 5 μg/ml (Life technologies, Cat. A11113803); Zeocin 100 μg/ml (InvivoGen, Cat. 11006-33-0); Geneticin 500 μg/ml (Life Technologies, Cat. 10131-027). Protein L (Life Technologies, 21189), was used as an artificial crosslinking agent and was mixed with the mAb² molecules in a 1:4 molar ratio. After a 24-hour incubation, cells were treated with 100 μl Promega Bio-Glo™ juciferase assay reagent (Promega cat no G7941) according to manufacturer's instructions and luminescence was measured with an integration time of 0.5 seconds on a plate reader with the Gen5 Software, BioTek. Luminescence values are a measure of the luciferase produced in response to the activation of the NF-κB signalling pathway by the clustering of CD137 induced by crosslinked Fcabs. The luminescence values were plotted versus the log concentration of Fcab and the resulting curves were fitted using the log (agonist) vs response equation in GraphPad Prism.

Hits were identified by having at least a 10-fold increase in luciferase signal when crosslinked with protein L as compared to when not crosslinked. These clones were determined to be capable of inducing CD137 clustering and subsequent activation of downstream signalling pathways. Of all clones tested, two were able to induce this 10-fold increase in luciferase on crosslinking, FS22-053 and FS22-172, though an $EC_{50}$ could not be determined for either. Both were selected for further characterisation in a DO11.10 T cell activation assay. Surprisingly, activity was not observed for the remaining clones in crosslinked conditions despite binding to CD137 target by BLI, perhaps indicating they were binding at an irrelevant epitope on CD137, or that the affinity of such clones was not sufficient to bind CD137 strongly enough to initiate the NF-κB signalling cascade. Overall, while more than 30 Fcabs were tested, only two Fcabs (FS22-053 and FS22-172) were identified from the naïve selections which exhibited the desired function in the NF-κB reporter assay when crosslinked and had little activity when not crosslinked.

2.4 Activity of the Selected Anti-CD137 Mock mAb² in a DO11.10 T Cell Activation Assay CD137 clustering via agonist molecules on activated T cells elicits T cell activation and downstream signalling resulting in, but not limited to, IL-2 production. Since FS22-053 and FS22-172 were identified as having activity in the NF-κB reporter assay, their ability to activate CD137 was tested in a T cell activation assay. A DO11.10 T cell activation assay using DO11.10 T cells engineered to overexpress human CD137 was developed and T cell activation was assessed by measuring IL-2 release.

DO11.10 T cells (National Jewish Health) were transduced with a lentiviral vector designed to overexpress mouse or human CD137 as described earlier. As well as FS22-053 and FS22-172, the following clones were tested in this DO11.10 T cell activation assay: FS22-007, FS22-033, FS22-042, FS22-049, FS22-050, FS22-052, FS22-054, (all in "mock" HeID1.3 mAb² format). Dilutions of mAb² or 20H4.9 positive control mAb either with or without recombinant Protein L (Life Technologies, 21189) crosslinker were prepared and added to DO11.10.hCD137 cells in a 96 well round bottom plate that had been coated overnight with 0.1 µg/ml anti-CD3 antibody (clone 17A2, BioLegend, 100208). After an 18-hour incubation, supernatants were collected and assayed with mouse IL-2 ELISA kit (eBioscience, 88-7024-86) following the manufacturer's instructions. Plates were read at 450 nm using the plate reader with the Gens Software, BioTek. Absorbance values of 570 nm were subtracted from those of 450 nm (Correction). The standard curve for calculation of cytokine concentration was based on four parameter logistic curve fit (Gens Software, BioTek). The concentration of mIL-2 was plotted vs the log concentration of mAb$^2$ or benchmark mAb and the resulting curves were fitted using the log (agonist) vs response equation in GraphPad Prism.

Clones FS22-053 and FS22-172 showed significantly enhanced activity when crosslinked with Protein L in this assay. FS22-053 had an activity of 126 nM when not crosslinked and an activity of 21 nM when crosslinked (an improvement of 6-fold), while FS22-172 had an activity of 950 nM when not crosslinked and an activity of 44 nM when crosslinked (an improvement of 22-fold). As a result, both clones were selected for affinity maturation.

Example 2.4 shows that FS22-053 and FS22-172 could drive clustering and activation of CD137 on the surface of DO11.10 T cells when crosslinked by Protein L in the mAb$^2$ formats tested.

Example 3: Affinity Maturation of Anti-Human CD137 Fcabs and Subsequent Characterisation As previously discussed, two clones were selected for affinity maturation based on their functional characteristics in the NF-κB reporter assay, DO11.10 T cell activation assays FS22-053 and FS22-172).
3.1 Affinity Maturation of FS22-053 and FS22-172

Four yeast displayed libraries were constructed from the FS22-053 and FS22-172 Fcab clones. Seven residues (at positions 15-16.1 according to IMGT) were randomised using ELLA primers in the AB loop of the CH3 domain of each clone to make libraries FS22-053 AB and FS22-172 AB. Five residues (at positions 92-94 and 97-98 according to IMGT) were randomised using ELLA primers in the EF loop of the CH3 domain resulting in libraries FS22-053 EF and FS22-172 EF.

For libraries FS22-053 AB and FS22-053 EF, and FS22-172 AB and FS22-172 EF, three or four selection rounds were performed on the yeast libraries to select for affinity matured clones using either dimeric hCD137-mFc-Avi antigen or monomeric hCD137-Avi-His antigen. Monomeric antigen was used in alternation with dimeric antigens to ensure clones retained affinity to the antigen and did not bind exclusively through avidity. The use of monomeric or dimeric antigen, as well as the concentration used was determined empirically during each round by flow cytometry, determined by whether enrichment against the monomeric or dimeric antigen was observed in the previous round. Whenever possible, a sorting gate above the parental was used to isolate affinity matured clones compared to the parental molecule. Selection pressure was increased up to 1 nM of dimeric antigen. During each selection round, individual clones were spotted on agar plates to assess the progress of the selection. Each clone was grown and induced individually and next its binding and structural parameters were determined by flow cytometry using biotinylated dimeric antigen as well as anti-CH2 structural markers as described earlier. This screening cascade was followed to allow the determination of selection success based on a sample of clones from the selection output and to allow for early screening of individual clones that could be subsequently produced as soluble proteins.

1152 yeast single clones in total were screened for binding to biotinylated recombinant antigen in an antigen binding flow cytometry as described earlier. Selections on the FS22-053 EF library resulted in enrichment of 138 unique loop sequences. Likewise, 30 unique loop sequences were isolated from the FS22-172 AB library. Libraries FS22-053 AB and FS22-172 EF did not contain any clones which showed any binding improvement over the parental clones. Sequence analysis across the best-binding clones from the FS22-053 EF and FS22-172 AB libraries revealed a conserved PPY sequence pattern in the AB loops. The presence of a conserved PPY motif may promote the formation of an extended binding region by introduction of a more rigid or exposed loop based upon the limited flexibility of proline residues. Alternatively, the PPY sequence may represent a specific conserved motif involved in binding for these clones as Proline rich sequences have been demonstrated to bind to aromatic sequences in SH3 domain proteins. Further, since the PPY conserved sequence has been selected for independently in two separate lineages of Fcabs, it may be important for epitope binding on CD137. Additionally, a conserved LE or LD sequence pattern in the EF loops of the CH3 domain of the clones of both the FS22-053 and FS22-172 lineages, which suggests this amino acid motif in the EF loop is required for improved binding.

In order to assess the progress of the selections and whether it would be necessary to recombine mutated AB and EF loops between affinity matured clones, the top five unique clones from the FS22-053 EF library (FS22-053-008, FS22-053-009, FS22-053-010, FS22-053-011, FS22-053-012) ranked by presenting specific binding to 10 nM dimeric human antigen (higher than 30% APC positive cells in a flow cytometry binding assay), and the top six unique clones from the FS22-172 AB library (FS22-172-001, FS22-172-002, FS22-172-003, FS22-172-004, FS22-172-005, FS22-172-006, all showing above 10% APC positive cells when screened with 10 nM dimeric human antigen in the same assay) were produced as mock mAb$^2$ (HelD1.3) and model mAb$^2$ (PD-L1) to assess functional and kinetic improvement of the randomised loops.
3.2 Construction of Anti-Human CD137 Fcabs in "Mock" and "Model" mAb$^2$ Format 16 affinity matured clones derived from the parental FS22-053 clone (FS22-053-001 to FS22-053-016), and 6 affinity matured clones derived from the parental FS22-172 clones (FS22-172-001 to FS22-172-006) were prepared in "mock" and "model" mAb$^2$ format. Clones FS22-053-001 to FS22-053-007 were not further pursued as they did not express in mAb$^2$ format at a level that allowed downstream purification for further testing and characterisation.

"Mock" mAb$^2$ antibodies comprising the anti-human CD137 Fcabs in HelD1.3 were prepared for further characterisation of the affinity matured Fcabs in mAb$^2$ format. These mAb$^2$ were prepared as described in Example 2.2.

"Model" mAb$^2$ were also produced comprising the anti-human CD137 Fcabs and also a PD-L1 binding Fab region (clone YW243.55.S70 from U.S. Pat. No. 8,217,149 B2). These were prepared in a similar manner to the method described in Example 2.2 by substitution of part of the CH3 of the anti-PD-L1 binding antibody containing the AB, CD and EF loops with the corresponding region of the Fcab. These PD-L1 model mAb$^2$ comprised a LALA mutation in the CH2 domain (AA). The introduction of the LALA mutation in the CH2 domain of human IgG1 is known to reduce Fc γ receptor binding (Bruhns, P., et al. (2009) and Hezareh M., et al. (2001)).

The CD137/HeID1.3 "mock" and CD137-AA/PD-L1 "model" mAb$^2$ were produced by transient expression in HEK293-6E cells and purified using mAb Select SuRe protein A columns.

3.3 Activity of Human Fcabs in Mock mAb$^2$ Format in Human NF-κB Reporter Cell Assay The functional activity of the affinity-matured anti-human CD137 Fcabs in mock mAb$^2$ (HeID1.3) format listed was tested in the same NF-κB luciferase assay described in Example 2.3. Luminescence was measured with an integration time of 0.5 seconds in a plate reader with the Gen5 Software, BioTek. As expected, none of the Fcabs showed activity without Protein L crosslinking (−XL). All affinity-matured CD137 Fcabs showed a vast improvement over parental CD137 Fcabs for which, while positive in this assay, calculation of an $EC_{50}$ value was not possible (see Example 2.3). FS22-053-008 and FS22-172-003 showed the best activity from each family with the lowest $EC_{50}$ (26.34 nM and 32.64 nM, respectively) when crosslinked with Protein L (+XL).

3.4 Activity of Affinity Matured Human Fcabs in Model mAb$^2$ Format in Human DO11.10 T Cell Activation Assay The functional activity of the affinitymatured human Fcabs in model mAb$^2$ (PD-L1 LALA) format was tested in a DO11.10 T cell activation assay, similar to the assay as described in Example 2.4.

HEK.mPD-L1 cells were produced by subcloning cDNA encoding mouse PD-L1 (SEQ ID NO: 187) into pcDNA5FRT vector (Life Technologies) using KpnI and NotI restriction sites and transforming the vectors into the FIp-In T-REx 293 cell line (Life Technologies, R780-07) using Lipofectamine 2000 (Life Technologies, 11668-019). Cells were grown in DMEM containing 10% FBS, 100 µg/ml Hygromycin B (Melford Laboratories Ltd, Z2475) and 15 µg/ml Blasticidin (Melford Laboratories Ltd, B1105) for 3-4 weeks until colonies of stably transformed cells had formed. These colonies were amplified in the presence of 1 µg/ml Doxycyclin (Sigma Aldrich, D9891) and tested for expression of PD-L1 using PE conjugated anti-mouse PD-L1 (MIH5) antibody (BD Biosciences, 558091).

Cells were detached using cell dissociation buffer, washed once with PBS and 2×10$^5$ cells were plated in wells of a 96-well plate and then incubated with antibody diluted 1:20 in PBS for 1 hour at 4° C. Cells were washed once in PBS and then measured on an Accuri C6 cytometer (BD Biosciences) and the data was analysed using FlowJoX. Expression of mouse PD-L1 was again confirmed.

The 15 clones produced in Example 3.2 in CD137/PD-L1 mAb$^2$ were tested in this DO11.10 T cell activation assay. Dilutions of mAb$^2$ or positive control mAb were prepared and added to either DO11.10.hCD137 (7.5×10$^3$ cells per well) and HEK.mPD-L1 cells (2×10$^4$ cells per well) or to Do11.10.hCD137 (7.5×10$^3$ cells per well) and HEK cells that were not transduced to express mPD-L1 (2×10$^4$ cells per well) in a 96 well flat bottom plate that had been coated overnight with 0.1 µg/ml anti-CD3 antibody (clone 17A2, BioLegend, 100208). After an 18-hour incubation, supernatants were collected and assayed with mouse IL-2 ELISA kit (eBioscience, 88-7024-86) following the manufacturer's instructions. Plates were read at 450 nm using the plate reader with the Gens Software, BioTek. Absorbance values of 570 nm were subtracted from those of 450 nm (Correction). The standard curve for calculation of cytokine concentration was based on four parameter logistic curve fit (Gens Software, BioTek). The concentration of mIL-2 was plotted vs the log concentration of mAb$^2$ or benchmark mAb and the resulting curves were fitted using the log (agonist) vs response equation in GraphPad Prism. T cell activation was detected by measuring the release of mIL-2.

No T cell activity was observed without crosslinking by binding to PD-L1 expressing cells. Upon crosslinking, all mAb$^2$ had potent T cell activity as seen by the release of high levels of mIL-2 and sub-nanmolar $EC_{50}$ values. All clones other than FS22-053-009 and FS22-172-005, had an $EC_{50}$ of less than 0.3 nM so were as good as, if not better than the positive control (anti-human CD137 mAb, G1-AA/20H4.9). The lowest $E_{max}$, which is a measure of maximum T cell activation, and might be relevant to greater T cell anti-tumour activity in vivo, observed was 7758 µg/ml which was higher than the positive control (anti-human CD137 mAb, G1-AA/20H4.9).

3.5 Primary Human CD8$^+$ T Cell Activation Assay

The ability of the Fcabs to activate CD137 on T cells overexpressing CD137 was shown in Example 3.3. To test the activity of the Fcabs on cells which have not been engineered to overexpress CD137, a primary human T cell assay was needed. Activated cytotoxic CD8$^+$ T cells are responsible for directly killing cancer cells and express CD137 on their cell surface (Ye et al, 2014). Clustering of CD137 is known to be essential to induce downstream signalling and further CD8$^+$ T cell activation. A CD8$^+$ T cell activation assay was therefore used to assess the ability of Fcabs (in mAb$^2$ format as detailed below) to drive clustering and subsequent downstream signalling of CD137. CD8$^+$ T cell activation was determined by the release of hIL-2.

To isolate T cells, peripheral blood mononuclear cells (PBMCs) were collected from leucocyte depletion cones, a by-product of platelet donations. Briefly, leucocyte cone contents were flushed with PBS and overlaid on a Ficoll (Sigma-Aldrich, 1440-02) gradient. PBMCs were collected by centrifugation and the cells that did not cross the Ficoll gradient were recovered. PBMCs were further washed with PBS and remaining red blood cells were lysed through the addition of 10 ml 1× red blood cell lysis buffer (eBioscience, 00-4300-54) according to the manufacturer's instructions. CD8$^+$ T cells were isolated from the PBMCs present in the eluant using the CD8$^+$ T cell isolation kit II (Miltenyi Biotec Ltd, 130-096-495) according to the manufacturer's instructions.

Incubation with an anti-CD3 antibody was used as a first signal to drive initial activation of the T cells. 96-well flat bottom tissue culture plates were coated with 8 µg/ml anti-CD3 antibody (Clone UCHT1, R&D Systems, MAB100-SP) in PBS overnight at 4° C. The plates were then washed 3 times with 200 µl PBS.

For cell-based crosslinking of affinity matured human CD137 Fcabs in PD-L1 model mAb$^2$ format, HEK293 cells overexpressing human PD-L1 (HEK.hPD-L1) were produced essentially as described in Example 5.3 but by subcloning cDNA encoding the human PD-L1 sequence (SEQ ID NO: 185) instead of mouse PD-L1. HEK.hPD-L1 cells were plated at 2×10$^5$ cells per well on to anti-CD3 antibody-coated (8 µg/ml) 96 well flat bottom plates in 100 µl T cell culture medium (RPMI medium (Life Technologies, 61870-044) with 10% FBS (Life Technologies), 1× Penicillin Streptomycin (Life Technologies, 15140122), 1 mM Sodium Pyruvate (Gibco, 11360-070), 10 mM Hepes (Sigma-Aldrich, H0887), 2 mM L-Glutamine (Sigma-Aldrich, G7513) and 50 µM 2-mercaptoethanol (Gibco, M6250)). Once HEK.hPD-L1 cells or HEK cells that were not transduced to express hPD-L1 had adhered after 4 hours incubation, all T cell culture medium was removed and replaced with 100 μl T cell culture medium containing T cells at a concentration of 5.0×10⁵ cells/ml resulting in 5.0×10⁴ cells/well.

mAb² were diluted in T cell medium at a 2× final concentration starting at 500 nM and a 1:3 titration was carried out. 100 μl of mAb² titration was added to the cells for a total assay volume of 200 μl and 1× concentration of antibody.

Positive control anti-CD137 antibody (Gi-AA/20H4.9) and negative control isotype IgG antibody (G1-AA/HelD1.3) were each diluted in T cell medium at a 2× final concentration starting at 500 nM containing 500 nM crosslinking agent (anti-human CH2, produced in house (Jefferis et al., 1985 and Jefferis et al., 1992) (mG1/MK1A6)) and a 1:3 titration was carried out. 100 μl of diluted positive control antibody/crosslinker mix or negative control IgG antibody/crosslinker mix was added to the cells for a total of 200 μl assay volume and 1× concentration of antibody.

The assay was incubated at 37° C., 5% $CO_2$ for 72 hours. Supernatants were collected and assayed with human IL-2 ELISA Ready-SET-Go! kit (eBioscience, Cat. 88-7025-88) following the manufacturer's instructions. Plates were read at 450 nm using the plate reader with the Gen5 Software, BioTek. Absorbance values of 630 nm were subtracted from those of 450 nm (Correction). The standard curve for calculation of cytokine concentration was based on a four-parameter logistic curve fit (Gen5 Software, BioTek). The concentration of human IL-2 (hIL-2) was plotted vs the log concentration of antibody and the resulting curves were fitted using the log (agonist) vs response equation in GraphPad Prism.

The positive control anti-human CD137 mAb, 20H4.9, shows an increase in hIL-2 release with an $EC_{50}$ of 0.5 nM when crosslinked with the anti-hCH2 antibody (mG1/MK1A6). All clones had activity in the assay, the majority displaying good potency with sub-nanomolar $EC_{50}$ s. mAb² containing Fcabs FS22-053-007, FS22-053-008, FS22-053-010, FS22-053-011, FS22-053-012, FS22-172-003, FS22-172-004, FS22-172-005 elicited the greatest T cell response with the lowest $EC_{50}$s in the range of 0.19- to 0.49 nM. A subset of the mAb² (containing Fcabs FS22-053-008, FS22-053-011, FS22-053-014, FS22-173-003 and FS22-172-004) were also tested without crosslinking by PD-L1 expressed on HEK cells and showed no activity in this assay, as expected. This confirms activity seen in the NF-kB assay and DO11.10 T cell activation assay.

3.6 Specificity Determination of Anti-Human CD137 Fcabs by Surface Plasmon Resonance (SPR)

The specificity of the anti-human CD137 Fcabs for human CD137 compared to other related TNFSFR family members was tested. 8 of the Fcabs were tested in mock mAb² (HelD1.3) format and measured by SPR in a Biacore T200 (GE Healthcare) by testing for binding to other human TNFRSF receptors: CD40, OX40 and GITR. Amine coupling (amine coupling kit, GE Healthcare, BR-1000-50) was used to coat human CD40, GITR and OX40 to approximately 1000 RU in Biacore CM5 chips (GE Healthcare, cat no 29149603). Dilutions of anti-human CD137 Fcabs in mock mAb² format (FS22-053-008/HelD1.3, FS22-053-009/HelD1.3, FS22-053-010/HelD1.3, FS22-053-011/HelD1.3, FS22-053-012/HelD1.3, FS22-053-014/HelD1.3, FS22-172-003/HelD1.3, FS22-172-004/HelD1.3) starting at 1 μM were prepared in HBS-EP+ buffer (BR100669) and injected for 3 min at 30 μl/min and then allowed to dissociate in buffer for 4 min. The chip was regenerated by injection of 10 mM glycine pH 2.5 for 12 s at 30 μl/min. Antibodies specific to the different TNFRSF members were used as positive controls to verify Biacore chip coating. Data was double reference subtracted and analysed using BIAevaluation 3.2 software. The Fcabs did not bind to any of the TNFRSF receptors tested, demonstrating their specificity for CD137. As a result, it is not expected that the Fcabs, or mAb² comprising the antigen-binding sites from these Fcabs, will elicit off-target binding to anything other than CD137.

3.7 Binding Affinity of Anti-Human CD137 Fcabs in Mock mAb² Format for Human, Cynomolgus and Mouse CD137 by SPR and Generation of FS22-053-017

The affinity of the anti-human CD137 Fcabs (FS22-053-008, FS22-053-011, FS22-053-014, FS22-172-004, FS22-172-004) in a mock mAb² format (see Example 3.2) for human, cynomolgus (cyno) and mouse CD137 was measured by SPR, to determine whether the Fcabs may be useful for testing in animal studies. An anti-human Fab capture antibody was immobilised on all four flow cells of a CM5 series S chip (GE Healthcare #BR-1005-30) to an average surface density of 6000 RU following the manufacturer's recommendations (GE Healthcare, human Fab capture Kit, #28958325). Immobilization at 25° C. and 10 μl/min flow rate achieved an average final response of 6000 RUs. Each mAb² was captured to approximately 150 RU by injecting a 3 μg/ml solution of mAb² diluted in HBS-EP+ buffer (GE Healthcare #BR1006-69) for 60 seconds at 30 μl/min. Then different concentrations of human, cyno or mouse CD137 antigen (unbiotinylated human, cyno or mouse CD137-mFc-Avi or human CD137-Avi-His) in HBS-EP+ buffer were flowed over the chip for 3 min at 60 μl/min and then allowed to dissociate for 10 minutes. After each antigen concentration the chip was regenerated by infecting 10 mM glycine pH 2.1 at a flow rate of 30 μl/min for 30 seconds. Buffer HBS-EP+ was injected before the highest concentration of antigen and after the lowest concentration of antigen for reference subtraction, and one of the concentrations at random was repeated twice. The binding kinetics were fit with a 1:1 Langmuir model to generate equilibrium binding constants ($K_D$) for each sample. Data analysis was performed with BiaEvaluation software version 3.2. The results are shown in Table 3.

Analysis of the results revealed an improved binding for both human and cynomolgus CD137 by all affinity matured clones, compared to the respective parent molecules. The binding affinity for the monomeric human CD137 antigens was weaker (by at least 100-fold) than for the dimeric human and cyno Fc-fusion antigens. As discussed in Example 2.1, the Fcabs were selected to preferentially bind to dimeric over monomeric forms of CD137 and this data confirms that the selection strategy was successful. This kinetic behaviour makes them less likely to bind to monomeric CD137 expressed at minimal levels on unstimulated T cells to result in reduced risk of liver or systemic toxicities associated with some anti-CD137 monoclonal antibody therapies.

The data also shows that the anti-human CD137 Fcabs bound to cynomolgus dimeric CD137 with comparable affinity to human dimeric CD137.

TABLE 3

| Fcab | Human dimeric CD137 $K_D$ (nM) | Cynomolgus dimeric CD137 $K_D$ (nM) | Human monomeric CD137 $K_D$ fold difference relative to human dimeric $K_D$ | Mouse dimeric CD137 $K_D$ (nM) |
| --- | --- | --- | --- | --- |
| FS22-053 | 38 | 34 | N/A | N/A |
| FS22-053-008 | 4.2 | 0.9 | 170-fold | N/A |
| FS22-053-011 | 5.5 | 1.3 | >200-fold | N/A |
| FS22-053-014 | 3.2 | 0.9 | 100-fold | 24 |
| FS22-172 | 52 | 203 | N/A | N/A |
| FS22-172-003 | 1.5 | 1.3 | >200-fold | N/A |
| FS22-172-004 | 4.3 | 3.5 | >200-fold | N/A |

N/A-not applicable as low signal did not allow $K_D$ determination

The ability of the Fcabs in a mock mAb² format to bind to mouse dimeric CD137 was also tested. None of the clones showed strong binding to the mouse antigen (as shown in the table where N/A indicates that no $K_D$ could be calculated) except for clone FS22-053-014 which was surprisingly found to have a $K_D$ of 24 nM for the mouse antigen. This was unexpected since mouse CD137 and human CD137 share less than 57% sequence homology.

Sequence analysis of FS22-053-014 revealed a potential sequence liability that could result in a post-translational aspartate isomerisation at position 98 in the EF loop of its CH3 domain. The aspartate (D) at position 98 was mutated to glutamate (E) by site-directed mutagenesis using the QuickChange II mutagenesis kit (Agilent, catalogue no. 200523) according to the manufacturer's recommendations, which yielded clone FS22-053-017.

Experiments were then carried out to confirm that this mutation did not negatively affect the binding affinity or functional activity of the FS22-053-017 clone as compared to the FS22-053-014 clone.

The equilibrium dissociation constant ($K_D$) of Fcab clone FS22-053-017 was compared to that of clone FS22-053-014 by SPR on a Biacore T200 system using the human CD137-mFc-Avi antigen and mouse PD-L1-mFc-Avi, respectively. The results showed very similar kinetic profiles to human antigen for both Fcab clones, thereby evidencing that mutating the aspartate at position 98 to a glutamate did not have a negative effect on binding to the human antigen. The results also showed that FS22-053-017 showed a 2-fold decrease in binding strength to the mouse CD137 antigen.

Fcab clone FS22-053-017 was sub-cloned and expressed as a HeID1.3 "mock" mAb² (see Example 2.2) and then compared to the FS22-053-014 clone, also in HeID1.3 mAb² format, in a human CD137 DO11.10 T cell activation assay as described in Example 2.4. G1-AA/20H4.9 was used as an anti-CD137 positive control and G1-AA/HeID1.3 as an IgG control. The mAb² were tested either without Protein L crosslinking or were crosslinked in a 1:4 ratio with Protein L.

The results showed that both FS22-053-17 Fcab in mock mAb² format FS22-053-014 Fcab in mock mAb² format had comparable activity when crosslinked by Protein L in the same DO11.10 T cell activation assay. Therefore, the mutagenesis carried out did not negatively impact functional activity. Both clones in mock mAb² format had no activity without crosslinking.

3.8 Summary of Affinity Maturation and Characterisation of Anti-Human CD137 Fcabs In summary, affinity matured anti-CD137 Fcabs were generated and prepared in a mAb² format, which were then characterised. mAb² containing these CD137 antigen-binding domains in the CH3 domain showed high levels of activity in a human NF-κB Reporter Cell assay and this activity was shown to be crosslink dependent. mAb² containing the antigen-binding domain from the FS22-053-008 and FS22-172-003 Fcabs showed the best activity in this assay.

Additionally, it was shown that when the mAb² were prepared from these Fcabs, such that they contained the CD137 antigen-binding domain and a PD-L1 binding Fab region as well as the LALA mutation in their CH2 domain to reduce or abrogate binding to Fcγ receptors, then the mAb² had potent T cell activity in a human DO11.10 T cell activation assay and this activity was shown to be dependent on crosslinking by binding to PD-L1 expressing cells. The mAb² were also shown to have crosslink-dependent activity in a primary human CD8⁺ T cell activation assay, providing further evidence that the mAb² containing these affinity matured CD137 antigen-binding domains are able to effectively induce agonism of CD137 and that this agonistic activity is conditional on crosslinking.

The mAb² containing the anti-human CD137 antigen-binding domain were also shown to be specific for CD137 and did not bind to other TNFRSF members. The mAb² were shown to preferentially bind human dimeric CD137 antigen over monomeric human CD137 antigen. Finally, these mAb² were shown to bind dimeric cynomolgus CD137 with comparable affinity to dimeric human CD137.

One Fcab clone, FS22-053-014, was surprisingly found to also be able to bind mouse CD137. Sequence analysis of the FS22-053-014 revealed a potential sequence liability, which was corrected by side directed mutagenesis to produce the FS22-053-017 clone. Characterisation of the FS22-053-017 revealed that it retained similar binding properties and showed similar functional activity in a human CD137 DO11.10 T cell activation assay as FS22-053-014.

Having demonstrated that mAb² containing the anti-human CD137 antigen-binding domain require crosslinking in order to cluster and activate CD137, the next aim was to prepare a mAb² that binds human PD-L1 in addition to CD137. It was hypothesised that binding of the mAb² to human PD-L1 via the Fab arms would cause crosslinking of the antibody molecules, which in turn would lead to clustering and activation of CD137 and that this activation would be dependent on the presence of human PD-L1 expression.

In order to prepare mAb² that bind human PD-L1 in addition to CD137, it was first necessary to generate mAbs that were able to bind PD-L1. The generation of these mAbs is described below.

Example 4: Isolation of Naïve Anti-PD-L1 mAb 280 02 G02

4.1 Selections

The "IONTAS 1" human antibody phage display library (IONTAS Ltd.) was employed to select for anti-PD-L1 clones. The antibody genes used to construct the IONTAS 1 library were derived from human lymphocytes (42 buffy coat donations) and one tonsil tissue sample. Both the buffy coats and tonsil tissue were obtained under Local Research Ethical Committee approval.

Three rounds of solid phase selections were performed with the IONTAS 1 antibody phage display library using antigen that was directly coated onto polystyrene Nunc tubes as described by Schofield et al, 2007. The first, second and third selection rounds employed human PD-L1-Fc-His, mouse PD-L1-rCD4-His and human PD-L1-Fc-His, respectively (see Example 1.3 for antigen details).

The selected variable heavy (VH) anti-PD-L1 antibody population was shuffled with a naïve variable light (VL) antibody population as described by Dyson et al., 2011, and this shuffled, rescued, antibody-phage-display population was employed in solution phase selections. Briefly, panning was performed with human PD-L1-rCD4-His (10 nM), human PD-L1-rCD4-His (200 µM) and mouse PD-L1-rCD4-His (10 nM) at rounds 1, 2 and 3, respectively, and this resulted in an output anti-PD-L1 scFv population termed "Selection 280". This scFv population contained human and mouse anti-PD-L1 binding scFvs, as determined by a phage polyclonal ELISA performed as described by Dyson et al., 2011, and displayed minimal cross-reactivity with human PD-1 or with rCD4 or Fc tags.

4.2 Screening: ELISA, Recombinant Blocking Assay, Cell-Based Blocking Assay 4.2.1 Monoclonal scFv ELISA The Selection 280 scFv population from Example 4.1 was screened by ELISA to identify the clones which bound best to human PD-L1. The scFv population was subcloned into the soluble scFv vector pSANG10 and *E. coli* cultures containing soluble scFvs were prepared as described (Martin et al., 2006; Studier, 2005). Soluble scFv were then used in a monoclonal ELISA with immobilised human PD-L1-rCD4-His as described by Schofield et al., 2007. Nunc Maxisorp plates (Thermo Fisher Scientific, 437111) were coated with human PD-L1-rCD4-His (5 µg/ml, PBS) overnight, blocked with 2% MPBS for 1 hour and the *E. coli* culture supernatant (1:2 dilution with 2×2% MPBS) was added and scFv were allowed to bind for 1 hour at room temperature. Bound scFv were detected with anti-FLAG M2 antibody (Sigma, F1804) labelled with europium. A total of 470 clones were screened and this resulted in the identification of 346 anti-PD-L1 clones with a binding signal for PD-L1 at least 10-fold above background compared with "empty" blocked wells containing no antigens. The 192 best anti-human PD-L1 clones assessed by primary ELISA signal were selected for further analysis.

4.2.2 Screening scFv in ELISA-Based PD-L1/PD-1 Blocking Assay

To identify clones that blocked the interaction between PD-L1 and PD-1, an ELISA was performed to screen for blocking scFvs. Briefly, nunc maxisorp plates (437111, Thermo Fisher Scientific) were coated with anti-rCD4 (domains 3 and 4) antibody (MCA1022, OX-68, Bio-Rad) overnight, blocked with 3% MPBS and incubated with human PD-1-rCD4-His (5 µg/ml in 3% MPBS) for 1 hour at room temperature. Human PD-L1-Fc-His (50 µl, 0.2 nM), was pre-mixed with *E. coli* culture supernatant containing scFv. The Nunc 96-well plates were washed 3 times with PBS, 0.1% Tween™-20 (PBS-T) and 3 times with PBS, then the human PD-L1-Fc-His/scFv mix was added and incubated for 1 hour at room temperature. The plates were washed and bound human PD-L1-Fc-His was detected using goat-anti-Fc-biotin (Jackson ImmunoResearch, 109-065-098, Laboratories, 0.1 µg/ml, 3% MPBS) and Streptavidin-Europium (Perkin Elmer, 1244-360) followed by DELFIA enhancement solution (Perkin Elmer, 4001-0010). Of 192 clones screened, 183 displayed at least 90% blocking activity compared with the medium control. The 183 anti-PD-L1 scFv clones identified were screened further for mouse PD-L1 cross-reactivity in a primary ELISA, as described in Example 4.2.1 above, but using immobilised mouse PD-L1-rCD4-His instead of human PD-L1. This identified 50 mouse cross-reactive anti-PD-L1 clones, which were candidates for conversion to IgG1 format.

4.2.3 Conversion of Blocking Anti-PD-L1 scFv Clones to IgG1 Format

The anti-PD-L1 scFv clones which blocked the interaction between PD-L1 and PD-1 were converted to IgG1 format by sub-cloning the VL and VH genes into the IgG1 expression plasmid pINT3-IgG1 and expressed in HEK293 at 4 ml scale as described by Chapple et al., 2006. The antibodies were batch affinity purified with Protein A sepharose beads (PC-A100) and *Proteus* "1-step batch" midi-spin columns (Generon, GEN-1SB08) according to the manufacturer's instructions. Dialysis of the purified antibodies was performed with GeBAflex maxi tubes, with an 8 kDa cut-off (Generon, D045). If necessary, the antibodies were concentrated to 2 µM by ultrafiltration.

4.2.4 Screening for PD-L1-PD-1 Blocking Activity in Jurkat-NFAT Reporter Co-Culture Assay The functional activity of the purified anti-PD-L1 mAbs was then assessed in a co-culture reporter assay screen. This screen was performed using the GloResponse NFAT-luc2/PD-1 stable Jurkat cell line (Promega, CS187102) and Thaw-and-Use PD-L1 cells (Promega, CS178103) in accordance with the manufacturer's instructions. The PD-L1 cells were plated in HAM'S-F12 medium containing 10% FBS. The next day media was removed and in parallel PD-1 Jurkat reporter cells (Promega, CS187102) were resuspended in assay medium (90% RPMI1640, 1% FBS). To the plate containing adhered PD-L1 cells was added 40 µl of assay media containing different antibodies at a 2× concentration (200 nM) followed by 40 µl of the PD-1 cell mix. The plate was incubated for 6 hours at 37° C., 5% CO2. BioGlo reagent (Promega, G7940, 80 µl) was added to each well and the luciferase output was read using a BMG pherastar plate reader. This identified antibody G1/280_02_G02 as capable of blocking the interaction of PD-L1 with PD-1 in a co-culture assay, as determined by increased luciferase activity compared to controls with no antibody. This activity was confirmed in a dose-response co-culture assay (doubling concentration range: 200 to 1.56 nM) resulting in a calculated half maximal effective concentration (EC50) of 4.2 nM.

4.3 Sequence Optimisation

Preliminary analysis of the sequence of the G1/280_02_G02 antibody resulted in the identification of a potential deamidation site in the VH-CDR2, specifically an NG motif at Kabat positions 54 to 55. As deamidation at this site could potentially affect binding, variant clones were produced in which the NG motif was changed to either NA, NS, SG or GG. These modifications did not result in any significant reduction in affinity for recombinant PD-L1 or potency in PD-L1 blocking activity, and the variant clone containing the NS modification, designated G1/280_02_G02_NS, was chosen for use in a light-chain shuffle.

4.4 Summary Naïve Selections

Phage selections strategies identified more than 50 anti-human PD-L1 binding clones with potent in vitro PD-1/PD-L1 blocking activity as well as mouse PD-L1 cross-reactivity. In particular, G1/280_02_G02 showed potent activation in a cell-based PD-L1 reporter assay and was therefore selected for further optimisation.

Example 5: Generating and Characterising Kappa Light Chain-Containing Anti-PD-L1 Clones The G1/280_02_G02_NS antibody possesses a lambda light chain. As most monoclonal antibodies used in a clinical context have kappa light chains (Jain et al., 2017), it was sought, by the use of a chain-shuffling campaign, to generate clones comprising the heavy chain of the G1/280_02_G02_NS antibody but paired with kappa light chains, which retained affinity for human PD-L1 and mouse cross-reactivity. The IONTAS™ kappa-light-chain library in the phage display plasmid pIONTAS-1 (kappa-library) was used to prepare a light-chain-shuffled library of scFv clones comprising the heavy chain of the G1/280_02_G02_NS antibody coupled with light chain variants.

5.1 Phage Selections and Screening Strategy

A number of phage-display solution selections were performed in three rounds using biotinylated human PD-L1-rCD4-His and mouse PD-L1-rCD4-His antigens (see Example 1.3 for antigen details). The selections were performed by decreasing the antigen concentrations in every round (varying from 100 to 0.02 nM) and for each round of selection a "no-antigen" control was used.

Six selection outputs were selected for screening, two from round 2 (nos. 871 and 872) and four from round 3 (nos. 887, 890, 891 and 894) using the soluble scFv expression system as described in section 1.3.1. A total of 1692 soluble scFv clones were screened for binding to immobilised antigen in ELISA (hu-PD-L1-rCD4-His antigen coated at 3 μg/mL in Dulbecco PBS, 50 μl, onto Maxisorb plates) using the assay described in Example 4.2.1 above employing DELFIA enhancement solution.

Of the 1692 clones screened, 1029 clones yielded a signal of more than 2000 RFU in the DELFIA assay, giving a success rate of around 61%. The top 736 clones were then selected and analysed using a secondary assay (affinity ranking) employing three concentrations of hPD-L1-rCD4-His antigen (1.0 nM, 0.2 nM, and 0.04 nM). From the 736 clones screened, the 48 clones which showed the greatest signal were selected for cloning and expression in IgG1 format. Clones were expressed in Expi293F™ (Fisher Scientific cat. no. 13479756) cells at 800 μl scale, and the culture supernatants were harvested on the 5$^{th}$ day post transfection for further screening in IgG1 format.

5.2 SPR Screening

All 48 antibodies were ranked by affinity using SPR (Biacore T200 instrument). For ranking, diluted supernatants (1:10 in running buffer made of 1×PBS and 0.002% Tween™-20) were immobilised onto a Protein-A chip (GE healthcare, product code: 29127556) and human PD-L1-rCD4-Hiswas flowed over the prepared surface at 50 nM concentration. The association ($k_a$) and dissociation ($k_d$) rate constants generated using this single injection were used to determine the dissociation constant ($K_D$). The $K_D$ values of the clones were compared with that of clone G1/280_02_G02_NS in Ig1 format (G1/280_02_G02_NS). Ten clones of unique sequence were identified that showed higher affinity for human PD-L1 than clone G1/280_02_G02_NS and were therefore subjected to full kinetic analysis together with clone G1/280_02_G02_NS.

Briefly, SPR experiments were performed using a BIAcore T200 instrument. Antibodies from diluted culture supernatant were captured on a Protein A chip (GE Healthcare, 29127556) over FC2 at a flow rate of 10 μl/min, with 60 seconds contact time. Typically, this resulted in 500-800 RU of antibody captured. Doubling dilutions of PD-L1-rCD4-His were injected from 50 nM at a flow rate of 30 μl/min, (Concentration range: 50 nM-0.05 nM) over FC1 and FC2. Association was measured over 180 seconds, and dissociation was measured over 300 seconds. All measurements were performed at 25° C. in PBS, pH 7.4, 0.05% Tween™_20. Kinetic parameters were determined by reference cell subtraction and fitting the sensogram experimental data assuming a 1:1 interaction using the BIAevaluation software (GE, BR-1005-97). The resulting data was fitted using BIAevaluation software and corresponding $k_a$, $k_d$, and $K_D$ values were calculated. Out of the ten clones tested, four antibodies, designated "G1/887_04_E12", "894_08_A05", "G1/894_08_E05" and "G1/887_04_G12", exhibited sub-nanomolar $K_D$ values, which were lower than the $K_D$ for G1/280_02_G02_NS. The affinity data obtained under the described screening conditions showed that the kappa light chain shuffle described in Example 5.1 allowed the heavy chain of the G1/280_02_G02_NS antibody to be paired not only with a lambda light chain but also with kappa light chains to produce antibodies with good, and in fact improved, affinity for recombinant human PD-1.

5.3 Characterisation of Kappa Clones in IgG1 Format 5.3.1 Cell Based PD-1/PD-L1 Blocking Assay The ability of the anti-PD-L1 clones containing a kappa light chain, G1/887_04_E12, G1/894_08_E05 and G1/887_04_G12, to block the interaction between PD-1 and PD-L1 was assessed in a bioluminescent cell-based assay using a PD-1/PD-L1 Blockade Bioassay product (Promega, J1250/J1255) in accordance with the manufacturer's recommendations. The blocking activity was compared to the G1/280_02_G02_NS clone.

Briefly, all antibodies were purified as described in Example 4.2.3 and tested at 3-fold dilutions from 100 nM to 35 μM (eight concentrations) in duplicates. All clones tested were shown to be potent inhibitors of the PD-1/PD-L1 interaction, with the three kappa light chain-containing clones G1/887_04_E12, G1/894_08_E05 and G1/884_04_G12 exhibiting even better $IC_{50}$ values than the lambda light chain-containing clone G1/280_02_G02_NS.

5.3.2 Affinities

The binding of the anti-PD-L1 mAbs G1/887_04_E12, G1/887_04_G12 and G1/894_08_E05 to recombinant human (biotinylated hPD-L1-Avi-His, Acro Biosystems, PD1-H82E5), cynomolgus (cPD-L1-His, Acro Biosystems, PD1-C52H4) and mouse PD-L1 (mPD-L1-His, Acro Biosystems, PD1-M5220) was then measured by SPR using a Biacore T200 processing unit (GE Healthcare). Affinities were compared to the 280_02_G02_NS clone in IgG1 format (G1-AA/280_02_G02_NS; the "AA" in this clone name denotes that this clone also contained the "LALA" mutation in the CH2 domain).

Briefly, the anti-PD-L1 mAbs, diluted in HBS-EP buffer (GE Healthcare, BR100188) at 2 μg/ml, were injected individually on flows cell 2, 3 and 4 of a Protein A chip (GE Healthcare, 29127556) at 30 μl/min to achieve a final response of approximately 110 RU. The recombinant human, cynomolgus and mouse PD-L1-His antigens, diluted in HBS-EP buffer, were injected on flow cell 1, 2, 3 or 4 as appropriate at a concentration range of 81 nM to 0.037 nM with 3-fold dilutions for 4 min at 75 μl/min and then allowed to dissociate in buffer for 10 min. Regeneration was achieved by injecting 10 mM glycine-HCL pH1.5 (GE Healthcare, Human Antibody Capture Kit, BR00356) for 30 sec at a rate of 30 μl/min. Subtracted data (flow cell 2-flow cell 1, flow cell 3-flow cell 1, or flow cell 4-flow cell 1) were analysed using BIAevaluation 3.2 Software (GE Healthcare) to identify binding using the model 1:1 binding with mass transfer, with refractive index (RI) constant 0. To determine the affinities of the mouse PD-L1 binding curves, the Rmax of the corresponding human binding profiles was used.

The binding data demonstrated that the G1-AA/280_02_G02_NS clone and the G1/894_08_E05, G1/887_04_E12 and G1/887_04_G12 clones bound to human and cynomolgus PD-L1 with low single-digit nanomolar or subnanomolar affinities and were fully human/cynomolgus cross-reactive. In comparison to the G1-AA1280_02_G02_NS clone, the binding affinities of the G1/894_08_E05, G1/887_04_E12 and G1/887_04_G12 clones were about 1.8 to 4.8 fold higher for human and 2.7 to 4.7 fold higher for cynomolgus PD-L1. The affinities of the clones for recombinant mouse PD-L1 were lower, with $K_D$ values ranging from 38 to 225 nM, with the highest affinity being observed for the G1/887_04_E12 clone. These data show that the heavy chain of the G1-AA/280_02_G02_NS antibody can be paired with both lambda and kappa light chains to produce antibodies with good (and in the case of kappa light chain pairing, sub-nanomolar) affinities for recombinant human and cynomolgus PD-L1, as well as some, albeit lower, affinity for recombinant mouse PD-L1.

5.3.3 Binding of Anti-PD-L1 mAbs to Cell Expressed PD-L1

The anti-human PD-L1 mAbs, G1/894_08_E05, G1/887_04_E12 and G1/887_04_G12 were then tested for binding to HEK293 cells expressing human PD-L1 (HEK-.hPD-L1 cells) using flow cytometry. Non-specific binding was also assessed by testing binding to HEK293 parental cells lacking human PD-L1 (Flp-In T-Rex 293 cell line, Life Technologies, R780-07).

cNDA encoding human PD-L1 (SEQ ID NO: 185) was subcloned into pcDNA™5/FRT vector (ThermoFisher Scientific Cat. No. V601020) using KpnI and NotI restriction sites and the vector was then transformed into Flp-In T-REx 293 cell line (Life Technologies, R780-07) using Lipofectamine 2000 (Life Technologies, 11668-019). Cells were grown in DMEM containing 10% FBS, 100 µg/ml Hygromycin B (Melford Laboratories Ltd, Z2475) and 15 µg/ml Blasticidin (Melford Laboratories Ltd, B11105) for 3-4 weeks until colonies of stably transformed cells had formed. These colonies were amplified in the presence of 1 µg/ml doxycyclin (Sigma Aldrich, D9891) and tested for expression of PD-L1 using PE-conjugated anti-human PD-L1 (MIH1) antibody (BD Biosciences, 557924). Cells were detached using cell dissociation buffer, washed once with PBS, plated at $2\times10^5$ cells in wells of a 96-well plate and then incubated with antibody diluted 1:20 in PBS for 1 hour at 4° C., before being washed again in PBS and measured using an Accuri C6 cytometer (BD Biosciences). The data was analysed using FlowJoX software. Expression of human PD-L1 was detected in the cell line.

The G1/894_08_E05, G1/887_04_E12 and G1/887_04_G12 clones were found to bind to cell surface human PD-L1 with $EC_5m$ values in the range of 0.26-0.29 nM. No binding to parental HEK293 cells was observed showing the specificity of the binding. Therefore, all mAb clones tested bound specifically to PD-L1, with no non-specific binding observed.

5.3.4 Activity of Anti-PD-L1 mAbs in Mixed Lymphocyte Reaction Assay

The activity of the anti-PD-L1 mAbs was tested in a Mixed Lymphocyte Reaction (MLR) assay. A MLR assay measures the cellular immune response that occurs between two allogeneic lymphocyte populations (same species but genetically distinct). The assay uses $CD4^+$ T cells from one donor and monocyte derived dendritic cells (iDCs) from another donor. As the immune cells contain physiological levels of immune checkpoint regulators, the MLR assay can be used to confirm that T cell activation is enhanced by the mAb in a human system.

Generation of Expanded $CD4^+$ T Cells

PBMCs were isolated from leukocyte cones by Ficoll gradient separation. $CD4^+$ T cells were isolated using a Human $CD4^+$ T Cell Isolation Kit (Miltenyi Biotec Ltd, 130-096-533) according to the manufacturer's instructions. Human T-Activator CD3/CD28 Dynabeads (Life Technologies, 11131 D) were resuspended by vortexing. Beads were transferred to a sterile 15 ml tube and 10 ml RPMI (Life Technologies, 61870044) with 10% FBS (Life Technologies, 10270106) and 1× Penicillin Streptomycin (Life Technologies, 15140122) was added to wash the Dynabeads. The supernatant was discarded. The required amount of $CD4^+$ T cells at $1.0\times10^6$ cells/ml in RPMI with 10% FBS and 1× Penicillin Streptomycin Solution and 50 IU/ml recombinant human IL-2 (Peprotech, 200-02-50 µg) with 3:1 bead to cell ratio was transferred to a T75 flask (Greiner Bio-one, 690195) and incubated at 37° C.+5% $CO_2$. After 3 days the cells were gently resuspended and counted. The cell density was maintained between $0.8-1\times10^6$ cells/ml by adding fresh media (RPMI-10% FBS+ Penicillin Streptomycin Solution 1×+50 IU/ml rhuIL-2) as needed. On day 7 or 8, the CD3/28 beads were removed and $CD4^+$ T cells were rested overnight at $1\times10^6$ cells/ml fresh media RPMI-10% FBS+ Penicillin Streptomycin Solution 1× with reduced 10 IU/ml rhuIL-2. The cells were stored frozen until required.

Differentiation of iDCs

Untouched monocytes were isolated from human PBMCs using a Human Pan Monocyte Isolation Kit, (Miltenyi Biotec Ltd, 130-096-537) following the manufacturer's instructions. Monocytes were differentiated to iDCs using Human Mo-DC Differentiation Medium (Miltenyi Biotec Ltd, 130-094-812) following the manufacturer's instructions.

Expanded T cells were thawed one day before the experiment, washed with AIM V Medium (Gibco, 12055-091) and incubated at 37° C., 5% $CO_2$ in AIM V Medium overnight. The anti-human PD-L1 mAbs, G1/894_08_E05, G1/887_04_E12 and G1/887_04_G12 were diluted at 4× the final concentration in triplicate in 50 µl AIM V Medium in 96 well round bottom plates (VWR, 734-1797). An anti-FITC antibody, designated 4420 (Bedzyk et al., 1989 and Bedzyk et al., 1990), containing the LALA mutation was included as negative control. A 3-fold dilution series starting from 30 nM to 0.002 nM was tested. Both $1\times10^4$ iDC cells suspended in 50 µl AIM V Medium and $1\times10^5$ expanded $CD4^+$ T cells suspended in 100 µl AIM V Medium were added to the antibody dilutions and incubated for 5 days at 37° C.+5% $CO_2$. The following controls were included: $CD4^+$ T cells alone, iDC alone, $CD4^+$ T cells+iDCs, and AIM V Medium only. Supernatants were harvested, samples were diluted (1:25) and interferon gamma (IFN-γ) concentrations measured using Human IFN gamma ELISA Ready-SET-Go! Kit (Life Technologies, 88-7316-77). Plates were read at 450 nm using the plate reader with the Gen5 Software, BioTek. Absorbance values of 630 nm were subtracted from those of 450 nm (Correction). The standard curve for calculation of cytokine concentration was based on a four parameter logistic curve fit (Gen5 Software, BioTek). The concentration of human IFN-γ was plotted vs the log concentration of antibody and the resulting curves were fitted using the log (agonist) vs response equation in Graph-Pad Prism.

The anti-human PD-L1 mAbs, G1/894_8_E05, G1/887_4_E12 and G1/887_4_G12, showed potent activity in the MLR assay with $EC_{50}$ values of less than 0.030 nM and a maximum level of IFN-γ ($E_{max}$) of greater than 10000 µg/ml. The $EC_{50}$ indicates the concentration of mAb at which half of the response is achieved, whereas the $E_{max}$ is an absolute value that indicates the maximum concentration of IFN-γ achieved in the assay. No activity was observed with the negative control G1-AA/4420 mAb as expected.

5.4 Activity of Anti-PD-L1 mAbs in a Mouse DO11.10 T Cell Activation Assay

As the anti-human PD-L1 mAbs G1/887_04_E12, G1/887_4_G12 and G1/894_08_E05 were shown to be weakly cross-reactive to mouse PD-L1 (see Example 5.3.2) their functional activity towards mouse PD-L1 was examined in an interleukin-2 (IL-2) release assay based on the DO11.10 OVA T-lymphocyte and LK35.2 B-lymphocyte hybridoma cell lines. IL-2 release is a marker of T cell activation. T cells expressing endogenous murine PD-1 were transfected with empty vector (pLVX). B-cells were transfected with a mouse PD-L1 construct.

5.4.1 Production of T Cell Lines with an Empty Vector

Lentiviral transduction methodology was used to generate DO11.10 cells (National Jewish Health) containing the empty lentiviral vector pLVX using the Lenti-X HTX Packaging System (Clontech, 631249). Lenti-X expression vector (pLVX) (Cat. No 631253) was co-transfected with a Lenti-X HTX Packaging Mix into the Lenti-X 293T Cell Line (Cat. No 632180) to generate virus. The DO11.10 cell line was transduced using the lentiviral particles produced with the Lenti-X HTX Packaging System.

5.4.2 Production of Antigen Presenting Cells Over-Expressing PD-L1

Lentiviral transduction methodology was used to generate LK35.2 B cell lymphoma cells (ATCC, HB-98) over-expressing mouse PD-L1 using the Lenti-X HTX Packaging System (Cat. No 631249). Lenti-X expression vector (pLVX) (Cat. No. 631253) containing, cDNA encoding mouse PD-L1 (SEQ ID NO: 187), was co-transfected with a Lenti-X HTX Packaging Mix into the Lenti-X 293T Cell Line (Cat. No. 632180) to generate virus. The LK35.2 cell line was transduced using the lentiviral vectors produced with the Lenti-X HTX Packaging System.

5.4.3 Mouse DO11.10 T Cell Activation Assay

Dilutions of the anti-PD-L1 mAbs G1/887_04_E12, G1/887_4_G12 and G1/894_08_E05 or the anti-FITC negative control mAb (G1-AA/4420) were prepared in experimental media (DMEM (Gibco, 61965-026), 10% FBS (Gibco, 10270-106), 1 mM Sodium Pyruvate (Gibco, 11360-070)). The mAbs were mixed 1:1 with $4 \times 10^5$/ml LK35.2 mPD-L1 cells in experimental media in presence of 2.46 μM OVA peptide (H-ISQAVHAAHAEINEAGR-OH (SEQ ID NO: 192) (Pepscan)) (100 μL LK35.2 mPD-L1 cells (B cell hybridoma transduced with a lentiviral vector containing mPD-L1 to overexpress mouse PD-L1)/mAb mix per well in 96-round bottom plate) and incubated at 37° C., 5% $CO_2$ for 1 hour. $2 \times 10^5$ DO11.10 pLVX cells (DO11.10 T cell hybridoma transduced with an empty lentiviral vector)/ml in 100 μl volume experimental media were added to 100 μl of the LK35.2 mPD-L1/(mAbs) mix. The cells were then mixed before being incubated at 37° C., 5% $CO_2$ for 24 hours. Supernatants were collected and assayed with mouse IL-2 ELISA kit (eBioscience, 88-7024-88 or R&D systems, SM2000) following the manufacturer's instructions. Plates were read at 450 nm using the plate reader with the Gen5 Software, BioTek. Absorbance values of 570 nm were subtracted from those of 450 nm (Correction). The standard curve for calculation of cytokine concentration was based on a four parameter logistic curve fit (Gen5 Software, BioTek). The concentration of mouse IL-2 was plotted vs the log concentration of mAb and the resulting curves were fitted using the log (agonist) vs response equation in GraphPad Prism.

The anti-human PD-L1 mAbs showed significant activity in the mouse T cell activation assay with potencies ($EC_{50}$) in the range of 1-4.4 nM. No activity was observed with the negative control mAb as expected. Of the three clones tested, G1/887_04_E12, which showed the highest affinity for recombinant mouse PD-L1, was also the most potent clone in the T cell activation assay. The differences in potency were smaller than the measured affinities which is likely due to the high overexpression of mouse PD-L1 on the LK35.2 cells in this assay.

5.5 Summary for Characterisation Kappa Clones in IgG1 Format

The anti-PD-L1 mAbs G1/894_08_E05, G1/887_04_E12, and G1/887_04_G12, containing the selected kappa light chains demonstrated cynomolgus and mouse PD-L1 cross-reactivity, showed specific binding to cell surface-expressed PD-L1, and showed even higher affinity for recombinant human and cynomolgus PD-L1 than the lambda light chain-containing clone G1/280_02_G02. The anti-PD-L1 mAbs G1/894_08_E05, G1/887_04_E12, and G1/887_04_G12 were shown to be potent activators of human T cells in vitro and to have functional mouse cross-reactivity.

Example 6: Sequence Optimisation of the PD-L1 mAbs 6.1 Identification and Removal of Potential Protein Deamidation Sites Analysis of the sequence of the G1/280_02_G02_NS clone resulted in the identification of the sequence NSNT in the H-CDR2 loop (at Kabat positions 54-57) as a potential deamidation site, which if deamidated could affect binding. The heavy chain of this clone was retained in all kappa light chain-containing clones obtained by the chain shuffling campaign described in Example 5, so this potential deamidation site was also present in clones G1/887_04_E12, G1/894_08_A05, G1/894_08_E05 and G1/887_4_G12. Using specific primers closest to germline sequence, the NSNT sequence was changed in the four kappa light chain-containing clones by site-directed mutagenesis to either GGST, SGGT or SGNA to produce the variant clones identified. At the same time as removing this potential deamidation site, the role of the proline residue at Kabat position 28 in the VH region of the G1/887_04_E12 clone, which was unintentionally introduced into the sequence of this antibody during the kappa light chain shuffle, was also investigated by reverting it back to a threonine residue as contained in the G1/280_02_G02_NS clone. The parent and resulting variant clones (all in IgG1 format) were transfected at 0.8 ml scale, and culture supernatants harvested five days after transfections were used to determine the affinities of the clones for human and cynomolgus PD-L1-rCD4-His by SPR. Cyno PD-L1-rCD4-His was generated as described in Example 1.3. With the exception of the variant clones derived from the G1/887_04_E12 clone, all variant clones retained their sub-nanomolar affinities for human and cynomolgus PD-L1 as compared to their respective parent clone.

The modified clones derived from the G1/894_08_A05, G1/894_08_E05 and G1/887_04_G12 parent clones all showed sub-nanomolar affinities for human and cynomolgus PD-L1 comparable to those of their respective parent clone, indicating that the GGST, SGGT and SGNA substitutions were well tolerated. The much reduced affinities of the G1/929_01_A01, G1/929_01_A02 and G1/929_01_A03 clones compared to their parent (G1/887_04_E12) were considered likely to be due to the removal of the proline in the VH region at Kabat position 28 rather than to the presence of the GGST, SGGT and SGNA substitutions in H-CDR2. It was surprising that this proline residue in the G1/887_04_E12 clone appeared to be important for its affinity for PD-L1. The variants derived from the three parent clones G1/887_04_E12, G1/894_08_E05 and G1/887_04_G12 which contained the SGGT substitution in their H-CDR2 (positions 54-57), namely clones G1/929_01_A02, G1/929_01_A08 and G1/929_01_A11, were selected for further characterisation on the basis that this SGGT substitution was closest to germline sequence.

Using site-directed mutagenesis, the potential deamidation site (NSNT at Kabat position 54 to 57) in the H-CDR2 loop of the G1/280_02_G02_NS clone was also modified to SGGT. Additionally, a further potential deamidation site (NS motif) identified at Kabat positions 31 to 32 in the CDR1 of the lambda light chain of this clone was modified to NY by mutating serine 32 (Kabat numbering) to a tyrosine, as tyrosine is found at this position in several germline sequences, such as IGLV2-8-01, IGLV2-8-02, IGLV2-8-03, IGLV2-11-01, IGLV2-11-02, IGLV2-11-03 and IGLV2-14-01, IGLV2-14-02, IGLV2-14-03, IGLV2-14-04. The combination of these modifications yielded the lambda light chain-containing clone G1/lam-G02v3, which was also selected for further characterisation.

Example 7: Characterisation of mAbs 7.1 Cloning and Production of Clones in mAb Format The threonine residue at Kabat position 28 in the VH region of the G1/929_01_A02 "SGGT" variant clone identified in Example 6 was mutated to a proline, as is present at the same position in its parent clone G1/887_04_E12, with a view to improving its affinity for human and cynomolgus PD-L1. Transient expression in HEK293-6E cells and purification using mAb Select SuRe protein A columns was used to produce this modified variant clone and the other three "SGGT" variant clones (G1/929_01_A08, G1/929_01_A11 and G1/lam-G02v3) identified in Example 6 in IgG1 format and with the LALA mutation to enable testing of their functional activity in the absence of effector function. The resulting mAbs were designated G1-AA/E12v2, G1-AA/E05v2, G1-AA/G12v2 and G1-AA/lamG02v3 (called either G1-AA/lamG02v3 or G1-AA/lambdav3). The heavy and light chain sequences respectively are shown in SEQ ID NO: 16 and SEQ ID NO: 17 for G1-AA/E12v2, SEQ ID NO: 27 and SEQ ID NO: 28 for G1-AA/E05v2, SEQ ID NO: 27 and SEQ ID NO: 33 for G1-AA/G12v2 and SEQ ID NO: 27 and SEQ ID NO: 44 for G1-AA/lam-G02v3.

7.2 Affinities of mAb for Human and Cynomolgus PD-L1

To determine whether the further sequence modifications present in G1-AA/lam-G02v3 (namely, NSNT to SGGT in the VH-CDR2, NS to NY in the VL-CDR1, and the LALA mutation) and the kappa light chain-containing mAb G1-AA/E12v2, G1-AA/E05v2, and G1-AA/G12v2 (namely, the LALA mutation and, in the G1-AA/E12v2 only, threonine to proline at Kabat position 28 in the VH region) had affected binding kinetics, the affinities of these anti-PD-L1 mAb for human and cynomolgus PD-L1 were determined as described in Example 5.3.2. The mAbs G1-AA/lam-G02v3, G1-AA/E05v2, G1-AA/E12v2 and G1-AA/G12v2 exhibited affinities for human and cynomolgus PD-L1 similar to those observed in Example 5.3 for mAbs G1-AA/ 280_02_G02_NS, G1/894_08_E05, G1/887_04_E12 and G1/887_04_G12, demonstrating that the binding affinities of the mAbs and mAb$^2$ tested were not affected by the modification of the potential deamidation sites or the introduction of the LALA mutation. The G1-AA/E12v2 mAb showed the lowest $K_D$ value of all four mAbs tested (0.21 nM for human PD-L1, and 0.37 nM for cynomolgus PD-L1). The results are shown in Table 4.

The VH of G1-AA/E12v2 mAb differs from G1/929_01_A02 region (Example 6) by one residue, E12v2 has a proline at Kabat position 28 whereas G1/929_01_A02 has a threonine at this position. G1/929_01_A02 had a greater than 10-fold lower affinity for both human and cynomolgus PD-L1 when compared to G1-AA/E12v2, this data demonstrates the importance of the proline residue at position 28 in the VH of clone E12v2 (Kabat nomenclature) for its affinity for human and cynomolgus PD-L1.

TABLE 4

| Clone | Human PD-L1-His $K_D$ (nM) | Cyno PD-L1-His $K_D$ (nM) |
|---|---|---|
| G1-AA/Iam-G02v3 | 1.34 | 2.45 |
| G1-AA/E05v2 | 0.50 | 0.89 |
| G1-AA/E12v2 | 0.21 | 0.37 |
| G1-AA/G12v2 | 0.44 | 0.75 |

7.3 Activity of Anti-Human PD-L1 mAbs in MLR

The anti-PD-L1 mAbs, G1-AA/E05v2, G1-AA/E12v2 and G1-AA/G05v2 were tested in a Mixed Lymphocyte Reaction (MLR) assay as described in Example 5.3.4. G1-AA/4420 was used as a negative control. The resulting data are shown in Table 5. The mAbs G1-AA/E05v2, G1-AA/E12v2 and G1-AA/G12v2 showed potent activity in the MLR assay with $EC_{50}$ values of less than 0.054 nM and a maximum level of IFN-γ ($E_{max}$) of greater than 600 μg/ml (Table 5). The $EC_{50}$ and especially the $E_{max}$ values were significantly different from those described in Example 5.3.4. This difference is believed to be due to donor variability, as the response depends on the allogenic reaction between T cells from one donor and the monocyte derived dendritic cells from another donor. The potency of the anti-human PD-L1 mAbs was consistent with the data described in Example 5.3.4, as was the ranking of the clones by order of potency. No activity was observed for the negative control G1-AA/4420 mAb as expected.

TABLE 5

| | Functional activity in MLR Assay | |
|---|---|---|
| Clone | $EC_{50}$ (nM) | $E_{max}$ (pg/ml) |
| G1-AA/E05v2 | 0.047 | 632 |
| G1-AA/E12v2 | 0.054 | 666 |
| G1-AA/G12v2 | 0.040 | 686 |
| G1-AA/4420 negative control | | No activity |

7.4 Expression, Purification and Analytical Characterisation of Anti-PD-L1 mAbs

The mAbs G1-AA/E05v2, G1-AA/E12v2 and G1-AA/G12v2 were produced at lab-scale and characterised by the standard analytical methods of SEC and Differential Scanning Calorimetry (DSC).

7.4.1 Lab Scale Expression and Purification of Anti-PD-L1 mAbs

DNA sequences encoding the mAbs G1-AA/E05v2, G1-AA/E12v2 and G1-AA/G12v2 were transfected into HEK293 6E (National Research Council Canada) cells using PEIpro (Polyplus, France). After 5 days, cell culture fluids were harvested, and purified on MabSelect Protein-A pre-packed columns using AKTAxpress instrument (both GE Healthcare, Uppsala, Sweden). Equilibration of the columns was carried out in 50 mM Tris, 250 mM NaCl at pH 7.0 followed by loading with harvested cell culture fluid. The resin was washed using 50 mM Tris, 250 mM NaCl at pH 7.0 and this was followed by eluting the mAb using buffer at pH of less than 3.5.

7.4.2 Analysis by SE-UPLC

Post-purification SE-UPLC was performed within 24 hours of purification (material was stored at 4° C.) using an Acquity H-Class Bio UPLC (Waters Corp. UK) to measure the percentage of monomer. An Acquity UPLC BEH200 SEC 1.7 mm column (4.6×150 mm) was used, the mobile phase consisted of 250 mM sodium phosphate, 100 mM L-Arginine at pH 6.8. Quantification of monomer, low molecular and high molecular weight species was performed using Empower software (Waters Corp. UK).

7.4.3 Thermostability

The melting temperature ($T_m$) of G1-AA/E05v2, G1-AA/E12v2 and G1-AA/G12v2 was measured using a Microcal VP-capillary differential scanning calorimeter (DSC). G1-AA/lam-G02v3 was included to assess the difference between the kappa and lambda light chain-containing mAbs. Samples were measured in sample buffer at a concentration of 0.2 mg/ml. The scan rate was set at 60° C./hr and data were collected between 35° C. and 100° C. Data analysis was performed with Origin 7.0 software. As the DSC peaks of the Fab and CH3 were overlapping, one value was reported.

TABLE 6

| mAb | Monomer purity post-Protein A % | Tm of Fab/CH3 |
|---|---|---|
| G1-AA/E05v2 | 99.48 ± 0.01% | 80.4-82.8° C. |
| G1-AA/E12v2 | 98.85 ± 0.07% | 81.4-84.1° C. |
| G1-AA/G12v2 | 99.83 ± 0.11% | 78.1-81.3° C. |
| G1-AA/Iam-G02v3 | 99.75 ± 0.25% | 68.1° C. |

A summary of the results is shown in Table 6. The three mAbs: G1-AA/E05v2, G1-AA/E12v2 and G1-AA/G12v2 showed favourable analytical characterisation parameters; monomer purity post-protein A was greater than 98% and the thermal stability of the Fab transition (Tm) was found to be at the higher end of transitions typically reported for IgG1, with G1-AA/E12v2 appearing to be the most thermally stable (Fab/CH3 $T_M$=81.484.10C). The lambda light chain mAb, G1-AA/lamG02v3, had a lower Tm than the three kappa light chain-containing mAbs.

Example 8: Production and Characterisation of Anti-Human CD137/PD-L1 mAb$^2$

8.1 Production of Anti-Human CD137/PD-L1 mAb$^2$

CD137/PD-L1 mAb$^2$ antibodies consisting of IgG1 molecules comprising the 3 anti-human CD137 Fcab clones FS22-053-008, FS22-053-017 and FS22-172-003 (see Example 3) were produced to allow characterisation of the Fcabs in a mAb$^2$ format. The CD137/PD-L1 mAb$^2$ were prepared by substituting part of the CH3 domain Fcabs comprising the AB, CD and EF loops, for the corresponding region of the CH3 domain of one of three anti-PD-L1 binding antibodies (G1-AA/E05v2, G1-AA/E12v2, G1-AA/G12v2; see Example 7.1). All resulting mAb$^2$ contained the LALA mutation. The CD137/PD-L1 mAb$^2$ were expressed transiently using PEIpro (Polyplus, France) in HEK293 6E (NRCC, Canada) cells. After 5 days, cell culture fluids were harvested, and purified on MabSelect Protein-A pre-packed columns using AKTAxpress instrument (both GE Healthcare, Uppsala, Sweden). Equilibration of the columns was carried out in 50 mM Tris-HCl, 250 mM NaCl, pH 7.0 followed by loading with harvested cell culture fluid. The resin was then subjected to wash in 50 mM Tris-HCl, 250 mM NaCl, pH 7.0 followed eluting the mAb$^2$ using buffer at pH<3.5.

To assess the amount of protein produced, IgG protein content was quantified by BioLayer Interferometry using the Octet QKe (ForteBio) platform with Protein A quantitation biosensors from PALL (18-5021). Proteins were purified by Protein A affinity chromatography using mAb SelectSure columns. Nine mAb$^2$ were purified using mAb Select SuRe Protein A columns (GE Healthcare, 11003494). The results are shown in Table 7.

TABLE 7

| CD137/PD-L1 mAb$^2$ | | | | |
|---|---|---|---|---|
| CD137 Fcab | PD-L1 Fab | mAb$^2$ | Titre in HEK transient expression (mg/L) | Yield (Protein A) |
| FS22-053-008-AA | E05v2 | FS22-053-008-AA/E05v2 | 88 | 69% |
| FS22-053-008-AA | E12v2 | FS22-053-008-AA/E12v2 | 113 | 74% |
| FS22-053-008-AA | G12v2 | FS22-053-008-AA/G12v2 | 108 | 88% |
| FS22-053-017-AA | E05v2 | FS22-053-017-AA/E05v2 | 61 | 88% |
| FS22-053-017-AA | E12v2 | FS22-053-017-AA/E12v2 | 198 | 65% |
| FS22-053-017-AA | G12v2 | FS22-053-017-AA/G12v2 | 89 | 81% |
| FS22-172-003-AA | E05v2 | FS22-172-003-AA/E05v2 | 127 | 82% |
| FS22-172-003-AA | E12v2 | FS22-172-003-AA/E12v2 | 260 | 76% |
| FS22-172-003-AA | G12v2 | FS22-172-003-AA/G12v2 | 229 | 69% |

All 9 CD137/PD-L1 mAb$^2$ antibodies were produced by transient expression in HEK 293 6E and obtained titres and protein A purification yields within typical range expected at the lab scale. FS22-172-003-AA-lam/G02v3 was also expressed and purified for further testing.

8.2 Biophysical Characterisation of mAb$^2$ by Size Exclusion Chromatography (SEC) and SDS-PAGE

8.2.1 Analysis by SE-HPLC

Post-purification SE-HPLC was performed on an Agilent 1100 series HPLC (Agilent, UK), fitted with a TSK-GEL SUPERSW3000 4.6 mm ID×30.0 cm column (Tosoh Bioscience) using 20 mM sodium phosphate, 200 mM sodium chloride, pH 6.8 as a mobile phase. Quantification of % monomer was performed using Chemstation software (Agilent, UK).

8.2.2 Analysis by CE-SDS

CE-SDS analysis was performed on a 2100 Bioanalyzer Capillary Electrophoresis System (Agilent, UK), according to manufacturer's instructions. For reducing conditions, DTT was added and samples were denatured at 70° C. for 5 minutes.

TABLE 8

| mAb² | Reduced CE-SDS Sum of % heavy chain + % light chain | SEC-HPLC % monomer |
|---|---|---|
| FS22-053-008-AA/E05v2 | 99.7% | 99.6% |
| FS22-053-008-AA/E12v2 | 99.6% | 98.9% |
| FS22-053-008-AA/G12v2 | Not tested | 62.6% |
| FS22-053-017-AA/E05v2 | 99.8% | 99.5% |
| FS22-053-017-AA/E12v2 | 99.7% | 99.6% |
| FS22-053-017-AA/G12v2 | 99.0% | 99.6% |
| FS22-172-003-AA/E05v2 | 99.2% | 99.1% |
| FS22-172-003-AA/E12v2 | 99.7% | 97.9% |
| FS22-172-003-AA/G12v2 | 99.6% | 99.3% |

A summary of analytical results is shown in Table 8. All mAb², except FS22-053-008-AA/G12v2, showed high purity post purification using Protein A; low level of soluble aggregation and fragmentation as showed by % monomer post protein A>95% and a high purity by reduced CE-SDS (>95%, sum of % heavy chain and % light chain). FS22-053-008-AA/G12v2 displayed aggregation post Protein A purification and as a result it was not progressed any further.

Example 9: Characterisation of mAb² Binding 9.1 Binding Affinity of Anti-Human CD137/PD-L1 mAb² for Human and Cynomolgus PD-L1 by SPR Binding of the anti-human CD137/PD-L1 mAb², FS22-172-003-AA/Iam-G02v3, FS22-172-003-AA/E05v2, FS22-053-008-AA/E05v2, FS22-172-003-AA/E12v2, FS22-053-008-AA/E12v2 and FS22-172-003-AA/G12v2 to recombinant human and cynomolgus PD-L1 antigens was then measured by SPR using a Biacore T200 processing unit (GE Healthcare).

Briefly, the anti-human CD137/PD-L1 mAb², diluted in HBS-EP buffer (GE Healthcare, BR100188) at 2 μg/ml, were injected individually on flows cell 2, 3 and 4 of a Protein A chip (GE Healthcare, 29127556) at 30 μl/min to achieve a final response of approximately 110 RU. Two different recombinant human PD-L1 antigens were used i.e. hPD-L1-His-Avi (see Example 1.3 for antigen details) and biotinylated hPD-L1-Avi-His (Acrobiosystems, PD-1-H82E5). Human and cynomolgus PD-L1-His (Acrobiosystems, PD-1-C52H4) antigens, diluted in HBS-EP buffer, were injected on flow cell 1, 2, 3 or 4 as appropriate at a concentration range of 81 nM to 0.037 nM with 3-fold dilutions for 4 min at 75 μl/min and then allowed to dissociate in buffer for 10 min. Regeneration was achieved by injecting 10 mM glycine-HCL pH1.5 (GE Healthcare, Human Antibody Capture Kit, BR00356) for 30 sec at a rate of 30 μl/min. Subtracted data (flow cell 2-flow cell 1, flow cell 3-flow cell 1, or flow cell 4-flow cell 1) were analysed using BIAevaluation 3.2 Software (GE Healthcare) to identify binding using the model 1:1 binding with mass transfer, with refractive index (RI) constant 0.

TABLE 9

| Clone | Human PD-L1-His $K_D$ (nM) | Cynomolgus PD-L1-His $K_D$ (nM) |
|---|---|---|
| FS22-172-003-AA/Iam-G02v3 | 1.54 | 1.91 |
| FS22-172-003-AA/E05v2 | 0.50 | 0.59 |

TABLE 9-continued

| Clone | Human PD-L1-His $K_D$ (nM) | Cynomolgus PD-L1-His $K_D$ (nM) |
|---|---|---|
| FS22-172-003-AA/E12v2 | 0.19 | 0.36 |
| FS22-172-003-AA/G12v2 | 0.49 | 0.53 |
| FS22-053-008-AA/E05v2 | 0.47 | 0.58 |
| FS22-053-008-AA/E12v2 | 0.19 | 0.25 |

The binding data demonstrated that each of the anti-human CD137/PD-L1 mAb² bound to human and cynomolgus PD-L1 with low to subnanomolar affinities and so were human/cynomolgus cross-reactive (Table 9). All mAb² clones bound to human and cynomolgus PD-L1 equally well with equivalent $K_D$ values for each antigen.

9.2 Binding Affinity of Anti-Human CD137/PD-L1 mAb² for Human and Cynomolgus CD137 by SPR The binding of the anti-human CD137/PD-L1 mAb² to recombinant dimeric human and cynomolgus CD137 antigens was also measured by SPR using a Biacore T200 processing unit (GE Healthcare).

Briefly, 20 μg/ml anti-human Fab antibody (GE Healthcare, Human Fab Capture kit 28958325) was coated on flow cells 1, 2, 3 and 4 of a Biacore sensor S chip CM5 (GE Healthcare, BR100530) achieving a final response of approximately 5000 RU. The mAb² clones, diluted in HBS-EP buffer (GE Healthcare, BR100188) at 2-5 μg/ml, were injected individually on flows cell 2, 3 and 4 at 30 μl/min to achieve a response of approximately 70 RU (200 RU for FS22-172-003-AA/E12v2). The recombinant dimeric antigens, human CD137-mFc-Avi or cynomolgus CD137-mFc-Avi (see Example 1.1 for antigen details) diluted in HBS-EP buffer, were injected on flow cell 1, 2, 3 or 4 as appropriate at a concentration range of 81 nM to 0.037 nM with 3-fold dilutions for 4 minutes at 70 μl/min and then allowed to dissociate in buffer for 10 minutes. Regeneration was achieved by injecting 10 mM glycine pH 2.1 (GE Healthcare, Human Fab Capture kit 28958325) for 60 seconds at a rate of 30 μl/min. Data analysis was performed as described in Example 9.1.

TABLE 10

| mAb² clone | Human CD137-mFc-Avi $K_D$ (nM) | Cyno CD137-mFc-Avi $K_D$ (nM) |
|---|---|---|
| FS22-172-003-AA/Iam-G02v3 | 1.3 | 2.2 |
| FS22-172-003-AA/E05v2 | 1.5 | 1.0 |
| FS22-172-003-AA/E12v2 | 0.7 | 0.8 |
| FS22-172-003-AA/G12v2 | 2.2 | 1.8 |
| FS22-053-008-AA/E05v2 | 2.8 | 1.1 |
| FS22-053-008-AA/E12v2 | 2.6 | 0.6 |

The binding data demonstrated that the anti-human CD137/PD-L1 mAb² clones bound to dimeric human and cynomolgus CD137 with low nanomolar affinities and were fully human/cynomolgus cross-reactive (Table 10). As expected, these results were similar to the binding data reported for these Fcab clones in "mock" mAb² format (Table 3, Example 3.7). The highest affinity for dimeric CD137 was observed for FS22-172-003-AA/E12v2, which affinity was subsequently also tested against monomeric CD137-His-Avi using the same method as described above. No binding of FS22-172-003-AA/E12v2 to monomeric CD137 up to 81 nM was detected, illustrating that the Fcab binding regions of the anti-human CD137/PD-L1 mAb² have a low affinity for monomeric CD137. These results are similar to those also observed for the FS22-053-008 CD137 Fcabs showing that the conversion of the Fcab to a mAb² format resulted in little change in binding to CD137.

9.3 Specificity Determination of Anti-Human CD137/PD-L1 mAb² by SPR 9.3.1 Specificity for Human PD-L1

To analyse specificity of the anti-human CD137/PD-L1 mAb², the binding of six mAb² (FS22-172-003-AA/lam-G02v3, FS22-172-003-AA/E05v2, FS22-053-008-AA/E05v2, FS22-172-003-AA/E12v2, FS22-053-008-AA/E12v2 and FS22-172-003-AA/G12v2) to other T cell targets was tested using SPR. The aim was to demonstrate specificity by showing no binding of the mAb² to the antigens PD-L2, CD80, PD-1, and B7-H3 at a concentration of 1 µM.

Flow cells on CM5 chips were immobilised with approximately 1000 RU of either human PD-L2-Fc (R&D Biosystems, 1224-PL), CD80-Fc (R&D Biosystems, 140-B1), PD-1-His (R&D Biosystems, 8986-PD), B7-H3-His (F-star in-house production, SEQ ID NO: 193), PD-L1-Fc (R&D Biosystems, 156-B7) and PD-L1-His (Acrobiosystems, PD-1-H83F3). Flow cell 1 was left for blank immobilisation. The mAb² were diluted to 1 µM and 1 nM in 1×HBS-EP buffer (GE Healthcare, product code BR100188), allowed to flow over the chip for 3 min and then allowed to dissociate for 4 min. A 30-seconds injection of 10 mM glycine pH 1.5 was used for regeneration. Positive control antibodies were injected at 50-100 nM to demonstrate the coating of each antigen. Binding levels were determined at the end of the association phase and compared.

All mAb² tested showed a high level of specificity with less than 10 RU of mAb² binding to the four antigens detected at 1 µM compared to a range of 105 to 570 RU of binding response detected at 1 nM for binding to either human PD-L1-Fc or PD-L1-His. These results demonstrated the high level of specificity of the anti-human CD137/PD-L1 mAb² for PD-L1 with no binding to the other T cell targets listed.

9.3.2 Specificity for Human CD137

It is expected that the specificity of the CD137 Fcab binding moiety is retained in the CD137/PD-L1 mAb² when compared to CD137/HeID1.3 mAb² (see Example 3.6). The specificity of FS22-172-003-AA/E12v2 for TNFR family members, OX40, GITR, CD40 and DR6 (R&D Biosystems) was analysed by SPR similarly as described in Example 9.3.1. At a concentration of 1 µM, FS22-172-003-AA/E12v2 bound with less than 7 RU to human OX40, GITR, CD40 and DR6 compared to 278 RU to human CD137-mFc. This result demonstrates the high level of specificity of the FS22-172-003-AA/E12v2 mAb² for CD137.

9.4 Simultaneous Binding of Anti-Human CD137/PD-L1 mAb² to Human PD-L1 and Human CD137 by SPR The ability of the FS22-172-003-AA/E12v2 mAb² to bind simultaneously to human CD137 and human PD-L1-His Avi (see Example 1.3 for antigen details) was tested by SPR on a Biacore T200. G1/S70 was used as control. Human PD-L1 His, diluted to 10 µg/ml in sodium acetate buffer pH 5.0 (GE Healthcare, 18-1069), was immobilised on a CM5 Sensor S chip (GE Healthcare, BR100530) to a surface density of approximately 1100 RU. One flow cell was activated and deactivated without any protein immobilised for background subtraction. The antibodies, diluted to 5 µg/ml in HBS-EP buffer, were captured at a flow rate of 30 µl/min to achieve a density of about 200-300 RU. Binding of human CD137-mFc-Avi was tested at 0 and 100 nM for 5 min at 30 µl/min, followed by a dissociation step of 2.5 min. The sensor chip was regenerated after each cycle with 20 mM NaOH for 60 seconds at a flow rate of 30 µl/min. FS22-172-003-AA/E12v2 was able to bind simultaneously to both human PD-L1 and human CD137, whereas the control G1/S70 only bound to human PD-L1.

9.5 Binding Affinity of Anti-Human CD137/PD-L1 mAb² to Cell Surface Expressed Human or Cynomolgus PD-L1 by Flow Cytometry To assess binding of the anti-human CD137/PD-L1 mAb² to cell surface human and cynomolgus PD-L1, HEK293 cells overexpressing human PD-L1 were generated. HEK293 cells overexpressing human PD-L1 (HEK.hPD-L1) were produced as described in Example 5.3.3. HEK293 cells overexpressing cynomolgus PD-L1 (HEK.cPD-L1) were also produced as described in Example 5.3.3, except the cDNA encoding cynomolgus PD-L1 (SEQ ID NO: 189) was subcloned into the pcDNA™5/FRT vector instead of the human PD-L1 sequence.

The anti-human CD137/PD-L1 mAb², FS22-172-003-AA/E12v2, was then tested for binding to HEK293 cells expressing human or cynomolgus PD-L1 using flow cytometry. Non-specific binding was also assessed by testing binding to HEK293 parental cells lacking human PD-L1 (Flp-In T-Rex 293 cell line, Life Technologies, R780-07). Binding affinities were compared with a positive control antibody G1-AA/E12v2 (SEQ ID NO: 16 and 17 for the heavy chain and light chain, respectively), the variable domains of which were cloned and expressed in the human IgG1 format comprising the LALA mutation in the CH2 domain (G1-AA format).

HEK293, HEK.hPD-L1 and HEK.cPD-L1 suspensions were prepared in FACS buffer (DPBS (Gibco, 14190-094) containing 0.5% BSA (Sigma, A7906)) and seeded at $1\times10^5$ cell/well in 100 µl in round bottomed 96-well plates (VWR, 734-1797). Cells were washed once in FACS buffer. mAb² FS22-172-003-AA/E12v2, mock mAb² FS22-172-003-AA/HeID1.3, mAb G1-AA/E12v2 and negative control mAb G1-AA/4420 were diluted (400 nM-0.005 nM, 5-fold dilutions) in 100 µl FACS buffer. The washed cells were resuspended in the diluted antibody mixture, incubated at 4° C. for 30 minutes, and then washed once in FACS buffer. 100 µl/well of secondary antibody (goat anti-human IgG Alexa Fluor 647 labelled antibody, Invitrogen, A21445) diluted 1:1000 in FACS buffer was then added, incubated for 20 mins at 4° C., and the cells washed again with FACS buffer and resuspended in 100 µl of PBS containing 7AAD (1:1000, Biotium, 40043) before being analysed using a Canto II flow cytometer (BD Bioscience). Dead cells were excluded and the fluorescence in the APC channel (638 nm 660/20) was measured. The geometric mean fluorescence intensity (GMFI) values were plotted vs the log concentration of antibody and the resulting curves were fitted using the log (agonist) vs response equation in GraphPad Prism.

The FS22-172-003-AA/E12v2 mAb² and G1-AA/E12v2 antibody were found to bind to cell surface human PD-L1 with $EC_{50}$ values in the range of 3.1-3.7 nM and cell surface cynomolgus PD-L1 with $EC_{50}$ values in the range 0.6-0.7 nM (see Table 11) No binding to HEK293 cells lacking PD-L1 overexpression was observed showing the specificity of the binding. Therefore, FS22-172-003-AA/E12v2 mAb² tested bound specifically to PD-L1, with no non-specific binding observed. These results show that the specificity to human and cyno PD-L1 observed for the PD-L1 mAb (see Example 5.3.3) is retained.

TABLE 11

|  | | FS22-172-003-AA/<br>E12v2<br>EC$_{50}$ (nM) | G1-AA/<br>E12v2<br>EC$_{50}$ (nM) |
|---|---|---|---|
| Human PD-L1 | EC$_{50}$ (nM) | 3.7 ± 0.4 | 3.1 |
| Cynomolgus PD-L1 | EC$_{50}$ (nM) | 0.7 ± 0.3 | 0.6 ± 0.3 |

TABLE 12

| Antigen | FS22-172-003-AA/<br>E12v2<br>(EC$_{50}$ (nM)) | FS22-172-003-AA/<br>HeID1.3<br>(EC$_{50}$ (nM)) | G1-AA/<br>MOR7480.1<br>(EC$_{50}$ (nM)) |
|---|---|---|---|
| Human CD137 | 6.2 ± 1.95 | 6.25 ± 2.03 | 1.48 ± 0.4 |
| Cynomolgus CD137 | 7.39 ± 6.07 | 9.09 ± 6.93 | 2.6 ± 1.85 |

9.6 Binding Affinity of Anti-Human CD137/PD-L1 mAb$^2$ to Cell Surface Expressed Human or Cynomolgus CD137 by Flow Cytometry DO11.10 cells (National Jewish Health) expressing full-length human (SEQ ID NO: 185) or cynomolgus CD137 (SEQ ID NO: 189), designated 'DO11.10.hCD137' and 'DO11.10.cCD137' respectively, were produced in order to present the antigen in a membrane-bound conformation, most similar to its natural form, for further characterisation of selected anti-human CD137/PD-L1 mAb$^2$. Details of the DO11.10.hCD137 and DO11.10.cCD137 cell production and confirmation of expression are described in Example 1.2.

The anti-human CD137/PD-L1 mAb$^2$ FS22-172-003-AA/E12v2 was tested for binding to cells expressing human or cynomolgus CD137 (DO11.10.hCD137 or DO11.10.cCD137) using flow cytometry. Non-specific binding was also assessed by testing binding to DO11.10 cells lacking CD137 expression. The variable domains of MOR7480.1 (US Patent No. 2012/0237498) were cloned and expressed in human IgG1 format comprising the LALA mutation in the CH2 domain (G1-AA format) and this was used as a positive control.

Briefly, DO11.10, DO11.10.hCD137 or DO11.10.cCD137 suspensions were prepared in FACS buffer (DPBS containing (Gibco, 14190-094) containing 0.5% BSA (Sigma, A7906)) and seeded at 1×10$^5$ cell/well in 100 µl in round bottomed 96-well plates (VWR, 734-1797). Cells were washed once in FACS buffer and mAb$^2$ FS22-172-003-AA/E12v2, mock mAb$^2$ FS22-172-003-AA/HeID1.3, antibody G1-AA/MOR7480.1 and negative control mAb G1-AA/4420 were diluted (400 nM-0.005 nM, 5-fold dilutions) in 100 µl FACS buffer. The washed cells were resuspended in the diluted antibody mixture, incubated at 4° C. for 30 minutes, and then washed once in FACS buffer. 100 µl/well of secondary antibody (goat anti-human IgG Alexa Fluor 647 labelled antibody, Invitrogen, A21445) diluted 1:1000 in FACS buffer was then added, the cells/antibody mixture was incubated for 20 mins at 4° C., and the cells were then washed again with FACS buffer and resuspended in 100 µl of PBS containing 7AAD (1:1000, Biotium, 40043) before being analysed using a Canto II flow cytometer (BD Bioscience). Dead cells were excluded and the fluorescence in the APC channel (638 nm 660/20) was measured. The geometric mean fluorescence intensity (GMFI) values were plotted vs the log concentration of antibody and the resulting curves were fitted using the log (agonist) vs response equation in GraphPad Prism.

The results are shown in Table 12. FS22-172-003-AA/E12v2 mAb$^2$ and FS22-172-003-AA/HeID1.3 mock mAb$^2$ were found to bind to cell surface-expressed human and cyno CD137 receptors with EC$_{50}$ values in the range of 4.8-9.1 nM, and the positive control mAb was found to bind to human and cyno CD137 receptors with an EC$_{50}$ value of 1.45 nM and 4.4 nM respectively. No binding to DO11.10 or HEK293 cells which did not overexpress CD137 was observed confirming the specificity of binding by the mAb$^2$.

9.7 Binding Affinity of Anti-Human CD137/PD-L1 mAb$^2$ to Endogenously Expressed CD137 and PD-L1 on Activated Primary Human T Cells The affinity of the anti-human CD137/PD-L1 mAb$^2$ for endogenously expressed CD137 and PD-L1 on activated primary human T cells was determined using flow cytometry. To isolate T cells, peripheral blood mononuclear cells (PBMCs) were isolated from leucocyte depletion cones, a by-product of platelet donations. Briefly, leucocyte cone contents were flushed with PBS and overlaid on a Ficoll (Sigma-Aldrich, 1440-02) gradient. PBMCs were isolated by centrifugation and the cells that did not cross the Ficoll gradient were recovered. PBMCs were further washed with PBS and remaining red blood cells were lysed through the addition of 10 ml 1× red blood cell lysis buffer (eBioscience, 00-4300-54) according to the manufacturer's instructions. Pan T cells were isolated from the PBMCs present in the eluent using the Pan T Cell Isolation kit II (Miltenyi Biotec Ltd, 130-095-130) according to the manufacturer's instructions. CD137 is rapidly expressed to high levels on activated CD8$^+$ T cells and also on activated CD4$^+$ T cells with lower levels (Xue-Zhong Yu et al, 2013), therefore Pan T cells were stimulated for 24 hours using Dynabeads™ Human T-Activator CD3/CD28 beads (Thermo, 11132D) according to manufacturer's instructions. Human T-Activator beads were washed from the T cells using a DynaMag™-15 Magnet (Thermo, 12301D) following manufacturer's instructions before being using a cell binding assay to test for binding of FS22-172-003-AA/E12v2 mAb$^2$, FS22-172-003-AA/HeID1.3 mock mAb$^2$, G1-AA/E12v2 positive control anti-human PD-L1 antibody, G1-AA/MOR7480.1 positive control anti-human CD137 antibody, G1-AA/4420 negative control antibody.

Stimulated pan human T cell suspensions were prepared in FACS buffer ((DPBS (Gibco, 14190-094) containing 0.5% BSA (Sigma, A7906)) and seeded at 1×10$^5$ cell/well in 100 µl in round bottomed 96-well plates (VWR, 734-1797). Cells were washed once in FACS buffer and mAb$^2$ FS22-172-003-AA/E12v2, mock mAb$^2$ FS22-172-003-AA/HeID1.3, positive control antibody G1-AA/E12v2, positive control antibody G1-AA/20H4.9, and negative control antibody G1-AA/4420 were diluted (80 nM-0.005 nM, 5-fold dilutions) in 100 µl FACS buffer. The washed cells were resuspended in the diluted antibody mixture containing anti-human CD4$^+$ FITC labelled antibody (BD Biosciences, 550628) and anti-human CD8' eFluor450 labelled antibody (Invitrogen, 48-0087-42) to differentiate between CD4$^+$ and CD8$^+$ T cells, incubated at 4° C. for 30 minutes, and then washed once in FACS buffer. 100 µl/well of secondary antibody (goat anti-human IgG Alexa Fluor 647 labelled antibody, Invitrogen, A21445) diluted 1:1000 in FACS buffer was then added, the cells/antibody mixture was incubated for 20 mins at 4° C., and the cells were then washed again with FACS buffer and resuspended in 100 µl of PBS containing 7AAD (1:1000, Biotium, 40043) before being analysed using a Canto II flow cytometer (BD Bioscience). Dead cells were excluded and the fluorescence in the APC channel (638 nm 660/20) was measured to show test antibody binding. The geometric Mean Fluorescence Intensity (GMFI) values were plotted vs the log concentration of antibody and the resulting curves were fitted using the log (agonist) vs response equation in GraphPad Prism.

Figure 2:
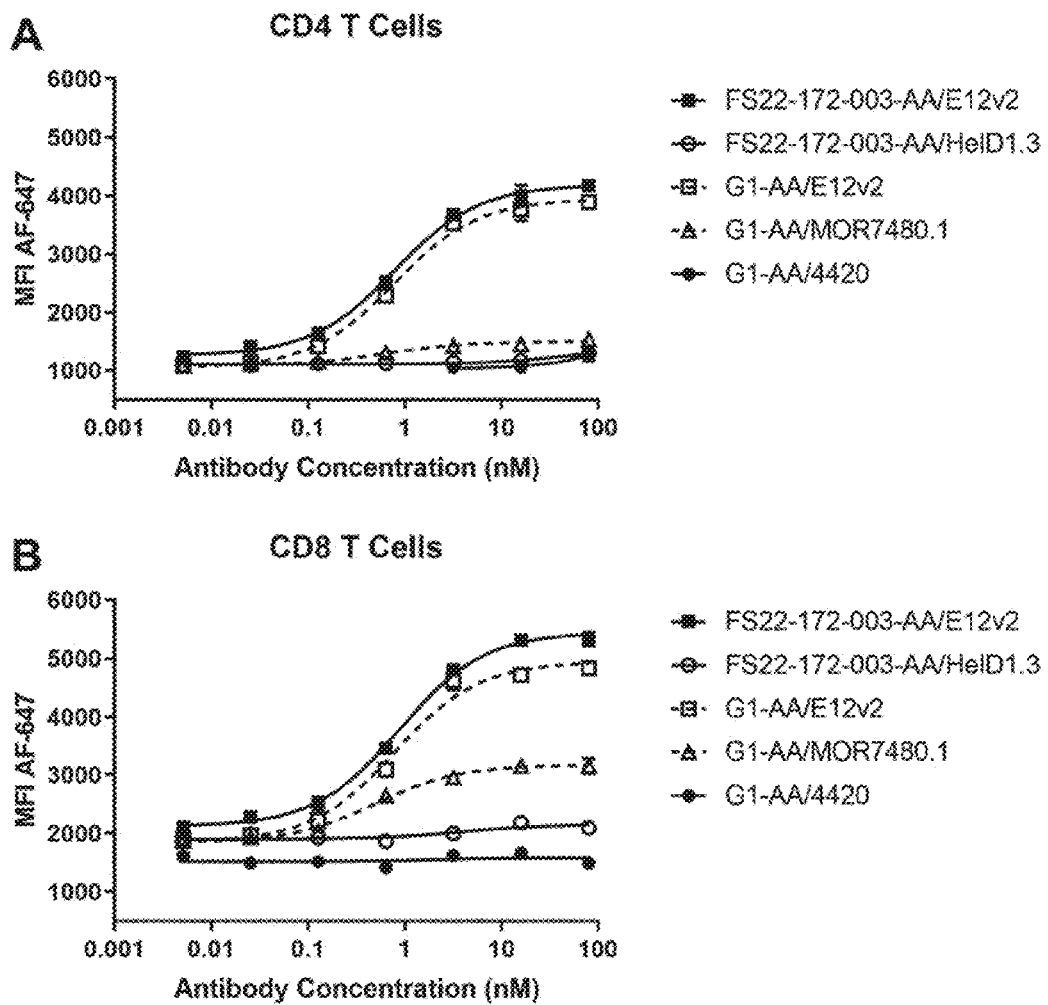
FIG. 2 shows that the CD137/PD-L1 mAb$^2$ FS22-172-003-AA/E12v2 is capable of binding to activated CD4$^+$ (FIG. 2A) and CD8$^+$ (FIG. 2B) T cells. The anti-human CD137/PD-L1 mAb$^2$ FS22-172-003-AA/E12v2 bound activated T cells with EC$_{50}$ values of 0.8 nM in the case of CD4$^+$ T cells and 0.9 nM in the case of CD8$^+$ T cells. The positive control anti-human PD-L1 antibody (G1-AA/E12v2) showed very similar affinity to the mAb$^2$ with EC$_{50}$ values of 0.8 nM for both cell types. The positive control anti-human CD137 antibody (G1-AA/MOR7480.1) showed low binding to CD4+ and CD8$^+$ cells, indicating the low level of CD137 expression on these cell types.

The FS22-172-003-AA/E12v2 mAb$^2$ was found to bind to stimulated human primary CD4$^+$ T cells and CD8$^+$ T cells as shown by the MFI values in FIG. 2. The PD-L1 positive control antibody G1-AA/E12v2 bound with similar MFI values as the mAb$^2$ to both CD4$^+$ and CD8$^+$ T cells, confirming that PD-L1 was expressed on the cells.

G1-AA/MOR7480.1, the CD137 positive control was found to bind to the same cells described above though the MFI was much lower than observed for either FS22-172-003-AA/E12v2 or G1-AA/E12v2. This is likely due to there being a lower level of CD137 expression on the cells, compared to PD-L1 expression. Further, the MFI value was higher for binding of G1-AA/MOR7480.1 to CD8$^+$ T cells than on CD4$^+$ T cells. As described earlier it is expected to observe lower CD137 expression on stimulated CD4$^+$ T cells than on CD8$^+$ T cells (Xue-Zhong Yu et al, 2013) which accounts for the low binding level of CD137 positive control antibody MOR7480.1 on CD4$^+$ T cells as opposed to CD8$^+$ T cells. This low CD137 expression seen on primary T cells, particularly on CD4$^+$ T cells, also likely accounts for seeing no or little binding of the Fcab in mock mAb$^2$ format (FS22-172-003-AA/HeID1.3).

9.8 Binding of Anti-Human CD137/PD-L1 mAb$^2$ to FcRn by SPR

The neonatal Fc receptor (FcRn) binding is critical for antibody recycling (Martins et al., 2016). The binding of FS22-172-003-AA/lam-G02v3, FS22-172-003-AA/E12v2 and FS22-053-008-AA/E12v2 mAb$^2$ to human and mouse FcRn was measured by SPR using BIAcore T200 (GE Healthcare). G1-AA/HeID1.3 was included as an isotype control IgG control lacking mutations in the CH3 domain.

Briefly, mAb$^2$ were individually coated on flow cell 2, 3 and 4 of Series S Sensor Chip CM5 (GE Healthcare, BR100530) to achieve a response of approximately 1000 RU. Flow cell 1 was activated/deactivated but left blank as a reference. Human FcRn (Acro Biosystems, FCM-H5286) or mouse FcRn (R&D systems, 9114-Fc) was dialysed and diluted in MHBS-EP+B pH 6.0 or pH 7.4 buffer (10 mM MES, FortéBio, 18-5026; 1×HBS-EP, GE Healthcare, BR100669; 0.1 mg/ml BSA, Sigma, A7906) and injected on flow cell 1, 2, 3 and 4 at 2000-3000 nM with 2-fold dilutions for 1 min at 80 µl/min and then allowed to dissociate in buffer for 3 min. Regeneration was not required. Subtracted data (flow cell 2-flow cell 1, flow cell 3-flow cell 1, or flow cell 4-flow cell 1) was analysed using Biacore T200 Evaluation Software 2.0 to identify binding using the model steady state affinity. The binding data are shown in Table 13 and demonstrated that FS22-172-003-AA/lam-G02v3, FS22-172-003-AA/E12v2 and FS22-053-008-AA/E12v2 mAb$^2$ bound to human or mouse FcRn at pH 6.0 with similar affinities as the control antibody G1-AA/HeID1.3. No binding was observed with human or mouse FcRn at pH7.4. This data showed that FcRn binding was retained by the mAb$^2$.

TABLE 13

| | Human FcRn $K_D$ (nM) | | Mouse FcRn $K_D$ (nM) | |
| --- | --- | --- | --- | --- |
| | pH 6.0 | pH 7.4 | pH 6.0 | pH 7.4 |
| FS22-172-003-AA/ Iam-G02v3 | 1.22 × 10$^{-6}$ | No binding | 1.67 × 10$^{-7}$ | No binding |
| FS22-172-003-AA/ E12v2 | 1.12 × 10$^{-6}$ | No binding | 1.58 × 10$^{-7}$ | No binding |

TABLE 13-continued

| | Human FcRn $K_D$ (nM) | | Mouse FcRn $K_D$ (nM) | |
| --- | --- | --- | --- | --- |
| | pH 6.0 | pH 7.4 | pH 6.0 | pH 7.4 |
| FS22-053-008-AA/ E12v2 | 9.98 × 10$^{-7}$ | No binding | 1.77 × 10$^{-7}$ | No binding |
| G1-AA/HeID1.3 | 1.23 × 10$^{-6}$ | No binding | 1.60 × 10$^{-7}$ | No binding |

9.9 Binding of Anti-Human CD137/PD-L1 mAb$^2$ to Cells Expressing Fcγ Receptors by Flow Cytometry Agonistic antibodies targeting TNFRSF members require crosslinking via Fcγ receptors to drive target clustering and activation to achieve in vivo activity (Li et al, 2013). However, in order to circumnavigate potential off-target effects such as systemic CD137 activation due to crosslinking by Fcγ receptor binding and to decrease the possibility of inducing ADCC of immune cells, for example T cells, that express both targets, it was decided to decrease the Fcγ receptor binding ability of the anti-human CD137/PD-L1 mAb$^2$ by introduction of a LALA mutation in the CH2 domain (see Example 3.2 for details on the LALA format). Cell binding by flow cytometry to CHO cells over-expressing only FcγRIIA (ECACC Cat No: 15042905), FcγRIIA (ECACC Cat No: 15042903), FcγRIIIA (ECACC Cat No: 15042902), FcγRIIIA (ECACC Cat No: 15042901), or FcγRIIB (ECACC Cat No: 15042907) was used to confirm that the presence of the LALA mutation in the CH2 domain of the anti-human CD137/PD-L1 mAb$^2$ had reduced its binding affinity for the previously mentioned Fcγ receptors.

Briefly, CHO.FcγRIIA.131H, CHO.FcγRIIA.131E, CHO.FcγRIIIA.158F, CHO.FcγRIIIA.158V, CHO.FcγRIIB, or CHO.WT suspensions were prepared in FACS buffer (DPBS containing (Gibco, 14190-094) containing 0.5% BSA (Sigma, A7906)) and seeded at 1×10$^5$ cell/well in 100 µl in round bottomed 96-well plates (VWR, 734-1797). Cells were washed once in FACS buffer and mAb$^2$ FS22-172-003-AA/E12v2, positive control for Fcγ receptor binding antibody G1/4420 and negative control for Fcγ receptor antibody G1-AA/4420 were diluted (500 nM-0.03 nM, 4-fold dilutions) in 100 µl FACS buffer. The washed cells were resuspended in the diluted antibody mixture, incubated at 4° C. for 30 minutes, and then washed once in FACS buffer. 100 µl/well of secondary antibody (goat anti-human IgG Alexa Fluor 488 labelled antibody, Stratech Scientific Ltd, 109-545-098-JIR) diluted 1:1000 in FACS buffer was then added, the cells/antibody mixture was incubated for 20 mins at 4° C., and the cells were then washed again with FACS buffer and resuspended in 100 µl of PBS containing 7AAD (1:1000, Biotium, 40043) before being analysed using a CytoFLEX flow cytometer (Beckman Coulter). Dead cells were excluded and the fluorescence in the FITC channel (488 nm 525/40) was measured. The geometric mean fluorescence intensity (GMFI) values were plotted vs the log concentration of antibody and the resulting curves were fitted using the log (agonist) vs response equation in GraphPad Prism.

Figure 3:
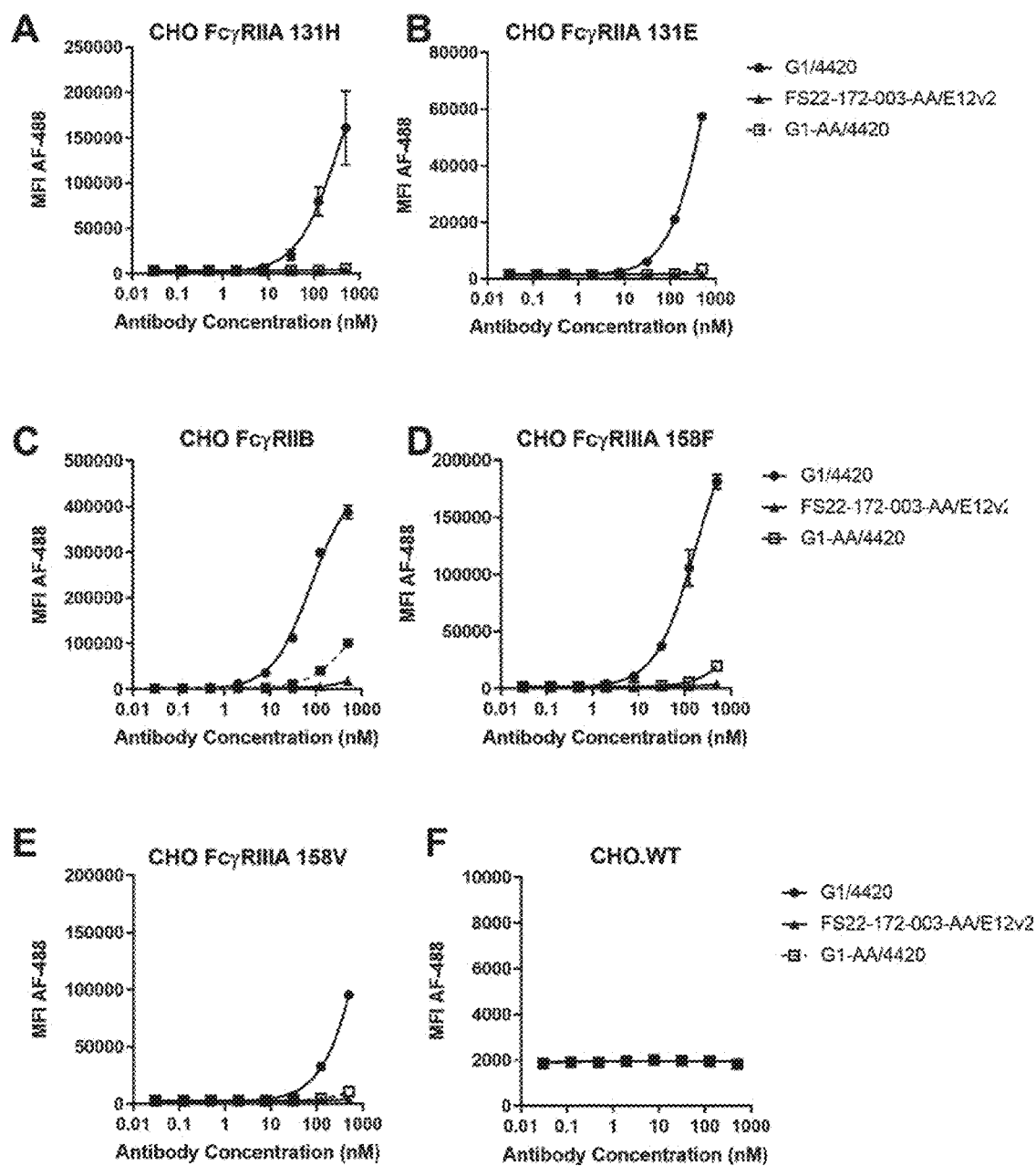
FIG. 3 shows that anti-human CD137/PD-L1 mAb$^2$ FS22-172-003-AA/E12v2 does not bind to Fcγ receptor over-expressing CHO cells. Anti-human CD137/PD-L1 mAb$^2$ FS22-172-003-AA/E12v2, the positive control antibody for Fcγ receptor binding, G1/4420, and the negative control antibody for no Fcγ receptor binding, G1-AA/4420, were tested in a cell binding assay against five different Fcγ receptor over-expressing CHO cell lines expressing (A) FcgRIIA 131H, (B) FcgRIIA 131E, (C) FcgRIIB, (D) FcgRIIIA 158F, (E) FcgRIIIA 158V, as well as (F) a CHO WT cell line used as a negative control. The anti-human CD137/PD-L1 mAb$^2$, which contained the LALA mutation in the CH2 region, did not bind any of the Fcγ receptors tested and neither did it bind non-specifically to CHO WT cells (closed black triangles). The positive control antibody bound Fcγ receptors (closed black circles) and the negative control antibody G1-AA/4420, which contained the LALA mutation in the CH2 region, did not bind Fcγ receptors (open grey squares), as expected.

The FS22-172-003-AA/E12v2 mAb$^2$ showed no binding (or bound below the level of the negative control antibody G1-AA/4420) to all the Fcγ receptor expressing cells tested (FIG. 3(A) FcgRIIA 131H, (B) FcgRIIA 131E, (C) FcgRIIB, (D) FcgRIIIA 158F, (E) FcgRIIIA 158V). This indicates that the LALA mutation decreases binding to FcγRIIA, FcγRIIIA, or FygRIIB which would also decrease mAb$^2$ crosslinking via these receptors in vivo.

Example 10: Characterisation of mAb² Function 10.1 Activity of Anti-Human CD137/PD-L1 mAb² in a Human Primary CD8⁺ T Cell Assay The human primary T cell assay described in Example 3.5 was used to test the activity of the mAb².

For cell-based crosslinking of anti-human CD137/PD-L1 mAb², HEK293 cells overexpressing hPD-L1 (HEK.hPD-L1) were produced essentially as described in Example 3.5. HEK.hPD-L1 cells have been engineered to express a high level of human PD-L1 and were used alongside MDA-MB-231 cells which express a medium level of human PD-L1 as well as SKBR3 cells which express a low level of human PD-L1 (Table 14) as quantified by Antibody Binding Capacity beads (Quantum Simply Cellular, Bans Laboratories, Inc. cat no. 816A) following manufacturer's instructions.

TABLE 14

| Cell line | Antibody Binding Capacity |
| --- | --- |
| HEK WT | 7463 (±971) |
| HEK.hPD-L1 | 702000 (±58000) |
| MDA-MB-231 | 137369 (±2429) |
| SKBR3 | 14734 (±239) |

The CD8⁺ T cells were isolated and activated using an anti-CD3 antibody as described in Example 3.5. HEK.hPD-L1 cells were plated at 2×10⁵ cells per well on to anti-CD3 antibody-coated (8 µg/ml) 96 well flat bottom plates in 100 µl T cell culture medium (RPMI medium (Life Technologies, 61870-044) with 10% FBS (Life Technologies), 1× Penicillin Streptomycin (Life Technologies, 15140122), 1 mM Sodium Pyruvate (Gibco, 11360-070), and 50 µM 2-mercaptoethanol (Gibco, M6250)). Once HEK.hPD-L1 cells or HEK cells that were not transduced to express hPD-L1 used as controls had adhered after 4 hours incubation, all T cell culture medium was removed and replaced with 100 µl T cell culture medium containing T cells at a concentration of 5.0×10⁵ cells/ml resulting in 5.0×10⁴ cells/well.

For cell-based crosslinking with lower more physiological levels of PD-L1 expression, the human breast adenocarcinoma cell line, MDA-MB-231 (ATCC HTB-26), was used with the same methodology as described for HEK.hPD-L1 cell-based crosslinking.

mAb² were diluted in T cell medium at a 2× final concentration starting at 50 nM and a 1:5 titration was carried out. 100 µl of mAb² titration was added to the cells for a total assay volume of 200 µl and 1× concentration of antibody.

Positive control anti-CD137 antibody (G1-AA/20H4.9) was diluted in T cell medium at a 2× final concentration starting at 50 nM containing 50 nM crosslinking agent (the anti-human CH2 antibody (mG1/MK1A6)) and a 1:5 titration was carried out. 100 µl of diluted positive control antibody/crosslinker mix was added to the cells for a total of 200 µl assay volume and 1× concentration of antibody.

The assay was incubated at 37° C., 5% CO₂ for 72 hours. Supernatants were collected and assayed with human IL-2 ELISA Ready-SET-Go! kit (eBioscience, Cat. 88-7025-88) following the manufacturer's instructions. Plates were read at 450 nm using the plate reader with the Gen5 Software, BioTek. Absorbance values of 630 nm were subtracted from those of 450 nm (Correction). The standard curve for calculation of cytokine concentration was based on a four-parameter logistic curve fit (Gen5 Software, BioTek). The concentration of human IL-2 (hIL-2) was plotted vs the log concentration of antibody and the resulting curves were fitted using the log (agonist) vs response equation in GraphPad Prism.

Figure 4:
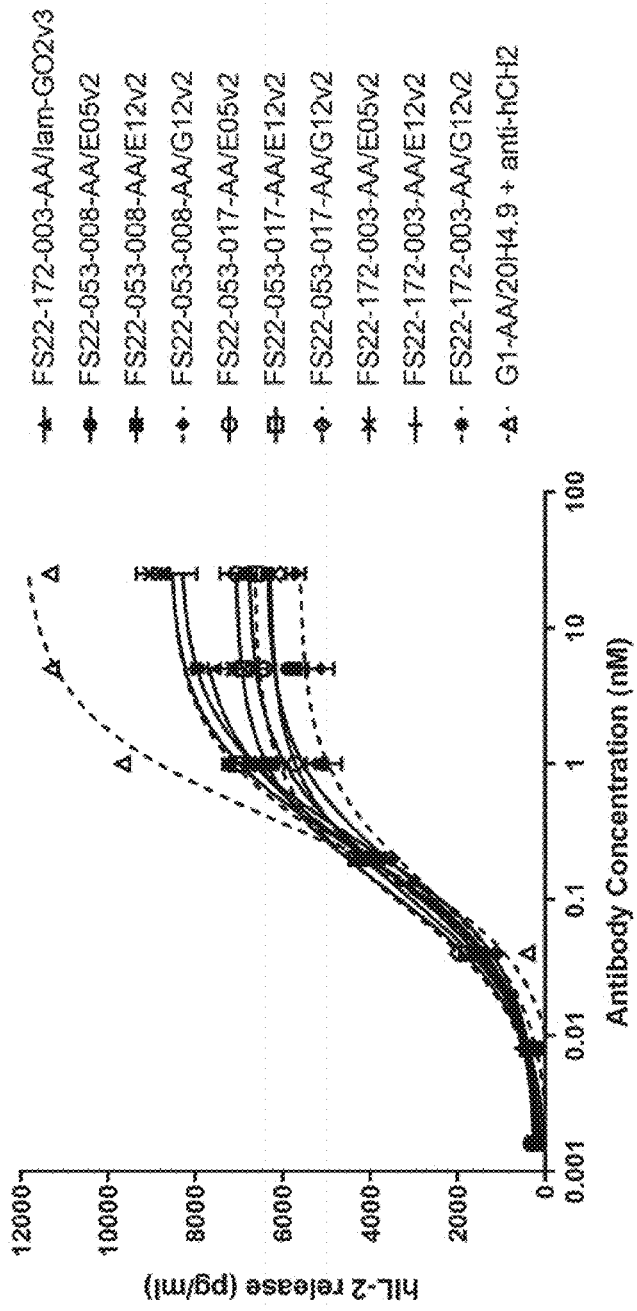
FIG. 4 shows release of human IL-2 (hIL-2) in a human primary CD8$^+$ T cell activation assay in the presence of anti-human CD137/PD-L1 mAb$^2$ or positive control anti-human CD137 antibody G1-AA/20H4.9. All mAb$^2$ tested drove CD137 clustering and activation of CD8$^+$ T cells only when the mAb$^2$ were crosslinked by HEK cells overexpressing human PD-L1 leading to release of human IL-2. The EC$_{50}$ values of the anti-human CD137/PD-L1 mAb$^2$ were smaller than the EC$_{50}$ value of the positive control anti-human CD137 antibody, G1-AA/20H4.9 when crosslinked with anti-human CH2 secondary antibody (closed black circles, dotted line), indicating that improved T cell activation was achieved with the mAb$^2$. All showed an increase in hIL-2 release and there was a larger release of IL-2 (E$_{max}$) with the positive control antibody than with the anti-human CD137/PD-L1 mAb$^2$.
Figure 5:
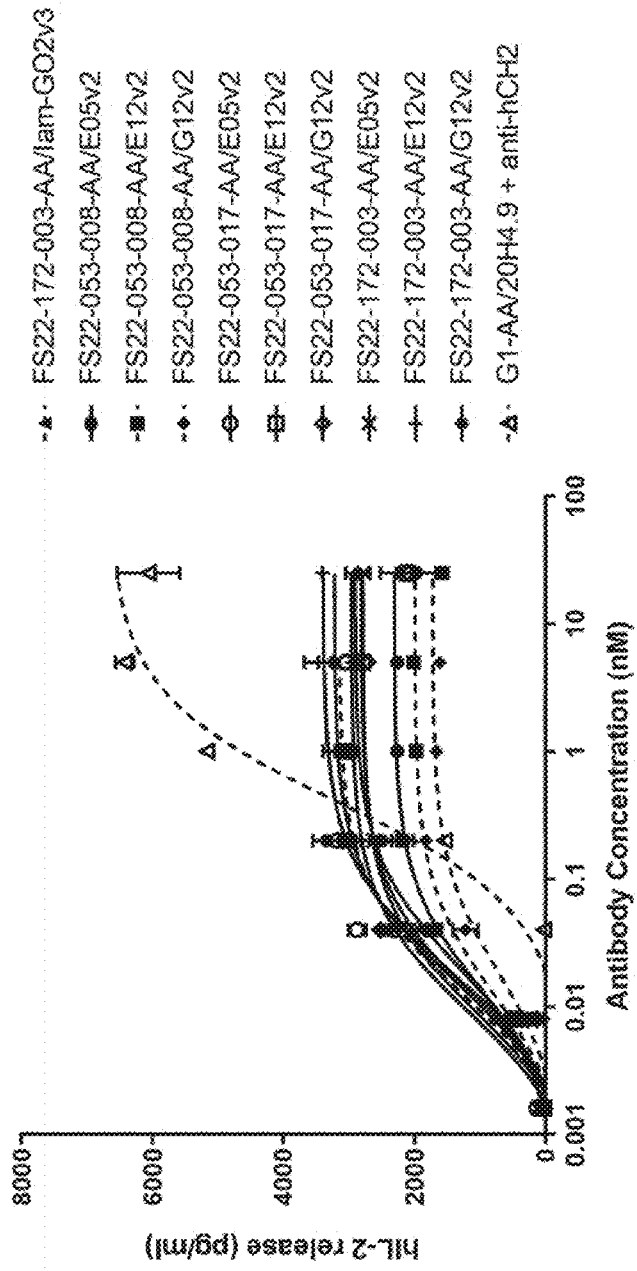
FIG. 5 shows release of human IL-2 (hIL-2) in a human primary CD8$^+$ T cell activation assay in the presence of anti-human CD137/PD-L1 mAb$^2$ or positive control anti-human CD137 antibody G1-AA/20H4.9. All mAb$^2$ tested drove CD137 clustering and activation of CD8$^+$ T cells only when the mAb$^2$ were crosslinked by MDA-MD-231 cells endogenously expressing human PD-L1 leading to release of human IL-2. The EC$_{50}$ values of the anti-human CD137/PD-L1 mAb$^2$ were smaller than the EC$_{50}$ value of the positive control anti-human CD137 antibody, G1-AA/20H4.9 when crosslinked with anti-human CH2 secondary antibody (closed black circles, dotted line) indicating that better activity was achieved with the mAb$^2$. All showed an increase in hIL-2 release and there was a larger release of IL-2 (E$_{max}$) with the positive control antibody than with the anti-human CD137/PD-L1 mAb$^2$.

Table 15 shows the $EC_{50}$ values and maximum response of IL-2 release observed in the T cell activation assay in the presence of the anti-human CD137/PD-L1 mAb² tested with cell-based crosslinking. The positive control anti-human CD137 mAb, 20H4.9, shows an increase in hIL-2 release with an $EC_{50}$ of 0.21 to 0.31 nM when crosslinked with anti-hCH2 antibody in either assay. All clones had activity in the assays, each displaying potency with sub-nanomolar $EC_{50}$ s. mAb² containing Fcab FS22-172-003 elicited the greatest T cell response with $EC_{50}$ s in the range of 0.19 to 0.31 nM in the HEK.hPD-L1 based assay and 0.01-0.02 nM in the MDA-MB-231 based assay. A subset of the mAb² (containing Fcabs FS22-053-008, FS22-053-011, FS22-053-014, FS22-173-003 and FS22-172-004) were also tested without crosslinking by PD-L1 expressed on HEK cells and showed no activity in this assay, as expected. FIG. 4 and FIG. 5 shows representative plots of IL-2 release for the T cell activation assay for mAb² listed in Table 15.

The FS22-053 and FS22-172 Fcab lineage was also tested in this assay using the lowest PD-L1 expressing human breast adenocarcinoma cell-line, SK-BR-3 (ATCC HTB-30). As expected the lower PD-L1 expression resulted in lower CD8⁺ T cell activation in line with the previous two assays (data not shown).

TABLE 15

| | $EC_{50}$ (nM) Donor 171115A | | $EC_{50}$ (nM) Donor 171115B | |
| --- | --- | --- | --- | --- |
| mAb² | HEK.hPD-L1 XL | MDA-MB-231 XL | HEK.hPD-L1 XL | MDA-MB-231 XL |
| FS22-053-008-AA/E05v2 | 0.16 | 0.01 | 0.11 | 0.02 |
| FS22-053-008-AA/E12v2 | 0.10 | 0.01 | 0.11 | 0.02 |
| FS22-053-008-AA/G12v2 | 0.13 | 0.02 | 0.12 | 0.02 |
| FS22-053-017-AA/E05v2 | 0.15 | 0.01 | 0.12 | 0.01 |
| FS22-053-017-AA/E12v2 | 0.11 | 0.01 | 0.12 | 0.01 |
| FS22-053-017-AA/G12v2 | 0.10 | 0.01 | 0.20 | 0.01 |
| FS22-172-003-AA/E05v2 | 0.27 | 0.02 | 0.19 | 0.02 |
| FS22-172-003-AA/E12v2 | 0.24 | 0.02 | 0.31 | 0.02 |
| FS22-172-003-AA/G12v2 | 0.21 | 0.02 | 0.22 | 0.01 |
| G1-AA/20H4.9 | 0.21 | 0.31 | 0.29 | 0.28 |

The results showed that the mAb² could bind to cells expressing different levels of PD-L1. Binding to the cell-expressed PD-L1 resulted in crosslinking of the mAb² such that they were able to bind to, cluster and activate CD137 on T cells, as measured by IL-2 production. The level of activation observed related to the level of crosslinking by binding PD-L1, where the mAb² bound to cells expressing higher levels of hPD-L1 (HEK.hPD-L1) there was greater activation, whereas lower levels of PD-L1 expression elicited less activation.

10.2 Activity of an Anti-Human CD137/PD-L1 mAb² Crosslinked with Different Populations of HEK.hPD-L1 Cells in a Human Primary CD8⁺ T Cell Activation Assay As the expression level of PD-L1 by different cell lines was observed to impact activation of CD137, it was decided to explore further the impact of PD-L1 expression on the functional activity of the mAb² tested. A similar assay to that described in Example 10.1 was performed, where the ratio of HEK.hPD-L1 to HEK.WT cells was varied in order to modulate the level of human PD-L1 expression in a population based approach.

Figure 6:
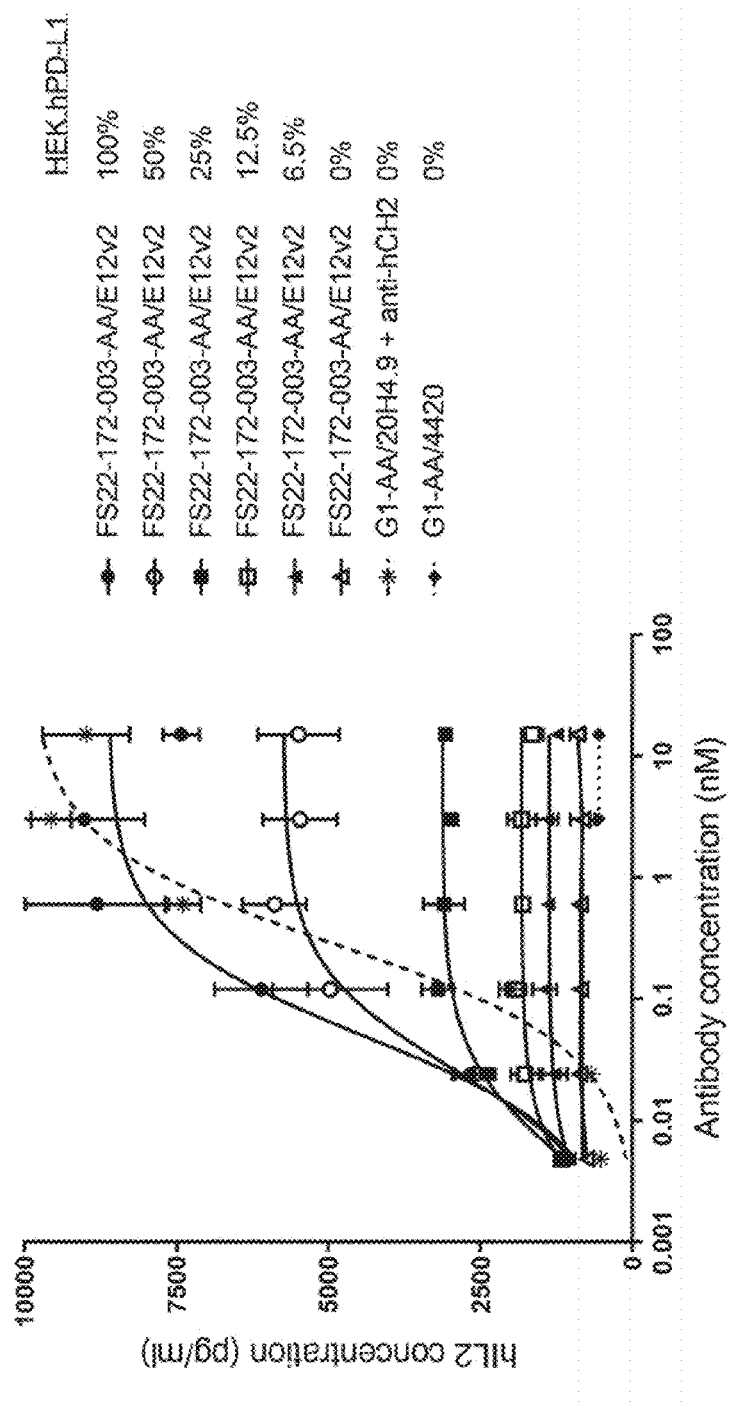
FIG. 6 shows release of human IL-2 (hIL-2) in a human primary CD8$^+$ T cell activation assay in the presence of anti-human CD137/PD-L1 mAb$^2$ FS22-172-003-AA/E12v2 or positive control anti-human CD137 antibody G1-AA/20H4.9. All mAb$^2$ tested drove CD137 clustering and activation of CD8$^+$ T cells only when the mAb$^2$ were crosslinked by HEK.hPD-L1 cells that comprised at least 6.5% of the total HEK cell population leading to release of human IL-2. The EC$_{50}$ values of the anti-human CD137/PD-L1 mAb$^2$ remained similar when modulating the percentage of HEK.hPD-L1 cells present in the assay, but the maximal activation (E$_{max}$) increased in relation to an increasing percentage of HEK.hPD-L1 crosslinking cells in the assay.

HEK.hPD-L1 cells and HEK cells that were not transduced to express hPD-L1 (HEK.WT) were plated in different ratios to provide the percentage of HEK.hPD-L1 cells of the total HEK cells present listed in FIG. 6 (100%, 50%, 25%, 12.5%, 6.5% or 0%). HEK cells were plated at $2 \times 10^5$ total HEK cells per well onto anti-CD3 antibody-coated (8 µg/ml) 96 well flat bottom plates in 100 µl T cell culture medium (RPMI medium (Life Technologies, 61870-044) with 10% FBS (Life Technologies), 1× Penicillin Streptomycin (Life Technologies, 15140122), 1 mM Sodium Pyruvate (Gibco, 11360-070), and 50 µM 2-mercaptoethanol (Gibco, M6250)). Once all HEK cells had adhered after 4 hours incubation, all T cell culture medium was removed and replaced with 100 µl T cell culture medium containing T cells at a concentration of $5.0 \times 10^5$ cells/ml resulting in $5.0 \times 10^4$ cells/well.

The assay was run with anti-human CD137/PD-L1 mAb2 FS22-172-003-AA/E12v2 but otherwise followed the protocol described in Example 10.1. The anti-CD137 positive control antibody G1-AA/20H4.9 was included with additional crosslinking via an anti-CH2 antibody. Antibody G1-AA/4420 was used as a negative control.

The results in FIG. 6 show that as the population of HEK.hPD-L1 cells increased, activity of the mAb$^2$ also increased, as illustrated by an increase in the maximum hIL-2 concentration observed. Where 100% of the HEK cell population present were HEK.hPD-L1, maximal crosslinking was achieved and the highest maximum hIL-2 concentration was observed. The positive control antibody G1-AA/20H4.9 also reached a similar maximum hIL-2 concentration when maximally artificially crosslinked by an anti-CH2 antibody.

The data supports the observation that the amount of PD-L1 present in the system (represented by testing cell lines expressing different levels of PD-L1 on their cell surface or by modulating the number of cells in a population which display PD-L1) controls the crosslinking of the mAb$^2$ and thereby dictates the level of CD137 agonism induced by the mAb$^2$. However, even where only low levels of PD-L1 are present, the mAb$^2$ was still capable of agonising CD137. The mAb$^2$ is therefore expected to have activity where PD-L1 is expressed in a system, and activated T cells that express CD137 are present. As the level of PD-L1 in the system increases, the agonism exerted is also expected to increase. In contrast to the mAb$^2$ which was still capable of inducing CD137 agonism in the presence of low levels of CD137, CD137/PD-L1 molecules which bind CD137 monovalently are expected to have low efficiency in the presence of low PD-L1 levels, as molecules bound to PD-L1 are likely to be too far apart to drive clustering of CD137, which is not expected to be an issue where the molecule can bind CD137 bivalently, as is the case in the mAb$^2$ of the invention.

10.3 Activity of Anti-Human CD137/PD-L1 mAb$^2$ in a Human Primary Mixed Lymphocyte Reaction Assay The activity of the anti-human CD137/PD-L1 mAb$^2$ was tested in a Mixed Lymphocyte Reaction (MLR) assay (see Example 5.3.4). The MLR assay used CD4$^+$ T cells from one donor and monocyte derived dendritic cells (iDCs) from another donor. As the immune cells contain physiological levels of immune checkpoint regulators, the MLR assay can be used to confirm that T cell activation is enhanced by the mAb$^2$ in a human system.

Expanded CD4$^+$ T cells and iDC were generated as described in Example 5.3.4.

Expanded T cells were thawed one day before the experiment, washed with AIM V Medium (Gibco, 12055-091) and incubated at 37° C., 5% CO2 in AIM V Medium overnight. The anti-CD137 and anti-PD-L1 antibodies and anti-human CD137/PD-L1 mAb$^2$ listed in Table 16 were diluted 4× the final concentration in triplicate in 50 µl AIMV Medium in 96 well round bottom plates (VWR, 734-1797). An anti-Cytomegalovirus (CMV) gH glycoprotein antibody, designated MSL109 (described in WO1994/016730 A1), containing the LALA mutation was included as negative control. A 3-fold dilution series starting from 30 nM to 0.002 nM was tested. $1 \times 10^4$ iDC cells suspended in 50 µl AIM V Medium and $1 \times 10^5$ expanded CD4$^+$ T cells suspended in 100 µl AIM V Medium were both added to the antibody dilutions and incubated for 5 days at 37° C.+5% CO2. The following negative controls were included: CD4$^+$ T cells alone, iDC alone, CD4$^+$ T cells+iDCs, and AIM V Medium only. Supernatants were harvested, samples were diluted (1:25) and interferon gamma (IFN-γ) concentrations measured using Human IFN gamma ELISA Ready-SET-Go! Kit (Life Technologies, 88-7316-77). Plates were read at 450 nm using the plate reader with the Gen5 Software, BioTek. Absorbance values of 630 nm were subtracted from those of 450 nm (Correction).

The standard curve for calculation of cytokine concentration was based on a four-parameter logistic curve fit (Gen5 Software, BioTek). The concentration of human IFN-γ was plotted vs the log concentration of antibody and the resulting curves were fitted using the log (agonist) vs response equation in GraphPad Prism.

The anti-human PD-L1 antibody G1/S70, showed potent activity in the MLR assay with an $EC_{50}$ value of 0.06 nM and a maximum level of IFN-γ ($E_{max}$) of 1135 µg/ml (Table 16, representative FIGS. 7A and 7B). The $EC_{50}$ indicates the concentration of mAb at which half of the agonistic response is achieved, whereas the $E_{max}$ is an absolute value that indicates the maximum concentration of IFN-γ achieved in the assay. No activity was observed with the negative control G1-AA/MSL109 antibody, as expected. The positive anti-human CD137 antibody control G1-AA/20H4.9, when crosslinked with anti-hCH2 antibody, did not elicit any activity, indicating that CD137 expression may be low and that PD-L1 blockade overwhelms CD137 signalling in this assay because PD-L1 blockade is very strong. Surprisingly, all anti-human CD137/PD-L1 mAb$^2$ tested in this assay showed very potent $EC_{50}$ values of less than 0.04 nM and high $E_{max}$ values in the range of 2626 to 3327 µg/ml. This indicates that the mAb$^2$ have increased potency in this assay above that of either of the PD-L1 and CD137 monoclonal antibodies.

TABLE 16

| Molecule(s) | Type | $EC_{50}$ (nM) | $E_{max}$ (pg/ml) |
| --- | --- | --- | --- |
| FS22-172-003-AA/E05v2 | mAb$^2$ | 0.03 | 2654 |
| FS22-172-003-AA/E12v2 | mAb$^2$ | 0.02 | 2626 |
| FS22-053-008-AA/E05v2 | mAb$^2$ | 0.02 | 2797 |
| FS22-053-008-AA/E12v2 | mAb$^2$ | 0.04 | 3128 |
| FS22-053-017-AA/E12v2 | mAb$^2$ | 0.04 | 3327 |
| G1-AA/20H4.9 + anti-human CH2 | CD137 mAb | N/A | N/A |
| G1/S70 | PD-L1 mAb | 0.06 | 1135 |
| G1-AA/MSL109 | Isotype | N/A | N/A |
| CD4$^+$ T cells alone | Cell control | N/A | N/A |
| iDC alone | Cell control | N/A | N/A |
| CD4$^+$ T cells + iDC alone | Cell control | N/A | N/A |

N/A-not applicable as low signal did not allow $EC_{50}$ determination

Following the same protocol described above, the activity of the anti-human CD137/PD-L1 mAb² FS22-172-003-AA/E12v2 was tested again in an MLR but this time against each component part (the anti-human FS22-172-003 Fcab in mock mAb² format and the anti-PD-L1 antibody G1-AA/E12v2), as well as the combination of the two.

The anti-human PD-L1 component antibody G1-AA/E12v2, showed potent activity in the MLR assay with an $EC_{50}$ value of 0.08 nM and a maximum level of IFN-γ ($E_{max}$) of 12421 µg/ml (Table 17; representative FIG. 7C). No activity was observed with the negative control G1-AA/4420 antibody, as expected, and no activity was observed with the anti-human Fcab FS22-173-003 in mock mAb² format. The positive anti-human CD137 antibody control, G1-AA/20H4.9, when crosslinked with anti-hCH2 antibody, did not elicit any activity, indicating that CD137 expression may be low and that PD-L1 blockade overwhelms the CD137 signalling in this assay because PD-L1 blockade is very strong as seen above. As expected, the anti-human CD137/PD-L1 FS22-172-003-AA/E12v2 mAb² showed a very potent $EC_{50}$ value of 0.07 nM and a high $E_{max}$ value of 17874 µg/ml. This indicates that the mAb² has increased potency in this assay above that of either of the anti-PD-L1 and anti-CD137 monoclonal antibodies alone or both in combination. The data also shows that the mAb² had greater potency than the combination of two antibodies comprising the Fcab and Fab binding sites of the mAb², respectively.

TABLE 17

| Molecule(s) | Type | $EC_{50}$ (nM) | $E_{max}$ (pg/ml) |
|---|---|---|---|
| FS22-172-003-AA/E12v2 | mAb² | 0.07 | 17874 |
| FS22-172-003-AA/HeID1.3 | mAb² | N/A | 3574 |
| G1-AA/E12v2 | PD-L1 mAb | 0.08 | 12421 |
| FS22-172-003-AA/ HeID1.3 + G1-AA/E12v2 | Component Combination | 0.06 | 12301 |
| G1-AA/20H4.9 + anti-human CH2 | CD137 mAb | 1.9 | 4307 |
| G1-AA/E12v2 + G1-AA/20H4.9 + anti-human CH2 | mAb Combination | 0.14 | 17525 |
| G1-AA/4420 | Isotype | N/A | N/A |
| CD4⁺ T cells alone | Cell control | N/A | N/A |
| iDC alone | Cell control | N/A | N/A |
| CD4⁺ T cells + iDC alone | Cell control | N/A | N/A |

N/A-not applicable as low signal did not allow $EC_{50}$ determination 10.4 Activity of Anti-Human CD137/PD-L1 mAb² in an Antigen Recall T Cell Activation Assay The activity of anti-human CD137/PD-L1 mAb² was tested in an antigen recall T cell activation assay by measuring the immune response to two distinct peptide pools containing physiologically relevant antigens. One pool comprised MHC class I-restricted peptides from Cytomegalovirus, Epstein-Barr virus, and Influenza virus (CEF) which test CD8⁺ T cell activation and the second pool comprised MHC class II-restricted peptides from Cytomegalovirus, Epstein-Barr virus, Influenza virus, and Tetanus toxin (CEFT), which tested CD4⁺ T cell activation. As human PBMCs from a single donor were used, and as the immune cells contained physiological levels of immune checkpoint regulators and were stimulated by antigen presentation rather than T cell receptor crosslinking by anti-CD3 antibody, the results of the assay confirm that antigen-driven T cell activation is enhanced by the mAb² in a human system.

Cryopreserved peripheral blood mononuclear cells (PBMCs) were thawed and counted and 1.9×10⁵ cells were seeded per well in to a 96 well flat bottom plate in 200 µl Roswell Park Memorial Institute (RPMI) media containing 10% fetal bovine serum (FBS)+1 ng/ml IL-2+5 ng/ml IL-7 and either 1 µg/ml CEF peptide pool (Thinkpeptides, cat no. PX-CEF-G) or 1 µg/ml CEFT peptide pool (Thinkpeptides, cat no. PX-CEFT-G). Cells were incubated at 37° C. with 5% CO₂ for 3 days. After 3 days, media was replenished by the addition of 22.5 µl fresh RPMI containing 10% FBS and maintaining 1 ng/ml IL-2 and 1 ng/ml IL-7. Cells were incubated at 37° C. with 5% CO₂ for a further 4 days.

Cells were collected and pooled together and then distributed across 96 well round bottom plates at 1×10⁵ cells per well in 150 µl RPMI containing 10% FBS+1 ng/ml IL-2+5 ng/ml IL-7 and either 1 µg/ml CEF peptide pool or 1 µg/ml CEFT peptide pool. mAb² were diluted in the same media as cells were seeded in and added to the cells.

Each of the positive control anti-CD137 antibody (G1-AA/20H4.9) and positive control anti-PD-L1 antibody (G1-AA/E12v2) were diluted in the same media as cells were seeded in, at a 2× final concentration starting at 400 nM containing 400 nM crosslinking agent (the anti-human CH2 antibody (MK1A6)) and a 1:5 titration was carried out. 50 µl of diluted either positive control antibody/crosslinker mix was added to the cells for a total of 200 µl assay volume and 1× concentration of antibody.

The assay was incubated at 37° C., 5% CO₂ for 72 hours. Supernatants were collected and assayed with an MSD U-PLEX kit (Meso Scale Discovery, cat no. K15067L-2) following the manufacturer's instructions. Plates were read on a MESO QuickPlex SQ 120 electrochemiluminescence plate reader instrument using a sample dilution of 1:5. A standard curve for the calculation of cytokine concentration was calculated using the MSD Discovery Workbench 4.0 software and the concentration of cytokine in the supernatant was fitted using the log (agonist) vs response equation in GraphPad Prism.

As shown in Table 18 and Table 19, the anti-human PD-L1 antibody G1-AA/E12v2, showed activity for both CD4⁺ and CD8⁺ T cell activation with an $EC_{50}$ value of 0.06 nM and 0.04 nM respectively ($E_{max}$ of 65840 µg/ml and 86613 µg/ml respectively). The $EC_{50}$ indicates the concentration of mAb at which half of the agonistic response is achieved, whereas the $E_{max}$ is an absolute value that indicates the maximum concentration of IFN-γ achieved in the assay. The positive anti-human CD137 antibody control G1-AA/20H4.9, when crosslinked with anti-hCH2 antibody, showed activity for CD8⁺ T cell activation, with an $EC_{50}$ value of 0.33 nM and an $E_{max}$ value of 116204 µg/ml, but did not elicit any activity for CD4⁺ T cell activation, indicating that CD137 expression may be higher on CD8⁺ T cells compared to CD4⁺ T cells. No activity was observed with the negative control G1-AA/4420 antibody, as expected. Surprisingly, the mAb² showed activation in both CD4⁺ T cell activation and CD8⁺ T cell activation assays with $EC_{50}$ values of 0.08 nM and 0.03 nM respectively. The mAb² could bind PBMC-expressed PD-L1 and had equivalent PD-L1 activity on both cell types. Further, binding to the PBMC-expressed PD-L1 resulted in crosslinking of the mAb² such that they were able to bind to, cluster and activate CD137 on both T cell subtypes, as measured by IFN-γ release. The maximum concentration of IFN-γ released by T cells treated with mAb² was higher than any of the positive control antibodies with $E_{max}$ values of 86680 µg/ml and 188242 µg/ml for CD4⁺ T cell activation and CD8⁺ T cell activation respectively. This indicates the mAb² has increased activity in this assay above that of either of the PD-L1 and CD137 monoclonal antibodies.

TABLE 18

CEFT peptide pool antigen recall assay values (CD4+ T cell activation)

| Molecule(s) | Type | $EC_{50}$ (nM) | $E_{max}$ (pg/ml) |
|---|---|---|---|
| FS22-172-003-AA/E12v2 | $mAb^2$ | 0.08 | 86680 |
| G1-AA/20H4.9 + anti-human CH2 | CD137 mAb | N/A | 12965 |
| G1-AA/E12v2 | PD-L1 mAb | 0.06 | 65840 |
| G1-AA/4420 | Isotype | N/A | N/A |

N/A - not applicable as low signal did not allow $EC_{50}$ determination

TABLE 19

CEF peptide pool antigen recall assay values (CD8+ T cell activation)

| Molecule(s) | Type | $EC_{50}$ (nM) | $E_{max}$ (pg/ml) |
|---|---|---|---|
| FS22-172-003-AA/E12v2 | $mAb^2$ | 0.03 | 188242 |
| G1-AA/20H4.9 + anti-human CH2 | CD137 mAb | 0.33 | 116204 |
| G1-AA/E12v2 | PD-L1 mAb | 0.04 | 86613 |
| G1-AA/4420 | Isotype | N/A | N/A |

N/A - not applicable as low signal did not allow $EC_{50}$ determination 10.5 Activity of Anti-Human CD137/PD-L1 $mAb^2$ in a PD-L1 Blockade Mouse DO11.10 T Cell Activation Assay The activity of FS22-172-003-AA/E12v2 was tested in a mouse DO11.10 T cell activation assay to investigate PD-L1 checkpoint blockade activity. The functional activity towards human PD-L1 was examined in an IL-2 release assay using DO11.10 OVA T cell and LK35.2 B cell hybridoma cells as described in Example 5.4.

Results are shown Table 20. The anti-human CD137/PD-L1 $mAb^2$ showed potent activity in the mouse DO11.10 T cell activation assay with an $EC_{50}$ value of 1.27 nM, which confirms that FS22-172-003-AA/E12v2 can bind PD-L1 and block the interaction of PD-L1 with PD-1. Its activity was similar to that of the positive control anti-human PD-L1 antibodies G1-AA/E12v2 and G1-AA/S70, indicating that no loss of anti-human PD-L1 activity occurred when G1-AA/E12v2 was incorporated in to the FS22-172-003-AA/E12v2 $mAb^2$ molecule.

TABLE 20

DO11.10 T cell activation assay values (mouse IL-2 release)

| Molecule(s) | Type | $EC_{50}$ (nM) | $E_{max}$ (pg/ml) |
|---|---|---|---|
| FS22-172-003-AA/E12v2 | $mAb^2$ | 1.27 | 424 |
| G1-AA/E12v2 | PD-L1 mAb | 1.19 | 480 |
| G1-AA/S70 | PD-L1 mAb | 1.4 | 498 |
| G1-AA/HelD1.3 | Human IgG1 isotype control mAb | N/A | N/A |

N/A - not applicable as low signal did not allow $EC_{50}$ determination

Example 11: Functional Cross Reactivity of Anti-Human CD137/PD-L1 $mAb^2$ in Cynomolqus Functional Assays 11.1 Activity of Anti-Human CD137/PD-L1 $mAb^2$ in a Cynomolgus DO11.10 T Cell Activation Assay CD137 clustering via agonist molecules on activated T cells elicits T cell activation and downstream signalling resulting in, but not limited to, IL-2 production. The ability of anti-human CD137/PD-L1 $mAb^2$ to activate DO11.10 cells expressing cynomolgus CD137 was tested in a T cell activation assay. A DO11.10 T cell activation assay using DO11.10 T cells engineered to overexpress cynomolgus CD137 was developed and T cell activation was assessed by measuring IL-2 release.

DO11.10 cells (National Jewish Health) expressing full-length cynomolgus CD137 (SEQ ID NO: 189) designated 'DO11.10.cCD137', were produced and expression of cynomolgus CD137 confirmed as described in Example 1.2.

The following anti-human CD137/PD-L1 $mAb^2$ were tested in this DO11.10 T cell activation assay: FS22-172-003-AA/lamG02v3, FS22-053-008-AA/E05v2, FS22-053-008-AA/E12v2, FS22-053-008-AA/G12v2, FS22-053-017-AA/E05v2, FS22-053-017-AA/E12v2, FS22-053-017-AA/G12v2, FS22-172-003-AA/E05v2, FS22-172-003-AA/E12v2, FS22-172-003-AA//G12v2. Dilutions of $mAb^2$ or G1-AA/MOR7480.1 positive control mAb either with or without anti-hCH2 antibody (mG1/MK1A6) crosslinker were prepared and added to DO11.10.cCD137 cells in a 96 well round bottom plate that had been coated overnight with 0.1 µg/ml anti-CD3 antibody (clone 17A2, BioLegend, 100208) and had been seeded with $2\times10^5$ HEK.cyPD-L1 cells to be used as cell-based crosslinking cells, which overexpress cynomolgus PD-L1. Cells over expressing cynomolgus PD-L1 were made as described in Example 5.3.3, using the cynomolgus PD-L1 as described in Example 9.5. After an 18-hour incubation, supernatants were collected and assayed with mouse IL-2 ELISA kit (eBioscience, 88-7024-86) following the manufacturer's instructions. Plates were read at 450 nm using the plate reader with the Gens Software, BioTek. Absorbance values of 570 nm were subtracted from those of 450 nm (Correction). The standard curve for calculation of cytokine concentration was based on four parameter logistic curve fit (Gens Software, BioTek). The concentration of mIL-2 was plotted vs the log concentration of $mAb^2$ or benchmark mAb and the resulting curves were fitted using the log (agonist) vs response equation in GraphPad Prism.

All anti-human CD137/PD-L1 $mAb^2$ tested in this assay showed activity in the presence of HEK cells overexpressing cynomolgus PD-L1 to crosslink the $mAb^2$, indicating that all $mAb^2$ are able to bind both cynomolgus PD-L1 and bind and cluster cynomolgus CD137 eliciting DO11.10 T cell activation as readout by IL-2 production (see Table 21 and FIG. 8). All anti-human CD137/PD-L1 $mAb^2$ showed similar activity with EC50 values in the range of 0.06 to 0.11 nM and $E_{max}$ values in the range of 8060 to 12300 µg/ml IL-2 only when crosslinked via cell-expressed cynomolgus PD-L1. In the absence of cynomolgus PD-L1, when the assay was carried out using HEK cells that do not express cynomolgus PD-L1, there was no activity as a result of no crosslinking. The positive control CD137 antibody G1-AA/MOR7480.1 which has been shown to be cynomolgus cross-reactive (Fisher et al, 2012) shows activity in this assay, when crosslinked with anti-CH2 however all anti-human CD137/PD-L1 $mAb^2$ are better both in terms of lower $EC_{50}$ values and higher $E_{max}$ values indicating cross-reactivity and better activity in a cynomolgus CD137 expressing system.

TABLE 21

| Molecule | Type | EC$_{50}$ (nM) (cross-linked) | E$_{max}$ (pg/ml) (cross-linked) |
| --- | --- | --- | --- |
| FS22-172-003-AA-Iam/GO2v3 | mAb$^2$ | 0.08 | 12304 |
| FS22-053-008-AA/E05V2 | mAb$^2$ | 0.06 | 8057 |
| FS22-053-008-AA/E12V2 | mAb$^2$ | 0.08 | 9010 |
| FS22-053-008-AA/G12V2 | mAb$^2$ | 0.07 | 9656 |
| FS22-053-017-AA/E05V2 | mAb$^2$ | 0.10 | 9021 |
| FS22-053-017-AA/E12V2 | mAb$^2$ | 0.11 | 9362 |
| FS22-053-017-AA/G12V2 | mAb$^2$ | 0.08 | 8933 |
| FS22-172-003-AA/E05V2 | mAb$^2$ | 0.08 | 10520 |
| FS22-172-003-AA/E12V2 | mAb$^2$ | 0.06 | 11291 |
| FS22-172-003-AA/G12V2 | mAb$^2$ | 0.06 | 11216 |
| G1-AA/MOR7480.1 | CD137 mAb | 0.71 | 5705 |

11.2 Activity of Anti-Human CD137/PD-L1 mAb$^2$ in a Cynomolgus Primary Mixed Leukocyte Reaction Assay The activity of the anti-human CD137/PD-L1 mAb$^2$ was tested in a cynomolgus Mixed Lymphocyte Reaction (MLR) assay. Similar to the human MLR assay described in Example 10.3 this assay measures a cellular immune assay response that occurs between two allogeneic lymphocyte populations (same species but genetically distinct). The assay uses CD4$^+$ T cells from one cynomolgus individual and CD14$^+$ monocytes from another individual. As the immune cells contain physiological levels of immune checkpoint regulators, the MLR assay can be used to confirm that T cell activation is enhanced by the mAb$^2$ in a cynomolgus system.

Isolation of CD4$^+$ T Cells

PBMCs were isolated from cynomolgus monkey blood samples by Ficoll gradient separation. CD4$^+$ T cells were isolated using a Non-human primate CD4$^+$ isolation kit (Miltenyi Biotec Ltd, 130-091-102) according to the manufacturer's instructions. The cells were used fresh in the MLR assay.

Isolation of CD14$^+$ Monocytes

Untouched monocytes were isolated from cynomolgus PBMCs using a Non-human primate CD14 isolation kit, (Miltenyi Biotec Ltd, 130-091-097) following the manufacturer's instructions. Monocytes were used fresh in the MLR assay.

MLR Assay

The anti-human CD137/PD-L1 mAb$^2$ FS22-172-003-AA/E12v2 and anti-human PD-L1 antibody G1-AA/E12v2 and isotype control antibody G1-AA/4420 were diluted 4× the final concentration in triplicate in 50 µl AIM V Medium in 96 well round bottom plates (VWR, 734-1797). An anti-hen egg lysozyme (HEL) antibody, designated HelD1.3 (described in Example 2.2), containing the LALA mutation was included as negative control. A 4-fold dilution series starting from 300 nM to 0.02 nM was tested. 7.5×10$^4$ monocyte cells suspended in 50 µl AIM V Medium and 7.5×10$^5$ CD4$^+$ T cells suspended in 100 µl AIM V Medium were both added to the antibody dilutions and incubated for 6 days at 37° C.+5% CO2. The following negative controls were included: CD4$^+$ T cells alone, CD14$^+$ monocytes alone, CD4$^+$ T cells+iDCs, and AIM V Medium only. Supernatants were harvested on day 2 and interleukin 2 (IL-2) concentrations were measured using a MILLIPLEX MAP Non-Human Primate Cytokine Magnetic Bead Panel (Merck Millipore, cat no. PRCYTOMAG-40K-01), supernatants were also harvested on day 6 and interferon gamma (IFN-γ) concentrations measured using the same kit. Samples analysed on Bio Plex 200 machines, from Bio-Rad.

Both anti-human CD137/PD-L1 mAb$^2$ showed activity in this assay indicating that the mAb$^2$ are capable of binding cynomolgus PD-L1 and subsequently bind and cluster cynomolgus CD137 at expression levels endogenous to freshly isolated cynomolgus immune cells resulting in cytokine release as a result of T cell activation (see FIG. 9).

11.3 Activity of Anti-Human CD137/PD-L1 mAb$^2$ in a Cynomolgus Primary PBMC Assay The activity of anti-human CD137/PD-L1 mAb$^2$ was tested in a cynomolgus primary PBMC assay. This assay measures a cellular immune assay response that occurs in a mixed population of PBMCs that have been stimulated with anti-CD3 mAb. The assay uses whole PBMCs from one cynomolgus individual and, as the immune cells contain physiological levels of immune checkpoint regulators, the PBMC assay can be used to confirm that T cell activation is enhanced by the mAb$^2$ in a cynomolgus system.

The experiment was performed essentially as described in Example 3.5 with the following deviations: the positive control anti-CD137 antibody (G1-AA/MOR7480.1) was diluted in the same media as cells were seeded in, at a 2× final concentration starting at 40 nM containing 40 nM crosslinking agent (the anti-human CH2 antibody (MK1A6) and a 1:4 titration was carried out. The mAb$^2$ (FS22-172-003-AA/E12v2) and the negative control antibody (G1-AA/HeID1.3) were diluted in the same manner without the crosslinking agent. 100 µl of diluted antibody/crosslinker mix was added to the cells for a total of 200 µl assay volume and 1× concentration of antibody. The assay was incubated at 37° C. with 5% CO$_2$ for 3 days. Supernatants were collected and assayed with an MSD V-Plex Proinflammatory Panel 1 (NHP) kit (Meso Scale Discovery, cat no. K15056D-2) following the manufacturer's instructions. Plates were read on a MESO QuickPlex SQ 120 electrochemiluminescence plate reader instrument. A standard curve for the calculation of cytokine concentration was calculated using the MSD Discovery Workbench 4.0 software and the concentration of cytokine in the supernatant was fitted using the log (agonist) vs response equation in GraphPad Prism.

FIG. 28A shows a representative plot of IFN-γ release from T cell activation in the cynomolgus PBMC assay and FIG. 28B shows a representative plot of IFN-γ release from T cell activation in the human PBMC assay.

The anti-human CD137 antibody G1-AA/MOR7480.1 when crosslinked with anti-hCH2 antibody, showed activity in both PBMC assays. No activity was observed with the negative control G1-AA/HeID1.3 antibody, as expected. Surprisingly, the mAb$^2$ showed similar activation in both PBMC assays with EC$_{50}$ values of 0.08 nM and 0.03 nM respectively. The EC$_{50}$ indicates the concentration of mAb at which half of the agonistic response is achieved. Therefore, the mAb$^2$ could bind to the PBMC-expressed PD-L1 resulted in crosslinking of the mAb$^2$ such that they were able to bind to, cluster and activate CD137 on both species' T cells, as measured by IFN-γ release. The maximum concentration of IFN-γ released by T cells treated with mAb$^2$ was higher than any of the positive control antibodies, indicating that the mAb$^2$ has increased activity in this assay above that of anti-CD137 monoclonal antibodies.

Example 12: Production of an Anti-Mouse CD137 Fcab

To test the activity of mAb$^2$ containing a CD137 antigen-binding region in in vivo mouse models, because of the risk of not being able to obtain mouse human cross-reactive Fcabs due to the low sequence homology between the mouse and human CD137 sequences, Fcabs which specifically bound to mouse CD137 were generated and characterised. After mouse CD137-binding Fcabs were generated, surprisingly, FS22-053-14 was subsequently found to be able to be mouse and human cross-reactive.

12.1 Naïve Selection of Anti-Mouse CD137 Fcabs

In order to select Fcabs that bind to human CD137, yeast and phage display selection campaigns were employed, similar to that previously described for selection of Fcabs binding to human CD137 (see Example 2.1). Recombinant mouse dimeric CD137 or cells expressing full-length mouse CD137 used as antigens (see Example 1).

In-house mCD137-mFc-Avi antigen and DO11.10 cells expressing mCD137 (DO11.10.mCD137) were used in selections using the six phage libraries. All round 3 recombinant antigen outputs (576 clones) and all round 3 cell selection outputs (576 clones) were screened by phage ELISA and for cell binding to Do11.10.mCD137 cells. 34 Fcab clone hits were subcloned and produced as HelD1.3 mAb$^2$ as described in Example 2.2.

The four naïve yeast libraries displaying CH1 to CH3 domains of human IgG1 previously used for selection of Fcabs binding to human CD137 were used for selections of Fcabs binding to mouse CD137. A total of 53 separate rounds of selections were performed to identify anti-mouse CD137 binders. In-house-produced, recombinant, dimeric, biotinylated mouse CD137 (mCD137-mFc-Avi) antigen was used to select binders from the yeast naïve libraries.

12.2 Characterisation of Anti-Mouse CD137 Fcabs from Naïve Selections

The specificity of the anti-mouse CD137 Fcabs for mouse CD137 was tested in HeID1.3 "mock" mAb$^2$ format and measured by BLI in an Octet QKe system by testing for binding of the Fcabs to other mouse TNFRSF receptors (CD40, OX40, GITR). Streptavidin biosensors (PALL ForteBio 18-5021) to coat 10 ng/μl mouse CD40, GITR, OX40 receptors (all obtained from R&D Systems and biotinylated using an EZ-Link Sulfo-NHS—SS-Biotin kit from Thermoscientific #21328). Anti-mouse CD137 Fcabs in mock mAb$^2$ format were diluted 1:1 in kinetic buffer (PALL 18-1092) to a final concentration of at least 1 μM. Antigen-coated sensors were dipped into the mAb$^2$ solutions for 180 seconds followed by 180 seconds in 1×kinetic buffer. Antibodies for each of the TNFRSF receptors were used as positive controls. The Fcab clones FS22m-055, FS22m-063, FS22m-066, FS22m-075, FS22m-135, FS22m-055, FS22m-063, FS22m-066 did not bind to any of the TNFRSF receptors tested, thus demonstrating their specificity for mouse CD137.

HEK.FRT.luc cells expressing the mouse CD137 sequence (SEQ ID NO: 187) were produced following the same methodology as previously described in Example 2.3. The mAb$^2$ containing the anti-mouse CD137 Fcabs previously selected were screened using this cell line, HEK.FRT-.luc.mCD137, according to the method described in Example 2.3. 56 mAb$^2$ were tested of which 29 were positive for NF-κB activity. Lob12.3 containing a human IgG1 Fc with a LALA mutation (G1-AA/Lob12.3), was used as a positive control anti-mouse CD137 mAb and showed an increase in luminescence confirming the assay's validity. HeID1.3, also containing a human IgG1 Fc with a LALA mutation, was used as a negative control human IgG isotype to rule out interference from the human IgG mock Fab in this assay. EC$_{50}$ s were calculated where possible and mAb$^2$ which did not reach a plateau in activity were disregarded in favour of mAb$^2$ which showed classic sigmoidal activity kinetics. mAb$^2$ were ranked in order of EC$_{50}$ and fold-change in activity upon Protein L crosslinking. FS22m-063 was selected based on it having the best EC$_{50}$ upon crosslinking (1.44 nM) and highest fold-change in activity upon crosslinking (27-fold).

12.3 Activity of FS22m-063, FS22-053-014 and FS22-053-017 Fcabs in Mock mAb$^2$ Format in Mouse CD137 DO11.10 T Cell Activation Assay The FS22-053-017 clone (in HeID1.3 mock mAb$^2$ format) was also compared against the murine CD137 binding Fcab clone FS22m-063 (also in HeID1.3 mock mAb$^2$ format), as well as the parental FS22-053-014 clone (in HeID1.3 mock mAb$^2$ format), in a mouse CD137 DO11.10 T cell activation assay as described in Example 2.4. The mAb$^2$ molecules were crosslinked with Protein L at a 4:1 molar ratio (mAb$^2$:Protein L). The results are shown in Table 22.

As expected, all of the molecules tested showed activity as measured by IL-2 release when crosslinked by Protein L but had no activity when not crosslinked. FS22m-063 which was selected to bind to mouse CD137 had the best activity in the assay, with an EC$_{50}$ of 0.39 nM when crosslinked. Both FS22-053-14 and FS22-053-017 had activity in the assay, indicating that function was not lost due to mutagenesis, though FS22-053-017 had a slight loss in activity with an EC$_{50}$ which was approximately 8-fold worse than FS22-053-14 when cross linked by Protein L. FIG. 10 shows that the affinity-matured human and murine cross-reactive CD137 Fcabs FS22-053-014 and FS22-053-017, and anti-mouse CD137 Fcab FS22m-063, in HeID1.3 mock mAb$^2$ format activate CD137 when crosslinked with Protein L leading to a release of mIL-2 in a DO11.10 T cell activation assay.

TABLE 22

| Fcab clone (in HeID1.3 mAb$^2$ format) or mAb | IL-2 release with or without Protein L crosslinking | | |
|---|---|---|---|
| | No XL | +XL E$_{max}$ (IL-2 pg/ml) | +XL EC$_{50}$ (nM) |
| FS22-053-014 | N/A | 28071 | 2.04 |
| FS22-053-017 | N/A | 41042 | 16.74 |
| FS22m-063 | N/A | 24175 | 0.39 |
| G1-AA/Lob12.3 + Protein L | N/A | 21332 | 2.26 |

N/A - not applicable as low signal did not allow EC$_{50}$ determination

Example 13: In Vitro Characterisation of Anti-Mouse CD137/PD-L1 mAb$^2$

To test the activity of mAb$^2$ containing a CD137 antigen-binding region in in vivo mouse models, FS22m-063 was chosen as the Fcab which showed the best activity in the T cell activation assay as described in Example 12.3.

13.1 Construction, Expression and Purification of Anti-Mouse CD137/PD-L1 mAb$^2$ Anti-mouse CD137/PD-L1 mAb$^2$ were produced comprising the anti-mouse CD137 Fcab FS22m-063 and also a PD-L1 binding Fab region (clone YW243.55.S70 from U.S. Pat. No. 8,217,149 B2). They were prepared similarly to the method described in Example 3.2 by substitution of part of the CH3 of the anti-PD-L1 binding antibody containing the AB, CD and EF loops with the corresponding region of the Fcab. These PD-L1 model mAb$^2$ comprised a LALA mutation in the CH2 domain (AA). The introduction of the LALA mutation in the CH2 domain of human IgG1 is known to reduce Fc γ receptor binding (Bruhns, P., et al. (2009) and Hezareh M., et al. (2001)).

FS22m-063-AA/PD-L1 mAb² were produced by transient expression in HEK293-6E cells and purified using mAb Select SuRe protein A columns.

13.2 Activity of Anti-Mouse CD137/PD-L1 mAb² in a Mouse Primary OT-1 T Cell Activation Assay To test the activity of the anti-mouse CD137/PD-L1 mAb² on cells which have not been engineered to overexpress CD137, a mouse primary T cell assay was needed. Activated cytotoxic CD8+ T cells are responsible for directly killing cancer cells and express CD137 on their cell surface (Ye et al, 2014). Clustering of CD137 is known to be essential to induce downstream signalling and further CD8+ T cell activation. A CD8+ T cell activation assay was therefore used to assess the ability of mAb² to drive clustering and subsequent downstream signalling of CD137. Whilst attempts were made to mirror the human CD8+ T cell activation assay identically, murine CD8+ T cells isolated from naïve C57BL/6 or Balb/c spleens did not show the activation potential required for such an assay. Therefore, an alternative antigen-specific CD8+ T cell activation assay was developed. CD8+ T cell activation was achieved by antigen stimulation of genetically modified OT-1 T cells, isolated from C57BL/6 OT-1 mice (Jackson Laboratory, Cat no. 003831) having a T cell receptor specific for ovalbumin peptide 257-264, and was determined by the release of IL-2.

To isolate CD8+ T cells, splenocytes were isolated from fresh OT-1 mouse spleens. Briefly, each spleen from a C57BL/6 OT-1 mouse was collected and stored in PBS before being transferred to a well of a 6-well tissue culture plate and mechanically disrupted with 2 needles. The disrupted spleen was passed through a 70 µm cell strainer and the strainer was rinsed with PBS. The cell suspension was then pelleted by centrifugation, the supernatant removed, and red blood cells were lysed through the addition of 10 ml 1× red blood cell lysis buffer (eBioscience, 00-4300-54) according to the manufacturer's instructions. Splenocytes were plated for T cell activation medium (IMDM, 5% FCS, 50 µM 2-Mercapto Ethanol, 1× Penstrep) containing 10 nM SIINFEKL peptide (SEQ ID NO: 194) InvivoGen, cat no. vac-sin) in 6-well plates at 10×10⁶ cells per well. Plates were incubated for 48 hours at 37'C with 5% CO2. After 48 hours CD8+ T cells were isolated by using a CD8+ T cell Isolation Kit (Miltenyi Biotec, 130-104-075) following manufacturer's instructions. Isolated and activated CD8+ T cells were plated in medium (IMDM, 5% FCS, 50 µM 2-Mercapto Ethanol, 1× Penstrep) supplemented with 30 U/ml IL-2 (Peprotech, AF-200-02) and kept at less than 1×10⁶ per ml at each daily split for 3 further days. After the three days of expansion cells were then used in the following assay.

Incubation with B16.F10 cells, which were cultured in the presence of IFN-γ to induce expression of PD-L1, and that were then pulsed with SIINFEKL peptide was used as a first signal to drive initial activation of the OT-1 T cells and were subsequently used to assess the efficacy of anti-mouse CD137/PD-L1 mAb² FS22m-063-AA/S70.

Briefly, B16.F10 cells were first cultured in the presence of 20 ng/ml murine IFN-γ (Peprotech, cat no. AF-315-05-100UG) to induce PD-L1 expression. These cells were then incubated with 500 nM SIINFEKL peptide for one hour at 37° C. before being seeded at 1.5×10⁴ cells per well in 100 µl media in a flat bottom 96-well plate. 2×10⁴ OT-1 cells per well were added to the B16.F10 cells in 50 µl media. Test antibodies (FS22m-063-AA/S70, G1-AA/S70, G1-AA/Lob12.3, FS22m-063-AA/HeID1.3) were prepared in a 1:4 titration starting at 160 nM (4× final concentration) and 50 µl of antibody mix was added to each well accordingly resulting in a final assay volume of 200 µl. The assay was incubated for 3 days at 37° C. with 5% $CO_2$. After 3 days, supernatants were harvested and an ELISA for mIFN-γ (eBioscience, cat no. 88-7314-88) was performed according to manufacturer's instructions.

As seen in FIG. 11 and in Table 23, the anti-mouse CD137/PD-L1 mAb² has the highest potency with an $EC_{50}$ value of 0.003 nM. This assay indicates that the mAb² has strong potency as a result of clustering of CD137 leading to increased agonism and CD8+ T cell activation.

TABLE 23

| Molecule | Type | $EC_{50}$ (nM) | $E_{max}$ (pg/ml) |
|---|---|---|---|
| FS22m-063-AA/S70 | mAb² | 0.003 | 23886 |
| G1-AA/S70 + G1-AA/Lob12.3 + anti-hCH2 | Positive control mAb combination | 0.02 | 24703 |
| G1-AA/S70 | PD-L1 mAb | 0.02 | 19477 |
| G1-AA/Lob12.3 + anti-hCH2 | CD137 mAb | 0.36 | 17833 |
| FS22m-063-AA/HeID1.3 | Mock mAb² | n/a | 3854 |

N/A means - not applicable as low signal did not allow $EC_{50}$ determination

Having shown activity in vitro and activity superior to positive antibody controls, it was desirable to then test the anti-mouse CD137/PD-L1 mAb² in a suitable in vivo syngeneic mouse tumour model.

Example 14: In Vivo Characterisation of Anti-Mouse CD137/PD-L1 mAb²

14.1 Activity of Anti-Mouse CD137/PD-L1 mAb² in a CT26 Syngeneic Mouse Tumour Model Having shown that the FS22m-063 Fcab is capable of driving clustering and activation of CD137 in vitro, it was desirable to test its ability to activate CD137 in vivo.

Preparation of FS22m-063 Fcab in mAb² Format for In Vivo Testing in Mice

A mAb² comprising the anti-mouse CD137 Fcab, FS22m-063, and a Fab region specific for PD-L1 using similar methodology to the model mAb² produced in Example 3.2 was prepared and tested for in vivo anti-tumour activity in a CT26 syngeneic mouse tumour model.

Controls: G1/Lob12.3, G1-AA/Lob12.3, G1/S70, G1-AA/4420.

Control antibodies for the in vivo experiments were produced by joining the variable heavy region of the anti-PD-L1 antibody S70 (clone YW243.55.S70 from U.S. Pat. No. 8,217,149 B2) to the human IgG1 (G1m17) constant region containing the LALA mutation, and the variable light region from the S70 antibody was joined to the human constant region (Lm1) via human kappa J-region. The anti-mouse CD137 antibody Lob12.3 (Taraban et al., 2002) in human IgG1 format with and without the LALA mutation in the constant region was used as an anti-mouse CD137 positive control antibody. The mAb² was generated by replacing the CH3 domain of the reformatted construct described above with FS22m-063 and was designated 'FS22m-063-AA/S70'.

Syngeneic mouse models are accepted as appropriate murine systems for testing the anti-tumour effect of inhibiting therapeutic targets and have been used extensively to validate development of human therapeutics. The CT26 syngeneic tumour model was used in this experiment as CT26 tumours are known to be highly immunogenic (Lechner et al, 2013) and partially respond to anti-CD137 antibody monotherapy (Kim et al, 2009) and express PD-L1 (Kleinovink, 2017).

Balb/c female mice (Charles River) aged 8-10 weeks and weighing 20-25 g each were rested for one week prior to the study start. All animals were micro-chipped and given a unique identifier. Each cohort had 12 mice. The CT26 colon carcinoma cell line (S.Rosenberg, NIH) was initially expanded, stored, and then pre-screened by IDEXX Bioresearch for pathogens using the IMPACT I protocol and shown to be pathogen-free. Each animal received $0.1 \times 10^6$ cells injected subcutaneously in the left flank in 100 µl DMEM. 7 days following tumour cell inoculation, mice which did not have tumours at this point were removed from the study.

The FS22m-063-AA/S70 mAb$^2$ and control antibodies (G1/Lob12.3, G1-AA/Lob12.3 (anti-CD137 positive controls), G1/S70 (positive control anti-PD-L1), G1-AA/4420 (isotype control)) were injected intraperitoneally into mice at 20 µg per mouse (a final concentration of ~1 mg/kg) in DPBS+1 mM arginine+0.05 Tween 80. Each mouse received the mAb$^2$ molecule or the control antibody or a combination of two control antibodies by 200 µl intraperitoneal (IP) injection on days 7, 9, and 11 following tumour inoculation. Accurate measurements of tumours were taken, any drug dosing due on the day in question was performed, and the mice were put under close observation for the remainder of the study. Tumour volume measurements were taken with callipers to determine the longest axis and the shortest axis of the tumour. The following formula was used to calculate the tumour volume:

$$L \times (S^2)/2$$

Where L=longest axis; S=shortest axis

As shown in FIG. 12, the FS22m-063-AA/S70 mAb$^2$ showed significant tumour growth inhibition compared to mice treated with some of the control antibodies. Statistical significance was shown pairwise for growth rates over the full time of study using the Mixed Model analysis comparing all groups. None of the mice showed signed of overt toxicity and all treatments were well tolerated indicating that a bispecific targeting CD137 and PD-L1 does not induce significant toxicity.

All animals containing tumours measuring equal or below 62.5 mm$^3$ were counted as fully responding animals (see Table 24). 28% of the animals treated with G1/Lob12.3 (anti-CD137 positive control without LALA mutation) were deemed to be tumour free at the end of the study, while 7% of the animals treated with G1-AA/Lob12.3 (anti-CD137 positive control with the LALA mutation) and 0% of FS22m-063-AA/S70 (anti-mouse CD137 Fcab FS22m-063 in a model PD-L1 mAb$^2$ format) treated mice were deemed tumour free. FS22m-063-AA/S70 induces significant tumour growth inhibition, in a CT26 syngeneic tumour model compared to IgG control treated mice. No animals treated with G1-AA/4420 (IgG control) or G1/S70 (PD-L1 positive control) were tumour free by the end of the study. The graphs in FIG. 17 show the tumour growth measurements in mm$^3$ for each animal over time.

TABLE 24

Number and percentage of tumour-free mice by study end in the CT26 syngeneic tumour study.

| Compound | Tumour-free mice by study end |
|---|---|
| G1-AA/4420 | 0/13 (0%) |
| G1-AA/Lob12.3 | 1/14 (7%) |
| G1/S70 | 0/14 (0%) |

TABLE 24-continued

Number and percentage of tumour-free mice by study end in the CT26 syngeneic tumour study.

| Compound | Tumour-free mice by study end |
|---|---|
| G1/Lob12.3 | 4/14 (28%) |
| G1-AA/Lob12.3 + G1/S70 | 1/14 (7%) |
| FS22m-063-AA/S70 | 0/14 (0%) |

The study shows that in mice with a fully functioning immune system, in a CT26 syngeneic mouse tumour model, CD137 agonism, presumably as a result of crosslinking via PD-L1, leads to a reduction in tumour growth, presumably through increased cytotoxic activity of CD8$^+$ T cells in the tumour.

Survival analysis (FIG. 18 and Table 25) showed that the FS22m-063-AA/S70 induced a significant survival benefit compared to isotype control (G1-AA/4420). Table 25 shows a summary of median survival in days for each group and pairwise statistical analyses (Log-rank) in CT26 syngeneic tumour model grown subcutaneously in Balb/c mice treated with G1-AA/4420 (IgG control), the combination of G1/S70 plus G1-AA/Lob12.3 and FS22m-063-AA/S70 (the anti-mouse CD137 Fcab FS22m-063 in a model PD-L1 mAb$^2$ format). FS22m-063-AA/S70 resulted in significantly increased survival compared to IgG control treated mice. FS22m-063-AA/S70 showed no significant survival benefit over the combination of G1/S70+G1-AA/Lob12.3.

TABLE 25

Median survival times for animals treated with each compound.

| Compound | Median Survival (Days) | p-values | Log-rank |
|---|---|---|---|
| FS22m-063-AA/S70 | 30.5 | | |
| G1/S70 + G1-AA/Lob12.3 | 27 | 0.2235 | Ns |
| G1-AA/4420 | 26 | 0.0058 | ** |

Having shown that in mice with a fully functioning immune system, in a CT26 syngeneic mouse tumour model, CDI137 agonism, presumably as a result of crosslinking via PD-L1, leads to a reduction in tumour growth, presumably through increased cytotoxic activity of CD8$^+$ T cells in the tumour, the study was repeated with the following deviations. The FS22m-063-AA/S70 mAb$^2$ and control antibodies G1-AA/Lob12.3 (positive control anti-CD137), G1/S70 (positive control anti-PD-L1), G1-AA/HeID1.3 (isotype control)) were injected intraperitoneally into mice at 200 µg per mouse (a final concentration of ~10 mg/kg) in DPBS+1 mM arginine+0.05 Tween 80. Each mouse received the mAb$^2$ molecule or the control antibody or a combination of two control antibodies by 200 µl intraperitoneal (IP) injection on days 7, 9, and 11 following tumour inoculation.

Treatment with FS22m-063-AA/S70 resulted in significant tumour growth inhibition (shown as tumour volume mean in FIG. 19) compared to the control antibodies.

Survival analysis (FIG. 20 and Table 26) showed that the FS22m-063-AA/S70 induced a significant survival benefit compared to isotype control (G1-AA/HeID1.3) and G1/S70. There was no significant survival benefit over G1-AA/Lob12.3

Table 26 shows a summary of median survival in days for each group and pairwise statistical analyses (Log-rank) in CT26 syngeneic tumour model grown subcutaneously in Balb/c mice treated with G1-AA/HeID1.3 (IgG control), G1/S70 (anti-PD-L1 positive control), G1-AA/Lob12.3 (anti-CD137 positive control) and FS22m-063-AA/S70 (anti-mouse CD137 Fcab FS22m-063 in a model PD-L1 mAb$^2$ format). FS22m-063-AA/S70 induced significant survival in a CT26 syngeneic tumour model compared to IgG control treated and CD137 positive control treated mice.

TABLE 26

Summary of median survival in days for each group and pairwise statistical analyses (Log-rank) in CT26 syngeneic tumour model.

| Compound | Median Survival (Days) | p-values Log-rank | |
|---|---|---|---|
| FS22m-063-AA/S70 | 48.5 | | |
| G1/S70 | 23.5 | 0.0057 | ** |
| G1-AA/Lob12.3 | 28 | 0.131 | Ns |
| G1-AA/HeID1.3 | 27 | 0.0149 | * |

14.2 Dose-Response Activity of Anti-Mouse CD137/PD-L1 mAb$^2$ in a CT26 Syngeneic Mouse Tumour Model Dose-Response Anti-Tumour Activity The anti-mouse CD137/PD-L1 mAb$^2$ FS22m-063-AA/S70 showed anti-tumour activity in the CT26 syngeneic tumour model at a dose of 20 μg per mouse (~1 mg/kg) dosed three times every two days (q2dx3). To investigate the optimum dose of FS22m-063-AA/S70 mAb$^2$ in vivo, a range of doses (2, 6, 20 and 200 μg/mouse, equivalent to approximately 0.1, 0.3, 1, and 10 mg/kg) were tested in the CT26 model at a q2dx3 dosing schedule as described above starting 7 days after tumour cell inoculation. The negative control antibody G1-AA/4420 was included at a dose of 200 μg per mouse (~10 mg/kg) with the same scheduling. The positive control antibody G1/Lob12.3 was included at a sub-optimal dose of 20 μg per mouse (~1 mg/kg) with the same scheduling.

Following the same protocol as described in Example 14.1, Balb/c female mice (Charles River) aged 8-10 weeks and weighing 20-25 g each were rested for one week prior to the study start. All animals were micro-chipped and given a unique identifier. Each cohort had 12 mice. The CT26 colon carcinoma cell line (ATCC CRL-2638) was initially expanded, stored, and then pre-screened by IDEXX Bioresearch for pathogens using the IMPACT I protocol and shown to be pathogen-free. Each animal received 0.1×10$^5$ cells injected subcutaneously in the left flank in 100 μl DMEM. 7 days following tumour cell inoculation, mice which did not have tumours at this point were removed from the study.

On study day 7, the FS22m-063-AA/S70 mAb$^2$ was injected intraperitoneally into mice at a final concentration according the dose range described above. Control antibodies (G1/Lob12.3 (CD137 positive control antibody), G1-AA/4420 (isotype control)) were injected intraperitoneally into mice at a final concentration of 20 μg per mouse (~1 mg/kg) and 200 μg per mouse (~10 mg/kg) respectively in DPBS+1 mM arginine+0.05 Tween 80. Each mouse received the mAb$^2$ molecule or the control antibody by 200 μl intraperitoneal (IP) injection on days 7, 9, and 11 following tumour inoculation (q2dx3). Accurate measurements of tumours were taken, any drug dosing due on the day in question was performed, and the mice were put under close observation for the remainder of the study. Tumour volume measurements were taken with callipers to determine the longest axis and the shortest axis of the tumour as described in Example 14.1

As shown in FIG. 13A, the FS22m-063-AA/S70 mAb$^2$ showed significant tumour growth inhibition compared to mice treated with the isotype control (G1-AA/4420) when dosed at ~0.3 mg/kg up to ~10 mg/kg Statistical significance was shown using the Mixed Model analysis comparing all groups Survival analysis, FIG. 13B and Table 27, shows that FS22m-63-AA/S70 mAb$^2$ induces a statistically significant survival benefit compared to isotype control in CT26 syngeneic model when dosed at levels above 0.3 mg/kg. Statistical significance performed using log rank (Mantel Cox) test. *P≤0.05; P≤0.01; *P≤0.001; ****P≤0.0001. None of the mice showed signed of overt toxicity and all treatments were well tolerated.

TABLE 27

| | | Statistical significance (log rank test) | | | |
|---|---|---|---|---|---|
| | Median | FS22m-063-AA/S70 | | | |
| Treatment | Survival (days) | 10 mg/kg | 1 mg/kg | 0.3 mg/kg | 0.1 mg/kg |
| FS22m-063-AA/S70 10 mg/kg | 39 | | | | |
| FS22m-063-AA/S70 1 mg/kg | 29 | ns | | | |
| FS22m-063-AA/S70 0.3 mg/kg | 24 | *** | * | | |
| FS22m-063-AA/S70 0.1 mg/kg | 21 | *** * | *** | ** | |
| G1-AA/4420 10 mg/kg | 21 | **** | ** | * | ns |

NS means not significant

The study shows that in mice with a fully functioning immune system, in a CT26 syngeneic mouse tumour model, CD137 agonism, presumably as a result of crosslinking via PD-L1, leads to a dose dependent reduction in tumour growth and a dose dependent increase in survival, presumably through increased cytotoxic activity of CD8$^+$ T cells in the tumour.

14.3 Dose-Response Mechanism of Action

The mechanism of action of the anti-mouse CD137/PD-L1 mAb$^2$ was assessed in the same CT26 tumour-bearing mouse model as described in Example 14.2. Blood, spleen and tumour tissue from CT26 tumour-bearing treated with FS22m-063-AA/S70 at four different doses (2, 6, 20 and 200 μg/mouse, equivalent to approximately 0.1, 0.3, 1, 10 mg/kg) as well as negative control antibody G1-AA/4420 was tested for T cell activation and proliferation markers known to be downstream effects of CD137 agonism (Fisher et al., 2012).

Following the same study protocol as described in this example at day 9 (48 hours after first dose), day 11 (48 hours after second dose) and at day 15 (96 hours after third and final dose) blood was collected in to EDTA-containing tubes by cardiac puncture, and spleen and tumour tissue was collected by dissection. Spleen and tumour tissue was disaggregated to single cell suspension by standard mechanical and enzymatic methods. Red blood cells were lysed once in red blood cell lysis buffer (eBioscience, cat no. 00-4300-54) according to manufacturer's instructions.

Red blood cells of the uncoagulated blood were lysed twice in red blood cell lysis buffer (eBioscience cat no 00-4300-54) according to manufacturer's instructions.

All samples were then treated the same. Cells were then washed once with PBS and samples stained with fixable viability dye (Invitrogen, cat no. 65-0865-14) at 1:3000 dilution in PBS following manufacturer's instructions. The cells were stained for flow cytometry for cell surface markers with an antibody staining panel (all but Ki67 and FoxP3 antibodies) (Table 28 below) in the presence of Fc block (eBioscience cat no 14-0161-86 at 1:50) for 30 minutes at 4° C. The cells were then fixed and permeabilized with the eBioscience Foxp3 staining kit (eBioscience cat no 00-5523-00) according to manufacturer's instructions. Cells were resuspended in 100 pl permeabilization buffer with Ki67 and Foxp3 antibodies in the presence of Fc block (all in 1:100 dilution) and incubated 30 minutes in the dark at room temperature. Cells were then washed once with permeabilization buffer and resuspended in 200 μl PBS+0.5% BSA. The cells were then analysed in a BD Fortessa flow cytometer. Data was analysed with FlowJoX, Excel and GraphPad Prism. The data plotted represents the T cell abundance and proliferation observed over time for CD4$^+$ and CD8$^+$ T cell subpopulations. The data is presented as the percentage of the parental population according to the population description in the Y axis.

As shown in FIG. 14B the CD8$^+$:CD4$^+$ percentage ratio increases in favour of CD8$^+$ T cells, both in the tumour and the periphery in line with an increased dose of anti-mouse CD137/PD-L1 mAb$^2$, indicating that the treatment causes a shift in the balance of the two T cell subpopulations likely to be as a result of increase CD8$^+$ T cell numbers. By day 15, the proliferation marker on CD8$^+$ T cells is increased in line with treatment dose level with highest proliferation seen at the highest dose level. This would indicate that CD8$^+$ T cells are proliferated which is a sign of activation and would account for the increased CD8$^+$ T cell numbers resulting in an increased CD8$^+$:CD4$^+$ T cell ratio.

Overall, this study has shown that increasing the dose level of anti-mouse CD137/PD-L1 results in more CD8$^+$ T cells in the tumour. The main role of CD8$^+$ T cells (often also called cytotoxic lymphocytes) is the killing of infected or malignant cells via 3 main mechanisms: 1) release of cytokines e.g. TNFα and IFN-γ, 2) production and release of cytotoxic granules and 3) expression of FasL. The presence of more CD8$^+$ T cells in the tumour following treatment with anti-mouse CD137/PD-L1 presumably results in cytotoxic activity via these mechanisms against the tumour, resulting in tumour control.

TABLE 28

| Target | Antibody Clone | Fluorophore | Company | Cat no. |
| --- | --- | --- | --- | --- |
| CD45 | 30-F11 | AF700 | eBioscience | 56-0451-82 |
| CD3 | 145-2C11 | PECy7 | eBioscience | 25-0031-82 |
| CD4$^+$ | RM4-5 | BUV395 | BD Biosciences | 740208 |
| CD8$^+$ | 53-6.7 | BUV737 | BD Biosciences | 564297 |
| FoxP3 | Fjk-16S | PerCP-Cy5.5 | Invitrogen | 45-5773-82 |
| CD44 | IM7 | BV650 | BioLegend | 103049 |
| CD62L | MEL-14 | Bv421 | BioLegend | 104435 |
| CD69 | H1.2F3 | Bv510 | BioLegend | 104532 |
| Ki67 | 16A8 | 647 | BioLegend | 652407 |
| PD-L1 | 10F.9G2 | Bv785 | BioLegend | 124331 |
| IgG | MK1A6 | FITC | Bio-Rad | MCA647F |
| Viability | n/a | 780 | Invitrogen | 65-0865-14 | n/a means not applicable 14.4 Activity of Anti-Mouse CD137/PD-L1 mAb$^2$ in a MC38 Syngeneic Mouse Tumour Model Syngeneic mouse models are accepted as appropriate murine systems for testing the anti-tumour effect of inhibiting therapeutic targets and have been used extensively to validate development of human therapeutics. The MC38 syngeneic tumour model was used in this experiment as MC38 tumours are known to be highly immunogenic and respond to anti-CD137 antibody monotherapy (Kocak et al, 2006) and express PD-L1 (Juneja et al, 2017).

C57BL/6 female mice (The Jackson Laboratory) aged 9-10 weeks and weighing 18 to 24 g each were rested for one week prior to the study start. All animals were microchipped and given a unique identifier. Each cohort had 12 mice. The MC38 colon carcinoma cell line (National Cancer Institute, USA) was initially expanded, stored, and then pre-screened for pathogens and shown to be pathogen-free. Each animal received 1×10$^6$ cells injected subcutaneously in the right flank in 100 μl in serum-free culture medium (Dulbecco's Modified Eagle Medium). 7 days following tumour cell inoculation, mice which did not have tumours at this point were removed from the study.

The FS22m-063-AA/S70 mAb$^2$ and control antibodies (G1-AA/Lob12.3 (CD137 positive control), G1-AA/S70 (positive control PD-L1), G1-AA/4420 (isotype control)) were injected intraperitoneally into mice at a fixed concentration of 20 μg per dose in DPBS+1 mM arginine+0.05 Tween 80. Each mouse received the mAb$^2$ molecule or the control antibody by 200 μl intraperitoneal (IP) injection on days 7, 9, and 11 following tumour inoculations. Accurate measurements of tumours were taken, any drug dosing due on the day in question was performed, and the mice were put under close observation for the remainder of the study. Tumour volume measurements were taken with callipers to determine the longest axis and the shortest axis of the tumour. The following formula was used to calculate the tumour volume:

$$L \times (S^2)/2$$

Where L=longest axis; S=shortest axis

As shown in FIG. 15, the FS22m-063-AA/S70 mAb$^2$ showed significant tumour growth inhibition compared to mice treated with any of the control antibodies. Statistical significance was shown pairwise for growth rates over the full time of study using a Mixed Model analysis comparing all groups. As shown in Table 29, unexpectedly all mice treated with FS22m-063-AA/S70 mAb$^2$ were tumour free at the end of the study, compared to only 4 of 12 mice treated with a combination of anti-PD-L1 and anti-CD137 antibodies (G1-AA/S70+G1-AA/Lob12.3) or the PD-L1 or CD137 antibodies alone. The graphs in FIG. 21 show the tumour growth measurements in mm$^3$ for each animal over time.

TABLE 29

| Group | % Tumour Free Mice | Number Tumour Free Mice |
| --- | --- | --- |
| G1-AA/Lob12.3 | 16% | 2/12 |
| G1-AA/4420 | 0% | 0/12 |
| G1-AA/S70 | 16% | 2/12 |
| G1-AA/S70 + G1-AA/Lob12.3 | 33% | 4/12 |
| FS22m-063-AA/S70 | 100% | 12/12 |

The study shows that in mice with a fully functioning immune system, in a second syngeneic tumour model, MC38, which shows suboptimal response to 1 mg/kg of PD-L1 mAb, surprisingly, 1 mg/kg of CD137/PD-L1 mAb$^2$ induces complete tumour regression in 100% of treated mice.

Survival analysis (FIG. 22 and Table 30) shows the summary of median survival in days for each treatment group treated with 3 doses of G1-AA/4420 (isotype control), G1-AA/S70 (anti-PD-L1 positive control), G1-AA/Lob12.3 (anti-CD137 positive control), the combination of G1-AA/S70 plus G1-AA/Lob12.3, and FS22m-063-AA/S70 (the anti-mouse CD137 Fcab FS22m-063 in a model PD-L1 mAb$^2$ format). Table 30 also shows pairwise statistical analyses (Log-rank). FS22m-063-AA/S70 induces full survival in a MC38 syngeneic tumour model, with 100% survival of the animals at the end of the study (labelled 'undefined'), compared to the IgG control treated mice.

TABLE 30

Median survival in MC38 tumour model

| Compound | Median Survival (Days) | p-values | Log-rank |
|---|---|---|---|
| FS22m-063-AA/S70 | undefined | | |
| G1-AA/S70 + G1-AA/Lob12.3 | 33.5 | 0.0006 | *** |
| G1-AA/Lob12.3 | 25 | 0.0001 | ** |
| G1-AA/S70 | 28 | <0.0001 | **** |
| G1-AA/4420 | 20 | <0.0001 | **** |

14.5 Activity of Anti-Mouse CD137/PD-L1 mAb$^2$ in a B16.F10 Syngeneic Mouse Tumour Model The B16.F10 syngeneic tumour model was used to test the anti-tumour activity of the anti-mouse CD137/PD-L1 mAb$^2$ (FS22m-063-AA/S70) in vivo. This model is seen as more challenging to treat with therapeutic antibodies (Baird, J. R., et al, 2013). Antibody G1-AA/4420 was used as an isotype control in the study. The B16.F10 syngeneic tumour model has not been previously shown to be sensitive to CD137 agonist antibodies. However, tumour infiltrating lymphocytes (TILs) isolated from B16.F10 tumours express CD137 (Curran. M., et al, 2013).

C57BL/6 female mice (Charles River) aged 8-10 weeks and weighing 20-25 g each were acclimatised for one week prior to the study start. All animals were micro-chipped and given a unique identifier. Each cohort had 10 mice. The B16.F10 melanoma cell line (ATCC cat no CRL-6475) was initially expanded, stored, and then pre-screened by IDEXXX Bioresearch for pathogens using the IMPACT I protocol and shown to be pathogen free. B16.F10 cells were thawed from −150° C. storage and added to 20 ml DMEM (Gibco, 61965-026) with 10% FCS (Gibco, 10270-106) in a T175 tissue culture flask. Each animal received 1×10$^6$ cells injected subcutaneously in the left flank.

20 µg of each antibody was injected into mice (~1 mg/kg) in 200 µl PBS. Each mouse received the antibodies by intraperitoneal (IP) injection every 2 days for 3 doses starting on day 7 post tumour cell inoculation. Tumour volumes were determined by measuring using callipers (as described in Example 14.1) and any drug dosing due on the day in question was performed, and the mice were subjected to close observation for the remainder of the trial. Tumour volumes were calculated as described in Example 14.1.

The trial was halted when humane endpoints were reached based on tumour volume and condition. Statistical analysis of growth rates was carried out pairwise over the full time of the study using the Mixed Model analysis.

There was significant slowing of tumour growth rate for the anti-mouse CD137/PD-L1 mAb$^2$ compared to isotype control antibody G1-AA/4420 (FIG. 16). FS22m-063-AA/S70 induced partial tumour growth inhibition in a B16.F10 syngeneic tumour model compared to IgG control treated mice. The graphs in FIG. 23 show the tumour growth measurements in mm$^3$ for each animal over time.

Survival analysis (Table 31) shows the summary of median survival in days for each group and pairwise statistical analyses (Log-rank) in the B16.F10 syngeneic tumour model grown subcutaneously in C57BL/6 mice treated with G1-AA/4420 (isotype control) and the anti-mouse CD137/PD-L1 mAb$^2$ FS22m-063-AA/S70. FS22m-063-AA/S70 induced increased survival in a B16.F10 syngeneic tumour model compared to IgG control treated mice.

TABLE 31

Median survival in the B16.F10 syngeneic tumour model

| Compound | Median Survival (Days) | p-values Log-rank |
|---|---|---|
| FS22m-063-AA/S70 | 23.5 | n/a |
| G1-AA/4420 | 19 | n/a |

This study showed that in mice with a fully functioning immune system, in a notoriously difficult to treat B16.F10 syngeneic mouse tumour model, CD137 agonism, presumably as a result of crosslinking via PD-L1, leads to a reduction in tumour growth, presumably through increased cytotoxic activity of CD8$^+$ T cells in the tumour.

14.6 Liver Pharmacology of Anti-Mouse CD137/PD-L1 mAb$^2$ in CT26 Syngeneic Mouse Tumour Bearing Model Anti-CD137 mAb treatment of solid tumour patients with urelumab in investigational clinical trials has resulted in severe treatment related immune events which have been shown to be related to the dose of urelumab administered. The effects of these immune events manifested in the liver as severe hepatoxicity (Segal, N. H., et al, 2017).

Preclinical mechanistic work undertaken in mice wherein animals were dosed using CD137 agonistic tool antibodies has shown similar hepatotoxicity. These studies showed a requirement for T cells and CD137 in the resultant hepatotoxicity (Niu, L., et al 2007 and Dubrot J, et al. 2010). Although poorly understood, the interplay between the myeloid and T cell compartments has also been shown to be important in initiating the inflammatory cascade leading to liver damage and hepatotoxicity (Bartkowiak, T et al., 2018). Therefore, these animal models have translational relevance for the clinic in predicting the risk of hepatoxicity in human patients following administration of other CD137 agonists and specifically a CD137/PD-L1 mAb$^2$.

Mice from the CT26 syngeneic tumour study described in Example 14.1 showed no overt signs of toxicity following repeated dosing with FS22m-063-AA/S70 mAb$^2$ which has CD137 agonist capacity upon PD-L1 crosslinking. To determine whether in these animals the immune activation observed as a result of treatment with ~1 mg/kg FS22m-063-AA/S70 mAb$^2$ (which correlated with anti-tumour immune activity) correlated with hepatotoxicity, liver samples were taken at necropsy for histological assessment. FS22m-063-AA/S70 mAb$^2$ and control mice were necropsied 4, 7 and 14 days after the last administration (three mice per group per timepoint) and liver samples were formalin fixed and paraffin embedded. Sections of liver were then cut and subjected to histopathological evaluation via hematoxilin and eosin staining and scoring of parameters of liver inflammation and damage by a certified pathologist. The methods for tissue preparation and histopathological staining by hematoxilin and eosin are highly standardised and well known within the art.

A scoring system was used to assess liver pathology in the hematoxilin and eosin stained sections. Liver was scored for pathology corresponding to hepatocellular necrosis, portal tract inflammation, degenerative hepatocytes and increased mitoses. The frequency of mice showing minimal, slight, moderate and marked effects within each group are shown in Table 32.

FS22m-063-AA/S70 mAb² treated animals have minimal liver pathology. Specifically:
- minimal to slight hepatocellular necrosis with mixed lymphocyte infiltrate in the parenchyma
- minimal to slight mixed inflammatory cells in periportal tracts
- minimal degenerative hepatocytes
- minimal to marked increased mitoses

TABLE 32

Liver findings

| Liver | G1/4420 (Isotype control) | | | FS22m-063-AA/S70 | | |
|---|---|---|---|---|---|---|
| | D4 | D7 | D14 | D4 | D7 | D14 |
| Hepatocellular necrosis, degeneration with mixed inflammatory cells (parenchymal) | | | | | | |
| Minimal | 3 | 3 | 3 | 2 | 2 | 3 |
| Slight | 0 | 0 | 0 | 1 | 1 | 0 |
| Mixed inflammatory cells (+/− SCN) in portal tracts | | | | | | |
| Minimal | 1 | 0 | 0 | 1 | 3 | 3 |
| Slight | 0 | 0 | 0 | 1 | 0 | 0 |
| Degenerative hepatocyte | | | | | | |
| Minimal | 0 | 0 | 0 | 0 | 0 | 0 |
| Increased mitoses | | | | | | |
| Minimal | 1 | 1 | 1 | 2 | 2 | 3 |
| Slight | 1 | 0 | 1 | 1 | 0 | 0 |
| Moderate | 0 | 0 | 0 | 0 | 0 | 0 |
| Marked | 0 | 0 | 0 | 0 | 0 | 0 |

These findings are not deemed to represent severe hepatoxicity, as observed with other examples of anti-CD137 agonist antibodies.

Given the relevance of preclinical studies in mice for risk assessment of severe hepatoxicity in human patients treated with CD137 agonist agents, these results indicate that a mAb² agonising CD137 via crosslinking mediated through PD-L1 binding has a low risk of inducing hepatoxicity in human patients treated at therapeutic doses.

14.7 Tumour and Peripheral Receptor Occupancy and Pharmacodynamic Effects of Anti-Mouse CD137/PD-L1 mAb² in a CT26 Syngeneic Mouse Tumour Model In Example 14.3, the anti-mouse CD137-PD-L1 mAb² FS22m-063-AA/S70 showed the ability to increase CD8⁺ T cells in the tumour after multiple doses. To investigate the extent of target binding on T cells, PD-L1 blockade and the effect FS22m-063-AA/S70 has on T cell proliferation, a single-dose pharmacodynamic study was run in the same CT26 syngeneic tumour model as described in Example 14.1.

Antibody G1-AA/4420 was used as a control. Anti-mouse CD137/PD-L1 mAb² and control antibodies for the in vivo experiments were produced as described in Example 14.1.

Following the same protocol as described in Example 14.1, Balb/c female mice (Charles River) aged 8-10 weeks and weighing 20-25 g each were rested for one week prior to the study start. All animals were micro-chipped and given a unique identifier. This study comprised 3 dosing groups, receiving either control antibody or mAb² at one of two doses over 8 time points (2 h, 6 h, 24 h, 48 h, 72 h, 96 h, 120 h, 192 h). Each dosing cohort had 64 mice (8 mice per timepoint). The CT26 colon carcinoma cell line (S.Rosenberg, NIH) was initially expanded, stored, and then pre-screened by IDEXX Bioresearch for pathogens using the IMPACT I protocol and shown to be pathogen-free. Each animal received $1 \times 10^5$ cells injected subcutaneously in the left flank in 100 µl DMEM. 7 days following tumour cell inoculation, mice which did not have tumours at this point were removed from the study. Each mouse received the test sample via a 100 µl intravenous (IV) injection on day 11 following tumour inoculation. In the groups receiving mAb², FS22m-063-AA/S70 mAb² was injected intravenously into mice at either 20 µg or 200 µg per mouse (a final concentration of ~1 mg/kg and ~10 mg/kg respectively) and in the group receiving control antibody G1-AA/4420 (isotype control) was injected intravenously into mice at 200 µg per mouse (a final concentration of ~10 mg/kg) in DPBS+1 mM arginine+0.05 Tween 80.

The tumour and peripheral blood receptor engagement and pharmacodynamic response as a result of dosing with the anti-mouse CD137/PD-L1 mAb² was assessed. Tumour tissue and blood from CT26 tumour-bearing mice treated with FS22m-063-AA/S70 (anti-mCD137/PD-L1 mAb²) at each of the doses, as well as negative control antibody G1-AA/4420, was tested for anti-mouse CD137/PD-L1 mAb²-bound positive T cells, T cell proliferation, and free PD-L1 not bound by anti-mouse CD137/PD-L1 mAb². Total CD137 expression was also assessed.

Blood (100 µl) was collected in to EDTA coated capillaries by tail vein bleeding and were lysed twice in red blood cell lysis buffer (eBioscience cat no 00-4300-54) according to manufacturer's instructions.

Tumour tissue was collected by dissection and was disaggregated to single cell suspension by standard mechanical and enzymatic methods. Any red blood cells remaining in the disaggregated tumour tissue were lysed once in red blood cell lysis buffer (eBioscience, cat no. 00-4300-54) according to manufacturer's instructions.

Cells were washed once with PBS and samples stained with fixable viability dye (Invitrogen, cat no. 65-0865-14) at 1:3000 dilution in PBS following manufacturer's instructions. The cells were stained for cell surface markers for flow cytometry with an antibody staining panel (all but Ki67 and FoxP3 antibodies) (Table 33 below) in the presence of Fc block (eBioscience cat no 14-0161-86 at 1:50) for 30 minutes at 4° C. The cells were then fixed and permeabilized with the eBioscience Foxp3 staining kit (eBioscience cat no 00-5523-00) according to manufacturer's instructions. Cells were resuspended in 100 µl permeabilization buffer with Ki67 and Foxp3 antibodies in the presence of Fc block and incubated for 30 minutes in the dark at room temperature. Cells were then washed once with permeabilization buffer and resuspended in 200 µl PBS+0.5% BSA. The cells were then analysed in a BD Fortessa flow cytometer. Data was analysed with FlowJoX, Excel and GraphPad Prism.

FIG. 24 shows the percentage of CD4$^+$ and CD8$^+$ T cells isolated from either blood or tumours that were positive for anti-IgG antibody bound to the mCD137/PD-L1 mAb$^2$ in the sample. As shown in FIG. 24, the T cells were positive for bound anti-mCD137/PD-L1 mAb$^2$ as soon as 2 hours after intravenous administration. There was a dose-dependent correlation in the longevity of binding, with anti-mCD137/PD-L1 mAb$^2$ no longer detected after 96 hr on T cells isolated from blood and tumour after administration of a 1 mg/kg dose, whereas anti-mCD137/PD-L1 mAb$^2$ was still detected between 120 hr and 192 h after administration of 10 mg/kg dose. As expected, minimal background staining was observed for the control antibody. Populations of T cells isolated from tumour that were positive for anti-mCD137/PD-L1 mAb$^2$ were larger at the outset compared to T cells isolated from blood. This could indicate that the levels of target expression, either CD137 or PD-L1, were higher on T cells isolated from the tumour, such that the anti-mCD137/PD-L1 was more efficiently targeted to the tumour compared to T cells in the blood.

FIG. 25 shows Ki67 detection as a marker for T cell proliferation on CD4$^+$ and CD8$^+$ T cells isolated from blood and tumours. As indicated in FIG. 25, when compared to control antibody, the anti-mCD137/PD-L1 mAb$^2$ resulted in increases in the frequency of Ki67 positive peripheral blood T cells indicating a pharmacodynamic (PD) response, i.e. that both targets are or have been at some point engaged resulting in the activation of T cells as seen by a proliferative response, at both dose levels tested. Since tumour infiltrating T cells are exposed to an inflammatory environment, the T cell populations isolated from the tumours exhibited a higher frequency of Ki67 positive proliferative T cells. In contrast, the base line frequency of Ki67 positive T cells was much lower in the blood. Both CD4$^+$ and CD8$^+$ T cells appeared to respond to anti-mCD137/PD-L1 treatment, indicating that CD137 on both cell types was engaged by mAb$^2$ and clustered together by binding PD-L1 leading to CD137 signalling and T cell activation resulting in increased proliferation. The effect appeared stronger for CD8$^+$ T cells which is in line with CD8$^+$ T cells expressing higher levels of CD137 than CD4$^+$ T cells. The data suggest that maximum effect is achieved at 1 mg/kg, although the duration of the response appears greater at 10 mg/kg, which could be related to a more prolonged receptor occupancy and therefore longer target engagement at the higher dose level. The more prolonged the receptor occupancy, the greater the PD response. In the tumour, T cells are already highly proliferative, and a dose-correlated increase in magnitude of proliferation on both CD4$^+$ and CD8$^+$ T cells over time was observed.

Samples from the control antibody G1-AA/4420 treated mice were spiked with 100 nM anti-mCD137/PD-L1 mAb$^2$ and acted as control for 100% PD-L1 receptor engagement. This was shown by the lack of binding from a competing anti-mPD-L1 antibody (clone 10F.9G2, see Table 33). Samples from tumours and blood of mice treated with anti-mCD137/PD-L1 showed near complete PD-L1 blockade at the 10 mg/kg dose for the full length of the study, as shown in FIG. 26 represented by 100% PD-L1 receptor occupancy. In samples from mice treated with 1 mg/kg anti-mCD137/PD-L1, the PD-L1 receptor engagement decreased after approximately 72 h on T cells present in blood and tumours, with PD-L1 receptor engagement on T cells present in blood decreased much faster than in T cells present in tumours. This data indicates a tumour-specific blockade of PD-L1 having both the advantage of inhibiting the PD-1/PD-L1 axis and retaining the anti-mCD137/PD-L1 mAb$^2$ in the tumour for longer than in the blood, which is expected to allow the full effect of the drug to persist in the tumour, whilst at the same time limiting off target effects in the periphery.

Overall, this study showed that increasing the dose of anti-mouse CD137/PD-L1 resulted in activation and proliferation of CD8$^+$ and CD4$^+$ T cells in the tumour as measured by the number of cells to which the mAb$^2$ bound, PD-L1 receptor engagement by the mAb$^2$ and increased expression of Ki67 as a marker of proliferation. Activated and proliferating CD8$^+$ and CD4$^+$ cells were also observed in the peripheral blood, acting as a further marker of anti-mouse CD137/PD-L1 induced activity. This dose-dependent T-cell activation supports the tumour growth inhibition previously observed in Example 14 upon administration of anti-mouse CD137/PD-L1.

The main role of CD8$^+$ T cells (often also called cytotoxic lymphocytes) is the killing of infected or malignant cells via 3 main mechanisms: 1) release of cytokines (e.g. TNFα and IFN-γ), 2) production and release of cytotoxic granules and 3) expression of Fas ligand. The presence of more CD8$^+$ T cells in the tumour following treatment with anti-mouse CD137/PD-L1 is expected to result in cytotoxic activity via these mechanisms against the tumour, resulting in tumour control. Whilst CD8$^+$ T cells are the overriding cytotoxic T cell that account for tumour cell killing, CD4$^+$ T cells play a pivotal role in adaptive immunity by recognising peptides presented by MHC class II molecules, becoming activated and producing IFN-γ and TNFα which both mediate protection from tumours (Zanetti, 2015, JI, 2015).

TABLE 33

| Target | Antibody Clone | Fluorophore | Company | Cat no. |
| --- | --- | --- | --- | --- |
| CD45 | 30-F11 | AF700 | eBioscience | 56-0451-82 |
| CD3 | 145-2C11 | BUV737 | BD Biosciences | 564618 |
| CD4 | RM4-5 | Bv786 | BD Biosciences | 563727 |
| CD8 | 53-6.7 | BUV395 | BD Biosciences | 563786 |
| FoxP3 | Fjk-16S | PerCP-Cy5.5 | Invitrogen | 45-5773-82 |
| CD4+4 | IM7 | BV650 | BioLegend | 103049 |
| CD62L | MEL-14 | Bv421 | BioLegend | 104435 |
| CD137 | 17B5 | PE | BioLegend | 106105 |
| Ki67 | 16A8 | PE-Cy7 | BioLegend | 652426 |
| PD-L1 | 10F.9G2 | Bv605 | BioLegend | 124321 |
| IgG | MK1A6 | FITC | Bio-Rad | MCA647F |
| Viability | n/a | e780 | Invitrogen | 65-0865-14 | n/a means not applicable

Example 15: Anti-Human CD137/PD-L1 mAb$^2$ Pharmacokinetics in Mouse

In order to determine the pharmacokinetics of anti-CD137/PD-L1 mAb$^2$ in mice, C57BL/6 female mice (see Example 14.4) but without MC38 tumours, i.e. tumour-free mice, were administered 100 µl anti-CD137/PD-L1 mAb$^2$ at 4 doses (25 mg/kg, 10 mg/kg, 3 mg/kg and 1 mg/kg) and monitored for 384 hours.

Microsampling of around 20 μl of whole blood was performed at 2, 6, 24, 48, 96, and 384 hours, and processed to isolate approximately 5 μl of serum. The amount of anti-CD137/PD-L1 mAb$^2$ present at each time point was determined using the Gyrolab xPlore system by Gyros Protein Technologies. A sandwich assay was performed using a Gyrolab Bioaffy 1000 CD (Product Number P0004253) with biotinylated goat anti-human IgG-(heavy and light chain) monkey adsorbed antibody (Cambridge Bioscience product number A80-319B) as capture antibody and goat anti-Human IgG-AlexaFluor® 647 (Cambridge Bioscience product number 2040-31) as detection antibody. A standard curve generated in the range of 8000-0.07 ng/ml was used to determine sample concentration, with samples undergoing dilution in Rexxip AN buffer as required (Gyros product number P0004994). Other buffers were used as per the manufacturer's recommendations. The average sample concentration from individual mice per time point (three mice per time point) was plotted (FIG. 27).

FIG. 27 shows the pharmacokinetics of anti-CD137/PD-L1 mAb$^2$, demonstrating that the mAb$^2$ has comparable terminal clearance to a standard human IgG in mice (Bergman et al, 1998).

Example 16: Pharmacokinetic/Pharmacodynamic Response to and Tolerability of Anti-Human CD137/PD-L1 mAb$^2$ in Cynomolqus Monkeys A preliminary dose range finding study was conducted to evaluate the pharmacokinetic/pharmacodynamic (PK/PD) response to and tolerability of anti-human CD137/PD-L2 mAb$^2$ in cynomolgus monkeys. Briefly, the FS22-172-003-AA/E12v2 mAb$^2$ was administered to cynomolgus monkeys via intravenous (IV) infusion as a single dose or as repeat doses. Standard toxicology parameters such as body weight, food consumption, clinical observations, haematology and blood chemistry were assessed for the evaluation of tolerability over the duration of the study.

The FS22-172-003-AA/E12v2 mAb$^2$ had a terminal half-life of approximately 6 days and was generally well tolerated up to 30 mg/kg dosed weekly as determined by clinical chemistry and histopathology results). Increased serum sPD-L1 levels (an indication of direct target engagement and cell activation) were observed in all animals on day 1, with peak achieved at 168 hours post end of infusion, following which the levels declined in line with the decline in the systemic levels of the FS22-172-003-AA/E12v2 mAb$^2$.

Consistent with the findings of the study to assess the PD response of the anti-mouse CD137/PD-L1 mAb$^2$ in a syngeneic mouse tumour model (Example 15), a drug-related increase in cell proliferation and activation was also observed in CD4$^+$ and CD8$^+$ Central Memory and Effector Memory T cells, which was measured by an increased expression of Ki67. Similar kinetics were observed for NK cells and a moderate but transient increase in the relative percentage and absolute counts of CD4$^+$ regulatory T cells (CD4$^+$ FoxP3$^+$).

Taken together these results strongly indicate that the anti-human FS22-172-003-AA/E12v2 mAb$^2$ has potent in vivo pharmacological activity in the cynomolgus monkey and is well tolerated up 30 mg/kg. Furthermore, the PK/PD data generated is in line with the surrogate molecule (FS22m-063-AA/S70) data, strengthening the rationale for the use of FS22-172-003-AA/E12v2 mAb$^2$ in the clinical setting.

```
CDR amino acid sequences of E12v2 mAb (Kabat)
VH CDR1 - SYGIS (SEQ ID NO: 1)

VH CDR2 - WISAYSGGTNYAQKLQG (SEQ ID NO: 2)

VH CDR3 - DLFPTIFGVSYYYY (SEQ ID NO: 3)

VL CDR1 - RASQSIGNRLA (SEQ ID NO: 4)

VL CDR2 - EASTSET (SEQ ID NO: 5)

VL CDR3 - QQSYSTPYT (SEQ ID NO: 6)

CDR amino acid sequences of E12v2 (IMGT)
VH CDR1 - GYPFTSYG (SEQ ID NO: 7)

VH CDR2 - ISAYSGGT (SEQ ID NO: 8)

VH CDR3 - ARDLFPTIFGVSYYYY (SEQ ID NO: 9)

VL CDR1 - QSIGNR (SEQ ID NO: 10)

VL CDR2 - EAS (SEQ ID NO: 11)

VL CDR3 - QQSYSTPYT (SEQ ID NO: 6)

VH domain amino acid sequence of E12v2 mAb (SEQ ID NO: 12)
IMGT CDRs (bold italics); Kabat CDRs (italics and underlined).
EVQLVQSGAEVKRPGASVKVSCKASGYPFTSYGIS*WVRQAPGQGLEWMGWISAYSGGTNYAQKLQ
GRVTMTTDTSTSTAYMELRSLRSDDTAVYYCARDLFPTIFGVSYYYYWGQGTLVTVSS VH domain nucleic acid sequence of E12v2 mAb (SEQ ID NO: 13)
GAAGTGCAGCTGGTGCAGTCCGGAGCCGAAGTCAAGAGGCCTGGAGCGTCCGTGAAGGTGTCC
TGCAAAGCCTCAGGATACCCCTTCACTTCGTACGGGATTTCCTGGGTCCGCCAAGCACCGGGTC
AAGGCTTGGAGTGGATGGGATGGATCAGCGCGTATTCCGGGGGAACCAACTACGCTCAAAAGC
TGCAGGGTCGCGTGACCATGACCACCGATACCTCCACCTCAACGGCCTACATGGAACTGAGATC
TCTGCGGAGCGACGACACTGCCGTGTACTACTGTGCCCGGGACCTGTTCCCCACTATCTTCGGA
GTGTCGTACTACTACTACTGGGGCCAGGGGACTCTCGTGACCGTGTCGAGC
```

VL domain amino acid sequence of E12v2 mAb (SEQ ID NO: 14)
IMGT CDRs (bold italics); Kabat CDRs (italics and underlined).
DIQMTQSPSTLSASVRDRVIITCRASQSIGNRLAWYQHKPGKAPKLLIYEASTSETGVPSRFSGSGSG
TDFTLTISSLQPEDFATYYCQQSYSTPYTFGQGTKLEIK VL domain nucleic acid sequence of E12v2 mAb (SEQ ID NO: 15)
GACATCCAGATGACGCAGAGCCCGTCTACCCTGTCCGCCTCCGTGAGAGATCGCGTGATCATCA
CCTGTCGGGCCAGCCAGTCCATCGGAAACCGCTTGGCGTGGTACCAGCACAAGCCTGGGAAGG
CTCCGAAGCTGCTCATCTACGAAGCCTCGACTTCGGAGACTGGTGTCCCTAGCCGGTTCAGCGG
ATCGGGATCAGGGACCGATTTCACTCTGACCATTTCCTCCCTGCAACCCGAGGACTTCGCCACC
TACTACTGCCAACAGTCATATTCCACCCCGTACACCTTCGGACAAGGCACCAAGCTCGAAATCAA
G Heavy chain amino acid sequence of G1-AA/E12v2 mAb (with LALA) (SEQ ID NO: 16)
VH domain (italics); IMGT CDRs (bold and italics); Kabat CDRs (italics and underlined); LALA
mutation (bold and underlined)
*EVQLVQSGAEVKRPGASVKVSCKASGYPFTSYGISWVRQAPGQGLEWMGWISAYSGGTNYAQKLQ
GRVTMTTDTSTSTAYMELRSLRSDDTAVYYCARDLFPTIFGVSYYYYWGQGTLVTVSS*ASTKGPSVF
PLAPSSKSTSGGTAALGCLVKDYFPEPVTVSWNSGALTSGVHTFPAVLQSSGLYSLSSVVTVPSSSL
GTQTYICNVNHKPSNTKVDKKVEPKSCDKTHTCPPCPAPEAAGGPSVFLFPPKPKDTLMISRTPEVT
CVVVDVSHEDPEVKFNWYVDGVEVHNAKTKPREEQYNSTYRVVSVLTVLHQDWLNGKEYKCKVSN
KALPAPIEKTISKAKGQPREPQVYTLPPSRDELTKNQVSLTCLVKGFYPSDIAVEWESNGQPENNYKT
TPPVLDSDGSFFLYSKLTVDKSRWQQGNVFSCSVMHEALHNHYTQKSLSLSPG Light chain amino acid sequence of G1-AA/E12v2 mAb (SEQ ID NO: 17)
VH domain (italics); IMGT CDRs (bold and italics); Kabat CDRs (italics and underlined)
*DIQMTQSPSTLSASVRDRVIITCRASQSIGNRLAWYQHKPGKAPKLLIYEASTSETGVPSRFSGSGSG
TDFTLTISSLQPEDFATYYCQQSYSTPYTFGQGTKLEIK*RTVAAPSVFIFPPSDEQLKSGTASVVCLLN
NFYPREAKVQWKVDNALQSGNSQESVTEQDSKDSTYSLSSTLTLSKADYEKHKVYACEVTHQGLSS
PVTKSFNRGEC CDR amino acid sequences of E05v2 mAb (Kabat)
VH CDR1 - SYGIS (SEQ ID NO: 1)

VH CDR2 - WISAYSGGTNYAQKLQG (SEQ ID NO: 2)

VH CDR3 - DLFPTIFGVSYYYY (SEQ ID NO: 3)

VL CDR1 - RASQSISGRLA (SEQ ID NO: 18)

VL CDR2 - EASNLES (SEQ ID NO: 19)

VL CDR3 - QQSYSTPRVT (SEQ ID NO: 20)

CDR amino acid sequences of E05v2 (IMGT)
VH CDR1 - GYTFTSYG (SEQ ID NO: 21)

VH CDR2 - ISAYSGGT (SEQ ID NO: 8)

VH CDR3 - ARDLFPTIFGVSYYYY (SEQ ID NO: 9)

VL CDR1 - QSISGR (SEQ ID NO: 22)

VL CDR2 - EAS (SEQ ID NO: 11)

VL CDR3 - QQSYSTPRVT (SEQ ID NO: 20)

VH domain amino acid sequence of E05v2 mAb (SEQ ID NO: 23)
IMGT CDRs (bold and italics); Kabat CDRs (italics and underlined)
*EVQLVQSGAEVKRPGASVKVSCKASGYTFTSYGISWVRQAPGQGLEWMGWISAYSGGTNYAQKLQ
GRVTMTTDTSTSTAYMELRSLRSDDTAVYYCARDLFPTIFGVSYYYYWGQGTLVTVSS*

VH domain nucleic acid sequence of E05v2 mAb (SEQ ID NO: 24)
GAAGTGCAGCTGGTGCAGTCCGGAGCCGAAGTCAAGAGGCCTGGAGCGTCCGTGAAGGTGTCC
TGCAAAGCCTCAGGATACACCTTCACTTCGTACGGGATTTCCTGGGTCCGCCAAGCACCGGGTC
AAGGCTTGGAGTGGATGGGATGGATCAGCGCGTATTCCGGGGGAACCAACTACGCTAAAAGC
TGCAGGGTCGCGTGACCATGACCACCGATACCTCCACCTCAACGGCCTACATGGAACTGAGATC
TCTGCGGAGCGACGACACTGCCGTGTACTACTGTGCCCGGGACCTGTTCCCCACTATCTTCGGA
GTGTCGTACTACTACTACTGGGGCCAGGGGACTCTCGTGACCGTGTCGAGC VL domain amino acid sequence of E05v2 mAb (SEQ ID NO: 25)
IMGT CDRs (bold and italics); Kabat CDRs (italics and underlined)
*DIQMTQSPSTLSASVGDRVTITCRASQSISGRLAWYQQKPGKAPNLLIYEASNLESGVPSRFSGSGS
GTEFTLTISSLQPEDFATYYCQQSYSTPRVTFGQGTKVEIK*

VL domain nucleic acid sequence of E05v2 mAb (SEQ ID NO: 26)
GACATTCAGATGACCCAATCCCCGTCCACGCTGAGCGCCTCCGTCGGTGATCGCGTGACAATCA
CTTGTCGGGCGTCGCAGTCCATCTCTGGAAGGCTCGCCTGGTACCAGCAGAAGCCTGGAAAGG
CTCCCAACCTCCTTATCTACGAAGCCAGCAACCTGGAGTCCGGAGTGCCTAGCCGGTTCAGCGG

```
ATCAGGGTCCGGTACCGAGTTCACCCTGACCATTTCCTCGCTCCAACCTGAGGACTTCGCCACC
TACTACTGCCAACAGTCCTATTCAACTCCGCGCGTGACCTTCGGCCAGGGCACTAAGGTCGAAA
TCAAA
```

Heavy chain amino acid sequence of G1-AA/E05v2 mAb (with LALA) (SEQ ID NO: 27)
VH domain (italics); IMGT CDRs (bold and italics); Kabat CDRs (italics and underlined); LALA
mutation (bold and underlined)

*EVQLVQSGAEVKRPGASVKVSCKASGYTFTSYGISWVRQAPGQGLEWMGWISAYSGGTNYAQKLQ*
*GRVTMTTDTSTSTAYMELRSLRSDDTAVYYCARDLFPTIFGVSYYYYWGQGTLVTVSS*ASTKGPSVF
PLAPSSKSTSGGTAALGCLVKDYFPEPVTVSWNSGALTSGVHTFPAVLQSSGLYSLSSVVTVPSSSL
GTQTYICNVNHKPSNTKVDKKVEPKSCDKTHTCPPCPAPEAAGGPSVFLFPPKPKDTLMISRTPEVT
CVVVDVSHEDPEVKFNWYVDGVEVHNAKTKPREEQYNSTYRVVSVLTVLHQDWLNGKEYKCKVSN
KALPAPIEKTISKAKGQPREPQVYTLPPSRDELTKNQVSLTCLVKGFYPSDIAVEWESNGQPENNYKT
TPPVLDSDGSFFLYSKLTVDKSRWQQGNVFSCSVMHEALHNHYTQKSLSLSPG

Light chain amino acid sequence of G1-AA/E05v2 mAb and FS22-172-003-AA/E05v2 and FS22-053-
008-AA/E05v2 mAb[2] (SEQ ID NO: 28)
VH domain (italics); IMGT CDRs (bold and italics); Kabat CDRs (italics and underlined)

*DIQMTQSPSTLSASVGDRVTITCRASQSISGRLAWYQQKPGKAPNLLIYEASNLESGVPSRFSGSGS*
*GTEFTLTISSLQPEDFATYYCQQSYSTPRVTFGQGTKVEIK*RTVAAPSVFIFPPSDEQLKSGTASVVCL
LNNFYPREAKVQWKVDNALQSGNSQESVTEQDSKDSTYSLSSTLTLSKADYEKHKVYACEVTHQGL
SSPVTKSFNRGEC

CDR amino acid sequences of G12v2 mAb (Kabat)
VH CDR1 - SYGIS (SEQ ID NO: 1)

VH CDR2 - WISAYSGGTNYAQKLQG (SEQ ID NO: 2)

VH CDR3 - DLFPTIFGVSYYYY (SEQ ID NO: 3)

VL CDR1 - RASQSISGRLA (SEQ ID NO: 18)

VL CDR2 - EASNLES (SEQ ID NO: 19)

VL CDR3 - QQSYSWPRT (SEQ ID NO: 29)

CDR amino acid sequences of G12v2 (IMGT)
VH CDR1 - GYTFTSYG (SEQ ID NO: 21)

VH CDR2 - ISAYSGGT (SEQ ID NO: 8)

VH CDR3 - ARDLFPTIFGVSYYYY (SEQ ID NO: 9)

VL CDR1 - QSISGR (SEQ ID NO: 22)

VL CDR2 - EAS (SEQ ID NO: 11)

VL CDR3 - QQSYSWPRT (SEQ ID NO: 29)

VH domain amino acid sequence of G12v2 mAb (SEQ ID NO: 23)
IMGT CDRs (bold and italics); Kabat CDRs (italics and underlined)

*EVQLVQSGAEVKRPGASVKVSCKASGYTFTSYGISWVRQAPGQGLEWMGWISAYSGGTNYAQKLQ*
*GRVTMTTDTSTSTAYMELRSLRSDDTAVYYCARDLFPTIFGVSYYYYWGQGTLVTVSS*

VH domain nucleic acid sequence of G12v2 mAb (SEQ ID NO: 24)
```
GAAGTGCAGCTGGTGCAGTCCGGAGCCGAAGTCAAGAGGCCTGGAGCGTCCGTGAAGGTGTCC
TGCAAAGCCTCAGGATACACCTTCACTTCGTACGGGATTTCCTGGGTCCGCCAAGCACCGGGTC
AAGGCTTGGAGTGGATGGGATGGATCAGCGCGTATTCCGGGGGAACCAACTACGCTCAAAAGC
TGCAGGGTCGCGTGACCATGACCACCGATACCTCCACCTCAACGGCCTACATGGAACTGAGATC
TCTGCGGAGCGACGACACTGCCGTGTACTACTGTGCCCGGGACCTGTTCCCCACTATCTTCGGA
GTGTCGTACTACTACTACTGGGGCCAGGGGACTCTCGTGACCGTGTCGAGC
```

VL domain amino acid sequence of G12v2 mAb (SEQ ID NO: 30)
IMGT CDRs (bold and italics); Kabat CDRs (italics and underlined)

*DIQMTQSPSTLSASVGDRVTITCRASQSISGRLAWYQQKPGKAPNLLIYEASNLESGVPSRFSGSGS*
*GTEFTLTISSLQPEDFATYYCQQSYSWPRTFGQGTKVEIK*

VL domain nucleic acid sequence of G12v2 mAb (SEQ ID NO: 31)
```
GACATTCAGATGACCCAGTCCCCGAGCACGCTGTCCGCAAGCGTGGGGGACAGAGTGACCATC
ACTTGCCGCGCCTCACAATCCATCAGCGGACGCTTGGCCTGGTACCAGCAGAAGCCCGGAAAG
GCCCCAAACCTTCTGATCTACGAAGCCTCGAACCTGGAGTCAGGCGTCCCTTCGCGGTTCTCTG
GCTCCGGTTCCGGAACTGAGTTCACCCTCACCATCTCGTCCCTGCAACCGGAAGATTTCGCCAC
CTACTACTGCCAACAGTCGTACTCCTGGCCCCGGACATTCGGACAGGGAACCAAAGTCGAGATT
AAG
```

Heavy chain amino acid sequence of G1-AA/G12v2 mAb (with LALA) (SEQ ID NO: 27)
VH domain (italics); IMGT CDRs (bold and italics); Kabat CDRs (italics and underlined); LALA
mutation (bold and underlined)

*EVQLVQSGAEVKRPGASVKVSCKASGYTFTSYGISWVRQAPGQGLEWMGWISAYSGGTNYAQKLQ*
*GRVTMTTDTSTSTAYMELRSLRSDDTAVYYCARDLFPTIFGVSYYYYWGQGTLVTVSS*ASTKGPSVF
PLAPSSKSTSGGTAALGCLVKDYFPEPVTVSWNSGALTSGVHTFPAVLQSSGLYSLSSVVTVPSSSL

```
GTQTYICNVNHKPSNTKVDKKVEPKSCDKTHTCPPCPAPEAAGGPSVFLFPPKPKDTLMISRTPEVT
CVVVDVSHEDPEVKFNWYVDGVEVHNAKTKPREEQYNSTYRVVSVLTVLHQDWLNGKEYKCKVSN
KALPAPIEKTISKAKGQPREPQVYTLPPSRDELTKNQVSLTCLVKGFYPSDIAVEWESNGQPENNYKT
TPPVLDSDGSFFLYSKLTVDKSRWQQGNVFSCSVMHEALHNHYTQKSLSLSPG
```

Light chain amino acid sequence of G1-AA/G12v2 mAb and FS22-172-003-AA/G12v2 and FS22-053-008-AA/G12v2 mAb² (SEQ ID NO: 33)
VH domain (italics); IMGT CDRs (bold and italics); Kabat CDRs (italics and underlined)
*DIQMTQSPSTLSASVGDRVTITCRAS<u>QSISGR</u>LAWYQQKPGKAPNLLIY<u>EASNLES</u>GVPSRFSGSGS*
*GTEFTLTISSLQPEDFATYYC<u>QQSYSWPRT</u>FGQGTKVEIK*RTVAAPSVFIFPPSDEQLKSGTASVVCL
LNNFYPREAKVQWKVDNALQSGNSQESVTEQDSKDSTYSLSSTLTLSKADYEKHKVYACEVTHQGL
SSPVTKSFNRGEC CDR amino acid sequences of lambdav3/lam-G02v3 mAb (Kabat)
VH CDR1 - SYGIS (SEQ ID NO: 1)

VH CDR2 - WISAYSGGTNYAQKLQG (SEQ ID NO: 2)

VH CDR3 - DLFPTIFGVSYYYY (SEQ ID NO: 3)

VL CDR1 - TGTSSDVGGYNYVS (SEQ ID NO: 34)

VL CDR2 - EVTNRPS (SEQ ID NO: 35)

VL CDR3 - SSFKRGSTLVV (SEQ ID NO: 36)

CDR amino acid sequences of lambdav3/lam-G02v3 (IMGT)
VH CDR1 - GYTFTSYG (SEQ ID NO: 21)

VH CDR2 - ISAYSGGT (SEQ ID NO: 8)

VH CDR3 - ARDLFPTIFGVSYYYY (SEQ ID NO: 9)

VL CDR1 - SSDVGGYNY (SEQ ID NO: 37)

VL CDR2 - EVT (SEQ ID NO: 38)

VL CDR3 - SSFKRGSTLVV (SEQ ID NO: 36)

VH domain amino acid sequence of lambdav3/lam-G02v3 mAb (SEQ ID NO: 23)
IMGT CDRs (bold and italics); Kabat CDRs (italics and underlined)
*EVQLVQSGAEVKRPGASVKVSCKASGYTFTSYGI**<u>SWVRQAPGQGLEWMGW</u>ISAYSGGTNYAQKLQ*
*GRVTMTTDTSTSTAYMELRSLRSDDTAVYYC<u>ARDLFPTIFGVSYYYY</u>WGQGTLVTVSS*

VH domain nucleic acid sequence of lambdav3/lam-G02v3 mAb (SEQ ID NO: 24)
```
GAAGTGCAGCTGGTGCAGTCCGGAGCCGAAGTCAAGAGGCCTGGAGCGTCCGTGAAGGTGTCC
TGCAAAGCCTCAGGATACACCTTCACTTCGTACGGGATTTCCTGGGTCCGCCAAGCACCGGGTC
AAGGCTTGGAGTGGATGGGATGGATCAGCGCGTATTCCGGGGGAACCAACTACGCTCAAAAGC
TGCAGGGTCGCGTGACCATGACCACCGATACCTCCACCTCAACGGCCTACATGGAACTGAGATC
TCTGCGGAGCGACGACACTGCCGTGTACTACTGTGCCCGGGACCTGTTCCCCACTATCTTCGGA
GTGTCGTACTACTACTACTGGGGCCAGGGGACTCTCGTGACCGTGTCGAGC
```

VL domain amino acid sequence of lambdav3/lam-G02v3 mAb (SEQ ID NO: 41)
IMGT CDRs (bold and italics); Kabat CDRs (italics and underlined)
*QSALTQPASVSGSPGQSITISCTGT<u>SSDVGGYNY</u>VSWYQQFPGKAPKLMIF**<u>EVT</u>NRPS*GVSDRFSGS
*KSDNTASLTISGLQAEDEAEYYC<u>SSFKRGSTLVV</u>FGGGTKLTVL*

VL domain nucleic acid sequence of lambdav3/lam-G02v3 mAb (SEQ ID NO: 42)
```
CAGTCGGCCCTTACTCAACCCGCGTCAGTCTCCGGTAGCCCCGGACAGTCCATCACGATTTCGT
GCACCGGAACCAGCAGCGATGTCGGGGGATACAACTACGTGTCCTGGTACCAGCAGTTCCCGG
GAAAGGCCCCTAAGCTGATGATCTTCGAAGTCACTAACAGACCTTCCGGAGTGTCGGACCGGTT
CTCCGGCTCCAAGTCCGACAACACTGCGAGCCTGACCATCTCGGGCCTGCAAGCCGAGGACGA
AGCCGAGTACTACTGTAGCTCATTCAAGCGCGGTTCCACCCTCGTGGTGTTCGGCGGTGGCACT
AAGCTCACCGTGCTGGGA
```

Heavy chain amino acid sequence of G1-AA/lambdav3/lam-G02v3 mAb (with LALA) (SEQ ID NO: 27)
VH domain (italics); IMGT CDRs (bold and italics); Kabat CDRs (italics and underlined); LALA
mutation (bold and underlined)
*EVQLVQSGAEVKRPGASVKVSCKASGYTFTSYGI**<u>SWVRQAPGQGLEWMGW</u>ISAYSGGTNYAQKLQ*
*GRVTMTTDTSTSTAYMELRSLRSDDTAVYYC<u>ARDLFPTIFGVSYYYY</u>WGQGTLVTVSS*ASTKGPSVF
PLAPSSKSTSGGTAALGCLVKDYFPEPVTVSWNSGALTSGVHTFPAVLQSSGLYSLSSVVTVPSSSL
GTQTYICNVNHKPSNTKVDKKVEPKSCDKTHTCPPCPAPEAAGGPSVFLFPPKPKDTLMISRTPEVT
CVVVDVSHEDPEVKFNWYVDGVEVHNAKTKPREEQYNSTYRVVSVLTVLHQDWLNGKEYKCKVSN
KALPAPIEKTISKAKGQPREPQVYTLPPSRDELTKNQVSLTCLVKGFYPSDIAVEWESNGQPENNYKT
TPPVLDSDGSFFLYSKLTVDKSRWQQGNVFSCSVMHEALHNHYTQKSLSLSPG -continued

```
Light chain amino acid sequence of G1-AA/lambdav3/lam-G02v3 mAb (SEQ ID NO: 44)
VL domain (italics); IMGT CDRs (bold and italics); Kabat CDRs (italics and underlined)
QSALTQPASVSGSPGQSITISCTGTSSDVGGYNYVSWYQQFPGKAPKLMIFEVTNRPSGVSDRFSGS
KSDNTASLTISGLQAEDEAEYYCSSFKRGSTLVVFGGGTKLTVLGQPAAAPSVTLFPPSSEELQANKA
TLVCLISDFYPGAVTVAWKADSSPVKAGVETTTPSKQSNNKYAASSYLSLTPEQWKSHRSYSCQVTH
EGSTVEKTVAPTECS Alternative definition of HCDR1 (IMGT) (SEQ ID NO: 45)
GYX₁FTSYG
where X₁ is P or T Alternative definition of LCDR1 (Kabat) (SEQ ID NO: 46)
RASQSIX₂X₃RLA
where X2 is S or G, X₃ is N or G Alternative definition of LCDR2 (Kabat) (SEQ ID NO: 47)
EASX₄X₅EX₆
Where X₄ is T or N; X₅ is S or L; X₆ is T or S Alternative definition of LCDR3 (Kabat) (SEQ ID NO: 48)
QQSYSX₇PX₈X₉T
Where X₇ is T or W; X₈ is absent or R; X₉ is Y, R, or V Alternative definition of LCDR1 (IMGT) (SEQ ID NO: 49)
QSIX₁₀X₁₁R
Where X₁₀ is G or S; X₁₁ is N or G Alternative definition of LCDR3 (IMGT) (SEQ ID NO: 50)
QQSYSX₁₂X₁₃X₁₄X₁₅T
Where X₁₂ is absent or T; X₁₃ is T, W, or P; X₁₄ is P or R; X₁₅ is Y or R HFW amino acid sequences IgG1 (Kabat)
HFW1 - EVQLVQSGAEVKRPGASVKVSCKASGYX16FT (SEQ ID NO: 51)
Where X₁₆ is P or T

HFW2 - WVRQAPGQGLEWMG (SEQ ID NO: 52)

HFW3 - RVTMTTDTSTSTAYMELRSLRSDDTAVYYCAR (SEQ ID NO: 53)

HFW4 - WGQGTLVTVSS (SEQ ID NO: 54)

HFW amino acid sequences of IgG1 (IMGT)
HFW1 - EVQLVQSGAEVKRPGASVKVSCKAS (SEQ ID NO: 55)

HFW2 - ISWVRQAPGQGLEWMGW (SEQ ID NO: 56)

HFW3 - NYAQKLQGRVTMTTDTSTSTAYMELRSLRSDDTAVYYC (SEQ ID NO: 57)

HFW4 - WGQGTLVTVSS (SEQ ID NO: 54)

LFW amino acid sequences of kappa light chain (Kabat)
LFW1 - DIQMTQSPSTLSASVRDRVIITC (SEQ ID NO: 58)

LFW2 - WYQHKPGKAPKLLIY (SEQ ID NO: 59)

LFW3 - GVPSRFSGSGSGTDFTLTISSLQPEDFATYYC (SEQ ID NO: 60)

LFW4 - FGQGTKLEIK (SEQ ID NO: 61)

LFW amino acid sequences of kappa light chain (IMGT)
LFW1 - DIQMTQSPSTLSASVRDRVIITCRAS (SEQ ID NO: 62)

LFW2 - LAWYQHKPGKAPKLLIY (SEQ ID NO: 63)

LFW3 - TSETGVPSRFSGSGSGTDFTLTISSLQPEDFATYYC (SEQ ID NO: 64)

LFW4 - FGQGTKLEIK (SEQ ID NO: 61)

LFW amino acid sequences of lambda light chain (Kabat)
LFW1 - QSALTQPASVSGSPGQSITISC (SEQ ID NO: 65)

LFW2 - WYQQFPGKAPKLMIF (SEQ ID NO: 66)

LFW3 - GVSDRFSGSKSDNTASLTISGLQAEDEAEYYC (SEQ ID NO: 67)

LFW4 - FGGGTKLTVL (SEQ ID NO: 68)
```

LFW amino acid sequences of lambda light chain (IMGT)
LFW1 - QSALTQPASVSGSPGQSITISCTGT (SEQ ID NO: 69)

LFW2 - VSWYQQFPGKAPKLMIF (SEQ ID NO: 70)

LFW3 - NRPSGVSDRFSGSKSDNTASLTISGLQAEDEAEYYC (SEQ ID NO: 71)

LFW4 - FGGGTKLTVL (SEQ ID NO: 68)

Amino acid sequences of WT CH3 domain structural loops
WT AB loop - RDELTKNQ (SEQ ID NO: 72)

WT CD loop - SNGQPENNY (SEQ ID NO: 73)

WT EF loop - DKSRWQQGNV (SEQ ID NO: 74)

Amino acid sequence of WT CH3 domain (SEQ ID NO: 75)
AB, CD and EF loops underlined
GQPREPQVYTLPPSRDELTKNQVSLTCLVKGFYPSDIAVEWESNGQPENNYKTTPPVLDSDGSFFLY
SKLTVDKSRWQQGNVFSCSVMHEALHNHYTQKSLSLSPG Amino acid sequence of the CH2 domain (SEQ ID NO: 76)
APELLGGPSVFLFPPKPKDTLMISRTPEVTCVVVDVSHEDPEVKFNWYVDGVEVHNAKTKPREEQYN
STYRVVSVLTVLHQDWLNGKEYKCKVSNKALPAPIEKTISKAK Amino acid sequence of the CH2 domain with LALA mutation (SEQ ID NO: 77)
LALA mutation underlined
APEAAGGPSVFLFPPKPKDTLMISRTPEVTCVVVDVSHEDPEVKFNWYVDGVEVHNAKTKPREEQY
NSTYRVVSVLTVLHQDWLNGKEYKCKVSNKALPAPIEKTISKAK Amino acid sequence of the CH2 domain with LALA mutation and P114A mutation (SEQ ID NO: 176)
LALA mutation underlined; P114A mutation bold and underlined
APEAAGGPSVFLFPPKPKDTLMISRTPEVTCVVVDVSHEDPEVKFNWYVDGVEVHNAKTKPREEQY
NSTYRVVSVLTVLHQDWLNGKEYKCKVSNKALAAPIEKTISKAK Amino acid sequence of PPY motif (SEQ ID NO: 78)
PPY Amino acid sequences of FS22-053-008 CH3 domain structural loop sequences
FS22-053-008 first sequence - NPPYLFS (SEQ ID NO: 79)

FS22-053-008 second sequence - DYWRWLE (SEQ ID NO: 80)

Amino acid sequence of FS22-053-008 CH3 domain (SEQ ID NO: 81)
First and second sequences underlined
GQPREPQVYTLPPSRDELNPPYLFSNQVSLTCLVKGFYPSDIAVEWESNGQPENNYKTTPPVLDSDG
SFFLYSKLTVDYWRWLEGNVFSCSVMHEALHNHYTQKSLSLSPG Nucleic acid sequence of FS22-053-008 CH3 domain (SEQ ID NO: 82)
GGACAGCCTCGAGAACCACAGGTGTACACCCTGCCCCCATCCCGGGATGAGCTGAACCCGCCG
TACCTGTTCTCTAACCAGGTCAGCCTGACCTGCCTGGTCAAAGGCTTCTATCCCAGCGACATCG
CCGTGGAGTGGGAGAGCAATGGGCAGCCGGAGAACAACTACAAGACCACGCCTCCCGTACTGG
ACTCCGACGGCTCCTTCTTCCTCTACAGCAAGCTCACCGTGGATTACTGGAGGTGGCTGGAAGG
GAACGTCTTCTCATGCTCCGTGATGCATGAGGCGCTGCACAACCACTACACTCAGAAGAGCTTG
TCCCTGTCGCCCGGT Amino acid sequences of FS22-053-009 CH3 domain structural loop sequences
FS22-053-009 first sequence - NPPYLFS (SEQ ID NO: 79)

FS22-053-009 second sequence - EHTRWLD (SEQ ID NO: 83)

Amino acid sequence of FS22-053-009 CH3 domain (SEQ ID NO: 84)
First and second sequences underlined
GQPREPQVYTLPPSRDELNPPYLFSNQVSLTCLVKGFYPSDIAVEWESNGQPENNYKTTPPVLDSDG
SFFLYSKLTVEHTRWLDGNVFSCSVMHEALHNHYTQKSLSLSPG Nucleic acid sequence of FS22-053-009 CH3 domain (SEQ ID NO: 85)
GGCCAGCCTCGAGAACCACAGGTGTACACCCTGCCCCCATCCCGGGATGAGCTGAACCCGCCG
TACCTGTTCTCTAACCAGGTCAGCCTGACCTGCCTGGTCAAAGGCTTCTATCCCAGCGACATCG
CCGTGGAGTGGGAGAGCAATGGGCAGCCGGAGAACAACTACAAGACCACGCCTCCCGTGCTGG
ACTCCGACGGCTCCTTCTTCCTCTACAGCAAGCTCACCGTGGAACATACTAGGTGGCTGGATGG
GAACGTCTTCTCATGCTCCGTGATGCATGAGGCTCTGCACAACCACTACACACAGAAGAGCCTC
TCCCTGTCTCCGGGT Amino acid sequences of Fcab FS22-053-011 CH3 domain structural loop sequences
FS22-053-011 first sequence - NPPYLFS (SEQ ID NO: 79)

FS22-053-011 second sequence - DYWRWTD (SEQ ID NO: 86)

Amino acid sequence of Fcab FS22-053-011 CH3 domain (SEQ ID NO: 87)
First and second sequences underlined
GQPREPQVYTLPPSRDEL<u>NPPYLFS</u>NQVSLTCLVKGFYPSDIAVEWESNGQPENNYKTTPPVLDSDG
SFFLYSKLTV<u>DYWRWTDG</u>NVFSCSVMHEALHNHYTQKSLSLSPG Nucleic acid sequence of Fcab FS22-053-011 CH3 domain (SEQ ID NO: 88)
GGCCAGCCTCGAGAACCACAGGTGTACACCCTGCCCCCATCCCGGGATGAGCTGAACCCGCCG
TACCTGTTTCTCTAACCAGGTCAGCCTGACCTGCCTGGTCAAAGGCTTCTATCCCAGCGACATCG
CCGTGGAGTGGGAGAGCAATGGGCAGCCGGAGAACAACTACAAGACCACGCCTCCCGTGCTGG
ACTCCGACGGCTCCTTCTTCCTCTACAGCAAGCTCACCGTGGATTACTGGAGGTGGACTGATGG
GAACGTCTTCTCATGCTCCGTGATGCATGAGGCTCTGCACAACCACTACACACAGAAGAGCCTC
TCCCTGTCTCCGGGT Amino acid sequences of Fcab FS22-053-017 CH3 domain structural loop sequences
FS22-053-017 first sequence - NPPYLFS (SEQ ID NO: 79)
FS22-053-017 second sequence - YHWRWLE (SEQ ID NO: 89)

Amino acid sequence of Fcab FS22-053-017 CH3 domain (SEQ ID NO: 90)
First and second sequences underlined
GQPREPQVYTLPPSRDEL<u>NPPYLFS</u>NQVSLTCLVKGFYPSDIAVEWESNGQPENNYKTTPPVLDSDG
SFFLYSKLTV<u>YHWRWLEG</u>NVFSCSVMHEALHNHYTQKSLSLSPG Nucleic acid sequence of Fcab FS22-053-017 CH3 domain (SEQ ID NO: 91)
GGACAGCCTCGAGAACCACAGGTGTACACTCTGCCCCCTCACGCGACGAACTCAATCCGCCCT
ACCTGTTCTCCAACCAAGTCTCCCTGACCTGTCTTGTGAAGGGTTTCTACCCATCCGATATCGCC
GTGGAGTGGGAGAGCAACGGACAGCCGGAGAACAACTATAAGACTACCCCGCCTGTGCTGGAC
TCGGACGGCAGCTTCTTCTTGTACTCCAAACTGACCGTGTACCACTGGCGGTGGCTGGAAGGGA
ACGTGTTTAGCTGCTCCGTCATGCATGAAGCCCTGCACAACCACTACACCCAGAAGTCCCTCTC
GCTCTCTCCGGGT Amino acid sequences of Fcab FS22-053-014 CH3 domain structural loop sequences
FS22-053-014 first sequence - NPPYLFS (SEQ ID NO: 79)

FS22-053-014 second sequence - YHWRWLD (SEQ ID NO: 92)

Amino acid sequence of Fcab FS22-053-014 CH3 domain (SEQ ID NO: 93)
First and second sequences underlined
GQPREPQVYTLPPSRDEL<u>NPPYLFS</u>NQVSLTCLVKGFYPSDIAVEWESNGQPENNYKTTPPVLDSDG
SFFLYSKLTV<u>YHWRWLDG</u>NVFSCSVMHEALHNHYTQKSLSLSPG Nucleic acid sequence of Fcab FS22-053-014 CH3 domain (SEQ ID NO: 94)
GGACAGCCTCGAGAGCCTCAAGTGTACACCCTGCCCCCATCCCGGGATGAGCTGAACCCGCCG
TACCTGTTCTCTAACCAGGTCAGCCTGACCTGCCTGGTCAAAGGCTTCTATCCCAGCGACATCG
CCGTGGAGTGGGAGAGCAATGGGCAGCCGGAGAACAACTACAAGACCACGCCTCCCGTGCTGG
ACTCCGACGGCTCCTTCTTCCTCTACAGCAAGCTCACCGTGTACCATTGGAGGTGGCTGGATGG
GAACGTCTTCTCATGCTCCGTGATGCATGAGGCGCTGCACAACCACTACACTCAGAAGAGCTTG
TCCCTGTCGCCCGGA Amino acid sequences of Fcab FS22-053-010 CH3 domain structural loop sequences
FS22-053-010 first sequence - NPPYLFS (SEQ ID NO: 79)

FS22-053-010 second sequence - DYMRWLD (SEQ ID NO: 95)

Amino acid sequence of Fcab FS22-053-010 CH3 domain (SEQ ID NO: 96)
First and second sequences underlined
GQPREPQVYTLPPSRDEL<u>NPPYLFS</u>NQVSLTCLVKGFYPSDIAVEWESNGQPENNYKTTPPVLDSDG
SFFLYSKLTV<u>DYMRWLDG</u>NVFSCSVMHEALHNHYTQKSLSLSPG Nucleic acid sequence of Fcab FS22-053-010 CH3 domain (SEQ ID NO: 97)
GGCCAGCCTCGAGAACCACAGGTGTACACCCTGCCCCCATCCCGGGATGAGCTGAACCCGCCG
TACCTGTTCTCTAACCAGGTCAGCCTGACCTGCCTGGTCAAAGGCTTCTATCCCAGCGACATCG
CCGTGGAGTGGGAGAGCAATGGGCAGCCGGAGAACAACTACAAGACCACGCCTCCCGTGCTGG
ACTCCGACGGCTCCTTCTTCCTCTACAGCAAGCTCACCGTGGATTACATGAGGTGGCTGGATGG
GAACGTCTTCTCATGCTCCGTGATGCATGAGGCTCTGCACAACCACTACACACAGAAGAGCCTC
TCCCTGTCTCCGGGT Amino acid sequences of Fcab FS22-053-012 CH3 domain structural loop sequences
FS22-053-012 first sequence - NPPYLFS (SEQ ID NO: 79)

FS22-053-012 second sequence - DHMRWLE (SEQ ID NO: 98)

Amino acid sequence of Fcab FS22-053-012 CH3 domain (SEQ ID NO: 99)
First and second sequences underlined
GQPREPQVYTLPPSRDEL<u>NPPYLFS</u>NQVSLTCLVKGFYPSDIAVEWESNGQPENNYKTTPPVLDSDG
SFFLYSKLTV<u>DHMRWLEG</u>NVFSCSVMHEALHNHYTQKSLSLSPG Nucleic acid sequence of Fcab FS22-053-012 CH3 domain (SEQ ID NO: 100)
GGCCAGCCTCGAGAACCACAGGTGTACACCCTGCCCCCATCCCGGGATGAGCTGAACCCGCCG
TACCTGTTCTCTAACCAGGTCAGCCTGACCTGCCTGGTCAAAGGCTTCTATCCCAGCGACATCG
CCGTGGAGTGGGAGAGCAATGGGCAGCCGGAGAACAACTACAAGACCACGCCTCCCGTGCTGG
ACTCCGACGGCTCCTTCTTCCTCTACAGCAAGCTCACCGTGGATCATATGAGGTGGCTGGAAGG
GAACGTCTTCTCATGCTCCGTGATGCATGAGGCTCTGCACAACCACTACACACAGAAGAGCCTC
TCCCTGTCTCCGGGT Amino acid sequences of Fcab FS22-053-013 CH3 domain structural loop sequences
FS22-053-013 first sequence - NPPYLFS (SEQ ID NO: 79)

FS22-053-013 second sequence - GYERWLE (SEQ ID NO: 101)

Amino acid sequence of Fcab FS22-053-013 CH3 domain (SEQ ID NO: 102)
First and second sequences underlined
GQPREPQVYTLPPSRDELNPPYLFSNQVSLTCLVKGFYPSDIAVEWESNGQPENNYKTTPPVLDSDG
SFFLYSKLTVGYERWLEGNVFSCSVMHEALHNHYTQKSLSLSPG Nucleic acid sequence of Fcab FS22-053-013 CH3 domain (SEQ ID NO: 103)
GGCCAGCCTCGAGAACCACAGGTGTACACCCTGCCCCCATCCCGGGATGAGCTGAACCCGCCG
TACCTGTTCTCTAACCAGGTCAGCCTGACCTGCCTGGTCAAAGGCTTCTATCCCAGCGACATCG
CCGTGGAGTGGGAGAGCAATGGGCAGCCGGAGAACAACTACAAGACCACGCCTCCCGTGCTGG
ACTCCGACGGCTCCTTCTTCCTCTACAGCAAGCTCACCGTGGGTTACGAAAGGTGGCTGGAAGG
GAACGTCTTCTCATGCTCCGTGATGCATGAGGCTCTGCACAACCACTACACACAGAAGAGCCTC
TCCCTGTCTCCGGGT Amino acid sequences of Fcab FS22-053-015 CH3 domain structural loop sequences
FS22-053-015 first sequence - NPPYLFS (SEQ ID NO: 79)

FS22-053-015 second sequence - DHWRWLQ (SEQ ID NO: 104)

Amino acid sequence of Fcab FS22-053-015 CH3 domain (SEQ ID NO: 105)
First and second sequences underlined
GQPREPQVYTLPPSRDELNPPYLFSNQVSLTCLVKGFYPSDIAVEWESNGQPENNYKTTPPVLDSDG
SFFLYSKLTVDHWRWLQGNVFSCSVMHEALHNHYTQKSLSLSPG Nucleic acid sequence of Fcab FS22-053-015 CH3 domain (SEQ ID NO: 106)
GGCCAGCCTCGAGAACCACAGGTGTACACCCTGCCCCCATCCCGGGATGAGCTGAACCCGCCG
TACCTGTTCTCTAACCAGGTCAGCCTGACCTGCCTGGTCAAAGGCTTCTATCCCAGCGACATCG
CCGTGGAGTGGGAGAGCAATGGGCAGCCGGAGAACAACTACAAGACCACGCCTCCCGTGTTGG
ACTCCGACGGCTCCTTCTTCCTCTACAGCAAGCTCACCGTGGATCATTGGAGGTGGCTGCAGGG
GAACGTCTTCTCATGCTCCGTGATGCATGAGGCTCTGCACAACCACTACACACAGAAGAGCCTC
TCCCTGTCTCCGGGT Amino acid sequences of Fcab FS22-053-016 CH3 domain structural loop sequences
FS22-053-016 first sequence - NPPYLFS (SEQ ID NO: 79)

FS22-053-016 second sequence - DYIRWLN (SEQ ID NO: 107)

Amino acid sequence of Fcab FS22-053-016 CH3 domain (SEQ ID NO: 108)
First and second sequences underlined
GQPREPQVYTLPPSRDELNPPYLFSNQVSLTCLVKGFYPSDIAVEWESNGQPENNYKTTPPVLDSDG
SFFLYSKLTVDYIRWLNGNVFSCSVMHEALHNHYTQKSLSLSPG Nucleic acid sequence of Fcab FS22-053-016 CH3 domain (SEQ ID NO: 109)
GGCCAGCCTCGAGAACCACAGGTGTACACCCTGCCCCCATCCCGGGATGAGCTGAACCCGCCG
TACCTGTTCTCTAACCAGGTCAGCCTGACCTGCCTGGTCAAAGGCTTCTATCCCAGCGACATCG
CCGTGGAGTGGGAGAGCAATGGGCAGCCGGAGAACAACTACAAGACCACGCCTCCCGTGCTGG
ACTCCGACGGCTCCTTCTTCCTCTACAGCAAGCTCACCGTGGATTACATCAGGTGGCTGAACGG
GAACGTCTTCTCATGCTCCGTGATGCATGAGGCTCTGCACAACCACTACACACAGAAGAGCCTC
TCCCTGTCTCCGGGT Amino acid sequences of FS22-053 CH3 domain structural loop sequences
FS22-053-008 first sequence - NPPYLFS (SEQ ID NO: 79)

FS22-053-008 second sequence - YYNRWQD (SEQ ID NO: 110)

Amino acid sequences of FS22-053 CH3 domain (SEQ ID NO: 111)
First and second sequences underlined
GQPREPQVYTLPPSRDELNPPYLFSNQVSLTCLVKGFYPSDIAVEWESNGQPENNYKTTPPVLDSDG
SFFLYSKLTVYYNRWQDGNVFSCSVMHEALHNHYTQKSLSLSPG Nucleic acid sequence of FS22-053 CH3 domain (SEQ ID NO: 112)
GGCCAGCCTCGAGAACCACAGGTGTACACCCTGCCCCCATCCCGGGATGAGCTGAACCCGCCG
TACCTGTTCTCTAACCAGGTCAGCCTGACCTGCCTGGTCAAAGGCTTCTATCCCAGCGACATCG
CCGTGGAGTGGGAGAGCAATGGGCAGCCGGAGAACAACTACAAGACCACGCCTCCCGTGCTGG
ACTCCGACGGCTCCTTCTTCCTCTACAGCAAGCTCACCGTGTATTATAACAGGTGGCAGGATGG
GAACGTCTTCTCATGCTCCGTGATGCATGAGGCTCTGCACAACCACTACACACAGAAGAGCCTC
TCCCTGTCTCCGGGT -continued Amino acid sequences of Fcab FS22-172-003 CH3 domain structural loop sequences
FS22-172-003 first sequence - PYIIPPY (SEQ ID NO: 113)

FS22-172-003 second sequence - GADRWLE (SEQ ID NO: 114)

Amino acid sequence of Fcab FS22-172-003 CH3 domain (SEQ ID NO: 115)
First and second sequences underlined
GQPREPQVYTLPPSRDELPYIIPPYNQVSLTCLVKGFYPSDIAVEWESNGQPENNYKTTPPVLDSDGS
FFLYSKLTVGADRWLEGNVFSCSVMHEALHNHYTQKSLSLSPG Nucleic acid sequence of Fcab FS22-172-003 CH3 domain (SEQ ID NO: 116)
GGACAGCCTCGAGAACCACAGGTGTACACCCTGCCCCCATCCCGGGATGAGCTGCCATACATC
ATCCCACCATACAACCAGGTCAGCCTGACCTGCCTGGTCAAAGGCTTCTATCCCAGCGACATCG
CCGTGGAGTGGGAGAGCAATGGGCAGCCGGAGAACAACTACAAGACCACGCCTCCCGTGCTGG
ACTCCGACGGCTCCTTCTTCCTCTACAGCAAGCTCACCGTGGGCGCAGATAGGTGGCTGGAAG
GGAACGTCTTCTCATGCTCCGTGATGCATGAGGCGCTGCACAACCACTACACTCAGAAGAGCTT
GTCCCTGTCGCCCGGT Amino acid sequences of Fcab FS22-172-002 CH3 domain structural loop sequences
FS22-172-002 first sequence - PFQMPPY (SEQ ID NO: 117)

FS22-172-002 second sequence - GADRWLE (SEQ ID NO: 114)

Amino acid sequence of Fcab FS22-172-002 CH3 domain (SEQ ID NO: 118)
First and second sequences underlined
GQPREPQVYTLPPSRDELPFQMPPYNQVSLTCLVKGFYPSDIAVEWESNGQPENNYKTTPPVLDSD
GSFFLYSKLTVGADRWLEGNVFSCSVMHEALHNHYTQKSLSLSPG Nucleic acid sequence of Fcab FS22-172-002 CH3 domain (SEQ ID NO: 119)
GGCCAGCCTCGAGAACCACAGGTGTACACCCTGCCCCCATCCCGGGATGAGCTGCCATTCCAG
ATGCCACCATACAACCAGGTCAGCCTGACCTGCCTGGTCAAAGGCTTCTATCCCAGCGACATCG
CCGTGGAGTGGGAGAGCAATGGGCAGCCGGAGAACAACTACAAGACCACGCCTCCCGTGCTGG
ACTCCGACGGCTCCTTCTTCCTCTACAGCAAGCTCACCGTGGGCGCAGATAGGTGGCTGGAAG
GGAACGTCTTCTCATGCTCCGTGATGCATGAGGCTCTGCACAACCACTACACACAGAAGAGCCT
CTCCCTGTCTCCGGGT Amino acid sequences of Fcab FS22-172-004 CH3 domain structural loop sequences
FS22-172-004 first sequence - NYIYPPY (SEQ ID NO: 120)

FS22-172-004 second sequence - GADRWLE (SEQ ID NO: 114)

Amino acid sequence of Fcab FS22-172-004 CH3 domain (SEQ ID NO: 121)
First and second sequences underlined
GQPREPQVYTLPPSRDELNYIYPPYNQVSLTCLVKGFYPSDIAVEWESNGQPENNYKTTPPVLDSDG
SFFLYSKLTVGADRWLEGNVFSCSVMHEALHNHYTQKSLSLSPG Nucleic acid sequence of Fcab FS22-172-004 CH3 domain (SEQ ID NO: 122)
GGACAGCCTCGAGAGCCTCAAGTGTACACCCTGCCCCCATCCCGGGATGAGCTGAACTACATCT
ACCCACCATACAACCAGGTCAGCCTGACCTGCCTGGTCAAAGGCTTCTATCCCAGCGACATCGC
CGTGGAGTGGGAGAGCAATGGGCAGCCGGAGAACAACTACAAGACCACGCCTCCCGTGCTGGA
CTCCGACGGCTCCTTCTTCCTCTACAGCAAGCTCACCGTGGGCGCAGATAGGTGGCTGGAAGG
GAACGTCTTCTCATGCTCCGTGATGCATGAGGCGCTGCACAACCACTACACTCAGAAGAGCTTG
TCCCTGTCGCCCGGA Amino acid sequences of Fcab FS22-172-001 CH3 domain structural loop sequences
FS22-172-001 first sequence - PFVMPPY (SEQ ID NO: 123)

FS22-172-001 second sequence - GADRWLE (SEQ ID NO: 114)

Amino acid sequence of Fcab FS22-172-001 CH3 domain (SEQ ID NO: 124)
First and second sequences underlined
GQPREPQVYTLPPSRDELPFVMPPYNQVSLTCLVKGFYPSDIAVEWESNGQPENNYKTTPPVLDSD
GSFFLYSKLTVGADRWLEGNVFSCSVMHEALHNHYTQKSLSLSPG Nucleic acid sequence of Fcab FS22-172-001 CH3 domain (SEQ ID NO: 125)
GGCCAGCCTCGAGAACCACAGGTGTACACCCTGCCCCCATCCCGGGATGAGCTGCCATTCGTT
ATGCCACCATACAACCAGGTCAGCCTGACCTGCCTGGTCAAAGGCTTCTATCCCAGCGACATCG
CCGTGGAGTGGGAGAGCAATGGGCAGCCGGAGAACAACTACAAGACCACGCCTCCCGTGCTGG
ACTCCGACGGCTCCTTCTTCCTCTACAGCAAGCTCACCGTGGGCGCAGATAGGTGGCTGGAAG
GGAACGTCTTCTCATGCTCCGTGATGCATGAGGCTCTGCACAACCACTACACACAGAAGAGCCT
CTCCCTGTCTCCGGGT Amino acid sequences of Fcab FS22-172-005 CH3 domain structural loop sequences
FS22-172-005 first sequence - QQVYPPY (SEQ ID NO: 126)

FS22-172-005 second sequence - GADRWLE (SEQ ID NO: 114)

Amino acid sequence of Fcab FS22-172-005 CH3 domain (SEQ ID NO: 127)
First and second sequences underlined
GQPREPQVYTLPPSRDELQQVYPPYNQVSLTCLVKGFYPSDIAVEWESNGQPENNYKTTPPVLDSD
GSFFLYSKLTVGADRWLEGNVFSCSVMHEALHNHYTQKSLSLSPG Nucleic acid sequence of Fcab FS22-172-005 CH3 domain (SEQ ID NO: 128)
GGCCAGCCTCGAGAACCACAGGTGTACACCCTGCCCCCATCCCGGGATGAGCTGCAGCAGGTT
TACCCACCATACAACCAGGTCAGCCTGACCTGCCTGGTCAAAGGCTTCTATCCCAGCGACATCG
CCGTGGAGTGGGAGAGCAATGGGCAGCCGGAGAACAACTACAAGACCACGCCTCCCGTGCTGG
ACTCCGACGGCTCCTTCTTCCTCTACAGCAAGCTCACCGTGGGCGCAGATAGGTGGCTGGAAG
GGAACGTCTTCTCATGCTCCGTGATGCATGAGGCTCTGCACAACCACTACACACAGAAGAGCCT
CTCCCTGTCTCCGGGT
Amino acid sequences of Fcab FS22-172-006 CH3 domain structural loop sequences
FS22-172-006 first sequence - RKYYPPY (SEQ ID NO: 129)
FS22-172-006 second sequence - GADRWLE (SEQ ID NO: 114)
Amino acid sequence of Fcab FS22-172-006 CH3 domain (SEQ ID NO: 130)
First and second sequences underlined
GQPREPQVYTLPPSRDELRKYYPPYNQLSLTCLVKGFYPSDIAVEWESNGQPENNYKTTPPVLDSD
GSFFLYSKLTVGADRWLEGNVFSCSVMHEALHNHYTQKSLSLSPG
Nucleic acid sequence of Fcab FS22-172-006 CH3 domain (SEQ ID NO: 131)
GGCCAGCCTCGAGAACCACAGGTGTACACCCTGCCCCCATCCCGGGATGAGCTGCGTAAATAC
TACCCGCCGTACAACCAGCTCAGCCTGACCTGCCTGGTCAAAGGCTTCTATCCCAGCGACATCG
CCGTGGAGTGGGAGAGCAATGGGCAGCCGGAGAACAACTACAAGACCACGCCTCCCGTGCTGG
ACTCCGACGGCTCCTTCTTCCTCTACAGCAAGCTCACCGTGGGCGCAGATAGGTGGCTGGAAG
GGAACGTCTTCTCATGCTCCGTGATGCATGAGGCTCTGCACAACCACTACACACAGAAGAGCCT
CTCCCTGTCTCCGGGT Amino acid sequences of Fcab FS22-172 CH3 domain structural loop sequences
FS22-172 first sequence - RKYYPPY (SEQ ID NO: 129)

FS22-172 second sequence - GADRWLE (SEQ ID NO: 114)

Amino acid sequence of Fcab FS22-172 CH3 domain (SEQ ID NO: 132)
First and second sequences underlined
GQPREPQVYTLPPSRDELRKYYPPYNQVSLTCLVKGFYPSDIAVEWESNGQPENNYKTTPPVLDSD
GSFFLYSKLTVGADRWLEGNVFSCSVMHEALHNHYTQKSLSLSPG Nucleic acid sequence of Fcab FS22-172 CH3 domain (SEQ ID NO: 133)
GGCCAGCCTCGAGAACCACAGGTGTACACCCTGCCCCCATCCCGGGATGAGCTGCGTAAATAC
TACCCGCCGTACAACCAGGTCAGCCTGACCTGCCTGGTCAAAGGCTTCTATCCCAGCGACATCG
CCGTGGAGTGGGAGAGCAATGGGCAGCCGGAGAACAACTACAAGACCACGCCTCCCGTGCTGG
ACTCCGACGGCTCCTTCTTCCTCTACAGCAAGCTCACCGTGGGGCAGATAGGTGGCTGGAAG
GGAACGTCTTCTCATGCTCCGTGATGCATGAGGCTCTGCACAACCACTACACACAGAAGAGCCT
CTCCCTGTCTCCGGGT Amino acid sequence of the heavy chain of FS22-172-003-AA/E12v2 mAb$^2$ with LALA mutation (SEQ ID NO: 134)
VH domain (italics); LALA mutation (bold underlined)
*EVQLVQSGAEVKRPGASVKVSCKASGYPFTSYGISWVRQAPGQGLEWMGWISAYSGGTNYAQKLQ*
*GRVTMTTDTSTSTAYMELRSLRSDDTAVYYCARDLFPTIFGVSYYYYWGQGTLVTVSS*ASTKGPSVF
PLAPSSKSTSGGTAALGCLVKDYFPEPVTVSWNSGALTSGVHTFPAVLQSSGLYSLSSVVTVPSSSL
GTQTYICNVNHKPSNTKVDKKVEPKSCDKTHTCPPCPAPEAAGGPSVFLFPPKPKDTLMISRTPEVT
CVVVDVSHEDPEVKFNWYVDGVEVHNAKTKPREEQYNSTYRVVSVLTVLHQDWLNGKEYKCKVSN
KALPAPIEKTISKAKGQPREPQVYTLPPSRDELPYIIPPYNQVSLTCLVKGFYPSDIAVEWESNGQPEN
NYKTTPPVLDSDGSFFLYSKLTVGADRWLEGNVFSCSVMHEALHNHYTQKSLSLSPG Nucleic acid sequence of the heavy chain of FS22-172-003-AA/E12v2 mAb$^2$ with LALA mutation
(SEQ ID NO: 135)
GAAGTTCAGCTGGTTCAGTCTGGCGCCGAAGTGAAAAGACCTGGCGCCTCTGTGAAGGTGTCCT
GCAAGGCTTCTGGCTACCCCTTTACCTCCTACGGCATCTCCTGGGTCCGACAGGCTCCTGGACA
AGGCTTGGAATGGATGGGCTGGATCTCCGCTTATTCCGGCGGCACCAATTACGCCCAGAAACTG
CAGGGCAGAGTGACCATGACCACCGACACCTCTACCTCCACCGCCTACATGGAACTGCGGTCC
CTGAGATCTGACGACACCGCCGTGTACTACTGCGCCAGAGATCTGTTCCCCACCATCTTCGGCG
TGTCCTACTACTACTATTGGGGCCAGGGCACCCTGGTCACCGTGTCCTCTGCTTCTACCAAGGG
ACCCAGCGTGTTCCCTCTGGCTCCTTCCAGCAAGTCTACCTCTGGCGGAACAGCTGCTCTGGGC
TGCCTGGTCAAGGACTACTTTCCTGAGCCTGTGACCGTGTCTTGGAACTCTGGCGCTCTGACAT
CTGGCGTGCACACCTTTCCAGCTGTGCTGCAGTCCTCCGGCCTGTACTCTCTGTCCTCTGTCGT
GACCGTGCCTTCCAGCTCTCTGGGAACCCAGACCTACATCTGCAATGTGAACCACAAGCCTTCC
AACACCAAGGTGGACAAGAAGGTGGAACCCAAGTCCTGCGACAAGACCCACACCTGTCCTCCAT
GTCCTGCTCCAGAAGCTGCTGGCGGCCCTTCCGTGTTTCTGTTCCCTCCAAAGCCTAAGGACAC
CCTGATGATCTCTCGGACCCCTGAAGTGACCTGCGTGGTGGTGGATGTGTCTCACGAGGACCCA
GAAGTGAAGTTCAATTGGTACGTGGACGGCGTGGAAGTGCACAACGCCAAGACCAAGCCTAGA
GAGGAACAGTACAACTCCACCTACAGAGTGGTGTCCGTGCTGACCGTGCTGCACCAGGATTGGC
TGAACGGCAAAGAGTACAAGTGCAAGGTGTCCAACAAGGCCCTGCCTGCTCCTATCGAAAAGAC
CATCTCCAAGGCCAAGGGCCAGCCTAGGGAACCCCAGGTTTACACCTTGCCTCCATCTCGGGAC
GAGCTGCCCTACATCATCCCTCCATACAACCAGGTGTCCCTGACCTGCCTCGTGAAGGGCTTCT
ACCCTTCCGATATCGCCGTGGAATGGGAGAGCAATGCCCAGCCTGAGAACAACTACAAGACAAC
CCCTCCTGTGCTGGACTCCGACGGCTCATTCTTTCTGTACTCCAAGCTGACAGTGGGCGCCGAC
AGATGGCTGGAAGGGAACGTGTTCTCCTGCAGCGTGATGCACGAGGCCCTGCACAATCACTACA
CACAGAAGTCCCTGTCTCTGTCCCCTGGC Amino acid sequence of the light chain of FS22-172-003-AA/E12v2 and FS22-053-008-AA/E12v2
mAb$^2$ (SEQ ID NO: 17)
DIQMTQSPSTLSASVRDRVIITCRASQSIGNRLAWYQHKPGKAPKLLIYEASTSETGVPSRFSGSGSG
TDFTLTISSLQPEDFATYYCQQSYSTPYTFGQGTKLEIKRTVAAPSVFIFPPSDEQLKSGTASVVCLLN -continued

NFYPREAKVQWKVDNALQSGNSQESVTEQDSKDSTYSLSSTLTLSKADYEKHKVYACEVTHQGLSS
PVTKSFNRGEC

Nucleic acid sequence of the light chain of FS22-172-003-AA/E12v2 mAb[2] (SEQ ID NO: 136)
GACATCCAGATGACCCAGTCTCCATCCACACTGTCCGCCTCTGTGCGGGACAGAGTGATCATCA
CCTGTAGAGCCAGCCAGTCCATCGGCAACAGACTGGCCTGGTATCAGCACAAGCCTGGCAAGG
CTCCCAAGCTGCTGATCTACGAGGCCTCCACATCTGAGACAGGCGTGCCCTCTAGATTCTCCGG
CTCTGGCTCTGGCACCGACTTTACCCTGACAATCTCCAGCCTGCAGCCTGAGGACTTCGCCACC
TACTACTGCCAGCAGTCCTACAGCACCCCTTACACCTTTGGCCAGGGCACCAAGCTGGAAATCA
AGCGTACGGTGGCCGCTCCCAGCGTGTTCATCTTCCCCCCAAGCGACGAGCAGCTGAAGAGCG
GCACCGCCAGCGTGGTGTGTCTGCTGAACAACTTCTACCCCAGGGAGGCCAAGGTGCAGTGGA
AGGTGGACAACGCCCTGCAGAGCGGCAACAGCCAGGAGAGCGTCACCGAGCAGGACAGCAAG
GACTCCACCTACAGCCTGAGCAGCACCCTGACCCTGAGCAAGGCCGACTACGAGAAGCACAAG
GTGTACGCCTGTGAGGTGACCCACCAGGGCCTGTCCAGCCCCGTGACCAAGAGCTTCAACAGG
GGCGAGTGC Amino acid sequence of the heavy chain of FS22-172-003-AA/E05v2 mAb[2] with LALA mutation (SEQ ID NO: 137)
VH domain (italics); LALA mutation (bold underlined)
*EVQLVQSGAEVKRPGASVKVSCKASGYTFTSYGISWVRQAPGQGLEWMGWISAYSGGTNYAQKLQ*
*GRVTMTTDTSTSTAYMELRSLRSDDTAVYYCARDLFPTIFGVSYYYYWGQGTLVTVSS*ASTKGPSVF
PLAPSSKSTSGGTAALGCLVKDYFPEPVTVSWNSGALTSGVHTFPAVLQSSGLYSLSSVVTVPSSSL
GTQTYICNVNHKPSNTKVDKKVEPKSCDKTHTCPPCPAPEAAGGPSVFLFPPKPKDTLMISRTPEVT
CVVVDVSHEDPEVKFNWYVDGVEVHNAKTKPREEQYNSTYRVVSVLTVLHQDWLNGKEYKCKVSN
KALPAPIEKTISKAKGQPREPQVYTLPPSRDELPYIIPPYNQVSLTCLVKGFYPSDIAVEWESNGQPEN
NYKTTPPVLDSDGSFFLYSKLTVGADRWLEGNVFSCSVMHEALHNHYTQKSLSLSPG Nucleic acid sequence of the heavy chain of FS22-172-003-AA/E05v2 mAb[2] with LALA mutation (SEQ ID NO: 138)
GAAGTGCAGCTGGTGCAGTCCGGAGCCGAAGTCAAGAGGCCTGGAGCGTCCGTGAAGGTGTCC
TGCAAAGCCTCAGGATACACCTTCACTTCGTACGGGATTTCCTGGGTCCGCCAAGCACCGGGTC
AAGGCTTGGAGTGGATGGGATGGATCAGCGCGTATTCCGGGGGAACCAACTACGCTCAAAAGC
TGCAGGGTCGCGTGACCATGACCACCGATACCTCCACCTCAACGGCCTACATGGAACTGAGATC
TCTGCGGAGCGACGACACTGCCGTGTACTACTGTGCCCGGGACCTGTTCCCCACTATCTTCGGA
GTGTCGTACTACTACTACTGGGGCCAGGGGACTCTCGTGACCGTGTCGAGCGCTAGCACTAAG
GGCCCGTCGGTGTTCCCGCTGGCCCCATCGTCCAAGAGCACATCAGGGGGTACCGCCGCCCTG
GGCTGCCTTGTGAAGGATTACTTTCCCGAGCCCGTCACAGTGTCCTGGAACAGCGGAGCCCTGA
CCTCCGGAGTGCATACTTTCCCGGCTGTGCTTCAGTCCTCTGGCCTGTACTCATTGTCCTCCGTG
GTCACCGTCCCTTCGTCCTCCCTGGGCACCCAGACCTATATCTGTAATGTCAACCATAAGCCCTC
GAACACCAAGGTCGACAAGAAGGTCGAGCCGAAGTCGTGCGACAAGACTCACACTTGCCCGCC
TTGCCCAGCCCCGGAAGCTGCCGGTGGTCCTTCGGTGTTCCTCTTCCCGCCCAAGCCGAAGGA
TACCCTGATGATCTCACGGACCCCCGAAGTGACCTGTGTGGTGGTGGACGTGTCCCACGAGGA
CCCGGAAGTGAAATTCAATTGGTACGTGGATGGAGTGGAAGTGCACAACGCCAAGACCAAGCCA
CGGGAAGAACAGTACAACTCTACCTACCGCGTGGTGTCCGTGCTCACTGTGCTGCACCAAGACT
GGCTGAACGGGAAGGAGTACAAGTGCAAAGTGTCCAACAAGGCGCTGCCTGCCCCAATTGAGA
AAACTATCTCGAAAGCCAAGGGACAGCCTCGAGAACCACAGGTGTACACCCTGCCCCCATCCCG
GGATGAGCTGCCATACATCATCCCACCATACAACCAGGTCAGCCTGACCTGCCTGGTCAAAGGC
TTCTATCCCAGCGACATCGCCGTGGAGTGGGAGAGCAATGGGCAGCCGGAGAACAACTACAAG
ACCACGCCTCCCGTGCTGGACTCCGACGGCTCCTTCTTCCTCTACAGCAAGCTCACCGTGGGCG
CAGATAGGTGGCTGGAAGGGAACGTCTTCTCATGCTCCGTGATGCATGAGGCGCTGCACAACCA
CTACACTCAGAAGAGCTTGTCCCTGTCGCCCGGT Nucleic acid sequence of the light chain of FS22-172-003-AA/E05v2 mAb[2] (SEQ ID NO: 139)
GACATTCAGATGACCCAATCCCCGTCCACGCTGAGCGCCTCCGTCGGTGATCGCGTGACAATCA
CTTGTCGGGCGTCGCAGTCCATCTCTGGAAGGCTCGCCTGGCAGCAGAAGCCTGGAAAGG
CTCCCAACCTCCTTATCTACGAAGCCAGCAACCTGGAGTCCGGAGTGCCTAGCCGGTTCAGCGG
ATCAGGGTCCGGTACCGAGTTCACCCTGACCATTTCCTCGCTCCAACCTGAGGACTTCGCCACC
TACTACTGCCAACAGTCCTATTCAACTCCGCGCGTGACCTTCGGCCAGGGCACTAAGGTCGAAA
TCAAAAGAACCGTGGCAGCCCCATCGGTGTTTATCTTCCCGCCCTCGGACGAACAGCTGAAGTC
AGGCACTGCTAGCGTGGTCTGTCTCCTGAACAATTTCTACCCGCGCGAAGCTAAGGTCCAGTGG
AAGGTCGACAACGCGCTGCAGTCCGGAAACAGCCAGGAGTCAGTGACCGAGCAGGACTCCAAG
GATTCCACTTATTCCCTGTCCTCCACCCTGACTTTGAGCAAGGCCGACTACGAGAAGCACAAAGT
GTACGCCTGCGAAGTGACCCATCAAGGGCTTTCGTCGCCCGTGACCAAGAGCTTCAACCGGGG
CGAATGC Amino acid(AA) sequence of the heavy chain of FS22-172-003-AA/G12v2 mAb[2] with LALA mutation (SEQ ID NO: 140)
VH domain (italics); LALA mutation (bold underlined)
*EVQLVQSGAEVKRPGASVKVSCKASGYTFTSYGISWVRQAPGQGLEWMGWISAYSGGTNYAQKLQ*
*GRVTMTTDTSTSTAYMELRSLRSDDTAVYYCARDLFPTIFGVSYYYYWGQGTLVTVSS*ASTKGPSVF
PLAPSSKSTSGGTAALGCLVKDYFPEPVTVSWNSGALTSGVHTFPAVLQSSGLYSLSSVVTVPSSSL
GTQTYICNVNHKPSNTKVDKKVEPKSCDKTHTCPPCPAPEAAGGPSVFLFPPKPKDTLMISRTPEVT
CVVVDVSHEDPEVKFNWYVDGVEVHNAKTKPREEQYNSTYRVVSVLTVLHQDWLNGKEYKCKVSN
KALPAPIEKTISKAKGQPREPQVYTLPPSRDELPYIIPPYNQVSLTCLVKGFYPSDIAVEWESNGQPEN
NYKTTPPVLDSDGSFFLYSKLTVGADRWLEGNVFSCSVMHEALHNHYTQKSLSLSPG Nucleic acid sequence of the heavy chain of FS22-172-003-AA/G12v2 mAb[2] with LALA mutation (SEQ ID NO: 141)
GAAGTGCAGCTGGTGCAGTCCGGAGCCGAAGTCAAGAGGCCTGGAGCGTCCGTGAAGGTGTCC
TGCAAAGCCTCAGGATACACCTTCACTTCGTACGGGATTTCCTGGGTCCGCCAAGCACCGGGTC
AAGGCTTGGAGTGGATGGGATGGATCAGCGCGTATTCCGGGGGAACCAACTACGCTCAAAAGC -continued
TGCAGGGTCGCGTGACCATGACCACCGATACCTCCACCTCAACGGCCTACATGGAACTGAGATC
TCTGCGGAGCGACGACACTGCCGTGTACTACTGTGCCCGGGACCTGTTCCCCACTATCTTCGGA
GTGTCGTACTACTACTACTGGGGCCAGGGGACTCTCGTGACCGTGTCGAGCGCTAGCACTAAG
GGCCCGTCGGTGTTCCCGCTGGCCCCATCGTCCAAGAGCACATCAGGGGGTACCGCCGCCCTG
GGCTGCCTTGTGAAGGATTACTTTCCCGAGCCCGTCACAGTGTCCTGGAACGGGAGCCCTGA
CCTCCGGAGTGCATACTTTCCCGGCTGTGCTTCAGTCCTCTGGCCTGTACTCATTGTCCTCCGTG
GTCACCGTCCCTTCGTCCTCCCTGGGCACCCAGACCTATATCTGTAATGTCAACCATAAGCCCTC
GAACACCAAGGTCGACAAGAAGGTCGAGCCGAAGTCGTGCGACAAGACTCACACTTGCCCGCC
TTGCCCAGCCCCGGAAGCTGCCGGTGGTCCTTCGGTGTTCCTCTTCCCGCCCAAGCCGAAGGA
TACCCTGATGATCTCACGGACCCCCGAAGTGACCTGTGTGGTGGTGGACGTGTCCCACGAGGA
CCCGGAAGTGAAATTCAATTGGTACGTGGATGGAGTGGAAGTGCACAACGCCAAGACCAAGCCA
CGGGAAGAACAGTACAACTCTACCTACCGCGTGGTGTCCGTGCTCACTGTGCTGCACCAAGACT
GGCTGAACGGGAAGGAGTACAAGTGCAAAGTGTCCAACAAGGCGCTGCCTGCCCCAATTGAGA
AAACTATCTCGAAAGCCAAGGGACAGCCTCGAGAACCACAGGTGTACACCCTGCCCCCATCCCG
GGATGAGCTGCCATACATCATCCCACCATACAACCAGGTCAGCCTGACCTGCCTGGTCAAAGGC
TTCTATCCCAGCGACATCGCCGTGGAGTGGGAGAGCAATGGGCAGCCGGAGAACAACTACAAG
ACCACGCCTCCCGTGCTGGACTCCGACGGCTCCTTCTTCCTCTACAGCAAGCTCACCGTGGGCG
CAGATAGGTGGCTGGAAGGGAACGTCTTCTCATGCTCCGTGATGCATGAGGCGCTGCACAACCA
CTACACTCAGAAGAGCTTGTCCCTGTCGCCCGGT Nucleic acid sequence of the light chain of FS22-172-003-AA/G12v2 mAb² (SEQ ID NO: 142)
GACATTCAGATGACCCAGTCCCCGAGCACGCTGTCCGCAAGCGTGGGGACAGAGTGACCATC
ACTTGCCGCGCCTCACAATCCATCAGCGGACGCTTGGCCTGGTACCAGCAGAAGCCCGGAAAG
GCCCCAAACCTTCTGATCTACGAAGCCTCGAACCTGGAGTCAGGCGTCCCTTCGCGGTTCTCTG
GCTCCGGTTCCGGAACTGAGTTCACCCTCACCATCTCGTCCCTGCAACCGGAAGATTTCGCCAC
CTACTACTGCCAACAGTCGTACTCCTGGCCCCGGACATTCGGACAGGGAACCAAAGTCGAGATT
AAGCGGACTGTGGCGGCTCCTAGCGTGTTCATCTTTCCCCCGTCCGACGAACAGCTGAAGTCCG
GTACCGCTAGCGTGGTCTGTCCTGAACAATTTCTACCCGCGCGAAGCTAAGGTCCAGTGGAA
GGTCGACAACGCGCTGCAGTCCGGAAACAGCCAGGAGTCAGTGACCGAGCAGGACTCCAAGGA
TTCCACTTATTCCCTGTCCTCCACCCTGACTTTGAGCAAGGCCGACTACGAGAAGCACAAAGTGT
ACGCCTGCGAAGTGACCCATCAAGGGCTTTCGTCGCCCGTGACCAAGAGCTTCAACCGGGGCG
AATGC AA sequence of the heavy chain of FS22-053-008-AA/E12v2 mAb² with LALA mutation (SEQ ID NO: 143)
VH domain (italics); LALA mutation (bold underlined)
*EVQLVQSGAEVKRPGASVKVSCKASGYPFTSYGISWVRQAPGQGLEWMGWISAYSGGTNYAQKLQ*
*GRVTMTTDTSTSTAYMELRSLRSDDTAVYYCARDLFPTIFGVSYYYYWGQGTLVTVSS*ASTKGPSVF
PLAPSSKSTSGGTAALGCLVKDYFPEPVTVSWNSGALTSGVHTFPAVLQSSGLYSLSSVVTVPSSSL
GTQTYICNVNHKPSNTKVDKKVEPKSCDKTHTCPPCPAPEAAGGPSVFLFPPKPKDTLMISRTPEVT
CVVVDVSHEDPEVKFNWYVDGVEVHNAKTKPREEQYNSTYRVVSVLTVLHQDWLNGKEYKCKVSN
KALPAPIEKTISKAKGQPREPQVYTLPPSRDELNPPYLFSNQVSLTCLVKGFYPSDIAVEWESNGQPE
NNYKTTPPVLDSDGSFFLYSKLTVDYWRWLEGNVFSCSVMHEALHNHYTQKSLSLSPG Nucleic acid sequence of the heavy chain of FS22-053-008-AA/E12v2 mAb² with LALA mutation (SEQ ID NO: 144)
GAAGTGCAGCTGGTGCAGTCCGGAGCCGAAGTCAAGAGGCCTGGAGCGTCCGTGAAGGTGTCC
TGCAAAGCCTCAGGATACCCCTTCACTTCGTACGGGATTTCCTGGGTCCGCCAAGCACCGGGTC
AAGGCTTGGAGTGGATGGGATGGATCAGCGCGTATTCCGGGGGAACCAACTACGCTCAAAAGC
TGCAGGGTCGCGTGACCATGACCACCGATACCTCCACCTCAACGGCCTACATGGAACTGAGATC
TCTGCGGAGCGACGACACTGCCGTGTACTACTGTGCCCGGGACCTGTTCCCCACTATCTTCGGA
GTGTCGTACTACTACTACTGGGGCCAGGGGACTCTCGTGACCGTGTCGAGCGCTAGCACTAAG
GGCCCGTCGGTGTTCCCGCTGGCCCCATCGTCCAAGAGCACATCAGGGGGTACCGCCGCCCTG
GGCTGCCTTGTGAAGGATTACTTTCCCGAGCCCGTCACAGTGTCCTGGAACAGCGGAGCCCTGA
CCTCCGGAGTGCATACTTTCCCGGCTGTGCTTCAGTCCTCTGGCCTGTACTCATTGTCCTCCGTG
GTCACCGTCCCTTCGTCCTCCCTGGGCACCCAGACCTATATCTGTAATGTCAACCATAAGCCCTC
GAACACCAAGGTCGACAAGAAGGTCGAGCCGAAGTCGTGCGACAAGACTCACACTTGCCCGCC
TTGCCCAGCCCCGGAAGCTGCCGGTGGTCCTTCGGTGTTCCTCTTCCCGCCCAAGCCGAAGGA
TACCCTGATGATCTCACGGACCCCCGAAGTGACCTGTGTGGTGGTGGACGTGTCCCACGAGGA
CCCGGAAGTGAAATTCAATTGGTACGTGGATGGAGTGGAAGTGCACAACGCCAAGACCAAGCCA
CGGGAAGAACAGTACAACTCTACCTACCGCGTGGTGTCCGTGCTCACTGTGCTGCACCAAGACT
GGCTGAACGGGAAGGAGTACAAGTGCAAAGTGTCCAACAAGGCGCTGCCTGCCCCAATTGAGA
AAACTATCTCGAAAGCCAAGGGACAGCCTCGAGAACCACAGGTGTACACCCTGCCCCCATCCCG
GGATGAGCTGAACCCGCTACCTGTTCTCTAACCAGGTCAGCCTGACCTGCCTGGTCAAAGGC
TTCTATCCCAGCGACATCGCCGTGGAGTGGGAGAGCAATGGGCAGCCGGAGAACAACTACAAG
ACCACGCCTCCCGTACTGGACTCCGACGGCTCCTTCTTCCTCTACAGCAAGCTCACCGTGGATT
ACTGGAGGTGGCTGGAAGGGAACGTCTTCTCATGCTCCGTGATGCATGAGGCGCTGCACAACC
ACTACACTCAGAAGAGCTTGTCCCTGTCGCCCGGT Nucleic acid sequence of the light chain of FS22-053-008-AA/E12v2 mAb² (SEQ ID NO: 145)
GACATCCAGATGACGCAGAGCCCGTCTACCCTGTCCGCCTCCGTGAGAGATCGCGTGATCATCA
CCTGTCGGGCCAGCCAGTCCATCGGAAACCGCTTGGCGTGGTACCAGCACAAGCCTGGGAAGG
CTCCGAAGCTGCTCATCTACGAAGCCTCGACTTCGGAGACTGGTGTCCCTAGCCGGTTCAGCGG
ATCGGGATCAGGGACCGATTTCACTCTGACCATTTCCTCCCTGCAACCCGAGGACTTCGCCACC
TACTACTGCCAACAGTCATATTCCACCCCGTACACCTTCGGACAAGGCACCAAGCTCGAAATCAA
GCGGACTGTCGCCGCACCTTCCGTGTTCATTTTCCCACCCTCCGACGAACAGCTGAAATCGGGT
ACAGCTAGCGTGGTCTGTCTCCTGAACAATTTCTACCCGCGCGAAGCTAAGGTCCAGTGGAAGG
TCGACAACGCGCTGCAGTCCGGAAACAGCCAGGAGTCAGTGACCGAGCAGGACTCCAAGGATT
CCACTTATTCCCTGTCCTCCACCCTGACTTTGAGCAAGGCCGACTACGAGAAGCACAAAGTGTAC
GCCTGCGAAGTGACCCATCAAGGGCTTTCGTCGCCCGTGACCAAGAGCTTCAACCGGGGCGAA
TGC AA sequence of the heavy chain of FS22-053-008-AA/E05v2 with LALA mutation (SEQ ID NO: 146)
VH domain (italics); LALA mutation (bold underlined)
*EVQLVQSGAEVKRPGASVKVSCKASGYTFTSYGISWVRQAPGQGLEWMGWISAYSGGTNYAQKLQ*
*GRVTMTDTSTSTAYMELRSLRSDDTAVYYCARDLFPTIFGVSYYYYWGQGTLVTVSS*ASTKGPSVF
PLAPSSKSTSGGTAALGCLVKDYFPEPVTVSWNSGALTSGVHTFPAVLQSSGLYSLSSVVTVPSSSL
GTQTYICNVNHKPSNTKVDKKVEPKSCDKTHTCPPCPAPEAAGGPSVFLFPPKPKDTLMISRTPEVT
CVVVDVSHEDPEVKFNWYVDGVEVHNAKTKPREEQYNSTYRVVSVLTVLHQDWLNGKEYKCKVSN
KALPAPIEKTISKAKGQPREPQVYTLPPSRDELNPPYLFSNQVSLTCLVKGFYPSDIAVEWESNGQPE
NNYKTTPPVLDSDGSFFLYSKLTVDYWRWLEGNVFSCSVMHEALHNHYTQKSLSLSPG Nucleic acid sequence of the heavy chain of FS22-053-008-AA/E05v2 mAb$^2$ with LALA mutation
(SEQ ID NO: 147)
GAAGTGCAGCTGGTGCAGTCCGGAGCCGAAGTCAAGAGGCCTGGAGCGTCCGTGAAGGTGTCC
TGCAAAGCCTCAGGATACACCTTCACTTCGTACGGGATTTCCTGGGTCCGCCAAGCACCGGGTC
AAGGCTTGGAGTGGATGGGATGGATCAGCGCGTATTCCGGGGGAACCAACTACGCTCAAAAGC
TGCAGGGTCGCGTGACCATGACCACCGATACCTCCACCTCAACGGCCTACATGGAACTGAGATC
TCTGCGGAGCGACGACACTGCCGTGTACTACTGTGCCCGGGACCTGTTCCCCACTATCTTCGGA
GTGTCGTACTACTACTACTGGGGCCAGGGGACTCTCGTGACCGTGTCGAGCGCTAGCACTAAG
GGCCCGTCGGTGTTCCCGCTGGCCCCATCGTCCAAGAGCACATCAGGGGGTACCGCCGCCCTG
GGCTGCCTTGTGAAGGATTACTTTCCCGAGCCCGTCACAGTGTCCTGGAACAGCGGAGCCCTGA
CCTCCGGAGTGCATACTTTCCCGGCTGTGCTTCAGTCCTCTGGCCTGTACTCATTGTCCTCCGTG
GTCACCGTCCCTTCGTCCTCCCTGGGCACCCAGACCTATATCTGTAATGTCAACCATAAGCCCTC
GAACACCAAGGTCGACAAGAAGGTCGAGCCGAAGTCGTGCGACAAGACTCACACTTGCCCGCC
TTGCCCAGCCCCGGAAGCTGCCGGTGGTCCTTCGGTGTTCCTCTTCCCGCCCAAGCCGAAGGA
TACCCTGATGATCTCACGGACCCCCGAAGTGACCTGTGTGGTGGTGGACGTGTCCCACGAGGA
CCCGGAAGTGAAATTCAATTGGTACGTGGATGGAGTGGAAGTGCACAACGCCAAGACCAAGCCA
CGGGAAGAACAGTACAACTCTACCTACCGCGTGGTGTCCGTGCTCACTGTGCTGCACCAAGACT
GGCTGAACGGGAAGGAGTACAAGTGCAAAGTGTCCAACAAGGCGCTGCCTGCCCCAATTGAGA
AAACTATCTCGAAAGCCAAGGGACAGCCTCGAGAACCACAGGTGTACACCCTGCCCCCATCCCG
GGATGAGCTGAACCCGCCGTACCTGTTCTCTAACCAGGTCAGCCTGACCTGCCTGGTCAAAGGC
TTCTATCCCAGCGACATCGCCGTGGAGTGGGAGAGCAATGGGCAGCCGGAGAACAACTACAAG
ACCACGCCTCCCGTACTGGACTCCGACGGCTCCTTCTTCCTCTACAGCAAGCTCACCGTGGATT
ACTGGAGGTGGCTGGAAGGGAACGTCTTCTCATGCTCCGTGATGCATGAGGCGCTGCACAACC
ACTACACTCAGAAGAGCTTGTCCCTGTCGCCCGGT Nucleic acid sequence of the light chain of FS22-053-008-AA/E05v2 mAb$^2$ (SEQ ID NO: 148)
GACATTCAGATGACCCAATCCCCGTCCACGCTGAGCGCCTCCGTCGGTGATCGCGTGACAATCA
CTTGTCGGGCGTCGCAGTCCATCTCTGGAAGGCTCGCCTGGTACCAGCAGAAGCCTGGAAAGG
CTCCCAACCTCCTTATCTACGAAGCCAGCAACCTGGAGTCCGGAGTGCCTAGCCGGTTCAGCGG
ATCAGGGTCCGGTACCGAGTTCACCCTGACCATTTCCTCGCTCCAACCTGAGGACTTCGCCACC
TACTACTGCCAACAGTCCTATTCAACTCCGCGCGTGACCTTCGGCCAGGGCACTAAGGTCGAAA
TCAAAAGAACCGTGGCAGCCCCCATCGGTGTTTATCTTCCCGCCTCCGACGAACAGCTGAAGTC
AGGCACTGCTAGCGTGGTCTGTCTCCTGAACAATTTCTACCCGCGCGAAGCTAAGGTCCAGTGG
AAGGTCGACAACGCGCTGCAGTCCGGAAACAGCCAGGAGTCAGTGACCGAGCAGGACTCCAAG
GATTCCACTTATTCCCTGTCCTCCACCCTGACTTTGAGCAAGGCCGACTACGAGAAGCACAAAGT
GTACGCCTGCGAAGTGACCCATCAAGGGCTTTCGTCGCCCGTGACCAAGAGCTTCAACCGGGG
CGAATGC AA sequence of the heavy chain of FS22-053-008-AA/G12v2 with LALA mutation (SEQ ID NO: 149)
VH domain (italics); LALA mutation (bold underlined)
*EVQLVQSGAEVKRPGASVKVSCKASGYTFTSYGISWVRQAPGQGLEWMGWISAYSGGTNYAQKLQ*
*GRVTMTDTSTSTAYMELRSLRSDDTAVYYCARDLFPTIFGVSYYYYWGQGTLVTVSS*ASTKGPSVF
PLAPSSKSTSGGTAALGCLVKDYFPEPVTVSWNSGALTSGVHTFPAVLQSSGLYSLSSVVTVPSSSL
GTQTYICNVNHKPSNTKVDKKVEPKSCDKTHTCPPCPAPEAAGGPSVFLFPPKPKDTLMISRTPEVT
CVVVDVSHEDPEVKFNWYVDGVEVHNAKTKPREEQYNSTYRVVSVLTVLHQDWLNGKEYKCKVSN
KALPAPIEKTISKAKGQPREPQVYTLPPSRDELNPPYLFSNQVSLTCLVKGFYPSDIAVEWESNGQPE
NNYKTTPPVLDSDGSFFLYSKLTVDYWRWLEGNVFSCSVMHEALHNHYTQKSLSLSPG Nucleic acid sequence of the heavy chain of FS22-053-008-AA/G12v2 mAb$^2$ with LALA mutation
(SEQ ID NO: 150)
GAAGTGCAGCTGGTGCAGTCCGGAGCCGAAGTCAAGAGGCCTGGAGCGTCCGTGAAGGTGTCC
TGCAAAGCCTCAGGATACACCTTCACTTCGTACGGGATTTCCTGGGTCCGCCAAGCACCGGGTC
AAGGCTTGGAGTGGATGGGATGGATCAGCGCGTATTCCGGGGGAACCAACTACGCTCAAAAGC
TGCAGGGTCGCGTGACCATGACCACCGATACCTCCACCTCAACGGCCTACATGGAACTGAGATC
TCTGCGGAGCGACGACACTGCCGTGTACTACTGTGCCCGGGACCTGTTCCCCACTATCTTCGGA
GTGTCGTACTACTACTACTGGGGCCAGGGGACTCTCGTGACCGTGTCGAGCGCTAGCACTAAG
GGCCCGTCGGTGTTCCCGCTGGCCCCATCGTCCAAGAGCACATCAGGGGGTACCGCCGCCCTG
GGCTGCCTTGTGAAGGATTACTTTCCCGAGCCCGTCACAGTGTCCTGGAACAGCGGAGCCCTGA
CCTCCGGAGTGCATACTTTCCCGGCTGTGCTTCAGTCCTCTGGCCTGTACTCATTGTCCTCCGTG
GTCACCGTCCCTTCGTCCTCCCTGGGCACCCAGACCTATATCTGTAATGTCAACCATAAGCCCTC
GAACACCAAGGTCGACAAGAAGGTCGAGCCGAAGTCGTGCGACAAGACTCACACTTGCCCGCC
TTGCCCAGCCCCGGAAGCTGCCGGTGGTCCTTCGGTGTTCCTCTTCCCGCCCAAGCCGAAGGA
TACCCTGATGATCTCACGGACCCCCGAAGTGACCTGTGTGGTGGTGGACGTGTCCCACGAGGA
CCCGGAAGTGAAATTCAATTGGTACGTGGATGGAGTGGAAGTGCACAACGCCAAGACCAAGCCA
CGGGAAGAACAGTACAACTCTACCTACCGCGTGGTGTCCGTGCTCACTGTGCTGCACCAAGACT
GGCTGAACGGGAAGGAGTACAAGTGCAAAGTGTCCAACAAGGCGCTGCCTGCCCCAATTGAGA
AAACTATCTCGAAAGCCAAGGGACAGCCTCGAGAACCACAGGTGTACACCCTGCCCCCATCCCG
GGATGAGCTGAACCCGCCGTACCTGTTCTCTAACCAGGTCAGCCTGACCTGCCTGGTCAAAGGC
TTCTATCCCAGCGACATCGCCGTGGAGTGGGAGAGCAATGGGCAGCCGGAGAACAACTACAAG
ACCACGCCTCCCGTACTGGACTCCGACGGCTCCTTCTTCCTCTACAGCAAGCTCACCGTGGATT

```
ACTGGAGGTGGCTGGAAGGGAACGTCTTCTCATGCTCCGTGATGCATGAGGCGCTGCACAACC
ACTACACTCAGAAGAGCTTGTCCCTGTCGCCCGGT
```

Nucleic acid sequence of the light chain of FS22-053-008-AA/G12v2 mAb² (SEQ ID NO: 151)
```
GACATTCAGATGACCCAGTCCCCGAGCACGCTGTCCGCAAGCGTGGGGGACAGAGTGACCATC
ACTTGCCGCGCCTCACAATCCATCAGCGGACGCTTGGCCTGGTACCAGCAGAAGCCCGGAAAG
GCCCCAAACCTTCTGATCTACGAAGCCTCGAACCTGGAGTCAGGCGTCCCTTCGCGGTTCTCTG
GCTCCGGTTCCGGAACTGAGTTCACCCTCACCATCTCGTCCCTGCAACCGGAAGATTTCGCCAC
CTACTACTGCCAACAGTCGTACTCCTGGCCCCGGACATTCGGACAGGGAACCAAAGTCGAGATT
AAGCGGACTGTGGCGGCTCCTAGCGTGTTCATCTTTCCCCCGTCCGACGAACAGCTGAAGTCCG
GTACCGCTAGCGTGGTCTGTCTCCTGAACAATTTCTACCCGCGCGAAGCTAAGGTCCAGTGGAA
GGTCGACAACGCGCTGCAGTCCGGAAACAGCCAGGAGTCAGTGACCGAGCAGGACTCCAAGGA
TTCCACTTATTCCCTGTCCTCCACCCTGACTTTGAGCAAGGCCGACTACGAGAAGCACAAAGTGT
ACGCCTGCGAAGTGACCCATCAAGGGCTTTCGTCGCCCGTGACCAAGAGCTTCAACCGGGGCG
AATGC
```

AA sequence of the heavy chain of FS22-053-017AA/E12v2 with LALA mutation (SEQ ID NO: 152)
VH domain (italics); LALA mutation (bold underlined)
*EVQLVQSGAEVKRPGASVKVSCKASGYPFTSYGISWVRQAPGQGLEWMGWISAYSGGTNYAQKLQ*
*GRVTMTTDTSTSTAYMELRSLRSDDTAVYYCARDLFPTIFGVSYYYYWGQGTLVTVSS*ASTKGPSVF
PLAPSSKSTSGGTAALGCLVKDYFPEPVTVSWNSGALTSGVHTFPAVLQSSGLYSLSSVVTVPSSSL
GTQTYICNVNHKPSNTKVDKKVEPKSCDKTHTCPPCPAPEAAGGPSVFLFPPKPKDTLMISRTPEVT
CVVVDVSHEDPEVKFNWYVDGVEVHNAKTKPREEQYNSTYR<u>V</u>VSVLTVLHQDWLNGKEYKCKVSN
KALPAPIEKTISKAKGQPREPQVYTLPPSRDELNPPYLFSNQVSLTCLVKGFYPSDIAVEWESNGQPE
NNYKTTPPVLDSDGSFFLYSKLTVYHWRWLEGNVFSCSVMHEALHNHYTQKSLSLSPG AA sequence of the heavy chain of FS22-053-017AA/E05v2 with LALA mutation (SEQ ID NO: 153)
VH domain (italics); LALA mutation (bold underlined)
*EVQLVQSGAEVKRPGASVKVSCKASGYPFTSYGISWVRQAPGQGLEWMGWISAYSGGTNYAQKLQ*
*GRVTMTTDTSTSTAYMELRSLRSDDTAVYYCARDLFPTIFGVSYYYYWGQGTLVTVSS*ASTKGPSVF
PLAPSSKSTSGGTAALGCLVKDYFPEPVTVSWNSGALTSGVHTFPAVLQSSGLYSLSSVVTVPSSSL
GTQTYICNVNHKPSNTKVDKKVEPKSCDKTHTCPPCPAPEAAGGPSVFLFPPKPKDTLMISRTPEVT
CVVVDVSHEDPEVKFNWYVDGVEVHNAKTKPREEQYNSTYR<u>V</u>VSVLTVLHQDWLNGKEYKCKVSN
KALPAPIEKTISKAKGQPREPQVYTLPPSRDELNPPYLFSNQVSLTCLVKGFYPSDIAVEWESNGQPE
NNYKTTPPVLDSDGSFFLYSKLTVYHWRWLEGNVFSCSVMHEALHNHYTQKSLSLSPG AA sequence of the heavy chain of FS22-053-017AA/G12v2 with LALA mutation (SEQ ID NO: 154)
VH domain (italics); LALA mutation (bold underlined)
*EVQLVQSGAEVKRPGASVKVSCKASGYPFTSYGISWVRQAPGQGLEWMGWISAYSGGTNYAQKLQ*
*GRVTMTTDTSTSTAYMELRSLRSDDTAVYYCARDLFPTIFGVSYYYYWGQGTLVTVSS*ASTKGPSVF
PLAPSSKSTSGGTAALGCLVKDYFPEPVTVSWNSGALTSGVHTFPAVLQSSGLYSLSSVVTVPSSSL
GTQTYICNVNHKPSNTKVDKKVEPKSCDKTHTCPPCPAPEAAGGPSVFLFPPKPKDTLMISRTPEVT
CVVVDVSHEDPEVKFNWYVDGVEVHNAKTKPREEQYNSTYR<u>V</u>VSVLTVLHQDWLNGKEYKCKVSN
KALPAPIEKTISKAKGQPREPQVYTLPPSRDELNPPYLFSNQVSLTCLVKGFYPSDIAVEWESNGQPE
NNYKTTPPVLDSDGSFFLYSKLTVYHWRWLEGNVFSCSVMHEALHNHYTQKSLSLSPG AA sequence of the heavy chain of FS22-172-003AA/lam-G02v3 with LALA mutation (SEQ ID NO: 155)
VH domain (italics); LALA mutation (bold underlined)
*EVQLVQSGAEVKRPGASVKVSCKASGYPFTSYGISWVRQAPGQGLEWMGWISAYSGGTNYAQKLQ*
*GRVTMTTDTSTSTAYMELRSLRSDDTAVYYCARDLFPTIFGVSYYYYWGQGTLVTVSS*ASTKGPSVF
PLAPSSKSTSGGTAALGCLVKDYFPEPVTVSWNSGALTSGVHTFPAVLQSSGLYSLSSVVTVPSSSL
GTQTYICNVNHKPSNTKVDKKVEPKSCDKTHTCPPCPAPEAAGGPSVFLFPPKPKDTLMISRTPEVT
CVVVDVSHEDPEVKFNWYVDGVEVHNAKTKPREEQYNSTYR<u>V</u>VSVLTVLHQDWLNGKEYKCKVSN
KALPAPIEKTISKAKGQPREPQVYTLPPSRDELNPPYLFSNQVSLTCLVKGFYPSDIAVEWESNGQPE
NYKTTPPVLDSDGSFFLYSKLTVGADRWLEGNVFSCSVMHEALHNHYTQKSLSLSPG AA sequence of the heavy chain of FS22-172-003AA/S70 with LALA mutation (SEQ ID NO: 156)
VH domain (italics); LALA mutation (bold underlined)
*EVQLVESGGGLVQPGGSLRLSCAASGFTFSDSWIHWVRQAPGKGLEWVAWISPYGGSTYYADSVK*
*GRFTISADTSKNTAYLQMNSLRAEDTAVYYCARRHWPGGFDYWGQGTLVTVSA*ASTKGPSVFPLAP
SSKSTSGGTAALGCLVKDYFPEPVTVSWNSGALTSGVHTFPAVLQSSGLYSLSSVVTVPSSSLGTQT
YICNVNHKPSNTKVDKKVEPKSCDKTHTCPPCPAPEAAGGPSVFLFPPKPKDTLMISRTPEVTCVVV
DVSHEDPEVKFNWYVDGVEVHNAKTKPREEQYNSTYR<u>V</u>VSVLTVLHQDWLNGKEYKCKVSNKALP
APIEKTISKAKGQPREPQVYTLPPSRDELPYIIPPYNQVSLTCLVKGFYPSDIAVEWESNGQPENNYKT
TPPVLDSDGSFFLYSKLTVGADRWLEGNVFSCSVMHEALHNHYTQKSLSLSPG AA sequence of the light chain of S70 (SEQ ID NO: 157)
VL domain (italics);
*DIQMTQSPSSLSASVGDRVTITCRASQDVSTAVAWYQQKPGKAPKLLIYSASFLYSGVPSRFSGSGS*
*GTDFTLTISSLQPEDFATYYCQQYLYHPATFGQGTKVEIK*RTVAAPSVFIFPPSDEQLKSGTASVVCLL
NNFYPREAKVQWKVDNALQSGNSQESVTEQDSKDSTYSLSSTLTLSKADYEKHKVYACEVTHQGLS
SPVTKSFNRGEC AA sequence of the heavy chain of FS22-172-003AA/HeID1.3 with LALA mutation (SEQ ID NO: 158)
VH domain (italics); LALA mutation (bold underlined)
*QVQLQESGPGLVRPSQTLSLTCTVSGSTFSGYGVNWVRQPPGRGLEWIGMIWGDGNTDYNSALKS*
*RVTMLVDTSKNQFSLRLSSVTAADTAVYYCARERDYRLDYWGQGTLVTVSS*ASTKGPSVFPLAPSS
KSTSGGTAALGCLVKDYFPEPVTVSWNSGALTSGVHTFPAVLQSSGLYSLSSVVTVPSSSLGTQTYI
CNVNHKPSNTKVDKKVEPKSCDKTHTCPPCPAPEAAGGPSVFLFPPKPKDTLMISRTPEVTCVVVDV
SHEDPEVKFNWYVDGVEVHNAKTKPREEQYNSTYR<u>V</u>VSVLTVLHQDWLNGKEYKCKVSNKALPAPI -continued EKTISKAKGQPREPQVYTLPPSRDELPYIIPPYNQVSLTCLVKGFYPSDIAVEWESNGQPENNYKTTP
PVLDSDGSFFLYSKLTVGADRWLEGNVFSCSVMHEALHNHYTQKSLSLSPG AA sequence of the light chain of HelD1.3 (SEQ ID NO: 159)
VL domain (italics)
*DIQMTQSPASLSASVGETVTITCRASGNIHNYLAWYQQKQGKSPQLLVYNAKTLADGVPSRFSGSGS*
*GTQYSLKINSLQPEDFGSYYCQHFWSTPRTFGGGTKLEIK*RTVAAPSVFIFPPSDEQLKSGTASVVCL
LNNFYPREAKVQWKVDNALQSGNSQESVTEQDSKDSTYSLSSTLTLSKADYEKHKVYACEVTHQGL
SSPVTKSFNRGEC AA sequence of the heavy chain of FS22m-063AA/S70 with LALA mutation (SEQ ID NO: 160)
VH domain (italics); LALA mutation (bold underlined)
*EVOLVESGGGLVQPGGSLRLSCAASGFTFSDSWIHWVRQAPGKGLEWVAWISPYGGSTYYADSVK*
*GRFTISADTSKNTAYLQMNSLRAEDTAVYYCARRHWPGGFDYWGQGTLVTVSA*ASTKGPSVFPLAP
SSKSTSGGTAALGCLVKDYFPEPVTVSWNSGALTSGVHTFPAVLQSSGLYSLSSVVTVPSSSLGTQT
YICNVNHKPSNTKVDKKVEPKSCDKTHTCPPCPAPEAAGGPSVFLFPPKPKDTLMISRTPEVTCVVV
DVSHEDPEVKFNWYVDGVEVHNAKTKPREEQYNSTYRVVSVLTVLHQDWLNGKEYKCKVSNKALP
APIEKTISKAKGQPREPQVYTLPPSRDEPYWSYVSLTCLVKGFYPSDIAVEWESNGQPENNYKTTPP
VLDSDGSFFLYSKLTVMNYRWELGNVFSCSVMHEALHNHYTQKSLSLSPG AA sequence of the heavy chain of FS22m-063AA/HeID1.3 with LALA mutation (SEQ ID NO: 161)
VH domain (italics); LALA mutation (bold underlined)
*QVQLQESGPGLVRPSQTLSLTCTVSGSTFSGYGVNWVRQPPGRGLEWIGMIWGDGNTDYNSALKS*
*RVTMLVDTSKNQFSLRLSSVTAADTAVYYCARERDYRLDYWGQGSLVTVSS*ASTKGPSVFPLAPSS
KSTSGGTAALGCLVKDYFPEPVTVSWNSGALTSGVHTFPAVLQSSGLYSLSSVVTVPSSSLGTQTYI
CNVNHKPSNTKVDKKVEPKSCDKTHTCPPCPAPEAAGGPSVFLFPPKPKDTLMISRTPEVTCVVVD
SHEDPEVKFNWYVDGVEVHNAKTKPREEQYNSTYRVVSVLTVLHQDWLNGKEYKCKVSNKALPAPI
EKTISKAKGQPREPQVYTLPPSRDEPYWSYVSLTCLVKGFYPSDIAVEWESNGQPENNYKTTPPVLD
SDGSFFLYSKLTVMNYRWELGNVFSCSVMHEALHNHYTQKSLSLSPG AA sequence of the heavy chain of G1-AA/E12v2 with LALA mutation (SEQ ID NO: 162)
VH domain (italics); LALA mutation (bold underlined)
*EVQLVQSGAEVKRPGASVKVSCKASGYPFTSYGISWVRQAPGQGLEWMGWISAYSGGTNYAQKLQ*
*GRVTMTTDTSTSTAYMELRSLRSDDTAVYYCARDLFPTIFGVSYYYYWGQGTLVTVSS*ASTKGPSVF
PLAPSSKSTSGGTAALGCLVKDYFPEPVTVSWNSGALTSGVHTFPAVLQSSGLYSLSSVVTVPSSSL
GTQTYICNVNHKPSNTKVDKKVEPKSCDKTHTCPPCPAPEAAGGPSVFLFPPKPKDTLMISRTPEVT
CVVVDVSHEDPEVKFNWYVDGVEVHNAKTKPREEQYNSTYRVVSVLTVLHQDWLNGKEYKCKVSN
KALPAPIEKTISKAKGQPREPQVYTLPPSRDELTKNQVSLTCLVKGFYPSDIAVEWESNGQPENNYKT
TPPVLDSDGSFFLYSKLTVDKSRWQQGNVFSCSVMHEALHNHYTQKSLSLSPG AA sequence of the heavy chain of G1/S70 (SEQ ID NO: 163)
VH domain (italics)
*EVOLVESGGGLVQPGGSLRLSCAASGFTFSDSWIHWVRQAPGKGLEWVAWISPYGGSTYYADSVK*
*GRFTISADTSKNTAYLQMNSLRAEDTAVYYCARRHWPGGFDYWGQGTLVTVSA*ASTKGPSVFPLAP
SSKSTSGGTAALGCLVKDYFPEPVTVSWNSGALTSGVHTFPAVLQSSGLYSLSSVVTVPSSSLGTQT
YICNVNHKPSNTKVDKKVEPKSCDKTHTCPPCPAPELLGGPSVFLFPPKPKDTLMISRTPEVTCVVVD
VSHEDPEVKFNWYVDGVEVHNAKTKPREEQYNSTYRVVSVLTVLHQDWLNGKEYKCKVSNKALPAP
IEKTISKAKGQPREPQVYTLPPSRDELTKNQVSLTCLVKGFYPSDIAVEWESNGQPENNYKTTPPVLD
SDGSFFLYSKLTVDKSRWQQGNVFSCSVMHEALHNHYTQKSLSLSPGK AA sequence of the heavy chain of G1-AA/S70 with LALA mutation (SEQ ID NO: 164)
VH domain (italics); LALA mutation (bold underlined)
*EVOLVESGGGLVQPGGSLRLSCAASGFTFSDSWIHWVRQAPGKGLEWVAWISPYGGSTYYADSVK*
*GRFTISADTSKNTAYLQMNSLRAEDTAVYYCARRHWPGGFDYWGQGTLVTVSA*ASTKGPSVFPLAP
SSKSTSGGTAALGCLVKDYFPEPVTVSWNSGALTSGVHTFPAVLQSSGLYSLSSVVTVPSSSLGTQT
YICNVNHKPSNTKVDKKVEPKSCDKTHTCPPCPAPEAAGGPSVFLFPPKPKDTLMISRTPEVTCVVVD
VSHEDPEVKFNWYVDGVEVHNAKTKPREEQYNSTYRVVSVLTVLHQDWLNGKEYKCKVSNKALPAP
IEKTISKAKGQPREPQVYTLPPSRDELTKNQVSLTCLVKGFYPSDIAVEWESNGQPENNYKTTPPVLD
SDGSFFLYSKLTVDKSRWQQGNVFSCSVMHEALHNHYTQKSLSLSPGK AA sequence of the heavy chain of G1/4420 (SEQ ID NO: 165)
VH domain (italics)
*EVKLDETGGGLVQPGRPMKLSCVASGFTFSDYWMNWVRQSPEKGLEWVAQIRNKPYNYETYYSDS*
*VKGRFTISRDDSKSSVYLQMNNLRVEDMGIYYCTGSYYGMDYWGQGTSVTVSS*ASTKGPSVFPLAP
SSKSTSGGTAALGCLVKDYFPEPVTVSWNSGALTSGVHTFPAVLQSSGLYSLSSVVTVPSSSLGTQT
YICNVNHKPSNTKVDKKVEPKSCDKTHTCPPCPAPELLGGPSVFLFPPKPKDTLMISRTPEVTCVVVD
VSHEDPEVKFNWYVDGVEVHNAKTKPREEQYNSTYRVVSVLTVLHQDWLNGKEYKCKVSNKALPAP
IEKTISKAKGQPREPQVYTLPPSRDELTKNQVSLTCLVKGFYPSDIAVEWESNGQPENNYKTTPPVLD
SDGSFFLYSKLTVDKSRWQQGNVFSCSVMHEALHNHYTQKSLSLSPGK AA sequence of the light chain of 4420 (SEQ ID NO: 166)
VL domain (italics)
*DVVMTQTPLSLPVSLGDQASISCRSSQSLVHSNGNTYLRWYLQKPGQSPKVLIYKVSNRFSGVPDRF*
*SGSGSGTDFTLKISRVEAEDLGVYFCSQSTHVPWTFGGGTKLEIK*RTVAAPSVFIFPPSDEQLKSGTA
SVVCLLNNFYPREAKVQWKVDNALQSGNSQESVTEQDSKDSTYSLSSTLTLSKADYEKHKVYACEV
THQGLSSPVTKSFNRGEC AA sequence of the heavy chain of G1-AA/4420 with LALA mutation (SEQ ID NO: 167)
VH domain (italics); LALA mutation (bold underlined)
*EVKLDETGGGLVQPGRPMKLSCVASGFTFSDYWMNWVRQSPEKGLEWVAQIRNKPYNYETYYSDS*
*VKGRFTISRDDSKSSVYLQMNNLRVEDMGIYYCTGSYYGMDYWGQGTSVTVSS*ASTKGPSVFPLAP -continued SSKSTSGGTAALGCLVKDYFPEPVTVSWNSGALTSGVHTFPAVLQSSGLYSLSSVVTVPSSSLGTQT
YICNVNHKPSNTKVDKKVEPKSCDKTHTCPPCPAPEAAGGPSVFLFPPKPKDTLMISRTPEVTCVVV
DVSHEDPEVKFNWYVDGVEVHNAKTKPREEQYNSTYRVVSVLTVLHQDWLNGKEYKCKVSNKALP
APIEKTISKAKGQPREPQVYTLPPSRDELTKNQVSLTCLVKGFYPSDIAVEWESNGQPENNYKTTPPV
LDSDGSFFLYSKLTVDKSRWQQGNVFSCSVMHEALHNHYTQKSLSLSPGK AA sequence of the heavy chain of G1-AA/HeID1.3 with LALA mutation (SEQ ID NO: 168)
VH domain (italics); LALA mutation (bold underlined)
*QVQLQESGPGLVRPSQTLSLTCTVSGSTFSGYGVNWVRQPPGRGLEWIGMIWGDGNTDYNSALKS*
*RVTMLVDTSKNQFSLRLSSVTAADTAVYYCARERDYRLDYWGQGSLVTVSS*ASTKGPSVFPLAPSS
KSTSGGTAALGCLVKDYFPEPVTVSWNSGALTSGVHTFPAVLQSSGLYSLSSVVTVPSSSLGTQTYI
CNVNHKPSNTKVDKKVEPKSCDKTHTCPPCPAPEAAGGPSVFLFPPKPKDTLMISRTPEVTCVVVDV
SHEDPEVKFNWYVDGVEVHNAKTKPREEQYNSTYRVVSVLTVLHQDWLNGKEYKCKVSNKALPAPI
EKTISKAKGQPREPQVYTLPPSRDELTKNQVSLTCLVKGFYPSDIAVEWESNGQPENNYKTTPPVLD
SDGSFFLYSKLTVDKSRWQQGNVFSCSVMHEALHNHYTQKSLSLSPGK AA sequence of the heavy chain of G1-AA/MLS109 with LALA mutation (SEQ ID NO: 169)
VH domain (italics); LALA mutation (bold underlined)
*EEQVLESGGGLVKPGGSLRLSCAASGFTFSPYSVFWVRQAPGKGLEWVSSINSDSTYKYYADSVKG*
*RFTISRDNAENSIFLQMNSLRAEDTAVYYCARDRSYYAFSSGSLSDYYYGLDVWGQGTTVIVSS*AST
KGPSVFPLAPSSKSTSGGTAALGCLVKDYFPEPVTVSWNSGALTSGVHTFPAVLQSSGLYSLSSVVT
VPSSSLGTQTYICNVNHKPSNTKVDKKVEPKSCDKTHTCPPCPAPEAAGGPSVFLFPPKPKDTLMIS
RTPEVTCVVVDVSHEDPEVKFNWYVDGVEVHNAKTKPREEQYNSTYRVVSVLTVLHQDWLNGKEY
KCKVSNKALPAPIEKTISKAKGQPREPQVYTLPPSRDELTKNQVSLTCLVKGFYPSDIAVEWESNGQP
ENNYKTTPPVLDSDGSFFLYSKLTVDKSRWQQGNVFSCSVMHEALHNHYTQKSLSLSPGK Amino acid sequence of the light chain of MLS109 (SEQ ID NO: 170)
VL domain (italics)
*DIVMTQSPLSLSVTPGEPASISCRSSQSLLHTNGYNYLDWYVQKPGQSPQLLIYLASNRASGVPDRFS*
*GSGSGTDFTLKISRVETEDVGVYYCMQALQIPRTFGQGTKVEIK*RTVAAPSVFIFPPSDEQLKSGTAS
VVCLLNNFYPREAKVQWKVDNALQSGNSQESVTEQDSKDSTYSLSSTLTLSKADYEKHKVYACEVT
HQGLSSPVTKSFNRGEC Amino acid sequences of FS22-172-003 CH3 domain AB and EF loops
AB loop - RDELPYIIPPYNQ (SEQ ID NO: 171)

EF loop - GADRWLEGNV (SEQ ID NO: 172)

Amino acid sequences of FS22-53-008 CH3 domain AB and EF loops
AB loop - RDELNPPYLFSNQ (SEQ ID NO: 173)

EF loop - DYWRWLEGNV (SEQ ID NO: 174)

Amino acid sequences of FS22-053-017 CH3 domain AB and EF loops
AB loop - RDELNPPYLFSNQ (SEQ ID NO: 173)

EF loop - YHWRWLEGNV (SEQ ID NO: 175)

Amino acid sequence of the heavy chain of G1/280 02 G02 (SEQ ID NO: 177)
VH domain (italics)
*EVQLVQSGAEVKRPGASVKVSCKASGYTFTSYGISWVRQAPGQGLEWMGWISAYNGNTNYAQKLQ*
*GRVTMTTDTSTSTAYMELRSLRSDDTAVYYCARDLFPTIFGVSYYYYWGQGTLVTVSS*ASTKGPSVF
PLAPSSKSTSGGTAALGCLVKDYFPEPVTVSWNSGALTSGVHTFPAVLQSSGLYSLSSVVTVPSSSL
GTQTYICNVNHKPSNTKVDKKVEPKSCDKTHTCPPCPAPELLGGPSVFLFPPKPKDTLMISRTPEVTC
VVVDVSHEDPEVKFNWYVDGVEVHNAKTKPREEQYNSTYRVVSVLTVLHQDWLNGKEYKCKVSNK
ALPAPIEKTISKAKGQPREPQVYTLPPSRDELTKNQVSLTCLVKGFYPSDIAVEWESNGQPENNYKTT
PPVLDSDGSFFLYSKLTVDKSRWQQGNVFSCSVMHEALHNHYTQKSLSLSPG Amino acid sequence of the light chain of G1/280 02 G02 (SEQ ID NO: 178)
VL domain (italics)
*QSALTQPASVSGSPGQSITISCTGTSSDVGGYNSVSWYQQFPGKAPKLMIFEVTNRPSGVSDRFSGS*
*KSDNTASLTISGLQAEDEAEYYCSSFKRGSTLVVFGGGTKLTVL*GQPAAAPSVTLFPPSSEELQANKA
TLVCLISDFYPGAVTVAWKADSSPVKAGVETTTPSKQSNNKYAASSYLSLTPEQWKSHRSYSCQVTH
EGSTVEKTVAPTECS Amino acid sequence of human PD-L1 (SEQ ID NO: 179)
Extracellular domain (italics); transmembrane and intracellular domains (bold)
*FTVTVPKDLYVVEYGSNMTIECKFPVEKQLDLAALIVYWEMEDKNIIQFVHGEEDLKVQHSSYRQRAR*
*LLKDQLSLGNAALQITDVKLQDAGVYRCMISYGGADYKRITVKVNAPYNKINQRILVVDPVTSEHELTC*
*QAEGYPKAEVIWTSSDHQVLSGKTTTTNSKREEKLFNVTSTLRINTTTNEIFYCTFRRLDPEENHTAEL*
*VIPELPLAHPPNER*THLVILGAILLCLGVALTFIFRLRKGRMMDVKKCGIQDTNSKKQSDTHLEET

Amino acid sequence of human PD-L1 extracellular domain (SEQ ID NO: 180)
FTVTVPKDLYVVEYGSNMTIECKFPVEKQLDLAALIVYWEMEDKNIIQFVHGEEDLKVQHSSYRQRAR
LLKDQLSLGNAALQITDVKLQDAGVYRCMISYGGADYKRITVKVNAPYNKINQRILVVDPVTSEHELTC
QAEGYPKAEVIWTSSDHQVLSGKTTTTNSKREEKLFNVTSTLRINTTTNEIFYCTFRRLDPEENHTAEL
VIPELPLAHPPNER -continued Amino acid sequence of mouse PD-L1 (SEQ ID NO: 181)
Extracellular domain (italics); transmembrane and intracellular domains (bold)
*FTITAPKDLYVVEYGSNVTMECRFPVERELDLLALVVYWEKEDEQVIQFVAGEEDLKPQHSNFRGRA*
*SLPKDQLLKGNAALQITDVKLQDAGVYCCIISYGGADYKRITLKVNAPYRKINQRISVDPATSEHELICQ*
*AEGYPEAEVIWTNSDHQPVSGKRSVTTSRTEGMLLNVTSSLRVNATANDVFYCTFWRSQPGQNHTA*
*ELIIPELPATHPPQNRTH*WVLLGSILLFLIVVSTVLLFLRKQVRMLDVEKCGVEDTSSKNRNDTQFEET

Amino acid sequence of mouse PD-L1 extracellular domain (SEQ ID NO: 182)
FTITAPKDLYVVEYGSNVTMECRFPVERELDLLALVVYWEKEDEQVIQFVAGEEDLKPQHSNFRGRA
SLPKDQLLKGNAALQITDVKLQDAGVYCCIISYGGADYKRITLKVNAPYRKINQRISVDPATSEHELICQ
AEGYPEAEVIWTNSDHQPVSGKRSVTTSRTEGMLLNVTSSLRVNATANDVFYCTFWRSQPGQNHTA
ELIIPELPATHPPQNRTH Amino acid sequence of cynomolgus PD-L1 (SEQ ID NO: 183)
Extracellular domain (italics); transmembrane and intracellular domains (bold)
*FTVTVPKDLYVVEYGSNMTIECKFPVEKQLDLTSLIVYWEMEDKNIIQFVHGEEDLKVQHSNYRQRAQ*
*LLKDQLSLGNAALRITDVKLQDAGVYRCMISYGGADYKRITVKVNAPYNKINQRILVVDPVTSEHELTC*
*QAEGYPKAEVIWTSSDHQVLSGKTTTTNSKREEKLLNVTSTLRINTTANEIFYCIFRRLDPEENHTAEL*
*VIPELPLALPPNERTH*LVILGAIFLLLGVALTFIFYLRKGRMMDMKKCGIRVTNSKKQRDTQLEETKG
PSARFDIPDEIPVIESKPNTLSIVLGTTLTVAMIIVATIFGYRRQKGRLRTLKL

Amino acid sequence of cynomolgus PD-L1 extracellular domain (SEQ ID NO: 184)
FTVTVPKDLYVVEYGSNMTIECKFPVEKQLDLTSLIVYWEMEDKVQHSNYRQRAQ
LLKDQLSLGNAALRITDVKLQDAGVYRCMISYGGADYKRITVKVNAPYNKINQRILVVDPVTSEHELTC
QAEGYPKAEVIWTSSDHQVLSGKTTTTNSKREEKLLNVTSTLRINTTANEIFYCIFRRLDPEENHTAEL
VIPELPLALPPNERTH Amino acid sequence of human CD137 (SEQ ID NO: 185)
Extracellular domain (italics); transmembrane and intracellular domains (bold)
*LQDPCSNCPAGTFCDNNRNQICSPCPPNSFSSAGGQRTCDICRQCKGVFRTRKECSSTSNAECDCT*
*PGFHCLGAGCSMCEQDCKQGQELTKKGCKDCCFGTFNDQKRGICRPWTNCSLDGKSVLVNGTKER*
*DVVCGPSPADLSPGASSVTPPAPAREPGHSPQ*IISFFLALTSTALLFLLFFLTLRFSVVKRGRKKLLYI
FKQPFMRPVQTTQEEDGCSCRFPEEEEGGCEL

Amino acid sequence of human CD137 extracellular domain (SEQ ID NO: 186)
LQDPCSNCPAGTFCDNNRNQICSPCPPNSFSSAGGQRTCDICRQCKGVFRTRKECSSTSNAECDCT
PGFHCLGAGCSMCEQDCKQGQELTKKGCKDCCFGTFNDQKRGICRPWTNCSLDGKSVLVNGTKER
DVVCGPSPADLSPGASSVTPPAPAREPGHSPQ Amino acid sequence of mouse CD137 (SEQ ID NO: 187)
Extracellular domain (italics); transmembrane and intracellular domains (bold)
*VQNSCDNCQPGTFCRKYNPVCKSCPPSTFSSIGGQPNCNICRVCAGYFRFKKFCSSTHNAECECIE*
*GFHCLGPQCTRCEKDCRPGQELTKQGCKTCSLGTFNDQNGTGVCRPWTNCSLDGRSVLKTGTTEK*
*DVVCGPPVVSFSPSTTISVTPEGGPGGHSLQVL*TLFLALTSALLLALIFITLLFSVLKWIRKKFPHIFKQ
PFKKTTGAAQEEDACSCRCPQEEEGGGGYEL

Amino acid sequence of mouse CD137 extracellular domain (SEQ ID NO: 188)
VQNSCDNCQPGTFCRKYNPVCKSCPPSTFSSIGGQPNCNICRVCAGYFRFKKFCSSTHNAECECIE
GFHCLGPQCTRCEKDCRPGQELTKQGCKTCSLGTFNDQNGTGVCRPWTNCSLDGRSVLKTGTTEK
DVVCGPPVVSFSPSTTISVTPEGGPGGHSLQVL Amino acid sequence of cynomolgus CD137 (SEQ ID NO: 189)
Extracellular domain (italics); transmembrane and intracellular domains (bold)
*LQDLCSNCPAGTFCDNNRSQICSPCPPNSFSSAGGQRTCDICRQCKGVFKTRKECSSTSNAECDCIS*
*GYHCLGAECSMCEQDCKQGQELTKKGCKDCCFGTFNDQKRGICRPWTNCSLDGKSVLVNGTKERD*
*VVCGPSPADLSPGASSATPPAPAREPGHSPQ*IIFFLALTSTVVLFLLFFLVLRFSVVKRSRKKLLYIFK
QPFMRPVQTTQEEDGCSCRFPEEEEGGCEL

Amino acid sequence of cynomolgus CD137 extracellular domain (SEQ ID NO: 190)
LQDLCSNCPAGTFCDNNRSQICSPCPPNSFSSAGGQRTCDICRQCKGVFKTRKECSSTSNAECDCIS
GYHCLGAECSMCEQDCKQGQELTKKGCKDCCFGTFNDQKRGICRPWTNCSLDGKSVLVNGTKERD
VVCGPSPADLSPGASSATPPAPAREPGHSPQ Amino acid sequence of the heavy chain of G1/HeID1.3 (SEQ ID NO: 191)
VH domain (italics)
QVQLQESGPGLVRPSQTLSLTCTVSGSTFSGYGVNWVRQPPGRGLEWIGMIWGDGNTDYNSALKS
RVTMLVDTSKNQFSLRLSSVTAADTAVYYCARERDYRLDYWGQGSLVTVSSASTKGPSVFPLAPSS
KSTSGGTAALGCLVKDYFPEPVTVSWNSGALTSGVHTFPAVLQSSGLYSLSSVVTVPSSSLGTQTYI
CNVNHKPSNTKVDKKVEPKSCDKTHTCPPCPAPELLGGPSVFLFPPKPKDTLMISRTPEVTCVVVDV
SHEDPEVKFNWYVDGVEVHNAKTKPREEQYNSTYRVVSVLTVLHQDWLNGKEYKCKVSNKALPAPI
EKTISKAKGQPREPQVYTLPPSRDELTKNQVSLTCLVKGFYPSDIAVEWESNGQPENNYKTTPPVLD
SDGSFFLYSKLTVDKSRWQQGNVFSCSVMHEALHNHYTQKSLSLSPG OVA peptide (SEQ ID NO: 192)
ISQAVHAAHAEINEAGR Amino acid sequence of Human B7-H3 extracellular domain (SEQ ID NO: 193)
ILEVQVPEDPVVALVGTDATLCCSFSPEPGFSLAQLNLIWQLTDTKQLVHSFAEGQDQGSAYANRTAL
FPDLLAQGNASLRLQRVRVADEGSFTCFVSIRDFGSAAVSLQVAAPYSKPSMTLEPNKDLRPGDTVTI
TCSSYQGYPEAEVFWQDGQGVPLTGNVTTSQMANEQGLFDVHSILRVVLGANGTYSCLVRNPVLQ -continued

```
QDAHSSVTITPQRSPTGAVEVQVPEDPVVALVGTDATLRCSFSPEPGFSLAQLNLIWQLTDTKQLVHS
FTEGRDQGSAYANRTALFPDLLAQGNASLRLQRVRVADEGSFTCFVSIRDFGSAAVSLQVAAPYSKP
SMTLEPNKDLRPGDTVTITCSSYRGYPEAEVFWQDGQGVPLTGNVTTSQMANEQGLFDVHSVLRVV
LGANGTYSCLVRNPVLQQDAHGSVTITGQPMT
```

SIINFEKL peptide (SEQ ID NO: 194)
SIINFEKL

Amino acid sequence of Human PD-L1-rCD4-His (SEQ ID NO: 195)
Signal peptide (underlined); Extracellular domain of PD-L1 (regular font); C-terminal rat CD4⁺
(domains 3 and 4) (italics); Junction between antigen and C-terminal fusion encoding a NotI restriction
site (bold and underlined); C-terminal hexahistidine tag (bold)

<u>MRIFAVFIFMTYWHLLNAFT</u>VTVPKDLYVVEYGSNMTIECKFPVEKQLDLAALIVYWEMEDKNIIQFVH
GEEDLKVQHSSYRQRARLLKDQLSLGNAALQITDVKLQDAGVYRCMISYGGADYKRITVKVNAPYNKI
NQRILVVDPVTSEHELTCQAEGYPKAEVIWTSSDHQVLSGKTTTTNSKREEKLFNVTSTLRINTTTNEI
FYCTFRRLDPEENHTAELVIPELPLAHPPNERT<u>AAA</u>*TSITAYKSEGESAEFSFPLNLGEESLQGELRW*
*KAEKAPSSQSWITFSLKNQKVSVQKSTSNPKFQ<u>LSE</u>TLPLTLQIPQVSLQFAGSGNLTLTLDRGILYQE*
*VNLVVMKVTQPDSNTLTCEVMGPTSPKMRLILKQENQEARVSRQEKVIQVQAPEAGVWQCLLSEGE*
*EVKMDSKIQVLSKGLN*GSHHHHHH

Amino acid sequence of Human PD-L1-Fc-His (SEQ ID NO: 196)
Signal peptide (underlined) Extracellular domain of PD-L1 (regular font) Human IgG1 Fc (italics)
Junction between antigen and C-terminal fusion encoding a NotI restriction site (bold and underlined)
C-terminal hexahistidine tag (bold)

<u>MRIFAVFIFMTYWHLLNAFT</u>VTVPKDLYVVEYGSNMTIECKFPVEKQLDLAALIVYWEMEDKNIIQFVH
GEEDLKVQHSSYRQRARLLKDQLSLGNAALQITDVKLQDAGVYRCMISYGGADYKRITVKVNAPYNKI
NQRILVVDPVTSEHELTCQAEGYPKAEVIWTSSDHQVLSGKTTTTNSKREEKLFNVTSTLRINTTTNEI
FYCTFRRLDPEENHTAELVIPELPLAHPPNERT<u>AAA</u>*DKTHTCPPCPAPELLGGPSVFLFPPKPKDTLMI*
*SRTPEVTCVVVDVSHEDPEVKFNWYVDGVEVHNA<u>KT</u>KPREEQYNSTYRVVSVLTVLHQDWLNGKE*
*YKCKVSNKALPAPIEKTISKAKGQPREPQVYTLPPSRDELTKNQVSLTCLVKGFYPSDIAVEWESNGQ*
*PENNYKTTPPVLDSDGSFFLYSKLTVDKSRWQQGNVFSCSVMHEALHNHYTQKSLSLSPGK*GSHHH
HHH

Amino acid sequence of Mouse PD-L1-rCD4-His (SEQ ID NO: 197)
Signal peptide (underlined); Extracellular domain of PD-L1 (regular font); C-terminal rat CD4⁺
(domains 3 and 4) (italics); Junction between antigen and C-terminal fusion encoding a NotI restriction
site (bold and underlined); C-terminal hexahistidine tag (bold)

<u>MRIFAGIIFTACCHLLRAFT</u>ITAPKDLYVVEYGSNVTMECRFPVERELDLLALVVYWEKEDEQVIQFVA
GEEDLKPQHSNFRGRASLPKDQLLKGNAALQITDVKLQDAGVYCCIISYGGADYKRITLKVNAPYRKIN
QRISVDPATSEHELICQAEGYPEAEVIWTNSDHQPVSGKRSVTTSRTEGMLLNVTSSLRVNATANDV
FYCTFWRSQPGQNHTAELIIPELPATHPPQNRT<u>AAA</u>*TSITAYKSEGESAEFSFPLNLGEESLQGELRW*
*KAEKAPSSQSWITFSLKNQKVSVQKSTSNPKFQ<u>LSE</u>TLPLTLQIPQVSLQFAGSGNLTLTLDRGILYQE*
*VNLVVMKVTQPDSNTLTCEVMGPTSPKMRLILKQENQEARVSRQEKVIQVQAPEAGVWQCLLSEGE*
*EVKMDSKIQVLSKGLN*GSHHHHHH

Amino acid sequence of Mouse PD-L1-Fc-His (SEQ ID NO: 198)
Signal peptide (underlined) Extracellular domain of PD-L1 (regular font) Human IgG1 Fc (italics)
Junction between antigen and C-terminal fusion encoding a NotI restriction site (bold and underlined)
C-terminal hexahistidine tag (bold)

<u>MRIFAGIIFTACCHLLRAFT</u>ITAPKDLYVVEYGSNVTMECRFPVERELDLLALVVYWEKEDEQVIQFVA
GEEDLKPQHSNFRGRASLPKDQLLKGNAALQITDVKLQDAGVYCCIISYGGADYKRITLKVNAPYRKIN
QRISVDPATSEHELICQAEGYPEAEVIWTNSDHQPVSGKRSVTTSRTEGMLLNVTSSLRVNATANDV
FYCTFWRSQPGQNHTAELIIPELPATHPPQNRT<u>AAA</u>*DKTHTCPPCPAPELLGGPSVFLFPPKPKDTL*
*MISRTPEVTCVVVDVSHEDPEVKFNWYVDGVEVH<u>NA</u>KTKPREEQYNSTYRVVSVLTVLHQDWLNGK*
*EYKCKVSNKALPAPIEKTISKAKGQPREPQVYTLPPSRDELTKNQVSLTCLVKGFYPSDIAVEWESNG*
*QPENNYKTTPPVLDSDGSFFLYSKLTVDKSRWQQGNVFSCSVMHEALHNHYTQKSLSLSPGK*GSHH
HHHH

Amino acid sequence of Human PD-L1-His-Avi (SEQ ID NO: 199)
Extracellular domain of PD-L1 (regular font) C-terminal hexahistidine tag (italics) Avi tag (bold)

FTVTVPKDLYVVEYGSNMTIECKFPVEKQLDLAALIVYWEMEDKNIIQFVHGEEDLKVQHSSYRQRAR
LLKDQLSLGNAALQITDVKLQDAGVYRCMISYGGADYKRITVKVNAPYNKINQRILVVDPVTSEHELTC
QAEGYPKAEVIWTSSDHQVLSGKTTTTNSKREEKLFNVTSTLRINTTTNEIFYCTFRRLDPEENHTAEL
VIPELPLAHPPNER*GSHHHHHH*GGGLNDIFEAQKIEWHE

Codon-optimised nucleic acid sequences encoding the FS22-172-003-AA/E12v2 heavy chain (SEQ
ID NO: 32)

```
AAGCTTGCCGCCACCATGGAATGGTCCTGGGTGTTCCTGTTCTTCCTGTCCGTGACCACCGGCG
TGCACTCTGAAGTTCAGCTGGTTCAGTCTGGCGCCGAAGTGAAAAGACCTGGCGCCTCTGTGAA
GGTGTCCTGCAAGGCTTCTGGCTACCCCTTTACCTCCTACGGCATCTCCTGGGTCCGACAGGCT
CCTGGACAAGGCTTGGAATGGATGGGCTGGATCTCCGCTTATTCCGGCGGCACCAATTACGCCC
AGAAACTGCAGGGCAGAGTGACCATGACCACCGACACCTCTACCTCCACCGCCTACATGGAACT
GCGGTCCCTGAGATCTGACGACACCGCCGTGTACTACTGCGCCAGAGATCTGTTCCCCACCATC
TTCGGCGTGTCCTACTACTACTATTGGGGCCAGGGCACCCTGGTCACCGTGTCCTCTGCTTCTA
CCAAGGGACCCAGCGTGTTCCCTCTGGCTCCTTCCAGCAAGTCTACCTCTGGCGGAACAGCTGC
TCTGGGCTGCCTGGTCAAGGACTACTTTCCTGAGCCTGTGACCGTGTCTTGGAACTCTGGCGCT
CTGACATCTGGCGTGCACACCTTTCCAGCTGTGCTGCAGTCCTCCGGCCTGTACTCTCTGTCCT
CTGTCGTGACCGTGCCTTCCAGCTCTCTGGGAACCCAGACCTACATCTGCAATGTGAACCACAA
GCCTTCCAACACCAAGGTGGACAAGAAGGTGGAACCCAAGTCCTGCGACAAGACCCACACCTGT
CCTCCATGTCCTGCTCCAGAAGCTGCTGGCGGCCCTTCCGTGTTTCTGTTCCCTCCAAAGCCTA
AGGACACCCTGATGATCTCTCGGACCCCTGAAGTGACCTGCGTGGTGGTGGATGTGTCTCACGA
```

```
                                                         -continued
GGACCCAGAAGTGAAGTTCAATTGGTACGTGGACGGCGTGGAAGTGCACAACGCCAAGACCAA
GCCTAGAGAGGAACAGTACAACTCCACCTACAGAGTGGTGTCCGTGCTGACCGTGCTGCACCAG
GATTGGCTGAACGGCAAAGAGTACAAGTGCAAGGTGTCCAACAAGGCCCTGCCTGCTCCTATCG
AAAAGACCATCTCCAAGGCCAAGGGCCAGCCTAGGGAACCCCAGGTTTACACCTTGCCTCCATC
TCGGGACGAGCTGCCCTACATCATCCCTCCATACAACCAGGTGTCCCTGACCTGCCTCGTGAAG
GGCTTCTACCCTTCCGATATCGCCGTGGAATGGGAGAGCAATGGCCAGCCTGAGAACAACTACA
AGACAACCCCTCCTGTGCTGGACTCCGACGGCTCATTCTTTCTGTACTCCAAGCTGACAGTGGG
CGCCGACAGATGGCTGGAAGGGAACGTGTTCTCCTGCAGCGTGATGCACGAGGCCCTGCACAA
TCACTACACACAGAAGTCCCTGTCTCTGTCCCCTGGCAAG TGATGAATTC Codon-optimised nucleic acid sequences encoding the FS22-172-003-AA/E12v2 light chain (SEQ ID
NO: 39)
AAGCTTGCCGCCACCATGTCTGTGCCTACACAGGTTCTGGGACTGCTGCTGCTGTGGCTGACCG
ACGCCAGATGCGACATCCAGATGACCCAGTCTCCATCCACACTGTCCGCCTCTGTGCGGGACAG
AGTGATCATCACCTGTAGAGCCAGCCAGTCCATCGGCAACAGACTGGCCTGGTATCAGCACAAG
CCTGGCAAGGCTCCCAAGCTGCTGATCTACGAGGCCTCCACATCTGAGACAGGCGTGCCCTCTA
GATTCTCCGGCTCTGGCTCTGGCACCGACTTTACCCTGACAATCTCCAGCCTGCAGCCTGAGGA
CTTCGCCACCTACTACTGCCAGCAGTCCTACAGCACCCCTTGGCCAGGGCACCAAG
CTGGAAATCAAGCGTACGGTGGCCGCTCCCAGCGTGTTCATCTTCCCCCCAAGCGACGAGCAG
CTGAAGAGCGGCACCGCCAGCGTGGTGTGTCTGCTGAACAACTTCTACCCCAGGGAGGCCAAG
GTGCAGTGGAAGGTGGACAACGCCCTGCAGAGCGGCAACAGCCAGGAGAGCGTCACCGAGCA
GGACAGCAAGGACTCCACCTACAGCCTGAGCAGCACCCTGACCCTGAGCAAGGCCGACTACGA
GAAGCACAAGGTGTACGCCTGTGAGGTGACCCACCAGGGCCTGTCCAGCCCCGTGACCAAGAG
CTTCAACAGGGGCGAGTGCTGATGAATTC
```

REFERENCES

All documents mentioned in this specification are incorporated herein by reference in their entirety.

Altschul S F, Gish W, Miller W, Myers E W, Lipman D J. Basic local alignment search tool. J. Mol. Biol. 215(3), 403-10 (1990).

Altschul S F, Madden T L, Schsffer A A, Zhang J, Zhang Z, Miller W, Lipman D J. Gapped BLAST and PSI-BLAST: a new generation of protein database search programs. Nucleic Acids Res. 25(17), 3389-402 (1997).

Bagshawe K D, Sharma S K, Springer C J, Antoniw P, Rogers G T, Burke P J, Melton R. Antibody-enzyme conjugates can generate cytotoxic drugs from inactive precursors at tumor sites. Antibody, Immunoconjugates and Radiopharmaceuticals 4, 915-922 (1991).

Baird J R et al. Immune-mediated regression of established B16F10 melanoma by intratumoral injection of attenuated Toxoplasma gondii protects against rechallenge. J Immunol. 190(1): 469-478 (2013).

Bartkowiak T, Curran M A. 4-1BB Agonists: Multi-Potent Potentiators of Tumor Immunity. Front Oncol. June 8; 5, 117 (2015).

Bartkowiak T et al. Activation of 4-1BB on Liver Myeloid Cells Triggers Hepatitis via an Interleukin-27-Dependent Pathway. Clin Cancer Res. 24(5), 1138-51 (2018).

Bergman I, Burckart G J, Pohl C R, Venkataramanan R, Barmada M A, Griffin J A And Cheung N V. Pharmacokinetics of IgG and IgM Anti-Ganglioside Antibodies in Rats and Monkeys After Intrathecal Administration. The Journal of Pharmacology and Experimental Therapeutics 284(1), 111-115 (1998)

Bitra A, Doukov T, Wang J, Picarda G, Benedict C A, Croft M, Zajonc D M. Crystal structure of murine 4-1BB and its interaction with 4-1 BBL support a role for galectin-9 in 4-1BB signaling. J Biol Chem. 293(4):1317-1329 (2017).

Brown M H, Barclay A N. Expression of immunoglobulin and scavenger receptor superfamily domains as chimeric proteins with domains 3 and 4 of CD4$^+$ for ligand analysis. Protein Eng. 7(4), 515-21 (1994).

Bruhns P, Iannascoli B, England P, Mancardi D A, Fernandez N, Jorieux S, Dasron M. Specificity and affinity of human Fcgamma receptors and their polymorphic variants for human IgG subclasses. Blood. 113(16):3716-25 (2009).

Chacon J A1, Wu R C, Sukhumalchandra P, Molldrem J J, Sarnaik A, Pilon-Thomas S, Weber J, Hwu P, Radvanyi L. Co-stimulation through 4-1BB/CD137 improves the expansion and function of CD8(+) melanoma tumor-infiltrating lymphocytes for adoptive T-cell therapy. PLoS One. 8(4):e60031 (2013).

Chapple S D, Crofts A M, Shadbolt S P, McCafferty J, Dyson M R. Multiplexed expression and screening for recombinant protein production in mammalian cells. BMC Biotechnol. 6:49 (2006).

Chester C, Ambulkar S, Kohrt H E. 4-1 BB agonism: adding the accelerator to cancer immunotherapy. Cancer Immunol Immunother. 65(10):1243-8 (2016).

Chester C, Sanmamed M F, Wang J, Melero I. Immunotherapy targeting 4-1BB: mechanistic rationale, clinical results, and future strategies. Blood. 131(1):49-57 (2018).

Claus C et al. A novel tumor-targeted 4-1BB agonist and its combination with T-cell bispecific antibodies: an off-the-shelf cancer immunotherapy alternative to CAR T-cells [abstract]. In: Proceedings of the American Association for Cancer Research Annual Meeting 2017. Cancer Res. 77 (2017).

Croft M. Co-stimulatory members of the TNFR family: keys to effective T-cell immunity? Nat Rev Immunol. 3(8):609-20 (2003).

Curran M A, Geiger T L, Montalvo W, Kim M, Reiner S L, Al-Shamkhani A, Sun J C, Allison J. P. Systemic 4-1 BB activation induces a novel T cell phenotype driven by high expression of Eomesodermin. J. Exp. Med. 210(4): 743-755 (2013).

Dubrot J et al. Treatment with anti-CD137 mAbs causes intense accumulations of liver T cells without selective antitumor immunotherapeutic effects in this organ. Cancer Immunol Immunother. 59(8):1223-1233 (2010).

Dyson M R, Zheng Y, Zhang C, Colwill K, Pershad K, Kay B K, Pawson T, McCafferty J: Mapping protein interactions by combining antibody affinity maturation and mass spectrometry. Anal. Biochem. 417(1), 25-35 (2011).

Fisher T S et al. Targeting of 4-1BB by monoclonal antibody PF-05082566 enhances T-cell function and promotes anti-tumor activity. Cancer Immunol Immunother. 61(10): 1721-33 (2012).

Grosso J, Inzunza D, Wu Q, Simon J, Singh P, Zhang X, Phillips T, Simmons P, Cogswell J. Programmed death-ligand 1 (PD-L1) expression in various tumor types. Journal for Immunotherapy of Cancer. 1(Suppl 1):P53. (2013).

Hasenhindl C, Traxlmayr M W, Wozniak-Knopp G, Jones P C, Stadlmayr G, Raker F, Obinger C. Stability assessment on a library scale: a rapid method for the evaluation of the commutability and insertion of residues in C-terminal loops of the CH3 domains of IgG1-Fc. Protein Eng. Des. Sel., 26(10), 675-82 (2013).

Hezareh M, Hessell A J, Jensen R C, van de Winkel J G, Parren P W. Effector function activities of a panel of mutants of a broadly neutralizing antibody against human immunodeficiency virus type 1. J Virol. 75(24):12161-8. (2001).

Hinner M J, Aiba, RSB., Wiedenmann A, Schlosser C, Allersdorfer A, Matschiner G, Rothe C, Moebius U, Kohrt H E, Olwill S A. Costimulatory T cell engagement via a novel bispecific anti-CD137/anti-HER2 protein. J. Immunotherapy Cancer 3 (Suppl 2): P187. (2015).

Holliger P, Hudson P J. Engineered antibody fragments and the rise of single domains. Nat Biotechnol. 23(9):1126-36 (2005).

Hu S, Shively L, Raubitschek A, Sherman M, Williams L E, Wong J Y, Shively J E, Wu A M. Minibody: A novel engineered anti-carcinoembryonic antigen antibody fragment (single-chain Fv-C H3) which exhibits rapid, high-level targeting of xenografts. Cancer Res. 56(13):3055-61 (1996).

Hurtado J C, Kim Y J, Kwon B S. Signals through 4-1BB are costimulatory to previously activated splenic T cells and inhibit activation-induced cell death. J Immunol. 15; 158(6):2600-9 (1997).

Idusogie E E, Presta L G, Gazzano-Santoro H, Totpal K, Wong P Y, Ultsch M, Meng Y G, Mulkerrin M G. Mapping of the C1q binding site on rituxan, a chimeric antibody with a human IgG1 Fc. J Immunol. 164(8), 4178-84 (2000).

Jain T et al. Biophysical properties of the clinical-stage antibody landscape. PNAS 114 (5), 944-949 (2017).

Jefferis R, Reimer C B, Skvaril F, de Lange G, Ling N R, Lowe J, Walker M R, Phillips D J, Aloisio C H, Wells T W. Evaluation of monoclonal antibodies having specificity for human IgG sub-classes: results of an IUIS/WHO collaborative study. Immunol. Lett. 1, 223-52 (1985).

Jefferis R, Reimer C B, Skvaril F, de Lange G G, Goodall D M, Bentley T L, Phillips D J, Vlug A, Harada S, Radl J. Evaluation of monoclonal antibodies having specificity for human IgG subclasses: results of the 2nd IUIS/WHO collaborative study. Immunol. Lett. 31(2), 143-68 (1992).

Juneja V R, McGuire K A, Manguso R T, LaFleur M W, Collins N, Haining W N, Freeman G J, Sharpe A H. PD-L1 on tumor cells is sufficient for immune evasion in immunogenic tumors and inhibits CD8$^+$ T cell cytotoxicity. J Exp Med. 214(4), 895-904 (2017).

Kabat E A, Wu T T, Perry H M, Gottesman K S, Foeller C. Sequences of Proteins of Immunological Interest, 5th ed. NIH Publication No. 91-3242. Washington, D.C.: U.S. Department of Health and Human Services (1991).

Kim Y H, Choi B K, Kim K H, Kang S W, Kwon B S. Combination Therapy with Cisplatin and Anti-4-1 BB. Cancer Res. 68(18), 7264-7269 (2009).

Klein C, Schaefer W, Regula J T. The use of CrossMAb technology for the generation of bi- and multispecific antibodies. MAbs 8(6), 1010-20 (2016).

Kleinovink J W, Marijt K A, Schoonderwoerd M J A, Hall T, Ossendorp F, Fransen M F. PD-L1 expression on malignant cells is no prerequisite for checkpoint therapy. Oncoimmunology. 6(4), e1294299 (2017).

Kocak E et al. Combination therapy with anti-CTL antigen-4 and anti-4-1BB antibodies enhances cancer immunity and reduces autoimmunity. Cancer Res. 15; 66(14), 7276-84 (2006).

Lechner M G et al. Immunogenicity of murine solid tumor models as a defining feature of in vivo behavior and response to immunotherapy. J Immunother. 36(9), 477-89 (2013).

Ledermann J A, Begent R H, Massof C, Kelly A M, Adam T, Bagshawe $K_D$. A phase-I study of repeated therapy with radiolabelled antibody to carcinoembryonic antigen using intermittent or continuous administration of cyclosporin A to supress the immune response. Int. J. Cancer 47(5), 659-64 (1991).

Lefranc M P et al. IMGTO, the international ImMunoGeneTics information System® 25 years on. Nucleic Acids Res. 43(Database issue):D413-22 (2015).

Lefranc M P et al. IMGT unique numbering for immunoglobulin and T cell receptor constant domains and Ig superfamily C-like domains. Dev. Comp. Immunol. 29(3), 185-203 (2005).

Li F. and Ravetech J V. Antitumor activities of agonistic anti-TNFR antibodies require differential FcγRIIB coengagement in vivo. Proc Natl Acad Sci USA, 110(48), 19501-6 (2013).

Link A et al. Preclinical pharmacology of MPO310: a 4-1BB/FAP bispecific DARPin drug candidate promoting tumor-restricted T cell co-stimulation [abstract]. In: Proceedings of the Annual Meeting of the American Association for Cancer Research; 2018 Apr. 14-18; Chicago (Ill.) Abstract nr 3752 (2018).

Makkouk A, Chester C, Kohrt H E. Rationale for anti-CD137 cancer immunotherapy. Eur J Cancer. 54, 112-119 (2016).

Martins J P, Kennedy P J, Santos H A, Barrias C, Sarmento B. A comprehensive review of the neonatal Fc receptor and its application in drug delivery. Pharmcol. Ther. 161, 22-39 (2016).

Niu L et al. Cytokine-mediated disruption of lymphocyte trafficking, hemopoiesis, and induction of lymphopenia, anemia, and thrombocytopenia in anti-CD137-treated mice. J Immunol. 178(7), 4194-4213 (2007).

Pérez-Ruiz E, Etxeberria I, Rodriguez-Ruiz, Melero I. Anti-CD137 and PD-1/PD-L1 Antibodies En Route toward Clinical Synergy. Clin. Cancer Res. 23, (18) (2017)

Reichen C et al. FAP-mediated tumor accumulation of a T-cell agonistic FAP/4-1 BB DARPin drug candidate analyzed by SPECT/CT and quantitative biodistribution [abstract]. In: Proceedings of the Annual Meeting of the American Association for Cancer Research; 2018 Apr. 14-18; Chicago (Ill.) Abstract nr 3029 (2018).

Schofield D J et al. Application of phage display to high throughput antibody generation and characterization. Genome Biol. 8(11), R254 (2007).

Segal N H et al. Phase I Study of Single-Agent Utomilumab (PF-05082566), a 4-1BB/CD137 Agonist, in Patients with Advanced Cancer. Clin Cancer Res. 24(8):1816-1823 (2018).

Segal N H et al. Results from an Integrated Safety Analysis of Urelumab, an Agonist Anti-CD137 Monoclonal Antibody. Clin Cancer Res. 23(8):1929-1936 (2017).

Shuford W W et al. 4-1BB costimulatory signals preferentially induce CD8$^+$ T cell proliferation and lead to the amplification in vivo of cytotoxic T cell responses. J Exp Med. 186(1), 47-55 (1997).

Smith T F, Waterman M S. Identification of common molecular subsequences. J. Mol. Biol. 147(1), 195-7 (1981).

Taraban V Y et al. Expression and costimulatory effects of the TNF receptor superfamily members CD134 (OX40) and CD137 (4-1BB), and their role in the generation of anti-tumor immune responses. Eur. J. Immunol. 32, 3617-3627 (2002).

Tello, D, Goldbaum, FA, Mariuzza, RA, Ysern, X, Schwarz, FP, Poljak, RJ. Three-dimensional structure and thermodynamics of antigen binding by anti-lysozyme antibodies, Biochem Soc. Trans., 21(4), 943-6 (1993).

Tolcher A W et al. Phase 1b Study of Utomilumab (PF-05082566), a 4-1 BB/CD137 Agonist, in Combination with Pembrolizumab (MK-3475) in Patients with Advanced Solid Tumors. Clin. Cancer Res. 23, 5349-57 (2017)

Wang X, Mathieu M, Brezski R J. IgG Fc engineering to modulate antibody effector functions. Protein Cell 9(1), 63-73 (2018).

Wen T, Bukczynski J, Watts T H. 4-1 BB ligand-mediated costimulation of human T cells induces CD4+ and CD8+ T cell expansion, cytokine production, and the development of cytolytic effector function. J Immunol. 168(10), 4897-906 (2002).

Wolfl M, Kuball J, Ho W Y, Nguyen H, Manley T J, Bleakley M, Greenberg P D. Activation-induced expression of CD137 permits detection, isolation, and expansion of the full repertoire of CD8+ T cells responding to antigen without requiring knowledge of epitope specificities. Blood. 110(1):201-10 (2007).

Won E Y, Cha K, Byun J S, Kim D U, Shin S, Ahn B, Kim Y H, Rice A J, Walz T, Kwon B S, Cho H S. The structure of the trimer of human 4-1BB ligand is unique among members of the tumor necrosis factor superfamily. J Biol Chem. 285(12), 9202-10 (2010).

Wozniak-Knopp G et al. Introducing antigen-binding sites in structural loops of immunoglobulin constant domains: Fc fragments with engineered HER2/neu-binding sites and antibody properties. Protein Eng Des Sel. 23(4), 289-97 (2010).

Ye Q, Song D G, Poussin M, Yamamoto T, Best A, Li C, Coukos G, Powell D J Jr. CD137 accurately identifies and enriches for naturally occurring tumor-reactive T cells in tumor. Clin Cancer Res. 20(1):44-55 (2014).

Yu X, Anasetti C. CH 10—T-cell costimulation in graft-versus-host disease and graft-versus-leukemia effect. Immune Biology of Allogeneic Hematopoietic Stem Cell Transplantation. 195-222 (2013).

Zanetti M. Tapping C D4 T Cells for Cancer Immunotherapy: The Choice of Personalized Genomics. J Immunol. 194:2049-2056 (2015).

The invention claimed is:

1. An antibody molecule that binds to programmed death-ligand 1 (PD-L1) and CD137, comprising:
   (a) a complementarity determining region (CDR)-based antigen-binding site for PD-L1; and
   (b) a CD137 antigen-binding site located in a CH3 domain of the antibody molecule;
   wherein the CDR-based antigen-binding site comprises the VH CDR1, VH CDR2, VH CDR3, VL CDR1, VL CDR2 and VL CDR3, defined according to the Kabat numbering scheme, set forth in:
   (i) SEQ ID NOs: 1, 2, 3, 4, 5 and 6, respectively;
   (ii) SEQ ID NOS: 1, 2, 3, 18, 19 and 20, respectively; or
   (iii) SEQ ID NOs: 1, 2, 3, 18, 19 and 29, respectively; and/or
   wherein the CDR-based antigen-binding site comprises the VH CDR1, VH CDR2, VH CDR3, VL CDR1, VL CDR2 and VL CDR3, defined according to the ImMunoGeneTics (IMGT) numbering scheme, set forth in:
   (iv) SEQ ID NOs: 7, 8, 9, 10, 11 and 6, respectively;
   (v) SEQ ID NOs: 21, 8, 9, 22, 11 and 20, respectively; or
   (vi) SEQ ID NOs: 21, 8, 9, 22, 11 and 29, respectively; and
   wherein the CD137 antigen-binding site comprises a first sequence and a second sequence located in the AB structural loop and the EF structural loop of the CH3 domain, respectively, wherein the first sequence and the second sequence are set forth in SEQ ID NOs: 113 and 114, SEQ ID NOs: 79 and 80, or SEQ ID NOs: 79 and 89, respectively.

2. The antibody molecule according to claim 1, wherein the antibody molecule comprises the VH domain and the VL domain set forth in:
   (i) SEQ ID NOs: 12 and 14, respectively;
   (ii) SEQ ID NOs: 23 and 25, respectively; or
   (iii) SEQ ID NOS: 23 and 30, respectively.

3. The antibody molecule according to claim 1, wherein the antibody molecule comprises:
   (i) the VH CDR1, VH CDR2, VH CDR2, VL CDR1, VL CDR2 and VL CDR3, defined according to the Kabat numbering scheme, set forth in SEQ ID NOs: 1, 2, 3, 4, 5 and 6, respectively;
   (ii) the VH CDR1, VH CDR2, VH CDR3, VL CDR1, VL CDR2 and VL CDR3, defined according to the IMGT numbering scheme, set forth in SEQ ID NOs: 7, 8, 9, 10, 11 and 6, respectively; and/or
   (iii) the VH domain and VL domain set forth in SEQ ID NOs: 12 and 14, respectively.

4. The antibody molecule according to claim 1, wherein
   (i) the first sequence is located between positions 14 and 17 of the CH3 domain of the antibody molecule; and/or
   (ii) wherein the second sequence is located between positions 91 and 99 of the CH3 domain of the antibody molecule; and
   wherein the amino acid residue numbering is according to the IMGT numbering scheme.

5. The antibody molecule according to claim 1, wherein the antibody molecule comprises the CH3 domain set forth in SEQ ID NO: 115, 81, or 90.

6. The antibody molecule according to claim 1, wherein the antibody molecule comprises the heavy chain and light chain set forth in:
   (i) SEQ ID NOs: 134 and 17, respectively;
   (ii) SEQ ID NOs: 137 and 28, respectively;
   (iii) SEQ ID NOs: 140 and 33, respectively;
   (iv) SEQ ID NOs: 143 and 17, respectively;
   (v) SEQ ID NOs: 146 and 28, respectively;
   (vi) SEQ ID NOs: 149 and 33, respectively;
   (vii) SEQ ID NOs: 152 and 17, respectively;
   (viii) SEQ ID NOs: 153 and 28, respectively;
   (ix) SEQ ID NOs: 154 and 33, respectively.

7. The antibody molecule according to claim 6, wherein the antibody molecule comprises the heavy chain and light chain set forth in SEQ ID NOs: 134 and 17, respectively.

8. The antibody molecule according to claim 1, wherein the antibody molecule comprises a CH2 domain, and wherein the antibody molecule has been modified to reduce or abrogate binding of the CH2 domain to one or more Fcγ receptors.

9. The antibody molecule according to claim 1, wherein the antibody molecule does not bind to one or more Fcγ receptors.

10. The antibody molecule according to claim 1, wherein binding of the antibody molecule to CD137 on an immune cell and to tumour cell-surface bound PD-L1 causes clustering of CD137 on the immune cell.

11. A nucleic acid molecule or molecules encoding the antibody molecule according to claim 1.

12. A vector or vectors comprising the nucleic acid molecule or molecules according to claim 11.

13. A recombinant host cell comprising the nucleic acid molecule(s) according to claim 11, or a vector(s) comprising the nucleic acid molecule(s) according to claim 11.

14. A method of producing the antibody molecule comprising culturing the recombinant host cell of claim 13 under conditions for production of the antibody molecule.

15. The method according to claim 14 further comprising isolating and/or purifying the antibody molecule.

16. A pharmaceutical composition comprising the antibody molecule according to claim 1 and a pharmaceutically acceptable excipient.

17. A method of treating cancer in an individual comprising administering to the individual a therapeutically effective amount of the antibody molecule according to claim 1.

18. The method according to claim 17, wherein the cancer is selected from the list consisting of: melanoma, bladder cancer, brain cancer, breast cancer, ovarian cancer, lung cancer, colorectal cancer, cervical cancer, liver cancer, head and neck cancer, pancreatic cancer, renal cancer, stomach cancer and Gastrointestinal Stromal Tumours (GISTs).

19. The method according to claim 17, wherein the method further comprises administering a therapeutically effective amount of a second therapeutic to the individual.

20. The antibody molecule according to claim 5, wherein the CH3 domain of the antibody molecule comprises a lysine residue (K) adjoined to the C-terminus of the CH3 domain sequence set forth in SEQ ID NOs: 115, 81, or 90.

21. The antibody molecule according to claim 6, wherein the CH3 domain of the antibody molecule comprises a lysine residue (K) adjoined to the C-terminus of the heavy chain sequence set forth in SEQ ID NOs: 134, 137, 140, 143, 146, 149, 152, 153, or 154.

22. The antibody molecule according to claim 7, wherein the CH3 domain of the antibody molecule comprises a lysine residue (K) adjoined to the C-terminus of the heavy chain sequence set forth in SEQ ID NO: 134.

23. The antibody molecule according to claim 1, wherein the first sequence and the second sequence located in the AB structural loop and the EF structural loop of the CH3 domain, respectively, are set forth in SEQ ID NOs: 113 and 114, respectively, or wherein the antibody molecule comprises the CH3 domain set forth in SEQ ID NO: 115.

24. The antibody molecule according to claim 1, wherein the first sequence and the second sequence located in the AB structural loop and the EF structural loop of the CH3 domain, respectively, are set forth in SEQ ID NOs: 79 and 80, respectively, or wherein the antibody molecule comprises the CH3 domain set forth in SEQ ID NO: 81.

25. The antibody molecule according to claim 1, wherein the first sequence and the second sequence located in the AB structural loop and the EF structural loop of the CH3 domain, respectively, are set forth in SEQ ID NOs: 79 and 89, respectively, or wherein the antibody molecule comprises the CH3 domain set forth in SEQ ID NO: 90.

* * * * *

```
                        SEQUENCE LISTING

<160> NUMBER OF SEQ ID NOS: 199

<210> SEQ ID NO 1
<211> LENGTH: 5
<212> TYPE: PRT
<213> ORGANISM: Artificial Sequence
<220> FEATURE:
<223> OTHER INFORMATION: E12v2 mAb (Kabat) VH CDR1

<400> SEQUENCE: 1

Ser Tyr Gly Ile Ser
1               5

<210> SEQ ID NO 2
<211> LENGTH: 17
<212> TYPE: PRT
<213> ORGANISM: Artificial Sequence
<220> FEATURE:
<223> OTHER INFORMATION: E12v2 mAb (Kabat) VH CDR2

<400> SEQUENCE: 2

Trp Ile Ser Ala Tyr Ser Gly Gly Thr Asn Tyr Ala Gln Lys Leu Gln
1               5                   10                  15

Gly

<210> SEQ ID NO 3
<211> LENGTH: 14
<212> TYPE: PRT
<213> ORGANISM: Artificial Sequence
<220> FEATURE:
<223> OTHER INFORMATION: E12v2 mAb (Kabat) VH CDR3

<400> SEQUENCE: 3

Asp Leu Phe Pro Thr Ile Phe Gly Val Ser Tyr Tyr Tyr Tyr
1               5                   10

<210> SEQ ID NO 4
```

```
<211> LENGTH: 11
<212> TYPE: PRT
<213> ORGANISM: Artificial Sequence
<220> FEATURE:
<223> OTHER INFORMATION: E12v2 mAb (Kabat) VL CDR1

<400> SEQUENCE: 4

Arg Ala Ser Gln Ser Ile Gly Asn Arg Leu Ala
1               5                   10

<210> SEQ ID NO 5
<211> LENGTH: 7
<212> TYPE: PRT
<213> ORGANISM: Artificial Sequence
<220> FEATURE:
<223> OTHER INFORMATION: E12v2 mAb (Kabat) VL CDR2

<400> SEQUENCE: 5

Glu Ala Ser Thr Ser Glu Thr
1               5

<210> SEQ ID NO 6
<211> LENGTH: 9
<212> TYPE: PRT
<213> ORGANISM: Artificial Sequence
<220> FEATURE:
<223> OTHER INFORMATION: E12v2 mAb (Kabat) VL CDR3

<400> SEQUENCE: 6

Gln Gln Ser Tyr Ser Thr Pro Tyr Thr
1               5

<210> SEQ ID NO 7
<211> LENGTH: 8
<212> TYPE: PRT
<213> ORGANISM: Artificial Sequence
<220> FEATURE:
<223> OTHER INFORMATION: E12v2 (IMGT) VH CDR1

<400> SEQUENCE: 7

Gly Tyr Pro Phe Thr Ser Tyr Gly
1               5

<210> SEQ ID NO 8
<211> LENGTH: 8
<212> TYPE: PRT
<213> ORGANISM: Artificial Sequence
<220> FEATURE:
<223> OTHER INFORMATION: E12v2 (IMGT) VH CDR2

<400> SEQUENCE: 8

Ile Ser Ala Tyr Ser Gly Gly Thr
1               5

<210> SEQ ID NO 9
<211> LENGTH: 16
<212> TYPE: PRT
<213> ORGANISM: Artificial Sequence
<220> FEATURE:
<223> OTHER INFORMATION: E12v2 (IMGT) VH CDR3

<400> SEQUENCE: 9

Ala Arg Asp Leu Phe Pro Thr Ile Phe Gly Val Ser Tyr Tyr Tyr Tyr
1               5                   10                  15

<210> SEQ ID NO 10
<211> LENGTH: 6
```

```
<212> TYPE: PRT
<213> ORGANISM: Artificial Sequence
<220> FEATURE:
<223> OTHER INFORMATION: E12v2 (IMGT) VL CDR1

<400> SEQUENCE: 10

Gln Ser Ile Gly Asn Arg
1               5

<210> SEQ ID NO 11
<211> LENGTH: 3
<212> TYPE: PRT
<213> ORGANISM: Artificial Sequence
<220> FEATURE:
<223> OTHER INFORMATION: E12v2 (IMGT) VL CDR2

<400> SEQUENCE: 11

Glu Ala Ser
1

<210> SEQ ID NO 12
<211> LENGTH: 123
<212> TYPE: PRT
<213> ORGANISM: Artificial Sequence
<220> FEATURE:
<223> OTHER INFORMATION: E12v2 mAb

<400> SEQUENCE: 12

Glu Val Gln Leu Val Gln Ser Gly Ala Glu Val Lys Arg Pro Gly Ala
1               5                   10                  15

Ser Val Lys Val Ser Cys Lys Ala Ser Gly Tyr Pro Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Ser Gly Gly Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Leu Phe Pro Thr Ile Phe Gly Val Ser Tyr Tyr Tyr Tyr
            100                 105                 110

Trp Gly Gln Gly Thr Leu Val Thr Val Ser Ser
        115                 120

<210> SEQ ID NO 13
<211> LENGTH: 369
<212> TYPE: DNA
<213> ORGANISM: Artificial Sequence
<220> FEATURE:
<223> OTHER INFORMATION: E12v2 mAb

<400> SEQUENCE: 13
gaagtgcagc tggtgcagtc cggagccgaa gtcaagaggc ctggagcgtc cgtgaaggtg     60
tcctgcaaag cctcaggata ccccttcact tcgtacggga tttcctgggt ccgccaagca    120
ccgggtcaag gcttggagtg gatgggatgg atcagcgcgt attccggggg aaccaactac    180
gctcaaaagc tgcagggtcg cgtgaccatg accaccgata cctccacctc aacggcctac    240
atggaactga gatctctgcg gagcgacgac actgccgtgt actactgtgc ccgggacctg    300
ttccccacta tcttcggagt gtcgtactac tactactggg gccaggggac tctcgtgacc    360
```

```
gtgtcgagc                                                              369
```

<210> SEQ ID NO 14
<211> LENGTH: 107
<212> TYPE: PRT
<213> ORGANISM: Artificial Sequence
<220> FEATURE:
<223> OTHER INFORMATION: E12v2 mAb  VL domain

<400> SEQUENCE: 14

Asp Ile Gln Met Thr Gln Ser Pro Ser Thr Leu Ser Ala Ser Val Arg
1               5                   10                  15

Asp Arg Val Ile Ile Thr Cys Arg Ala Ser Gln Ser Ile Gly Asn Arg
            20                  25                  30

Leu Ala Trp Tyr Gln His Lys Pro Gly Lys Ala Pro Lys Leu Leu Ile
        35                  40                  45

Tyr Glu Ala Ser Thr Ser Glu Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Tyr
                85                  90                  95

Thr Phe Gly Gln Gly Thr Lys Leu Glu Ile Lys
            100                 105

<210> SEQ ID NO 15
<211> LENGTH: 321
<212> TYPE: DNA
<213> ORGANISM: Artificial Sequence
<220> FEATURE:
<223> OTHER INFORMATION: E12v2 mAb  VL domain

<400> SEQUENCE: 15

```
gacatccaga tgacgcagag cccgtctacc ctgtccgcct ccgtgagaga tcgcgtgatc     60
atcacctgtc gggccagcca gtccatcgga aaccgcttgg cgtggtacca gcacaagcct    120
gggaaggctc cgaagctgct catctacgaa gcctcgactt cggagactgg tgtccctagc    180
cggttcagcg gatcgggatc aggaccgat ttcactctga ccatttcctc cctgcaaccc     240
gaggacttcg ccacctacta ctgccaacag tcatattcca ccccgtacac cttcggacaa    300
ggcaccaagc tcgaaatcaa g                                              321
```

<210> SEQ ID NO 16
<211> LENGTH: 452
<212> TYPE: PRT
<213> ORGANISM: Artificial Sequence
<220> FEATURE:
<223> OTHER INFORMATION: G1-AA/E12v2 mAb (with LALA) heavy chain

<400> SEQUENCE: 16

Glu Val Gln Leu Val Gln Ser Gly Ala Glu Val Lys Arg Pro Gly Ala
1               5                   10                  15

Ser Val Lys Val Ser Cys Lys Ala Ser Gly Tyr Pro Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Ser Gly Gly Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

```
Met Glu Leu Arg Ser Leu Arg Ser Asp Asp Thr Ala Val Tyr Tyr Cys
                85                  90                  95

Ala Arg Asp Leu Phe Pro Thr Ile Phe Gly Val Ser Tyr Tyr Tyr Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Ala
225                 230                 235                 240

Ala Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
        355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly
    450

<210> SEQ ID NO 17
<211> LENGTH: 214
<212> TYPE: PRT
<213> ORGANISM: Artificial Sequence
<220> FEATURE:
```

<223> OTHER INFORMATION: G1-AA/E12v2 mAb light chain

<400> SEQUENCE: 17

Asp Ile Gln Met Thr Gln Ser Pro Ser Thr Leu Ser Ala Ser Val Arg
1               5                   10                  15

Asp Arg Val Ile Ile Thr Cys Arg Ala Ser Gln Ser Ile Gly Asn Arg
            20                  25                  30

Leu Ala Trp Tyr Gln His Lys Pro Gly Lys Ala Pro Lys Leu Leu Ile
        35                  40                  45

Tyr Glu Ala Ser Thr Ser Glu Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 18
<211> LENGTH: 11
<212> TYPE: PRT
<213> ORGANISM: Artificial Sequence
<220> FEATURE:
<223> OTHER INFORMATION: E05v2 mAb (Kabat) VL CDR1

<400> SEQUENCE: 18

Arg Ala Ser Gln Ser Ile Ser Gly Arg Leu Ala
1               5                   10

<210> SEQ ID NO 19
<211> LENGTH: 7
<212> TYPE: PRT
<213> ORGANISM: Artificial Sequence
<220> FEATURE:
<223> OTHER INFORMATION: E05v2 mAb (Kabat) VL CDR2

<400> SEQUENCE: 19

Glu Ala Ser Asn Leu Glu Ser
1               5

<210> SEQ ID NO 20
<211> LENGTH: 10
<212> TYPE: PRT
<213> ORGANISM: Artificial Sequence
<220> FEATURE:
<223> OTHER INFORMATION: E05v2 mAb (Kabat) VL CDR3

<400> SEQUENCE: 20

Gln Gln Ser Tyr Ser Thr Pro Arg Val Thr
1               5                   10

<210> SEQ ID NO 21
<211> LENGTH: 8
<212> TYPE: PRT
<213> ORGANISM: Artificial Sequence
<220> FEATURE:
<223> OTHER INFORMATION: E05v2 VH CDR1

<400> SEQUENCE: 21

Gly Tyr Thr Phe Thr Ser Tyr Gly
1               5

<210> SEQ ID NO 22
<211> LENGTH: 6
<212> TYPE: PRT
<213> ORGANISM: Artificial Sequence
<220> FEATURE:
<223> OTHER INFORMATION: E05v2 VL CDR1

<400> SEQUENCE: 22

Gln Ser Ile Ser Gly Arg
1               5

<210> SEQ ID NO 23
<211> LENGTH: 123
<212> TYPE: PRT
<213> ORGANISM: Artificial Sequence
<220> FEATURE:
<223> OTHER INFORMATION: E05v2 mAb VH domain

<400> SEQUENCE: 23

Glu Val Gln Leu Val Gln Ser Gly Ala Glu Val Lys Arg Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Ser Gly Gly Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Leu Phe Pro Thr Ile Phe Gly Val Ser Tyr Tyr Tyr Tyr
            100                 105                 110

Trp Gly Gln Gly Thr Leu Val Thr Val Ser Ser
        115                 120

<210> SEQ ID NO 24
<211> LENGTH: 369
<212> TYPE: DNA
<213> ORGANISM: Artificial Sequence
<220> FEATURE:
<223> OTHER INFORMATION: E05v2 mAb VH domain

<400> SEQUENCE: 24
gaagtgcagc tggtgcagtc cggagccgaa gtcaagaggc ctggagcgtc cgtgaaggtg      60
tcctgcaaag cctcaggata caccttcact tcgtacggga tttcctgggt ccgccaagca     120

```
ccgggtcaag gcttggagtg gatgggatgg atcagcgcgt attccggggg aaccaactac    180
gctcaaaagc tgcagggtcg cgtgaccatg accaccgata cctccacctc aacggcctac    240
atggaactga gatctctgcg gagcgacgac actgccgtgt actactgtgc ccgggacctg    300
ttccccacta tcttcggagt gtcgtactac tactactggg gccagggggac tctcgtgacc    360 gtgtcgagc                                                             369
```

```
<210> SEQ ID NO 25
<211> LENGTH: 108
<212> TYPE: PRT
<213> ORGANISM: Artificial Sequence
<220> FEATURE:
<223> OTHER INFORMATION: E05v2 mAb VL domain

<400> SEQUENCE: 25

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Gly Arg
            20                  25                  30

Leu Ala Trp Tyr Gln Gln Lys Pro Gly Lys Ala Pro Asn Leu Leu Ile
        35                  40                  45

Tyr Glu Ala Ser Asn Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Arg
                85                  90                  95

Val Thr Phe Gly Gln Gly Thr Lys Val Glu Ile Lys
            100                 105
```

```
<210> SEQ ID NO 26
<211> LENGTH: 324
<212> TYPE: DNA
<213> ORGANISM: Artificial Sequence
<220> FEATURE:
<223> OTHER INFORMATION: E05v2 mAb VL domain

<400> SEQUENCE: 26
gacattcaga tgacccaatc cccgtccacg ctgagcgcct ccgtcggtga tcgcgtgaca     60
atcacttgtc gggcgtcgca gtccatctct ggaaggctcg cctggtacca gcagaagcct    120
ggaaaggctc ccaacctcct tatctacgaa gccagcaacc tggagtccgg agtgcctagc    180
cggttcagcg gatcagggtc cggtaccgag ttcaccctga ccatttcctc gctccaacct    240
gaggacttcg ccacctacta ctgccaacag tcctattcaa ctccgcgcgt gaccttcggc    300
cagggcacta aggtcgaaat caaa                                            324
```

```
<210> SEQ ID NO 27
<211> LENGTH: 452
<212> TYPE: PRT
<213> ORGANISM: Artificial Sequence
<220> FEATURE:
<223> OTHER INFORMATION: Heavy chain amino acid sequence of G1-AA/E05v2
      mAb

<400> SEQUENCE: 27

Glu Val Gln Leu Val Gln Ser Gly Ala Glu Val Lys Arg Pro Gly Ala
1               5                   10                  15

Ser Val Lys Val Ser Cys Lys Ala Ser Gly Tyr Thr Phe Thr Ser Tyr
```

-continued

```
                 20                  25                  30
Gly Ile Ser Trp Val Arg Gln Ala Pro Gly Gln Gly Leu Glu Trp Met
             35                  40                  45
Gly Trp Ile Ser Ala Tyr Ser Gly Gly Thr Asn Tyr Ala Gln Lys Leu
         50                  55                  60
Gln Gly Arg Val Thr Met Thr Thr Asp Thr Ser Thr Ser Thr Ala Tyr
 65                  70                  75                  80
Met Glu Leu Arg Ser Leu Arg Ser Asp Asp Thr Ala Val Tyr Tyr Cys
                 85                  90                  95
Ala Arg Asp Leu Phe Pro Thr Ile Phe Gly Val Ser Tyr Tyr Tyr Tyr
             100                 105                 110
Trp Gly Gln Gly Thr Leu Val Thr Val Ser Ser Ala Ser Thr Lys Gly
         115                 120                 125
Pro Ser Val Phe Pro Leu Ala Pro Ser Ser Lys Ser Thr Ser Gly Gly
     130                 135                 140
Thr Ala Ala Leu Gly Cys Leu Val Lys Asp Tyr Phe Pro Glu Pro Val
145                 150                 155                 160
Thr Val Ser Trp Asn Ser Gly Ala Leu Thr Ser Gly Val His Thr Phe
             165                 170                 175
Pro Ala Val Leu Gln Ser Ser Gly Leu Tyr Ser Leu Ser Ser Val Val
         180                 185                 190
Thr Val Pro Ser Ser Ser Leu Gly Thr Gln Thr Tyr Ile Cys Asn Val
     195                 200                 205
Asn His Lys Pro Ser Asn Thr Lys Val Asp Lys Lys Val Glu Pro Lys
210                 215                 220
Ser Cys Asp Lys Thr His Thr Cys Pro Pro Cys Pro Ala Pro Glu Ala
225                 230                 235                 240
Ala Gly Gly Pro Ser Val Phe Leu Phe Pro Pro Lys Pro Lys Asp Thr
             245                 250                 255
Leu Met Ile Ser Arg Thr Pro Glu Val Thr Cys Val Val Val Asp Val
         260                 265                 270
Ser His Glu Asp Pro Glu Val Lys Phe Asn Trp Tyr Val Asp Gly Val
     275                 280                 285
Glu Val His Asn Ala Lys Thr Lys Pro Arg Glu Glu Gln Tyr Asn Ser
    290                 295                 300
Thr Tyr Arg Val Val Ser Val Leu Thr Val Leu His Gln Asp Trp Leu
305                 310                 315                 320
Asn Gly Lys Glu Tyr Lys Cys Lys Val Ser Asn Lys Ala Leu Pro Ala
             325                 330                 335
Pro Ile Glu Lys Thr Ile Ser Lys Ala Lys Gly Gln Pro Arg Glu Pro
         340                 345                 350
Gln Val Tyr Thr Leu Pro Pro Ser Arg Asp Glu Leu Thr Lys Asn Gln
     355                 360                 365
Val Ser Leu Thr Cys Leu Val Lys Gly Phe Tyr Pro Ser Asp Ile Ala
    370                 375                 380
Val Glu Trp Glu Ser Asn Gly Gln Pro Glu Asn Asn Tyr Lys Thr Thr
385                 390                 395                 400
Pro Pro Val Leu Asp Ser Asp Gly Ser Phe Phe Leu Tyr Ser Lys Leu
             405                 410                 415
Thr Val Asp Lys Ser Arg Trp Gln Gln Gly Asn Val Phe Ser Cys Ser
         420                 425                 430
Val Met His Glu Ala Leu His Asn His Tyr Thr Gln Lys Ser Leu Ser
     435                 440                 445
```

```
<210> SEQ ID NO 28
<211> LENGTH: 215
<212> TYPE: PRT
<213> ORGANISM: Artificial Sequence
<220> FEATURE:
<223> OTHER INFORMATION: Light chain amino acid sequence of G1-AA/E05v2
      mAb and FS22-172-003-AA/E05v2 and FS22-053-008-AA/E05v2 mAb2

<400> SEQUENCE: 28

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Gly Arg
            20                  25                  30

Leu Ala Trp Tyr Gln Gln Lys Pro Gly Lys Ala Pro Asn Leu Leu Ile
        35                  40                  45

Tyr Glu Ala Ser Asn Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Arg
                85                  90                  95

Val Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 29
<211> LENGTH: 9
<212> TYPE: PRT
<213> ORGANISM: Artificial Sequence
<220> FEATURE:
<223> OTHER INFORMATION: G12v2 mAb (Kabat) VL CDR3

<400> SEQUENCE: 29

Gln Gln Ser Tyr Ser Trp Pro Arg Thr
1               5

<210> SEQ ID NO 30
<211> LENGTH: 107
<212> TYPE: PRT
<213> ORGANISM: Artificial Sequence
<220> FEATURE:
<223> OTHER INFORMATION: G12v2 mAb VL domain

<400> SEQUENCE: 30
```

```
Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Gly Arg
            20                  25                  30

Leu Ala Trp Tyr Gln Lys Pro Gly Lys Ala Pro Asn Leu Leu Ile
        35                  40                  45

Tyr Glu Ala Ser Asn Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65              70                  75                  80

Glu Asp Phe Ala Thr Tyr Tyr Cys Gln Gln Ser Tyr Ser Trp Pro Arg
                85                  90                  95

Thr Phe Gly Gln Gly Thr Lys Val Glu Ile Lys
            100                 105
```

<210> SEQ ID NO 31
<211> LENGTH: 321
<212> TYPE: DNA
<213> ORGANISM: Artificial Sequence
<220> FEATURE:
<223> OTHER INFORMATION: G12v2 mAb VL domain

<400> SEQUENCE: 31

```
gacattcaga tgacccagtc cccgagcacg ctgtccgcaa gcgtggggga cagagtgacc      60
atcacttgcc gcgcctcaca atccatcagc ggacgcttgg cctggtacca gcagaagccc    120
ggaaaggccc caaaccttct gatctacgaa gcctcgaacc tggagtcagg cgtcccttcg    180
cggttctctg gctccggttc cggaactgag ttcaccctca ccatctcgtc cctgcaaccg    240
gaagatttcg ccacctacta ctgccaacag tcgtactcct ggccccggac attcggacag    300
ggaaccaaag tcgagattaa g                                              321
```

<210> SEQ ID NO 32
<211> LENGTH: 1456
<212> TYPE: DNA
<213> ORGANISM: Artificial Sequence
<220> FEATURE:
<223> OTHER INFORMATION: Codon-optimised nucleic acid sequences encoding
      the FS22-172-003-AA/E12v2 heavy chain

<400> SEQUENCE: 32

```
aagcttgccg ccaccatgga atggtcctgg gtgttcctgt tcttcctgtc cgtgaccacc      60
ggcgtgcact ctgaagttca gctggttcag tctggcgccg aagtgaaaag acctggcgcc    120
tctgtgaagg tgtcctgcaa ggcttctggc tacccctttt cctcctacgg catctcctgg    180
gtccgacagg ctcctggaca aggcttggaa tggatgggct ggatctccgc ttattccggc    240
ggcaccaatt acgcccagaa actgcagggc agagtgacca tgaccaccga cacctctacc    300
tccaccgcct acatggaact gcggtccctg agatctgacg acaccgccgt gtactactgc    360
gccagagatc tgttccccac catcttcggc gtgtcctact actactattg gggccagggc    420
accctggtca ccgtgtcctc tgcttctacc aagggaccca gcgtgttccc tctggctcct    480
tccagcaagt ctacctctgg cggaacagct gctctgggct gcctggtcaa ggactacttt    540
cctgagcctg tgaccgtgtc ttggaactct ggcgctctga catctggcgt gcacaccttt    600
ccagctgtgc tgcagtcctc cggcctgtac tctctgtcct ctgtcgtgac cgtgccttcc    660
agctctctgg gaacccagac ctacatctgc aatgtgaacc acaagccttc caacaccaag    720
```

```
gtggacaaga aggtggaacc caagtcctgc gacaagaccc acacctgtcc tccatgtcct    780
gctccagaag ctgctggcgg cccttccgtg tttctgttcc ctccaaagcc taaggacacc    840
ctgatgatct ctcggacccc tgaagtgacc tgcgtggtgg tggatgtgtc tcacgaggac    900
ccagaagtga agttcaattg gtacgtggac ggcgtggaag tgcacaacgc caagaccaag    960
cctagagagg aacagtacaa ctccacctac agagtggtgt ccgtgctgac cgtgctgcac   1020
caggattggc tgaacggcaa agagtacaag tgcaaggtgt ccaacaaggc cctgcctgct   1080
cctatcgaaa agaccatctc caaggccaag ggccagccta gggaacccca ggtttacacc   1140
ttgcctccat ctcgggacga gctgcccac atcatccctc catacaacca ggtgtccctg    1200
acctgcctcg tgaagggctt ctaccttcc gatatcgccg tggaatggga gagcaatggc    1260
cagcctgaga caactacaa gacaacccct cctgtgctgg actccgacgg ctcattcttt    1320
ctgtactcca agctgacagt gggcgccgac agatggctgg aagggaacgt gttctcctgc   1380
agcgtgatgc acgaggccct gcacaatcac tacacacaga gtccctgtc tctgtcccct    1440
ggcaagtgat gaattc                                                  1456
```

<210> SEQ ID NO 33
<211> LENGTH: 214
<212> TYPE: PRT
<213> ORGANISM: Artificial Sequence
<220> FEATURE:
<223> OTHER INFORMATION: Light chain amino acid sequence of G1-AA/G12v2
mAb and FS22-172-003-AA/G12v2 and FS22-053-008-AA/G12v2 mAb2

<400> SEQUENCE: 33

```
Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Gly Arg
            20                  25                  30

Leu Ala Trp Tyr Gln Gln Lys Pro Gly Lys Ala Pro Asn Leu Leu Ile
        35                  40                  45

Tyr Glu Ala Ser Asn Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Ser Tyr Ser Trp Pro Arg
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 34
<211> LENGTH: 14
<212> TYPE: PRT
<213> ORGANISM: Artificial Sequence
<220> FEATURE:
<223> OTHER INFORMATION: lambdav3/lam-G02v3 mAb (Kabat) VL CDR1

<400> SEQUENCE: 34

Thr Gly Thr Ser Ser Asp Val Gly Gly Tyr Asn Tyr Val Ser
1               5                   10

<210> SEQ ID NO 35
<211> LENGTH: 7
<212> TYPE: PRT
<213> ORGANISM: Artificial Sequence
<220> FEATURE:
<223> OTHER INFORMATION: lambdav3/lam-G02v3 mAb (Kabat) VL CDR2

<400> SEQUENCE: 35

Glu Val Thr Asn Arg Pro Ser
1               5

<210> SEQ ID NO 36
<211> LENGTH: 11
<212> TYPE: PRT
<213> ORGANISM: Artificial Sequence
<220> FEATURE:
<223> OTHER INFORMATION: lambdav3/lam-G02v3 mAb (Kabat) VL CDR3

<400> SEQUENCE: 36

Ser Ser Phe Lys Arg Gly Ser Thr Leu Val Val
1               5                   10

<210> SEQ ID NO 37
<211> LENGTH: 9
<212> TYPE: PRT
<213> ORGANISM: Artificial Sequence
<220> FEATURE:
<223> OTHER INFORMATION: lambdav3/lam-G02v3 (IMGT) VL CDR1

<400> SEQUENCE: 37

Ser Ser Asp Val Gly Gly Tyr Asn Tyr
1               5

<210> SEQ ID NO 38
<211> LENGTH: 3
<212> TYPE: PRT
<213> ORGANISM: Artificial Sequence
<220> FEATURE:
<223> OTHER INFORMATION: lambdav3/lam-G02v3 (IMGT) VL CDR2

<400> SEQUENCE: 38

Glu Val Thr
1

<210> SEQ ID NO 39
<211> LENGTH: 727
<212> TYPE: DNA
<213> ORGANISM: Artificial Sequence
<220> FEATURE:
<223> OTHER INFORMATION: Codon-optimised nucleic acid sequences encoding
      the FS22-172-003-AA/E12v2 light chain

<400> SEQUENCE: 39
aagcttgccg ccaccatgtc tgtgcctaca caggttctgg gactgctgct gctgtggctg     60
accgacgcca gatgcgacat ccagatgacc cagtctccat ccacactgtc cgcctctgtg    120

```
cgggacagag tgatcatcac ctgtagagcc agccagtcca tcggcaacag actggcctgg      180
tatcagcaca agcctggcaa ggctcccaag ctgctgatct acgaggcctc cacatctgag      240
acaggcgtgc cctctagatt ctccggctct ggctctggca ccgactttac cctgacaatc      300
tccagcctgc agcctgagga cttcgccacc tactactgcc agcagtccta cagcaccct       360 tacacctttg gccagggcac caagctggaa atcaagcgta cggtggccgc tcccagcgtg      420
ttcatcttcc ccccaagcga cgagcagctg aagagcggca ccgccagcgt ggtgtgtctg      480
ctgaacaact tctaccccag ggaggccaag gtgcagtgga aggtggacaa cgccctgcag      540
agcggcaaca gccaggagag cgtcaccgag caggacagca aggactccac ctacagcctg      600
agcagcaccc tgaccctgag caaggccgac tacgagaagc acaaggtgta cgcctgtgag      660
gtgacccacc agggcctgtc cagccccgtg accaagagct caacaggggg cgagtgctga      720
tgaattc                                                               727

<210> SEQ ID NO 40

<400> SEQUENCE: 40

000

<210> SEQ ID NO 41
<211> LENGTH: 111
<212> TYPE: PRT
<213> ORGANISM: Artificial Sequence
<220> FEATURE:
<223> OTHER INFORMATION: lambdav3/lam-G02v3 mAb  VL domain

<400> SEQUENCE: 41

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln Phe Pro Gly Lys Ala Pro Lys Leu
        35                  40                  45

Met Ile Phe Glu Val Thr Asn Arg Pro Ser Gly Val Ser Asp Arg Phe
    50                  55                  60

Ser Gly Ser Lys Ser Asp Asn Thr Ala Ser Leu Thr Ile Ser Gly Leu
65                  70                  75                  80

Gln Ala Glu Asp Glu Ala Glu Tyr Tyr Cys Ser Ser Phe Lys Arg Gly
                85                  90                  95

Ser Thr Leu Val Val Phe Gly Gly Gly Thr Lys Leu Thr Val Leu
            100                 105                 110

<210> SEQ ID NO 42
<211> LENGTH: 336
<212> TYPE: DNA
<213> ORGANISM: Artificial Sequence
<220> FEATURE:
<223> OTHER INFORMATION: lambdav3/lam-G02v3 mAb  VL domain

<400> SEQUENCE: 42
cagtcggccc ttactcaacc cgcgtcagtc tccggtagcc ccggacagtc catcacgatt       60
tcgtgcaccg gaaccagcag cgatgtcggg ggatacaact acgtgtcctg gtaccagcag      120
ttcccgggaa aggcccctaa gctgatgatc ttcgaagtca ctaacagacc ttccggagtg      180
tcggaccggt tctccggctc caagtccgac aacactgcga gcctgaccat ctcgggcctg      240
```

```
caagccgagg acgaagccga gtactactgt agctcattca agcgcggttc caccctcgtg    300
gtgttcggcg gtggcactaa gctcaccgtg ctggga                              336
```

<210> SEQ ID NO 43

<400> SEQUENCE: 43

000

<210> SEQ ID NO 44
<211> LENGTH: 217
<212> TYPE: PRT
<213> ORGANISM: Artificial Sequence
<220> FEATURE:
<223> OTHER INFORMATION: Light chain amino acid sequence of
      G1-AA/lambdav3/lam-G02v3 mAb

<400> SEQUENCE: 44

```
Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln Phe Pro Gly Lys Ala Pro Lys Leu
        35                  40                  45

Met Ile Phe Glu Val Thr Asn Arg Pro Ser Gly Val Ser Asp Arg Phe
    50                  55                  60

Ser Gly Ser Lys Ser Asp Asn Thr Ala Ser Leu Thr Ile Ser Gly Leu
65              70                  75                  80

Gln Ala Glu Asp Glu Ala Glu Tyr Tyr Cys Ser Ser Phe Lys Arg Gly
            85                  90                  95

Ser Thr Leu Val Val Phe Gly Gly Gly Thr Lys Leu Thr Val Leu Gly
        100                 105                 110

Gln Pro Ala Ala Ala Pro Ser Val Thr Leu Phe Pro Pro Ser Ser Glu
    115                 120                 125

Glu Leu Gln Ala Asn Lys Ala Thr Leu Val Cys Leu Ile Ser Asp Phe
130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
            165                 170                 175

Tyr Ala Ala Ser Ser Tyr Leu Ser Leu Thr Pro Glu Gln Trp Lys Ser
        180                 185                 190

His Arg Ser Tyr Ser Cys Gln Val Thr His Glu Gly Ser Thr Val Glu
    195                 200                 205

Lys Thr Val Ala Pro Thr Glu Cys Ser
    210                 215
```

<210> SEQ ID NO 45
<211> LENGTH: 8
<212> TYPE: PRT
<213> ORGANISM: Artificial Sequence
<220> FEATURE:
<223> OTHER INFORMATION: Alternative definition of HCDR1 (IMGT)
<220> FEATURE:
<221> NAME/KEY: MISC_FEATURE
<222> LOCATION: (3)..(3)
<223> OTHER INFORMATION: X = P or T

<400> SEQUENCE: 45

Gly Tyr Xaa Phe Thr Ser Tyr Gly

```
1               5

<210> SEQ ID NO 46
<211> LENGTH: 11
<212> TYPE: PRT
<213> ORGANISM: Artificial Sequence
<220> FEATURE:
<223> OTHER INFORMATION: Alternative definition of LCDR1 (Kabat)
<220> FEATURE:
<221> NAME/KEY: MISC_FEATURE
<222> LOCATION: (7)..(7)
<223> OTHER INFORMATION: X = S or G
<220> FEATURE:
<221> NAME/KEY: MISC_FEATURE
<222> LOCATION: (8)..(8)
<223> OTHER INFORMATION: X = N or G

<400> SEQUENCE: 46

Arg Ala Ser Gln Ser Ile Xaa Xaa Arg Leu Ala
1               5                   10

<210> SEQ ID NO 47
<211> LENGTH: 7
<212> TYPE: PRT
<213> ORGANISM: Artificial Sequence
<220> FEATURE:
<223> OTHER INFORMATION: Alternative definition of LCDR2 (Kabat)
<220> FEATURE:
<221> NAME/KEY: MISC_FEATURE
<222> LOCATION: (4)..(4)
<223> OTHER INFORMATION: X = T or N
<220> FEATURE:
<221> NAME/KEY: MISC_FEATURE
<222> LOCATION: (5)..(5)
<223> OTHER INFORMATION: X = S or L
<220> FEATURE:
<221> NAME/KEY: MISC_FEATURE
<222> LOCATION: (7)..(7)
<223> OTHER INFORMATION: X = T or S

<400> SEQUENCE: 47

Glu Ala Ser Xaa Xaa Glu Xaa
1               5

<210> SEQ ID NO 48
<211> LENGTH: 10
<212> TYPE: PRT
<213> ORGANISM: Artificial Sequence
<220> FEATURE:
<223> OTHER INFORMATION: Alternative definition of LCDR3 (Kabat)
<220> FEATURE:
<221> NAME/KEY: MISC_FEATURE
<222> LOCATION: (6)..(6)
<223> OTHER INFORMATION: X = T or W
<220> FEATURE:
<221> NAME/KEY: MISC_FEATURE
<222> LOCATION: (8)..(8)
<223> OTHER INFORMATION: X = absent or R
<220> FEATURE:
<221> NAME/KEY: MISC_FEATURE
<222> LOCATION: (9)..(9)
<223> OTHER INFORMATION: X = Y, R or V

<400> SEQUENCE: 48

Gln Gln Ser Tyr Ser Xaa Pro Xaa Xaa Thr
1               5                   10

<210> SEQ ID NO 49
<211> LENGTH: 6
<212> TYPE: PRT
<213> ORGANISM: Artificial Sequence
<220> FEATURE:
```

```
<223> OTHER INFORMATION: Alternative definition of LCDR1 (IMGT)
<220> FEATURE:
<221> NAME/KEY: MISC_FEATURE
<222> LOCATION: (4)..(4)
<223> OTHER INFORMATION: X = G or S
<220> FEATURE:
<221> NAME/KEY: MISC_FEATURE
<222> LOCATION: (5)..(5)
<223> OTHER INFORMATION: X = N or G

<400> SEQUENCE: 49

Gln Ser Ile Xaa Xaa Arg
1               5

<210> SEQ ID NO 50
<211> LENGTH: 10
<212> TYPE: PRT
<213> ORGANISM: Artificial Sequence
<220> FEATURE:
<223> OTHER INFORMATION: Alternative definition of LCDR3 (IMGT)
<220> FEATURE:
<221> NAME/KEY: MISC_FEATURE
<222> LOCATION: (6)..(6)
<223> OTHER INFORMATION: X = absent or T
<220> FEATURE:
<221> NAME/KEY: MISC_FEATURE
<222> LOCATION: (7)..(7)
<223> OTHER INFORMATION: X = T, W or P
<220> FEATURE:
<221> NAME/KEY: MISC_FEATURE
<222> LOCATION: (8)..(8)
<223> OTHER INFORMATION: X = P or R
<220> FEATURE:
<221> NAME/KEY: MISC_FEATURE
<222> LOCATION: (9)..(9)
<223> OTHER INFORMATION: X = Y or R

<400> SEQUENCE: 50

Gln Gln Ser Tyr Ser Xaa Xaa Xaa Xaa Thr
1               5                   10

<210> SEQ ID NO 51
<211> LENGTH: 30
<212> TYPE: PRT
<213> ORGANISM: Artificial Sequence
<220> FEATURE:
<223> OTHER INFORMATION: IgG1 (Kabat) HFW1
<220> FEATURE:
<221> NAME/KEY: MISC_FEATURE
<222> LOCATION: (28)..(28)
<223> OTHER INFORMATION: X = P or T

<400> SEQUENCE: 51

Glu Val Gln Leu Val Gln Ser Gly Ala Glu Val Lys Arg Pro Gly Ala
1               5                   10                  15

Ser Val Lys Val Ser Cys Lys Ala Ser Gly Tyr Xaa Phe Thr
            20                  25                  30

<210> SEQ ID NO 52
<211> LENGTH: 14
<212> TYPE: PRT
<213> ORGANISM: Artificial Sequence
<220> FEATURE:
<223> OTHER INFORMATION: IgG1 (Kabat) HFW2

<400> SEQUENCE: 52

Trp Val Arg Gln Ala Pro Gly Gln Gly Leu Glu Trp Met Gly
1               5                   10

<210> SEQ ID NO 53
```

<211> LENGTH: 32
<212> TYPE: PRT
<213> ORGANISM: Artificial Sequence
<220> FEATURE:
<223> OTHER INFORMATION: IgG1 (Kabat) HFW3

<400> SEQUENCE: 53

Arg Val Thr Met Thr Thr Asp Thr Ser Thr Ser Ala Tyr Met Glu
1               5                   10                  15

Leu Arg Ser Leu Arg Ser Asp Asp Thr Ala Val Tyr Tyr Cys Ala Arg
            20                  25                  30

<210> SEQ ID NO 54
<211> LENGTH: 11
<212> TYPE: PRT
<213> ORGANISM: Artificial Sequence
<220> FEATURE:
<223> OTHER INFORMATION: IgG1 (Kabat) HFW4

<400> SEQUENCE: 54

Trp Gly Gln Gly Thr Leu Val Thr Val Ser Ser
1               5                   10

<210> SEQ ID NO 55
<211> LENGTH: 25
<212> TYPE: PRT
<213> ORGANISM: Artificial Sequence
<220> FEATURE:
<223> OTHER INFORMATION: IgG1 (IMGT) HFW1

<400> SEQUENCE: 55

Glu Val Gln Leu Val Gln Ser Gly Ala Glu Val Lys Arg Pro Gly Ala
1               5                   10                  15

Ser Val Lys Val Ser Cys Lys Ala Ser
            20                  25

<210> SEQ ID NO 56
<211> LENGTH: 17
<212> TYPE: PRT
<213> ORGANISM: Artificial Sequence
<220> FEATURE:
<223> OTHER INFORMATION: IgG1 (IMGT) HFW2

<400> SEQUENCE: 56

Ile Ser Trp Val Arg Gln Ala Pro Gly Gln Gly Leu Glu Trp Met Gly
1               5                   10                  15

Trp

<210> SEQ ID NO 57
<211> LENGTH: 38
<212> TYPE: PRT
<213> ORGANISM: Artificial Sequence
<220> FEATURE:
<223> OTHER INFORMATION: IgG1 (IMGT) HFW3

<400> SEQUENCE: 57

Asn Tyr Ala Gln Lys Leu Gln Gly Arg Val Thr Met Thr Thr Asp Thr
1               5                   10                  15

Ser Thr Ser Thr Ala Tyr Met Glu Leu Arg Ser Leu Arg Ser Asp Asp
            20                  25                  30

Thr Ala Val Tyr Tyr Cys
        35

<210> SEQ ID NO 58

```
<211> LENGTH: 23
<212> TYPE: PRT
<213> ORGANISM: Artificial Sequence
<220> FEATURE:
<223> OTHER INFORMATION: kappa light chain (Kabat) LFW1

<400> SEQUENCE: 58

Asp Ile Gln Met Thr Gln Ser Pro Ser Thr Leu Ser Ala Ser Val Arg
1               5                   10                  15

Asp Arg Val Ile Ile Thr Cys
            20

<210> SEQ ID NO 59
<211> LENGTH: 15
<212> TYPE: PRT
<213> ORGANISM: Artificial Sequence
<220> FEATURE:
<223> OTHER INFORMATION: kappa light chain (Kabat) LFW2

<400> SEQUENCE: 59

Trp Tyr Gln His Lys Pro Gly Lys Ala Pro Lys Leu Leu Ile Tyr
1               5                   10                  15

<210> SEQ ID NO 60
<211> LENGTH: 32
<212> TYPE: PRT
<213> ORGANISM: Artificial Sequence
<220> FEATURE:
<223> OTHER INFORMATION: kappa light chain (Kabat) LFW3

<400> SEQUENCE: 60

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 61
<211> LENGTH: 10
<212> TYPE: PRT
<213> ORGANISM: Artificial Sequence
<220> FEATURE:
<223> OTHER INFORMATION: kappa light chain (Kabat) LFW4

<400> SEQUENCE: 61

Phe Gly Gln Gly Thr Lys Leu Glu Ile Lys
1               5                   10

<210> SEQ ID NO 62
<211> LENGTH: 26
<212> TYPE: PRT
<213> ORGANISM: Artificial Sequence
<220> FEATURE:
<223> OTHER INFORMATION: kappa light chain (IMGT) LFW1

<400> SEQUENCE: 62

Asp Ile Gln Met Thr Gln Ser Pro Ser Thr Leu Ser Ala Ser Val Arg
1               5                   10                  15

Asp Arg Val Ile Ile Thr Cys Arg Ala Ser
            20                  25

<210> SEQ ID NO 63
<211> LENGTH: 17
<212> TYPE: PRT
<213> ORGANISM: Artificial Sequence
<220> FEATURE:
<223> OTHER INFORMATION: kappa light chain (IMGT) LFW2
```

<400> SEQUENCE: 63

Leu Ala Trp Tyr Gln His Lys Pro Gly Lys Ala Pro Lys Leu Leu Ile
1               5                   10                  15

Tyr

<210> SEQ ID NO 64
<211> LENGTH: 36
<212> TYPE: PRT
<213> ORGANISM: Artificial Sequence
<220> FEATURE:
<223> OTHER INFORMATION: kappa light chain (IMGT) LFW3

<400> SEQUENCE: 64

Thr Ser Glu Thr Gly Val Pro Ser Arg Phe Ser Gly Ser Gly Ser Gly
1               5                   10                  15

Thr Asp Phe Thr Leu Thr Ile Ser Ser Leu Gln Pro Glu Asp Phe Ala
            20                  25                  30

Thr Tyr Tyr Cys
            35

<210> SEQ ID NO 65
<211> LENGTH: 22
<212> TYPE: PRT
<213> ORGANISM: Artificial Sequence
<220> FEATURE:
<223> OTHER INFORMATION: lambda light chain (Kabat) LFW1

<400> SEQUENCE: 65

Gln Ser Ala Leu Thr Gln Pro Ala Ser Val Ser Gly Ser Pro Gly Gln
1               5                   10                  15

Ser Ile Thr Ile Ser Cys
            20

<210> SEQ ID NO 66
<211> LENGTH: 15
<212> TYPE: PRT
<213> ORGANISM: Artificial Sequence
<220> FEATURE:
<223> OTHER INFORMATION: lambda light chain (Kabat) LFW2

<400> SEQUENCE: 66

Trp Tyr Gln Gln Phe Pro Gly Lys Ala Pro Lys Leu Met Ile Phe
1               5                   10                  15

<210> SEQ ID NO 67
<211> LENGTH: 32
<212> TYPE: PRT
<213> ORGANISM: Artificial Sequence
<220> FEATURE:
<223> OTHER INFORMATION: lambda light chain (Kabat) LFW3

<400> SEQUENCE: 67

Gly Val Ser Asp Arg Phe Ser Gly Ser Lys Ser Asp Asn Thr Ala Ser
1               5                   10                  15

Leu Thr Ile Ser Gly Leu Gln Ala Glu Asp Glu Ala Glu Tyr Tyr Cys
            20                  25                  30

<210> SEQ ID NO 68
<211> LENGTH: 10
<212> TYPE: PRT
<213> ORGANISM: Artificial Sequence
<220> FEATURE:
<223> OTHER INFORMATION: lambda light chain (Kabat) LFW4

```
<400> SEQUENCE: 68

Phe Gly Gly Gly Thr Lys Leu Thr Val Leu
1               5                   10

<210> SEQ ID NO 69
<211> LENGTH: 25
<212> TYPE: PRT
<213> ORGANISM: Artificial Sequence
<220> FEATURE:
<223> OTHER INFORMATION: lambda light chain (IMGT) LFW1

<400> SEQUENCE: 69

Gln Ser Ala Leu Thr Gln Pro Ala Ser Val Ser Gly Ser Pro Gly Gln
1               5                   10                  15

Ser Ile Thr Ile Ser Cys Thr Gly Thr
            20                  25

<210> SEQ ID NO 70
<211> LENGTH: 17
<212> TYPE: PRT
<213> ORGANISM: Artificial Sequence
<220> FEATURE:
<223> OTHER INFORMATION: lambda light chain (IMGT) LFW2

<400> SEQUENCE: 70

Val Ser Trp Tyr Gln Gln Phe Pro Gly Lys Ala Pro Lys Leu Met Ile
1               5                   10                  15

Phe

<210> SEQ ID NO 71
<211> LENGTH: 36
<212> TYPE: PRT
<213> ORGANISM: Artificial Sequence
<220> FEATURE:
<223> OTHER INFORMATION: lambda light chain (IMGT) LFW3

<400> SEQUENCE: 71

Asn Arg Pro Ser Gly Val Ser Asp Arg Phe Ser Gly Ser Lys Ser Asp
1               5                   10                  15

Asn Thr Ala Ser Leu Thr Ile Ser Gly Leu Gln Ala Glu Asp Glu Ala
            20                  25                  30

Glu Tyr Tyr Cys
        35

<210> SEQ ID NO 72
<211> LENGTH: 8
<212> TYPE: PRT
<213> ORGANISM: Artificial Sequence
<220> FEATURE:
<223> OTHER INFORMATION: WT CH3 domain structural AB loop

<400> SEQUENCE: 72

Arg Asp Glu Leu Thr Lys Asn Gln
1               5

<210> SEQ ID NO 73
<211> LENGTH: 9
<212> TYPE: PRT
<213> ORGANISM: Artificial Sequence
<220> FEATURE:
<223> OTHER INFORMATION: WT CH3 domain structural CD loop

<400> SEQUENCE: 73
```

```
Ser Asn Gly Gln Pro Glu Asn Asn Tyr
1               5
```

<210> SEQ ID NO 74
<211> LENGTH: 10
<212> TYPE: PRT
<213> ORGANISM: Artificial Sequence
<220> FEATURE:
<223> OTHER INFORMATION: WT CH3 domain structural EF loop

<400> SEQUENCE: 74

```
Asp Lys Ser Arg Trp Gln Gln Gly Asn Val
1               5                   10
```

<210> SEQ ID NO 75
<211> LENGTH: 106
<212> TYPE: PRT
<213> ORGANISM: Artificial Sequence
<220> FEATURE:
<223> OTHER INFORMATION: WT CH3 domain

<400> SEQUENCE: 75

```
Gly Gln Pro Arg Glu Pro Gln Val Tyr Thr Leu Pro Pro Ser Arg Asp
1               5                   10                  15

Glu Leu Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly
            100                 105
```

<210> SEQ ID NO 76
<211> LENGTH: 110
<212> TYPE: PRT
<213> ORGANISM: Artificial Sequence
<220> FEATURE:
<223> OTHER INFORMATION: CH2 domain

<400> SEQUENCE: 76

```
Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys
            100                 105                 110
```

<210> SEQ ID NO 77
<211> LENGTH: 110
<212> TYPE: PRT
<213> ORGANISM: Artificial Sequence
<220> FEATURE:
<223> OTHER INFORMATION: CH2 domain with LALA mutation

<400> SEQUENCE: 77

Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys
            100                 105                 110

<210> SEQ ID NO 78
<211> LENGTH: 3
<212> TYPE: PRT
<213> ORGANISM: Artificial Sequence
<220> FEATURE:
<223> OTHER INFORMATION: PPY motif

<400> SEQUENCE: 78

Pro Pro Tyr
1

<210> SEQ ID NO 79
<211> LENGTH: 7
<212> TYPE: PRT
<213> ORGANISM: Artificial Sequence
<220> FEATURE:
<223> OTHER INFORMATION: synthetic

<400> SEQUENCE: 79

Asn Pro Pro Tyr Leu Phe Ser
1               5

<210> SEQ ID NO 80
<211> LENGTH: 7
<212> TYPE: PRT
<213> ORGANISM: Artificial Sequence
<220> FEATURE:
<223> OTHER INFORMATION: FS22-053-008 CH3 domain structural loop
      sequence

<400> SEQUENCE: 80

Asp Tyr Trp Arg Trp Leu Glu
1               5

<210> SEQ ID NO 81
<211> LENGTH: 111
<212> TYPE: PRT
<213> ORGANISM: Artificial Sequence
<220> FEATURE:
<223> OTHER INFORMATION: FS22-053-008 CH3 domain

<400> SEQUENCE: 81

```
Gly Gln Pro Arg Glu Pro Gln Val Tyr Thr Leu Pro Pro Ser Arg Asp
1               5                   10                  15

Glu Leu Asn Pro Pro Tyr Leu Phe Ser Asn Gln Val Ser Leu Thr Cys
            20                  25                  30

Leu Val Lys Gly Phe Tyr Pro Ser Asp Ile Ala Val Glu Trp Glu Ser
        35                  40                  45

Asn Gly Gln Pro Glu Asn Asn Tyr Lys Thr Thr Pro Pro Val Leu Asp
    50                  55                  60

Ser Asp Gly Ser Phe Phe Leu Tyr Ser Lys Leu Thr Val Asp Tyr Trp
65              70                  75                  80

Arg Trp Leu Glu Gly Asn Val Phe Ser Cys Ser Val Met His Glu Ala
                85                  90                  95

Leu His Asn His Tyr Thr Gln Lys Ser Leu Ser Leu Ser Pro Gly
            100                 105                 110

<210> SEQ ID NO 82
<211> LENGTH: 333
<212> TYPE: DNA
<213> ORGANISM: Artificial Sequence
<220> FEATURE:
<223> OTHER INFORMATION: FS22-053-008 CH3 domain

<400> SEQUENCE: 82
ggacagcctc gagaaccaca ggtgtacacc ctgcccccat cccgggatga gctgaacccg      60
ccgtacctgt tctctaacca ggtcagcctg acctgcctgg tcaaaggctt ctatcccagc     120
gacatcgccg tggagtggga gagcaatggg cagccggaga caactacaa gaccacgcct      180 cccgtactgg actccgacgg ctccttcttc ctctacagca agctcaccgt ggattactgg     240
aggtggctgg aagggaacgt cttctcatgc tccgtgatgc atgaggcgct gcacaaccac     300
tacactcaga gagcttgtc cctgtcgccc ggt                                   333

<210> SEQ ID NO 83
<211> LENGTH: 7
<212> TYPE: PRT
<213> ORGANISM: Artificial Sequence
<220> FEATURE:
<223> OTHER INFORMATION: FS22-053-009 CH3 domain structural loop
      sequence

<400> SEQUENCE: 83

Glu His Thr Arg Trp Leu Asp
1               5

<210> SEQ ID NO 84
<211> LENGTH: 111
<212> TYPE: PRT
<213> ORGANISM: Artificial Sequence
<220> FEATURE:
<223> OTHER INFORMATION: FS22-053-009 CH3 domain

<400> SEQUENCE: 84

Gly Gln Pro Arg Glu Pro Gln Val Tyr Thr Leu Pro Pro Ser Arg Asp
1               5                   10                  15

Glu Leu Asn Pro Pro Tyr Leu Phe Ser Asn Gln Val Ser Leu Thr Cys
            20                  25                  30

Leu Val Lys Gly Phe Tyr Pro Ser Asp Ile Ala Val Glu Trp Glu Ser
        35                  40                  45

Asn Gly Gln Pro Glu Asn Asn Tyr Lys Thr Thr Pro Pro Val Leu Asp
    50                  55                  60
```

Ser Asp Gly Ser Phe Phe Leu Tyr Ser Lys Leu Thr Val Glu His Thr
65                  70                  75                  80

Arg Trp Leu Asp Gly Asn Val Phe Ser Cys Ser Val Met His Glu Ala
                85                  90                  95

Leu His Asn His Tyr Thr Gln Lys Ser Leu Ser Leu Ser Pro Gly
            100                 105                 110

<210> SEQ ID NO 85
<211> LENGTH: 333
<212> TYPE: DNA
<213> ORGANISM: Artificial Sequence
<220> FEATURE:
<223> OTHER INFORMATION: FS22-053-009 CH3 domain

<400> SEQUENCE: 85
ggccagcctc gagaaccaca ggtgtacacc ctgcccccat cccgggatga gctgaacccg      60
ccgtacctgt tctctaacca ggtcagcctg acctgcctgg tcaaaggctt ctatcccagc     120
gacatcgccg tggagtggga gagcaatggg cagccggaga caactacaa gaccacgcct      180 cccgtgctgg actccgacgg ctccttcttc ctctacagca agctcaccgt ggaacatact     240
aggtggctga tgggaacgt cttctcatgc tccgtgatgc atgaggctct gcacaaccac      300
tacacacaga gagcctctc cctgtctccg ggt                                   333

<210> SEQ ID NO 86
<211> LENGTH: 7
<212> TYPE: PRT
<213> ORGANISM: Artificial Sequence
<220> FEATURE:
<223> OTHER INFORMATION: Fcab FS22-053-011 CH3 domain structural loop
      sequence

<400> SEQUENCE: 86

Asp Tyr Trp Arg Trp Thr Asp
1               5

<210> SEQ ID NO 87
<211> LENGTH: 111
<212> TYPE: PRT
<213> ORGANISM: Artificial Sequence
<220> FEATURE:
<223> OTHER INFORMATION: Fcab FS22-053-011 CH3 domain

<400> SEQUENCE: 87

Gly Gln Pro Arg Glu Pro Gln Val Tyr Thr Leu Pro Pro Ser Arg Asp
1               5                   10                  15

Glu Leu Asn Pro Pro Tyr Leu Phe Ser Asn Gln Val Ser Leu Thr Cys
            20                  25                  30

Leu Val Lys Gly Phe Tyr Pro Ser Asp Ile Ala Val Glu Trp Glu Ser
        35                  40                  45

Asn Gly Gln Pro Glu Asn Asn Tyr Lys Thr Thr Pro Pro Val Leu Asp
    50                  55                  60

Ser Asp Gly Ser Phe Phe Leu Tyr Ser Lys Leu Thr Val Asp Tyr Trp
65                  70                  75                  80

Arg Trp Thr Asp Gly Asn Val Phe Ser Cys Ser Val Met His Glu Ala
                85                  90                  95

Leu His Asn His Tyr Thr Gln Lys Ser Leu Ser Leu Ser Pro Gly
            100                 105                 110

<210> SEQ ID NO 88

```
<211> LENGTH: 333
<212> TYPE: DNA
<213> ORGANISM: Artificial Sequence
<220> FEATURE:
<223> OTHER INFORMATION: Fcab FS22-053-011 CH3 domain

<400> SEQUENCE: 88
ggccagcctc gagaaccaca ggtgtacacc ctgcccccat cccgggatga gctgaacccg      60
ccgtacctgt tctctaacca ggtcagcctg acctgcctgg tcaaaggctt ctatcccagc     120
gacatcgccg tggagtggga gagcaatggg cagccggaga caactacaa gaccacgcct      180 cccgtgctgg actccgacgg ctccttcttc tctacagca agctcaccgt ggattactgg      240
aggtggactg atgggaacgt cttctcatgc tccgtgatgc atgaggctct gcacaaccac     300
tacacacaga gagcctctc cctgtctccg ggt                                    333

<210> SEQ ID NO 89
<211> LENGTH: 7
<212> TYPE: PRT
<213> ORGANISM: Artificial Sequence
<220> FEATURE:
<223> OTHER INFORMATION: Fcab FS22-053-017 CH3 domain structural loop
      sequence

<400> SEQUENCE: 89

Tyr His Trp Arg Trp Leu Glu
1               5

<210> SEQ ID NO 90
<211> LENGTH: 111
<212> TYPE: PRT
<213> ORGANISM: Artificial Sequence
<220> FEATURE:
<223> OTHER INFORMATION: Fcab FS22-053-017 CH3 domain

<400> SEQUENCE: 90

Gly Gln Pro Arg Glu Pro Gln Val Tyr Thr Leu Pro Pro Ser Arg Asp
1               5                   10                  15

Glu Leu Asn Pro Pro Tyr Leu Phe Ser Asn Gln Val Ser Leu Thr Cys
                20                  25                  30

Leu Val Lys Gly Phe Tyr Pro Ser Asp Ile Ala Val Glu Trp Glu Ser
            35                  40                  45

Asn Gly Gln Pro Glu Asn Asn Tyr Lys Thr Thr Pro Pro Val Leu Asp
        50                  55                  60

Ser Asp Gly Ser Phe Phe Leu Tyr Ser Lys Leu Thr Val Tyr His Trp
65                  70                  75                  80

Arg Trp Leu Glu Gly Asn Val Phe Ser Cys Ser Val Met His Glu Ala
                85                  90                  95

Leu His Asn His Tyr Thr Gln Lys Ser Leu Ser Leu Ser Pro Gly
            100                 105                 110

<210> SEQ ID NO 91
<211> LENGTH: 333
<212> TYPE: DNA
<213> ORGANISM: Artificial Sequence
<220> FEATURE:
<223> OTHER INFORMATION: Fcab FS22-053-017 CH3 domain

<400> SEQUENCE: 91
ggacagcctc gagaaccaca ggtgtacact ctgcccccct cacgcgacga actcaatccg      60
ccctacctgt tctccaacca agtctccctg acctgtcttg tgaagggttt ctacccatcc     120
```

```
gatatcgccg tggagtggga gagcaacgga cagccggaga caactataa gactaccccg      180 cctgtgctgg actcggacgg cagcttcttc ttgtactcca aactgaccgt gtaccactgg      240
cggtggctgg aagggaacgt gtttagctgc tccgtcatgc atgaagccct gcacaaccac      300
tacacccaga gtccctctc gctctctccg ggt                                    333
```

<210> SEQ ID NO 92
<211> LENGTH: 7
<212> TYPE: PRT
<213> ORGANISM: Artificial Sequence
<220> FEATURE:
<223> OTHER INFORMATION: Fcab FS22-053-014 CH3 domain structural loop
      sequence

<400> SEQUENCE: 92

Tyr His Trp Arg Trp Leu Asp
1               5

<210> SEQ ID NO 93
<211> LENGTH: 111
<212> TYPE: PRT
<213> ORGANISM: Artificial Sequence
<220> FEATURE:
<223> OTHER INFORMATION: Fcab FS22-053-014 CH3 domain

<400> SEQUENCE: 93

Gly Gln Pro Arg Glu Pro Gln Val Tyr Thr Leu Pro Pro Ser Arg Asp
1               5                   10                  15

Glu Leu Asn Pro Pro Tyr Leu Phe Ser Asn Gln Val Ser Leu Thr Cys
                20                  25                  30

Leu Val Lys Gly Phe Tyr Pro Ser Asp Ile Ala Val Glu Trp Glu Ser
            35                  40                  45

Asn Gly Gln Pro Glu Asn Asn Tyr Lys Thr Thr Pro Pro Val Leu Asp
        50                  55                  60

Ser Asp Gly Ser Phe Phe Leu Tyr Ser Lys Leu Thr Val Tyr His Trp
65                  70                  75                  80

Arg Trp Leu Asp Gly Asn Val Phe Ser Cys Ser Val Met His Glu Ala
                85                  90                  95

Leu His Asn His Tyr Thr Gln Lys Ser Leu Ser Leu Ser Pro Gly
                100                 105                 110

<210> SEQ ID NO 94
<211> LENGTH: 333
<212> TYPE: DNA
<213> ORGANISM: Artificial Sequence
<220> FEATURE:
<223> OTHER INFORMATION: Fcab FS22-053-014 CH3 domain

<400> SEQUENCE: 94

```
ggacagcctc gagagcctca gtgtacacc ctgcccccat cccgggatga gctgaacccg       60
ccgtacctgt tctctaacca ggtcagcctg acctgcctgg tcaaaggctt ctatcccagc      120
gacatcgccg tggagtggga gagcaatggg cagccggaga caactacaa gaccacgcct       180 cccgtgctgg actccgacgg ctccttcttc ctctacagca agctcaccgt gtaccattgg      240
aggtggctga tgggaacgt cttctcatgc tccgtgatgc atgaggcgct gcacaaccac       300
tacactcaga gagcttgtc cctgtcgccc gga                                    333
```

<210> SEQ ID NO 95
<211> LENGTH: 7
<212> TYPE: PRT

<213> ORGANISM: Artificial Sequence
<220> FEATURE:
<223> OTHER INFORMATION: Fcab FS22-053-010 CH3 domain structural loop
      sequence

<400> SEQUENCE: 95

Asp Tyr Met Arg Trp Leu Asp
1               5

<210> SEQ ID NO 96
<211> LENGTH: 111
<212> TYPE: PRT
<213> ORGANISM: Artificial Sequence
<220> FEATURE:
<223> OTHER INFORMATION: Fcab FS22-053-010 CH3 domain

<400> SEQUENCE: 96

Gly Gln Pro Arg Glu Pro Gln Val Tyr Thr Leu Pro Pro Ser Arg Asp
1               5                   10                  15

Glu Leu Asn Pro Pro Tyr Leu Phe Ser Asn Gln Val Ser Leu Thr Cys
            20                  25                  30

Leu Val Lys Gly Phe Tyr Pro Ser Asp Ile Ala Val Glu Trp Glu Ser
        35                  40                  45

Asn Gly Gln Pro Glu Asn Asn Tyr Lys Thr Thr Pro Pro Val Leu Asp
    50                  55                  60

Ser Asp Gly Ser Phe Phe Leu Tyr Ser Lys Leu Thr Val Asp Tyr Met
65                  70                  75                  80

Arg Trp Leu Asp Gly Asn Val Phe Ser Cys Ser Val Met His Glu Ala
                85                  90                  95

Leu His Asn His Tyr Thr Gln Lys Ser Leu Ser Leu Ser Pro Gly
            100                 105                 110

<210> SEQ ID NO 97
<211> LENGTH: 333
<212> TYPE: DNA
<213> ORGANISM: Artificial Sequence
<220> FEATURE:
<223> OTHER INFORMATION: Fcab FS22-053-010 CH3 domain

<400> SEQUENCE: 97
ggccagcctc gagaaccaca ggtgtacacc ctgcccccat cccgggatga gctgaacccg      60
ccgtacctgt tctctaacca ggtcagcctg acctgcctgg tcaaaggctt ctatcccagc     120
gacatcgccg tggagtggga gagcaatggg cagccggaga caactacaa gaccacgcct      180 cccgtgctgg actccgacgg ctccttcttc ctctacagca agctcaccgt ggattacatg     240
aggtggctgg atgggaacgt cttctcatgc tccgtgatgc atgaggctct gcacaaccac     300
tacacacaga gagcctctc cctgtctccg ggt                                   333

<210> SEQ ID NO 98
<211> LENGTH: 7
<212> TYPE: PRT
<213> ORGANISM: Artificial Sequence
<220> FEATURE:
<223> OTHER INFORMATION: Fcab FS22-053-012 CH3 domain structural loop
      sequence

<400> SEQUENCE: 98

Asp His Met Arg Trp Leu Glu
1               5

<210> SEQ ID NO 99

```
<211> LENGTH: 111
<212> TYPE: PRT
<213> ORGANISM: Artificial Sequence
<220> FEATURE:
<223> OTHER INFORMATION: Fcab FS22-053-012 CH3 domain

<400> SEQUENCE: 99
```

Gly Gln Pro Arg Glu Pro Gln Val Tyr Thr Leu Pro Pro Ser Arg Asp
1               5                   10                  15

Glu Leu Asn Pro Pro Tyr Leu Phe Ser Asn Gln Val Ser Leu Thr Cys
                20                  25                  30

Leu Val Lys Gly Phe Tyr Pro Ser Asp Ile Ala Val Glu Trp Glu Ser
            35                  40                  45

Asn Gly Gln Pro Glu Asn Asn Tyr Lys Thr Thr Pro Pro Val Leu Asp
        50                  55                  60

Ser Asp Gly Ser Phe Phe Leu Tyr Ser Lys Leu Thr Val Asp His Met
65                  70                  75                  80

Arg Trp Leu Glu Gly Asn Val Phe Ser Cys Ser Val Met His Glu Ala
                85                  90                  95

Leu His Asn His Tyr Thr Gln Lys Ser Leu Ser Leu Ser Pro Gly
            100                 105                 110

```
<210> SEQ ID NO 100
<211> LENGTH: 333
<212> TYPE: DNA
<213> ORGANISM: Artificial Sequence
<220> FEATURE:
<223> OTHER INFORMATION: Fcab FS22-053-012 CH3 domain

<400> SEQUENCE: 100
ggccagcctc gagaaccaca ggtgtacacc ctgcccccat cccgggatga gctgaacccg      60
ccgtacctgt tctctaacca ggtcagcctg acctgcctgg tcaaaggctt ctatcccagc     120
gacatcgccg tggagtggga gagcaatggg cagccggaga caactacaa gaccacgcct      180
cccgtgctgg actccgacgg ctccttcttc ctctacagca agctcaccgt ggatcatatg     240
aggtggctgg aagggaacgt cttctcatgc tccgtgatgc atgaggctct gcacaaccac     300
tacacacaga gagcctctc cctgtctccg ggt                                  333

<210> SEQ ID NO 101
<211> LENGTH: 7
<212> TYPE: PRT
<213> ORGANISM: Artificial Sequence
<220> FEATURE:
<223> OTHER INFORMATION: Fcab FS22-053-013 CH3 domain structural loop
      sequence

<400> SEQUENCE: 101
```

Gly Tyr Glu Arg Trp Leu Glu
1               5

```
<210> SEQ ID NO 102
<211> LENGTH: 111
<212> TYPE: PRT
<213> ORGANISM: Artificial Sequence
<220> FEATURE:
<223> OTHER INFORMATION: Fcab FS22-053-013 CH3 domain

<400> SEQUENCE: 102
```

Gly Gln Pro Arg Glu Pro Gln Val Tyr Thr Leu Pro Pro Ser Arg Asp
1               5                   10                  15

Glu Leu Asn Pro Pro Tyr Leu Phe Ser Asn Gln Val Ser Leu Thr Cys

```
            20                  25                  30

Leu Val Lys Gly Phe Tyr Pro Ser Asp Ile Ala Val Glu Trp Glu Ser
            35                  40                  45

Asn Gly Gln Pro Glu Asn Asn Tyr Lys Thr Thr Pro Pro Val Leu Asp
        50                  55                  60

Ser Asp Gly Ser Phe Phe Leu Tyr Ser Lys Leu Thr Val Gly Tyr Glu
65                  70                  75                  80

Arg Trp Leu Glu Gly Asn Val Phe Ser Cys Ser Val Met His Glu Ala
                85                  90                  95

Leu His Asn His Tyr Thr Gln Lys Ser Leu Ser Leu Ser Pro Gly
            100                 105                 110

<210> SEQ ID NO 103
<211> LENGTH: 333
<212> TYPE: DNA
<213> ORGANISM: Artificial Sequence
<220> FEATURE:
<223> OTHER INFORMATION: Fcab FS22-053-013 CH3 domain

<400> SEQUENCE: 103
ggccagcctc gagaaccaca ggtgtacacc ctgcccccat cccgggatga gctgaacccg      60
ccgtacctgt tctctaacca ggtcagcctg acctgcctgg tcaaaggctt ctatcccagc     120
gacatcgccg tggagtggga gagcaatggg cagccggaga caactacaa gaccacgcct      180 cccgtgctgg actccgacgg ctccttcttc ctctacagca agctcaccgt gggttacgaa     240
aggtggctgg aagggaacgt cttctcatgc tccgtgatgc atgaggctct gcacaaccac     300
tacacacaga gagcctctc cctgtctccg ggt                                   333

<210> SEQ ID NO 104
<211> LENGTH: 7
<212> TYPE: PRT
<213> ORGANISM: Artificial Sequence
<220> FEATURE:
<223> OTHER INFORMATION: Fcab FS22-053-015 CH3 domain structural loop
      sequence

<400> SEQUENCE: 104

Asp His Trp Arg Trp Leu Gln
1               5

<210> SEQ ID NO 105
<211> LENGTH: 111
<212> TYPE: PRT
<213> ORGANISM: Artificial Sequence
<220> FEATURE:
<223> OTHER INFORMATION: Fcab FS22-053-015 CH3 domain

<400> SEQUENCE: 105

Gly Gln Pro Arg Glu Pro Gln Val Tyr Thr Leu Pro Pro Ser Arg Asp
1               5                   10                  15

Glu Leu Asn Pro Pro Tyr Leu Phe Ser Asn Gln Val Ser Leu Thr Cys
            20                  25                  30

Leu Val Lys Gly Phe Tyr Pro Ser Asp Ile Ala Val Glu Trp Glu Ser
            35                  40                  45

Asn Gly Gln Pro Glu Asn Asn Tyr Lys Thr Thr Pro Pro Val Leu Asp
        50                  55                  60

Ser Asp Gly Ser Phe Phe Leu Tyr Ser Lys Leu Thr Val Asp His Trp
65                  70                  75                  80

Arg Trp Leu Gln Gly Asn Val Phe Ser Cys Ser Val Met His Glu Ala
```

Leu His Asn His Tyr Thr Gln Lys Ser Leu Ser Leu Ser Pro Gly
            100                 105                 110

<210> SEQ ID NO 106
<211> LENGTH: 333
<212> TYPE: DNA
<213> ORGANISM: Artificial Sequence
<220> FEATURE:
<223> OTHER INFORMATION: Fcab FS22-053-015 CH3 domain

<400> SEQUENCE: 106

```
ggccagcctc gagaaccaca ggtgtacacc ctgcccccat cccgggatga gctgaacccg    60
ccgtacctgt tctctaacca ggtcagcctg acctgcctgg tcaaaggctt ctatcccagc    120
gacatcgccg tggagtggga gagcaatggg cagccggaga caactacaa gaccacgcct    180
cccgtgttgg actccgacgg ctccttcttc ctctacagca agctcaccgt ggatcattgg   240
aggtggctgc aggggaacgt cttctcatgc tccgtgatgc atgaggctct gcacaaccac   300
tacacacaga gagcctctc cctgtctccg ggt                                  333
```

<210> SEQ ID NO 107
<211> LENGTH: 7
<212> TYPE: PRT
<213> ORGANISM: Artificial Sequence
<220> FEATURE:
<223> OTHER INFORMATION: Fcab FS22-053-016 CH3 domain structural loop
      sequence

<400> SEQUENCE: 107

Asp Tyr Ile Arg Trp Leu Asn
1               5

<210> SEQ ID NO 108
<211> LENGTH: 111
<212> TYPE: PRT
<213> ORGANISM: Artificial Sequence
<220> FEATURE:
<223> OTHER INFORMATION: Fcab FS22-053-016 CH3 domain

<400> SEQUENCE: 108

Gly Gln Pro Arg Glu Pro Gln Val Tyr Thr Leu Pro Pro Ser Arg Asp
1               5                   10                  15

Glu Leu Asn Pro Pro Tyr Leu Phe Ser Asn Gln Val Ser Leu Thr Cys
            20                  25                  30

Leu Val Lys Gly Phe Tyr Pro Ser Asp Ile Ala Val Glu Trp Glu Ser
        35                  40                  45

Asn Gly Gln Pro Glu Asn Asn Tyr Lys Thr Thr Pro Pro Val Leu Asp
    50                  55                  60

Ser Asp Gly Ser Phe Phe Leu Tyr Ser Lys Leu Thr Val Asp Tyr Ile
65                  70                  75                  80

Arg Trp Leu Asn Gly Asn Val Phe Ser Cys Ser Val Met His Glu Ala
                85                  90                  95

Leu His Asn His Tyr Thr Gln Lys Ser Leu Ser Leu Ser Pro Gly
            100                 105                 110

<210> SEQ ID NO 109
<211> LENGTH: 333
<212> TYPE: DNA
<213> ORGANISM: Artificial Sequence
<220> FEATURE:
<223> OTHER INFORMATION: Fcab FS22-053-016 CH3 domain

<400> SEQUENCE: 109

```
ggccagcctc gagaaccaca ggtgtacacc ctgcccccat cccgggatga gctgaacccg        60
ccgtacctgt tctctaacca ggtcagcctg acctgcctgg tcaaaggctt ctatcccagc       120
gacatcgccg tggagtggga gagcaatggg cagccggaga caactacaa gaccacgcct        180
cccgtgctgg actccgacgg ctccttcttc ctctacagca agctcaccgt ggattacatc       240
aggtggctga acgggaacgt cttctcatgc tccgtgatgc atgaggctct gcacaaccac       300
tacacacaga gagcctctcc cctgtctccg ggt                                    333
```

<210> SEQ ID NO 110
<211> LENGTH: 7
<212> TYPE: PRT
<213> ORGANISM: Artificial Sequence
<220> FEATURE:
<223> OTHER INFORMATION: FS22-053 CH3 domain structural loop sequence

<400> SEQUENCE: 110

Tyr Tyr Asn Arg Trp Gln Asp
1               5

<210> SEQ ID NO 111
<211> LENGTH: 111
<212> TYPE: PRT
<213> ORGANISM: Artificial Sequence
<220> FEATURE:
<223> OTHER INFORMATION: FS22-053 CH3 domain

<400> SEQUENCE: 111

Gly Gln Pro Arg Glu Pro Gln Val Tyr Thr Leu Pro Pro Ser Arg Asp
1               5                   10                  15

Glu Leu Asn Pro Pro Tyr Leu Phe Ser Asn Gln Val Ser Leu Thr Cys
            20                  25                  30

Leu Val Lys Gly Phe Tyr Pro Ser Asp Ile Ala Val Glu Trp Glu Ser
        35                  40                  45

Asn Gly Gln Pro Glu Asn Asn Tyr Lys Thr Thr Pro Pro Val Leu Asp
    50                  55                  60

Ser Asp Gly Ser Phe Phe Leu Tyr Ser Lys Leu Thr Val Tyr Tyr Asn
65                  70                  75                  80

Arg Trp Gln Asp Gly Asn Val Phe Ser Cys Ser Val Met His Glu Ala
                85                  90                  95

Leu His Asn His Tyr Thr Gln Lys Ser Leu Ser Leu Ser Pro Gly
            100                 105                 110

<210> SEQ ID NO 112
<211> LENGTH: 333
<212> TYPE: DNA
<213> ORGANISM: Artificial Sequence
<220> FEATURE:
<223> OTHER INFORMATION: FS22-053 CH3 domain

<400> SEQUENCE: 112

```
ggccagcctc gagaaccaca ggtgtacacc ctgcccccat cccgggatga gctgaacccg        60
ccgtacctgt tctctaacca ggtcagcctg acctgcctgg tcaaaggctt ctatcccagc       120
gacatcgccg tggagtggga gagcaatggg cagccggaga caactacaa gaccacgcct        180
cccgtgctgg actccgacgg ctccttcttc ctctacagca agctcaccgt gtattataac       240
aggtggcagg atgggaacgt cttctcatgc tccgtgatgc atgaggctct gcacaaccac       300
```

-continued

```
tacacacaga agagcctctc cctgtctccg ggt                                    333
```

<210> SEQ ID NO 113
<211> LENGTH: 7
<212> TYPE: PRT
<213> ORGANISM: Artificial Sequence
<220> FEATURE:
<223> OTHER INFORMATION: Fcab FS22-172-003 CH3 domain structural loop
      sequence

<400> SEQUENCE: 113

Pro Tyr Ile Ile Pro Pro Tyr
1               5

<210> SEQ ID NO 114
<211> LENGTH: 7
<212> TYPE: PRT
<213> ORGANISM: Artificial Sequence
<220> FEATURE:
<223> OTHER INFORMATION: Fcab FS22-172-003 CH3 domain structural loop
      sequence

<400> SEQUENCE: 114

Gly Ala Asp Arg Trp Leu Glu
1               5

<210> SEQ ID NO 115
<211> LENGTH: 111
<212> TYPE: PRT
<213> ORGANISM: Artificial Sequence
<220> FEATURE:
<223> OTHER INFORMATION: Fcab FS22-172-003 CH3 domain

<400> SEQUENCE: 115

Gly Gln Pro Arg Glu Pro Gln Val Tyr Thr Leu Pro Pro Ser Arg Asp
1               5                   10                  15

Glu Leu Pro Tyr Ile Ile Pro Pro Tyr Asn Gln Val Ser Leu Thr Cys
                20                  25                  30

Leu Val Lys Gly Phe Tyr Pro Ser Asp Ile Ala Val Glu Trp Glu Ser
            35                  40                  45

Asn Gly Gln Pro Glu Asn Asn Tyr Lys Thr Thr Pro Pro Val Leu Asp
        50                  55                  60

Ser Asp Gly Ser Phe Phe Leu Tyr Ser Lys Leu Thr Val Gly Ala Asp
65                  70                  75                  80

Arg Trp Leu Glu Gly Asn Val Phe Ser Cys Ser Val Met His Glu Ala
                85                  90                  95

Leu His Asn His Tyr Thr Gln Lys Ser Leu Ser Leu Ser Pro Gly
            100                 105                 110

<210> SEQ ID NO 116
<211> LENGTH: 333
<212> TYPE: DNA
<213> ORGANISM: Artificial Sequence
<220> FEATURE:
<223> OTHER INFORMATION: Fcab FS22-172-003 CH3 domain

<400> SEQUENCE: 116

```
ggacagcctc gagaaccaca ggtgtacacc ctgcccccat cccgggatga gctgccatac     60
atcatcccac catacaacca ggtcagcctg acctgcctgg tcaaaggctt ctatcccagc    120
gacatcgccg tggagtggga gagcaatggg cagccggaga caactacaa gaccacgcct     180 cccgtgctgg actccgacgg ctccttcttc ctctacagca agctcaccgt gggcgcagat    240
```

```
aggtggctgg aagggaacgt cttctcatgc tccgtgatgc atgaggcgct gcacaaccac    300
tacactcaga gagcttgtcc cctgtcgccc ggt                                 333
```

<210> SEQ ID NO 117
<211> LENGTH: 7
<212> TYPE: PRT
<213> ORGANISM: Artificial Sequence
<220> FEATURE:
<223> OTHER INFORMATION: Fcab FS22-172-002 CH3 domain structural loop
      sequence

<400> SEQUENCE: 117

Pro Phe Gln Met Pro Pro Tyr
1               5

<210> SEQ ID NO 118
<211> LENGTH: 111
<212> TYPE: PRT
<213> ORGANISM: Artificial Sequence
<220> FEATURE:
<223> OTHER INFORMATION: Fcab FS22-172-002 CH3 domain

<400> SEQUENCE: 118

Gly Gln Pro Arg Glu Pro Gln Val Tyr Thr Leu Pro Pro Ser Arg Asp
1               5                   10                  15

Glu Leu Pro Phe Gln Met Pro Pro Tyr Asn Gln Val Ser Leu Thr Cys
            20                  25                  30

Leu Val Lys Gly Phe Tyr Pro Ser Asp Ile Ala Val Glu Trp Glu Ser
        35                  40                  45

Asn Gly Gln Pro Glu Asn Asn Tyr Lys Thr Thr Pro Pro Val Leu Asp
    50                  55                  60

Ser Asp Gly Ser Phe Phe Leu Tyr Ser Lys Leu Thr Val Gly Ala Asp
65                  70                  75                  80

Arg Trp Leu Glu Gly Asn Val Phe Ser Cys Ser Val Met His Glu Ala
                85                  90                  95

Leu His Asn His Tyr Thr Gln Lys Ser Leu Ser Leu Ser Pro Gly
            100                 105                 110

<210> SEQ ID NO 119
<211> LENGTH: 333
<212> TYPE: DNA
<213> ORGANISM: Artificial Sequence
<220> FEATURE:
<223> OTHER INFORMATION: Fcab FS22-172-002 CH3 domain

<400> SEQUENCE: 119

```
ggccagcctc gagaaccaca ggtgtacacc ctgccccat cccgggatga gctgccattc     60
cagatgccac catacaacca ggtcagcctg acctgcctgg tcaaaggctt ctatcccagc   120
gacatcgccg tggagtggga gagcaatggg cagccggaga caactacaa gaccacgcct    180 cccgtgctgg actccgacgg ctccttcttc ctctacagca agctcaccgt gggcgcagat   240
aggtggctgg aagggaacgt cttctcatgc tccgtgatgc atgaggctct gcacaaccac   300
tacacacaga gagcctctc cctgtctccg ggt                                  333
```

<210> SEQ ID NO 120
<211> LENGTH: 7
<212> TYPE: PRT
<213> ORGANISM: Artificial Sequence
<220> FEATURE:
<223> OTHER INFORMATION: Fcab FS22-172-004 CH3 domain structural loop
      sequence -continued

<400> SEQUENCE: 120

Asn Tyr Ile Tyr Pro Pro Tyr
1               5

<210> SEQ ID NO 121
<211> LENGTH: 111
<212> TYPE: PRT
<213> ORGANISM: Artificial Sequence
<220> FEATURE:
<223> OTHER INFORMATION: Fcab FS22-172-004 CH3 domain

<400> SEQUENCE: 121

Gly Gln Pro Arg Glu Pro Gln Val Tyr Thr Leu Pro Pro Ser Arg Asp
1               5                   10                  15

Glu Leu Asn Tyr Ile Tyr Pro Pro Tyr Asn Gln Val Ser Leu Thr Cys
            20                  25                  30

Leu Val Lys Gly Phe Tyr Pro Ser Asp Ile Ala Val Glu Trp Glu Ser
        35                  40                  45

Asn Gly Gln Pro Glu Asn Asn Tyr Lys Thr Thr Pro Pro Val Leu Asp
    50                  55                  60

Ser Asp Gly Ser Phe Phe Leu Tyr Ser Lys Leu Thr Val Gly Ala Asp
65                  70                  75                  80

Arg Trp Leu Glu Gly Asn Val Phe Ser Cys Ser Val Met His Glu Ala
                85                  90                  95

Leu His Asn His Tyr Thr Gln Lys Ser Leu Ser Leu Ser Pro Gly
            100                 105                 110

<210> SEQ ID NO 122
<211> LENGTH: 333
<212> TYPE: DNA
<213> ORGANISM: Artificial Sequence
<220> FEATURE:
<223> OTHER INFORMATION: Fcab FS22-172-004 CH3 domain

<400> SEQUENCE: 122
ggacagcctc gagagcctca agtgtacacc ctgcccccat cccgggatga gctgaactac      60
atctacccac catacaacca ggtcagcctg acctgcctgg tcaaaggctt ctatcccagc     120
gacatcgccg tggagtggga gagcaatggg cagccggaga caactacaa gaccacgcct      180
cccgtgctgg actccgacgg ctccttcttc ctctacagca agctcaccgt gggcgcagat     240
aggtggctgg aagggaacgt cttctcatgc tccgtgatgc atgaggcgct gcacaaccac     300
tacactcaga agagcttgtc cctgtcgccc gga                                  333

<210> SEQ ID NO 123
<211> LENGTH: 7
<212> TYPE: PRT
<213> ORGANISM: Artificial Sequence
<220> FEATURE:
<223> OTHER INFORMATION: Fcab FS22-172-001 CH3 domain structural loop
      sequence

<400> SEQUENCE: 123

Pro Phe Val Met Pro Pro Tyr
1               5

<210> SEQ ID NO 124
<211> LENGTH: 111
<212> TYPE: PRT
<213> ORGANISM: Artificial Sequence
<220> FEATURE:

<223> OTHER INFORMATION: Fcab FS22-172-001 CH3 domain

<400> SEQUENCE: 124

Gly Gln Pro Arg Glu Pro Gln Val Tyr Thr Leu Pro Pro Ser Arg Asp
1               5                   10                  15

Glu Leu Pro Phe Val Met Pro Pro Tyr Asn Gln Val Ser Leu Thr Cys
            20                  25                  30

Leu Val Lys Gly Phe Tyr Pro Ser Asp Ile Ala Val Glu Trp Glu Ser
        35                  40                  45

Asn Gly Gln Pro Glu Asn Asn Tyr Lys Thr Thr Pro Pro Val Leu Asp
    50                  55                  60

Ser Asp Gly Ser Phe Phe Leu Tyr Ser Lys Leu Thr Val Gly Ala Asp
65                  70                  75                  80

Arg Trp Leu Glu Gly Asn Val Phe Ser Cys Ser Val Met His Glu Ala
                85                  90                  95

Leu His Asn His Tyr Thr Gln Lys Ser Leu Ser Leu Ser Pro Gly
            100                 105                 110

<210> SEQ ID NO 125
<211> LENGTH: 333
<212> TYPE: DNA
<213> ORGANISM: Artificial Sequence
<220> FEATURE:
<223> OTHER INFORMATION: Fcab FS22-172-001 CH3 domain

<400> SEQUENCE: 125

```
ggccagcctc gagaaccaca ggtgtacacc ctgcccccat cccgggatga gctgccattc      60
gttatgccac catacaacca ggtcagcctg acctgcctgg tcaaaggctt ctatccagc      120
gacatcgccg tggagtggga gagcaatggg cagccggaga caactacaa gaccacgcct       180
cccgtgctgg actccgacgg ctccttcttc ctctacagca agctcaccgt gggcgcagat      240
aggtggctgg aagggaacgt cttctcatgc tccgtgatgc atgaggctct gcacaaccac      300
tacacacaga gagcctctc cctgtctccg ggt                                    333
```

<210> SEQ ID NO 126
<211> LENGTH: 7
<212> TYPE: PRT
<213> ORGANISM: Artificial Sequence
<220> FEATURE:
<223> OTHER INFORMATION: Fcab FS22-172-005 CH3 domain structural loop
      sequence

<400> SEQUENCE: 126

Gln Gln Val Tyr Pro Pro Tyr
1               5

<210> SEQ ID NO 127
<211> LENGTH: 111
<212> TYPE: PRT
<213> ORGANISM: Artificial Sequence
<220> FEATURE:
<223> OTHER INFORMATION: Fcab FS22-172-005 CH3 domain

<400> SEQUENCE: 127

Gly Gln Pro Arg Glu Pro Gln Val Tyr Thr Leu Pro Pro Ser Arg Asp
1               5                   10                  15

Glu Leu Gln Gln Val Tyr Pro Pro Tyr Asn Gln Val Ser Leu Thr Cys
            20                  25                  30

Leu Val Lys Gly Phe Tyr Pro Ser Asp Ile Ala Val Glu Trp Glu Ser
        35                  40                  45

Asn Gly Gln Pro Glu Asn Asn Tyr Lys Thr Thr Pro Pro Val Leu Asp
            50                  55                  60

Ser Asp Gly Ser Phe Phe Leu Tyr Ser Lys Leu Thr Val Gly Ala Asp
 65                  70                  75                  80

Arg Trp Leu Glu Gly Asn Val Phe Ser Cys Ser Val Met His Glu Ala
                 85                  90                  95

Leu His Asn His Tyr Thr Gln Lys Ser Leu Ser Leu Ser Pro Gly
                100                 105                 110

<210> SEQ ID NO 128
<211> LENGTH: 333
<212> TYPE: DNA
<213> ORGANISM: Artificial Sequence
<220> FEATURE:
<223> OTHER INFORMATION: Fcab FS22-172-005 CH3 domain

<400> SEQUENCE: 128
ggccagcctc gagaaccaca ggtgtacacc ctgcccccat cccgggatga gctgcagcag     60
gtttacccac catacaacca ggtcagcctg acctgcctgg tcaaaggctt ctatcccagc    120
gacatcgccg tggagtggga gagcaatggg cagccggaga caactacaa gaccacgcct     180 cccgtgctgg actccgacgg ctccttcttc ctctacagca agctcaccgt gggcgcagat    240
aggtggctgg aagggaacgt cttctcatgc tccgtgatgc atgaggctct gcacaaccac    300
tacacacaga gagcctctc cctgtctccg ggt                                  333

<210> SEQ ID NO 129
<211> LENGTH: 7
<212> TYPE: PRT
<213> ORGANISM: Artificial Sequence
<220> FEATURE:
<223> OTHER INFORMATION: Fcab FS22-172-006 CH3 domain structural loop
      sequence

<400> SEQUENCE: 129

Arg Lys Tyr Tyr Pro Pro Tyr
1               5

<210> SEQ ID NO 130
<211> LENGTH: 111
<212> TYPE: PRT
<213> ORGANISM: Artificial Sequence
<220> FEATURE:
<223> OTHER INFORMATION: Fcab FS22-172-006 CH3 domain

<400> SEQUENCE: 130

Gly Gln Pro Arg Glu Pro Gln Val Tyr Thr Leu Pro Pro Ser Arg Asp
1                5                  10                  15

Glu Leu Arg Lys Tyr Tyr Pro Pro Tyr Asn Gln Leu Ser Leu Thr Cys
                20                  25                  30

Leu Val Lys Gly Phe Tyr Pro Ser Asp Ile Ala Val Glu Trp Glu Ser
                35                  40                  45

Asn Gly Gln Pro Glu Asn Asn Tyr Lys Thr Thr Pro Pro Val Leu Asp
            50                  55                  60

Ser Asp Gly Ser Phe Phe Leu Tyr Ser Lys Leu Thr Val Gly Ala Asp
 65                  70                  75                  80

Arg Trp Leu Glu Gly Asn Val Phe Ser Cys Ser Val Met His Glu Ala
                 85                  90                  95

Leu His Asn His Tyr Thr Gln Lys Ser Leu Ser Leu Ser Pro Gly
                100                 105                 110

<210> SEQ ID NO 131
<211> LENGTH: 333
<212> TYPE: DNA
<213> ORGANISM: Artificial Sequence
<220> FEATURE:
<223> OTHER INFORMATION: Fcab FS22-172-006 CH3 domain

<400> SEQUENCE: 131

```
ggccagcctc gagaaccaca ggtgtacacc ctgcccccat cccgggatga gctgcgtaaa      60
tactacccgc cgtacaacca gctcagcctg acctgcctgg tcaaaggctt ctatcccagc     120
gacatcgccg tggagtggga gagcaatggg cagccggaga caactacaa gaccacgcct      180
cccgtgctgg actccgacgg ctccttcttc ctctacagca agctcaccgt gggcgcagat     240
aggtggctgg aagggaacgt cttctcatgc tccgtgatgc atgaggctct gcacaaccac     300
tacacacaga gagcctctcc cctgtctccg ggt                                  333
```

<210> SEQ ID NO 132
<211> LENGTH: 111
<212> TYPE: PRT
<213> ORGANISM: Artificial Sequence
<220> FEATURE:
<223> OTHER INFORMATION: Fcab FS22-172 CH3 domain

<400> SEQUENCE: 132

```
Gly Gln Pro Arg Glu Pro Gln Val Tyr Thr Leu Pro Pro Ser Arg Asp
  1               5                  10                  15
Glu Leu Arg Lys Tyr Tyr Pro Pro Tyr Asn Gln Val Ser Leu Thr Cys
                 20                  25                  30
Leu Val Lys Gly Phe Tyr Pro Ser Asp Ile Ala Val Glu Trp Glu Ser
             35                  40                  45
Asn Gly Gln Pro Glu Asn Asn Tyr Lys Thr Thr Pro Pro Val Leu Asp
         50                  55                  60
Ser Asp Gly Ser Phe Phe Leu Tyr Ser Lys Leu Thr Val Gly Ala Asp
 65                  70                  75                  80
Arg Trp Leu Glu Gly Asn Val Phe Ser Cys Ser Val Met His Glu Ala
                 85                  90                  95
Leu His Asn His Tyr Thr Gln Lys Ser Leu Ser Leu Ser Pro Gly
                100                 105                 110
```

<210> SEQ ID NO 133
<211> LENGTH: 333
<212> TYPE: DNA
<213> ORGANISM: Artificial Sequence
<220> FEATURE:
<223> OTHER INFORMATION: Fcab FS22-172 CH3 domain

<400> SEQUENCE: 133

```
ggccagcctc gagaaccaca ggtgtacacc ctgcccccat cccgggatga gctgcgtaaa      60
tactacccgc cgtacaacca ggtcagcctg acctgcctgg tcaaaggctt ctatcccagc     120
gacatcgccg tggagtggga gagcaatggg cagccggaga caactacaa gaccacgcct      180
cccgtgctgg actccgacgg ctccttcttc ctctacagca agctcaccgt gggcgcagat     240
aggtggctgg aagggaacgt cttctcatgc tccgtgatgc atgaggctct gcacaaccac     300
tacacacaga gagcctctcc cctgtctccg ggt                                  333
```

<210> SEQ ID NO 134
<211> LENGTH: 457

-continued

```
<212> TYPE: PRT
<213> ORGANISM: Artificial Sequence
<220> FEATURE:
<223> OTHER INFORMATION: heavy chain of FS22-172-003-AA/E12v2 mAb2 with
      LALA mutation

<400> SEQUENCE: 134
```

| | | | | | | | | | | | | | | | |
|---|---|---|---|---|---|---|---|---|---|---|---|---|---|---|---|
| Glu | Val | Gln | Leu | Val | Gln | Ser | Gly | Ala | Glu | Val | Lys | Arg | Pro | Gly | Ala |
| 1 | | | | 5 | | | | | 10 | | | | | 15 | |
| Ser | Val | Lys | Val | Ser | Cys | Lys | Ala | Ser | Gly | Tyr | Pro | Phe | Thr | Ser | Tyr |
| | | | 20 | | | | | 25 | | | | | 30 | | |
| Gly | Ile | Ser | Trp | Val | Arg | Gln | Ala | Pro | Gly | Gln | Gly | Leu | Glu | Trp | Met |
| | | 35 | | | | | 40 | | | | | 45 | | | |
| Gly | Trp | Ile | Ser | Ala | Tyr | Ser | Gly | Gly | Thr | Asn | Tyr | Ala | Gln | Lys | Leu |
| 50 | | | | | 55 | | | | | 60 | | | | | |
| Gln | Gly | Arg | Val | Thr | Met | Thr | Thr | Asp | Thr | Ser | Thr | Ser | Thr | Ala | Tyr |
| 65 | | | | 70 | | | | | 75 | | | | | 80 | |
| Met | Glu | Leu | Arg | Ser | Leu | Arg | Ser | Asp | Asp | Thr | Ala | Val | Tyr | Tyr | Cys |
| | | | | 85 | | | | | 90 | | | | | 95 | |
| Ala | Arg | Asp | Leu | Phe | Pro | Thr | Ile | Phe | Gly | Val | Ser | Tyr | Tyr | Tyr | Tyr |
| | | | 100 | | | | | 105 | | | | | 110 | | |
| Trp | Gly | Gln | Gly | Thr | Leu | Val | Thr | Val | Ser | Ser | Ala | Ser | Thr | Lys | Gly |
| | | 115 | | | | | 120 | | | | | 125 | | | |
| Pro | Ser | Val | Phe | Pro | Leu | Ala | Pro | Ser | Ser | Lys | Ser | Thr | Ser | Gly | Gly |
| 130 | | | | | 135 | | | | | 140 | | | | | |
| Thr | Ala | Ala | Leu | Gly | Cys | Leu | Val | Lys | Asp | Tyr | Phe | Pro | Glu | Pro | Val |
| 145 | | | | 150 | | | | | 155 | | | | | 160 | |
| Thr | Val | Ser | Trp | Asn | Ser | Gly | Ala | Leu | Thr | Ser | Gly | Val | His | Thr | Phe |
| | | | | 165 | | | | | 170 | | | | | 175 | |
| Pro | Ala | Val | Leu | Gln | Ser | Ser | Gly | Leu | Tyr | Ser | Leu | Ser | Ser | Val | Val |
| | | | 180 | | | | | 185 | | | | | 190 | | |
| Thr | Val | Pro | Ser | Ser | Ser | Leu | Gly | Thr | Gln | Thr | Tyr | Ile | Cys | Asn | Val |
| | | 195 | | | | | 200 | | | | | 205 | | | |
| Asn | His | Lys | Pro | Ser | Asn | Thr | Lys | Val | Asp | Lys | Lys | Val | Glu | Pro | Lys |
| 210 | | | | | 215 | | | | | 220 | | | | | |
| Ser | Cys | Asp | Lys | Thr | His | Thr | Cys | Pro | Pro | Cys | Pro | Ala | Pro | Glu | Ala |
| 225 | | | | | 230 | | | | | 235 | | | | | 240 |
| Ala | Gly | Gly | Pro | Ser | Val | Phe | Leu | Phe | Pro | Pro | Lys | Pro | Lys | Asp | Thr |
| | | | | 245 | | | | | 250 | | | | | 255 | |
| Leu | Met | Ile | Ser | Arg | Thr | Pro | Glu | Val | Thr | Cys | Val | Val | Val | Asp | Val |
| | | | 260 | | | | | 265 | | | | | 270 | | |
| Ser | His | Glu | Asp | Pro | Glu | Val | Lys | Phe | Asn | Trp | Tyr | Val | Asp | Gly | Val |
| | | 275 | | | | | 280 | | | | | 285 | | | |
| Glu | Val | His | Asn | Ala | Lys | Thr | Lys | Pro | Arg | Glu | Glu | Gln | Tyr | Asn | Ser |
| | | 290 | | | | | 295 | | | | | 300 | | | |
| Thr | Tyr | Arg | Val | Val | Ser | Val | Leu | Thr | Val | Leu | His | Gln | Asp | Trp | Leu |
| 305 | | | | | 310 | | | | | 315 | | | | | 320 |
| Asn | Gly | Lys | Glu | Tyr | Lys | Cys | Lys | Val | Ser | Asn | Lys | Ala | Leu | Pro | Ala |
| | | | | 325 | | | | | 330 | | | | | 335 | |
| Pro | Ile | Glu | Lys | Thr | Ile | Ser | Lys | Ala | Lys | Gly | Gln | Pro | Arg | Glu | Pro |
| | | | 340 | | | | | 345 | | | | | 350 | | |
| Gln | Val | Tyr | Thr | Leu | Pro | Pro | Ser | Arg | Asp | Glu | Leu | Pro | Tyr | Ile | Ile |
| | | 355 | | | | | 360 | | | | | 365 | | | |
| Pro | Pro | Tyr | Asn | Gln | Val | Ser | Leu | Thr | Cys | Leu | Val | Lys | Gly | Phe | Tyr |
| 370 | | | | | 375 | | | | | 380 | | | | | |

```
Pro Ser Asp Ile Ala Val Glu Trp Glu Ser Asn Gly Gln Pro Glu Asn
385                 390                 395                 400

Asn Tyr Lys Thr Thr Pro Pro Val Leu Asp Ser Asp Gly Ser Phe Phe
                405                 410                 415

Leu Tyr Ser Lys Leu Thr Val Gly Ala Asp Arg Trp Leu Glu Gly Asn
            420                 425                 430

Val Phe Ser Cys Ser Val Met His Glu Ala Leu His Asn His Tyr Thr
        435                 440                 445

Gln Lys Ser Leu Ser Leu Ser Pro Gly
    450                 455
```

<210> SEQ ID NO 135
<211> LENGTH: 1371
<212> TYPE: DNA
<213> ORGANISM: Artificial Sequence
<220> FEATURE:
<223> OTHER INFORMATION: heavy chain of FS22-172-003-AA/E12v2 mAb2 with LALA mutation

<400> SEQUENCE: 135

| | | | | | |
|---|---|---|---|---|---|
| gaagttcagc | tggttcagtc | tggcgccgaa | gtgaaaagac | ctggcgcctc | tgtgaaggtg | 60 |
| tcctgcaagg | cttctggcta | cccctttacc | tcctacggca | tctcctgggt | ccgacaggct | 120 |
| cctggacaag | cttggaatg | gatgggctgg | atctccgctt | attccggcgg | caccaattac | 180 |
| gcccagaaac | tgcagggcag | agtgaccatg | accaccgaca | cctctacctc | caccgcctac | 240 |
| atggaactgc | ggtccctgag | atctgacgac | accgccgtgt | actactgcgc | cagagatctg | 300 |
| ttccccacca | tcttcggcgt | gtcctactac | tactattggg | gccagggcac | cctggtcacc | 360 |
| gtgtcctctg | cttctaccaa | gggacccagc | gtgttcccct | ggctccttc | cagcaagtct | 420 |
| acctctggcg | gaacagctgc | tctgggctgc | ctggtcaagg | actactttcc | tgagcctgtg | 480 |
| accgtgtctt | ggaactctgg | cgctctgaca | tctggcgtgc | acaccttcc | agctgtgctg | 540 |
| cagtcctccg | gcctgtactc | tctgtcctct | gtcgtgaccg | tgccttccag | ctctctggga | 600 |
| acccagacct | acatctgcaa | tgtgaaccac | aagccttcca | acaccaaggt | ggacaagaag | 660 |
| gtggaaccca | gtcctgcga | caagacccac | acctgtcctc | catgtcctgc | tccagaagct | 720 |
| gctggcggcc | cttccgtgtt | tctgttccct | ccaaagccta | aggacaccct | gatgatctct | 780 |
| cggacccctg | aagtgacctg | cgtggtggtg | gatgtgtctc | acgaggaccc | agaagtgaag | 840 |
| ttcaattggt | acgtggacgg | cgtggaagtg | cacaacgcca | agaccaagcc | tagagaggaa | 900 |
| cagtacaact | ccacctacag | agtggtgtcc | gtgctgaccg | tgctgcacca | ggattggctg | 960 |
| aacggcaaag | agtacaagtg | caaggtgtcc | aacaaggccc | tgcctgctcc | tatcgaaaag | 1020 |
| accatctcca | aggccaaggg | ccagcctagg | gaacccagg | tttacacctt | gcctccatct | 1080 |
| cgggacgagc | tgccctacat | catccctcca | tacaaccagg | tgtccctgac | ctgcctcgtg | 1140 |
| aagggcttct | accctccga | tatcgccgtg | gaatgggaga | gcaatggcca | gcctgagaac | 1200 |
| aactacaaga | caccccctcc | tgtgctggac | tccgacggct | cattctttct | gtactccaag | 1260 |
| ctgacagtgg | gcgccgacag | atggctggaa | gggaacgtgt | tctcctgcag | cgtgatgcac | 1320 |
| gaggccctgc | acaatcacta | cacacagaag | tccctgtctc | tgtcccctgg | c | 1371 |

<210> SEQ ID NO 136
<211> LENGTH: 642
<212> TYPE: DNA
<213> ORGANISM: Artificial Sequence
<220> FEATURE:

-continued

<223> OTHER INFORMATION: light chain of FS22-172-003-AA/E12v2 mAb2

<400> SEQUENCE: 136

```
gacatccaga tgacccagtc tccatccaca ctgtccgcct ctgtgcggga cagagtgatc      60
atcacctgta gagccagcca gtccatcggc aacagactgg cctggtatca gcacaagcct     120
ggcaaggctc ccaagctgct gatctacgag gcctccacat ctgagacagg cgtgccctct     180
agattctccg gctctggctc tggcaccgac tttacccctg aaatctccag cctgcagcct     240
gaggacttcg ccacctacta ctgccagcag tcctacagca cccccttacac ctttggccag    300
ggcaccaagc tggaaatcaa gcgtacggtg gccgctccca gcgtgttcat cttccccca      360
agcgacgagc agctgaagag cggcaccgcc agcgtggtgt gtctgctgaa caacttctac     420
cccagggagg ccaaggtgca gtggaaggtg gacaacgccc tgcagagcgg caacagccag     480
gagagcgtca ccgagcagga cagcaaggac tccacctaca gcctgagcag caccctgacc     540
ctgagcaagg ccgactacga aaagcacaag gtgtacgcct gtgaggtgac ccaccagggc     600
ctgtccagcc ccgtgaccaa gagcttcaac agggggcgagt gc                       642
```

<210> SEQ ID NO 137
<211> LENGTH: 457
<212> TYPE: PRT
<213> ORGANISM: Artificial Sequence
<220> FEATURE:
<223> OTHER INFORMATION: heavy chain of FS22-172-003-AA/E05v2 mAb2 with LALA mutation

<400> SEQUENCE: 137

```
Glu Val Gln Leu Val Gln Ser Gly Ala Glu Val Lys Arg Pro Gly Ala
 1               5                  10                  15
Ser Val Lys Val Ser Cys Lys Ala Ser Gly Tyr Thr Phe Thr Ser Tyr
            20                  25                  30
Gly Ile Ser Trp Val Arg Gln Ala Pro Gly Gln Gly Leu Glu Trp Met
        35                  40                  45
Gly Trp Ile Ser Ala Tyr Ser Gly Gly Thr Asn Tyr Ala Gln Lys Leu
    50                  55                  60
Gln Gly Arg Val Thr Met Thr Thr Asp Thr Ser Thr Ser Thr Ala Tyr
65                  70                  75                  80
Met Glu Leu Arg Ser Leu Arg Ser Asp Asp Thr Ala Val Tyr Tyr Cys
                85                  90                  95
Ala Arg Asp Leu Phe Pro Thr Ile Phe Gly Val Ser Tyr Tyr Tyr Tyr
            100                 105                 110
Trp Gly Gln Gly Thr Leu Val Thr Val Ser Ser Ala Ser Thr Lys Gly
        115                 120                 125
Pro Ser Val Phe Pro Leu Ala Pro Ser Ser Lys Ser Thr Ser Gly Gly
    130                 135                 140
Thr Ala Ala Leu Gly Cys Leu Val Lys Asp Tyr Phe Pro Glu Pro Val
145                 150                 155                 160
Thr Val Ser Trp Asn Ser Gly Ala Leu Thr Ser Gly Val His Thr Phe
                165                 170                 175
Pro Ala Val Leu Gln Ser Ser Gly Leu Tyr Ser Leu Ser Ser Val Val
            180                 185                 190
Thr Val Pro Ser Ser Ser Leu Gly Thr Gln Thr Tyr Ile Cys Asn Val
        195                 200                 205
Asn His Lys Pro Ser Asn Thr Lys Val Asp Lys Lys Val Glu Pro Lys
    210                 215                 220
```

Ser Cys Asp Lys Thr His Thr Cys Pro Pro Cys Pro Ala Pro Glu Ala
225                 230                 235                 240

Ala Gly Gly Pro Ser Val Phe Leu Phe Pro Pro Lys Pro Lys Asp Thr
            245                 250                 255

Leu Met Ile Ser Arg Thr Pro Glu Val Thr Cys Val Val Val Asp Val
        260                 265                 270

Ser His Glu Asp Pro Glu Val Lys Phe Asn Trp Tyr Val Asp Gly Val
    275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Pro Tyr Ile Ile
        355                 360                 365

Pro Pro Tyr Asn Gln Val Ser Leu Thr Cys Leu Val Lys Gly Phe Tyr
370                 375                 380

Pro Ser Asp Ile Ala Val Glu Trp Glu Ser Asn Gly Gln Pro Glu Asn
385                 390                 395                 400

Asn Tyr Lys Thr Thr Pro Pro Val Leu Asp Ser Asp Gly Ser Phe Phe
                405                 410                 415

Leu Tyr Ser Lys Leu Thr Val Gly Ala Asp Arg Trp Leu Glu Gly Asn
            420                 425                 430

Val Phe Ser Cys Ser Val Met His Glu Ala Leu His Asn His Tyr Thr
        435                 440                 445

Gln Lys Ser Leu Ser Leu Ser Pro Gly
    450                 455

<210> SEQ ID NO 138
<211> LENGTH: 1371
<212> TYPE: DNA
<213> ORGANISM: Artificial Sequence
<220> FEATURE:
<223> OTHER INFORMATION: heavy chain of FS22-172-003-AA/E05v2 mAb2 with
      LALA mutation

<400> SEQUENCE: 138
gaagtgcagc tggtgcagtc cggagccgaa gtcaagaggc tggagcgtc cgtgaaggtg      60 tcctgcaaag cctcaggata caccttcact tcgtacggga tttcctgggt ccgccaagca    120
ccgggtcaag gcttggagtg gatgggatgg atcagcgcgt attccggggg aaccaactac    180
gctcaaaagc tgcagggtcg cgtgaccatg accaccgata cctccacctc aacggcctac    240
atggaactga gatctctgcg gagcgacgac actgccgtgt actactgtgc ccgggacctg    300
ttccccacta tcttcggagt gtcgtactac tactactggg gccaggggac tctcgtgacc    360
gtgtcgagcg ctagcactaa gggcccgtcg gtgttcccgc tggccccatc gtccaagagc    420
acatcagggg gtaccgccgc cctgggctgc cttgtgaagg attactttcc cgagcccgtc    480
acagtgtcct ggaacagcgg agccctgacc tccggagtgc atactttccc ggctgtgctt    540
cagtcctctg gcctgtactc attgtcctcc gtggtcaccg tcccttcgtc ctccctgggc    600
acccagacct atatctgtaa tgtcaaccat aagccctcga acaccaaggt cgacaagaag    660
gtcgagccga agtcgtgcga caagactcac acttgcccgc cttgcccagc cccggaagct    720

```
gccggtggtc cttcggtgtt cctcttcccg cccaagccga aggataccct gatgatctca    780 cggaccccg aagtgacctg tgtggtggtg acgtgtccc acgaggaccc ggaagtgaaa     840
ttcaattggt acgtggatgg agtggaagtg cacaacgcca agaccaagcc acgggaagaa    900
cagtacaact ctacctaccg cgtggtgtcc gtgctcactg tgctgcacca agactggctg    960
aacgggaagg agtacaagtg caaagtgtcc aacaaggcgc tgcctgcccc aattgagaaa    1020
actatctcga agccaagggg acagcctcga gaaccacagg tgtacaccct gcccccatcc    1080
cgggatgagc tgccatacat catcccacca taccaaccag tcagcctgac ctgcctggtc    1140
aaaggcttct atcccagcga catcgccgtg gagtgggaga gcaatgggca gccggagaac    1200
aactacaaga ccacgcctcc cgtgctggac tccgacggct ccttcttcct ctacagcaag    1260
ctcaccgtgg cgcagatag gtggctgaa gggaacgtct tctcatgctc cgtgatgcat     1320
gaggcgctgc acaaccacta cactcagaag agcttgtccc tgtcgcccgg t             1371
```

<210> SEQ ID NO 139
<211> LENGTH: 645
<212> TYPE: DNA
<213> ORGANISM: Artificial Sequence
<220> FEATURE:
<223> OTHER INFORMATION: light chain of FS22-172-003-AA/E05v2 mAb2

<400> SEQUENCE: 139

```
gacattcaga tgacccaatc cccgtccacg ctgagcgcct ccgtcggtga tcgcgtgaca    60
atcacttgtc gggcgtcgca gtccatctct ggaaggctcg cctggtacca gcagaagcct    120
ggaaaggctc ccaacctcct tatctacgaa gccagcaacc tggagtccgg agtgcctagc    180
cggttcagcg gatcagggtc cggtaccgag ttcaccctga ccatttcctc gctccaacct    240
gaggacttcg ccacctacta ctgccaacag tcctattcaa ctccgcgcgt gaccttcggc    300
cagggcacta aggtcgaaat caaaagaacc gtggcagccc catcggtgtt tatcttcccg    360
ccctcggacg aacagctgaa gtcaggcact gctagcgtgg tctgtctcct gaacaatttc    420
tacccgcgcg aagctaaggt ccagtggaag gtcgacaacg cgctgcagtc cggaaacagc    480
caggagtcag tgaccgagca ggactccaag gattccactt attccctgtc ctccaccctg    540
actttgagca aggccgacta cgagaagcac aaagtgtacg cctgcgaagt gacccatcaa    600
gggctttcgt cgcccgtgac caagagcttc aaccggggcg aatgc                   645
```

<210> SEQ ID NO 140
<211> LENGTH: 457
<212> TYPE: PRT
<213> ORGANISM: Artificial Sequence
<220> FEATURE:
<223> OTHER INFORMATION: heavy chain of FS22-172-003-AA/G12v2 mAb2 with
    LALA mutation

<400> SEQUENCE: 140

```
Glu Val Gln Leu Val Gln Ser Gly Ala Glu Val Lys Arg Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Ser Gly Gly Thr Asn Tyr Ala Gln Lys Leu
    50                  55                  60

Gln Gly Arg Val Thr Met Thr Thr Asp Thr Ser Thr Ser Thr Ala Tyr
```

```
                65                  70                  75                  80
        Met Glu Leu Arg Ser Leu Arg Ser Asp Asp Thr Ala Val Tyr Tyr Cys
                        85                  90                  95

Ala Arg Asp Leu Phe Pro Thr Ile Phe Gly Val Ser Tyr Tyr Tyr Tyr
                    100                 105                 110

Trp Gly Gln Gly Thr Leu Val Thr Val Ser Ser Ala Ser Thr Lys Gly
                    115                 120                 125

Pro Ser Val Phe Pro Leu Ala Pro Ser Ser Lys Ser Thr Ser Gly Gly
                    130                 135                 140

Thr Ala Ala Leu Gly Cys Leu Val Lys Asp Tyr Phe Pro Glu Pro Val
        145                 150                 155                 160

Thr Val Ser Trp Asn Ser Gly Ala Leu Thr Ser Gly Val His Thr Phe
                        165                 170                 175

Pro Ala Val Leu Gln Ser Ser Gly Leu Tyr Ser Leu Ser Ser Val Val
                    180                 185                 190

Thr Val Pro Ser Ser Ser Leu Gly Thr Gln Thr Tyr Ile Cys Asn Val
                    195                 200                 205

Asn His Lys Pro Ser Asn Thr Lys Val Asp Lys Lys Val Glu Pro Lys
                    210                 215                 220

Ser Cys Asp Lys Thr His Thr Cys Pro Pro Cys Pro Ala Pro Glu Ala
        225                 230                 235                 240

Ala Gly Gly Pro Ser Val Phe Leu Phe Pro Pro Lys Pro Lys Asp Thr
                        245                 250                 255

Leu Met Ile Ser Arg Thr Pro Glu Val Thr Cys Val Val Val Asp Val
                    260                 265                 270

Ser His Glu Asp Pro Glu Val Lys Phe Asn Trp Tyr Val Asp Gly Val
                    275                 280                 285

Glu Val His Asn Ala Lys Thr Lys Pro Arg Glu Glu Gln Tyr Asn Ser
                    290                 295                 300

Thr Tyr Arg Val Val Ser Val Leu Thr Val Leu His Gln Asp Trp Leu
        305                 310                 315                 320

Asn Gly Lys Glu Tyr Lys Cys Lys Val Ser Asn Lys Ala Leu Pro Ala
                        325                 330                 335

Pro Ile Glu Lys Thr Ile Ser Lys Ala Lys Gly Gln Pro Arg Glu Pro
                    340                 345                 350

Gln Val Tyr Thr Leu Pro Pro Ser Arg Asp Glu Leu Pro Tyr Ile Ile
                    355                 360                 365

Pro Pro Tyr Asn Gln Val Ser Leu Thr Cys Leu Val Lys Gly Phe Tyr
                370                 375                 380

Pro Ser Asp Ile Ala Val Glu Trp Glu Ser Asn Gly Gln Pro Glu Asn
        385                 390                 395                 400

Asn Tyr Lys Thr Thr Pro Pro Val Leu Asp Ser Asp Gly Ser Phe Phe
                        405                 410                 415

Leu Tyr Ser Lys Leu Thr Val Gly Ala Asp Arg Trp Leu Glu Gly Asn
                    420                 425                 430

Val Phe Ser Cys Ser Val Met His Glu Ala Leu His Asn His Tyr Thr
                    435                 440                 445

Gln Lys Ser Leu Ser Leu Ser Pro Gly
                    450                 455

<210> SEQ ID NO 141
<211> LENGTH: 1371
<212> TYPE: DNA
<213> ORGANISM: Artificial Sequence
```

<220> FEATURE:
<223> OTHER INFORMATION: heavy chain of FS22-172-003-AA/G12v2 mAb2 with LALA mutation

<400> SEQUENCE: 141

```
gaagtgcagc tggtgcagtc cggagccgaa gtcaagaggc ctggagcgtc cgtgaaggtg      60
tcctgcaaag cctcaggata caccttcact tcgtacggga tttcctgggt ccgccaagca     120
ccgggtcaag gcttggagtg gatgggatgg atcagcgcgt attccggggg aaccaactac     180
gctcaaaagc tgcagggtcg cgtgaccatg accaccgata cctccacctc aacggcctac     240
atggaactga gatctctgcg gagcgacgac actgccgtgt actactgtgc ccgggacctg     300
ttccccacta tcttcggagt gtcgtactac tactactggg gccagggac tctcgtgacc     360
gtgtcgagcg ctagcactaa gggcccgtcg gtgttcccgc tggccccatc gtccaagagc     420
acatcagggg gtaccgccgc cctgggctgc cttgtgaagg attactttcc cgagcccgtc     480
acagtgtcct ggaacagcgg agccctgacc tccggagtgc atacctttcc ggctgtgctt     540
cagtcctctg gcctgtactc attgtcctcc gtggtcaccg tcccttcgtc ctccctgggc     600
acccagacct atatctgtaa tgtcaaccat aagccctcga acaccaaggt cgacaagaag     660
gtcgagccga agtcgtgcga caagactcac acttgcccgc cttgcccagc cccggaagct     720
gccggtggtc cttcggtgtt cctcttcccg cccaagccga aggatacct gatgatctca     780
cggaccccg aagtgacctg tgtggtggtg gacgtgtccc acgaggaccc ggaagtgaaa     840
ttcaattggt acgtggatgg agtggaagtg cacaacgcca agaccaagcc acgggaagaa     900
cagtacaact ctacctaccg cgtggtgtcc gtgctcactg tgctgcacca agactggctg     960
aacgggaagg agtacaagtg caaagtgtcc aacaaggcgc tgcctgcccc aattgagaaa    1020
actatctcga agccaagggg acagcctcga gaaccacagg tgtacaccct gccccatcc    1080
cgggatgagc tgccatacat catcccacca tacaaccagg tcagcctgac ctgcctggtc    1140
aaaggcttct atcccagcga catcgccgtg gagtgggaga gcaatgggca gccggagaac    1200
aactacaaga ccacgcctcc cgtgctggac tccgacggct ccttcttcct ctacagcaag    1260
ctcaccgtgg gcgcagatag gtggctgaa gggaacgtct tctcatgctc cgtgatgcat    1320
gaggcgctgc acaaccacta cactcagaag agcttgtccc tgtcgcccgg t            1371
```

<210> SEQ ID NO 142
<211> LENGTH: 642
<212> TYPE: DNA
<213> ORGANISM: Artificial Sequence
<220> FEATURE:
<223> OTHER INFORMATION: light chain of FS22-172-003-AA/G12v2 mAb2

<400> SEQUENCE: 142

```
gacattcaga tgacccagtc cccgagcacg ctgtccgcaa gcgtggggga cagagtgacc      60
atcacttgcc gcgcctcaca atccatcagc ggacgcttgg cctggtacca gcagaagccc     120
ggaaaggccc caaaccttct gatctacgaa gcctcgaacc tggagtcagg cgtcccttcg     180
cggttctctg gctccggttc cggaactgag ttcaccctca ccatctcgtc cctgcaaccg     240
gaagatttcg ccacctacta ctgccaacag tcgtactcct ggccccggac attcggacag     300
ggaaccaaag tcgagattaa gcggactgtg gcggctccta gcgtgttcat ctttccccg     360
tccgacgaac agctgaagtc cggtaccgct agcgtggtct gtctcctgaa caatttctac     420
ccgcgcgaag ctaaggtcca gtggaaggtc gacaacgcgc tgcagtccgg aaacagccag     480
gagtcagtga ccgagcagga ctccaaggat tccacttatt ccctgtcctc caccctgact     540
```

```
ttgagcaagg ccgactacga gaagcacaaa gtgtacgcct gcgaagtgac ccatcaaggg    600
ctttcgtcgc ccgtgaccaa gagcttcaac cggggcgaat gc                       642
```

<210> SEQ ID NO 143
<211> LENGTH: 457
<212> TYPE: PRT
<213> ORGANISM: Artificial Sequence
<220> FEATURE:
<223> OTHER INFORMATION: heavy chain of FS22-053-008-AA/E12v2 mAb2 with
      LALA mutation

<400> SEQUENCE: 143

Glu Val Gln Leu Val Gln Ser Gly Ala Glu Val Lys Arg Pro Gly Ala
1               5                   10                  15

Ser Val Lys Val Ser Cys Lys Ala Ser Gly Tyr Pro Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Ser Gly Gly Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Leu Phe Pro Thr Ile Phe Gly Val Ser Tyr Tyr Tyr Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Ala
225                 230                 235                 240

Ala Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

```
Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Asn Pro Pro Tyr
        355                 360                 365

Leu Phe Ser Asn Gln Val Ser Leu Thr Cys Leu Val Lys Gly Phe Tyr
    370                 375                 380

Pro Ser Asp Ile Ala Val Glu Trp Glu Ser Asn Gly Gln Pro Glu Asn
385                 390                 395                 400

Asn Tyr Lys Thr Thr Pro Pro Val Leu Asp Ser Asp Gly Ser Phe Phe
                405                 410                 415

Leu Tyr Ser Lys Leu Thr Val Asp Tyr Trp Arg Trp Leu Glu Gly Asn
            420                 425                 430

Val Phe Ser Cys Ser Val Met His Glu Ala Leu His Asn His Tyr Thr
        435                 440                 445

Gln Lys Ser Leu Ser Leu Ser Pro Gly
    450                 455
```

<210> SEQ ID NO 144
<211> LENGTH: 1371
<212> TYPE: DNA
<213> ORGANISM: Artificial Sequence
<220> FEATURE:
<223> OTHER INFORMATION: heavy chain of FS22-053-008-AA/E12v2 mAb2 with LALA mutation

<400> SEQUENCE: 144

```
gaagtgcagc tggtgcagtc cggagccgaa gtcaagaggc ctggagcgtc cgtgaaggtg      60
tcctgcaaag cctcaggata ccccttcact tcgtacggga tttcctgggt ccgccaagca     120
ccgggtcaag gcttggagtg gatgggatgg atcagcgcgt attccggggg aaccaactac     180
gctcaaaagc tgcagggtcg cgtgaccatg accaccgata cctccacctc aacggcctac     240
atggaactga gatctctgcg gagcgacgac actgccgtgt actactgtgc ccgggacctg     300
ttccccacta tcttcggagt gtcgtactac tactactggg gccagggac tctcgtgacc     360
gtgtcgagcg ctagcactaa gggcccgtcg gtgttcccgc tggccccatc gtccaagagc     420
acatcagggg gtaccgccgc cctgggctgc cttgtgaagg attactttcc cgagcccgtc     480
acagtgtcct ggaacagcgg agccctgacc tccggagtgc atactttccc ggctgtgctt     540
cagtcctctg gcctgtactc attgtcctcc gtggtcaccg tcccttcgtc ctccctgggc     600
acccagacct atatctgtaa tgtcaaccat aagccctcga acaccaaggt cgacaagaag     660
gtcgagccga gtcgtgcgaa caagactcac acttgcccgc cttgcccagc cccggaagct     720
gccggtggtc cttcggtgtt cctcttcccg cccaagccga aggataccct gatgatctca     780
cggaccccg aagtgacctg tgtggtggtg gacgtgtccc acgaggaccc ggaagtgaaa     840
ttcaattggt acgtggatgg agtggaagtg cacaacgcca agaccaagcc acgggaagaa     900
cagtacaact ctacctaccg cgtggtgtcc gtgctcactg tgctgcacca agactggctg     960
aacgggaagg agtacaagtg caaagtgtcc aacaaggcgc tgcctgcccc aattgagaaa    1020
actatctcga aagccaaggg acagcctcga gaaccacagg tgtacaccct gccccatcc    1080
cgggatgagc tgaacccgcc gtacctgttc tctaaccagg tcagcctgac ctgcctggtc    1140
aaaggcttct atcccagcga catcgccgtg gagtgggaga gcaatgggca gccggagaac    1200
aactacaaga ccacgcctcc cgtactggac tccgacggct ccttcttcct ctacagcaag    1260
ctcaccgtgg attactggag gtggctggaa gggaacgtct tctcatgctc cgtgatgcat    1320
```
gaggcgctgc acaaccacta cactcagaag agcttgtccc tgtcgccggg t             1371

<210> SEQ ID NO 145
<211> LENGTH: 642
<212> TYPE: DNA
<213> ORGANISM: Artificial Sequence
<220> FEATURE:
<223> OTHER INFORMATION: Light chain of FS22-053-008-AA/E12v2 mAb2 with
      LALA mutation

<400> SEQUENCE: 145
gacatccaga tgacgcagag cccgtctacc ctgtccgcct ccgtgagaga tcgcgtgatc      60
atcacctgtc gggccagcca gtccatcgga aaccgcttgg cgtggtacca gcacaagcct     120
gggaaggctc cgaagctgct catctacgaa gcctcgactt cggagactgg tgtccctagc     180
cggttcagcg gatcgggatc agggaccgat ttcactctga ccatttcctc cctgcaaccc     240
gaggacttcg ccacctacta ctgccaacag tcatattcca ccccgtacac cttcggacaa     300
ggcaccaagc tcgaaatcaa gcggactgtc gccgcacctt ccgtgttcat tttcccaccc     360
tccgacgaac agctgaaatc gggtacagct agcgtggtct gtctcctgaa caatttctac     420
ccgcgcgaag ctaaggtcca gtggaaggtc gacaacgcgc tgcagtccgg aaacagccag     480
gagtcagtga ccgagcagga ctccaaggat tccacttatt ccctgtcctc caccctgact     540
ttgagcaagg ccgactacga aagcacaaa gtgtacgcct gcgaagtgac ccatcaaggg     600
ctttcgtcgc ccgtgaccaa gagcttcaac cggggcgaat gc                        642

<210> SEQ ID NO 146
<211> LENGTH: 457
<212> TYPE: PRT
<213> ORGANISM: Artificial Sequence
<220> FEATURE:
<223> OTHER INFORMATION: heavy chain of FS22-053-008-AA/E05v2 with LALA
      mutation

<400> SEQUENCE: 146

Glu Val Gln Leu Val Gln Ser Gly Ala Glu Val Lys Arg Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Ser Gly Gly Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Leu Phe Pro Thr Ile Phe Gly Val Ser Tyr Tyr Tyr Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
               180                 185                 190

Thr Val Pro Ser Ser Ser Leu Gly Thr Gln Thr Tyr Ile Cys Asn Val
            195                 200                 205

Asn His Lys Pro Ser Asn Thr Lys Val Asp Lys Lys Val Glu Pro Lys
210                 215                 220

Ser Cys Asp Lys Thr His Thr Cys Pro Pro Cys Pro Ala Pro Glu Ala
225                 230                 235                 240

Ala Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Asn Pro Pro Tyr
        355                 360                 365

Leu Phe Ser Asn Gln Val Ser Leu Thr Cys Leu Val Lys Gly Phe Tyr
    370                 375                 380

Pro Ser Asp Ile Ala Val Glu Trp Glu Ser Asn Gly Gln Pro Glu Asn
385                 390                 395                 400

Asn Tyr Lys Thr Thr Pro Pro Val Leu Asp Ser Asp Gly Ser Phe Phe
                405                 410                 415

Leu Tyr Ser Lys Leu Thr Val Asp Tyr Trp Arg Trp Leu Glu Gly Asn
            420                 425                 430

Val Phe Ser Cys Ser Val Met His Glu Ala Leu His Asn His Tyr Thr
        435                 440                 445

Gln Lys Ser Leu Ser Leu Ser Pro Gly
    450                 455

<210> SEQ ID NO 147
<211> LENGTH: 1371
<212> TYPE: DNA
<213> ORGANISM: Artificial Sequence
<220> FEATURE:
<223> OTHER INFORMATION: heavy chain of FS22-053-008-AA/E05v2 with LALA
      mutation

<400> SEQUENCE: 147
gaagtgcagc tggtgcagtc cggagccgaa gtcaagaggc ctggagcgtc cgtgaaggtg      60
tcctgcaaag cctcaggata caccttcact tcgtacggga tttcctgggt ccgccaagca     120
ccgggtcaag gcttggagtg gatgggatgg atcagcgcgt attccggggg aaccaactac     180
gctcaaaagc tgcagggtcg cgtgaccatg accaccgata cctccacctc aacgcctac      240 atggaactga gatctctgcg gagcgacgac actgccgtgt actactgtgc ccgggacctg     300
ttccccacta tcttcggagt gtcgtactac tactactggg gccaggggac tctcgtgacc     360
gtgtcgagcg ctagcactaa gggcccgtcg gtgttcccgc tggccccatc gtccaagagc     420

```
acatcagggg gtaccgccgc cctgggctgc cttgtgaagg attactttcc cgagcccgtc    480
acagtgtcct ggaacagcgg agccctgacc tccggagtgc atactttccc ggctgtgctt    540
cagtcctctg gcctgtactc attgtcctcc gtggtcaccg tcccttcgtc ctccctgggc    600
acccagacct atatctgtaa tgtcaaccat aagccctcga acaccaaggt cgacaagaag    660
gtcgagccga agtcgtgcga caagactcac acttgcccgc cttgcccagc cccggaagct    720
gccggtggtc cttcggtgtt cctcttcccg cccaagccag aggataccct gatgatctca    780
cggacccccg aagtgacctg tgtggtggtg gacgtgtccc acgaggaccc ggaagtgaaa    840
ttcaattggt acgtggatgg agtggaagtg cacaacgcca agaccaagcc acgggaagaa    900
cagtacaact ctacctaccg cgtggtgtcc gtgctcactg tgctgcacca agactggctg    960
aacgggaagg agtacaagtg caaagtgtcc aacaaggcgc tgcctgcccc aattgagaaa   1020
actatctcga aagccaaggg acagcctcga gaaccacagg tgtacaccct gcccccatcc   1080
cgggatgagc tgaacccgcc gtacctgttc tctaaccagg tcagcctgac ctgcctggtc   1140
aaaggcttct atcccagcga catcgccgtg gagtgggaga gcaatgggca gccggagaac   1200
aactacaaga ccacgcctcc cgtactggac tccgacggct ccttcttcct ctacagcaag   1260
ctcaccgtgg attactggag gtggctgaa gggaacgtct tctcatgctc cgtgatgcat    1320
gaggcgctgc acaaccacta cactcagaag agcttgtccc tgtcgcccgg t             1371

<210> SEQ ID NO 148
<211> LENGTH: 645
<212> TYPE: DNA
<213> ORGANISM: Artificial Sequence
<220> FEATURE:
<223> OTHER INFORMATION: light chain of FS22-053-008-AA/E05v2 with LALA
      mutation

<400> SEQUENCE: 148
gacattcaga tgacccaatc cccgtccacg ctgagcgcct ccgtcggtga tcgcgtgaca     60
atcacttgtc gggcgtcgca gtccatctct ggaaggctcg cctggtacca gcagaagcct    120
ggaaaggctc ccaacctcct tatctacgaa gccagcaacc tggagtccgg agtgcctagc    180
cggttcagcg gatcagggtc cggtaccgag ttcaccctga ccatttcctc gctccaacct    240
gaggacttcg ccacctacta ctgccaacag tcctattcaa ctccgcgcgt gaccttcggc    300
cagggcacta aggtcgaaat caaaagaacc gtggcagccc atcggtgtt tatcttcccg    360 ccctcggacg aacagctgaa gtcaggcact gctagcgtgg tctgtctcct gaacaatttc    420
tacccgcgcg aagctaaggt ccagtggaag gtcgacaacg cgctgcagtc cggaaacagc    480
caggagtcag tgaccgagca ggactccaag gattccactt attccctgtc ctccaccctg    540
actttgagca aggccgacta cgagaagcac aaagtgtacg cctgcgaagt gacccatcaa    600
gggctttcgt cgcccgtgac caagagcttc aaccggggcg aatgc                    645

<210> SEQ ID NO 149
<211> LENGTH: 457
<212> TYPE: PRT
<213> ORGANISM: Artificial Sequence
<220> FEATURE:
<223> OTHER INFORMATION: heavy chain of FS22-053-008-AA/G12v2 with LALA
      mutation

<400> SEQUENCE: 149

Glu Val Gln Leu Val Gln Ser Gly Ala Glu Val Lys Arg Pro Gly Ala
1               5                   10                  15
```

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Ser Gly Gly Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Leu Phe Pro Thr Ile Phe Gly Val Ser Tyr Tyr Tyr Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Ala
225                 230                 235                 240

Ala Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Asn Pro Pro Tyr
        355                 360                 365

Leu Phe Ser Asn Gln Val Ser Leu Thr Cys Leu Val Lys Gly Phe Tyr
    370                 375                 380

Pro Ser Asp Ile Ala Val Glu Trp Glu Ser Asn Gly Gln Pro Glu Asn
385                 390                 395                 400

Asn Tyr Lys Thr Thr Pro Pro Val Leu Asp Ser Asp Gly Ser Phe Phe
                405                 410                 415

Leu Tyr Ser Lys Leu Thr Val Asp Tyr Trp Arg Trp Leu Glu Gly Asn
            420                 425                 430

Val Phe Ser Cys Ser Val Met His Glu Ala Leu His Asn His Tyr Thr

Gln Lys Ser Leu Ser Leu Ser Pro Gly
    450             455

<210> SEQ ID NO 150
<211> LENGTH: 1371
<212> TYPE: DNA
<213> ORGANISM: Artificial Sequence
<220> FEATURE:
<223> OTHER INFORMATION: heavy chain of FS22-053-008-AA/G12v2 with LALA
      mutation

<400> SEQUENCE: 150

| gaagtgcagc tggtgcagtc cggagccgaa gtcaagaggc tggagcgtc cgtgaaggtg | 60 |
| tcctgcaaag cctcaggata caccttcact tcgtacggga tttcctgggt ccgccaagca | 120 |
| ccgggtcaag gcttggagtg gatgggatgg atcagcgcgt attccggggg aaccaactac | 180 |
| gctcaaaagc tgcagggtcg cgtgaccatg accaccgata cctccacctc aacggcctac | 240 |
| atggaactga gatctctgcg gagcgacgac actgccgtgt actactgtgc ccgggacctg | 300 |
| ttccccacta tcttcggagt gtcgtactac tactactggg gccaggggac tctcgtgacc | 360 |
| gtgtcgagcg ctagcactaa gggcccgtcg gtgttcccgc tggccccatc gtccaagagc | 420 |
| acatcagggg gtaccgccgc cctgggctgc cttgtgaagg attactttcc gagcccgtc | 480 |
| acagtgtcct ggaacagcgg agccctgacc tccggagtgc atactttccc ggctgtgctt | 540 |
| cagtcctctg gcctgtactc attgtcctcc gtggtcaccg tcccttcgtc ctccctgggc | 600 |
| acccagacct atatctgtaa tgtcaaccat aagccctcga acaccaaggt cgacaagaag | 660 |
| gtcgagccga agtcgtgcga caagactcac acttgcccgc cttgcccagc ccggaagct | 720 |
| gccggtggtc cttcggtgtt cctcttcccg cccaagccga aggataccct gatgatctca | 780 |
| cggacccccg aagtgacctg tgtggtggtg gacgtgtccc acgaggaccc ggaagtgaaa | 840 |
| ttcaattggt acgtggatgg agtggaagtg cacaacgcca agaccaagcc acgggaagaa | 900 |
| cagtacaact ctacctaccg cgtggtgtcc gtgctcactg tgctgcacca agactggctg | 960 |
| aacgggaagg agtacaagtg caaagtgtcc aacaaggcgc tgcctgcccc aattgagaaa | 1020 |
| actatctcga aagccaaggg acagcctcga gaaccacagg tgtacaccct gcccccatcc | 1080 |
| cgggatgagc tgaacccgcc gtacctgttc tctaaccagg tcagcctgac ctgcctggtc | 1140 |
| aaaggcttct atcccagcga catcgccgtg gagtgggaga gcaatgggca gccggagaac | 1200 |
| aactacaaga ccacgcctcc cgtactggac tccgacggct ccttcttcct ctacagcaag | 1260 |
| ctcaccgtgg attactggag gtggctggaa gggaacgtct tctcatgctc cgtgatgcat | 1320 |
| gaggcgctgc acaaccacta cactcagaag agcttgtccc tgtcgcccgg t | 1371 |

<210> SEQ ID NO 151
<211> LENGTH: 642
<212> TYPE: DNA
<213> ORGANISM: Artificial Sequence
<220> FEATURE:
<223> OTHER INFORMATION: Light chain of FS22-053-008-AA/G12v2 with LALA
      mutation

<400> SEQUENCE: 151

| gacattcaga tgacccagtc cccgagcacg ctgtccgcaa gcgtggggga cagagtgacc | 60 |
| atcacttgcc gcgcctcaca atccatcagc ggacgcttgg cctggtacca gcagaagccc | 120 |
| ggaaaggccc caaaccttct gatctacgaa gcctcgaacc tggagtcagg cgtcccttcg | 180 |

-continued

```
cggttctctg gctccggttc cggaactgag ttcacccctca ccatctcgtc cctgcaaccg    240
gaagatttcg ccacctacta ctgccaacag tcgtactcct ggccccggac attcggacag    300
ggaaccaaag tcgagattaa gcggactgtg gcggctccta gcgtgttcat ctttcccccg    360
tccgacgaac agctgaagtc cggtaccgct agcgtggtct gtctcctgaa caatttctac    420
ccgcgcgaag ctaaggtcca gtggaaggtc gacaacgcgc tgcagtccgg aaacagccag    480
gagtcagtga ccgagcagga ctccaaggat tccacttatt ccctgtcctc caccctgact    540
ttgagcaagg ccgactacga aagcacaaa gtgtacgcct gcgaagtgac ccatcaaggg    600
ctttcgtcgc ccgtgaccaa gagcttcaac cggggcgaat gc                       642
```

<210> SEQ ID NO 152
<211> LENGTH: 457
<212> TYPE: PRT
<213> ORGANISM: Artificial Sequence
<220> FEATURE:
<223> OTHER INFORMATION: heavy chain of FS22-053-017AA/E12v2 with LALA mutation

<400> SEQUENCE: 152

```
Glu Val Gln Leu Val Gln Ser Gly Ala Glu Val Lys Arg Pro Gly Ala
1               5                   10                  15

Ser Val Lys Val Ser Cys Lys Ala Ser Gly Tyr Pro Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Ser Gly Gly Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Leu Phe Pro Thr Ile Phe Gly Val Ser Tyr Tyr Tyr Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Ala
225                 230                 235                 240

Ala Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
```

```
              275                 280                 285
Glu Val His Asn Ala Lys Thr Lys Pro Arg Glu Glu Gln Tyr Asn Ser
    290                 295                 300
Thr Tyr Arg Val Val Ser Val Leu Thr Val Leu His Gln Asp Trp Leu
305                 310                 315                 320
Asn Gly Lys Glu Tyr Lys Cys Lys Val Ser Asn Lys Ala Leu Pro Ala
            325                 330                 335
Pro Ile Glu Lys Thr Ile Ser Lys Ala Lys Gly Gln Pro Arg Glu Pro
            340                 345                 350
Gln Val Tyr Thr Leu Pro Pro Ser Arg Asp Glu Leu Asn Pro Pro Tyr
            355                 360                 365
Leu Phe Ser Asn Gln Val Ser Leu Thr Cys Leu Val Lys Gly Phe Tyr
    370                 375                 380
Pro Ser Asp Ile Ala Val Glu Trp Glu Ser Asn Gly Gln Pro Glu Asn
385                 390                 395                 400
Asn Tyr Lys Thr Thr Pro Pro Val Leu Asp Ser Asp Gly Ser Phe Phe
            405                 410                 415
Leu Tyr Ser Lys Leu Thr Val Tyr His Trp Arg Trp Leu Glu Gly Asn
            420                 425                 430
Val Phe Ser Cys Ser Val Met His Glu Ala Leu His Asn His Tyr Thr
    435                 440                 445
Gln Lys Ser Leu Ser Leu Ser Pro Gly
    450                 455

<210> SEQ ID NO 153
<211> LENGTH: 457
<212> TYPE: PRT
<213> ORGANISM: Artificial Sequence
<220> FEATURE:
<223> OTHER INFORMATION: heavy chain of FS22-053-017AA/E05v2 with LALA
      mutation

<400> SEQUENCE: 153

Glu Val Gln Leu Val Gln Ser Gly Ala Glu Val Lys Arg Pro Gly Ala
1               5                   10                  15
Ser Val Lys Val Ser Cys Lys Ala Ser Gly Tyr Thr Phe Thr Ser Tyr
            20                  25                  30
Gly Ile Ser Trp Val Arg Gln Ala Pro Gly Gln Gly Leu Glu Trp Met
        35                  40                  45
Gly Trp Ile Ser Ala Tyr Ser Gly Gly Thr Asn Tyr Ala Gln Lys Leu
    50                  55                  60
Gln Gly Arg Val Thr Met Thr Thr Asp Thr Ser Thr Ser Thr Ala Tyr
65                  70                  75                  80
Met Glu Leu Arg Ser Leu Arg Ser Asp Asp Thr Ala Val Tyr Tyr Cys
                85                  90                  95
Ala Arg Asp Leu Phe Pro Thr Ile Phe Gly Val Ser Tyr Tyr Tyr Tyr
            100                 105                 110
Trp Gly Gln Gly Thr Leu Val Thr Val Ser Ser Ala Ser Thr Lys Gly
        115                 120                 125
Pro Ser Val Phe Pro Leu Ala Pro Ser Ser Lys Ser Thr Ser Gly Gly
    130                 135                 140
Thr Ala Ala Leu Gly Cys Leu Val Lys Asp Tyr Phe Pro Glu Pro Val
145                 150                 155                 160
Thr Val Ser Trp Asn Ser Gly Ala Leu Thr Ser Gly Val His Thr Phe
                165                 170                 175
```

```
Pro Ala Val Leu Gln Ser Ser Gly Leu Tyr Ser Leu Ser Ser Val Val
                180                 185                 190

Thr Val Pro Ser Ser Ser Leu Gly Thr Gln Thr Tyr Ile Cys Asn Val
            195                 200                 205

Asn His Lys Pro Ser Asn Thr Lys Val Asp Lys Lys Val Glu Pro Lys
        210                 215                 220

Ser Cys Asp Lys Thr His Thr Cys Pro Pro Cys Pro Ala Pro Glu Ala
225                 230                 235                 240

Ala Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Asn Pro Pro Tyr
        355                 360                 365

Leu Phe Ser Asn Gln Val Ser Leu Thr Cys Leu Val Lys Gly Phe Tyr
370                 375                 380

Pro Ser Asp Ile Ala Val Glu Trp Glu Ser Asn Gly Gln Pro Glu Asn
385                 390                 395                 400

Asn Tyr Lys Thr Thr Pro Pro Val Leu Asp Ser Asp Gly Ser Phe Phe
                405                 410                 415

Leu Tyr Ser Lys Leu Thr Val Tyr His Trp Arg Trp Leu Glu Gly Asn
            420                 425                 430

Val Phe Ser Cys Ser Val Met His Glu Ala Leu His Asn His Tyr Thr
        435                 440                 445

Gln Lys Ser Leu Ser Leu Ser Pro Gly
450                 455

<210> SEQ ID NO 154
<211> LENGTH: 457
<212> TYPE: PRT
<213> ORGANISM: Artificial Sequence
<220> FEATURE:
<223> OTHER INFORMATION: heavy chain of FS22-053-017AA/G12v2 with LALA
      mutation

<400> SEQUENCE: 154

Glu Val Gln Leu Val Gln Ser Gly Ala Glu Val Lys Arg Pro Gly Ala
1               5                   10                  15

Ser Val Lys Val Ser Cys Lys Ala Ser Gly Tyr Thr Phe Thr Ser Tyr
                20                  25                  30

Gly Ile Ser Trp Val Arg Gln Ala Pro Gly Gln Gly Leu Glu Trp Met
            35                  40                  45

Gly Trp Ile Ser Ala Tyr Ser Gly Gly Thr Asn Tyr Ala Gln Lys Leu
        50                  55                  60

Gln Gly Arg Val Thr Met Thr Thr Asp Thr Ser Thr Ser Thr Ala Tyr
65                  70                  75                  80
```

Met Glu Leu Arg Ser Leu Arg Ser Asp Asp Thr Ala Val Tyr Tyr Cys
                85                  90                  95

Ala Arg Asp Leu Phe Pro Thr Ile Phe Gly Val Ser Tyr Tyr Tyr Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Ala
225                 230                 235                 240

Ala Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Asn Pro Pro Tyr
        355                 360                 365

Leu Phe Ser Asn Gln Val Ser Leu Thr Cys Leu Val Lys Gly Phe Tyr
    370                 375                 380

Pro Ser Asp Ile Ala Val Glu Trp Glu Ser Asn Gly Gln Pro Glu Asn
385                 390                 395                 400

Asn Tyr Lys Thr Thr Pro Pro Val Leu Asp Ser Asp Gly Ser Phe Phe
                405                 410                 415

Leu Tyr Ser Lys Leu Thr Val Tyr His Trp Arg Trp Leu Glu Gly Asn
            420                 425                 430

Val Phe Ser Cys Ser Val Met His Glu Ala Leu His Asn His Tyr Thr
        435                 440                 445

Gln Lys Ser Leu Ser Leu Ser Pro Gly
    450                 455

<210> SEQ ID NO 155
<211> LENGTH: 457
<212> TYPE: PRT
<213> ORGANISM: Artificial Sequence
<220> FEATURE:

<223> OTHER INFORMATION: heavy chain of FS22-172-003AA/1am-G02v3 with LALA mutation

<400> SEQUENCE: 155

| | | | | | | | | | | | | | | | |
|---|---|---|---|---|---|---|---|---|---|---|---|---|---|---|---|
| Glu | Val | Gln | Leu | Val | Gln | Ser | Gly | Ala | Glu | Lys | Arg | Pro | Gly | Ala |
| 1 | | | | 5 | | | | | 10 | | | | | 15 |
| Ser | Val | Lys | Val | Ser | Cys | Lys | Ala | Ser | Gly | Tyr | Thr | Phe | Thr | Ser | Tyr |
| | | | 20 | | | | | 25 | | | | | 30 | | |
| Gly | Ile | Ser | Trp | Val | Arg | Gln | Ala | Pro | Gly | Gln | Gly | Leu | Glu | Trp | Met |
| | | 35 | | | | | 40 | | | | | 45 | | | |
| Gly | Trp | Ile | Ser | Ala | Tyr | Ser | Gly | Gly | Thr | Asn | Tyr | Ala | Gln | Lys | Leu |
| 50 | | | | | 55 | | | | | 60 | | | | | |
| Gln | Gly | Arg | Val | Thr | Met | Thr | Thr | Asp | Thr | Ser | Thr | Ser | Thr | Ala | Tyr |
| 65 | | | | 70 | | | | | 75 | | | | | 80 | |
| Met | Glu | Leu | Arg | Ser | Leu | Arg | Ser | Asp | Asp | Thr | Ala | Val | Tyr | Tyr | Cys |
| | | | | 85 | | | | | 90 | | | | | 95 | |
| Ala | Arg | Asp | Leu | Phe | Pro | Thr | Ile | Phe | Gly | Val | Ser | Tyr | Tyr | Tyr |
| | | | 100 | | | | | 105 | | | | | 110 | |
| Trp | Gly | Gln | Gly | Thr | Leu | Val | Thr | Val | Ser | Ser | Ala | Ser | Thr | Lys | Gly |
| | | 115 | | | | | 120 | | | | | 125 | | | |
| Pro | Ser | Val | Phe | Pro | Leu | Ala | Pro | Ser | Ser | Lys | Ser | Thr | Ser | Gly | Gly |
| 130 | | | | | 135 | | | | | 140 | | | | | |
| Thr | Ala | Ala | Leu | Gly | Cys | Leu | Val | Lys | Asp | Tyr | Phe | Pro | Glu | Pro | Val |
| 145 | | | | 150 | | | | | 155 | | | | | 160 | |
| Thr | Val | Ser | Trp | Asn | Ser | Gly | Ala | Leu | Thr | Ser | Gly | Val | His | Thr | Phe |
| | | | | 165 | | | | | 170 | | | | | 175 | |
| Pro | Ala | Val | Leu | Gln | Ser | Ser | Gly | Leu | Tyr | Ser | Leu | Ser | Ser | Val | Val |
| | | | 180 | | | | | 185 | | | | | 190 | | |
| Thr | Val | Pro | Ser | Ser | Leu | Gly | Thr | Gln | Thr | Tyr | Ile | Cys | Asn | Val |
| | | 195 | | | | | 200 | | | | | 205 | | | |
| Asn | His | Lys | Pro | Ser | Asn | Thr | Lys | Val | Asp | Lys | Lys | Val | Glu | Pro | Lys |
| | 210 | | | | | 215 | | | | | 220 | | | | |
| Ser | Cys | Asp | Lys | Thr | His | Thr | Cys | Pro | Pro | Cys | Pro | Ala | Pro | Glu | Ala |
| 225 | | | | | 230 | | | | | 235 | | | | | 240 |
| Ala | Gly | Gly | Pro | Ser | Val | Phe | Leu | Phe | Pro | Pro | Lys | Pro | Lys | Asp | Thr |
| | | | | 245 | | | | | 250 | | | | | 255 | |
| Leu | Met | Ile | Ser | Arg | Thr | Pro | Glu | Val | Thr | Cys | Val | Val | Val | Asp | Val |
| | | | | 260 | | | | | 265 | | | | | 270 | |
| Ser | His | Glu | Asp | Pro | Glu | Val | Lys | Phe | Asn | Trp | Tyr | Val | Asp | Gly | Val |
| | | | 275 | | | | | 280 | | | | | 285 | | |
| Glu | Val | His | Asn | Ala | Lys | Thr | Lys | Pro | Arg | Glu | Glu | Gln | Tyr | Asn | Ser |
| | | | 290 | | | | | 295 | | | | | 300 | | |
| Thr | Tyr | Arg | Val | Val | Ser | Val | Leu | Thr | Val | Leu | His | Gln | Asp | Trp | Leu |
| 305 | | | | | 310 | | | | | 315 | | | | | 320 |
| Asn | Gly | Lys | Glu | Tyr | Lys | Cys | Lys | Val | Ser | Asn | Lys | Ala | Leu | Pro | Ala |
| | | | | 325 | | | | | 330 | | | | | 335 | |
| Pro | Ile | Glu | Lys | Thr | Ile | Ser | Lys | Ala | Lys | Gly | Gln | Pro | Arg | Glu | Pro |
| | | | 340 | | | | | 345 | | | | | 350 | | |
| Gln | Val | Tyr | Thr | Leu | Pro | Pro | Ser | Arg | Asp | Glu | Leu | Thr | Tyr | Ile | Ile |
| | | | | 355 | | | | | 360 | | | | | 365 | |
| Pro | Pro | Tyr | Asn | Gln | Val | Ser | Leu | Thr | Cys | Leu | Val | Lys | Gly | Phe | Tyr |
| | 370 | | | | | 375 | | | | | 380 | | | | |
| Pro | Ser | Asp | Ile | Ala | Val | Glu | Trp | Glu | Ser | Asn | Gly | Gln | Pro | Glu | Asn |
| 385 | | | | | 390 | | | | | 395 | | | | | 400 |

```
Asn Tyr Lys Thr Thr Pro Pro Val Leu Asp Ser Asp Gly Ser Phe Phe
                405                 410                 415

Leu Tyr Ser Lys Leu Thr Val Gly Ala Asp Arg Trp Leu Glu Gly Asn
                420                 425                 430

Val Phe Ser Cys Ser Val Met His Glu Ala Leu His Asn His Tyr Thr
                435                 440                 445

Gln Lys Ser Leu Ser Leu Ser Pro Gly
    450                 455

<210> SEQ ID NO 156
<211> LENGTH: 452
<212> TYPE: PRT
<213> ORGANISM: Artificial Sequence
<220> FEATURE:
<223> OTHER INFORMATION: heavy chain of FS22-172-003AA/S70 with LALA
      mutation

<400> SEQUENCE: 156

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
                20                  25                  30

Trp Ile His Trp Val Arg Gln Ala Pro Gly Lys Gly Leu Glu Trp Val
            35                  40                  45

Ala Trp Ile Ser Pro Tyr Gly Gly Ser Thr Tyr Tyr Ala Asp Ser Val
        50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
                100                 105                 110

Leu Val Thr Val Ser Ala Ala Ser Thr Lys Gly Pro Ser Val Phe Pro
            115                 120                 125

Leu Ala Pro Ser Ser Lys Ser Thr Ser Gly Gly Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
```

```
                    290                 295                 300
Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
                340                 345                 350

Pro Pro Ser Arg Asp Glu Leu Pro Tyr Ile Ile Pro Pro Tyr Asn Gln
            355                 360                 365

Val Ser Leu Thr Cys Leu Val Lys Gly Phe Tyr Pro Ser Asp Ile Ala
            370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Gly Ala Asp Arg Trp Leu Glu Gly Asn Val Phe Ser Cys Ser
                420                 425                 430

Val Met His Glu Ala Leu His Asn His Tyr Thr Gln Lys Ser Leu Ser
            435                 440                 445

Leu Ser Pro Gly
    450

<210> SEQ ID NO 157
<211> LENGTH: 214
<212> TYPE: PRT
<213> ORGANISM: Artificial Sequence
<220> FEATURE:
<223> OTHER INFORMATION: light chain of S70

<400> SEQUENCE: 157

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Leu Tyr His Pro Ala
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
```

Phe Asn Arg Gly Glu Cys
        210

<210> SEQ ID NO 158
<211> LENGTH: 450
<212> TYPE: PRT
<213> ORGANISM: Artificial Sequence
<220> FEATURE:
<223> OTHER INFORMATION: heavy chain of FS22-172-003AA/HelD1.3 with LALA
      mutation

<400> SEQUENCE: 158

Gln Val Gln Leu Gln Glu Ser Gly Pro Gly Leu Val Arg Pro Ser Gln
1               5                   10                  15

Thr Leu Ser Leu Thr Cys Thr Val Ser Gly Ser Thr Phe Ser Gly Tyr
            20                  25                  30

Gly Val Asn Trp Val Arg Gln Pro Pro Gly Arg Gly Leu Glu Trp Ile
        35                  40                  45

Gly Met Ile Trp Gly Asp Gly Asn Thr Asp Tyr Asn Ser Ala Leu Lys
    50                  55                  60

Ser Arg Val Thr Met Leu Val Asp Thr Ser Lys Asn Gln Phe Ser Leu
65                  70                  75                  80

Arg Leu Ser Ser Val Thr Ala Ala Asp Thr Ala Val Tyr Tyr Cys Ala
                85                  90                  95

Arg Glu Arg Asp Tyr Arg Leu Asp Tyr Trp Gly Gln Gly Ser Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

```
Lys Ala Lys Gly Gln Pro Arg Glu Pro Gln Val Tyr Thr Leu Pro Pro
            340                 345                 350

Ser Arg Asp Glu Leu Pro Tyr Ile Ile Pro Pro Tyr Asn Gln Val Ser
            355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
            405                 410                 415

Gly Ala Asp Arg Trp Leu Glu Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly
    450
```

<210> SEQ ID NO 159
<211> LENGTH: 214
<212> TYPE: PRT
<213> ORGANISM: Artificial Sequence
<220> FEATURE:
<223> OTHER INFORMATION: light chain of HelD1.3

<400> SEQUENCE: 159

```
Asp Ile Gln Met Thr Gln Ser Pro Ala Ser Leu Ser Ala Ser Val Gly
1               5                   10                  15

Glu Thr Val Thr Ile Thr Cys Arg Ala Ser Gly Asn Ile His Asn Tyr
            20                  25                  30

Leu Ala Trp Tyr Gln Gln Lys Gln Gly Lys Ser Pro Gln Leu Leu Val
        35                  40                  45

Tyr Asn Ala Lys Thr Leu Ala Asp Gly Val Pro Ser Arg Phe Ser Gly
50                  55                  60

Ser Gly Ser Gly Thr Gln Tyr Ser Leu Lys Ile Asn Ser Leu Gln Pro
65                  70                  75                  80

Glu Asp Phe Gly Ser Tyr Tyr Cys Gln His Phe Trp Ser Thr Pro Arg
            85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 160
<211> LENGTH: 447

<212> TYPE: PRT
<213> ORGANISM: Artificial Sequence
<220> FEATURE:
<223> OTHER INFORMATION: heavy chain of FS22m-063AA/S70 with LALA mutation

<400> SEQUENCE: 160

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ala Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Pro Tyr Trp Ser Tyr Val Ser Leu Thr Cys
        355                 360                 365

Leu Val Lys Gly Phe Tyr Pro Ser Asp Ile Ala Val Glu Trp Glu Ser
    370                 375                 380
```

```
Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Met Asn Tyr
                405                 410                 415

Arg Trp Glu Leu Gly Asn Val Phe Ser Cys Ser Val Met His Glu Ala
            420                 425                 430

Leu His Asn His Tyr Thr Gln Lys Ser Leu Ser Leu Ser Pro Gly
        435                 440                 445
```

<210> SEQ ID NO 161
<211> LENGTH: 445
<212> TYPE: PRT
<213> ORGANISM: Artificial Sequence
<220> FEATURE:
<223> OTHER INFORMATION: heavy chain of FS22m-063AA/HelD1.3 with LALA mutation

<400> SEQUENCE: 161

```
Gln Val Gln Leu Gln Glu Ser Gly Pro Gly Leu Val Arg Pro Ser Gln
1               5                   10                  15

Thr Leu Ser Leu Thr Cys Thr Val Ser Gly Ser Thr Phe Ser Gly Tyr
            20                  25                  30

Gly Val Asn Trp Val Arg Gln Pro Pro Gly Arg Gly Leu Glu Trp Ile
        35                  40                  45

Gly Met Ile Trp Gly Asp Gly Asn Thr Asp Tyr Asn Ser Ala Leu Lys
    50                  55                  60

Ser Arg Val Thr Met Leu Val Asp Thr Ser Lys Asn Gln Phe Ser Leu
65                  70                  75                  80

Arg Leu Ser Ser Val Thr Ala Ala Asp Thr Ala Val Tyr Tyr Cys Ala
                85                  90                  95

Arg Glu Arg Asp Tyr Arg Leu Asp Tyr Trp Gly Gln Gly Ser Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
```

```
                290                 295                 300
Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
                340                 345                 350

Ser Arg Asp Glu Pro Tyr Trp Ser Tyr Val Ser Leu Thr Cys Leu Val
                355                 360                 365

Lys Gly Phe Tyr Pro Ser Asp Ile Ala Val Glu Trp Glu Ser Asn Gly
                370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Met Asn Tyr Arg Trp
                405                 410                 415

Glu Leu Gly Asn Val Phe Ser Cys Ser Val Met His Glu Ala Leu His
                420                 425                 430

Asn His Tyr Thr Gln Lys Ser Leu Ser Leu Ser Pro Gly
                435                 440                 445

<210> SEQ ID NO 162
<211> LENGTH: 452
<212> TYPE: PRT
<213> ORGANISM: Artificial Sequence
<220> FEATURE:
<223> OTHER INFORMATION: heavy chain of G1-AA/E12v2 with LALA mutation

<400> SEQUENCE: 162

Glu Val Gln Leu Val Gln Ser Gly Ala Glu Val Lys Arg Pro Gly Ala
1               5                   10                  15

Ser Val Lys Val Ser Cys Lys Ala Ser Gly Tyr Pro Phe Thr Ser Tyr
                20                  25                  30

Gly Ile Ser Trp Val Arg Gln Ala Pro Gly Gln Gly Leu Glu Trp Met
            35                  40                  45

Gly Trp Ile Ser Ala Tyr Ser Gly Gly Thr Asn Tyr Ala Gln Lys Leu
50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Leu Phe Pro Thr Ile Phe Gly Val Ser Tyr Tyr Tyr Tyr
                100                 105                 110

Trp Gly Gln Gly Thr Leu Val Thr Val Ser Ser Ala Ser Thr Lys Gly
                115                 120                 125

Pro Ser Val Phe Pro Leu Ala Pro Ser Ser Lys Ser Thr Ser Gly Gly
            130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
                180                 185                 190

Thr Val Pro Ser Ser Ser Leu Gly Thr Gln Thr Tyr Ile Cys Asn Val
                195                 200                 205

Asn His Lys Pro Ser Asn Thr Lys Val Asp Lys Lys Val Glu Pro Lys
```

```
            210                 215                 220
Ser Cys Asp Lys Thr His Thr Cys Pro Pro Cys Pro Ala Pro Glu Ala
225                 230                 235                 240

Ala Gly Gly Pro Ser Val Phe Leu Phe Pro Pro Lys Pro Lys Asp Thr
            245                 250                 255

Leu Met Ile Ser Arg Thr Pro Glu Val Thr Cys Val Val Val Asp Val
                260                 265                 270

Ser His Glu Asp Pro Glu Val Lys Phe Asn Trp Tyr Val Asp Gly Val
            275                 280                 285

Glu Val His Asn Ala Lys Thr Lys Pro Arg Glu Glu Gln Tyr Asn Ser
        290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
        355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly
    450

<210> SEQ ID NO 163
<211> LENGTH: 448
<212> TYPE: PRT
<213> ORGANISM: Artificial Sequence
<220> FEATURE:
<223> OTHER INFORMATION: heavy chain of G1/S70

<400> SEQUENCE: 163

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ala Ala Ser Thr Lys Gly Pro Ser Val Phe Pro
```

115                 120                 125
Leu Ala Pro Ser Ser Lys Ser Thr Ser Gly Gly Thr Ala Ala Leu Gly
            130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 164
<211> LENGTH: 448
<212> TYPE: PRT
<213> ORGANISM: Artificial Sequence
<220> FEATURE:
<223> OTHER INFORMATION: heavy chain of G1-AA/S70 with LALA mutation

<400> SEQUENCE: 164

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val

```
            35                  40                  45
Ala Trp Ile Ser Pro Tyr Gly Gly Ser Thr Tyr Tyr Ala Asp Ser Val
 50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Arg Arg His Trp Pro Gly Gly Phe Asp Tyr Trp Gly Gln Gly Thr
                100                 105                 110

Leu Val Thr Val Ser Ala Ala Ser Thr Lys Gly Pro Ser Val Phe Pro
                115                 120                 125

Leu Ala Pro Ser Ser Lys Ser Thr Ser Gly Gly Thr Ala Ala Leu Gly
                130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
                180                 185                 190

Ser Leu Gly Thr Gln Thr Tyr Ile Cys Asn Val Asn His Lys Pro Ser
                195                 200                 205

Asn Thr Lys Val Asp Lys Lys Val Glu Pro Lys Ser Cys Asp Lys Thr
210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Asp Val Ser His Glu Asp Pro
                260                 265                 270

Glu Val Lys Phe Asn Trp Tyr Val Asp Gly Val Glu Val His Asn Ala
                275                 280                 285

Lys Thr Lys Pro Arg Glu Glu Gln Tyr Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
                340                 345                 350

Pro Pro Ser Arg Asp Glu Leu Thr Lys Asn Gln Val Ser Leu Thr Cys
                355                 360                 365

Leu Val Lys Gly Phe Tyr Pro Ser Asp Ile Ala Val Glu Trp Glu Ser
                370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly Lys
                435                 440                 445

<210> SEQ ID NO 165
```

```
<211> LENGTH: 448
<212> TYPE: PRT
<213> ORGANISM: Artificial Sequence
<220> FEATURE:
<223> OTHER INFORMATION: heavy chain of G1/4420

<400> SEQUENCE: 165

Glu Val Lys Leu Asp Glu Thr Gly Gly Gly Leu Val Gln Pro Gly Arg
1               5                   10                  15

Pro Met Lys Leu Ser Cys Val Ala Ser Gly Phe Thr Phe Ser Asp Tyr
            20                  25                  30

Trp Met Asn Trp Val Arg Gln Ser Pro Glu Lys Gly Leu Glu Trp Val
        35                  40                  45

Ala Gln Ile Arg Asn Lys Pro Tyr Asn Tyr Glu Thr Tyr Tyr Ser Asp
    50                  55                  60

Ser Val Lys Gly Arg Phe Thr Ile Ser Arg Asp Asp Ser Lys Ser Ser
65                  70                  75                  80

Val Tyr Leu Gln Met Asn Asn Leu Arg Val Glu Asp Met Gly Ile Tyr
                85                  90                  95

Tyr Cys Thr Gly Ser Tyr Tyr Gly Met Asp Tyr Trp Gly Gln Gly Thr
            100                 105                 110

Ser Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380
```

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
            405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
            435                 440                 445

<210> SEQ ID NO 166
<211> LENGTH: 219
<212> TYPE: PRT
<213> ORGANISM: Artificial Sequence
<220> FEATURE:
<223> OTHER INFORMATION: light chain of 4420

<400> SEQUENCE: 166

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu Arg Trp Tyr Leu Gln Lys Pro Gly Gln Ser
            35                  40                  45

Pro Lys Val Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Trp Thr Phe Gly Gly Gly Thr Lys Leu Glu Ile Lys
            100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
            195                 200                 205

Pro Val Thr Lys Ser Phe Asn Arg Gly Glu Cys
    210                 215

<210> SEQ ID NO 167
<211> LENGTH: 448
<212> TYPE: PRT
<213> ORGANISM: Artificial Sequence
<220> FEATURE:
<223> OTHER INFORMATION: heavy chain of G1-AA/4420 with LALA mutation

<400> SEQUENCE: 167

Glu Val Lys Leu Asp Glu Thr Gly Gly Gly Leu Val Gln Pro Gly Arg
1               5                   10                  15

Pro Met Lys Leu Ser Cys Val Ala Ser Gly Phe Thr Phe Ser Asp Tyr

-continued

```
                20                  25                  30
Trp Met Asn Trp Val Arg Gln Ser Pro Glu Lys Gly Leu Glu Trp Val
            35                  40                  45
Ala Gln Ile Arg Asn Lys Pro Tyr Asn Tyr Glu Thr Tyr Tyr Ser Asp
        50                  55                  60
Ser Val Lys Gly Arg Phe Thr Ile Ser Arg Asp Asp Ser Lys Ser Ser
65                  70                  75                  80
Val Tyr Leu Gln Met Asn Asn Leu Arg Val Glu Asp Met Gly Ile Tyr
                85                  90                  95
Tyr Cys Thr Gly Ser Tyr Tyr Gly Met Asp Tyr Trp Gly Gln Gly Thr
            100                 105                 110
Ser Val Thr Val Ser Ser Ala Ser Thr Lys Gly Pro Ser Val Phe Pro
        115                 120                 125
Leu Ala Pro Ser Ser Lys Ser Thr Ser Gly Gly Thr Ala Ala Leu Gly
    130                 135                 140
Cys Leu Val Lys Asp Tyr Phe Pro Glu Pro Val Thr Val Ser Trp Asn
145                 150                 155                 160
Ser Gly Ala Leu Thr Ser Gly Val His Thr Phe Pro Ala Val Leu Gln
                165                 170                 175
Ser Ser Gly Leu Tyr Ser Leu Ser Ser Val Val Thr Val Pro Ser Ser
            180                 185                 190
Ser Leu Gly Thr Gln Thr Tyr Ile Cys Asn Val Asn His Lys Pro Ser
        195                 200                 205
Asn Thr Lys Val Asp Lys Lys Val Glu Pro Lys Ser Cys Asp Lys Thr
    210                 215                 220
His Thr Cys Pro Pro Cys Pro Ala Pro Glu Ala Ala Gly Gly Pro Ser
225                 230                 235                 240
Val Phe Leu Phe Pro Pro Lys Pro Lys Asp Thr Leu Met Ile Ser Arg
                245                 250                 255
Thr Pro Glu Val Thr Cys Val Val Val Asp Val Ser His Glu Asp Pro
            260                 265                 270
Glu Val Lys Phe Asn Trp Tyr Val Asp Gly Val Glu Val His Asn Ala
        275                 280                 285
Lys Thr Lys Pro Arg Glu Glu Gln Tyr Asn Ser Thr Tyr Arg Val Val
    290                 295                 300
Ser Val Leu Thr Val Leu His Gln Asp Trp Leu Asn Gly Lys Glu Tyr
305                 310                 315                 320
Lys Cys Lys Val Ser Asn Lys Ala Leu Pro Ala Pro Ile Glu Lys Thr
                325                 330                 335
Ile Ser Lys Ala Lys Gly Gln Pro Arg Glu Pro Gln Val Tyr Thr Leu
            340                 345                 350
Pro Pro Ser Arg Asp Glu Leu Thr Lys Asn Gln Val Ser Leu Thr Cys
        355                 360                 365
Leu Val Lys Gly Phe Tyr Pro Ser Asp Ile Ala Val Glu Trp Glu Ser
    370                 375                 380
Asn Gly Gln Pro Glu Asn Asn Tyr Lys Thr Thr Pro Pro Val Leu Asp
385                 390                 395                 400
Ser Asp Gly Ser Phe Phe Leu Tyr Ser Lys Leu Thr Val Asp Lys Ser
                405                 410                 415
Arg Trp Gln Gln Gly Asn Val Phe Ser Cys Ser Val Met His Glu Ala
            420                 425                 430
Leu His Asn His Tyr Thr Gln Lys Ser Leu Ser Leu Ser Pro Gly Lys
        435                 440                 445
```

<210> SEQ ID NO 168
<211> LENGTH: 446
<212> TYPE: PRT
<213> ORGANISM: Artificial Sequence
<220> FEATURE:
<223> OTHER INFORMATION: heavy chain of G1-AA/HelD1.3 with LALA mutation

<400> SEQUENCE: 168

```
Gln Val Gln Leu Gln Glu Ser Gly Pro Gly Leu Val Arg Pro Ser Gln
1               5                   10                  15

Thr Leu Ser Leu Thr Cys Thr Val Ser Gly Ser Thr Phe Ser Gly Tyr
            20                  25                  30

Gly Val Asn Trp Val Arg Gln Pro Pro Gly Arg Gly Leu Glu Trp Ile
        35                  40                  45

Gly Met Ile Trp Gly Asp Gly Asn Thr Asp Tyr Asn Ser Ala Leu Lys
    50                  55                  60

Ser Arg Val Thr Met Leu Val Asp Thr Ser Lys Asn Gln Phe Ser Leu
65                  70                  75                  80

Arg Leu Ser Ser Val Thr Ala Ala Asp Thr Ala Val Tyr Tyr Cys Ala
                85                  90                  95

Arg Glu Arg Asp Tyr Arg Leu Asp Tyr Trp Gly Gln Gly Ser Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365
```

```
Lys Gly Phe Tyr Pro Ser Asp Ile Ala Val Glu Trp Glu Ser Asn Gly
            370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
            435                 440                 445

<210> SEQ ID NO 169
<211> LENGTH: 460
<212> TYPE: PRT
<213> ORGANISM: Artificial Sequence
<220> FEATURE:
<223> OTHER INFORMATION: heavy chain of G1-AA/MLS109 with LALA mutation

<400> SEQUENCE: 169

Glu Glu Gln Val Leu Glu Ser Gly Gly Gly Leu Val Lys Pro Gly Gly
1               5                   10                  15

Ser Leu Arg Leu Ser Cys Ala Ala Ser Gly Phe Thr Phe Ser Pro Tyr
            20                  25                  30

Ser Val Phe Trp Val Arg Gln Ala Pro Gly Lys Gly Leu Glu Trp Val
        35                  40                  45

Ser Ser Ile Asn Ser Asp Ser Thr Tyr Lys Tyr Tyr Ala Asp Ser Val
    50                  55                  60

Lys Gly Arg Phe Thr Ile Ser Arg Asp Asn Ala Glu Asn Ser Ile Phe
65                  70                  75                  80

Leu Gln Met Asn Ser Leu Arg Ala Glu Asp Thr Ala Val Tyr Tyr Cys
                85                  90                  95

Ala Arg Asp Arg Ser Tyr Tyr Ala Phe Ser Ser Gly Ser Leu Ser Asp
            100                 105                 110

Tyr Tyr Tyr Gly Leu Asp Val Trp Gly Gln Gly Thr Thr Val Ile Val
        115                 120                 125

Ser Ser Ala Ser Thr Lys Gly Pro Ser Val Phe Pro Leu Ala Pro Ser
    130                 135                 140

Ser Lys Ser Thr Ser Gly Gly Thr Ala Ala Leu Gly Cys Leu Val Lys
145                 150                 155                 160

Asp Tyr Phe Pro Glu Pro Val Thr Val Ser Trp Asn Ser Gly Ala Leu
                165                 170                 175

Thr Ser Gly Val His Thr Phe Pro Ala Val Leu Gln Ser Ser Gly Leu
            180                 185                 190

Tyr Ser Leu Ser Ser Val Val Thr Val Pro Ser Ser Ser Leu Gly Thr
        195                 200                 205

Gln Thr Tyr Ile Cys Asn Val Asn His Lys Pro Ser Asn Thr Lys Val
    210                 215                 220

Asp Lys Lys Val Glu Pro Lys Ser Cys Asp Lys Thr His Thr Cys Pro
225                 230                 235                 240

Pro Cys Pro Ala Pro Glu Ala Ala Gly Gly Pro Ser Val Phe Leu Phe
                245                 250                 255

Pro Pro Lys Pro Lys Asp Thr Leu Met Ile Ser Arg Thr Pro Glu Val
            260                 265                 270

Thr Cys Val Val Val Asp Val Ser His Glu Asp Pro Glu Val Lys Phe
        275                 280                 285
```

```
Asn Trp Tyr Val Asp Gly Val Glu Val His Asn Ala Lys Thr Lys Pro
            290                 295                 300

Arg Glu Glu Gln Tyr Asn Ser Thr Tyr Arg Val Val Ser Val Leu Thr
305                 310                 315                 320

Val Leu His Gln Asp Trp Leu Asn Gly Lys Glu Tyr Lys Cys Lys Val
                325                 330                 335

Ser Asn Lys Ala Leu Pro Ala Pro Ile Glu Lys Thr Ile Ser Lys Ala
            340                 345                 350

Lys Gly Gln Pro Arg Glu Pro Gln Val Tyr Thr Leu Pro Pro Ser Arg
            355                 360                 365

Asp Glu Leu Thr Lys Asn Gln Val Ser Leu Thr Cys Leu Val Lys Gly
            370                 375                 380

Phe Tyr Pro Ser Asp Ile Ala Val Glu Trp Glu Ser Asn Gly Gln Pro
385                 390                 395                 400

Glu Asn Asn Tyr Lys Thr Thr Pro Pro Val Leu Asp Ser Asp Gly Ser
                405                 410                 415

Phe Phe Leu Tyr Ser Lys Leu Thr Val Asp Lys Ser Arg Trp Gln Gln
                420                 425                 430

Gly Asn Val Phe Ser Cys Ser Val Met His Glu Ala Leu His Asn His
            435                 440                 445

Tyr Thr Gln Lys Ser Leu Ser Leu Ser Pro Gly Lys
    450                 455                 460

<210> SEQ ID NO 170
<211> LENGTH: 219
<212> TYPE: PRT
<213> ORGANISM: Artificial Sequence
<220> FEATURE:
<223> OTHER INFORMATION: light chain of MLS109

<400> SEQUENCE: 170

Asp Ile Val Met Thr Gln Ser Pro Leu Ser Leu Ser Val Thr Pro Gly
1               5                   10                  15

Glu Pro Ala Ser Ile Ser Cys Arg Ser Ser Gln Ser Leu Leu His Thr
                20                  25                  30

Asn Gly Tyr Asn Tyr Leu Asp Trp Tyr Val Gln Lys Pro Gly Gln Ser
            35                  40                  45

Pro Gln Leu Leu Ile Tyr Leu Ala Ser Asn Arg Ala Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Thr Glu Asp Val Gly Val Tyr Tyr Cys Met Gln Ala
                85                  90                  95

Leu Gln Ile Pro Arg Thr Phe Gly Gln Gly Thr Lys Val Glu Ile Lys
                100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
        130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190
```

```
Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 171
<211> LENGTH: 13
<212> TYPE: PRT
<213> ORGANISM: Artificial Sequence
<220> FEATURE:
<223> OTHER INFORMATION: FS22-172-003 CH3 domain AB loop

<400> SEQUENCE: 171

Arg Asp Glu Leu Pro Tyr Ile Ile Pro Pro Tyr Asn Gln
1               5                   10

<210> SEQ ID NO 172
<211> LENGTH: 10
<212> TYPE: PRT
<213> ORGANISM: Artificial Sequence
<220> FEATURE:
<223> OTHER INFORMATION: FS22-172-003 CH3 domain EF loop

<400> SEQUENCE: 172

Gly Ala Asp Arg Trp Leu Glu Gly Asn Val
1               5                   10

<210> SEQ ID NO 173
<211> LENGTH: 13
<212> TYPE: PRT
<213> ORGANISM: Artificial Sequence
<220> FEATURE:
<223> OTHER INFORMATION: FS22-53-008 CH3 domain AB loop

<400> SEQUENCE: 173

Arg Asp Glu Leu Asn Pro Pro Tyr Leu Phe Ser Asn Gln
1               5                   10

<210> SEQ ID NO 174
<211> LENGTH: 10
<212> TYPE: PRT
<213> ORGANISM: Artificial Sequence
<220> FEATURE:
<223> OTHER INFORMATION: FS22-53-008 CH3 domain EF loop

<400> SEQUENCE: 174

Asp Tyr Trp Arg Trp Leu Glu Gly Asn Val
1               5                   10

<210> SEQ ID NO 175
<211> LENGTH: 10
<212> TYPE: PRT
<213> ORGANISM: Artificial Sequence
<220> FEATURE:
<223> OTHER INFORMATION: FS22-053-017 CH3 domain EF loop

<400> SEQUENCE: 175

Tyr His Trp Arg Trp Leu Glu Gly Asn Val
1               5                   10

<210> SEQ ID NO 176
<211> LENGTH: 110
<212> TYPE: PRT
<213> ORGANISM: Artificial Sequence
<220> FEATURE:
<223> OTHER INFORMATION: CH2 domain with LALA mutation and P114A
``` mutation

<400> SEQUENCE: 176

Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
            85                  90                  95

Ala Leu Ala Ala Pro Ile Glu Lys Thr Ile Ser Lys Ala Lys
            100                 105                 110

<210> SEQ ID NO 177
<211> LENGTH: 452
<212> TYPE: PRT
<213> ORGANISM: Artificial Sequence
<220> FEATURE:
<223> OTHER INFORMATION: heavy chain of G1/280_02_G02

<400> SEQUENCE: 177

Glu Val Gln Leu Val Gln Ser Gly Ala Glu Val Lys Arg Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
            85                  90                  95

Ala Arg Asp Leu Phe Pro Thr Ile Phe Gly Val Ser Tyr Tyr Tyr Tyr
            100                 105                 110

Trp Gly Gln Gly Thr Leu Val Thr Val Ser Ser Ala Ser Thr Lys Gly
            115                 120                 125

Pro Ser Val Phe Pro Leu Ala Pro Ser Ser Lys Ser Thr Ser Gly Gly
            130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
            165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
            195                 200                 205

Asn His Lys Pro Ser Asn Thr Lys Val Asp Lys Lys Val Glu Pro Lys
            210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly
    450

<210> SEQ ID NO 178
<211> LENGTH: 217
<212> TYPE: PRT
<213> ORGANISM: Artificial Sequence
<220> FEATURE:
<223> OTHER INFORMATION: light chain of G1/280_02_G02

<400> SEQUENCE: 178

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Ser Val Ser Trp Tyr Gln Gln Phe Pro Gly Lys Ala Pro Lys Leu
        35                  40                  45

Met Ile Phe Glu Val Thr Asn Arg Pro Ser Gly Val Ser Asp Arg Phe
    50                  55                  60

Ser Gly Ser Lys Ser Asp Asn Thr Ala Ser Leu Thr Ile Ser Gly Leu
65                  70                  75                  80

Gln Ala Glu Asp Glu Ala Glu Tyr Tyr Cys Ser Ser Phe Lys Arg Gly
                85                  90                  95

Ser Thr Leu Val Val Phe Gly Gly Gly Thr Lys Leu Thr Val Leu Gly
            100                 105                 110

Gln Pro Ala Ala Ala Pro Ser Val Thr Leu Phe Pro Pro Ser Ser Glu
        115                 120                 125

Glu Leu Gln Ala Asn Lys Ala Thr Leu Val Cys Leu Ile Ser Asp Phe
    130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Pro Thr Glu Cys Ser
    210                 215

<210> SEQ ID NO 179
<211> LENGTH: 272
<212> TYPE: PRT
<213> ORGANISM: Homo sapiens

<400> SEQUENCE: 179

Phe Thr Val Thr Val Pro Lys Asp Leu Tyr Val Val Glu Tyr Gly Ser
1               5                   10                  15

Asn Met Thr Ile Glu Cys Lys Phe Pro Val Glu Lys Gln Leu Asp Leu
            20                  25                  30

Ala Ala Leu Ile Val Tyr Trp Glu Met Glu Asp Lys Asn Ile Ile Gln
        35                  40                  45

Phe Val His Gly Glu Glu Asp Leu Lys Val Gln His Ser Ser Tyr Arg
    50                  55                  60

Gln Arg Ala Arg Leu Leu Lys Asp Gln Leu Ser Leu Gly Asn Ala Ala
65                  70                  75                  80

Leu Gln Ile Thr Asp Val Lys Leu Gln Asp Ala Gly Val Tyr Arg Cys
                85                  90                  95

Met Ile Ser Tyr Gly Gly Ala Asp Tyr Lys Arg Ile Thr Val Lys Val
            100                 105                 110

Asn Ala Pro Tyr Asn Lys Ile Asn Gln Arg Ile Leu Val Val Asp Pro
        115                 120                 125

Val Thr Ser Glu His Glu Leu Thr Cys Gln Ala Glu Gly Tyr Pro Lys
    130                 135                 140

Ala Glu Val Ile Trp Thr Ser Ser Asp His Gln Val Leu Ser Gly Lys
145                 150                 155                 160

Thr Thr Thr Thr Asn Ser Lys Arg Glu Glu Lys Leu Phe Asn Val Thr
                165                 170                 175

Ser Thr Leu Arg Ile Asn Thr Thr Asn Glu Ile Phe Tyr Cys Thr
            180                 185                 190

Phe Arg Arg Leu Asp Pro Glu Glu Asn His Thr Ala Glu Leu Val Ile
        195                 200                 205

Pro Glu Leu Pro Leu Ala His Pro Pro Asn Glu Arg Thr His Leu Val
    210                 215                 220

Ile Leu Gly Ala Ile Leu Leu Cys Leu Gly Val Ala Leu Thr Phe Ile
225                 230                 235                 240

Phe Arg Leu Arg Lys Gly Arg Met Met Asp Val Lys Lys Cys Gly Ile
                245                 250                 255

Gln Asp Thr Asn Ser Lys Lys Gln Ser Asp Thr His Leu Glu Glu Thr
            260                 265                 270

<210> SEQ ID NO 180
<211> LENGTH: 220
<212> TYPE: PRT

<213> ORGANISM: Homo sapiens

<400> SEQUENCE: 180

Phe Thr Val Thr Val Pro Lys Asp Leu Tyr Val Val Glu Tyr Gly Ser
1               5                   10                  15

Asn Met Thr Ile Glu Cys Lys Phe Pro Val Glu Lys Gln Leu Asp Leu
            20                  25                  30

Ala Ala Leu Ile Val Tyr Trp Glu Met Glu Asp Lys Asn Ile Ile Gln
        35                  40                  45

Phe Val His Gly Glu Glu Asp Leu Lys Val Gln His Ser Ser Tyr Arg
    50                  55                  60

Gln Arg Ala Arg Leu Leu Lys Asp Gln Leu Ser Leu Gly Asn Ala Ala
65                  70                  75                  80

Leu Gln Ile Thr Asp Val Lys Leu Gln Asp Ala Gly Val Tyr Arg Cys
                85                  90                  95

Met Ile Ser Tyr Gly Gly Ala Asp Tyr Lys Arg Ile Thr Val Lys Val
            100                 105                 110

Asn Ala Pro Tyr Asn Lys Ile Asn Gln Arg Ile Leu Val Val Asp Pro
        115                 120                 125

Val Thr Ser Glu His Glu Leu Thr Cys Gln Ala Glu Gly Tyr Pro Lys
    130                 135                 140

Ala Glu Val Ile Trp Thr Ser Ser Asp His Gln Val Leu Ser Gly Lys
145                 150                 155                 160

Thr Thr Thr Thr Asn Ser Lys Arg Glu Glu Lys Leu Phe Asn Val Thr
                165                 170                 175

Ser Thr Leu Arg Ile Asn Thr Thr Asn Glu Ile Phe Tyr Cys Thr
                180                 185                 190

Phe Arg Arg Leu Asp Pro Glu Glu Asn His Thr Ala Glu Leu Val Ile
            195                 200                 205

Pro Glu Leu Pro Leu Ala His Pro Pro Asn Glu Arg
    210                 215                 220

<210> SEQ ID NO 181
<211> LENGTH: 272
<212> TYPE: PRT
<213> ORGANISM: Mus musculus

<400> SEQUENCE: 181

Phe Thr Ile Thr Ala Pro Lys Asp Leu Tyr Val Val Glu Tyr Gly Ser
1               5                   10                  15

Asn Val Thr Met Glu Cys Arg Phe Pro Val Glu Arg Glu Leu Asp Leu
            20                  25                  30

Leu Ala Leu Val Val Tyr Trp Glu Lys Glu Asp Glu Gln Val Ile Gln
        35                  40                  45

Phe Val Ala Gly Glu Glu Asp Leu Lys Pro Gln His Ser Asn Phe Arg
    50                  55                  60

Gly Arg Ala Ser Leu Pro Lys Asp Gln Leu Leu Lys Gly Asn Ala Ala
65                  70                  75                  80

Leu Gln Ile Thr Asp Val Lys Leu Gln Asp Ala Gly Val Tyr Cys Cys
                85                  90                  95

Ile Ile Ser Tyr Gly Gly Ala Asp Tyr Lys Arg Ile Thr Leu Lys Val
            100                 105                 110

Asn Ala Pro Tyr Arg Lys Ile Asn Gln Arg Ile Ser Val Asp Pro Ala
        115                 120                 125

Thr Ser Glu His Glu Leu Ile Cys Gln Ala Glu Gly Tyr Pro Glu Ala

```
                130                 135                 140
Glu Val Ile Trp Thr Asn Ser Asp His Gln Pro Val Ser Gly Lys Arg
145                 150                 155                 160

Ser Val Thr Thr Ser Arg Thr Glu Gly Met Leu Leu Asn Val Thr Ser
                165                 170                 175

Ser Leu Arg Val Asn Ala Thr Ala Asn Asp Val Phe Tyr Cys Thr Phe
            180                 185                 190

Trp Arg Ser Gln Pro Gly Gln Asn His Thr Ala Glu Leu Ile Ile Pro
        195                 200                 205

Glu Leu Pro Ala Thr His Pro Pro Gln Asn Arg Thr His Trp Val Leu
210                 215                 220

Leu Gly Ser Ile Leu Leu Phe Leu Ile Val Val Ser Thr Val Leu Leu
225                 230                 235                 240

Phe Leu Arg Lys Gln Val Arg Met Leu Asp Val Glu Lys Cys Gly Val
                245                 250                 255

Glu Asp Thr Ser Ser Lys Asn Arg Asn Asp Thr Gln Phe Glu Glu Thr
            260                 265                 270

<210> SEQ ID NO 182
<211> LENGTH: 221
<212> TYPE: PRT
<213> ORGANISM: Mus musculus

<400> SEQUENCE: 182

Phe Thr Ile Thr Ala Pro Lys Asp Leu Tyr Val Val Glu Tyr Gly Ser
1               5                   10                  15

Asn Val Thr Met Glu Cys Arg Phe Pro Val Glu Arg Glu Leu Asp Leu
                20                  25                  30

Leu Ala Leu Val Val Tyr Trp Glu Lys Glu Asp Glu Gln Val Ile Gln
            35                  40                  45

Phe Val Ala Gly Glu Glu Asp Leu Lys Pro Gln His Ser Asn Phe Arg
        50                  55                  60

Gly Arg Ala Ser Leu Pro Lys Asp Gln Leu Leu Lys Gly Asn Ala Ala
65                  70                  75                  80

Leu Gln Ile Thr Asp Val Lys Leu Gln Asp Ala Gly Val Tyr Cys Cys
                85                  90                  95

Ile Ile Ser Tyr Gly Gly Ala Asp Tyr Lys Arg Ile Thr Leu Lys Val
            100                 105                 110

Asn Ala Pro Tyr Arg Lys Ile Asn Gln Arg Ile Ser Val Asp Pro Ala
        115                 120                 125

Thr Ser Glu His Glu Leu Ile Cys Gln Ala Glu Gly Tyr Pro Glu Ala
    130                 135                 140

Glu Val Ile Trp Thr Asn Ser Asp His Gln Pro Val Ser Gly Lys Arg
145                 150                 155                 160

Ser Val Thr Thr Ser Arg Thr Glu Gly Met Leu Leu Asn Val Thr Ser
                165                 170                 175

Ser Leu Arg Val Asn Ala Thr Ala Asn Asp Val Phe Tyr Cys Thr Phe
            180                 185                 190

Trp Arg Ser Gln Pro Gly Gln Asn His Thr Ala Glu Leu Ile Ile Pro
        195                 200                 205

Glu Leu Pro Ala Thr His Pro Pro Gln Asn Arg Thr His
    210                 215                 220

<210> SEQ ID NO 183
<211> LENGTH: 328
```

```
<212> TYPE: PRT
<213> ORGANISM: Macaca fascicularis

<400> SEQUENCE: 183

Phe Thr Val Thr Val Pro Lys Asp Leu Tyr Val Val Glu Tyr Gly Ser
1               5                   10                  15

Asn Met Thr Ile Glu Cys Lys Phe Pro Val Glu Lys Gln Leu Asp Leu
            20                  25                  30

Thr Ser Leu Ile Val Tyr Trp Glu Met Glu Asp Lys Asn Ile Ile Gln
        35                  40                  45

Phe Val His Gly Glu Glu Asp Leu Lys Val Gln His Ser Asn Tyr Arg
    50                  55                  60

Gln Arg Ala Gln Leu Leu Lys Asp Gln Leu Ser Leu Gly Asn Ala Ala
65                  70                  75                  80

Leu Arg Ile Thr Asp Val Lys Leu Gln Asp Ala Gly Val Tyr Arg Cys
                85                  90                  95

Met Ile Ser Tyr Gly Gly Ala Asp Tyr Lys Arg Ile Thr Val Lys Val
            100                 105                 110

Asn Ala Pro Tyr Asn Lys Ile Asn Gln Arg Ile Leu Val Val Asp Pro
        115                 120                 125

Val Thr Ser Glu His Glu Leu Thr Cys Gln Ala Glu Gly Tyr Pro Lys
    130                 135                 140

Ala Glu Val Ile Trp Thr Ser Ser Asp His Gln Val Leu Ser Gly Lys
145                 150                 155                 160

Thr Thr Thr Thr Asn Ser Lys Arg Glu Glu Lys Leu Leu Asn Val Thr
                165                 170                 175

Ser Thr Leu Arg Ile Asn Thr Thr Ala Asn Glu Ile Phe Tyr Cys Ile
            180                 185                 190

Phe Arg Arg Leu Asp Pro Glu Glu Asn His Thr Ala Glu Leu Val Ile
        195                 200                 205

Pro Glu Leu Pro Leu Ala Leu Pro Pro Asn Glu Arg Thr His Leu Val
    210                 215                 220

Ile Leu Gly Ala Ile Phe Leu Leu Gly Val Ala Leu Thr Phe Ile
225                 230                 235                 240

Phe Tyr Leu Arg Lys Gly Arg Met Met Asp Met Lys Lys Cys Gly Ile
                245                 250                 255

Arg Val Thr Asn Ser Lys Lys Gln Arg Asp Thr Gln Leu Glu Glu Thr
            260                 265                 270

Lys Gly Pro Ser Ala Arg Phe Asp Ile Pro Asp Glu Ile Pro Val Ile
        275                 280                 285

Glu Ser Lys Pro Asn Thr Leu Ser Ile Val Leu Gly Thr Thr Leu Thr
    290                 295                 300

Val Ala Met Ile Ile Val Ala Thr Ile Phe Gly Tyr Arg Arg Gln Lys
305                 310                 315                 320

Gly Arg Leu Arg Thr Leu Lys Leu
                325

<210> SEQ ID NO 184
<211> LENGTH: 222
<212> TYPE: PRT
<213> ORGANISM: Macaca fascicularis

<400> SEQUENCE: 184

Phe Thr Val Thr Val Pro Lys Asp Leu Tyr Val Val Glu Tyr Gly Ser
1               5                   10                  15
```

```
Asn Met Thr Ile Glu Cys Lys Phe Pro Val Glu Lys Gln Leu Asp Leu
             20                  25                  30

Thr Ser Leu Ile Val Tyr Trp Glu Met Glu Asp Lys Asn Ile Ile Gln
         35                  40                  45

Phe Val His Gly Glu Glu Asp Leu Lys Val Gln His Ser Asn Tyr Arg
     50                  55                  60

Gln Arg Ala Gln Leu Leu Lys Asp Gln Leu Ser Leu Gly Asn Ala Ala
 65                  70                  75                  80

Leu Arg Ile Thr Asp Val Lys Leu Gln Asp Ala Gly Val Tyr Arg Cys
                 85                  90                  95

Met Ile Ser Tyr Gly Gly Ala Asp Tyr Lys Arg Ile Thr Val Lys Val
            100                 105                 110

Asn Ala Pro Tyr Asn Lys Ile Asn Gln Arg Ile Leu Val Val Asp Pro
        115                 120                 125

Val Thr Ser Glu His Glu Leu Thr Cys Gln Ala Glu Gly Tyr Pro Lys
    130                 135                 140

Ala Glu Val Ile Trp Thr Ser Asp His Gln Val Leu Ser Gly Lys Thr
145                 150                 155                 160

Thr Thr Thr Thr Asn Ser Lys Arg Glu Glu Lys Leu Leu Asn Val Thr
                165                 170                 175

Ser Thr Leu Arg Ile Asn Thr Thr Ala Asn Glu Ile Phe Tyr Cys Ile
            180                 185                 190

Phe Arg Arg Leu Asp Pro Glu Glu Asn His Thr Ala Glu Leu Val Ile
        195                 200                 205

Pro Glu Leu Pro Leu Ala Leu Pro Pro Asn Glu Arg Thr His
    210                 215                 220

<210> SEQ ID NO 185
<211> LENGTH: 232
<212> TYPE: PRT
<213> ORGANISM: Homo sapiens

<400> SEQUENCE: 185

Leu Gln Asp Pro Cys Ser Asn Cys Pro Ala Gly Thr Phe Cys Asp Asn
1               5                  10                  15

Asn Arg Asn Gln Ile Cys Ser Pro Cys Pro Pro Asn Ser Phe Ser Ser
             20                  25                  30

Ala Gly Gly Gln Arg Thr Cys Asp Ile Cys Arg Gln Cys Lys Gly Val
         35                  40                  45

Phe Arg Thr Arg Lys Glu Cys Ser Ser Thr Ser Asn Ala Glu Cys Asp
     50                  55                  60

Cys Thr Pro Gly Phe His Cys Leu Gly Ala Gly Cys Ser Met Cys Glu
 65                  70                  75                  80

Gln Asp Cys Lys Gln Gly Gln Glu Leu Thr Lys Lys Gly Cys Lys Asp
                 85                  90                  95

Cys Cys Phe Gly Thr Phe Asn Asp Gln Lys Arg Gly Ile Cys Arg Pro
            100                 105                 110

Trp Thr Asn Cys Ser Leu Asp Gly Lys Ser Val Leu Val Asn Gly Thr
        115                 120                 125

Lys Glu Arg Asp Val Val Cys Gly Pro Ser Pro Ala Asp Leu Ser Pro
    130                 135                 140

Gly Ala Ser Ser Val Thr Pro Pro Ala Pro Ala Arg Glu Pro Gly His
145                 150                 155                 160

Ser Pro Gln Ile Ile Ser Phe Phe Leu Ala Leu Thr Ser Thr Ala Leu
                165                 170                 175
```

Leu Phe Leu Leu Phe Phe Leu Thr Leu Arg Phe Ser Val Val Lys Arg
                180                 185                 190

Gly Arg Lys Lys Leu Leu Tyr Ile Phe Lys Gln Pro Phe Met Arg Pro
            195                 200                 205

Val Gln Thr Thr Gln Glu Glu Asp Gly Cys Ser Cys Arg Phe Pro Glu
210                 215                 220

Glu Glu Glu Gly Gly Cys Glu Leu
225                 230

<210> SEQ ID NO 186
<211> LENGTH: 163
<212> TYPE: PRT
<213> ORGANISM: Homo sapiens

<400> SEQUENCE: 186

Leu Gln Asp Pro Cys Ser Asn Cys Pro Ala Gly Thr Phe Cys Asp Asn
1               5                   10                  15

Asn Arg Asn Gln Ile Cys Ser Pro Cys Pro Asn Ser Phe Ser Ser
            20                  25                  30

Ala Gly Gly Gln Arg Thr Cys Asp Ile Cys Arg Gln Cys Lys Gly Val
            35                  40                  45

Phe Arg Thr Arg Lys Glu Cys Ser Ser Thr Ser Asn Ala Glu Cys Asp
50                  55                  60

Cys Thr Pro Gly Phe His Cys Leu Gly Ala Gly Cys Ser Met Cys Glu
65                  70                  75                  80

Gln Asp Cys Lys Gln Gly Gln Glu Leu Thr Lys Lys Gly Cys Lys Asp
                85                  90                  95

Cys Cys Phe Gly Thr Phe Asn Asp Gln Lys Arg Gly Ile Cys Arg Pro
            100                 105                 110

Trp Thr Asn Cys Ser Leu Asp Gly Lys Ser Val Leu Val Asn Gly Thr
        115                 120                 125

Lys Glu Arg Asp Val Val Cys Gly Pro Ser Pro Ala Asp Leu Ser Pro
130                 135                 140

Gly Ala Ser Ser Val Thr Pro Pro Ala Pro Ala Arg Glu Pro Gly His
145                 150                 155                 160

Ser Pro Gln

<210> SEQ ID NO 187
<211> LENGTH: 233
<212> TYPE: PRT
<213> ORGANISM: Mus musculus

<400> SEQUENCE: 187

Val Gln Asn Ser Cys Asp Asn Cys Gln Pro Gly Thr Phe Cys Arg Lys
1               5                   10                  15

Tyr Asn Pro Val Cys Lys Ser Cys Pro Pro Ser Thr Phe Ser Ser Ile
            20                  25                  30

Gly Gly Gln Pro Asn Cys Asn Ile Cys Arg Val Cys Ala Gly Tyr Phe
            35                  40                  45

Arg Phe Lys Lys Phe Cys Ser Ser Thr His Asn Ala Glu Cys Glu Cys
50                  55                  60

Ile Glu Gly Phe His Cys Leu Gly Pro Gln Cys Thr Arg Cys Glu Lys
65                  70                  75                  80

Asp Cys Arg Pro Gly Gln Glu Leu Thr Lys Gln Gly Cys Lys Thr Cys
                85                  90                  95

```
Ser Leu Gly Thr Phe Asn Asp Gln Asn Gly Thr Gly Val Cys Arg Pro
        100                 105                 110

Trp Thr Asn Cys Ser Leu Asp Gly Arg Ser Val Leu Lys Thr Gly Thr
        115                 120                 125

Thr Glu Lys Asp Val Val Cys Gly Pro Pro Val Ser Phe Ser Pro
130                 135                 140

Ser Thr Thr Ile Ser Val Thr Pro Glu Gly Gly Pro Gly Gly His Ser
145                 150                 155                 160

Leu Gln Val Leu Thr Leu Phe Leu Ala Leu Thr Ser Ala Leu Leu Leu
                165                 170                 175

Ala Leu Ile Phe Ile Thr Leu Leu Phe Ser Val Leu Lys Trp Ile Arg
        180                 185                 190

Lys Lys Phe Pro His Ile Phe Lys Gln Pro Phe Lys Lys Thr Thr Gly
        195                 200                 205

Ala Ala Gln Glu Glu Asp Ala Cys Ser Cys Arg Cys Pro Gln Glu Glu
        210                 215                 220

Glu Gly Gly Gly Gly Gly Tyr Glu Leu
225                 230

<210> SEQ ID NO 188
<211> LENGTH: 164
<212> TYPE: PRT
<213> ORGANISM: Mus musculus

<400> SEQUENCE: 188

Val Gln Asn Ser Cys Asp Asn Cys Gln Pro Gly Thr Phe Cys Arg Lys
1               5                   10                  15

Tyr Asn Pro Val Cys Lys Ser Cys Pro Pro Ser Thr Phe Ser Ser Ile
                20                  25                  30

Gly Gly Gln Pro Asn Cys Asn Ile Cys Arg Val Cys Ala Gly Tyr Phe
            35                  40                  45

Arg Phe Lys Lys Phe Cys Ser Ser Thr His Asn Ala Glu Cys Glu Cys
    50                  55                  60

Ile Glu Gly Phe His Cys Leu Gly Pro Gln Cys Thr Arg Cys Glu Lys
65                  70                  75                  80

Asp Cys Arg Pro Gly Gln Glu Leu Thr Lys Gln Gly Cys Lys Thr Cys
                85                  90                  95

Ser Leu Gly Thr Phe Asn Asp Gln Asn Gly Thr Gly Val Cys Arg Pro
            100                 105                 110

Trp Thr Asn Cys Ser Leu Asp Gly Arg Ser Val Leu Lys Thr Gly Thr
        115                 120                 125

Thr Glu Lys Asp Val Val Cys Gly Pro Pro Val Ser Phe Ser Pro
130                 135                 140

Ser Thr Thr Ile Ser Val Thr Pro Glu Gly Gly Pro Gly Gly His Ser
145                 150                 155                 160

Leu Gln Val Leu

<210> SEQ ID NO 189
<211> LENGTH: 231
<212> TYPE: PRT
<213> ORGANISM: Macaca fascicularis

<400> SEQUENCE: 189

Leu Gln Asp Leu Cys Ser Asn Cys Pro Ala Gly Thr Phe Cys Asp Asn
1               5                   10                  15

Asn Arg Ser Gln Ile Cys Ser Pro Cys Pro Pro Asn Ser Phe Ser Ser
```

```
                20                  25                  30
Ala Gly Gly Gln Arg Thr Cys Asp Ile Cys Arg Gln Cys Lys Gly Val
            35                  40                  45

Phe Lys Thr Arg Lys Glu Cys Ser Ser Thr Ser Asn Ala Glu Cys Asp
        50                  55                  60

Cys Ile Ser Gly Tyr His Cys Leu Gly Ala Glu Cys Ser Met Cys Glu
65                  70                  75                  80

Gln Asp Cys Lys Gln Gly Gln Glu Leu Thr Lys Lys Gly Cys Lys Asp
                85                  90                  95

Cys Cys Phe Gly Thr Phe Asn Asp Gln Lys Arg Gly Ile Cys Arg Pro
            100                 105                 110

Trp Thr Asn Cys Ser Leu Asp Gly Lys Ser Val Leu Val Asn Gly Thr
        115                 120                 125

Lys Glu Arg Asp Val Val Cys Gly Pro Ser Pro Ala Asp Leu Ser Pro
    130                 135                 140

Gly Ala Ser Ser Ala Thr Pro Pro Ala Pro Ala Arg Glu Pro Gly His
145                 150                 155                 160

Ser Pro Gln Ile Ile Phe Phe Leu Ala Leu Thr Ser Thr Val Val Leu
                165                 170                 175

Phe Leu Leu Phe Phe Leu Val Leu Arg Phe Ser Val Val Lys Arg Ser
            180                 185                 190

Arg Lys Lys Leu Leu Tyr Ile Phe Lys Gln Pro Phe Met Arg Pro Val
        195                 200                 205

Gln Thr Thr Gln Glu Glu Asp Gly Cys Ser Cys Arg Phe Pro Glu Glu
    210                 215                 220

Glu Glu Gly Gly Cys Glu Leu
225                 230

<210> SEQ ID NO 190
<211> LENGTH: 163
<212> TYPE: PRT
<213> ORGANISM: Macaca fascicularis

<400> SEQUENCE: 190

Leu Gln Asp Leu Cys Ser Asn Cys Pro Ala Gly Thr Phe Cys Asp Asn
1               5                   10                  15

Asn Arg Ser Gln Ile Cys Ser Pro Cys Pro Pro Asn Ser Phe Ser Ser
            20                  25                  30

Ala Gly Gly Gln Arg Thr Cys Asp Ile Cys Arg Gln Cys Lys Gly Val
        35                  40                  45

Phe Lys Thr Arg Lys Glu Cys Ser Ser Thr Ser Asn Ala Glu Cys Asp
    50                  55                  60

Cys Ile Ser Gly Tyr His Cys Leu Gly Ala Glu Cys Ser Met Cys Glu
65                  70                  75                  80

Gln Asp Cys Lys Gln Gly Gln Glu Leu Thr Lys Lys Gly Cys Lys Asp
                85                  90                  95

Cys Cys Phe Gly Thr Phe Asn Asp Gln Lys Arg Gly Ile Cys Arg Pro
            100                 105                 110

Trp Thr Asn Cys Ser Leu Asp Gly Lys Ser Val Leu Val Asn Gly Thr
        115                 120                 125

Lys Glu Arg Asp Val Val Cys Gly Pro Ser Pro Ala Asp Leu Ser Pro
    130                 135                 140

Gly Ala Ser Ser Ala Thr Pro Pro Ala Pro Ala Arg Glu Pro Gly His
145                 150                 155                 160
```

Ser Pro Gln

<210> SEQ ID NO 191
<211> LENGTH: 445
<212> TYPE: PRT
<213> ORGANISM: Artificial Sequence
<220> FEATURE:
<223> OTHER INFORMATION: heavy chain of G1/HelD1.3

<400> SEQUENCE: 191

```
Gln Val Gln Leu Gln Glu Ser Gly Pro Gly Leu Val Arg Pro Ser Gln
1               5                   10                  15

Thr Leu Ser Leu Thr Cys Thr Val Ser Gly Ser Thr Phe Ser Gly Tyr
            20                  25                  30

Gly Val Asn Trp Val Arg Gln Pro Pro Gly Arg Gly Leu Glu Trp Ile
        35                  40                  45

Gly Met Ile Trp Gly Asp Gly Asn Thr Asp Tyr Asn Ser Ala Leu Lys
    50                  55                  60

Ser Arg Val Thr Met Leu Val Asp Thr Ser Lys Asn Gln Phe Ser Leu
65                  70                  75                  80

Arg Leu Ser Ser Val Thr Ala Ala Asp Thr Ala Val Tyr Tyr Cys Ala
                85                  90                  95

Arg Glu Arg Asp Tyr Arg Leu Asp Tyr Trp Gly Gln Gly Ser Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
```

```
            355                 360                 365
Lys Gly Phe Tyr Pro Ser Asp Ile Ala Val Glu Trp Glu Ser Asn Gly
        370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly
        435                 440                 445

<210> SEQ ID NO 192
<211> LENGTH: 17
<212> TYPE: PRT
<213> ORGANISM: Artificial Sequence
<220> FEATURE:
<223> OTHER INFORMATION: OVA peptide

<400> SEQUENCE: 192

Ile Ser Gln Ala Val His Ala Ala His Ala Glu Ile Asn Glu Ala Gly
1               5                   10                  15

Arg

<210> SEQ ID NO 193
<211> LENGTH: 434
<212> TYPE: PRT
<213> ORGANISM: Homo sapiens

<400> SEQUENCE: 193

Ile Leu Glu Val Gln Val Pro Glu Asp Pro Val Val Ala Leu Val Gly
1               5                   10                  15

Thr Asp Ala Thr Leu Cys Cys Ser Phe Ser Pro Glu Pro Gly Phe Ser
            20                  25                  30

Leu Ala Gln Leu Asn Leu Ile Trp Gln Leu Thr Asp Thr Lys Gln Leu
        35                  40                  45

Val His Ser Phe Ala Glu Gly Gln Asp Gln Gly Ser Ala Tyr Ala Asn
    50                  55                  60

Arg Thr Ala Leu Phe Pro Asp Leu Leu Ala Gln Gly Asn Ala Ser Leu
65                  70                  75                  80

Arg Leu Gln Arg Val Arg Val Ala Asp Glu Gly Ser Phe Thr Cys Phe
                85                  90                  95

Val Ser Ile Arg Asp Phe Gly Ser Ala Ala Val Ser Leu Gln Val Ala
            100                 105                 110

Ala Pro Tyr Ser Lys Pro Ser Met Thr Leu Glu Pro Asn Lys Asp Leu
        115                 120                 125

Arg Pro Gly Asp Thr Val Thr Ile Thr Cys Ser Ser Tyr Gln Gly Tyr
    130                 135                 140

Pro Glu Ala Glu Val Phe Trp Gln Asp Gly Gln Gly Val Pro Leu Thr
145                 150                 155                 160

Gly Asn Val Thr Thr Ser Gln Met Ala Asn Glu Gln Gly Leu Phe Asp
                165                 170                 175

Val His Ser Ile Leu Arg Val Val Leu Gly Ala Asn Gly Thr Tyr Ser
            180                 185                 190

Cys Leu Val Arg Asn Pro Val Leu Gln Gln Asp Ala His Ser Ser Val
        195                 200                 205
```

```
Thr Ile Thr Pro Gln Arg Ser Pro Thr Gly Ala Val Glu Val Gln Val
    210                 215                 220

Pro Glu Asp Pro Val Val Ala Leu Val Gly Thr Asp Ala Thr Leu Arg
225                 230                 235                 240

Cys Ser Phe Ser Pro Glu Pro Gly Phe Ser Leu Ala Gln Leu Asn Leu
                245                 250                 255

Ile Trp Gln Leu Thr Asp Thr Lys Gln Leu Val His Ser Phe Thr Glu
            260                 265                 270

Gly Arg Asp Gln Gly Ser Ala Tyr Ala Asn Arg Thr Ala Leu Phe Pro
        275                 280                 285

Asp Leu Leu Ala Gln Gly Asn Ala Ser Leu Arg Leu Gln Arg Val Arg
    290                 295                 300

Val Ala Asp Glu Gly Ser Phe Thr Cys Phe Val Ser Ile Arg Asp Phe
305                 310                 315                 320

Gly Ser Ala Ala Val Ser Leu Gln Val Ala Ala Pro Tyr Ser Lys Pro
                325                 330                 335

Ser Met Thr Leu Glu Pro Asn Lys Asp Leu Arg Pro Gly Asp Thr Val
            340                 345                 350

Thr Ile Thr Cys Ser Ser Tyr Arg Gly Tyr Pro Glu Ala Glu Val Phe
        355                 360                 365

Trp Gln Asp Gly Gln Gly Val Pro Leu Thr Gly Asn Val Thr Thr Ser
    370                 375                 380

Gln Met Ala Asn Glu Gln Gly Leu Phe Asp Val His Ser Val Leu Arg
385                 390                 395                 400

Val Val Leu Gly Ala Asn Gly Thr Tyr Ser Cys Leu Val Arg Asn Pro
                405                 410                 415

Val Leu Gln Gln Asp Ala His Gly Ser Val Thr Ile Thr Gly Gln Pro
            420                 425                 430

Met Thr

<210> SEQ ID NO 194
<211> LENGTH: 8
<212> TYPE: PRT
<213> ORGANISM: Artificial Sequence
<220> FEATURE:
<223> OTHER INFORMATION: SIINFEKL peptide

<400> SEQUENCE: 194

Ser Ile Ile Asn Phe Glu Lys Leu
1               5

<210> SEQ ID NO 195
<211> LENGTH: 433
<212> TYPE: PRT
<213> ORGANISM: Homo sapiens

<400> SEQUENCE: 195

Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
            20                  25                  30

Gly Ser Asn Met Thr Ile Glu Cys Lys Phe Pro Val Glu Lys Gln Leu
        35                  40                  45

Asp Leu Ala Ala Leu Ile Val Tyr Trp Glu Met Glu Asp Lys Asn Ile
    50                  55                  60

Ile Gln Phe Val His Gly Glu Glu Asp Leu Lys Val Gln His Ser Ser
65                  70                  75                  80
```

```
Tyr Arg Gln Arg Ala Arg Leu Leu Lys Asp Gln Leu Ser Leu Gly Asn
                85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
        115                 120                 125

Lys Val Asn Ala Pro Tyr Asn Lys Ile Asn Gln Arg Ile Leu Val Val
    130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
            180                 185                 190

Val Thr Ser Thr Leu Arg Ile Asn Thr Thr Thr Asn Glu Ile Phe Tyr
        195                 200                 205

Cys Thr Phe Arg Arg Leu Asp Pro Glu Glu Asn His Thr Ala Glu Leu
    210                 215                 220

Val Ile Pro Glu Leu Pro Leu Ala His Pro Pro Asn Glu Arg Thr Ala
225                 230                 235                 240

Ala Ala Thr Ser Ile Thr Ala Tyr Lys Ser Glu Gly Glu Ser Ala Glu
                245                 250                 255

Phe Ser Phe Pro Leu Asn Leu Gly Glu Glu Ser Leu Gln Gly Glu Leu
            260                 265                 270

Arg Trp Lys Ala Glu Lys Ala Pro Ser Ser Gln Ser Trp Ile Thr Phe
        275                 280                 285

Ser Leu Lys Asn Gln Lys Val Ser Val Gln Lys Ser Thr Ser Asn Pro
    290                 295                 300

Lys Phe Gln Leu Ser Glu Thr Leu Pro Leu Thr Leu Gln Ile Pro Gln
305                 310                 315                 320

Val Ser Leu Gln Phe Ala Gly Ser Gly Asn Leu Thr Leu Thr Leu Asp
                325                 330                 335

Arg Gly Ile Leu Tyr Gln Glu Val Asn Leu Val Val Met Lys Val Thr
            340                 345                 350

Gln Pro Asp Ser Asn Thr Leu Thr Cys Glu Val Met Gly Pro Thr Ser
        355                 360                 365

Pro Lys Met Arg Leu Ile Leu Lys Gln Glu Asn Gln Glu Ala Arg Val
    370                 375                 380

Ser Arg Gln Glu Lys Val Ile Gln Val Gln Ala Pro Glu Ala Gly Val
385                 390                 395                 400

Trp Gln Cys Leu Leu Ser Glu Gly Glu Val Lys Met Asp Ser Lys
                405                 410                 415

Ile Gln Val Leu Ser Lys Gly Leu Asn Gly Ser His His His His
            420                 425                 430

His

<210> SEQ ID NO 196
<211> LENGTH: 477
<212> TYPE: PRT
<213> ORGANISM: Homo sapiens

<400> SEQUENCE: 196

Met Arg Ile Phe Ala Val Phe Ile Phe Met Thr Tyr Trp His Leu Leu
1               5                   10                  15
```

Asn Ala Phe Thr Val Thr Val Pro Lys Asp Leu Tyr Val Val Glu Tyr
            20                  25                  30

Gly Ser Asn Met Thr Ile Glu Cys Lys Phe Pro Val Glu Lys Gln Leu
            35                  40                  45

Asp Leu Ala Ala Leu Ile Val Tyr Trp Glu Met Glu Asp Lys Asn Ile
50                  55                  60

Ile Gln Phe Val His Gly Glu Glu Asp Leu Lys Val Gln His Ser Ser
65                  70                  75                  80

Tyr Arg Gln Arg Ala Arg Leu Leu Lys Asp Gln Leu Ser Leu Gly Asn
                85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
            115                 120                 125

Lys Val Asn Ala Pro Tyr Asn Lys Ile Asn Gln Arg Ile Leu Val Val
130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
            180                 185                 190

Val Thr Ser Thr Leu Arg Ile Asn Thr Thr Asn Glu Ile Phe Tyr
            195                 200                 205

Cys Thr Phe Arg Arg Leu Asp Pro Glu Glu Asn His Thr Ala Glu Leu
            210                 215                 220

Val Ile Pro Glu Leu Pro Leu Ala His Pro Pro Asn Glu Arg Thr Ala
225                 230                 235                 240

Ala Ala Asp Lys Thr His Thr Cys Pro Pro Cys Pro Ala Pro Glu Leu
            245                 250                 255

Leu Gly Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
            275                 280                 285

Ser His Glu Asp Pro Glu Val Lys Phe Asn Trp Tyr Val Asp Gly Val
            290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Ala Leu Pro Ala
            340                 345                 350

Pro Ile Glu Lys Thr Ile Ser Lys Ala Lys Gly Gln Pro Arg Glu Pro
            355                 360                 365

Gln Val Tyr Thr Leu Pro Pro Ser Arg Asp Glu Leu Thr Lys Asn Gln
            370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Val Leu Asp Ser Asp Gly Ser Phe Phe Leu Tyr Ser Lys Leu
            420                 425                 430

```
Thr Val Asp Lys Ser Arg Trp Gln Gln Gly Asn Val Phe Ser Cys Ser
        435                 440                 445

Val Met His Glu Ala Leu His Asn His Tyr Thr Gln Lys Ser Leu Ser
450                 455                 460

Leu Ser Pro Gly Lys Gly Ser His His His His His
465                 470                 475
```

<210> SEQ ID NO 197
<211> LENGTH: 432
<212> TYPE: PRT
<213> ORGANISM: Mus musculus

<400> SEQUENCE: 197

```
Met Arg Ile Phe Ala Gly Ile Ile Phe Thr Ala Cys Cys His Leu Leu
1               5                   10                  15

Arg Ala Phe Thr Ile Thr Ala Pro Lys Asp Leu Tyr Val Val Glu Tyr
            20                  25                  30

Gly Ser Asn Val Thr Met Glu Cys Arg Phe Pro Val Glu Arg Glu Leu
        35                  40                  45

Asp Leu Leu Ala Leu Val Val Tyr Trp Glu Lys Glu Asp Glu Gln Val
    50                  55                  60

Ile Gln Phe Val Ala Gly Glu Glu Asp Leu Lys Pro Gln His Ser Asn
65                  70                  75                  80

Phe Arg Gly Arg Ala Ser Leu Pro Lys Asp Gln Leu Leu Lys Gly Asn
                85                  90                  95

Ala Ala Leu Gln Ile Thr Asp Val Lys Leu Gln Asp Ala Gly Val Tyr
            100                 105                 110

Cys Cys Ile Ile Ser Tyr Gly Gly Ala Asp Tyr Lys Arg Ile Thr Leu
        115                 120                 125

Lys Val Asn Ala Pro Tyr Arg Lys Ile Asn Gln Arg Ile Ser Val Asp
    130                 135                 140

Pro Ala Thr Ser Glu His Glu Leu Ile Cys Gln Ala Glu Gly Tyr Pro
145                 150                 155                 160

Glu Ala Glu Val Ile Trp Thr Asn Ser Asp His Gln Pro Val Ser Gly
                165                 170                 175

Lys Arg Ser Val Thr Thr Ser Arg Thr Glu Gly Met Leu Leu Asn Val
            180                 185                 190

Thr Ser Ser Leu Arg Val Asn Ala Thr Ala Asn Asp Val Phe Tyr Cys
        195                 200                 205

Thr Phe Trp Arg Ser Gln Pro Gly Gln Asn His Thr Ala Glu Leu Ile
    210                 215                 220

Ile Pro Glu Leu Pro Ala Thr His Pro Pro Gln Asn Arg Thr Ala Ala
225                 230                 235                 240

Ala Thr Ser Ile Thr Ala Tyr Lys Ser Glu Gly Glu Ser Ala Glu Phe
                245                 250                 255

Ser Phe Pro Leu Asn Leu Gly Glu Glu Ser Leu Gln Gly Glu Leu Arg
            260                 265                 270

Trp Lys Ala Glu Lys Ala Pro Ser Ser Gln Ser Trp Ile Thr Phe Ser
        275                 280                 285

Leu Lys Asn Gln Lys Val Ser Val Gln Lys Ser Thr Ser Asn Pro Lys
    290                 295                 300

Phe Gln Leu Ser Glu Thr Leu Pro Leu Thr Leu Gln Ile Pro Gln Val
305                 310                 315                 320

Ser Leu Gln Phe Ala Gly Ser Gly Asn Leu Thr Leu Thr Leu Asp Arg
                325                 330                 335
```

```
Gly Ile Leu Tyr Gln Glu Val Asn Leu Val Val Met Lys Val Thr Gln
            340                 345                 350

Pro Asp Ser Asn Thr Leu Thr Cys Glu Val Met Gly Pro Thr Ser Pro
            355                 360                 365

Lys Met Arg Leu Ile Leu Lys Gln Glu Asn Gln Glu Ala Arg Val Ser
370                 375                 380

Arg Gln Glu Lys Val Ile Gln Val Gln Ala Pro Glu Ala Gly Val Trp
385                 390                 395                 400

Gln Cys Leu Leu Ser Glu Gly Glu Val Lys Met Asp Ser Lys Ile
            405                 410                 415

Gln Val Leu Ser Lys Gly Leu Asn Gly Ser His His His His His
            420                 425                 430

<210> SEQ ID NO 198
<211> LENGTH: 476
<212> TYPE: PRT
<213> ORGANISM: Mus musculus

<400> SEQUENCE: 198

Met Arg Ile Phe Ala Gly Ile Ile Phe Thr Ala Cys Cys His Leu Leu
1               5                   10                  15

Arg Ala Phe Thr Ile Thr Ala Pro Lys Asp Leu Tyr Val Val Glu Tyr
            20                  25                  30

Gly Ser Asn Val Thr Met Glu Cys Arg Phe Pro Val Glu Arg Glu Leu
        35                  40                  45

Asp Leu Leu Ala Leu Val Val Tyr Trp Glu Lys Glu Asp Glu Gln Val
50                  55                  60

Ile Gln Phe Val Ala Gly Glu Glu Asp Leu Lys Pro Gln His Ser Asn
65                  70                  75                  80

Phe Arg Gly Arg Ala Ser Leu Pro Lys Asp Gln Leu Leu Lys Gly Asn
                85                  90                  95

Ala Ala Leu Gln Ile Thr Asp Val Lys Leu Gln Asp Ala Gly Val Tyr
            100                 105                 110

Cys Cys Ile Ile Ser Tyr Gly Gly Ala Asp Tyr Lys Arg Ile Thr Leu
        115                 120                 125

Lys Val Asn Ala Pro Tyr Arg Lys Ile Asn Gln Arg Ile Ser Val Asp
130                 135                 140

Pro Ala Thr Ser Glu His Glu Leu Ile Cys Gln Ala Glu Gly Tyr Pro
145                 150                 155                 160

Glu Ala Glu Val Ile Trp Thr Asn Ser Asp His Gln Pro Val Ser Gly
                165                 170                 175

Lys Arg Ser Val Thr Thr Ser Arg Thr Glu Gly Met Leu Leu Asn Val
            180                 185                 190

Thr Ser Ser Leu Arg Val Asn Ala Thr Ala Asn Asp Val Phe Tyr Cys
        195                 200                 205

Thr Phe Trp Arg Ser Gln Pro Gly Gln Asn His Thr Ala Glu Leu Ile
210                 215                 220

Ile Pro Glu Leu Pro Ala Thr His Pro Pro Gln Asn Arg Thr Ala Ala
225                 230                 235                 240

Ala Asp Lys Thr His Thr Cys Pro Pro Cys Pro Ala Pro Glu Leu Leu
                245                 250                 255

Gly Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
```

```
            275                 280                 285
His Glu Asp Pro Glu Val Lys Phe Asn Trp Tyr Val Asp Gly Val Glu
    290                 295                 300

Val His Asn Ala Lys Thr Lys Pro Arg Glu Glu Gln Tyr Asn Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Ala Leu Pro Ala Pro
            340                 345                 350

Ile Glu Lys Thr Ile Ser Lys Ala Lys Gly Gln Pro Arg Glu Pro Gln
        355                 360                 365

Val Tyr Thr Leu Pro Pro Ser Arg Asp Glu Leu Thr Lys Asn Gln Val
    370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Val Leu Asp Ser Asp Gly Ser Phe Phe Leu Tyr Ser Lys Leu Thr
            420                 425                 430

Val Asp Lys Ser Arg Trp Gln Gln Gly Asn Val Phe Ser Cys Ser Val
        435                 440                 445

Met His Glu Ala Leu His Asn His Tyr Thr Gln Lys Ser Leu Ser Leu
    450                 455                 460

Ser Pro Gly Lys Gly Ser His His His His His
465                 470                 475

<210> SEQ ID NO 199
<211> LENGTH: 245
<212> TYPE: PRT
<213> ORGANISM: Homo sapiens

<400> SEQUENCE: 199

Phe Thr Val Thr Val Pro Lys Asp Leu Tyr Val Val Glu Tyr Gly Ser
1               5                   10                  15

Asn Met Thr Ile Glu Cys Lys Phe Pro Val Glu Lys Gln Leu Asp Leu
            20                  25                  30

Ala Ala Leu Ile Val Tyr Trp Glu Met Glu Asp Lys Asn Ile Ile Gln
        35                  40                  45

Phe Val His Gly Glu Glu Asp Leu Lys Val Gln His Ser Ser Tyr Arg
    50                  55                  60

Gln Arg Ala Arg Leu Leu Lys Asp Gln Leu Ser Leu Gly Asn Ala Ala
65                  70                  75                  80

Leu Gln Ile Thr Asp Val Lys Leu Gln Asp Ala Gly Val Tyr Arg Cys
                85                  90                  95

Met Ile Ser Tyr Gly Gly Ala Asp Tyr Lys Arg Ile Thr Val Lys Val
            100                 105                 110

Asn Ala Pro Tyr Asn Lys Ile Asn Gln Arg Ile Leu Val Val Asp Pro
        115                 120                 125

Val Thr Ser Glu His Glu Leu Thr Cys Gln Ala Glu Gly Tyr Pro Lys
    130                 135                 140

Ala Glu Val Ile Trp Thr Ser Ser Asp His Gln Val Leu Ser Gly Lys
145                 150                 155                 160

Thr Thr Thr Thr Asn Ser Lys Arg Glu Glu Lys Leu Phe Asn Val Thr
                165                 170                 175
```

```
Ser Thr Leu Arg Ile Asn Thr Thr Thr Asn Glu Ile Phe Tyr Cys Thr
            180             185                 190

Phe Arg Arg Leu Asp Pro Glu Glu Asn His Thr Ala Glu Leu Val Ile
        195             200             205

Pro Glu Leu Pro Leu Ala His Pro Pro Asn Glu Arg Gly Ser His His
    210             215             220

His His His His Gly Gly Gly Leu Asn Asp Ile Phe Glu Ala Gln Lys
225             230             235                 240

Ile Glu Trp His Glu
            245
```